US009796719B2

(12) United States Patent
Desroy et al.

(10) Patent No.: US 9,796,719 B2
(45) Date of Patent: Oct. 24, 2017

(54) COMPOUNDS AND PHARMACEUTICAL COMPOSITIONS THEREOF FOR THE TREATMENT OF INFLAMMATORY DISORDERS

(71) Applicant: GALAPAGOS NV, Mechelen (BE)

(72) Inventors: Nicolas Desroy, Romainville (FR); Bertrand Heckmann, Romainville (FR); Reginald Christophe Xavier Brys, Mechelen (BE); Agnès Marie Joncour, Romainville (FR); Christophe Peixoto, Romainville (FR); Xavier Marie Bock, Romainville (FR); Christopher Gaëtan Housseman, Romainville (FR)

(73) Assignee: GALAPAGOS NV, Mechelen (BE)

( * ) Notice: Subject to any disclaimer, the term of this patent is extended or adjusted under 35 U.S.C. 154(b) by 0 days.

(21) Appl. No.: 14/898,327

(22) PCT Filed: Jun. 12, 2014

(86) PCT No.: PCT/EP2014/062241
§ 371 (c)(1),
(2) Date: Dec. 14, 2015

(87) PCT Pub. No.: WO2014/202458
PCT Pub. Date: Dec. 24, 2014

(65) Prior Publication Data
US 2016/0214986 A1 Jul. 28, 2016

Related U.S. Application Data

(60) Provisional application No. 61/836,831, filed on Jun. 19, 2013.

(51) Int. Cl.
| | | |
|---|---|---|
| *C07D 487/04* | (2006.01) | |
| *C07D 519/00* | (2006.01) | |
| *A61K 45/06* | (2006.01) | |
| *A61K 31/4985* | (2006.01) | |
| *A61K 31/5025* | (2006.01) | |
| *A61K 31/506* | (2006.01) | |
| *A61K 31/5377* | (2006.01) | |

(Continued)

(52) U.S. Cl.
CPC ........ *C07D 487/04* (2013.01); *A61K 31/4985* (2013.01); *A61K 31/506* (2013.01); *A61K 31/5025* (2013.01); *A61K 31/5377* (2013.01); *A61K 31/5383* (2013.01); *A61K 31/541* (2013.01); *A61K 31/551* (2013.01); *A61K 45/06* (2013.01); *C07D 519/00* (2013.01)

(58) Field of Classification Search
CPC .................................................. C07D 401/01
See application file for complete search history.

(56) References Cited

U.S. PATENT DOCUMENTS

| | | |
|---|---|---|
| 8,227,603 B2 | 7/2012 | Russell et al. |
| 8,993,590 B2 | 3/2015 | Desroy et al. |
| 9,249,141 B2 | 2/2016 | Desroy et al. |

FOREIGN PATENT DOCUMENTS

| | | |
|---|---|---|
| WO | 2008/138842 A1 | 11/2008 |
| WO | 2010/063352 A1 | 6/2010 |

(Continued)

OTHER PUBLICATIONS

Bandoh, K., et al., "Lysophosphatidic acid (LPA) receptors of the EDG family are differentially activated by LPA species. Structure-activity relationship of cloned LPA receptors." *FEBS Lett.*, vol. 478, pp. 159-165 (2000).
Baumforth, K.R.N., et al., "Induction of autotaxin by the Epstein-Barr virus promotes the growth and survival of Hodgkin lymphoma cells", *Blood*, vol. 106, pp. 2138-2146 (2005).
Bozinovski, S., et al., "Serum amyloid a is a biomarker of acute exacerbations of chronic obstructive pulmonary disease", *Am. J. Respir. Crit. Care Med.*, vol. 177, pp. 269-278 (2008).

(Continued)

*Primary Examiner* — Paul V Ward
(74) *Attorney, Agent, or Firm* — Heslin Rothenberg Farley & Mesiti P.C.

(57) ABSTRACT

The present invention discloses compounds according to Formula I:

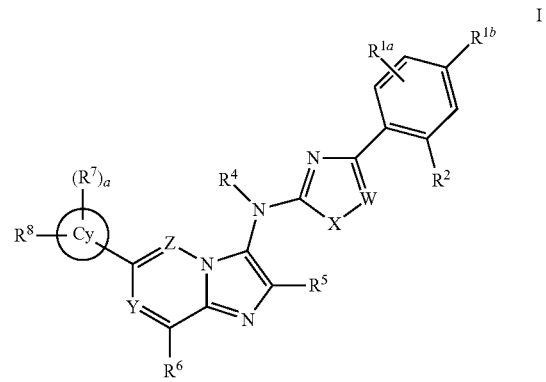

Wherein $R^{1a}$, $R^{1b}$, $R^2$, $R^4$, $R^5$, $R^6$, $R^7$, $R^8$, W, X, Y, Z, Cy, and the subscript a are as defined herein. The present invention relates to compounds inhibiting autotaxin (NPP2 or ENPP2), methods for their production, pharmaceutical compositions comprising the same, and methods of treatment using the same, for the prophylaxis and/or treatment of diseases involving fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering the compound of the invention.

15 Claims, No Drawings

(51) Int. Cl.
A61K 31/5383 (2006.01)
A61K 31/541 (2006.01)
A61K 31/551 (2006.01)

(56) References Cited

FOREIGN PATENT DOCUMENTS

| | | |
|---|---|---|
| WO | 2011/054922 A1 | 5/2011 |
| WO | 2012/166415 A1 | 12/2012 |

OTHER PUBLICATIONS

Braddock, D.T., "Autotaxin and lipid signaling pathways as anti-cancer targets", Curr Opin Investig Drugs, vol. 11, pp. 629-637 (2010).
Bush, K.A., et al., "Reduction of joint inflammation and bone erosion in rat adjuvant arthritis by treatment with interleukin-17 receptor IgGl Fc fusion protein", Arthritis & Rheumatism, vol. 46, pp. 802-805 (2002).
Castelino, F.V., et al., "Genetic deletion or pharmacologic antagonism of LPA1 ameliorates dermal fibrosis in a scleroderma mouse model", Arthritis Rheum, vol. 63, pp. 1405-1415 (2011).
Corley, E.G., et al., "Direct Synthesis of 4-Arylpiperidines via Palladium/Copper(I)-Cocatalyzed Negishi Coupling of a 4-Piperidylzinc Iodide with Aromatic Halides and Triflates", J. Org. Chem., vol. 69, pp. 5120-5123 (2004).
David, M., et al., "Cancer Cell Expression of Autotaxin Controls Bone Metastasis Formation in Mouse through Lysophosphatidic Acid-Dependent Activation of Osteoclasts", PLoS One, vol. 5, No. 3, pp. e9741 (2010).
Demedts, I.K., et al., "Elevated MMP-12 protein levels in induced sputum from patients with COPD", Thorax, vol. 61, pp. 196-201 (2006).
Eagan, T.M., et al., "Neutrophil gelatinase-associated lipocalin: A biomarker in copd", Chest, vol. 138, No. 4, pp. 888-895 (2010).
Emo, J., et al., "Lpa2 is a negative regulator of dendritic cell activation and murine models of allergic lung inflammation", J Immunol, vol. 188, No. 8, pp. 3784-3790 (2012).
Federico, L., et al., "Autotaxin and Its Product Lysophosphatidic Acid Suppress Brown Adipose Differentiation and Promote Diet-Induced Obesity in Mice", Molecular Endocrinology, vol. 26, pp. 786-797 (2012).
Ferry, G., et al., "Autotaxin Is Released from Adipocytes, Catalyzes Lysophosphatidic Acid Synthesis, and Activates Preadipocyte Proliferation Up-Regulated Expression With Adipocyte Differentiation and Obesity", J. Biol. Chem., vol. 278, pp. 18162-18169 (2003).
Gaetano, C.G., et al., "Inhibition of autotaxin production or activity blocks lysophosphatidylcholine-induced migration of human breast cancer and melanoma cells", Mol. Carcinog., vol. 48, No. 9, pp. 801-809 (2009).
Ganguly, K., et al., "Candidate genes controlling pulmonary function in mice: transcript profiling and predicted protein structure", Physiol. Genomics, vol. 31, pp. 410-421 (2007).
Gardell, S.E., et al., "Emerging medicinal roles for lysophospholipid signaling", Trends in Molecular Medicine, vol. 12, No. 2, pp. 65-75 (2006).
Gennero, I., et al., "Absence of the lysophosphatidic acid receptor LPA1 results in abnormal bone development and decreased bone mass", Bone, vol. 49, pp. 395-403 (2011).
Georas, S.N., et al., "Lysophosphatidic acid is detectable in human bronchoalveolar lavage fluids at baseline and increased after segmental allergen challenge", Clinical & Experimental Allergy, vol. 37, pp. 311-322 (2006).
Gierse, J., et al., "A Novel Autotaxin Inhibitor Reduces Lysophosphatidic Acid Levels in Plasma and the Site of Inflammation", J Pharmacol Exp Ther, vol. 334, No. 1, pp. 310-317 (2010).
Hausmann, J., et al., "Structural basis for substrate discrimination and integrin binding by autotaxin", Nat Struct Mol Biol, vol. 18, No. 2, pp. 198-204 (2011).
Inoue, M., et al., "Lysophosphatidylcholine induces neuropathic pain through an action of autotaxin to generate lysophosphatidic acid", Neuroscience, vol. 152, pp. 296-298 (2008).
Iyer, P., et al., "Autotaxin-Lysophosphatidic Acid Axis Is a Novel Molecular Target for Lowering Intraocular Pressure", PLoS One, vol. 7, No. 8, pp. e42627 (2012).
Jou, I.-M., et al., "Thrombospondin 1 as an effective gene therapeutic strategy in collagen-induced arthritis", Arthritis & Rheumatism, vol. 52, No. 1, pp. 339-344 (2005).
Kanda, H., et al., "Autotaxin, a lysophosphatidic acid-producing ectoenzyme, promotes lymphocyte entry into secondary lymphoid organs", Nat Immunol, vol. 9, No. 4, pp. 415-423 (2008).
Khachigian, L.M., "Collagen antibody-induced arthritis", Nat. Protocols, vol. 1, No. 5, pp. 2512-2516 (2006).
Kishi, Y., et al., "Autotaxin Is Overexpressed in Glioblastoma Multiforme and Contributes to Cell Motility of Glioblastoma by Converting Lysophosphatidylcholine to Lysophosphatidic Acid", J. Biol. Chem., vol. 281, pp. 17492-17500 (2006).
Kolonko, K.J., et al., "Stabilization of Ketone and Aldehyde Enols by Formation of Hydrogen Bonds to Phosphazene Enolates and Their Aldol Products", J. Am. Chem. Soc., vol. 130, pp. 9668-9669 (2008).
Kremer, A.E., et al., "Lysophosphatidic Acid Is a Potential Mediator of Cholestatic Pruritus", Gastroenterology, vol. 139, No. 3, pp. 1008-1018.el. (2010).
Lin, H.-S., et al., "Anti-rheumatic activities of histone deacetylase (HDAC) inhibitors in vivo in collagen-induced arthritis in rodents", British Journal of Pharmacology, vol. 150, pp. 862-872 (2007).
Lin, M.-E., et al., "Lysophosphatidic acid (LPA) receptors: signaling properties and disease relevance", Prostaglandins Other Lipid Mediat, vol. 91, No. 3-4, pp. 130-138 (2010).
Llinas, L., et al., "Similar gene expression profiles in smokers and patients with moderate COPD", Pulmonary Pharmacology & Therapeutics, vol. 24, pp. 32-41 (2011).
Matas-Rico, E., et al., "Deletion of lysophosphatidic acid receptor LPA1 reduces neurogenesis in the mouse dentate gyrus", Mol Cell Neurosci, vol. 39, No. 3, pp. 342-355 (2008).
Van Meeteren, L.A., et al., "Autotaxin, a Secreted Lysophospholipase D, Is Essential for Blood Vessel Formation during Development", Mol Cell Biol, vol. 26, No. 13, pp. 5015-5022 (2006).
Murph, M., et al., "Sharpening the edges of understanding the structure/function of the LPA1 receptor", Biochim Biophys Acta, vol. 1781, No. 9, pp. 547-557 (2008).
Nakao, I., et al., "Identification of Pendrin as a Common Mediator for Mucus Production in Bronchial Asthma and Chronic Obstructive Pulmonary Disease", J Immunol, vol. 180, pp. 6262-6269 (2008).
Nakasaki, T., et al., "Involvement of the Lysophosphatidic Acid-Generating Enzyme Autotaxin in Lymphocyte-Endothelial Cell Interactions", Am J Pathol, vol. 173, No. 5, pp. 1566-1576 (2008).
Nikitopoulou, I., et al., "Autotaxin expression from synovial fibroblasts is essential for the pathogenesis of modeled arthritis", J Exp Med, vol. 209, No. 5, pp. 925-933 (2012).
Nishida, K., et al., "Histone deacetylase inhibitor suppression of autoantibody-mediated arthritis in mice via regulation of p16INK4a and p21WAF1/Cip1 expression", Arthritis & Rheumatism, vol. 50, No. 10, pp. 3365-3376 (2004).
Nouh, M.A.A.M., et al., "Expression of Autotaxin and Acylglycerol kinase in prostate cancer: Association with cancer development and progression", Cancer Science, vol. 100, No. 9, pp. 1631-1638 (2009).
Oikonomou, N., et al., "Pulmonary Autotaxin Expression Contributes to the Pathogenesis of Pulmonary Fibrosis", American Journal of Respiratory Cell and Molecular Biology, vol. 47, No. 5, pp. 566-574 (2012).
Oste, L., et al., "A high throughput method of measuring bone architectural disturbance in a murine CIA model by micro-CT morphometry", (Copenhagen), (2007).
Panupinthu, N., et al., "Lysophosphatidic acid production and action: critical new players in breast cancer initiation and progression", Br J Cancer, vol. 102, pp. 941-946 (2010).
Pradère, J.-P., et al., "LPA1 Receptor Activation Promotes Renal Interstitial Fibrosis", JASN, vol. 18, pp. 3110-3118 (2007).

(56) References Cited

OTHER PUBLICATIONS

Rall, L.C., et al., "Rheumatoid cachexia: metabolic abnormalities, mechanisms and interventions", *Rheumatology*, vol. 43, pp. 1219-1223 (2004).
Salvemini, D., et al., "Amelioration of joint disease in a rat model of collagen-induced arthritis by M40403, a superoxide dismutase mimetic", *Arthritis Rheum.*, vol. 44, No. 12, pp. 2909-2921 (2001).
Shelton, D.L., et al., "Nerve growth factor mediates hyperalgesia and cachexia in auto-immune arthritis", *Pain*, vol. 116, pp. 8-16 (2005).
Sims, N.A., et al., "Targeting osteoclasts with zoledronic acid prevents bone destruction in collagen-induced arthritis", *Arthritis & Rheumatism*, vol. 50, No. 7, pp. 2338-2346 (2004).
Stassar, M.J.J.G., et al., "Identification of human renal cell carcinoma associated genes by suppression subtractive hybridization", *Br J Cancer*, vol. 85, No. 9, pp. 1372-1382 (2001).
Sumida, H., et al., "LPA4 regulates blood and lymphatic vessel formation during mouse embryogenesis" *Blood*, vol. 116, pp. 5060-5070 (2010).
Tager, A.M., et al., "The lysophosphatidic acid receptor LPA1 links pulmonary fibrosis to lung injury by mediating fibroblast recruitment and vascular leak", *Nat Med*, vol. 14, No. 1, pp. 45-54 (2008).
Tanaka, M., et al., "Autotaxin Stabilizes Blood Vessels and Is Required for Embryonic Vasculature by Producing Lysophosphatidic Acid", *J. Biol. Chem.*, vol. 281, pp. 25822-25830 (2006).
Tania, M., et al., "Autotaxin: A protein with two faces", *Biochemical and Biophysical Research Communications*, vol. 401, pp. 493-497 (2010).
Tilley, A.E., et al., "Biologic Phenotyping of the Human Small Airway Epithelial Response to Cigarette Smoking", *PLoS One*, vol. 6, No. 7, pp. e22798 (2011).
Vidot, S., et al., "Autotaxin delays apoptosis induced by carboplatin in ovarian cancer cells", *Cellular Signalling*, vol. 22, pp. 926-935 (2010).
Walsmith, J., et al., "Tumor necrosis factor-alpha production is associated with less body cell mass in women with rheumatoid arthritis", *J. Rheumatol.*, vol. 31, pp. 23-29 (2004).
Walters, D.M., et al., "Mouse Models of Bleomycin-Induced Pulmonary Fibrosis", In Current Protocols in Pharmacology, 40, 5.46.1-5.46.17. (2001).
Wirtz, S., et al., "Mouse models of inflammatory bowel disease", *Advanced Drug Delivery Reviews*, vol. 59, pp. 1073-1083 (2007).
Wu, J.-M., et al., "Autotaxin expression and its connection with the TNF-alpha-NF-$_K$B axis in human hepatocellular carcinoma", *Mol Cancer*, vol. 9, No. 71 (2010).
Xu, X., et al., "Inhibition of Tumor Growth and Angiogenesis by a Lysophosphatidic Acid Antagonist in a Engineered Three-dimensional Lung Cancer Xenograft Model", *Cancer*, vol. 116, No. 7, pp. 1739-1750 (2010).
Xu, M.Y., et al., "Lysophosphatidic Acid Induces $\alpha v \beta 6$ Integrin-Mediated TGF-$\beta$ Activation via the LPA2 Receptor and the Small G Protein G$\alpha$q", *The American Journal of Pathology*, vol. 174, No. 4, pp. 1264-1279 (2009).
Ye, X., et al., "LPA3-mediated lysophosphatidic acid signalling in implantation and embryo spacing", *Nature* vol. 435, No. 7038, pp. 104-108 (2005).
Zhang, H., et al., "Dual Activity Lysophosphatidic Acid Receptor Pan-Antagonist/Autotaxin Inhibitor Reduces Breast Cancer Cell Migration In vitro and Causes Tumor Regression In vivo", *Cancer Res*, vol. 69, No. 13, pp. 5441-5449 (2009).
Zhao, Y., et al., "Lysophosphatidic acid (LPA) and its Receptors: Role in Airway Inflammation and Remodeling", *Biochim Biophys Acta*, vol. 1831, No. 1, pp. 86-92 (2013).
Zhao, J., et al., "Autotaxin induces lung epithelial cell migration through lysoPLD activity-dependent and -independent pathways", *Biochem J*, vol. 439, No. 1, pp. 45-55 (2011).
Zhao, Y., et al., "Role of lysophosphatidic acid receptor LPA2 in the development of allergic airway inflammation in a murine model of asthma", *Respir Res*, vol. 10, pp. 114 (2009).
De Alba, J., et al., "House Dust Mite Induces Direct Airway Inflammation In Vivo: Implications for Future Disease Therapy?", *European Respiratory Journal*, vol. 35, No. 6, pp. 1377-1387 (2010).
Grimm, S. W., et al., "The Conduct of in Vitro Studies to Address Time-Dependent Inhibition of Drug-Metabolizing Enzymes: A Perspective of the Pharmaceutical Research and Manufacturers of America", *Drug Metabolism and Disposition*, vol. 37, No. 7, pp. 1355-1370 (2009).
Kudlacz, E., et al., "The JAK-3 Inhibitor CP-690550 is a Potent Anti-Inflammatory Agent in a Murine Model of Pulmonary Eosinophilia", *European Journal of Pharmacology*, vol. 582, pp. 154-161 (2008).
McGinnity, D. F., et al, "Evaluation of Fresh and Cryopreserved Hepatocytes As In Vitro Drug Metabolism Tools for the Prediction of Metabolic Clearance", *Drug Metabolism and Disposition*, vol. 32, No. 11, pp. 1247-1253 (2004).
Nials, A. T., et al., "Mouse Models of Allergic Asthma: Acute and Chronic Allergen Challenge", *Disease Models & Mechanisms*, vol. 1, pp. 213-220 (2008).
Park, G. Y., et al, "Autotaxin Production of Lysophosphatidic Acid Mediates Allergic Asthmatic Inflammation", *The American Thoracic Society*, pp. 1-92 (2013).
Sina, C., et al., "G Protein-Coupled Receptor 43 Is Essential for Neutrophil Recruitment during Intestinal Inflammation", *The Journal of Immunology*, vol. 183, pp. 7514-7522 (2009).
Wirtz, S., et al., "Chemically Induced Mouse Models of Intestinal Inflammation", *Nature Protocols*, vol. 2, No. 3, pp. 541-546 (2007).
International Search Report for International Application PCT/EP2014/062241 dated Jul. 25, 2014.

COMPOUNDS AND PHARMACEUTICAL COMPOSITIONS THEREOF FOR THE TREATMENT OF INFLAMMATORY DISORDERS

CROSS REFERENCE TO RELATED APPLICATIONS

This application is a national stage filing under section 371 of International Application No. PCT/EP2014/062241, filed on Jun. 12, 2014, and published in English on Dec. 24, 2014 as WO 2014/202458 A1, which claims priority to U.S. Provisional Application No. 61/836,831 filed on Jun. 19, 2013, the entire contents of said applications being hereby incorporated herein by reference.

FIELD OF THE INVENTION

The present invention relates to compounds that are inhibitors of autotaxin, also known as ectonucleotide pyrophosphatase/phosphodiesterase 2 (NPP2 or ENPP2), that is involved in fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases. The present invention also provides methods for the production of a compound of the invention, pharmaceutical compositions comprising a compound of the invention, methods for the prophylaxis and/or treatment of diseases involving fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering a compound of the invention.

BACKGROUND OF THE INVENTION

Autotaxin (ATX; also known as ENPP2 (ectonucleotide pyrophosphatase/phosphodiesterase 2) or lysophospholipase D) is a ~120 kDa protein that belongs to the ENPP family of enzymes which is composed of seven members, out of which ENPP1 and ENPP3 are the closest to ATX. Whereas ENPP1 and ENPP3 are active in converting ATP into pyrophosphate (a regulator of mineralization and calcification processes in bone), ATX is the only ENPP enzyme with lysophospholipase D (lysoPLD) activity and is responsible for the hydrolysis of lysophosphatidylcholine (LPC) to produce the bioactive lipid lysophosphatidic acid (LPA). Several pieces of evidence have established ATX as the main source of LPA in blood. For example, blood LPA and ATX levels have been shown to be strongly correlated in humans. In addition, LPA levels are reduced by 50% in mice carrying a heterozygous null mutation of ATX (Tanaka et al. 2006). Due to the importance of LPA as a biological mediator, the levels of bio-active LPA are expected to be strictly spatially and temporally controlled. The relatively short half life of circulating LPA (~3 min) in mice is in line with this expectation. In the circulation, where LPC levels are very high (100-200 µM, mainly albumin-bound), ATX is constitutively active but newly produced LPA is rapidly degraded by membrane-bound phosphatases and levels of plasma LPA are thereby kept low (in the low µM range). This is confirmed by the fact that in cell-free plasma ex vivo, LPA levels increase at a steady rate. In addition, LPA in blood is bound to serum albumin, which might further reduce the levels of bio-active LPA. Besides this first level of control of LPA levels, the spatial control of LPA production is ensured by the capacity of ATX to bind to cell surface molecules such as integrins and heparan sulphate proteoglycans (HSPs) to facilitate LPA release near to its cognate receptors. Several pieces of evidence support this hypothesis. First, the structural studies of ATX are supporting the fact that the ATX structure is compatible with such a process (Hausmann et al. 2011). In addition, several reports indicated how ATX is involved in lymphocyte homing through the interaction with cell surface integrins (Kanda et al. 2008). It was shown, for example, that ATX can be induced on high endothelial venules (HEVs) on sites of inflammation. This ATX expressed by HEVs acts on HEVs in situ to facilitate lymphocyte binding to endothelial cells (Nakasaki et al. 2008). As such, ATX not only drives the formation of LPA but, through these cellular interactions, also ensures specificity in LPA signaling.

ATX is widely expressed, with highest mRNA levels detected in brain, lymph nodes, kidney, and testis. Originally discovered as 'autocrine motility factor' in melanoma cells, ATX has emerged as the key LPA-producing enzyme in plasma and tissues. Unfortunately, embryonic lethality has hampered studies of the importance of ATX in adult life. This embryonic lethality reflects the key role of LPA in various developmental processes, vasculogenesis in particular. Knock-out studies of the LPA receptors have been more informative in terms of unraveling the physiological role of LPA. LPA acts through at least six distinct (G protein)-coupled receptors (LPA1-6) found on the surface of different cell types, three of which belong to the edg receptor family and three to the non-edg receptor family. LPA interacts with specific G protein-coupled receptors (GPCRs), namely LPA1 (also known as EDG2), LPA2 (also known as EDG4), LPA3 (also known as EDG7), LPA4 (also known as GPR23/p2y9), LPA5 (also known as GPR92/93), LPA6 (also known as p2y5). LPA has also been described to interact with three other GPCRs (GPR87, p2y10, GPR35). In addition, a preference of LPA receptors for specific LPA species has been demonstrated (Bandoh et al. 2000). As such, the specificity of the LPA activities is controlled by the expression pattern of the LPA receptors and their downstream signaling route.

The main part of the LPA responses are mediated through trimeric G-proteins and include but are not limited to mitogen-activated protein kinase (MAPK) activation, adenylyl cyclase (AC) inhibition/activation, phospholipase C (PLC) activation/$Ca^{2+}$ mobilization, arachidonic acid release, Akt/PKB activation, and the activation of small GTPases, Rho, ROCK, Rac, and Ras. Other pathways that are affected by LPA receptor activation include cell division cycle 42/GTP-binding protein (Cdc42), proto-oncogene serine/threonine-protein kinase Raf (c-RAF), proto-oncogene tyrosine-protein kinase Src (c-src), extracellular signal-regulated kinase (ERK), focal adhesion kinase (FAK), guanine nucleotide exchange factor (GEF), glycogen synthase kinase 3b (GSK3b), c-jun amino-terminal kinase (JNK), MEK, myosin light chain II (MLC II), nuclear factor kB (NF-kB), N-methyl-D-aspartate (NMDA) receptor activation, phosphatidylinositol3-kinase (PI3K), protein kinase A (PKA), protein kinase C (PKC), and ras-related C3 botulinum toxin substrate 1 (RACl). The actual pathway is influenced by cell type, expression level of a receptor or signaling protein, receptor usage, and LPA concentration (Tania et al. 2010). LPA has a broad range of physiological actions and various cellular effects (for example blood pressure regulation, platelet activation, smooth muscle contraction, cell growth, cell rounding, neurite retraction, actin stress fiber formation and cell migration). In addition, a preference of LPA receptors for specific LPA species has been demonstrated (Bandoh et al. 2000). The knock-out studies for these receptors indicated a role in bone development (Gennero et al. 2011), and neurogenesis (Matas-Rico et al. 2008), embryo implantation (Ye et al. 2005) and the formation of blood and lymphatic vessels (Sumida et al. 2010).

With regard to pathophysiology, a role for LPA and LPA receptors has been claimed in various patho-physiological conditions such as proliferative diseases, neuropathic pain, inflammation, autoimmune diseases, fibrosis, lymphocyte tracking in lymph nodes, obesity, diabetes, or embryonic blood vessel formation.

The role of LPA in lung fibrosis has been well described in literature and also an involvement in asthma has been claimed. The present inventors however are the first to report a link to chronic obstructive pulmonary disease COPD.

Several lines of evidence suggest a role for ATX in the control of lung function in disease through effects on lung epithelial cells, fibroblasts and smooth muscle cells. In general, inflammatory conditions in the lung are often described as associated with increased ATX and LPA levels. Instillation of LPS in mice, for example, induces increased ATX and LPA levels in the broncho-alveolar lavage (BAL) fluid (J. Zhao et al. 2011). Also in humans, a segmental LPS challenge led to increased LPA levels (Georas et al. 2007). Overall, the role of LPA in activating lung epithelial cells, the first line of defense to inhaled noxious stimuli, towards increased cytokine and chemokine production and migration have been extensively described (Y. Zhao and Natarajan 2013). Exogenous LPA promotes inflammatory responses by regulating the expression of chemokines, cytokines, and cytokine receptors in lung epithelial cells. In addition to the modulation of inflammatory responses, LPA regulates cytoskeleton rearrangement and confers protection against lung injury by enhancing lung epithelial cell barrier integrity and remodeling.

In the asthmatic individual, the release of normal repair mediators, including LPA, is exaggerated or the actions of the repair mediators are inappropriately prolonged leading to inappropriate airway remodeling. Major structural features of the remodeled airway observed in asthma include a thickened lamina reticularis (the basement membrane-like structure just beneath the airway epithelial cells), increased numbers and activation of myofibroblasts, thickening of the smooth muscle layer, increased numbers of mucus glands and mucus secretions, and alterations in the connective tissue and capillary bed throughout the airway wall. ATX and/or LPA may contribute to these structural changes in the airway, for example ATX and/or LPA are involved in acute airway hyperresponsiveness in asthma. The lumen of the remodeled asthmatic airway is narrower due to the thickening of the airway wall, thus decreasing airflow. Additionally, LPA contributes to the long-term structural remodeling and the acute hyperresponsiveness of the asthmatic airway, for example LPA contributes to the hyper-responsiveness that is a primary feature of acute exacerbations of asthma. Reports describing the role of LPA in asthma generated different conclusions, ranging from a protective role (Y. Zhao et al. 2009) to a negative role (Emo et al. 2012). The testing of autotaxin inhibitors in models for airway diseases as described herein allows for the clarification of the potential of this enzyme as a drug target.

Fibroblast proliferation and contraction and extracellular matrix secretion stimulated by LPA contributes to the fibroproliferative features of other airway diseases, such as the peribronchiolar fibrosis present in chronic bronchitis, and interstitial lung diseases and severe asthma. LPA plays a role in the fibrotic interstitial lung diseases and obliterative bronchiolitis, where both collagen and myofibroblasts are increased. Studies related to IPF (idiopathic pulmonary fibrosis) indicated an increase in LPA levels in the BAL fluid of patients (Tager et al. 2008). Further LPA1 knock-out and inhibitor studies revealed a key role for LPA in fibrotic processes in lung and were complemented by studies using cell-specific knock-out mice lacking ATX in bronchial epithelial cells and macrophages. These mice were shown to be less sensitive to models of lung fibrosis (Oikonomou et al. 2012). A role for LPA in other fibrotic diseases (kidney and skin) was based on similar types of observations (Pradere et al. 2007), (Castelino et al. 2011). The role of LPA in lung remodeling relates to the effects of LPA on both lung fibroblasts (through LPA1) and epithelial cells (through LPA2) (M. Y. Xu et al. 2009) have demonstrated that LPA2 plays a key role in the activation of TGFβ in epithelial cells under fibrotic conditions. The role of LPA in remodeling and fibrosis is relevant to COPD, IPF and asthma, diseases in which lung remodeling as a long term outcome will limit lung function. Finally, of interest towards lung diseases, in mice, ATX is one of the three main QTLs that appear to be associated with differences in lung function (Ganguly et al. 2007).

One prominent area of research interest is the role of ATX-LPA signaling in cancer (Braddock 2010). Although cancer-specific mutations in ATX have not been identified so far, overexpression of ATX or individual LPA receptors in xenografted and transgenic mice promotes tumour formation, angiogenesis and metastasis. Conversely, ATX knockdown in mammary carcinoma cells reduces their metastatic spread to bone. Several human cancers show elevated ATX and/or aberrant LPA receptor expression patterns, as revealed by microarray analyses. Autotaxin is viewed as a pro-metastatic enzyme. It has initially been isolated from the conditioned medium of human melanoma cells that stimulates a myriad of biological activities, including angiogenesis and the promotion of cell growth, migration, survival, and differentiation through the production of LPA (M.-E. Lin, Herr, and Chun 2010). LPA contributes to tumorigenesis by increasing motility and invasiveness of cells. The initiation, progression and metastasis of cancer involve several concurrent and sequential processes including cell proliferation and growth, survival and anti-apoptosis, migration of cells, penetration of foreign cells into defined tissues and/or organs, and promotion of angiogenesis.

Therefore, the control of each of these processes by LPA signaling in physiological and pathophysiological conditions underscores the potential therapeutic usefulness of modulating LPA signaling pathways for the treatment of cancer. In particular, LPA has been implicated in the initiation or progression of ovarian cancer, prostate cancer, breast cancer, melanoma, head and neck cancer, bowel cancer (colorectal cancer), thyroid cancer, glioblastoma, follicular lymphoma and other cancers (Gardell, Dubin, and Chun 2006; Murph et al. 2008; Kishi et al. 2006).

Furthermore, autotaxin is implicated in the invasive and metastatic process of tumor cells, since ectopic overexpression of autotaxin is frequently observed in malignant tumor tissues such as ovarian cancer (Vidot et al. 2010), breast cancer (Panupinthu, Lee, and Mills 2010; Zhang et al. 2009), prostate cancer (Nouh et al. 2009), renal cancer, Hodgkin lymphoma (Baumforth et al. 2005), hepatocellular carcinoma (Wu et al. 2010), lung cancer (X. Xu and Prestwich 2010), and glioblastoma (Kishi et al. 2006). Autotaxin overexpression has also been found in a variety of tumors such as malignant melanoma, teratocarcinoma, neuroblastoma, non-small-cell lung cancer, renal cell carcinoma (Stassar et al. 2001).

Furthermore, expression of autotaxin by cancer cells controls osteolytic bone metastasis formation. In particular, LPA stimulates directly cancer growth and metastasis, and osteoclast differentiation. Therefore, targeting the autotaxin/LPA signaling route has also been found to be beneficial in patients with bone metastases (David et al. 2010). Finally, the inhibition of autotaxin seems to provide a beneficial adjuvant to chemotherapy for preventing tumor growth and metastasis in patients with high autotaxin expression in their tumors (Gaetano et al. 2009).

Upregulation of the autotaxin-LPA signaling pathway has been observed in a variety of inflammatory conditions. For example, pro-inflammatory effects of LPA include degranulation of mast cells, contraction of smooth-muscle cells and release of cytokines from dendritic cells. As an indication for its general role in inflammation, LPA and autotaxin activity have been shown to be induced by carageenan injection into the mouse air pouch model, which is used to develop anti-inflammatory drugs, including cyclooxygenase inhibitors for arthritis. Furthermore, a reduction in plasma and air pouch LPA has been observed in this rat air pouch model using an autotaxin inhibitor, confirming the role of autotaxin during inflammation as a major source of LPA (Gierse et al. 2010). It has been observed that autotaxin inhibitors reduce LPA and PGE2 and also reduce inflammatory pain.

As another general role in inflammatory diseases, LPA has been shown to induce chemokinesis in T-cells. Intravenous injection of enzymatically inactive autotaxin has been shown to attenuate the homing of T-cells to lymphoid tissues, likely by competing with endogenous autotaxin and exerting a dominant-negative effect. In certain instances, autotaxin facilitates lymphocyte entry into lymphoid organs (Kanda et al. 2008). Therefore an autotaxin inhibitor may block lymphocyte migration into secondary lymphoid organs and be of benefit in autoimmune diseases.

Specifically in rheumatoid arthritis, an increased expression of ATX in synovial fibroblasts from RA patients was demonstrated and ablation of ATX expression in mesenchymal cells (including synovial fibroblasts) resulted in attenuated symptoms in mouse models for rheumatoid arthritis (Nikitopoulou et al. 2012). As such, the role of autotaxin in rheumatoid arthritis has been strongly established.

Several lines of evidence suggest a role for LPA in vascular injury and atherosclerosis. These relate to the role of LPA in modulating endothelial barrier function and the phenotype of vascular smooth muscle cells and the action of LPA as a weak platelet agonist. Platelets have been identified as important participants in LPA production in the circulation in some settings, mainly by providing sufficient LPC amounts. Plasma autotaxin associates with platelets during aggregation and concentrates in arterial thrombus, and activated but not resting platelets bind recombinant autotaxin in an integrin-dependent manner. Experimental induction of thrombocytopenia in rats, using an anti-platelet antibody, decreases the production of LPA in serum by almost 50%, which suggests a role for LPA during clotting. In some instances, transgenic overexpression of autotaxin elevates circulating LPA levels and induces a bleeding diathesis and attenuation of thrombosis in mice. Intravascular administration of exogenous LPA recapitulates the prolonged bleeding time observed in autotaxin-Tg mice. Finally, autotaxin +/−mice, which have ~50% normal plasma LPA levels, are more prone to thrombosis.

In addition to a role in blood clotting, LPA has multiple effects on the endothelial monolayer permeability increase, and endothelial cells, in particular in critical aspects of angiogenesis such as cell migration stimulation and invasion. Furthermore, LPA also exerts migratory and contractile effects on vascular smooth muscle cells: autotaxin-mediated LPA production and subsequent LPA signaling contributes to vascular development by stimulating endothelial cell migration and invasion as well as regulating adhesive interactions with the extracellular matrix and smooth muscle cells. For example, similar vascular defects have been observed in autotaxin-deficient mice and in mice lacking genes involved in cell migration and adhesion (van Meeteren et al. 2006). Therefore an autotaxin inhibitor may have benefit in some diseases involving dysregulated angiogenesis.

LPA induces neuropathic pain as well as demyelination and pain-related protein expression changes via LPA1 (Inoue et al. 2008). ATX heterozygous knockout mice show about 50% recovery of nerve injury-induced neuropathic pain compared to wild type mice. Lysophosphatidylcholine (LPC), also known as lyso-lecithin, is known to induce neuropathic pain. It has been observed that LPC-induced neuropathic pain is partially reduced in ATX heterozygous knockout mice. These results support the idea that LPA is produced by autotaxin resulting in neuropathic pain (M.-E. Lin, Herr, and Chun 2010).

Autotaxin is also implicated in metabolic diseases, in particular obesity and diabetes (Federico et al. 2012). In some instances, autotaxin is responsible for the lysoPLD activity released by adipocytes and exerts a paracrine control on preadipocyte growth via an LPA-dependent mechanism. In addition, autotaxin is upregulated during adipocyte differentiation and in genetic obesity. In certain instances, autotaxin mRNA is upregulated in adipocytes from db/db mice suggesting that the upregulation of autotaxin is related to the severe type 2 diabetes phenotype and adipocyte insuline resistance. In some instances, upregulation of adipocyte autotaxin is associated with type 2 diabetes in human (Ferry et al. 2003). The relationship between adipocyte and autotaxin biology suggests the use of an autotaxin inhibitor for the treatment of metabolic diseases.

Finally, two other conditions clearly related to autotaxin biology are cholestatic pruritus (Kremer et al. 2010) and regulation of ocular pressure (Iyer et al. 2012).

The current therapies are not satisfactory and therefore there remains a need to identify further compounds that may be of use in the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases. The present invention therefore provides compounds, methods for their manufacture and pharmaceutical compositions comprising a compound of the invention together with a suitable pharmaceutical carrier. The present invention also provides for the use of a compound of the invention in the preparation of a medicament for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

SUMMARY OF THE INVENTION

The present invention is based on the identification of novel compounds, and their ability to act as inhibitors of autotaxin and that they may be useful for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases. The present invention also provides methods for the production of these compounds, pharmaceutical compositions comprising these compounds and methods for the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering the compounds of the invention.

Accordingly, in a first aspect of the invention, the compounds of the invention are provided having a Formula (I):

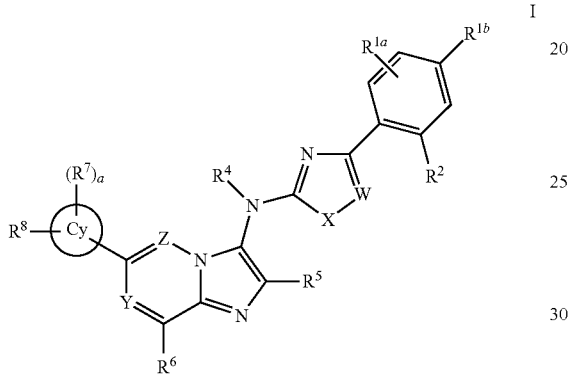

wherein
$R^{1a}$ is H, halo or $C_{1-4}$ alkyl;
$R^{1b}$ is:
    halo,
    $C_{1-4}$ alkyl (which alkyl is optionally substituted with one or more independently selected halo), or
    $C_{1-4}$ alkoxy (which alkoxy is optionally substituted with one or more independently selected halo);
X is —S—, —O—, —N=CH—, —CH=N— or —CH=CH—;
W is N, or $CR^3$
when W is N, $R^2$ is:
    H,
    —CN,
    halo,
    $C_{1-4}$ alkyl (which alkyl is optionally substituted with one or more independently selected OH, or CN),
    —C(=O)CH$_3$,
    —C(=O)CF$_3$,
    —C(=O)OCH$_3$,
    —C(=O)NH$_2$, or
    —NHC(=O)CH$_3$, or
when W is $CR^3$, one of $R^2$ or $R^3$ is:
    H,
    —CN,
    halo,
    $C_{1-4}$ alkyl (which alkyl is optionally substituted with one or more independently selected OH, or CN),
    —C(=O)CH$_3$,
    —C(=O)CF$_3$,
    —C(=O)OCH$_3$,
    —C(=O)NH$_2$,
    —NHC(=O)CH$_3$, and the other is H, or $C_{1-4}$ alkyl;
$R^4$ is $C_{1-4}$ alkyl;
$R^5$ is $C_{1-4}$ alkyl optionally substituted with one or more independently selected CN, OH, halo, or —C(=O)NH$_2$;
one of Y and Z is CH and the other is N;
$R^6$ is selected from H, —CH$_3$ and halo;
Cy is:
    $C_{4-10}$ cycloalkyl,
    4-10 membered mono or bicyclic heterocycloalkyl containing one or more heteroatoms independently selected from O, N, and S, or
    4-7 membered heterocycloalkenyl containing 1 double bond, containing one or more heteroatoms independently selected from O, N, and S;
each $R^7$ is independently selected from:
    OH,
    oxo,
    halo, and
    $C_{1-4}$ alkyl (which alkyl is optionally substituted with one or more independently selected OH, or $C_{1-4}$ alkoxy);
the subscript a is 0, 1 or 2;
$R^8$ is -(L$_1$W$_1$)$_m$-L$_2$-G$_1$,
wherein
    L$_1$ is absent, or is —O—, —C(=O)—, —NR$^i$, —NR$^h$C(=O)—, or —SO$_2$—;
    W$_1$ is $C_{1-4}$ alkylene;
    the subscript m is 0, or 1;
    L$_2$ is absent, or is —O—, —C(=O)—, —C(=O)O—, —OC(=O)—, —C(=O)—C(=O)—, —C(=O)—C(=O)NR$^a$—,
        —NR$^b$—, —C(=O)NR$^c$—, —NR$^d$C(=O)—, —NR$^j$C(=O)O—, —SO$_2$—, —SO$_2$NR$^e$— or NR$^f$SO$_2$—;
    G$_1$ is
        H,
        —CN,
        $C_{1-4}$ alkyl (which alkyl is optionally substituted with one or more independently selected CN, OH, halo or phenyl),
        $C_{3-7}$ cycloalkyl (which cycloalkyl is optionally substituted with —NH$_2$),
        5-6 membered heterocycloalkenyl containing 1 double bond containing one or more heteroatoms independently selected from O, N, and S, (which heterocycloalkenyl is optionally substituted with one or more independently selected $R^9$ groups),
        4-10 membered mono, bi or spirocyclic heterocycloalkyl containing one or more heteroatoms independently selected from O, N, and S, (which heterocycloalkyl is optionally substituted with one or more independently selected $R^9$ groups), or
        5-6 membered heteroaryl containing one or more heteroatoms independently selected from O, N, and S, (which heteroaryl is optionally substituted with one or more independently selected $R^{10}$ groups), or
each $R^9$ is oxo, or $R^{10}$;
each $R^{10}$ is:
    —OH,
    halo,
    —CN,
    $C_{1-4}$ alkyl (which alkyl is optionally substituted with one or more independently selected OH, halo, or phenyl),
    $C_{1-4}$ alkoxy,
    $C_{3-7}$ cycloalkyl, phenyl,
—SO$_2$CH$_3$,
—C(=O)C$_{1-4}$ alkoxy,
—C(=O)C$_{1-4}$ alkyl, or
—NR$^g$C(=O)C$_{1-4}$ alkyl; and
each R$^a$, R$^b$, R$^c$, R$^d$, R$^e$, R$^f$, R$^g$, R$^h$, R$^i$, and R$^j$ is independently selected from H, and C$_{1-4}$ alkyl.

In one aspect, the compounds of the invention are inhibitors of autotaxin. Furthermore, the compounds of the invention may exhibit low clearance, possibly resulting in low therapeutic dose levels.

In a more particular aspect, the compounds of the invention are active in vivo against IPF and/or COPD.

In a particular aspect, the compounds of the invention are provided for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In yet another aspect, the present invention provides a method of treating a mammal having, or at risk of having a disease disclosed herein. In a particular aspect, the present invention provides a method of treating a mammal having, or at risk of having fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In a further aspect, the present invention provides pharmaceutical compositions comprising a compound of the invention, and a pharmaceutical carrier, excipient or diluent. In a particular aspect, the pharmaceutical composition may additionally comprise further therapeutically active ingredients suitable for use in combination with the compounds of the invention. In a more particular aspect, the further therapeutically active ingredient is an agent for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

Moreover, the compounds of the invention, useful in the pharmaceutical compositions and treatment methods disclosed herein, are pharmaceutically acceptable as prepared and used.

In a further aspect of the invention, this invention provides a method of treating a mammal, in particular humans, afflicted with a condition selected from among those listed herein, and particularly fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases, which method comprises administering an effective amount of the pharmaceutical composition or compounds of the invention as described herein.

The present invention also provides pharmaceutical compositions comprising a compound of the invention, and a suitable pharmaceutical carrier, excipient or diluent for use in medicine. In a particular aspect, the pharmaceutical composition is for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In additional aspects, this invention provides methods for synthesizing the compounds of the invention, with representative synthetic protocols and pathways disclosed later on herein.

Other objects and advantages will become apparent to those skilled in the art from a consideration of the ensuing detailed description.

It will be appreciated that compounds of the invention may be metabolized to yield biologically active metabolites.

DETAILED DESCRIPTION OF THE INVENTION

Definitions

The following terms are intended to have the meanings presented therewith below and are useful in understanding the description and intended scope of the present invention.

When describing the invention, which may include compounds, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term 'substituted' is to be defined as set out below. It should be further understood that the terms 'groups' and 'radicals' can be considered interchangeable when used herein.

The articles 'a' and 'an' may be used herein to refer to one or to more than one (i.e. at least one) of the grammatical objects of the article. By way of example 'an analogue' means one analogue or more than one analogue.

As used herein the term 'LPA' relates to lysophosphatidic acid which is a member of the membrane-derived bioactive lipid mediators, further comprising sphingosine-1-phosphate (S1P), lysophosphatidylcholine (LPC), and sphingosylphosphorylcholine (SPC). LPA interacts with specific G protein-coupled receptors (GPCRs), namely LPA$_1$, LPA$_2$, LPA$_3$, LPA$_4$, LPA$_5$, LPA$_6$, LPA$_7$, LPA$_8$, in an autocrine and paracrine fashion, to activate intracellular signaling pathways, and in turn produce a variety of biological responses.

'Alkyl' means straight or branched aliphatic hydrocarbon with the number of carbon atoms specified. Particular alkyl groups have 1 to 8 carbon atoms. More particular is lower alkyl which has 1 to 6 carbon atoms. A further particular group has 1 to 4 carbon atoms. Exemplary straight chained groups include methyl, ethyl n-propyl, and n-butyl. Branched means that one or more lower alkyl groups such as methyl, ethyl, propyl or butyl is attached to a linear alkyl chain, exemplary branched chain groups include isopropyl, iso-butyl, t-butyl and isoamyl.

'Alkoxy' refers to the group —OR$^{26}$ where R$^{26}$ is alkyl with the number of carbon atoms specified. Particular alkoxy groups are methoxy, ethoxy, n-propoxy, isopropoxy, n-butoxy, tert-butoxy, sec-butoxy, n-pentoxy, n-hexoxy, and 1,2-dimethylbutoxy. Particular alkoxy groups are lower alkoxy, i.e. with between 1 and 6 carbon atoms. Further particular alkoxy groups have between 1 and 4 carbon atoms.

'Alkylene' refers to divalent alkene radical groups having the number of carbon atoms specified, in particular having 1 to 6 carbon atoms and more particularly 1 to 4 carbon atoms which can be straight-chained or branched. This term is exemplified by groups such as methylene (—CH₂—), ethylene (—CH₂—CH₂—), or —CH(CH₃)— and the like.

'Alkenyl' refers to monovalent olefinically (unsaturated) hydrocarbon groups with the number of carbon atoms specified. Particular alkenyl has 2 to 8 carbon atoms, and more particularly, from 2 to 6 carbon atoms, which can be straight-chained or branched and having at least 1 and particularly from 1 to 2 sites of olefinic unsaturation. Particular alkenyl groups include ethenyl (—CH═CH₂), n-propenyl (—CH₂CH═CH₂), isopropenyl (—C(CH₃)═CH₂) and the like.

'Amino' refers to the radical —NH₂.

'Aryl' refers to a monovalent aromatic hydrocarbon group derived by the removal of one hydrogen atom from a single carbon atom of a parent aromatic ring system. In particular aryl refers to an aromatic ring structure, monocyclic or polycyclic, with the number of ring atoms specified. Specifically, the term includes groups that include from 6 to 10 ring members. Where the aryl group is a monocyclic ring system it preferentially contains 6 carbon atoms. Particularly aryl groups include phenyl, naphthyl, indenyl, and tetrahydronaphthyl.

'Cycloalkyl' refers to a non-aromatic hydrocarbyl ring structure, monocyclic or polycyclic, with the number of ring atoms specified. A cycloalkyl may have from 3 to 10 carbon atoms, and in particular from 3 to 7 carbon atoms. Such cycloalkyl groups include, by way of example, single ring structures such as cyclopropyl, cyclobutyl, cyclopentyl, cyclohexyl, and cycloheptyl.

'Cyano' refers to the radical —CN.

'Halo' or 'halogen' refers to fluoro (F), chloro (Cl), bromo (Br) and iodo (I). Particular halo groups are either fluoro or chloro.

'Hetero' when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g. heteroalkyl, cycloalkyl, e.g. heterocycloalkyl, aryl, e.g. heteroaryl, and the like having from 1 to 4, and particularly from 1 to 3 heteroatoms, more typically 1 or 2 heteroatoms, for example a single heteroatom.

'Heteroaryl' means an aromatic ring structure, monocyclic or polycyclic, that includes one or more heteroatoms independently selected from O, N and S and the number of ring atoms specified. In particular, the aromatic ring structure may have from 5 to 10 ring members. The heteroaryl group can be, for example, a five membered or six membered monocyclic ring or a bicyclic structure formed from fused five and six membered rings or two fused six membered rings or, by way of a further example, two fused five membered rings. Each ring may contain up to four heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Examples of five membered monocyclic heteroaryl groups include but are not limited to pyrrole, furan, thiophene, imidazole, furazan, oxazole, oxadiazole, oxatriazole, isoxazole, thiazole, isothiazole, thiadiazole, pyrazole, triazole and tetrazole groups.

Examples of six membered monocyclic heteroaryl groups include but are not limited to pyridine, pyrazine, pyridazine, pyrimidine and triazine. Particular examples of bicyclic heteroaryl groups containing a five membered ring fused to another five membered ring include but are not limited to imidazothiazole and imidazoimidazole. Particular examples of bicyclic heteroaryl groups containing a six membered ring fused to a five membered ring include but are not limited to benzofuran, benzothiophene, benzoimidazole, benzoxazole, isobenzoxazole, benzisoxazole, benzthiazole, benzisothiazole, isobenzofuran, indole, isoindole, isoindolone, indolizine, indoline, isoindoline, purine (e.g. adenine, guanine), indazole, imidazopyridines, imidazopyrimidines, imidazopyrazines, pyrazolopyrimidine, triazolopyrimidine, benzodioxole and pyrazolopyridine groups. Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups. Particular heteroaryl groups are those derived from thiophene, pyrrole, benzothiophene, benzofuran, indole, pyridine, quinoline, imidazole, thiazole, oxazole and pyrazine.

Examples of representative heteroaryls include the following:

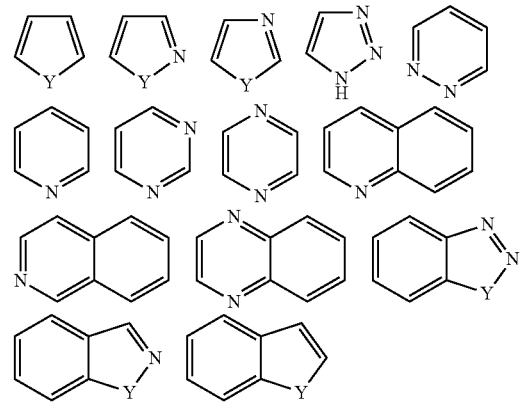

wherein each Y is selected from >C(═O), NH, O and S.

As used herein, the term 'heterocycloalkyl' means a stable non-aromatic ring structure, mono-cyclic or polycyclic, that includes one or more heteroatoms independently selected from O, N and S and the number of ring atoms specified. The non-aromatic ring structure may have from 4 to 10 ring members, and in particular from 4 to 7 ring members. A fused heterocyclic ring system may include carbocyclic rings and need only to include one heterocyclic ring. Examples of heterocyclic rings include, but are not limited to, morpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, pyran, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazine, and N-alkyl piperazines such as N-methyl piperazine. Further examples include thiomorpholine and its S-oxide and S,S-dioxide (particularly thiomorpholine). Still further examples include azetidine, piperidone, piperazone, and N-alkyl piperidines such as N-methyl piperidine. Particular examples of heterocycloalkyl groups are shown in the following illustrative examples:

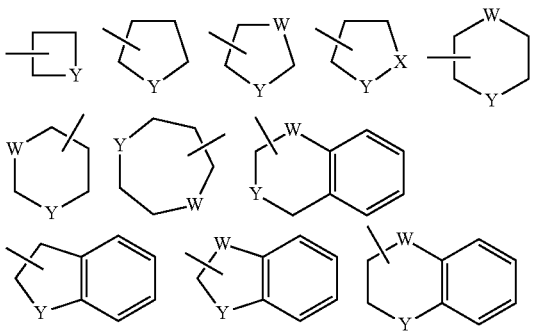

wherein each W is selected from $CH_2$, NH, O and S; and each Y is selected from NH, O, C(=O), $SO_2$, and S.

As used herein, the term 'heterocycloalkenyl' means a 'heterocycloalkyl', which comprises at least one double bond. Particular examples of heterocycloalkenyl groups are shown in the following illustrative examples:

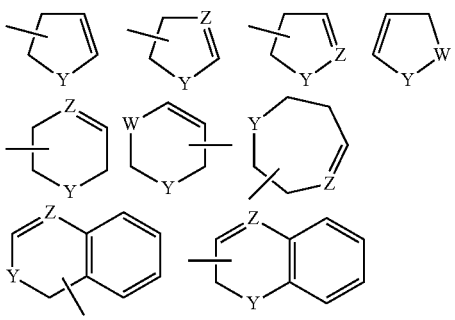

wherein each W is selected from $CH_2$, NH, O and S; each Y is selected from NH, O, C(=O), $SO_2$, and S; and each Z is selected from N or CH.

'Hydroxyl' refers to the radical —OH.

'Oxo' refers to the radical =O.

'Substituted' refers to a group in which one or more hydrogen atoms are each independently replaced with the same or different substituent(s).

Sulfo' or 'sulfonic acid' refers to a radical such as —$SO_3H$.

'Thiol' refers to the group —SH.

As used herein, term 'substituted with one or more' refers to one to four substituents. In one embodiment it refers to one to three substituents. In further embodiments it refers to one or two substituents. In a yet further embodiment it refers to one substituent.

'Thioalkoxy' refers to the group —$SR^{26}$ where $R^{26}$ is alkyl with the number of carbon atoms specified. Particular thioalkoxy groups are thiomethoxy, thioethoxy, n-thiopropoxy, isothiopropoxy, n-thiobutoxy, tert-thiobutoxy, sec-thiobutoxy, n-thiopentoxy, n-thiohexoxy, and 1,2-dimethyl-thiobutoxy. More particular thioalkoxy groups are lower thioalkoxy, i.e. with between 1 and 6 carbon atoms. Further particular alkoxy groups have between 1 and 4 carbon atoms.

One having ordinary skill in the art of organic synthesis will recognize that the maximum number of heteroatoms in a stable, chemically feasible heterocyclic ring, whether it is aromatic or non aromatic, is determined by the size of the ring, the degree of unsaturation and the valence of the heteroatoms. In general, a heterocyclic ring may have one to four heteroatoms so long as the heteroaromatic ring is chemically feasible and stable.

'Pharmaceutically acceptable' means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

'Pharmaceutically acceptable salt' refers to a salt of a compound of the invention that is pharmaceutically acceptable and that possesses the desired pharmacological activity of the parent compound. In particular, such salts are non-toxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g. an alkali metal ion, an alkaline earth ion, or an aluminum ion; or coordinates with an organic base such as ethanolamine, diethanolamine, triethanolamine, N-methylglucamine and the like. Salts further include, by way of example only, sodium, potassium, calcium, magnesium, ammonium, tetraalkylammonium, and the like; and when the compound contains a basic functionality, salts of non toxic organic or inorganic acids, such as hydrochloride, hydrobromide, tartrate, mesylate, acetate, maleate, oxalate and the like. The term 'pharmaceutically acceptable cation' refers to an acceptable cationic counter-ion of an acidic functional group. Such cations are exemplified by sodium, potassium, calcium, magnesium, ammonium, tetraalkylammonium cations, and the like.

'Pharmaceutically acceptable vehicle' refers to a diluent, adjuvant, excipient or carrier with which a compound of the invention is administered.

'Prodrugs' refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like.

'Solvate' refers to forms of the compound that are associated with a solvent, usually by a solvolysis reaction. This physical association includes hydrogen bonding. Conventional solvents include water, ethanol, acetic acid and the like. The compounds of the invention may be prepared e.g. in crystalline form and may be solvated or hydrated. Suitable solvates include pharmaceutically acceptable solvates, such as hydrates, and further include both stoichiometric solvates and non-stoichiometric solvates. In certain instances the solvate will be capable of isolation, for example when one or more solvent molecules are incorporated in the crystal lattice of the crystalline solid. 'Solvate' encompasses both solution-phase and isolable solvates. Representative solvates include hydrates, ethanolates and methanolates.

'Subject' includes humans. The terms 'human', 'patient' and 'subject' are used interchangeably herein.

'Effective amount' means the amount of a compound of the invention that, when administered to a subject for treating a disease, is sufficient to effect such treatment for the disease. The 'effective amount' can vary depending on the compound, the disease and its severity, and the age, weight, etc., of the subject to be treated.

'Preventing' or 'prevention' refers to a reduction in risk of acquiring or developing a disease or disorder (i.e. causing at least one of the clinical symptoms of the disease not to develop in a subject that may be exposed to a disease-causing agent, or predisposed to the disease in advance of disease onset).

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Treating' or 'treatment' of any disease or disorder refers, in one embodiment, to ameliorating the disease or disorder (i.e. arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g. stabilization of a discernible symptom), physiologically (e.g. stabilization of a physical parameter), or both. In a further embodiment, 'treating' or 'treatment' relates to slowing the progression of the disease.

As used herein the term 'fibrotic diseases' refers to diseases characterized by excessive scarring due to excessive production, deposition, and contraction of extracellular matrix, and are that are associated with the abnormal accumulation of cells and/or fibronectin and/or collagen and/or increased fibroblast recruitment and include but are not limited to fibrosis of individual organs or tissues such as the heart, kidney, liver, joints, lung, pleural tissue, peritoneal tissue, skin, cornea, retina, musculoskeletal and digestive tract. In particular, the term fibrotic diseases refers to idiopathic pulmonary fibrosis (IPF); cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease); radiation induced fibrosis; chronic obstructive pulmonary disease (COPD); scleroderma; bleomycin induced pulmonary fibrosis; chronic asthma; silicosis; asbestos induced pulmonary fibrosis; acute respiratory distress syndrome (ARDS); kidney fibrosis; tubulointerstitium fibrosis; glomerular nephritis; focal segmental glomerular sclerosis; IgA nephropathy; hypertension; Alport; gut fibrosis; liver fibrosis; cirrhosis; alcohol induced liver fibrosis; toxic/drug induced liver fibrosis; hemochromatosis; nonalcoholic steatohepatitis (NASH); biliary duct injury; primary biliary cirrhosis; infection induced liver fibrosis; viral induced liver fibrosis; and autoimmune hepatitis; corneal scarring; hypertrophic scarring; Dupuytren disease, keloids, cutaneous fibrosis; cutaneous scleroderma; systemic sclerosis, spinal cord injury/fibrosis; myelofibrosis; vascular restenosis; atherosclerosis; arteriosclerosis; Wegener's granulomatosis; Peyronie's disease, or chronic lymphocytic. More particularly, the term 'fibrotic diseases' refers to idiopathic pulmonary fibrosis (IPF).

As used herein the term 'proliferative disease(s)' refers to conditions such as cancer (e.g. uterine leiomyosarcoma or prostate cancer), myeloproliferative disorders (e.g. polycythemia vera, essential thrombocytosis and myelofibrosis), leukemia (e.g. acute myeloid leukaemia, acute and chronic lymphoblastic leukemia), multiple myeloma, psoriasis, restenosis, scleroderma or fibrosis. In particular the term refers to cancer, leukemia, multiple myeloma and psoriasis.

As used herein, the term 'cancer' refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types (such as but not limited to, melanoma, lymphoma, leukaemia, fibrosarcoma, rhabdomyosarcoma, and mastocytoma) and types of tissue carcinoma (such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma). In particular, the term 'cancer' refers to acute lymphoblastic leukemia, acute myeloidleukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-celllymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, asopharyngeal cancer, neuroblastoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Ewing sarcoma family of tumors, sarcoma, kaposi, Sezary syndrome, skin cancer, small cell Lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor As used herein the term 'leukemia' refers to neoplastic diseases of the blood and blood forming organs. Such diseases can cause bone marrow and immune system dysfunction, which renders the host highly susceptible to infection and bleeding. In particular the term leukemia refers to acute myeloid leukaemia (AML), and acute lymphoblastic leukemia (ALL) and chronic lymphoblastic leukaemia (CLL).

As used herein the term 'inflammatory diseases' refers to the group of conditions including, rheumatoid arthritis, osteoarthritis, juvenile idiopathic arthritis, psoriasis, psoriatic arthritis, allergic airway disease (e.g. asthma, rhinitis), chronic obstructive pulmonary disease (COPD), inflammatory bowel diseases (e.g. Crohn's disease, ulcerative colitis), endotoxin-driven disease states (e.g. complications after bypass surgery or chronic endotoxin states contributing to e.g. chronic cardiac failure), and related diseases involving cartilage, such as that of the joints. Particularly the term refers to rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly the term refers to rheumatoid arthritis, and chronic obstructive pulmonary disease (COPD).

As used herein the term 'autoimmune disease(s)' refers to the group of diseases including obstructive airways disease, including conditions such as COPD, asthma (e.g. intrinsic asthma, extrinsic asthma, dust asthma, infantile asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly the term refers to COPD, asthma, systemic lupus erythematosis, type I diabetes mellitus and inflammatory bowel disease.

As used herein, the term 'respiratory disease' refers to diseases affecting the organs that are involved in breathing, such as the nose, throat, larynx, eustachian tubes, trachea, bronchi, lungs, related muscles (e.g., diaphragm and intercostals), and nerves. In particular, examples of respiratory diseases include asthma, adult respiratory distress syndrome and allergic (extrinsic) asthma, non-allergic (intrinsic) asthma, acute severe asthma, chronic asthma, clinical asthma, nocturnal asthma, allerGen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation, cystic fibrosis, and hypoxia.

As used herein the term 'allergy' refers to the group of conditions characterized by a hypersensitivity disorder of the immune system including, allergic airway disease (e.g. asthma, rhinitis), sinusitis, eczema and hives, as well as food allergies or allergies to insect venom.

As used herein the term 'asthma' as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate the cause.

As used herein the term 'cardiovascular disease' refers to diseases affecting the heart or blood vessels or both. In particular, cardiovascular disease includes arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart, kidney or other organ or tissue; endotoxic, surgical, or traumatic shock; hypertension, valvular heart disease, heart failure, abnormal blood pressure; vasoconstriction (including that associated with migraines); vascular abnormality, inflammation, insufficiency limited to a single organ or tissue.

As used herein the term 'neurodegenerative diseases' refers to disorders that are associated with atrophy of the affected central or peripheral structures of the nervous system. In particular, the term 'neurodegenerative diseases' refers to diseases such as Alzheimer's disease and other dementias, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

As used herein the term 'dermatological disorder' refers to a skin disorder. In particular, dermatological disorders include proliferative or inflammatory disorders of the skin such as, atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, Sjogren-Larsso Syndrome, or urticaria.

As used herein the term 'abnormal angiogenesis associated disease' refers to diseases caused by the dysregulation of the processes mediating angiogenesis. In particular, abnormal angiogenesis associated disease refers to atherosclerosis, hypertension, tumor growth, inflammation, rheumatoid arthritis, wet-form macular degeneration, choroidal neovascularization, retinal neovascularization, and diabetic retinopathy.

'Compound(s) of the invention', and equivalent expressions, are meant to embrace compounds of the Formula(e) as herein described, which expression includes the pharmaceutically acceptable salts, and the solvates, e.g. hydrates, and the solvates of the pharmaceutically acceptable salts where the context so permits. Similarly, reference to intermediates, whether or not they themselves are claimed, is meant to embrace their salts, and solvates, where the context so permits.

When ranges are referred to herein, for example but without limitation, $C_{1-8}$ alkyl, the citation of a range should be considered a representation of each member of said range.

Other derivatives of the compounds of this invention have activity in both their acid and acid derivative forms, but in the acid sensitive form often offers advantages of solubility, tissue compatibility, or delayed release in the mammalian organism (Bundgaard 1992). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particularly useful prodrugs. In some cases it is desirable to prepare double ester type prodrugs such as (acyloxy)alkyl esters or ((alkoxycarbonyl)oxy)alkylesters. Particular such prodrugs are the $C_{1-8}$ alkyl, $C_{2-8}$ alkenyl, $C_{6-10}$ optionally substituted aryl, and ($C_{6-10}$ aryl)-($C_{1-4}$ alkyl) esters of the compounds of the invention.

As used herein, the term 'isotopic variant' refers to a compound that contains unnatural proportions of isotopes at one or more of the atoms that constitute such compound. For example, an 'isotopic variant' of a compound can contain one or more non-radioactive isotopes, such as for example, deuterium ($^2H$ or D), carbon-13 ($^{13}C$), nitroGen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radioactive isotopes tritium, i.e. $^3H$, and carbon-14, i.e. $^{14}C$ are particularly useful for this purpose in view of their ease of incorporation and ready means of detection. Further, compounds may be prepared that are substituted with positron emitting isotopes, such as $^{11}C$, $^{18}F$, $^{15}O$ and $^{13}N$, and would be useful in Positron Emission Topography (PET) studies for examining substrate receptor occupancy.

All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed 'isomers'. Isomers that differ in the arrangement of their atoms in space are termed 'stereoisomers'.

Stereoisomers that are not mirror images of one another are termed 'diastereomers' and those that are non-superimposable mirror images of each other are termed 'enantiomers'. When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e. as (+) or (−)-isomers respectively). A chiral compound can exist as either individual enantiomer or as a mixture thereof. A mixture containing equal proportions of the enantiomers is called a 'racemic mixture'.

'Tautomers' refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

The compounds of the invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

It will be appreciated that compounds of the invention may be metabolized to yield biologically active metabolites.

The Invention

The present invention is based on the identification of novel compounds, and their ability to act as inhibitors of autotaxin and that they may be useful for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

The present invention also provides methods for the production of these compounds, pharmaceutical compositions comprising these compounds and methods for the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases by administering the compounds of the invention.

Accordingly, in a first aspect of the invention, the compounds of the invention are provided having a Formula (I):

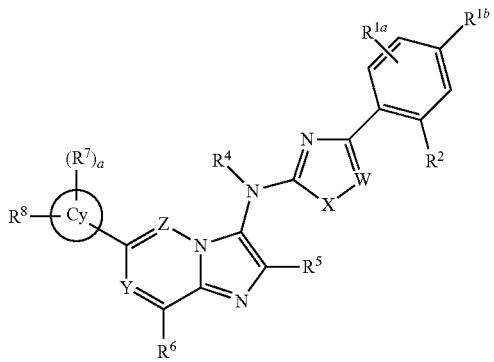

wherein
$R^{1a}$ is H, halo or $C_{1-4}$ alkyl;
$R^{1b}$ is:
 halo,
 $C_{1-4}$ alkyl (which alkyl is optionally substituted with one or more independently selected halo), or
 $C_{1-4}$ alkoxy (which alkoxy is optionally substituted with one or more independently selected halo);
X is —S—, —O—, —N=CH—, —CH=N— or —CH=CH—;
W is N, or $CR^3$
when W is N, $R^2$ is:
 H,
 —CN,
 halo,
 $C_{1-4}$ alkyl (which alkyl is optionally substituted with one or more independently selected OH, or CN),
 —C(=O)CH$_3$,
 —C(=O)CF$_3$,
 —C(=O)OCH$_3$,
 —C(=O)NH$_2$, or
 —NHC(=O)CH$_3$, or
when W is $CR^3$, one of $R^2$ or $R^3$ is:
 H,
 —CN,
 halo,
 $C_{1-4}$ alkyl (which alkyl is optionally substituted with one or more independently selected OH, or CN),
 —C(=O)CH$_3$,
 —C(=O)CF$_3$,
 —C(=O)OCH$_3$,
 —C(=O)NH$_2$, or
 —NHC(=O)CH$_3$,
 and the other is H, or $C_{1-4}$ alkyl;
$R^4$ is $C_{1-4}$ alkyl;
$R^5$ is $C_{1-4}$ alkyl optionally substituted with one or more independently selected CN, OH, halo, or —C(=O)NH$_2$;
one of Y and Z is CH and the other is N;
$R^6$ is selected from H, —CH$_3$ and halo;
Cy is:
 $C_{4-10}$ cycloalkyl,
 4-10 membered mono or bicyclic heterocycloalkyl containing one or more heteroatoms independently selected from O, N, and S, or
 4-7 membered heterocycloalkenyl containing 1 double bond, containing one or more heteroatoms independently selected from O, N, and S;

each $R^7$ is independently selected from:
 OH,
 oxo,
 halo, and
 $C_{1-4}$ alkyl (which alkyl is optionally substituted with one or more independently selected OH, or $C_{1-4}$ alkoxy);
the subscript a is 0, 1 or 2;
$R^8$ is -(L$_1$-W$_1$)$_m$-L$_2$-G$_1$,
 wherein
  L$_1$ is absent, or is —O—, —C(=O)—, —NR$^i$, —NR$^h$C(=O)—, or —SO$_2$—;
  W$_1$ is $C_{1-4}$ alkylene;
  the subscript m is 0, or 1;
  L$_2$ is absent, or is —O—, —C(=O)—, —C(=O)O—, —OC(=O)—, —C(=O)—C(=O)—, —C(=O)—C(=O)NR$^a$—, —NR$^b$—, —C(=O)NR$^c$—, —NR$^d$C(=O)—, —NR$^j$C(=O)O—, —SO$_2$—, —SO$_2$NR$^e$— or —NR$^f$SO$_2$—;
  G$_1$ is
   H,
   —CN,
   $C_{1-4}$ alkyl (which alkyl is optionally substituted with one or more independently selected CN, OH, halo or phenyl),
   $C_{3-7}$ cycloalkyl (which cycloalkyl is optionally substituted with NH$_2$),
   5-6 membered heterocycloalkenyl containing 1 double bond containing one or more heteroatoms independently selected from O, N, and S (which heterocycloalkenyl is optionally substituted with one or more independently selected $R^9$ groups),
   4-10 membered mono, bi or spirocyclic heterocycloalkyl containing one or more heteroatoms independently selected from O, N, and S (which heterocycloalkyl is optionally substituted with one or more independently selected $R^9$ groups), or
   5-6 membered heteroaryl containing one or more heteroatoms independently selected from O, N, and S (which heteroaryl is optionally substituted with one or more independently selected $R^{10}$ groups), or
each $R^9$ is oxo, or $R^{10}$;
each $R^{10}$ is:
 —OH,
 halo,
 —CN,
 $C_{1-4}$ alkyl (which alkyl is optionally substituted with one or more independently selected OH, halo, or phenyl),
 $C_{1-4}$ alkoxy,
 $C_{3-7}$ cycloalkyl,
 phenyl,
 —SO$_2$CH$_3$,
 —C(=O)C$_{1-4}$ alkoxy,
 —C(=O)C$_{1-4}$ alkyl, or
 —NR$^g$C(=O)C$_{1-4}$ alkyl; and
each $R^a$, $R^b$, $R^c$, $R^d$, $R^e$, $R^f$, $R^g$, $R^h$, $R^i$, and $R^j$ is independently selected from H, and $C_{1-4}$ alkyl;

In one embodiment, a compound of the invention is according to Formula I, wherein $R^{1a}$ is H.

In one embodiment, a compound of the invention is according to Formula I, wherein $R^{1a}$ is halo. In a particular embodiment, $R^{1a}$ is F, Cl, or Br. In a more particular embodiment, $R^{1a}$ is F, or Cl. In a most particular embodiment, $R^{1a}$ is F.

In one embodiment, a compound of the invention is according to Formula I, wherein $R^{1a}$ is $C_{1-4}$ alkyl. In a particular embodiment, $R^{1a}$ is —CH$_3$, —CH$_2$—CH$_3$, —CH$_2$—CH$_2$—CH$_3$, —CH(CH$_3$)$_2$. In a more particular embodiment, $R^{1a}$ is —CH$_3$, or —CH$_2$—CH$_3$.

In one embodiment, a compound of the invention is according to Formula I, wherein $R^{1b}$ is halo. In a particular embodiment, $R^{1b}$ is F, Cl, or Br. In a more particular embodiment, $R^{1b}$ is F, or Cl. In a most particular embodiment, $R^{1b}$ is F.

In one embodiment, a compound of the invention is according to Formula I, wherein $R^{1b}$ is $C_{1-4}$ alkyl. In a particular embodiment, $R^{1b}$ is —CH$_3$, —CH$_2$—CH$_3$, —CH$_2$—CH$_2$—CH$_3$, —CH(CH$_3$)$_2$. In a more particular embodiment, $R^{1b}$ is —CH$_3$, or —CH$_2$—CH$_3$.

In one embodiment, a compound of the invention is according to Formula I, wherein $R^{1b}$ is $C_{1-4}$ alkyl substituted with one or more independently selected halo. In a particular embodiment, $R^{1b}$ is —CF$_3$, or —CH$_2$—CF$_3$. In a more particular embodiment, $R^{1b}$ is —CF$_3$.

In one embodiment, a compound of the invention is according to Formula I, wherein $R^{1b}$ is $C_{1-4}$ alkoxy. In a particular embodiment, $R^{1b}$ is —OCH$_3$, —OCH$_2$—CH$_3$, —OCH$_2$—CH$_2$—CH$_3$, —OCH(CH$_3$)$_2$. In a more particular embodiment, $R^{1b}$ is —OCH$_3$, or —OCH$_2$—CH$_3$. In a most particular embodiment, $R^{1b}$ is —OCH$_3$.

In one embodiment, a compound of the invention is according to Formula I, wherein $R^{1b}$ is $C_{1-4}$ alkoxy substituted with one or more independently selected halo. In a more particular embodiment, $R^{1b}$ is —OCF$_3$, —OCH$_2$—CHF$_2$ or —OCH$_2$—CF$_3$. In a most particular embodiment, $R^{1b}$ is —OCF$_3$.

In one embodiment, a compound of the invention is according to Formula I, wherein X is —S—, —O—, —N═CH—, —CH═N— or —CH═CH—. In a particular embodiment, X is —S—, or —O—.

In one embodiment, a compound of the invention is according to Formula I, wherein W is N, and $R^2$ is as previously defined. In a particular embodiment, $R^2$ is H, —CN, —C(═O)CH$_3$, —C(═O)CF$_3$, —C(═O)OCH$_3$, —C(═O)NH$_2$, or —NHC(═O)CH$_3$. In a more particular embodiment, $R^2$ is —CN.

In one embodiment, a compound of the invention is according to Formula I, wherein W is N, and $R^2$ is as previously defined. In a particular embodiment, $R^2$ is halo. In a more particular embodiment, $R^2$ is F, Cl, or Br. In a most particular embodiment, $R^2$ is F, or Cl.

In one embodiment, a compound of the invention is according to Formula I, wherein W is N, and $R^2$ is as previously defined. In a particular embodiment, $R^2$ is $C_{1-4}$ alkyl. In another particular embodiment, $R^2$ is $C_{1-4}$ alkyl substituted with one or more independently selected OH, and CN. In yet another particular embodiment, $R^2$ is $C_{1-4}$ alkyl substituted with one OH, or CN. In a more particular embodiment, $R^2$ is —CH$_3$, —CH$_2$—CH$_3$, —CH$_2$—OH, or —CH$_2$—CN. In a most particular embodiment, $R^2$ is —CH$_2$—OH, or —CH$_2$—CN.

In another embodiment, a compound of the invention is according to Formula I, wherein W is CR$^3$, and $R^2$ and $R^3$ are as previously defined. In a particular embodiment, $R^2$ is H, —CN, —C(═O)CH$_3$, —C(═O)CF$_3$, —C(═O)OCH$_3$, —C(═O)NH$_2$, or —NHC(═O)CH$_3$, and $R^3$ is H, or $C_{1-4}$ alkyl. In another particular embodiment, $R^2$ is H, or $C_{1-4}$ alkyl, and $R^3$ is H, —CN, —C(═O)CH$_3$, —C(═O)CF$_3$, —C(═O)OCH$_3$, —C(═O)NH$_2$, or —NHC(═O)CH$_3$. In a more particular embodiment, $R^2$ is H, —CN, —C(═O)CH$_3$, —C(═O)CF$_3$, —C(═O)OCH$_3$, —C(═O)NH$_2$, or —NHC(═O)CH$_3$, and $R^3$ is H, —CH$_3$, or —CH$_2$—CH$_3$. In another more particular embodiment, $R^2$ is H, —CH$_3$, or —CH$_2$—CH$_3$, and $R^3$ is H, —CN, —C(═O)CH$_3$, —C(═O)CF$_3$, —C(═O)OCH$_3$, —C(═O)NH$_2$, or —NHC(═O)CH$_3$. In a most particular embodiment, $R^2$ is CN, and $R^3$ is H, —CH$_3$, or —CH$_2$—CH$_3$. In another most particular embodiment, $R^2$ is H, —CH$_3$, or —CH$_2$—CH$_3$, and $R^3$ is —CN.

In another embodiment, a compound of the invention is according to Formula I, wherein W is CR$^3$, and $R^2$ and $R^3$ are as previously defined. In a particular embodiment, $R^2$ is halo, and $R^3$ is H, or $C_{1-4}$ alkyl. In another particular embodiment, $R^2$ is H, or $C_{1-4}$ alkyl, and $R^3$ is halo. In a more particular embodiment, $R^2$ is F, Cl, or Br, and $R^3$ is H, —CH$_3$, or —CH$_2$—CH$_3$. In another more particular embodiment, $R^2$ is H, —CH$_3$, or —CH$_2$—CH$_3$, and $R^3$ is F, Cl, or Br. In a most particular embodiment, $R^2$ is F, or Cl, and $R^3$ is H, —CH$_3$, or —CH$_2$—CH$_3$. In another most particular embodiment, $R^2$ is H, —CH$_3$, or —CH$_2$—CH$_3$, and $R^3$ is F, or Cl.

In another embodiment, a compound of the invention is according to Formula I, wherein W is CR$^3$, and $R^2$ and $R^3$ are as previously defined. In a particular embodiment, $R^2$ is $C_{1-4}$ alkyl, and $R^3$ is H, or $C_{1-4}$ alkyl. In another particular embodiment, $R^2$ is H, or $C_{1-4}$ alkyl, and $R^3$ is $C_{1-4}$ alkyl. In a more particular embodiment, $R^2$ is —CH$_3$, or —CH$_2$—CH$_3$, and $R^3$ is H, —CH$_3$, or —CH$_2$—CH$_3$. In another more particular embodiment, $R^2$ is H, —CH$_3$, or —CH$_2$—CH$_3$, and $R^3$ is —CH$_3$, or —CH$_2$—CH$_3$.

In another embodiment, a compound of the invention is according to Formula I, wherein W is CR$^3$, and $R^2$ and $R^3$ are as previously defined. In a particular embodiment, $R^2$ is $C_{1-4}$ alkyl substituted with OH, or CN, and $R^3$ is H, or $C_{1-4}$ alkyl. In another particular embodiment, $R^2$ is H, or $C_{1-4}$ alkyl, and $R^3$ is $C_{1-4}$ alkyl substituted with OH, or CN. In a more particular embodiment, $R^2$ is —CH$_2$—OH, or —CH$_2$—CN, and $R^3$ is H, —CH$_3$, or —CH$_2$—CH$_3$. In another more particular embodiment, $R^2$ is H, —CH$_3$, or —CH$_2$—CH$_3$, and $R^3$ is —CH$_2$—OH, or —CH$_2$—CN.

In one embodiment, a compound of the invention is according to Formula II:

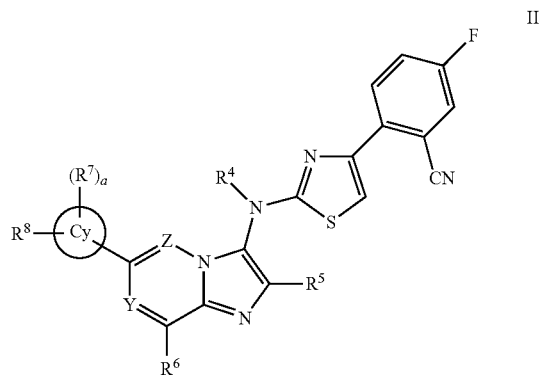

wherein the subscript a, Y, Z, $R^4$, $R^5$, $R^6$, $R^7$, and $R^8$ are as described above.

In another embodiment, a compound of the invention is according to Formula III:

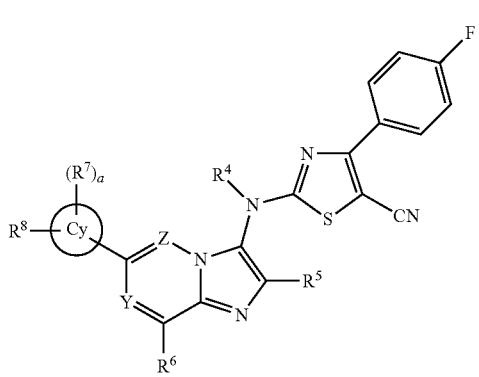

wherein the subscript a, Y, Z, $R^4$, $R^5$, $R^6$, $R^7$, and $R^8$ are as described above.

In one embodiment, a compound of the invention is according to Formula I, II or III, wherein $R^4$ is $C_{1-4}$ alkyl. In a particular embodiment, $R^4$ is —$CH_3$, or —$CH_2$—$CH_3$. In a more particular embodiment, $R^4$ is —$CH_3$.

In one embodiment, a compound of the invention is according to Formula I, II or III, wherein $R^5$ is $C_{1-4}$ alkyl. In a particular embodiment, $R^5$ is —$CH_3$, —$CH_2$—$CH_3$ or —$CH_2$—$CH_2$—$CH_3$. In a more particular embodiment, $R^5$ is —$CH_3$, or —$CH_2$—$CH_3$. In a most particular embodiment, $R^5$ is —$CH_2$—$CH_3$.

In one embodiment, a compound of the invention is according to Formula I, II or III, wherein $R^5$ is $C_{1-4}$ alkyl substituted with one or more independently selected CN, OH, halo, and —C(=O)$NH_2$. In a particular embodiment, $R^5$ is $C_{1-4}$ alkyl substituted with one CN, OH, halo, or —C(=O)$NH_2$. In a more particular embodiment, $R^5$ is —$CH_3$, —$CH_2$—$CH_3$, —$CH_2$—$CH_2$—$CH_3$, —$CH_2$—$CH_2$—$CH_2$—$CH_3$, —CH($CH_3$)$_2$, or —$CH_2$—CH($CH_3$)$_2$, each of which is substituted with one CN, OH, halo, or —C(=O)$NH_2$. In another more particular embodiment, $R^5$ is —$CH_3$, —$CH_2$—$CH_3$, —$CH_2$—$CH_2$—$CH_3$, —$CH_2$—$CH_2$—$CH_2$—$CH_3$, or —$CH_2$—CH($CH_3$)$_2$, each of which is substituted with one —CN, OH, F, or —C(=O)$NH_2$. In a most particular embodiment, $R^5$ is —$CH_2$—$CH_2$—CN, —$CH_2$—$CH_2$—OH, —$CH_2$—$CF_3$, or —$CH_2$—$CH_2$—C(=O)$NH_2$.

In one embodiment, a compound of the invention is according to Formula I, II or III, wherein Cy is $C_{3-10}$ cycloalkyl. In a particular embodiment, Cy is cyclobutyl, cyclopentyl or cyclohexyl. In a more particular embodiment, Cy is cyclohexyl.

In one embodiment, a compound of the invention is according to Formula I, II or III, wherein Cy is 4-10 membered mono or bicyclic heterocycloalkyl containing one or more heteroatoms independently selected from O, N, and S. In a particular embodiment, Cy is oxetanyl, azetidinyl, tetrahydrofuranyl, pyrrolidinyl, tetrahydropyranyl, piperidinyl, piperazinyl, morpholinyl, or thiomorpholinyl. In a more particular embodiment, Cy is piperidinyl. In another more particular embodiment, Cy is piperazinyl.

In one embodiment, a compound of the invention is according to Formula I, II or III, wherein Cy is 4-7 membered heterocycloalkenyl containing 1 double bond, containing one or more heteroatoms independently selected from O, N, and S. In a particular embodiment, Cy is dihydrofuranyl, dihydrothiazolyl, dihydrooxazolyl, dihydropyranyl, tetrahydropyridinyl, or dihydrothiopyranyl. In a more particular embodiment, Cy is dihydrooxazolyl.

In one embodiment, a compound of the invention is according to Formula I, II or III, wherein the subscript a is 1 or 2, and $R^7$ is OH, oxo, or halo. In a particular embodiment, $R^7$ is OH, oxo, F, or Cl.

In one embodiment, a compound of the invention is according to Formula I, II or III, wherein the subscript a is 1 or 2, and $R^7$ is $C_{1-4}$ alkyl. In a particular embodiment, $R^7$ is —$CH_3$, —$CH_2$—$CH_3$, or —CH($CH_3$)$_2$. In a more particular embodiment, $R^7$ is —$CH_3$.

In one embodiment, a compound of the invention is according to Formula I, II or III, wherein the subscript a is 1 or 2, and $R^7$ is $C_{1-4}$ alkyl substituted with OH, or $C_{1-4}$ alkoxy. In a particular embodiment, $R^7$ is —$CH_3$, —$CH_2$—$CH_3$, or —CH($CH_3$)$_2$, each of which is substituted with OH, or $C_{1-4}$ alkoxy. In a more particular embodiment, $R^7$ is $CH_2$—OH, or $CH_2$—O$CH_3$.

In one embodiment, a compound of the invention is according to Formula I, II or III, wherein the subscript a is 0.

In one embodiment, a compound of the invention is according to Formula IVa, IVb, IVc or IVd:

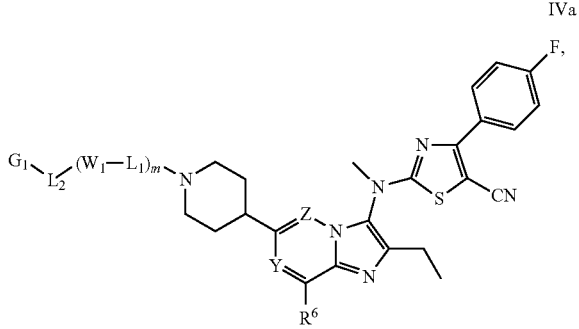

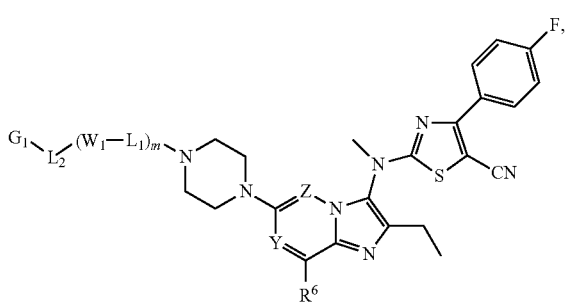

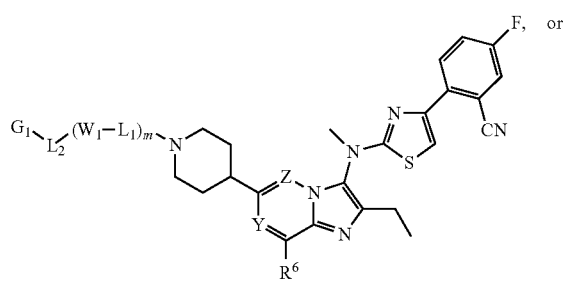

IVd

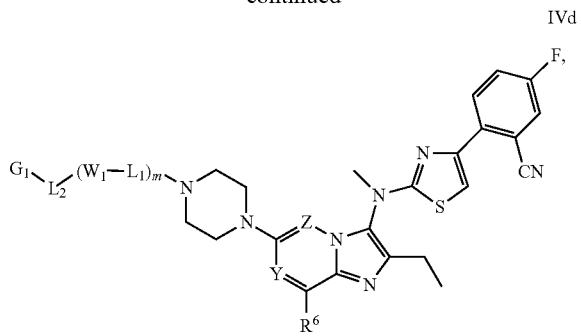

wherein Y, Z, R$^6$, L$_1$, W$_1$, L$_2$, G$_1$ and the subscript m are as previously described.

In one embodiment, a compound of the invention is according to Formula I-IVd, wherein the subscript m is 1, and L$_1$ is absent.

In one embodiment, a compound of the invention is according to Formula I-IVd, wherein the subscript m is 1, L$_1$ is —NR$^i$—, and R$^i$ is as previously described. In a particular embodiment, R$^i$ is H.

In another particular embodiment, R$^i$ is CH$_3$, —CH$_2$—CH$_3$, or —CH(CH$_3$)$_2$.

In one embodiment, a compound of the invention is according to Formula I-IVd, wherein the subscript m is 1, L$_1$ is —NR$^h$C(=O)—, and R$^h$ is as previously described. In a particular embodiment, R$^h$ is H. In another particular embodiment, R$^h$ is CH$_3$, —CH$_2$—CH$_3$, or —CH(CH$_3$)$_2$.

In one embodiment, a compound of the invention is according to Formula I-IVd, wherein the subscript m is 1, and L$_1$ is —C(=O)—, or —SO$_2$—.

In one embodiment, a compound of the invention is according to Formula I-IVd, wherein the subscript m is 1, and W$_1$ is C$_{1-4}$ alkylene. In a particular embodiment, W$_1$ is —CH$_2$—, —CH$_2$—CH$_2$—, —C(CH$_3$)H—, —CH$_2$—CH$_2$—CH$_2$— or —CH$_2$—C(CH$_3$)H—. In a more particular embodiment, W$_1$ is —CH$_2$—, or —C(CH$_3$)H—.

In one embodiment, a compound of the invention is according to Formula I-IVd, wherein the subscript m is 0.

In one embodiment, a compound of the invention is according to Formula I-IVd, wherein L$_2$ is absent.

In one embodiment, a compound of the invention is according to Formula I-IVd, wherein L$_2$ is —O—.

In one embodiment, a compound of the invention is according to Formula I-IVd, wherein L$_2$ is —O—, —C(=O)—, —C(=O)O—, —OC(=O)—C(=O)—C(=O)—, or —SO$_2$—.

In one embodiment, a compound of the invention is according to Formula I-IVd, wherein L$_2$ is —C(=O)—C(=O)NR$^a$—, and R$^a$ is as previously described. In a particular embodiment, R$^a$ is H. In another particular embodiment, R$^a$ is CH$_3$, —CH$_2$—CH$_3$, or —CH(CH$_3$)$_2$.

In one embodiment, a compound of the invention is according to Formula I-IVd, wherein L$_2$ is —NR$^b$—, and R$^b$ is as previously described. In a particular embodiment, R$^b$ is H. In another particular embodiment, R$^b$ is CH$_3$, —CH$_2$—CH$_3$, or —CH(CH$_3$)$_2$.

In one embodiment, a compound of the invention is according to Formula I-IVd, wherein L$_2$ is —C(=O)NR$^c$—, and R$^c$ is as previously described. In a particular embodiment, R$^c$ is H. In another particular embodiment, R$^c$ is CH$_3$, —CH$_2$—CH$_3$, or —CH(CH$_3$)$_2$.

In one embodiment, a compound of the invention is according to Formula I-IVd, wherein L$_2$ is —NR$^d$C(=O)—, and R$^d$ is as previously described. In a particular embodiment, R$^d$ is H. In another particular embodiment, R$^d$ is CH$_3$, —CH$_2$—CH$_3$, or —CH(CH$_3$)$_2$.

In one embodiment, a compound of the invention is according to Formula I-IVd, wherein L$_2$ is —NR$^j$C(=O)O—, and R$^j$ is as previously described. In a particular embodiment, R$^j$ is H. In another particular embodiment, R$^j$ is —CH$_3$, —CH$_2$—CH$_3$, or —CH(CH$_3$)$_2$.

In one embodiment, a compound of the invention is according to Formula I-IVd, wherein L$_2$ is —SO$_2$NR$^e$—, and R$^e$ is as previously described. In a particular embodiment, R$^e$ is H. In another particular embodiment, R$^e$ is —CH$_3$, —CH$_2$—CH$_3$, or —CH(CH$_3$)$_2$.

In one embodiment, a compound of the invention is according to Formula I-IVd, wherein L$_2$ is —NR$^f$SO$_2$—, and R$^f$ is as previously described. In a particular embodiment, R$^f$ is H. In another particular embodiment, R$^f$ is —CH$_3$, —CH$_2$—CH$_3$, or —CH(CH$_3$)$_2$.

In one embodiment, a compound of the invention is according to Formula I-IVd, wherein G$_1$ is H, or CN.

In one embodiment, a compound of the invention is according to Formula I-IVd, wherein G$_1$ is C$_{1-4}$ alkyl. In a particular embodiment, G$_1$ is —CH$_3$, or —CH$_2$—CH$_3$.

In one embodiment, a compound of the invention is according to Formula I-IVd, wherein G$_1$ is C$_{1-4}$ alkyl substituted with —CN, OH, halo or phenyl. In a particular embodiment, G$_1$ is —CH$_3$, —CH$_2$—CH$_3$, or —CH(CH$_3$)$_2$, each of which is substituted with —CN, OH, halo or phenyl. In a more particular embodiment, G$_1$ is —CF$_3$, —CH$_2$—Cl, —CH$_2$—CN, —CH$_2$—OH or CH$_2$-Ph.

In one embodiment, a compound of the invention is according to Formula I-IVd, wherein G$_1$ is C$_{3-7}$ cycloalkyl. In a particular embodiment, G$_1$ is cyclopropyl, cyclobutyl, cyclopropyl, or cyclohexyl.

In one embodiment, a compound of the invention is according to Formula I-IVd, wherein G$_1$ is C$_{3-7}$ cycloalkyl substituted with —NH$_2$. In a particular embodiment, G$_1$ is cyclopropyl, cyclobutyl, cyclopropyl, or cyclohexyl, each of which is substituted with —NH$_2$.

In one embodiment, a compound of the invention is according to Formula I-IVd, wherein G$_1$ is 5-6 membered heterocycloalkenyl containing 1 double bond, containing one to three heteroatoms independently selected from O, N, and S. In a particular embodiment, G$_1$ is dihydrofuranyl, dihydrothiazolyl, dihydrooxazolyl, dihydropyranyl, or dihydrothiopyranyl.

In one embodiment, a compound of the invention is according to Formula I-IVd, wherein G$_1$ is 5-6 membered heterocycloalkenyl containing 1 double bond, containing one to three heteroatoms independently selected from O, N, and S, substituted with one or more independently selected R$^9$, and R$^9$ is as previously defined. In another embodiment, G$_1$ is 5-6 membered heterocycloalkenyl containing 1 double bond, containing one to three heteroatoms independently selected from O, N, and S, substituted with one or two independently selected R$^9$, and R$^9$ is as previously defined. In a particular embodiment, G$_1$ is dihydrofuranyl, dihydrothiazolyl, dihydrooxazolyl, dihydropyranyl, or dihydrothiopyranyl, each of which is substituted with one or two independently selected R$^9$, and R$^9$ is as previously defined.

In one embodiment, a compound of the invention is according to Formula I-IVd, wherein G$_1$ is 4-10 membered mono, bi or spirocyclic heterocycloalkyl containing one to three heteroatoms independently selected from O, N, and S. In a particular embodiment, G$_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane.

In one embodiment, a compound of the invention is according to Formula I-IVd, wherein $G_1$ is 4-10 membered mono, bi or spirocyclic heterocycloalkyl containing one to three heteroatoms independently selected from O, N, and S, substituted with one or more independently selected $R^9$, and $R^9$ is as previously defined. In another embodiment, $G_1$ is 4-10 membered mono, bi or spirocyclic heterocycloalkyl containing one to three heteroatoms independently selected from O, N, and S, substituted with one or two independently selected $R^9$, and $R^9$ is as previously defined. In a particular embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptanes, each of which is substituted with one or two independently selected $R^9$, and $R^9$ is as previously defined.

In one embodiment, a compound of the invention is according to Formula I-IVd, wherein $R^9$ is oxo.

In another embodiment, a compound of the invention is according to Formula I-IVd, wherein $R^9$ is $R^{10}$.

In one embodiment, a compound of the invention is according to Formula I-IVd, wherein $R^{10}$ is selected from OH, F, Cl, and —CN.

In one embodiment, a compound of the invention is according to Formula I-IVd, wherein $R^{10}$ is $C_{1-4}$ alkyl. In a particular embodiment, $R^{10}$ is selected from —CH$_3$, —CH$_2$—CH$_3$, and —CH(CH$_3$)$_2$. In a more particular embodiment, $R^{10}$ is selected from —CH$_3$, and —CH$_2$—CH$_3$.

In one embodiment, a compound of the invention is according to Formula I-IVd, wherein $R^{10}$ is $C_{1-4}$ alkyl substituted with one or more independently selected OH, halo, or phenyl. In a further embodiment, $R^{10}$ is $C_{1-4}$ alkyl substituted with one to three independently selected OH, halo, or phenyl. In a more particular embodiment, $R^{10}$ is —CH$_3$, —CH$_2$—CH$_3$, or —CH(CH$_3$)$_2$, each of which is substituted with one to three independently selected OH, halo, or phenyl. In a most particular embodiment, $R^{10}$ is —CF$_3$, —CH$_2$—CH$_2$—OH, or —CH$_2$-phenyl.

In one embodiment, a compound of the invention is according to Formula I-IVd, wherein $R^{10}$ is $C_{1-4}$ alkoxy. In a particular embodiment, $R^{10}$ is selected from —OCH$_3$, —OCH$_2$—CH$_3$, and —OC(CH$_3$)$_3$. In a particular embodiment, $R^{10}$ is —OCH$_3$.

In one embodiment, a compound of the invention is according to Formula I-IVd, wherein $R^{10}$ is selected from —SO$_2$CH$_3$, —C(=O)C$_{1-4}$ alkoxy, and —C(=O)C$_{1-4}$ alkyl. In a particular embodiment, $R^{10}$ is selected from —SO$_2$CH$_3$, —C(=O)OCH$_3$, —C(=O)OCH$_2$CH$_3$, —C(=O)OCH(CH$_3$)$_2$, —C(=O)CH$_3$, —C(=O)CH$_2$CH$_3$, and —C(=O)OCH(CH$_3$)$_2$. In a most particular embodiment, $R^{10}$ is selected from —SO$_2$CH$_3$, —C(=O)OCH$_3$, and —C(=O)CH$_3$.

In one embodiment, a compound of the invention is according to Formula I-IVd, wherein $R^{10}$ is NR$^g$C(=O)C$_{1-4}$ alkyl, and $R^g$ is as described previously. In a particular embodiment, $R^{10}$ is —NR$^g$C(=O)CH$_3$, or —NR$^g$C(=O)CH$_2$CH$_3$, and $R^g$ is as described previously. In a more particular embodiment, $R^{10}$ is —NR$^g$C(=O)CH$_3$, or —NR$^g$C(=O)CH$_2$CH$_3$, and $R^g$ is H, —CH$_3$, or —CH$_2$CH$_3$. In a most particular embodiment, $R^{10}$ is —NHC(O)CH$_3$, or —NHC(=O)CH$_2$CH$_3$.

In one embodiment, a compound of the invention is according to Formula I-IVd, wherein $G_1$ is 4-7 membered heterocycloalkyl containing one or more heteroatoms independently selected selected from O, N, and S, each of which is substituted with one or two independently selected $R^9$ groups, and $R^9$ is oxo. In a further particular embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane, each of which is substituted with one or two independently selected $R^9$ groups, and $R^9$ is oxo.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane, each of which is substituted with one or two independently selected $R^9$ groups, $R^9$ is $R^{10}$, and $R^{10}$ is as previously described. In a particular embodiment, $R^{10}$ is selected from OH, F, Cl, and —CN.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane, each of which is substituted with one or two independently selected $R^9$ groups, $R^9$ is $R^{10}$, and $R^{10}$ is as previously described. In a particular embodiment, $R^{10}$ is selected $C_{1-4}$ alkyl. In a more particular embodiment, $R^{10}$ is selected from —CH$_3$, —CH$_2$—CH$_3$, and —CH(CH$_3$)$_2$. In a most particular embodiment, $R^{10}$ is selected from —CH$_3$, and —CH$_2$—CH$_3$.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane, each of which is substituted with one or two independently selected $R^9$ groups, $R^9$ is $R^{10}$, and $R^{10}$ is as previously described. In a particular embodiment, $R^{10}$ is $C_{1-4}$ alkyl substituted with one or more independently selected OH, halo, or phenyl. In a further embodiment, $R^{10}$ is $C_{1-4}$ alkyl substituted with one to three independently selected OH, halo, or phenyl. In a more particular embodiment, $R^{10}$ is —CH$_3$, —CH$_2$—CH$_3$, or —CH(CH$_3$)$_2$, each of which is substituted with one to three independently selected OH, halo, or phenyl. In a most particular embodiment, $R^{10}$ is —CF$_3$, —CH$_2$—CH$_2$—OH, or —CH$_2$-phenyl.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane, each of which is substituted with one or two independently selected $R^9$ groups, $R^9$ is $R^{10}$, and $R^{10}$ is as previously described. In a particular embodiment, $R^{10}$ is $C_{1-4}$ alkoxy. In a more particular embodiment, $R^{10}$ is selected from —OCH$_3$, —OCH$_2$—CH$_3$, and —OC(CH$_3$)$_3$. In a most particular embodiment, $R^{10}$ is —OCH$_3$.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane, each of which is substituted with one or two independently selected $R^9$ groups, $R^9$ is $R^{10}$, and $R^{10}$ is as previously described. In a particular embodiment, $R^{10}$ is selected from —SO$_2$CH$_3$, —C(=O)C$_{1-4}$ alkoxy, and —C(=O)C$_{1-4}$ alkyl. In a more particular embodiment, $R^{10}$ is selected from —SO$_2$CH$_3$, —C(=O)OCH$_3$, —C(=O)OCH$_2$CH$_3$, —C(=O)OCH(CH$_3$)$_2$, —C(=O)CH$_3$, —C(=O)CH$_2$CH$_3$, and —C(=O)OCH(CH$_3$)$_2$. In a most particular embodiment, $R^{10}$ is selected from —SO$_2$CH$_3$, —C(=O)OCH$_3$, and —C(=O)CH$_3$.

In one embodiment, a compound of the invention is according to Formula I-IVd, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-Diaza-spiro[3.3]heptane, each of which is substituted with one or two independently selected $R^9$ groups, $R^9$ is $R^{10}$, and $R^{10}$ is as previously described. In a particular embodiment, $R^{10}$ is —NR$^g$C(=O)C$_{1-4}$ alkyl, and $R^g$ is as described previously. In a particular embodiment, $R^{10}$ is NR$^g$C(=O)CH$_3$, or —NR$^g$C(=O)CH$_2$CH$_3$, and W is as described previously. In a more particular embodiment, $R^{10}$ is —NR$^g$C(=O)CH$_3$, or —NR$^g$C(=O)CH$_2$CH$_3$, and $R^g$ is H, —CH$_3$, or —CH$_2$CH$_3$. In a most particular embodiment, $R^{10}$ is —NHC(=O)CH$_3$, or —NHC(=O)CH$_2$CH$_3$.

In one embodiment, a compound of the invention is according to Formula Va, Vb, Vc, or Vd:

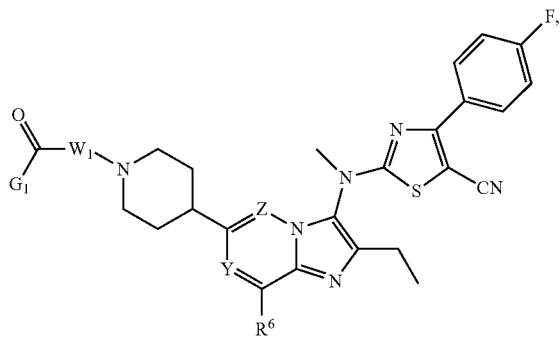

Va

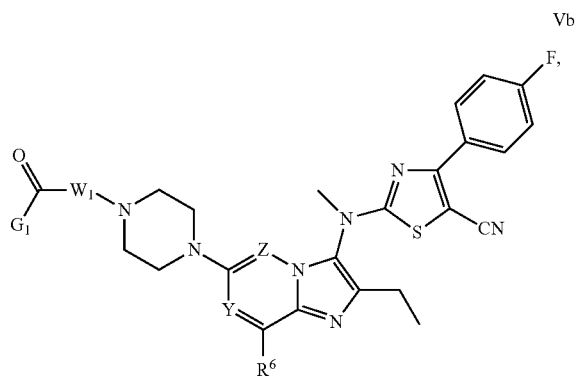

Vb

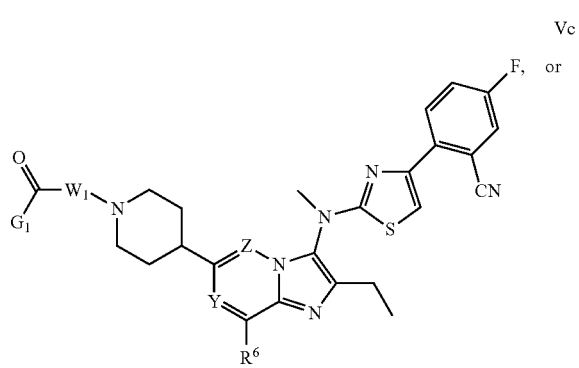

Vc, or

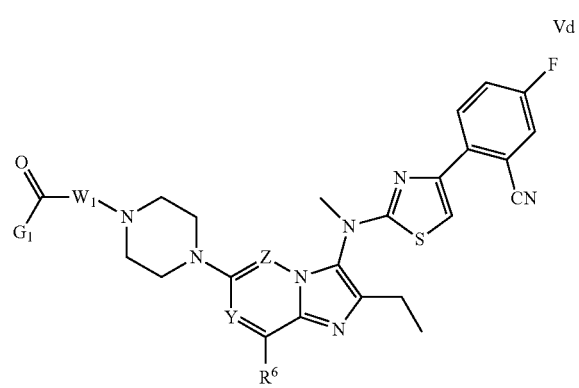

Vd wherein Y, Z, $R^6$, $W_1$, and $G_1$ are as described above.

In one embodiment, a compound of the invention is according to Formula Va-Vd, wherein $W_1$ is $C_{1-4}$ alkylene. In a particular embodiment, $W_1$ is —CH$_2$—, —CH$_2$—CH$_2$—, —C(CH$_3$)H—, —CH$_2$—CH$_2$—CH$_2$— or —CH$_2$—C(CH$_3$)H—. In a more particular embodiment, $W_1$ is —CH$_2$—, or —C(CH$_3$)H—. In a most particular embodiment, $W_1$ is —CH$_2$—.

In one embodiment, a compound of the invention is according to Formula VIa, VIb, VIc, or VId:

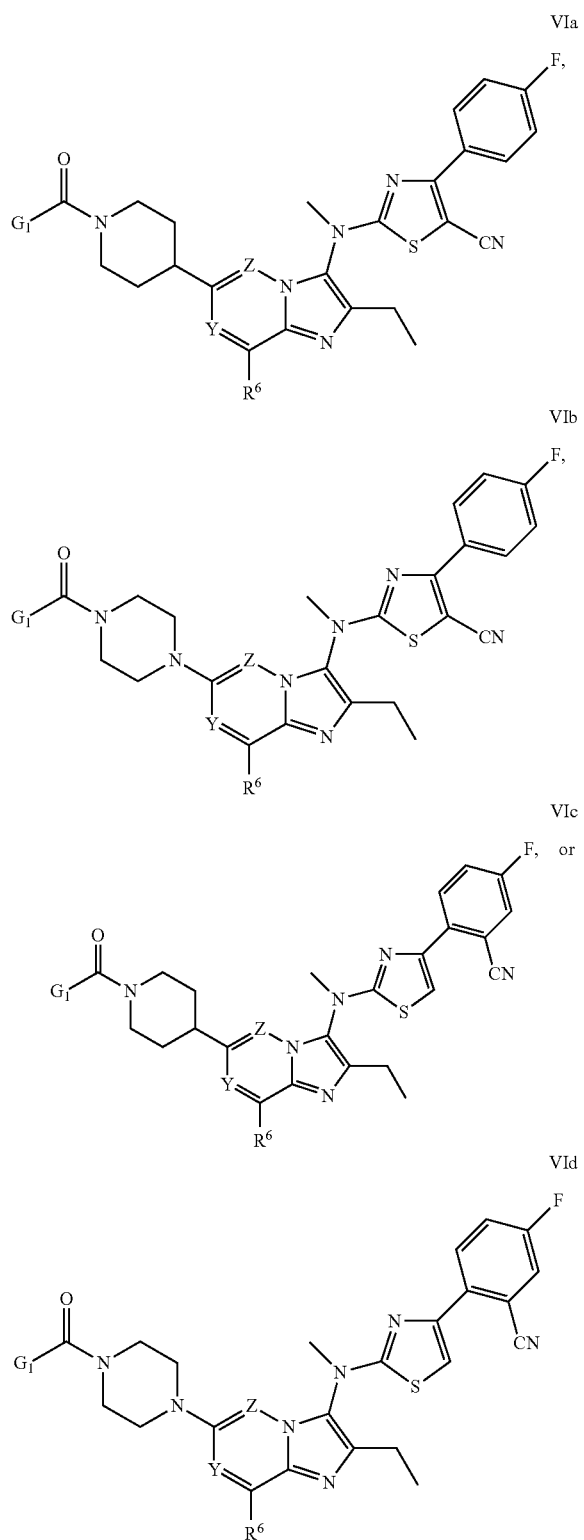

wherein Y, Z, R⁶, and G₁ are as described above.

In one embodiment, a compound of the invention is according to Formula Va-VId, wherein $G_1$ is 4-7 membered heterocycloalkyl containing one or more heteroatoms independently selected from O, N, and S. In a particular embodiment, $G_1$ is oxetanyl, azetidinyl, tetrahydrofuranyl, pyrolidinyl, tetrahydropyranyl, piperidinyl, piperazinyl, morpholinyl, or thiomorpholinyl. In a more particular embodiment, $G_1$ is azetidinyl.

In one embodiment, a compound of the invention is according to Formula Va-VId, wherein $G_1$ is 4-7 membered heterocycloalkyl containing one or more heteroatoms independently selected from O, N, and S, which heterocycle is substituted with one or more independently selected $R^9$ groups. In a further embodiment, $G_1$ is 4-7 membered heterocycloalkyl containing one or more heteroatoms independently selected from O, N, and S, which heterocycle is substituted with one or two independently selected $R^9$ groups. In a particular embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups. In a more particular embodiment, $G_1$ is azetidinyl substituted with one or two independently selected $R^9$ groups.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, and $R^9$ is oxo. In a further particular embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, and $R^9$ is oxo.

In one embodiment, a compound of the invention is according to Formula Va-VId, wherein $G_1$ is 4-7 membered heterocycloalkyl containing one or more heteroatoms independently selected selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is selected from OH, F, Cl, and —CN. In a more particular embodiment, $G_1$ is azetidinyl substituted with one or two independently selected $R^9$ groups, $R^9$ is $R^{10}$, and $R^{10}$ is as previously described. In a most particular embodiment, $R^{10}$ is selected from OH, F, Cl, and —CN.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is selected $C_{1-4}$ alkyl. In a more particular embodiment, $R^{10}$ is selected from —CH₃, —CH₂—CH₃, and —CH(CH₃)₂. In a most particular embodiment, $R^{10}$ is selected from —CH₃, and —CH₂—CH₃.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is $C_{1-4}$ alkyl substituted with one or more independently selected OH, halo, phenyl. In a further embodiment, $R^{10}$ is $C_{1-4}$ alkyl substituted with one to three independently selected OH, halo, and phenyl. In a more particular embodiment, $R^{10}$ is —$CH_3$, —$CH_2$—$CH_3$, and —$CH(CH_3)_2$, each of which is substituted with one to three independently selected OH, halo, and phenyl. In a most particular embodiment, $R^{10}$ is —$CF_3$, —$CH_2$—$CH_2$—OH, and —$CH_2$-phenyl.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is $C_{1-4}$ alkoxy. In a more particular embodiment, $R^{10}$ is selected from —$OCH_3$, —$OCH_2$—$CH_3$, and —$OC(CH_3)_3$. In a most particular embodiment, $R^{10}$ is —$OCH_3$.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is selected from —$SO_2CH_3$, —$C(=O)C_{1-4}$ alkoxy, and —$C(=O)C_{1-4}$ alkyl. In a more particular embodiment, $R^{10}$ is selected from —$SO_2CH_3$, —$C(=O)OCH_3$, —$C(=O)OCH_2CH_3$, —$C(=O)OCH(CH_3)_2$, —$C(=O)CH_3$, —$C(=O)CH_2CH_3$, and —$C(=O)OCH(CH_3)_2$. In a most particular embodiment, $R^{10}$ is selected from —$SO_2CH_3$, —$C(=O)OCH_3$, and —$C(=O)CH_3$.

In one embodiment, a compound of the invention is according to Formula Va-VId, wherein $G_1$ is 4-7 membered heterocycloalkyl containing one or more heteroatoms independently selected from O, N, and S, each of which is substituted with one or two independently selected $R^9$ groups, $R^9$ is $R^{10}$, and $R^{10}$ is as previously described. In a further embodiment, $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups, $R^9$ is $R^{10}$, and $R^{10}$ is as previously described. In a particular embodiment, $R^{10}$ is $NR^gC(=O)C_{1-4}$ alkyl, and $R^g$ is as described previously. In a particular embodiment, $R^{10}$ is $NR^gC(=O)CH_3$, or —$NR^gC(=O)CH_2CH_3$, and $R^g$ is as described previously. In a more particular embodiment, $R^{10}$ is —$NR^gC(=O)CH_3$, or —$NR^gC(=O)CH_2CH_3$, and W is H, —$CH_3$, or —$CH_2CH_3$. In a most particular embodiment, $R^{10}$ is —$NHC(=O)CH_3$, or $NHC(=O)CH_2CH_3$.

In one embodiment, a compound of the invention is according to Formula I-VId, wherein $R^6$ is H, —$CH_3$ or halo. In a particular embodiment, $R^6$ is H, —$CH_3$, F, or Cl. In a more particular embodiment, $R^6$ is H, —$CH_3$, or F. In a more particular embodiment, $R^6$ is H.

In one embodiment, a compound of the invention is according to Formula I-VId, wherein Y is N and Z is CH.

In one embodiment, a compound of the invention is according to Formula I-VId, wherein Y is CH and Z is N.

In one embodiment, a compound of the invention according to Formula I is selected from:
2-((2-ethyl-6-(piperazin-1-yl)imidazo[1,2-a]pyrazin-3-yl)(methyl)amino)-4-(4-fluorophenyl)thiazole-5-carbonitrile,
2-((2-ethyl-6-(4-(2-(3-hydroxyazetidin-1-yl)-2-oxoethyl)piperazin-1-yl)imidazo[1,2-a]pyrazin-3-yl)(methyl)amino)-4-(4-fluorophenyl)thiazole-5-carbonitrile,
2-((6-(4-(2-(3,3-difluoroazetidin-1-yl)-2-oxoethyl)piperazin-1-yl)-2-ethylimidazo[1,2-a]pyrazin-3-yl)(methyl)amino)-4-(4-fluorophenyl)thiazole-5-carbonitrile,
2-((6-(4-(2-(azetidin-1-yl)-2-oxoethyl)piperazin-1-yl)-2-ethylimidazo[1,2-a]pyrazin-3-yl)(methyl)amino)-4-(4-fluorophenyl)thiazole-5-carbonitrile,
2-(4-(3-((5-cyano-4-(4-fluorophenyl)thiazol-2-yl)(methyl)amino)-2-ethylimidazo[1,2-a]pyrazin-6-yl)piperazin-1-yl)-N,N-dimethylacetamide,
(R)-2-((2-ethyl-6-(4-(2-(3-hydroxypyrrolidin-1-yl)-2-oxoethyl)piperazin-1-yl)imidazo[1,2-a]pyrazin-3-yl)(methyl)amino)-4-(4-fluorophenyl)thiazole-5-carbonitrile,
(S)-2-((2-ethyl-6-(4-(2-(3-hydroxypyrrolidin-1-yl)-2-oxoethyl)piperazin-1-yl)imidazo[1,2-a]pyrazin-3-yl)(methyl)amino)-4-(4-fluorophenyl)thiazole-5-carbonitrile,
2-((2-ethyl-6-(4-(2-oxo-2-(pyrrolidin-1-yl)ethyl)piperazin-1-yl)imidazo[1,2-a]pyrazin-3-yl)(methyl)amino)-4-(4-fluorophenyl)thiazole-5-carbonitrile,
2-(4-(3-((5-cyano-4-(4-fluorophenyl)thiazol-2-yl)(methyl)amino)-2-ethylimidazo[1,2-a]pyrazin-6-yl)piperazin-1-yl)-N-methylacetamide,
2-((2-ethyl-6-(4-(2-morpholino-2-oxoethyl)piperazin-1-yl)imidazo[1,2-a]pyrazin-3-yl)(methyl)amino)-4-(4-fluorophenyl)thiazole-5-carbonitrile,
2-((2-ethyl-6-(4-(2-(3-fluoroazetidin-1-yl)-2-oxoethyl)piperazin-1-yl)imidazo[1,2-a]pyrazin-3-yl)(methyl)amino)-4-(4-fluorophenyl)thiazole-5-carbonitrile,
2-((2-ethyl-6-(4-(2-(3-hydroxyazetidin-1-yl)acetoyl)piperazin-1-yl)imidazo[1,2-a]pyrazin-3-yl)(methyl)amino)-4-(4-fluorophenyl)thiazole-5-carbonitrile,
1-(azetidin-1-yl)-2-(4-(2-ethyl-3-((4-(4-fluorophenyl)thiazol-2-yl)(methyl)amino)imidazo[1,2-a]pyrazin-6-yl)piperazin-1-yl)ethanone,
2-(4-(2-ethyl-3-((4-(4-fluorophenyl)thiazol-2-yl)(methyl)amino)imidazo[1,2-a]pyrazin-6-yl)piperazin-1-yl)-1-(3-hydroxyazetidin-1-yl)ethanone,
2-(2-((2-ethyl-6-(piperazin-1-yl)imidazo[1,2-a]pyrazin-3-yl)(methyl)amino)thiazol-4-yl)-5-fluorobenzonitrile,
2-(2-((2-ethyl-6-(4-(2-(3-hydroxyazetidin-1-yl)-2-oxoethyl)piperazin-1-yl)imidazo[1,2-a]pyrazin-3-yl)(methyl)amino) thiazol-4-yl)-5-fluorobenzonitrile,
2-(6-((2-ethyl-6-(4-(2-(3-hydroxyazetidin-1-yl)-2-oxoethyl)piperazin-1-yl)imidazo[1,2-a]pyrazin-3-yl)(methyl)amino)pyridin-2-yl)-5-fluorobenzonitrile,
2-(2-((2-ethyl-6-(4-(2-(3-hydroxyazetidin-1-yl)-2-oxoethyl)piperazin-1-yl)imidazo[1,2-a]pyrazin-3-yl)(methyl)amino)pyrimidin-4-yl)-5-fluorobenzonitrile,
2-((2-ethyl-6-(4-(2-(3-hydroxyazetidin-1-yl)-2-oxoethyl)piperazin-1-yl)imidazo[1,2-a]pyrazin-3-yl)(methyl)amino)-4-(4-fluorophenyl)pyrimidine-5-carbonitrile, 2-((2-ethyl-6-(1-(methyl sulfonyl)-1,2,3,6-tetrahydropyridin-4-yl)imidazo[1,2-a]pyrazin-3-yl)(methyl)amino)-4-(4-fluorophenyl)thiazole-5-carbonitrile, 2-((2-ethyl-6-(1-(2-(3-hydroxyazetidin-1-yl)-2-oxoethyl)-1,2,3,6-tetrahydropyridin-4-yl)imidazo[1,2-a]pyrazin-3-yl)(methyl)amino)-4-(4-fluorophenyl)thiazole-5-carbonitrile, 2-((2-ethyl-6-(piperidin-4-yl)imidazo[1,2-a]pyrazin-3-yl)(methyl)amino)-4-(4-fluorophenyl)thiazole-5-carbonitrile, 2-((2-ethyl-6-(1-(2-(3-hydroxyazetidin-1-yl)-2-oxoethyl)piperidin-4-yl)imidazo[1,2-a]pyrazin-3-yl)(methyl)amino)-4-(4-fluorophenyl)thiazole-5-carbonitrile, (R)-2-((2-ethyl-6-(1-(2-(3-hydroxypyrrolidin-1-yl)-2-oxoethyl)piperidin-4-yl)imidazo[1,2-a]pyrazin-3-yl)(methyl)amino)-4-(4-fluorophenyl)thiazole-5-carbonitrile, (S)-2-((2-ethyl-6-(1-(2-(3-hydroxypyrrolidin-1-yl)-2-oxoethyl)piperidin-4-yl)imidazo[1,2-a]pyrazin-3-yl)(methyl)amino)-4-(4-fluorophenyl)thiazole-5-carbonitrile, 2-(4-(2-ethyl-3-((4-(4-fluorophenyl)thiazol-2-yl)(methyl)amino)imidazo[1,2-b]pyridazin-6-yl)piperazin-1-yl)-1-(3-hydroxyazetidin-1-yl)ethanone, 2-((2-ethyl-6-(4-(2-(3-hydroxyazetidin-1-yl)-2-oxoethyl)piperazin-1-yl)imidazo[1,2-b]pyridazin-3-yl)(methyl)amino)-4-(4-fluorophenyl)thiazole-5-carbonitrile, 2-(4-(2-ethyl-3-((4-(4-fluorophenyl)thiazol-2-yl)(methyl)amino)imidazo[1,2-b]pyridazin-6-yl)piperazin-1-yl)-1-(2-methylpyrrolidin-1-yl)ethanone, 2-(4-(2-ethyl-3-((4-(4-fluorophenyl)thiazol-2-yl)(methyl)amino)imidazo[1,2-b]pyridazin-6-yl)piperazin-1-yl)-1-(2-(hydroxymethyl)pyrrolidin-1-yl)ethanone, 2-(4-(2-ethyl-3-((4-(4-fluorophenyl)thiazol-2-yl)(methyl)amino)imidazo[1,2-b]pyridazin-6-yl)piperazin-1-yl)-N-methylacetamide, 1-(3,3-difluoropyrrolidin-1-yl)-2-(4-(2-ethyl-3-(4-fluorophenyl)thiazol-2-yl)(methyl)amino)imidazo[1,2-b]pyridazin-6-yl)piperazin-1-yl)ethanone, 1-(2,5-dimethylpyrrolidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone, (R)-2-(4-(2-ethyl-3-((4-(4-fluorophenyl)thiazol-2-yl)(methyl)amino)imidazo[1,2-b]pyridazin-6-yl)piperazin-1-yl)-1-(3-hydroxypyrrolidin-1-yl)ethanone, (S)-2-(4-(2-ethyl-3-((4-(4-fluorophenyl) thiazol-2-yl)(methyl)amino)imidazo[1,2-b]pyridazin-6-yl)piperazin-1-yl)-1-(3-hydroxypyrrolidin-1-yl)ethanone, 2-(4-(2-ethyl-3-((4-(4-fluorophenyl)thiazol-2-yl)(methyl)amino)imidazo[1,2-b]pyridazin-6-yl)piperazin-1-yl)-N-(2-hydroxyethyl)acetamide, 1-(azetidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone, 2-(4-(2-ethyl-3-((4-(4-fluorophenyl)thiazol-2-yl)(methyl)amino)imidazo[1,2-b]pyridazin-6-yl)piperazin-1-yl)-N-isopropyl-N-methylacetamide, N-(2-ethyl-6-(4-(oxetan-3-yl)piperazin-1-yl)imidazo[1,2-b]pyridazin-3-yl)-4-(4-fluorophenyl)-N-methylthiazol-2-amine, N-(2-ethyl-6-(4-(tetrahydro-2H-pyran-4-yl)piperazin-1-yl)imidazo[1,2-b]pyridazin-3-yl)-4-(4-fluorophenyl)-N-methylthiazol-2-amine, 5-((4-(2-ethyl-3-((4-(4-fluorophenyl)thiazol-2-yl)(methyl)amino)imidazo[1,2-b]pyridazin-6-yl)piperazin-1-yl)methyl)oxazolidin-2-one, 5-((4-(2-ethyl-3-((4-(4-fluorophenyl)-5-(hydroxymethyl)thiazol-2-yl)(methyl)amino)imidazo[1,2-b]pyridazin-6-yl)piperazin-1-yl)methyl)oxazolidin-2-one, 2-(4-(2-ethyl-3-((4-(4-fluorophenyl)thiazol-2-yl)(methyl)amino)imidazo[1,2-b]pyridazin-6-yl)piperazin-1-yl)-N,N-dimethylacetamide, 2-(4-(2-ethyl-3-((4-(4-fluorophenyl)-5-(hydroxymethyl)thiazol-2-yl)(methyl)amino)imidazo[1,2-b]pyridazin-6-yl)piperazin-1-yl)-N,N-dimethylacetamide, 2-(4-(3-((5-cyano-4-(4-fluorophenyl)thiazol-2-yl)(methyl)amino)-2-ethylimidazo[1,2-b]pyridazin-6-yl)piperazin-1-yl)-N,N-dimethylacetamide, 2-(4-(2-ethyl-3-((4-(4-fluorophenyl)-5-(2,2,2-trifluoroacetoyl)thiazol-2-yl)(methyl)amino)imidazo[1,2-b]pyridazin-6-yl)piperazin-1-yl)-N,N-dimethylacetamide, 1-(2-(4-(2-ethyl-3-(4-fluorophenyl)thiazol-2-yl)(methyl)amino)imidazo[1,2-b]pyridazin-6-yl)piperazin-1-yl)ethyl)pyrrolidin-2-one, (4-(2-ethyl-3-((4-(4-fluorophenyl)thiazol-2-yl)(methyl)amino)imidazo[1,2-b]pyridazin-6-yl)piperazin-1-yl)(tetrahydrofuran-2-yl)methanone, N-(2-ethyl-6-(4-((tetrahydrofuran-2-yl)methyl)piperazin-1-yl)imidazo[1,2-b]pyridazin-3-yl)-4-(4-fluorophenyl)-N-methylthiazol-2-amine, 3-(4-(2-ethyl-3-((4-(4-fluorophenyl)thiazol-2-yl)(methyl)amino)imidazo[1,2-b]pyridazin-6-yl)piperazin-1-yl)propan-1-ol, 3-(4-(2-ethyl-3-((4-(4-fluorophenyl)-5-(hydroxymethyl)thiazol-2-yl)(methyl)amino)imidazo[1,2-b]pyridazin-6-yl)piperazin-1-yl)propan-1-ol, 3-(4-(2-ethyl-3-((4-(4-fluorophenyl)thiazol-2-yl)(methyl)amino)imidazo[1,2-b]pyridazin-6-yl)piperazin-1-yl)propanenitrile, 3-(4-(2-ethyl-3-((4-(4-fluorophenyl)thiazol-2-yl)(methyl)amino)imidazo[1,2-b]pyridazin-6-yl)piperazin-1-yl)propanamide, N-(2-ethyl-6-(4-(2-methoxyethyl)piperazin-1-yl)imidazo[1,2-b]pyridazin-3-yl)-4-(4-fluorophenyl)-N-methylthiazol-2-amine, 2-(4-(2-ethyl-3-((4-(4-fluorophenyl)thiazol-2-yl)(methyl)amino)imidazo[1,2-b]pyridazin-6-yl)piperazin-1-yl)-N-isopropylacetamide, 2-(4-(2-ethyl-3-((4-(4-fluorophenyl)thiazol-2-yl)(methyl)amino)imidazo[1,2-b]pyridazin-6-yl)piperazin-1-yl)-1-(pyrrolidin-1-yl)ethanone, tert-butyl 2-(4-(2-ethyl-3-((4-(4-fluorophenyl)thiazol-2-yl)(methyl)amino)imidazo[1,2-b]pyridazin-6-yl)piperazin-1-yl)ethylcarbamate, N-(2-(4-(2-ethyl-3-(4-fluorophenyl)thiazol-2-yl)(methyl)amino)imidazo[1,2-b]pyridazin-6-yl)piperazin-1-yl)ethyl)acetamide, ethyl 2-(4-(2-ethyl-3-((4-(4-fluorophenyl)thiazol-2-yl)(methyl)amino)imidazo[1,2-b]pyridazin-6-yl)piperazin-1-yl)ethylcarbamate, (S)-tert-butyl 4-(2-ethyl-3-((4-(4-fluorophenyl)thiazol-2-yl)(methyl)amino)imidazo[1,2-b]pyridazin-6-yl)-2-(hydroxymethyl)piperazine-1-carboxylate, (S)-(4-(2-ethyl-3-((4-(4-fluorophenyl)thiazol-2-yl)(methyl)amino)imidazo[1,2-b]pyridazin-6-yl)piperazin-2-yl)methanol, (S)-7-(2-ethyl-3-((4-(4-fluorophenyl)thiazol-2-yl)(methyl)amino)imidazo[1,2-b]pyridazin-6-yl)tetrahydro-1H-oxazolo[3,4-a]pyrazin-3(5H)-one, (S)—N-(2-ethyl-6-(3-(methoxymethyl)-4-(methylsulfonyl)piperazin-1-yl)imidazo[1,2-b]pyridazin-3-yl)-4-(4-fluorophenyl)-N-methylthiazol-2-amine, (S)-(1-(3-(dimethylamino)propyl sulfonyl)-4-(2-ethyl-3-((4-(4-fluorophenyl)thiazol-2-yl)(methyl)amino)imidazo[1,2-b]pyridazin-6-yl)piperazin-2-yl)methanol, (S)-2-(4-(2-ethyl-3-((4-(4-fluorophenyl) thiazol-2-yl) (methyl)amino)imidazo[1,2-b]pyridazin-6-yl)-2-(hydroxymethyl)piperazin-1-yl)-1-(pyrrolidin-1-yl)ethanone, (S)-2-(4-(2-ethyl-3-((4-(4-fluorophenyl) thiazol-2-yl) (methyl)amino)imidazo[1,2-b]pyridazin-6-yl)-2-(hydroxymethyl)piperazin-1-yl)-1-morpholinoethanone, (S)-8-(2-ethyl-3-((4-(4-fluorophenyl)thiazol-2-yl)(methyl) amino)imidazo[1,2-b]pyridazin-6-yl)hexahydropyrazino [2,1-c][1,4]oxazin-4(1H)-one, (S)-(4-(2-ethyl-3-((4-(4-fluorophenyl)thiazol-2-yl)(methyl) amino)imidazo[1,2-b]pyridazin-6-yl)-1-(methyl sulfonyl) piperazin-2-yl)methanol, (S)-(4-(2-ethyl-3-((4-(4-fluorophenyl)-5-(hydroxymethyl) thiazol-2-yl)(methyl)amino)imidazo[1,2-b]pyridazin-6-yl)-1-(methyl sulfonyl)piperazin-2-yl)methanol, (R)-(4-(2-ethyl-3-((4-(4-fluorophenyl)thiazol-2-yl)(methyl) amino)imidazo[1,2-b]pyridazin-6-yl)-1-(methyl sulfonyl) piperazin-2-yl)methanol, 3-(4-(2-ethyl-3-((4-(4-fluorophenyl)thiazol-2-yl)(methyl) amino)imidazo[1,2-b]pyridazin-6-yl)piperazin-1-yl)-1-(4-methoxybenzyl)pyrrolidin-2-one, N-(2-ethyl-6-(4-(ethyl sulfonyl)piperazin-1-yl)imidazo[1,2-b]pyridazin-3-yl)-4-(4-fluorophenyl)-N-methylthiazol-2-amine, 2-(4-(2-ethyl-3-((4-(4-fluorophenyl)thiazol-2-yl)(methyl) amino)imidazo[1,2-b]pyridazin-6-yl)-1-(methyl sulfonyl) piperazin-2-yl)ethanol, 2-(4-(2-ethyl-3-((4-(4-fluoro-2-methylphenyl) thiazol-2-yl) (methyl)amino)imidazo[1,2-b]pyridazin-6-yl)piperazin-1-yl)-N,N-dimethylacetamide, tert-butyl-(1R,4S)-5-(2-ethyl-3-(4-fluorophenyl)thiazol-2-yl)(methyl)amino)imidazo[1,2-b]pyridazin-6-yl)-2,5-diazabicyclo[2.2.1]heptane-2-carboxylate, 1-((1R,4S)-5-(2-ethyl-3-((4-(4-fluorophenyl)thiazol-2-yl) (methyl)amino)imidazo[1,2-b]pyridazin-6-yl)-2,5-diazabicyclo[2.2.1]heptan-2-yl)ethanone, N-(2-ethyl-6-((1S,4R)-5-(methylsulfonyl)-2,5-diazabicyclo [2.2.1]heptan-2-yl)imidazo[1,2-b]pyridazin-3-yl)-4-(4-fluorophenyl)-N-methylthiazol-2-amine, N-(2-ethyl-6-(3-azaspiro[5.5]undecan-3-yl)imidazo[1,2-b] pyridazin-3-yl)-4-(4-fluorophenyl)-N-methylthiazol-2-amine, N-(2-ethyl-6-morpholinoimidazo[1,2-b]pyridazin-3-yl)-4-(4-fluorophenyl)-N-methylthiazol-2-amine, 6-(1,1-Dioxo-thiomorpholin-4-yl)-2-ethyl-imidazo[1,2-b] pyridazin-3-yl)-[4-(4-fluoro-phenyl)-thiazol-2-yl]-methyl-amine, N-(6-(4-(dimethylamino)piperidin-1-yl)-2-ethylimidazo[1, 2-b]pyridazin-3-yl)-4-(4-fluorophenyl)-N-methylthiazol-2-amine, tert-butyl 1-(2-ethyl-3-((4-(4-fluorophenyl)thiazol-2-yl) (methyl)amino)imidazo[1,2-b]pyridazin-6-yl)piperidin-4-ylcarbamate, N-(6-(4-aminopiperidin-1-yl)-2-ethylimidazo[1,2-b] pyridazin-3-yl)-4-(4-fluorophenyl)-N-methylthiazol-2-amine, N-(1-(2-ethyl-3-((4-(4-fluorophenyl)thiazol-2-yl)(methyl) amino)imidazo[1,2-b]pyridazin-6-yl)piperidin-4-yl) methanesulfonamide, N-(1-(2-ethyl-3-((4-(4-fluorophenyl)thiazol-2-yl)(methyl) amino)imidazo[1,2-b]pyridazin-6-yl)piperidin-4-yl)tetrahydro-2H-pyran-4-carboxamide, N-(1-(2-ethyl-3-((4-(4-fluorophenyl)thiazol-2-yl)(methyl) amino)imidazo[1,2-b]pyridazin-6-yl)piperidin-4-yl)-2-hydroxyacetamide, N-(1-(2-ethyl-3-((4-(4-fluorophenyl)thiazol-2-yl)(methyl) amino)imidazo[1,2-b]pyridazin-6-yl)piperidin-4-yl)-3-methyloxetane-3-carboxamide, tert-butyl 4-(1-(2-ethyl-3-((4-(4-fluorophenyl)thiazol-2-yl) (methyl)amino)imidazo[1,2-b]pyridazin-6-yl)piperidin-4-ylcarbamoyl)piperidine-1-carboxylate, N-(1-(2-ethyl-3-((4-(4-fluorophenyl)thiazol-2-yl)(methyl) amino)imidazo[1,2-b]pyridazin-6-yl)piperidin-4-yl)piperidine-4-carboxamide, N-(1-(2-ethyl-3-((4-(4-fluorophenyl)thiazol-2-yl)(methyl) amino)imidazo[1,2-b]pyridazin-6-yl)piperidin-4-yl)pyrrolidine-1-carboxamide, 1-(2-ethyl-3-((4-(4-fluorophenyl)thiazol-2-yl)(methyl) amino)imidazo[1,2-b]pyridazin-6-yl)piperidin-4-ol, 1-(2-ethyl-3-((4-(4-fluorophenyl)thiazol-2-yl)(methyl) amino)imidazo[1,2-b]pyridazin-6-yl)piperidin-3-ol, N-ethyl-2-(1-(2-ethyl-3-((4-(4-fluorophenyl)thiazol-2-yl) (methyl)amino)imidazo[1,2-b]pyridazin-6-yl)piperidin-3-yloxy)acetamide, (1-(2-ethyl-3-((4-(4-fluorophenyl)thiazol-2-yl)(methyl) amino)imidazo[1,2-b]pyridazin-6-yl)piperidin-4-yl) methanol, (1-(2-ethyl-3-((4-(4-fluorophenyl)thiazol-2-yl)(methyl) amino)imidazo[1,2-b]pyridazin-6-yl)piperidin-3-yl) methanol, 1-(2-Ethyl-3-{[4-(4-fluoro-phenyl)-thiazol-2-yl]-methyl-amino}-imidazo[1,2-b]pyridazin-6-yl)-piperidine-4-carboxylic acid ethyl ester, 1-(2-ethyl-3-((4-(4-fluorophenyl)thiazol-2-yl)(methyl) amino)imidazo[1,2-b]pyridazin-6-yl)piperidine-4-carboxylic acid, 1-(2-ethyl-3-((4-(4-fluorophenyl)thiazol-2-yl)(methyl) amino)imidazo[1,2-b]pyridazin-6-yl)-N-(2-hydroxyethyl)piperidine-4-carboxamide, 1-(2-ethyl-3-((4-(4-fluorophenyl)thiazol-2-yl)(methyl) amino)imidazo[1,2-b]pyridazin-6-yl)piperidine-4-carboxamide, 1-(2-ethyl-3-((4-(4-fluorophenyl)thiazol-2-yl)(methyl) amino)imidazo[1,2-b]pyridazin-6-yl)piperidine-3-carboxamide,

[1-(2-Ethyl-3-{[4-(4-fluoro-phenyl)-thiazol-2-yl]-methyl-amino}-imidazo[1,2-b]pyridazin-6-yl)-piperidin-3-ylmethyl]-carbamic acid tert-butyl ester, N-(6-(3-(aminomethyl)piperidin-1-yl)-2-ethylimidazo[1,2-b]pyridazin-3-yl)-4-(4-fluorophenyl)-N-methylthiazol-2-amine, N-((1-(2-ethyl-3-((4-(4-fluorophenyl)thiazol-2-yl)(methyl) amino)imidazo[1,2-b]pyridazin-6-yl)piperidin-3-yl) methyl)methane sulfonamide,

[1-(2-Ethyl-3-{[4-(4-fluoro-phenyl)-thiazol-2-yl]-methyl-amino}-imidazo[1,2-b]pyridazin-6-yl)-piperidin-4-ylmethyl]-carbamic acid tert-butyl ester, N-(6-(4-(aminomethyl)piperidin-1-yl)-2-ethylimidazo[1,2-b]pyridazin-3-yl)-4-(4-fluorophenyl)-N-methylthiazol-2-amine, N-((1-(2-ethyl-3-((4-(4-fluorophenyl)thiazol-2-yl)(methyl) amino)imidazo[1,2-b]pyridazin-6-yl)piperidin-4-yl) methyl)methane sulfonamide, 3-((1-(2-ethyl-3-((4-(4-fluorophenyl)thiazol-2-yl)(methyl) amino)imidazo[1,2-b]pyridazin-6-yl)piperidin-4-yl) methyl)-1,1-dimethylurea, N-((1-(2-ethyl-3-((4-(4-fluorophenyl)thiazol-2-yl)(methyl) amino)imidazo[1,2-b]pyridazin-6-yl)piperidin-4-yl) methyl)tetrahydro-2H-pyran-4-carboxamide, 2-(1-(2-ethyl-3-((4-(4-fluorophenyl)thiazol-2-yl)(methyl) amino)imidazo[1,2-b]pyridazin-6-yl)piperidin-4-yl)-N,N-dimethylacetamide, N-(2-ethyl-6-(4-morpholinopiperidin-1-yl)imidazo[1,2-b]pyridazin-3-yl)-4-(4-fluorophenyl)-N-methylthiazol-2-amine,
N-(2-ethyl-6-(3-morpholinopiperidin-1-yl)imidazo[1,2-b]pyridazin-3-yl)-4-(4-fluorophenyl)-N-methylthiazol-2-amine,
N-(6-(1,4'-bipiperidin-1'-yl)-2-ethylimidazo[1,2-b]pyridazin-3-yl)-4-(4-fluorophenyl)-N-methylthiazol-2-amine,
1'-(2-ethyl-3-((4-(4-fluorophenyl)thiazol-2-yl)(methyl)amino)imidazo[1,2-b]pyridazin-6-yl)-1,3'-bipiperidin-4-ol,
N-(2-ethyl-6-(4-phenylpiperidin-1-yl)imidazo[1,2-b]pyridazin-3-yl)-4-(4-fluorophenyl)-N-methylthiazol-2-amine,
N-cyclopropyl-1-(2-ethyl-3-((4-(4-fluorophenyl)thiazol-2-yl)(methyl)amino)imidazo[1,2-b]pyridazin-6-yl)piperidine-4-sulfonamide,
1-(4-(2-ethyl-3-((4-(4-fluorophenyl)thiazol-2-yl)(methyl)amino)imidazo[1,2-b]pyridazin-6-yl)-1,4-diazepan-1-yl)ethanone,
N-(2-ethyl-6-(4-(methylsulfonyl)-1,4-diazepan-1-yl)imidazo[1,2-b]pyridazin-3-yl)-4-(4-fluorophenyl)-N-methylthiazol-2-amine,
N-(2-ethyl-6-(8-oxa-2-azaspiro[4.5]decan-2-yl)imidazo[1,2-b]pyridazin-3-yl)-4-(4-fluorophenyl)-N-methylthiazol-2-amine,
7-(2-ethyl-3-(4-fluorophenyl)thiazol-2-yl)(methyl)amino)imidazo[1,2-b]pyridazin-6-yl)-1-oxa-3,7-diazaspiro[4.4]nonan-2-one,
7-(2-ethyl-3-(4-fluorophenyl)thiazol-2-yl)(methyl)amino)imidazo[1,2-b]pyridazin-6-yl)-3-methyl-1-oxa-3,7-diazaspiro[4.4]nonan-2-one,
7-(2-ethyl-3-((4-(4-fluorophenyl)-5-(hydroxymethyl)thiazol-2-yl)(methyl)amino)imidazo[1,2-b]pyridazin-6-yl)-3-methyl-1-oxa-3,7-diazaspiro[4.4]nonan-2-one,
7-(2-ethyl-3-(4-fluorophenyl)thiazol-2-yl)(methyl)amino)imidazo[1,2-b]pyridazin-6-yl)-2,7-diazaspiro[4.4]nonane-1,3-dione,
tert-butyl 5-(2-ethyl-3-((4-(4-fluorophenyl)thiazol-2-yl)(methyl)amino)imidazo[1,2-b]pyridazin-6-yl)hexahydropyrrolo[3,4-c]pyrrole-2 (1H)-carboxylate,
N-(2-ethyl-6-(5-(methylsulfonyl)hexahydropyrrolo[3,4-c]pyrrol-2 (1H)-yl)imidazo[1,2-b]pyridazin-3-yl)-4-(4-fluorophenyl)-N-methylthiazol-2-amine,
1-(5-(2-ethyl-3-((4-(4-fluorophenyl)thiazol-2-yl)(methyl)amino)imidazo[1,2-b]pyridazin-6-yl)hexahydropyrrolo[3,4-c]pyrrol-2 (1H)-yl)ethanone,
N-(6-(5-(3-chloropropyl sulfonyl)hexahydropyrrolo[3,4-c]pyrrol-2 (1H)-yl)-2-ethylimidazo[1,2-b]pyridazin-3-yl)-4-(4-fluorophenyl)-N-methylthiazol-2-amine,
N-(6-(5-(3-(dimethylamino)propyl sulfonyl)hexahydropyrrolo[3,4-c]pyrrol-2 (1H)-yl)-2-ethylimidazo[1,2-b]pyridazin-3-yl)-4-(4-fluorophenyl)-N-methylthiazol-2-amine,
N-(2-ethyl-6-(5-(3-morpholinopropylsulfonyl)hexahydropyrrolo[3,4-c]pyrrol-2 (1H)-yl)imidazo[1,2-b]pyridazin-3-yl)-4-(4-fluorophenyl)-N-methylthiazol-2-amine,
(S)-1-(2-ethyl-3-((4-(4-fluorophenyl)thiazol-2-yl)(methyl)amino)imidazo[1,2-b]pyridazin-6-yl)pyrrolidine-3-carbonitrile,
1-(2-ethyl-3-(4-fluorophenyl)thiazol-2-yl)(methyl)amino)imidazo[1,2-b]pyridazin-6-yl)pyrrolidin-3-ol,
1-(2-ethyl-3-(4-fluorophenyl)thiazol-2-yl)(methyl)amino)imidazo[1,2-b]pyridazin-6-yl)pyrrolidin-3-yl formate,
N-(2-ethyl-6-(3-thiomorpholinopyrrolidin-1-yl)imidazo[1,2-b]pyridazin-3-yl)-4-(4-fluorophenyl)-N-methylthiazol-2-amine,
1-(3-((5-chloro-4-(4-fluorophenyl) thiazol-2-yl)(methyl)amino)-2-ethylimidazo[1,2-b]pyridazin-6-yl)pyrrolidin-3-one,
tert-butyl 1-(2-ethyl-3-((4-(4-fluorophenyl)thiazol-2-yl)(methyl)amino)imidazo[1,2-b]pyridazin-6-yl)pyrrolidin-3-ylcarbamate,
N-(6-(3-aminopyrrolidin-1-yl)-2-ethylimidazo[1,2-b]pyridazin-3-yl)-4-(4-fluorophenyl)-N-methylthiazol-2-amine,
methyl 2-(1-(2-ethyl-3-((4-(4-fluorophenyl)thiazol-2-yl)(methyl)amino)imidazo[1,2-b]pyridazin-6-yl)pyrrolidin-3-ylamino)acetate,
N-(1-(2-ethyl-3-((4-(4-fluorophenyl)thiazol-2-yl)(methyl)amino)imidazo[1,2-b]pyridazin-6-yl)pyrrolidin-3-yl)-2-hydroxyacetamide,
N-(1-(2-ethyl-3-((4-(4-fluorophenyl)thiazol-2-yl)(methyl)amino)imidazo[1,2-b]pyridazin-6-yl)pyrrolidin-3-yl) methane sulfonamide,
(S)-1-(2-ethyl-3-((4-(4-fluorophenyl)thiazol-2-yl)(methyl)amino)imidazo[1,2-b]pyridazin-6-yl)pyrrolidine-2-carboxylic acid,
1-(2-Ethyl-3-{[4-(4-fluoro-phenyl)-thiazol-2-yl]-methyl-amino}-imidazo[1,2-b]pyridazin-6-yl)-pyrrolidine-3-carboxylic acid methyl ester,
1-(2-ethyl-3-(4-fluorophenyl)thiazol-2-yl)(methyl)amino) imidazo[1,2-b]pyridazin-6-yl)-N-(2-hydroxyethyl)pyrrolidine-3-carboxamide,
(1-(2-ethyl-3-((4-(4-fluorophenyl)thiazol-2-yl)(methyl)amino)imidazo[1,2-b]pyridazin-6-yl)pyrrolidin-3-yl)(morpholino)methanone,
(1-(2-ethyl-3-((4-(4-fluorophenyl)thiazol-2-yl)(methyl)amino)imidazo[1,2-b]pyridazin-6-yl)pyrrolidin-2-yl)methanol,
(1-(2-ethyl-3-((4-(4-fluorophenyl)thiazol-2-yl)(methyl)amino)imidazo[1,2-b]pyridazin-6-yl)pyrrolidin-3-yl) methanol,
(1-(2-ethyl-3-((4-(4-fluorophenyl)-5-(hydroxymethyl)thiazol-2-yl)(methyl)amino)imidazo[1,2-b]pyridazin-6-yl)pyrrolidin-3-yl)methanol,
3-(4-(1-(2-ethyl-3-(4-fluorophenyl)thiazol-2-yl)(methyl)amino)imidazo[1,2-b]pyridazin-6-yl)-3-yl)piperazin-1-yl)propan-1-ol,
4-(1-(2-ethyl-3-((4-(4-fluorophenyl)thiazol-2-yl)(methyl)amino)imidazo[1,2-b]pyridazin-6-yl)piperazin-2-one,
N-(2-ethyl-6-(3-morpholinopyrrolidin-1-yl)imidazo[1,2-b]pyridazin-3-yl)-4-(4-fluorophenyl)-N-methylthiazol-2-amine,
(2-((2-ethyl-6-(3-morpholinopyrrolidin-1-yl)imidazo[1,2-b]pyridazin-3-yl)(methyl)amino)-4-(4-fluorophenyl)thiazol-5-yl)methanol,
2-((2-ethyl-6-(3-morpholinopyrrolidin-1-yl)imidazo[1,2-b]pyridazin-3-yl)(methyl)amino)-4-(4-fluorophenyl)thiazole-5-carbonitrile,
{6-[3-(1,1-Dioxo-thiomorpholin-4-yl)-pyrrolidin-1-yl]-2-ethyl-imidazo[1,2-b]pyridazin-3-yl}-[4-(4-fluoro-phenyl)-thiazol-2-yl]-methyl-amine,
N-(2-ethyl-6-(3-(piperidin-1-yl)pyrrolidin-1-yl)imidazo[1,2-b]pyridazin-3-yl)-4-(4-fluorophenyl)-N-methylthiazol-2-amine,
1-(1-(2-ethyl-3-((4-(4-fluorophenyl)thiazol-2-yl)(methyl)amino)imidazo[1,2-b]pyridazin-6-yl)pyrrolidin-3-yl)piperidin-4-ol, (1-(2-ethyl-3-((4-(4-fluorophenyl)thiazol-2-yl)(methyl)amino)imidazo[1,2-b]pyridazin-6-yl)azetidin-3-yl)methanol,

[1-(2-Ethyl-3-{[4-(4-fluoro-phenyl)-thiazol-2-yl]-methyl-amino}-imidazo[1,2-b]pyridazin-6-yl)-azetidin-3-yl]-carbamic acid tert-butyl ester, 2-(1-(2-ethyl-3-((4-(4-fluorophenyl)thiazol-2-yl)(methyl)amino)imidazo[1,2-b]pyridazin-6-yl)azetidin-3-ylamino)-1-(3-hydroxyazetidin-1-yl)ethanone, 2-(1-(2-ethyl-3-((4-(4-fluorophenyl)thiazol-2-yl)(methyl)amino)imidazo[1,2-b]pyridazin-6-yl)azetidin-3-ylamino)-N,N-dimethylacetamide, 2-(1-(2-ethyl-3-((4-(4-fluorophenyl)thiazol-2-yl)(methyl)amino)imidazo[1,2-b]pyridazin-6-yl)azetidin-3-ylamino)-N-methylacetamide, N-(1-(2-ethyl-3-((4-(4-fluorophenyl)thiazol-2-yl)(methyl)amino)imidazo[1,2-b]pyridazin-6-yl)azetidin-3-yl)methane sulfonamide, (1-(2-ethyl-3-((4-(4-fluorophenyl)thiazol-2-yl)(methyl)amino)imidazo[1,2-b]pyridazin-6-yl)azetidin-3-yl)(3-hydroxypyrrolidin-1-yl)methanone, 2-((2-ethyl-6-(4-((2-oxooxazolidin-5-yl)methyl)piperazin-1-yl)imidazo[1,2-b]pyridazin-3-yl)(methyl)amino)-4-(4-fluorophenyl)thiazole-5-carbonitrile, (S)-2-((2-ethyl-6-(3-(hydroxymethyl)-4-(methylsulfonyl)piperazin-1-yl)imidazo[1,2-b]pyridazin-3-yl)(methyl)amino)-4-(4-fluorophenyl)thiazole-5-carbonitrile, 2-((2-ethyl-6-(2-oxo-1-oxa-3,7-diazaspiro[4.5]decan-7-yl)imidazo[1,2-b]pyridazin-3-yl)(methyl)amino)-4-(4-fluorophenyl)thiazole-5-carbonitrile, 2-((2-ethyl-6-(3-methyl-2-oxo-1-oxa-3,7-diazaspiro[4.5]decan-7-yl)imidazo[1,2-b]pyridazin-3-yl)(methyl)amino)-4-(4-fluorophenyl)thiazole-5-carbonitrile, 2-((2-ethyl-6-(3-methyl-2-oxo-1-oxa-3,7-diazaspiro[4.4]nonan-7-yl)imidazo[1,2-b]pyridazin-3-yl)(methyl)amino)-4-(4-fluorophenyl)thiazole-5-carbonitrile, tert-butyl 7-(3-cyano-4-(4-fluorophenyl)thiazol-2-yl)(methyl)amino)-2-ethylimidazo[1,2-b]pyridazin-6-yl)-2,7-diazaspiro[4.4]nonane-2-carboxylate, 2-((2-ethyl-6-(2,7-diazaspiro[4.4]nonan-2-yl)imidazo[1,2-b]pyridazin-3-yl)(methyl)amino)-4-(4-fluorophenyl)thiazole-5-carbonitrile, 2-((6-(7-acetoyl-2,7-diazaspiro[4.4]nonan-2-yl)-2-ethylimidazo[1,2-b]pyridazin-3-yl)(methyl)amino)-4-(4-fluorophenyl)thiazole-5-carbonitrile, methyl (1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl), N-((1-(3-cyano-4-(4-fluorophenyl)thiazol-2-yl)(methyl)amino)-2-ethylimidazo[1,2-b]pyridazin-6-yl)-3-hydroxypyrrolidin-3-yl)methyl)acetamide, N-((1-(3-cyano-4-(4-fluorophenyl)thiazol-2-yl)(methyl)amino)-2-ethylimidazo[1,2-b]pyridazin-6-yl)-3-hydroxypyrrolidin-3-yl)methyl)isobutyramide, 2-((2-ethyl-6-(3-hydroxypyrrolidin-1-yl)imidazo[1,2-b]pyridazin-3-yl)(methyl)amino)-4-(4-fluorophenyl)thiazole-5-carbonitrile, 2-((2-ethyl-6-(3-oxopyrrolidin-1-yl)imidazo[1,2-b]pyridazin-3-yl)(methyl)amino)-4-(4-fluorophenyl)thiazole-5-carbonitrile, 2-((2-ethyl-6-(3-(hydroxymethyl)pyrrolidin-1-yl)imidazo[1,2-b]pyridazin-3-yl)(methyl)amino)-4-(4-fluorophenyl)thiazole-5-carbonitrile, (S)-2-((2-ethyl-6-(3-(2-(3-hydroxyazetidin-1-yl)-2-oxoethylamino)pyrrolidin-1-yl)imidazo[1,2-b]pyridazin-3-yl)(methyl)amino)-4-(4-fluorophenyl)thiazole-5-carbonitrile, (S)-2-(1-(3-cyano-4-(4-fluorophenyl)thiazol-2-yl)(methyl)amino)-2-ethylimidazo[1,2-b]pyridazin-6-yl)pyrrolidin-3-ylamino)-N,N-dimethylacetamide, (R)-2-((2-ethyl-6-(3-(2-(3-hydroxyazetidin-1-yl)-2-oxoethylamino)pyrrolidin-1-yl)imidazo[1,2-b]pyridazin-3-yl)(methyl)amino)-4-(4-fluorophenyl)thiazole-5-carbonitrile, (R)-2-(1-(3-cyano-4-(4-fluorophenyl)thiazol-2-yl)(methyl)amino)-2-ethylimidazo[1,2-b]pyridazin-6-yl)pyrrolidin-3-ylamino)-N,N-dimethylacetamide, 2-((6-(3-((2S,6R)-2,6-dimethylmorpholino)pyrrolidin-1-yl)-2-ethylimidazo[1,2-b]pyridazin-3-yl)(methyl)amino)-4-(4-fluorophenyl)thiazole-5-carbonitrile, 2-((2-ethyl-6-(3-(4-(hydroxymethyl)piperidin-1-yl)pyrrolidin-1-yl)imidazo[1,2-b]pyridazin-3-yl)(methyl)amino)-4-(4-fluorophenyl)thiazole-5-carbonitrile, 2-((6-(3-(4-acetoylpiperazin-1-yl)pyrrolidin-1-yl)-2-ethylimidazo[1,2-b]pyridazin-3-yl)(methyl)amino)-4-(4-fluorophenyl)thiazole-5-carbonitrile, N-(1-(1-(3-((5-cyano-4-(4-fluorophenyl)thiazol-2-yl)(methyl)amino)-2-ethylimidazo[1,2-b]pyridazin-6-yl)pyrrolidin-3-yl)piperidin-4-yl)-N-methylacetamide, 2-((2-ethyl-6-(3-(4-hydroxypiperidin-1-yl)pyrrolidin-1-yl)imidazo[1,2-b]pyridazin-3-yl)(methyl)amino)-4-(4-fluorophenyl)thiazole-5-carbonitrile, 2-((2-ethyl-6-(3-(4-methoxypiperidin-1-yl)pyrrolidin-1-yl)imidazo[1,2-b]pyridazin-3-yl)(methyl)amino)-4-(4-fluorophenyl)thiazole-5-carbonitrile, 2-((2-ethyl-6-((3 S,4S)-3-hydroxy-4-morpholinopyrrolidin-1-yl)imidazo[1,2-b]pyridazin-3-yl)(methyl)amino)-4-(4-fluorophenyl)thiazole-5-carbonitrile, 1-(2-ethyl-3-((4-(4-fluorophenyl)-5-(hydroxymethyl)thiazol-2-yl)(methyl)amino)imidazo[1,2-b]pyridazin-6-yl)pyrrolidin-3-ol, (2-((2-ethyl-6-(8-oxa-2-azaspiro[4.5]decan-2-yl)imidazo[1,2-b]pyridazin-3-yl)(methyl)amino)-4-(4-fluorophenyl)thiazol-5-yl)methanol,

[1-(3-{[5-Cyano-4-(4-fluoro-phenyl)-thiazol-2-yl]-methyl-amino}-2-ethyl-imidazo[1,2-b]pyridazin-6-yl)-azetidin-3-yl]-carbamic acid tert-butyl ester, 2-((6-(3-aminoazetidin-1-yl)-2-ethylimidazo[1,2-b]pyridazin-3-yl)(methyl)amino)-4-(4-fluorophenyl)thiazole-5-carbonitrile, 2-((2-ethyl-6-(3-(2-(3-hydroxyazetidin-1-yl)-2-oxoethylamino)azetidin-1-yl)imidazo[1,2-b]pyridazin-3-yl)(methyl)amino)-4-(4-fluorophenyl)thiazole-5-carbonitrile, N-(1-(3-cyano-4-(4-fluorophenyl)thiazol-2-yl)(methyl)amino)-2-ethylimidazo[1,2-b]pyridazin-6-yl)azetidin-3-yl)methane sulfonamide, 2-((2-ethyl-6-(3-(morpholine-4-carbonyl)azetidin-1-yl)imidazo[1,2-b]pyridazin-3-yl)(methyl)amino)-4-(4-fluorophenyl)thiazole-5-carbonitrile, 2-((2-ethyl-6-(3-(3-hydroxypyrrolidine-1-carbonyl)azetidin-1-yl)imidazo[1,2-b]pyridazin-3-yl)(methyl)amino)-4-(4-fluorophenyl)thiazole-5-carbonitrile, 4-(2-Ethyl-3-{[4-(4-fluoro-phenyl)-thiazol-2-yl]-methyl-amino}-imidazo[1,2-b]pyridazin-6-yl)-3,6-dihydro-2H-pyridine-1-carboxylic acid tert-butyl ester, N-(2-ethyl-6-(1-(methyl sulfonyl)-1,2,3,6-tetrahydropyridin-4-yl)imidazo[1,2-b]pyridazin-3-yl)-4-(4-fluorophenyl)-N-methylthiazol-2-amine, (3-((4-(4-fluorophenyl)thiazol-2-yl)(methyl)amino)-6-(1-(methyl sulfonyl)-1,2,3,6-tetrahydropyridin-4-yl)imidazo[1,2-b]pyridazin-2-yl)methanol, 2-(3-(4-fluorophenyl)thiazol-2-yl)(methyl)amino)-6-(1-(methyl sulfonyl)-1,2,3,6-tetrahydropyridin-4-yl)imidazo[1,2-b]pyridazin-2-yl)acetonitrile, 3-(3-((4-(4-fluorophenyl)thiazol-2-yl)(methyl)amino)-6-(1-(methyl sulfonyl)piperidin-4-yl)imidazo[1,2-b]pyridazin-2-yl)propanamide, 3-(3-((4-(4-fluorophenyl)thiazol-2-yl)(methyl)amino)-6-(1-(methyl sulfonyl)piperidin-4-yl)imidazo[1,2-b]pyridazin-2-yl)propanenitrile, 3-(3-((4-(4-fluorophenyl)-5-(2,2,2-trifluoroacetoyl)thiazol-2-yl)(methyl)amino)-6-(1-(methyl sulfonyl)piperidin-4-yl)imidazo[1,2-b]pyridazin-2-yl)propanenitrile, 3-(3-((4-(4-fluorophenyl)thiazol-2-yl)(methyl)amino)-6-(1-(methyl sulfonyl)piperidin-4-yl)imidazo[1,2-b]pyridazin-2-yl)propan-1-ol, 2-(4-(2-ethyl-3-((4-(4-fluorophenyl)thiazol-2-yl)(methyl)amino)imidazo[1,2-b]pyridazin-6-yl)piperidin-1-yl)-1-(3-hydroxyazetidin-1-yl)ethanone, 2-(4-(2-ethyl-3-((4-(4-fluorophenyl)thiazol-2-yl)(methyl)amino)imidazo[1,2-b]pyridazin-6-yl)piperidin-1-yl)-N,N-dimethylacetamide, 2-(4-(2-ethyl-3-((4-(4-fluorophenyl)-5-(hydroxymethyl)thiazol-2-yl)(methyl)amino)imidazo[1,2-b]pyridazin-6-yl)piperidin-1-yl)-N,N-dimethylacetamide, 2-(2-ethyl-6-(1-(methyl sulfonyl)-1,2,3,6-tetrahydropyridin-4-yl)imidazo[1,2-b]pyridazin-3-yl)(methyl)amino) thiazol-4-yl)-5-fluorobenzonitrile, 2-(2-ethyl-6-(1-(methyl sulfonyl)piperidin-4-yl)imidazo[1,2-b]pyridazin-3-yl)(methyl)amino) thiazol-4-yl)-5-fluorobenzonitrile, 2-(2-ethyl-6-(1-(methyl sulfonyl)piperidin-4-yl)imidazo[1,2-b]pyridazin-3-yl)(methyl)amino)-5-(hydroxymethyl)thiazol-4-yl)-5-fluorobenzonitrile, 2-(2-ethyl-6-(1-(2-(3-hydroxyazetidin-1-yl)-2-oxoethyl)piperidin-4-yl)imidazo[1,2-b]pyridazin-3-yl)(methyl)amino) thiazol-4-yl)-5-fluorobenzonitrile, 2-(4-(3-((4-(2-cyano-4-fluorophenyl)thiazol-2-yl)(methyl)amino)-2-ethylimidazo[1,2-b]pyridazin-6-yl)piperidin-1-yl)-N,N-dimethylacetamide, 2-(4-(3-((4-(2-cyano-4-fluorophenyl)thiazol-2-yl)(methyl)amino)-2-ethylimidazo[1,2-b]pyridazin-6-yl)piperidin-1-yl)-N-methylacetamide, 2-(2-ethyl-6-(1-(2-(3-hydroxyazetidin-1-yl)-2-oxoethyl)piperidin-4-yl)imidazo[1,2-b]pyridazin-3-yl)(methyl)amino)-5-methylthiazol-4-yl)-5-fluorobenzonitrile, 2-(4-(3-((4-(2-cyano-4-fluorophenyl)-5-methylthiazol-2-yl)(methyl)amino)-2-ethylimidazo[1,2-b]pyridazin-6-yl)piperidin-1-yl)-N-methylacetamide, 2-((2-ethyl-6-(1-(2-(3-hydroxyazetidin-1-yl)-2-oxoethyl)piperidin-4-yl)imidazo[1,2-b]pyridazin-3-yl)(methyl)amino)-4-(4-fluorophenyl)thiazole-5-carbonitrile, 2-(6-((2-ethyl-6-(1-(2-(3-hydroxyazetidin-1-yl)-2-oxoethyl)piperidin-4-yl)imidazo[1,2-b]pyridazin-3-yl)(methyl)amino)pyridin-2-yl)-5-fluorobenzonitrile, 2-(4-(2-ethyl-3-((6-(4-fluorophenyl)pyridin-2-yl)(methyl)amino)imidazo[1,2-b]pyridazin-6-yl)piperidin-1-yl)-1-(3-hydroxyazetidin-1-yl)ethanone, 2-(4-(2-ethyl-3-((4-(4-fluorophenyl)pyrimidin-2-yl)(methyl)amino)imidazo[1,2-b]pyridazin-6-yl)piperidin-1-yl)-1-(3-hydroxyazetidin-1-yl)ethanone, 2-(4-(2-ethyl-3-((2-(4-fluorophenyl)pyrimidin-4-yl)(methyl)amino)imidazo[1,2-b]pyridazin-6-yl)piperidin-1-yl)-1-(3-hydroxyazetidin-1-yl)ethanone, 2-((2-ethyl-6-(1-(2-(3-hydroxyazetidin-1-yl)-2-oxoethyl)piperidin-4-yl)imidazo[1,2-b]pyridazin-3-yl)(methyl)amino)-6-(4-fluorophenyl)nicotinonitrile, 6-((2-ethyl-6-(1-(2-(3-hydroxyazetidin-1-yl)-2-oxoethyl)piperidin-4-yl)imidazo[1,2-b]pyridazin-3-yl)(methyl)amino)-2-(4-fluorophenyl)nicotinonitrile, 2-(5-((2-ethyl-6-(piperidin-4-yl)imidazo[1,2-b]pyridazin-3-yl)(methyl)amino)-1,2,4-thiadiazol-3-yl)-5-fluorobenzonitrile, and 2-(5-ethyl-6-(1-(2-(3-hydroxyazetidin-1-yl)-2-oxoethyl)piperidin-4-yl)imidazo[1,2-b]pyridazin-3-yl)(methyl)amino)-1,2,4-thiadiazol-3-yl)-5-fluorobenzonitrile.

In one embodiment a compound of the invention is not an isotopic variant.

In one aspect a compound of the invention according to any one of the embodiments herein described is present as the free base.

In one aspect a compound of the invention according to any one of the embodiments herein described is a pharmaceutically acceptable salt.

In one aspect a compound of the invention according to any one of the embodiments herein described is a solvate of the compound.

In one aspect a compound of the invention according to any one of the embodiments herein described is a solvate of a pharmaceutically acceptable salt of a compound.

While specified groups for each embodiment have generally been listed above separately, a compound of the invention includes one in which several or each embodiment in the above Formula, as well as other formulae presented herein, is selected from one or more of particular members or groups designated respectively, for each variable. Therefore, this invention is intended to include all combinations of such embodiments within its scope.

While specified groups for each embodiment have generally been listed above separately, a compound of the invention may be one for which one or more variables (for example, R groups) is selected from one or more embodiments according to any of the Formula(e) listed above. Therefore, the present invention is intended to include all combinations of variables from any of the disclosed embodiments within its scope.

Alternatively, the exclusion of one or more of the specified variables from a group or an embodiment, or combinations thereof is also contemplated by the present invention.

In certain aspects, the present invention provides prodrugs and derivatives of the compounds according to the formulae above. Prodrugs are derivatives of the compounds of the invention, which have metabolically cleavable groups and become by solvolysis or under physiological conditions the compounds of the invention, which are pharmaceutically active, in vivo. Such examples include, but are not limited to, choline ester derivatives and the like, N-alkylmorpholine esters and the like.

Other derivatives of the compounds of this invention have activity in both their acid and acid derivative forms, but the acid sensitive form often offers advantages of solubility, tissue compatibility, or delayed release in the mammalian organism (Bundgaard 1992). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are preferred prodrugs. In some cases it is desirable to prepare double ester type prodrugs such as (acyloxy)alkyl esters or ((alkoxycarbonyl)oxy)alkylesters. Particularly useful are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds of the invention.

Clauses

1) A compound according to Formula I:

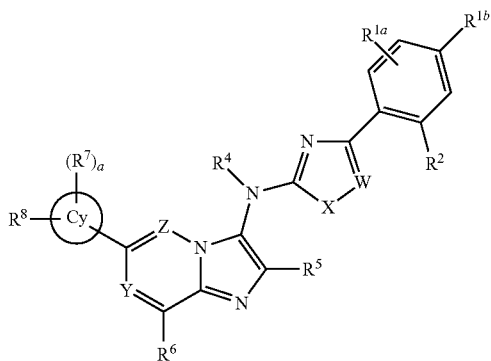

wherein
$R^{1a}$ is H, halo or $C_{1-4}$ alkyl; $R^{1b}$ is:
   halo,
   $C_{1-4}$ alkyl (which alkyl is optionally substituted with one or more independently selected halo), or
   $C_{1-4}$ alkoxy (which alkoxy is optionally substituted with one or more independently selected halo);
X is —S—, —O—, —N=CH—, —CH=N— or —CH=CH—;
W is N, or $CR^3$
when W is N, $R^2$ is:
   H,
   —CN,
   halo,
   $C_{1-4}$ alkyl (which alkyl is optionally substituted with one or more independently selected OH, or CN),
   —C(=O)CH$_3$,
   —C(=O)CF$_3$,
   —C(=O)OCH$_3$,
   —C(=O)NH$_2$,
   —NHC(=O)CH$_3$, or
when W is $CR^3$, one of $R^2$ or $R^3$ is:
   H,
   —CN,
   halo,
   $C_{1-4}$ alkyl (which alkyl is optionally substituted with one or more independently selected OH, or CN),
   —C(=O)CH$_3$,
   —C(=O)CF$_3$,
   —C(=O)OCH$_3$,
   —C(=O)NH$_2$,
   —NHC(=O)CH$_3$,
   and the other is H, or $C_{1-4}$ alkyl;
$R^4$ is $C_{1-4}$ alkyl;
$R^5$ is $C_{1-4}$ alkyl optionally substituted with one or more independently selected CN, OH, halo, or —C(=O)NH$_2$;
one of Y and Z is CH and the other is N;
$R^6$ is selected from H, —CH$_3$ and halo;

Cy is:
   $C_{4-10}$ cycloalkyl,
   4-10 membered mono or bicyclic heterocycloalkyl containing one or more heteroatoms independently selected from O, N, and S, or
   4-7 membered heterocycloalkenyl containing 1 double bond, containing one or more heteroatoms independently selected from O, N, and S;
each $R^7$ is independently selected from:
   OH,
   oxo,
   halo, and
   $C_{1-4}$ alkyl (which alkyl is optionally substituted with one or more independently selected OH, or $C_{1-4}$ alkoxy);
the subscript a is 0, 1 or 2;
$R^8$ is -(L$_1$-W$_1$)$_m$-L$_2$-G$_1$,
   wherein
      L$_1$ is absent, or is —O—, —C(=O)—, —NR$^i$—, —NR$^h$C(=O)—, or —SO$_2$—;
      W$_1$ is $C_{1-4}$ alkylene;
      the subscript m is 0, or 1;
      L$_2$ is absent, or is —O—, —C(=O)—, —C(=O)O—, —OC(=O)—, —C(=O)—C(=O)—, —C(=O)—C(=O)NR$^a$—, —NR$^b$—, —C(=O)NR$^c$—, —NR$^d$C(=O)—, —NR$^j$C(=O)O—, —SO$_2$—, —SO$_2$NR$^e$— or NR$^f$SO$_2$—;
      G$_1$ is
         H,
         —CN,
         $C_{1-4}$ alkyl (which alkyl is optionally substituted with one or more independently selected CN, OH, halo or phenyl),
         $C_{3-7}$ cycloalkyl (which cycloalkyl is optionally substituted with NH$_2$),
         5-6 membered heterocycloalkenyl containing 1 double bond containing one or more heteroatoms independently selected from O, N, and S, (which heterocycloalkenyl is optionally substituted with one or more independently selected $R^9$ groups),
         4-10 membered mono, bi or spirocyclic heterocycloalkyl containing one or more heteroatoms independently selected from O, N, and S, (which heterocycloalkyl is optionally substituted with one or more independently selected $R^9$ groups), or
         5-6 membered heteroaryl containing one or more heteroatoms independently selected from O, N, and S, (which heteroaryl is optionally substituted with one or more independently selected $R^{10}$ groups), or
each $R^9$ is oxo, or $R^{10}$;
each $R^{10}$ is:
   —OH,
   halo,
   —CN,
   $C_{1-4}$ alkyl (which alkyl is optionally substituted with one or more independently selected OH, halo, or phenyl), C$_{1-4}$ alkoxy, C$_{3-7}$ cycloalkyl, phenyl,

—SO$_2$CH$_3$,

—C(=O)C$_{1-4}$ alkoxy,

—C(=O)C$_{1-4}$ alkyl, or

—NR$^g$C(=O)C$_{1-4}$ alkyl; and each R$^a$, R$^b$, R$^c$, R$^d$, R$^e$, R$^f$, R$^g$, R$^h$, R$^i$, and R$^j$ is independently selected from H, or C$_{1-4}$ alkyl; or a pharmaceutically acceptable salt, or a solvate, or a pharmaceutically acceptable salt of a solvate thereof; or a biologically active metabolite thereof 2) A compound or pharmaceutically acceptable salt thereof, according to clause 1, wherein R$^{1a}$ is F, Cl, —CH$_3$ or C$_2$H$_5$.

3) A compound or pharmaceutically acceptable salt thereof, according to clause 1, wherein R$^{1a}$ is H.

4) A compound or pharmaceutically acceptable salt thereof, according to any one of clauses 1-3, wherein R$^{1b}$ is F, Cl, —CH$_3$, —C$_2$H$_5$, —CF$_3$, —OCH$_3$, or —OCF$_3$.

5) A compound or pharmaceutically acceptable salt thereof, according to any one of clauses 1-3, wherein R$^{1b}$ is F.

6) A compound or pharmaceutically acceptable salt thereof, according to any one of clauses 1-5, wherein X is —S— or —O—.

7) A compound or pharmaceutically acceptable salt thereof, according to any one of clauses 1-5, wherein X is —S—.

8) A compound or pharmaceutically acceptable salt thereof, according to any one of clauses 1-5, wherein W is N.

9) A compound or pharmaceutically acceptable salt thereof, according to any one of clauses 1-5, wherein W is CR$^3$.

10) A compound or pharmaceutically acceptable salt thereof, according to clause 9, wherein R$^3$ is H, CN, F, or Cl.

11) A compound or pharmaceutically acceptable salt thereof, according to clause 1, wherein the compound is according to Formula II:

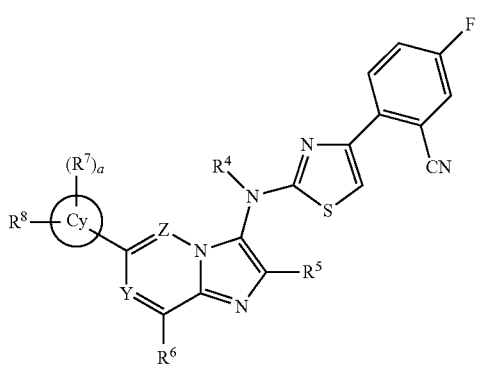

II wherein the subscript a, Y, Z, R$^4$, R$^5$, R$^6$, and R$^7$ are according to clause 1.

12) A compound or pharmaceutically acceptable salt thereof, according to clause 1, wherein the compound is according to Formula III:

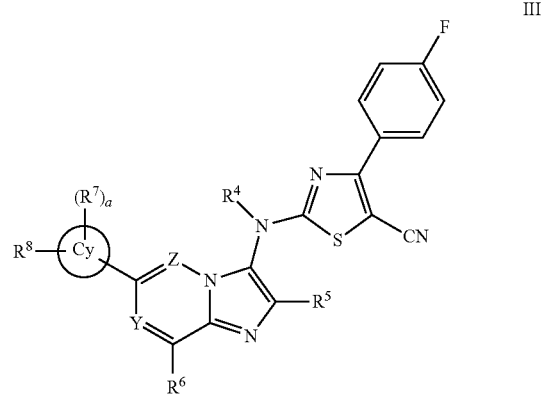

III wherein the subscript a, Y, Z, R$^4$, R$^5$, R$^6$, and R$^7$ are according to clause 1.

13) A compound or pharmaceutically acceptable salt thereof, according to any one of clauses 1-12, wherein R$^4$ is —CH$_3$, or C$_2$H$_5$.

14) A compound or pharmaceutically acceptable salt thereof, according to any one of clauses 1-12, wherein R$^4$ is —CH$_3$.

15) A compound or pharmaceutically acceptable salt thereof, according to any one of clauses 1-14, wherein R$^5$ is C$_{1-4}$ alkyl.

16) A compound or pharmaceutically acceptable salt thereof, according to any one of clauses 1-14, wherein R$^5$ is —CH$_3$, or C$_2$H$_5$.

17) A compound or pharmaceutically acceptable salt thereof, according to any one of clauses 1-14, wherein R$^5$ is C$_{1-4}$ alkyl substituted with one CN, OH, halo, or —C(=O)NH$_2$.

18) A compound or pharmaceutically acceptable salt thereof, according to clause 17, wherein R$^5$ is —CH$_3$, C$_2$H$_5$ or C$_3$H$_7$ substituted with one CN, OH, halo, or —C(=O)NH$_2$.

19) A compound or pharmaceutically acceptable salt thereof, according to clause 17, wherein R$^5$ is —CH$_2$—CH$_2$—CN, —CH$_2$—CH$_2$—OH, —CH$_2$—CF$_3$, or —CH$_2$—CH$_2$—C(=O)NH$_2$.

20) A compound or pharmaceutically acceptable salt thereof, according to any one of clauses 1-19, wherein Cy is C$_{3-10}$ cycloalkyl.

21) A compound or pharmaceutically acceptable salt thereof, according to clause 20, wherein Cy is cyclobutyl, cyclopentyl or cyclohexyl.

22) A compound or pharmaceutically acceptable salt thereof, according to any one of clauses 1-19, wherein Cy is 4-10 membered mono or bicyclic heterocycloalkyl containing one or more heteroatoms independently selected from O, N, and S.

23) A compound or pharmaceutically acceptable salt thereof, according to clause 22, wherein Cy is oxetanyl, azetidinyl, tetrahydropyranyl, pyrolidinyl, tetrahydropyranyl, piperidinyl, piperazinyl, morpholinyl, or thiomorpholinyl.

24) A compound or pharmaceutically acceptable salt thereof, according to any one of clauses 1-19, wherein Cy is 4-7 membered heterocycloalkenyl containing 1 double bond, containing one or more heteroatoms independently selected from O, N, and S.

25) A compound or pharmaceutically acceptable salt thereof, according to clause 24, wherein Cy is dihydrofuranyl, dihydrothiazolyl, dihydrooxazolyl, dihydropyranyl, or dihydrothiopyranyl.
26) A compound or pharmaceutically acceptable salt thereof, according to any one of clauses 1-25, wherein the subscript a is 1 or 2, and $R^7$ is OH, oxo, F, Cl, or $CH_3$.
27) A compound or pharmaceutically acceptable salt thereof, according to any one of clauses 1-25, wherein the subscript a is 0.
28) A compound or pharmaceutically acceptable salt thereof, according to any one of clauses 1-27, wherein $R^8$ is -$(L_1$-$W_1)_m$-$L_2$-$G_1$.
29) A compound according to Formula I, II, or III, wherein the compound is according to Formula IVa, IVb, IVc or IVd:

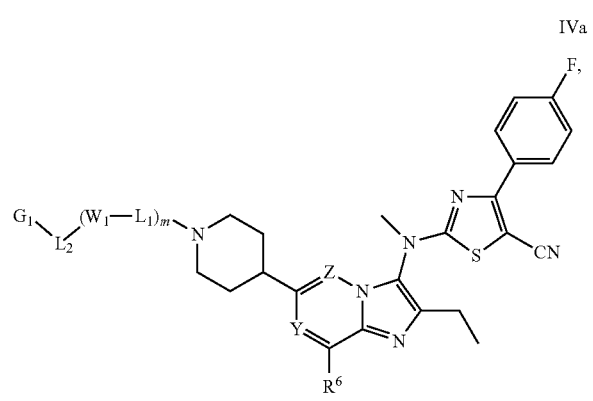

IVa

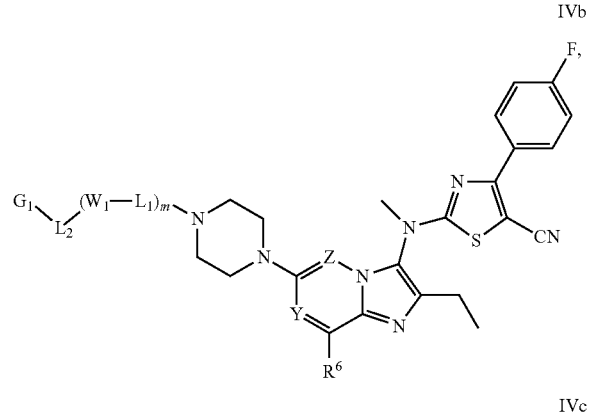

IVb

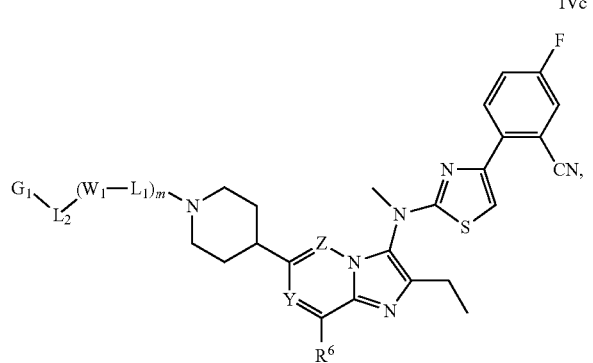

IVc or

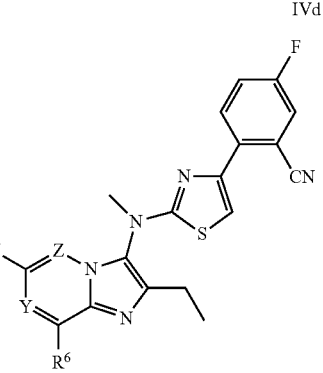

IVd wherein Y, Z, $R^6$, $L_1$, $W_1$, $L_2$, $G_1$ and the subscript m are according to clause 1.
30) A compound or pharmaceutically acceptable salt thereof, according to clause 28, or 29, wherein the subscript m is 1, $L_1$ is absent.
31) A compound or pharmaceutically acceptable salt thereof, according to clause 28, or 29, wherein the subscript m is 1, $L_1$ is —C(=O)—, or —$SO_2$—.
32) A compound or pharmaceutically acceptable salt thereof, according to any one of clauses 28-31, wherein the subscript m is 1, and $W_1$ is $C_{1-4}$ alkylene.
33) A compound or pharmaceutically acceptable salt thereof, according to clause 32, wherein the subscript m is 1, $L_1$ is as defined above and $W_1$ is —$CH_2$—, —$CH_2$—$CH_2$—, —$C(CH_3)H$—, —$CH_2$—$CH_2$—$CH_2$—, or —$CH_2$—$C(CH_3)H$—.
34) A compound or pharmaceutically acceptable salt thereof, according to clause 28, or 29, wherein the subscript m is 0.
35) A compound or pharmaceutically acceptable salt thereof, according to any one of clauses 28-34, wherein $L_2$ is absent.
36) A compound or pharmaceutically acceptable salt thereof, according to any one of clauses 28-34, wherein $L_2$ is —O—.
37) A compound or pharmaceutically acceptable salt thereof, according to any one of clauses 28-34, wherein $L_2$ is —C(=O)—.
38) A compound or pharmaceutically acceptable salt thereof, according to any one of clauses 28-34, wherein $L_2$ is —C(=O)O— or —OC(=O)—.
39) A compound or pharmaceutically acceptable salt thereof, according to any one of clauses 28-34, wherein $L_2$ is —C(=O)—C(=O)$NR^a$—.
40) A compound or pharmaceutically acceptable salt thereof, according to clause 39, wherein W is H.
41) A compound or pharmaceutically acceptable salt thereof, according to any one of clauses 28-34, wherein $L_2$ is —$NR^b$—.
42) A compound or pharmaceutically acceptable salt thereof, according to clause 41, wherein $R^b$ is H.
43) A compound or pharmaceutically acceptable salt thereof, according to any one of clauses 28-34, wherein $L_2$ is —C(=O)$NR^c$—.
44) A compound or pharmaceutically acceptable salt thereof, according to clause 41, wherein W is H, —$CH_3$, or $CH_2$—$CH_3$.
45) A compound or pharmaceutically acceptable salt thereof, according to any one of clauses 28-34, wherein $L_2$ is —$NR^d$C(=O)—.

46) A compound or pharmaceutically acceptable salt thereof, according to clause 45, wherein $R^d$ is H, —$CH_3$, or $CH_2$—$CH_3$.
47) A compound or pharmaceutically acceptable salt thereof, according to any one of clauses 28-34, wherein $L_2$ is —$SO_2$—.
48) A compound or pharmaceutically acceptable salt thereof, according to any one of clauses 28-34, wherein $L_2$ is —$SO_2NR^e$—.
49) A compound or pharmaceutically acceptable salt thereof, according to clause 48, wherein W is H, —$CH_3$, or $CH_2$—$CH_3$.
50) A compound or pharmaceutically acceptable salt thereof, according to any one of clauses 28-34, wherein $L_2$ is $NR^fSO_2$—.
51) A compound or pharmaceutically acceptable salt thereof, according to clause 50, wherein $R^f$ is H, —$CH_3$, or $CH_2$—$CH_3$.
52) A compound or pharmaceutically acceptable salt thereof, according to any one of clauses 28-51, wherein $G_1$ is H, or CN.
53) A compound or pharmaceutically acceptable salt thereof, according to any one of clauses 28-51, wherein $G_1$ is $C_{1-4}$ alkyl.
54) A compound or pharmaceutically acceptable salt thereof, according to clause 53, wherein $G_1$ is —$CH_3$, or $CH_2$—$CH_3$.
55) A compound or pharmaceutically acceptable salt thereof, according to any one of clauses 28-51, wherein $G_1$ is $C_{1-4}$ alkyl substituted with CN, OH, halo or phenyl.
56) A compound or pharmaceutically acceptable salt thereof, according to clause 55, wherein $G_1$ is —$CF_3$, —$CH_2$—Cl, —$CH_2$—CN, —$CH_2$—OH or $CH_2$-Ph.
57) A compound or pharmaceutically acceptable salt thereof, according to any one of clauses 28-51, wherein $G_1$ is $C_{3-7}$ cycloalkyl.
58) A compound or pharmaceutically acceptable salt thereof, according to clause 57, wherein $G_1$ is cyclopropyl, cyclobutyl, cyclopropyl, or cyclohexyl.
59) A compound or pharmaceutically acceptable salt thereof, according to any one of clauses 28-51, wherein $G_1$ is $C_{3-7}$ cycloalkyl substituted with $NH_2$.
60) A compound or pharmaceutically acceptable salt thereof, according to clause 59, wherein $G_1$ is cyclopropyl, cyclobutyl, cyclopropyl, or cyclohexyl, each of which is substituted with $NH_2$.
61) A compound or pharmaceutically acceptable salt thereof, according to any one of clauses 28-51, wherein $G_1$ is 5-6 membered heterocycloalkenyl containing 1 double bond containing one to three heteroatoms independently selected from O, N, and S.
62) A compound or pharmaceutically acceptable salt thereof, according to clause 61, wherein $G_1$ is dihydrofuranyl, dihydrothiazolyl, dihydrooxazolyl, dihydropyranyl, or dihydrothiopyranyl.
63) A compound or pharmaceutically acceptable salt thereof, according to any one of clauses 28-51, wherein $G_1$ is 4-10 membered mono, bi or spirocyclic heterocycloalkyl containing one to three heteroatoms independently selected from O, N, and S.
64) A compound or pharmaceutically acceptable salt thereof, according to clause 63, wherein $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane.
65) A compound or pharmaceutically acceptable salt thereof, according to any one of clauses 28-51, wherein $G_1$ is 4-10 membered mono, bi or spirocyclic heterocycloalkyl containing one to three heteroatoms independently selected from O, N, and S, substituted with one or two independently selected $R^9$.
66) A compound or pharmaceutically acceptable salt thereof, according to clause 65, wherein $G_1$ is oxetanyl, azetidinyl, tetrahydrofuranyl, pyrolidinyl, tetrahydropyranyl, piperidinyl, piperazinyl, morpholinyl, thiomorpholinyl, or 2,6-diaza-spiro[3.3]heptane, each of which is substituted with one or two independently selected $R^9$.
67) A compound or pharmaceutically acceptable salt thereof, according to clause 65 or 66, wherein $R^9$ is oxo.
68) A compound or pharmaceutically acceptable salt thereof, according to clause 65 or 66, wherein $R^9$ is $R^{10}$ and $R^{10}$ is selected from OH, F, Cl, and —CN.
69) A compound or pharmaceutically acceptable salt thereof, according to clause 65 or 66, wherein $R^9$ is $R^{10}$ and $R^{10}$ is selected from —$CH_3$, —$CH_2$—$CH_3$, —$CF_3$, —$CH_2$—$CH_2$—OH, and —$CH_2$-phenyl,
70) A compound or pharmaceutically acceptable salt thereof, according to clause 65 or 66, wherein $R^9$ is $R^{10}$ and $R^{10}$ is selected from —$OCH_3$, —$OCH_2$—$CH_3$, and —$OC(CH_3)_3$.
71) A compound or pharmaceutically acceptable salt thereof, according to clause 65 or 66, wherein $R^9$ is $R^{10}$ and $R^{10}$ is selected from —$SO_2CH_3$, —C(=O)$OCH_3$, and —C(=O)$CH_3$.
72) A compound or pharmaceutically acceptable salt thereof, according to clause 65 or 66, wherein each $R^9$ is $R^{10}$ and $R^{10}$ is —$NR^gC$(=O)$CH_3$, or —$NR^gC$(=O)$CH_2CH_3$.
73) A compound or pharmaceutically acceptable salt thereof, according to clause 72, wherein each W is H, —$CH_3$, or —$CH_2CH_3$.
74) A compound or pharmaceutically acceptable salt thereof, according to any one of clauses 28-51, wherein $G_1$ is 5-6 membered heteroaryl containing one to three heteroatoms independently selected from O, N, and S.
75) A compound or pharmaceutically acceptable salt thereof, according to clause 74, wherein $G_1$ is furanyl, thienyl, pyrolyl, pyrazolyl, imidazolyl, triazolyl, oxazolyl, oxadiazolyl, thiazolyl, thiadiazolyl, pyridyl, pyrazinyl, or pyrimidyl.
76) A compound or pharmaceutically acceptable salt thereof, according to any one of clauses 28-51, wherein $G_1$ is 5-6 membered heteroaryl containing one to three heteroatoms independently selected from O, N, and S, substituted with one or two independently selected $R^{10}$.
77) A compound or pharmaceutically acceptable salt thereof, according to clause 76, wherein $G_1$ is furanyl, thienyl, pyrolyl, pyrazolyl, imidazolyl, triazolyl, oxazolyl, oxadiazolyl, thiazolyl, thiadiazolyl, pyridyl, pyrazinyl, or pyrimidyl, each of which is substituted with one or two independently selected $R^{10}$.
78) A compound or pharmaceutically acceptable salt thereof, according to clause 77, wherein $R^{10}$ is selected from OH, F, Cl, and —CN.
79) A compound or pharmaceutically acceptable salt thereof, according to clause 77, wherein $R^{10}$ is selected from —$CH_3$, —$CH_2$—$CH_3$, —$CF_3$, —$CH_2$—$CH_2$—OH, and —$CH_2$-phenyl.
80) A compound or pharmaceutically acceptable salt thereof, according to clause 77, wherein $R^{10}$ is selected from —$OCH_3$, —$OCH_2$—$CH_3$, and —$OC(CH_3)_3$.
81) A compound or pharmaceutically acceptable salt thereof, according to clause 77, wherein $R^{10}$ is selected from —$SO_2CH_3$, —C(=O)$OCH_3$, and —C(=O)$CH_3$.

82) A compound or pharmaceutically acceptable salt thereof, according to clause 77, wherein each $R^{10}$ is —$NR^gC(=O)CH_3$, or —$NR^gC(=O)CH_2CH_3$.

83) A compound or pharmaceutically acceptable salt thereof, according to clause 82, wherein each $R^g$ is H, —$CH_3$, or —$CH_2CH_3$.

84) A compound according to clause 1, wherein the compound is according to Formula Va, Vb, Vc, or Vd:

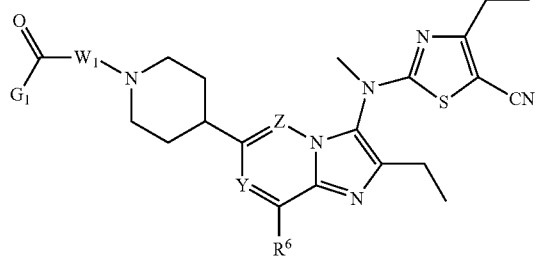

Va

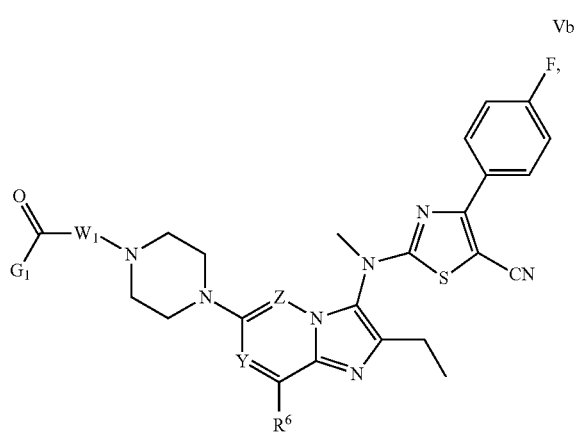

Vb

Vc

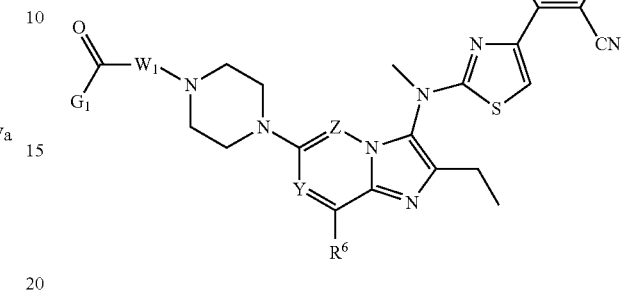

Vd wherein Y, Z, $R^6$, $W_1$, and $G_1$ are according to clause 1.

85) A compound or pharmaceutically acceptable salt thereof, according to clause 84, wherein $W_1$ is $C_{1-4}$ alkylene.

86) A compound or pharmaceutically acceptable salt thereof, according to clause 85, wherein the subscript m is 1, $L_1$ is as defined above and $W_1$ is —$CH_2$—, —$CH_2$—$CH_2$—, —$C(CH_3)H$—, —$CH_2$—$CH_2$—$CH_2$—, or —$CH_2$—$C(CH_3)H$—.

87) A compound according to clause 1, wherein the compound is according to Formula VIa, VIb, VIc, or VId:

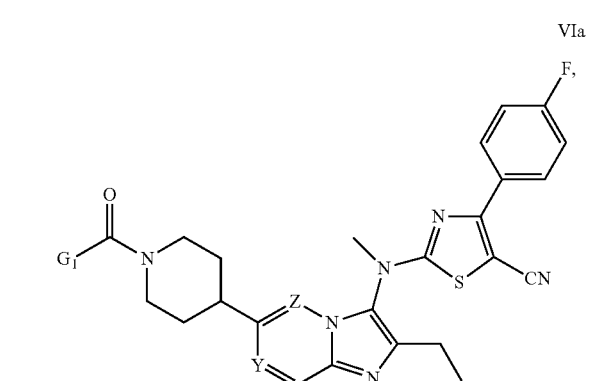

VIa

VIb

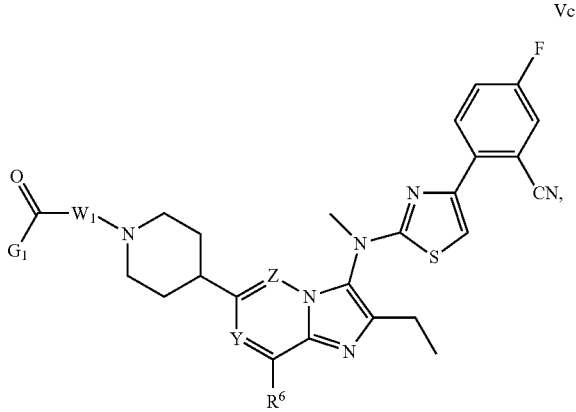

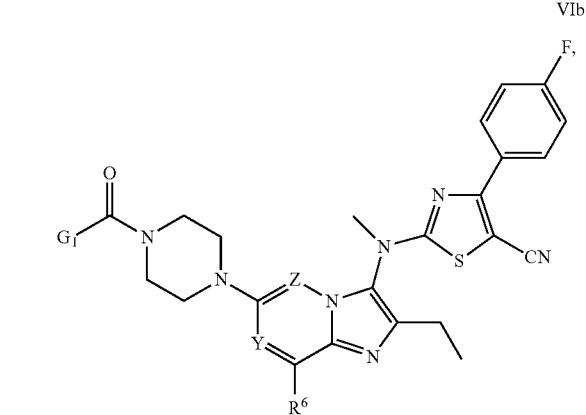

-continued

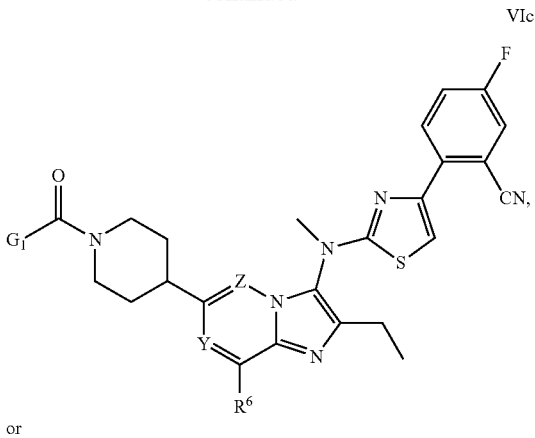

VIc or

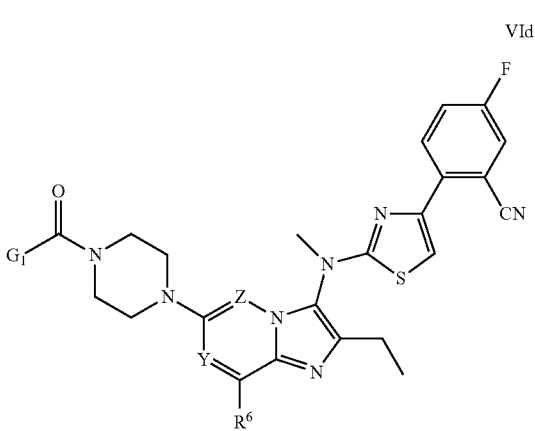

VId wherein Y, Z, R⁶, and G₁ are according to clause 1.

88) A compound or pharmaceutically acceptable salt thereof, according to any one of clauses 84-87, wherein G₁ is 4-7 membered heterocycloalkyl containing one or more heteroatoms independently selected from O, N, and S.

89) A compound or pharmaceutically acceptable salt thereof, according to clause 88, wherein G₁ is oxetanyl, azetidinyl, tetrahydrofuranyl, pyrolidinyl, tetrahydropyranyl, piperidinyl, piperazinyl, morpholinyl, or thiomorpholinyl.

90) A compound or pharmaceutically acceptable salt thereof, according to any one of clauses 84-87, wherein G₁ is 4-7 membered heterocycloalkyl containing one or more heteroatoms independently selected from O, N, and S, which heterocycloalkyl is substituted with one or two independently selected R⁹ groups.

91) A compound or pharmaceutically acceptable salt thereof, according to clause 90, wherein G₁ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected R⁹ groups.

92) A compound or pharmaceutically acceptable salt thereof, according to clause 90 or 91, wherein R⁹ is oxo.

93) A compound or pharmaceutically acceptable salt thereof, according to clause 90 or 91, wherein R⁹ is R¹⁰ and R¹⁰ is selected from OH, F, Cl, and —CN.

94) A compound or pharmaceutically acceptable salt thereof, according to clause 90 or 91, wherein R⁹ is R¹⁰ and R¹⁰ is selected from —CH₃, —CH₂—CH₃, —CF₃, —CH₂—CH₂—OH, and —CH₂-phenyl, 95) A compound or pharmaceutically acceptable salt thereof, according to clause 90 or 91, wherein R⁹ is R¹⁰ and R¹⁰ is selected from —OCH₃, —OCH₂—CH₃, and —OC(CH₃)₃.

96) A compound or pharmaceutically acceptable salt thereof, according to clause 90 or 91, wherein R⁹ is R¹⁰ and R¹⁰ is selected from —SO₂CH₃, —C(=O)OCH₃, and —C(=O)CH₃.

97) A compound or pharmaceutically acceptable salt thereof, according to clause 90 or 91, wherein R⁹ is R¹⁰ and R¹⁰ is NR^gC(=O)CH₃, or NR^gC(=O)CH₂CH₃.

98) A compound or pharmaceutically acceptable salt thereof, according to clause 90 or 91, wherein each W is H, —CH₃, or —CH₂CH₃.

99) A compound or pharmaceutically acceptable salt thereof, according to anyone of clauses 1-98, wherein R⁶ is H, —CH₃ or F.

100) A compound or pharmaceutically acceptable salt thereof, according to anyone of clauses 1-98, wherein R⁶ is —CH₃.

101) A compound or pharmaceutically acceptable salt thereof, according to anyone of clauses 1-100, wherein Y is N and Z is CH.

102) A compound or pharmaceutically acceptable salt thereof, according to anyone of clauses 1-100, wherein Y is CH and Z is N.

103) A compound or pharmaceutically acceptable salt thereof, according to anyone of clauses 1-102, wherein the compound is selected from the compounds of Table II.

104) A pharmaceutical composition comprising a pharmaceutically acceptable carrier and a pharmaceutically effective amount of a compound according to any one of clauses 1-103.

105) A pharmaceutical composition according to clause 104, comprising a further therapeutic agent.

106) A compound or pharmaceutically acceptable salt thereof, according to any one of clauses 1-103, or a pharmaceutical composition according to clause 104 or 105, for use in medicine.

107) A compound or pharmaceutically acceptable salt thereof, according to any one of clauses 1-103, or a pharmaceutical composition according to clause 104 or 105, for use in the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

108) A compound or pharmaceutically acceptable salt thereof, according to any one of clauses 1-103, or a pharmaceutical composition according to clause 104 or 105, for use in the treatment of inflammatory pulmonary fibrosis.

109) The use of a compound or pharmaceutically acceptable salt thereof or the pharmaceutical composition according to clause 107 or 108, wherein said compound or pharmaceutical composition is administered in combination with a further therapeutic agent.

110) A method for the treatment, or prevention of diseases or conditions selected from fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases, comprising administering an amount of compound according to any one of clauses 1 to 103, or the pharmaceutical composition according any one of clauses 104 or 105, sufficient to effect said treatment, or prevention.

111) A method for the treatment, or prevention of inflammatory pulmonary fibrosis, comprising administering an amount of compound according to any one of clauses 1 to 103, or the pharmaceutical composition according any one of clauses 104 or 105, sufficient to effect said treatment, or prevention.
112) The method according to clause 110 or 111, wherein the compound, or the pharmaceutical composition, is administered in combination with a further therapeutic agent.
113) The pharmaceutical composition according to clause 105, or the use according to clause 109, or the method according to clause 112, wherein the further therapeutic agent is for the treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.
114) The pharmaceutical composition according to clause 105, or the use according to clause 109, or the method according to clause 112, wherein the further therapeutic agent is for the treatment of inflammatory pulmonary fibrosis.

Pharmaceutical Compositions

When employed as a pharmaceutical, a compound of the invention is typically administered in the form of a pharmaceutical composition. Such compositions can be prepared in a manner well known in the pharmaceutical art and comprise at least one active compound of the invention according to Formula I. Generally, a compound of the invention is administered in a pharmaceutically effective amount. The amount of compound of the invention actually administered will typically be determined by a physician, in the light of the relevant circumstances, including the condition to be treated, the chosen route of administration, the actual compound of the invention administered, the age, weight, and response of the individual patient, the severity of the patient's symptoms, and the like.

The pharmaceutical compositions of this invention can be administered by a variety of routes including oral, rectal, transdermal, subcutaneous, intra-articular, intravenous, intramuscular, and intranasal. Depending on the intended route of delivery, a compound of the invention is preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term 'unit dosage forms' refers to physically discrete units suitable as unitary dosages for human subjects and other mammals, each unit containing a predetermined quantity of active material calculated to produce the desired therapeutic effect, in association with a suitable pharmaceutical excipient, vehicle or carrier. Typical unit dosage forms include prefilled, premeasured ampules or syringes of the liquid compositions or pills, tablets, capsules or the like in the case of solid compositions. In such compositions, the compound of the invention according to Formula I is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or non-aqueous vehicle with buffers, suspending and dispensing agents, colorants, flavors and the like. Solid forms may include, for example, any of the following ingredients, or compound of the inventions of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint or orange flavoring.

Injectable compositions are typically based upon injectable sterile saline or phosphate-buffered saline or other injectable carriers known in the art. As before, the active compound of the invention according to Formula I in such compositions is typically a minor component, often being from about 0.05 to 10% by weight with the remainder being the injectable carrier and the like.

Transdermal compositions are typically formulated as a topical ointment or cream containing the active ingredient (s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

A compound of the invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

A compound of the invention can also be administered in sustained release forms or from sustained release drug delivery systems. A description of representative sustained release materials can be found in Remington's Pharmaceutical Sciences.

The following formulation examples illustrate representative pharmaceutical compositions that may be prepared in accordance with this invention. The present invention, however, is not limited to the following pharmaceutical compositions.

Formulation 1—Tablets

A compound of the invention according to Formula I may be admixed as a dry powder with a dry gelatin binder in an approximate 1:2 weight ratio. A minor amount of magnesium stearate may be added as a lubricant. The mixture may be formed into 240-270 mg tablets (80-90 mg of active compound of the invention according to Formula I per tablet) in a tablet press.

Formulation 2—Capsules

A compound of the invention according to Formula I may be admixed as a dry powder with a starch diluent in an approximate 1:1 weight ratio. The mixture may be filled into 250 mg capsules (125 mg of active compound of the invention according to Formula I per capsule).

Formulation 3—Liquid

A compound of the invention according to Formula I (125 mg), may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color may be diluted with water and added with stirring. Sufficient water may then be added with stirring. Further sufficient water may be then added to produce a total volume of 5 mL.

Formulation 4—Tablets

A compound of the invention according to Formula I may be admixed as a dry powder with a dry gelatin binder in an approximate 1:2 weight ratio. A minor amount of magnesium stearate may be added as a lubricant. The mixture may be formed into 450-900 mg tablets (150-300 mg of active compound of the invention according to Formula I) in a tablet press.

Formulation 5—Injection

A compound of the invention according to Formula I may be dissolved or suspended in a buffered sterile saline injectable aqueous medium to a concentration of approximately 5 mg/mL.

Formulation 6—Topical

Stearyl alcohol (250 g) and a white petrolatum (250 g) may be melted at about 75° C. and then a mixture of A compound of the invention according to Formula I (50 g) methylparaben (0.25 g), propylparaben (0.15 g), sodium lauryl sulfate (10 g), and propylene glycol (120 g) dissolved in water (about 370 g) may be added and the resulting mixture may be stirred until it congeals.

Methods of Treatment

In one embodiment, the present invention provides compounds of the invention, or pharmaceutical compositions comprising a compound of the invention, for use in medicine. In a particular embodiment, the present invention provides compounds of the invention or pharmaceutical compositions comprising a compound of the invention, for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In another embodiment, the present invention provides compounds of the invention, or pharmaceutical compositions comprising a compound of the invention for use in the manufacture of a medicament for use in the prophylaxis and/or treatment of fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases.

In one embodiment, the present invention provides pharmaceutical compositions comprising a compound of the invention, and another therapeutic agent. In a particular embodiment, the other therapeutic agent is a fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases treatment agent.

In additional method of treatment aspects, this invention provides methods of prophylaxis and/or treatment of a mammal afflicted with fibrotic diseases, proliferative diseases, inflammatory diseases, autoimmune diseases, respiratory diseases, cardiovascular diseases, neurodegenerative diseases, dermatological disorders, and/or abnormal angiogenesis associated diseases, which methods comprise the administration of an effective amount of a compound of the invention or one or more of the pharmaceutical compositions herein described for the treatment or prophylaxis of said condition.

In one embodiment, the present invention provides compounds of the invention or pharmaceutical compositions comprising a compound of the invention, for use in the prophylaxis and/or treatment of fibrotic diseases. In a particular embodiment, the fibrotic disease is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, and autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, or chronic lymphocytic. More particularly, the fibrotic diseases is idiopathic pulmonary fibrosis (IPF).

In another embodiment, the present invention provides compounds of the invention, or pharmaceutical compositions comprising a compound of the invention for use in the manufacture of a medicament for use in the prophylaxis and/or treatment of fibrotic diseases. In a particular embodiment, the fibrotic disease is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, and autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, or chronic lymphocytic. More particularly, the fibrotic disease is idiopathic pulmonary fibrosis (IPF).

In additional method of treatment aspects, this invention provides methods of prophylaxis and/or treatment of a mammal afflicted with fibrotic diseases, which methods comprise the administration of an effective amount of a compound of the invention or one or more of the pharmaceutical compositions herein described for the treatment or prophylaxis of said condition. In a particular embodiment, the fibrotic disease is selected from idiopathic pulmonary fibrosis (IPF), cystic fibrosis, other diffuse parenchymal lung diseases of different etiologies including iatrogenic drug-induced fibrosis, occupational and/or environmental induced fibrosis, granulomatous diseases (sarcoidosis, hypersensitivity pneumonia), collagen vascular disease, alveolar proteinosis, langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, chronic obstructive pulmonary disease (COPD), scleroderma, bleomycin induced pulmonary fibrosis, chronic asthma, silicosis, asbestos induced pulmonary fibrosis, acute respiratory distress syndrome (ARDS), kidney fibrosis, tubulointerstitium fibrosis, glomerular nephritis, focal segmental glomerular sclerosis, IgA nephropathy, hypertension, Alport, gut fibrosis, liver fibrosis, cirrhosis, alcohol induced liver fibrosis, toxic/drug induced liver fibrosis, hemochromatosis, nonalcoholic steatohepatitis (NASH), biliary duct injury, primary biliary cirrhosis, infection induced liver fibrosis, viral induced liver fibrosis, and autoimmune hepatitis, corneal scarring, hypertrophic scarring, Dupuytren disease, keloids, cutaneous fibrosis, cutaneous scleroderma, systemic sclerosis, spinal cord injury/fibrosis, myelofibrosis, vascular restenosis, atherosclerosis, arteriosclerosis, Wegener's granulomatosis, Peyronie's disease, or chronic lymphocytic. More particularly, the fibrotic disease is idiopathic pulmonary fibrosis (IPF).

A particular regimen of the present method comprises the administration to a subject suffering from a fibrotic disease of an effective amount of a compound of the invention according to Formula I for a period of time sufficient to reduce the level of fibrosis in the subject, and preferably terminate the processes responsible for said fibrosis. A special embodiment of the method comprises administering of an effective amount of a compound of the invention according to Formula I to a subject patient suffering from to the development of idiopathic pulmonary fibrosis, for a period of time sufficient to reduce or prevent idiopathic pulmonary fibrosis of said patient, and preferably terminate, the processes responsible for said idiopathic pulmonary fibrosis.

In one embodiment, the present invention provides compounds of the invention or pharmaceutical compositions comprising a compound of the invention, for use in the prophylaxis and/or treatment of proliferative diseases. In a particular embodiment, the proliferative disease is selected from cancer, leukemia, multiple myeloma and psoriasis.

In another embodiment, the present invention provides compounds of the invention, or pharmaceutical compositions comprising a compound of the invention for use in the manufacture of a medicament for use in the prophylaxis and/or treatment of proliferative diseases. In a particular embodiment, the proliferative disease is selected from cancer, leukemia, multiple myeloma and psoriasis.

In additional method of treatment aspects, this invention provides methods of prophylaxis and/or treatment of a mammal afflicted with proliferative diseases, which methods comprise the administration of an effective amount of a compound of the invention or one or more of the pharmaceutical compositions herein described for the treatment or prophylaxis of said condition. In a particular embodiment, the proliferative disease is selected from cancer, leukemia, multiple myeloma and psoriasis.

In one embodiment, the present invention provides compounds of the invention or pharmaceutical compositions comprising a compound of the invention, for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In another embodiment, the present invention provides compounds of the invention, or pharmaceutical compositions comprising a compound of the invention for use in the manufacture of a medicament for use in the prophylaxis and/or treatment of inflammatory diseases. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly, the inflammatory disease is selected from rheumatoid arthritis, and chronic obstructive pulmonary disease (COPD).

In additional method of treatment aspects, this invention provides methods of prophylaxis and/or treatment of a mammal afflicted with inflammatory diseases, which methods comprise the administration of an effective amount of a compound of the invention or one or more of the pharmaceutical compositions herein described for the treatment or prophylaxis of said condition. In a particular embodiment, the inflammatory disease is selected from rheumatoid arthritis, osteoarthritis, allergic airway disease (e.g. asthma), chronic obstructive pulmonary disease (COPD) and inflammatory bowel diseases (e.g. Crohn's disease and ulcerative colitis). More particularly the inflammatory disease is selected from rheumatoid arthritis, and chronic obstructive pulmonary disease (COPD).

In one embodiment, the present invention provides compounds of the invention or pharmaceutical compositions comprising a compound of the invention, for use in the prophylaxis and/or treatment of autoimmune diseases. In a particular embodiment, the autoimmune disease is selected from COPD, asthma (e.g. intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly, the autoimmune disease is selected from COPD, asthma, systemic lupus erythematosis, type I diabetes mellitus and inflammatory bowel disease.

In another embodiment, the present invention provides compounds of the invention, or pharmaceutical compositions comprising a compound of the invention for use in the manufacture of a medicament for use in the prophylaxis and/or treatment of autoimmune diseases. In a particular embodiment, the autoimmune disease is selected from COPD, asthma (e.g. intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly, the autoimmune disease is selected from COPD, asthma, systemic lupus erythematosis, type I diabetes mellitus and inflammatory bowel disease.

In additional method of treatment aspects, this invention provides methods of prophylaxis and/or treatment of a mammal afflicted with autoimmune diseases, which methods comprise the administration of an effective amount of a compound of the invention or one or more of the pharmaceutical compositions herein described for the treatment or prophylaxis of said condition. In a particular embodiment, the autoimmune disease is selected from COPD, asthma (e.g. intrinsic asthma, extrinsic asthma, dust asthma, infantily asthma) particularly chronic or inveterate asthma (for example late asthma and airway hyperreponsiveness), bronchitis, including bronchial asthma, systemic lupus erythematosus (SLE), cutaneous lupus erythrematosis, lupus nephritis, dermatomyositis, Sjogren's syndrome, multiple sclerosis, psoriasis, dry eye disease, type I diabetes mellitus and complications associated therewith, atopic eczema (atopic dermatitis), thyroiditis (Hashimoto's and autoimmune thyroiditis), contact dermatitis and further eczematous dermatitis, inflammatory bowel disease (e.g. Crohn's disease and ulcerative colitis), atherosclerosis and amyotrophic lateral sclerosis. Particularly, the autoimmune disease is selected from COPD, asthma, systemic lupus erythematosis, type I diabetes mellitus and inflammatory bowel disease.

In one embodiment, the present invention provides compounds of the invention or pharmaceutical compositions comprising a compound of the invention, for use in the prophylaxis and/or treatment of respiratory diseases. In a particular embodiment, the respiratory disease is selected from asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In another embodiment, the present invention provides compounds of the invention, or pharmaceutical compositions comprising a compound of the invention for use in the manufacture of a medicament for use in the prophylaxis and/or treatment of respiratory diseases. In a particular embodiment, the respiratory disease is selected from asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In additional method of treatment aspects, this invention provides methods of prophylaxis and/or treatment of a mammal afflicted with respiratory diseases, which methods comprise the administration of an effective amount of a compound of the invention or one or more of the pharmaceutical compositions herein described for the treatment or prophylaxis of said condition. In a particular embodiment, the respiratory disease is selected from asthma, adult respiratory distress syndrome and allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, isocapnic hyperventilation, child onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In one embodiment, the present invention provides compounds of the invention or pharmaceutical compositions comprising a compound of the invention, for use in the prophylaxis and/or treatment of cardiovascular diseases. In a particular embodiment, the cardiovascular disease is selected from arrhythmia (atrial or ventricular or both), atherosclerosis and its sequelae, angina, cardiac rhythm disturbances, myocardial ischemia, myocardial infarction, cardiac or vascular aneurysm, vasculitis, stroke, peripheral obstructive arteriopathy of a limb, an organ, or a tissue, reperfusion injury following ischemia of the brain, heart, kidney or other organ or tissue, endotoxic, surgical, or traumatic shock, hypertension, valvular heart disease, heart failure, abnormal blood pressure, shock, vasoconstriction (including that associated with migraines), vascular abnormality, inflammation, insufficiency limited to a single organ or tissue.

In another embodiment, the present invention provides compounds of the invention, or pharmaceutical compositions comprising a compound of the invention for use in the manufacture of a medicament for use in the prophylaxis and/or treatment of cardiovascular diseases. In a particular embodiment, the cardiovascular disease is selected from arrhythmia (atrial or ventricular or both), atherosclerosis and its sequelae, angina, cardiac rhythm disturbances, myocardial ischemia, myocardial infarction, cardiac or vascular aneurysm, vasculitis, stroke, peripheral obstructive arteriopathy of a limb, an organ, or a tissue, reperfusion injury following ischemia of the brain, heart, kidney or other organ or tissue, endotoxic, surgical, or traumatic shock, hypertension, valvular heart disease, heart failure, abnormal blood pressure, shock, vasoconstriction (including that associated with migraines), vascular abnormality, inflammation, insufficiency limited to a single organ or tissue.

In additional method of treatment aspects, this invention provides methods of prophylaxis and/or treatment of a mammal afflicted with cardiovascular diseases, which methods comprise the administration of an effective amount of a compound of the invention or one or more of the pharmaceutical compositions herein described for the treatment or prophylaxis of said condition. In a particular embodiment, the cardiovascular disease is selected from arrhythmia (atrial or ventricular or both), atherosclerosis and its sequelae, angina, cardiac rhythm disturbances, myocardial ischemia, myocardial infarction, cardiac or vascular aneurysm, vasculitis, stroke, peripheral obstructive arteriopathy of a limb, an organ, or a tissue, reperfusion injury following ischemia of the brain, heart, kidney or other organ or tissue, endotoxic, surgical, or traumatic shock, hypertension, valvular heart disease, heart failure, abnormal blood pressure, shock, vasoconstriction (including that associated with migraines), vascular abnormality, inflammation, insufficiency limited to a single organ or tissue.

In one embodiment, the present invention provides compounds of the invention or pharmaceutical compositions comprising a compound of the invention, for use in the prophylaxis and/or treatment of neurodegenerative diseases. In a particular embodiment, the neurodegenerative disease is selected from Alzheimer's disease and other dementias, brain cancer, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

In another embodiment, the present invention provides compounds of the invention, or pharmaceutical compositions comprising a compound of the invention for use in the manufacture of a medicament for use in the prophylaxis and/or treatment of neurodegenerative diseases. In a particular embodiment, the neurodegenerative disease is selected from Alzheimer's disease and other dementias, brain cancer, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

In additional method of treatment aspects, this invention provides methods of prophylaxis and/or treatment of a mammal afflicted with neurodegenerative diseases, which methods comprise the administration of an effective amount of a compound of the invention or one or more of the pharmaceutical compositions herein described for the treatment or prophylaxis of said condition. In a particular embodiment, the neurodegenerative disease is selected from Alzheimer's disease and other dementias, brain cancer, degenerative nerve diseases, encephalitis, epilepsy, genetic brain disorders, head and brain malformations, hydrocephalus, stroke, Parkinson's disease, multiple sclerosis, amyotrophic lateral sclerosis (ALS or Lou Gehrig's Disease), Huntington's disease, and prion diseases.

In one embodiment, the present invention provides compounds of the invention or pharmaceutical compositions comprising a compound of the invention, for use in the prophylaxis and/or treatment of dermatological disorders. In a particular embodiment, the dermatological disease is selected from atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, or Sjogren-Larsso Syndrome.

In another embodiment, the present invention provides compounds of the invention, or pharmaceutical compositions comprising a compound of the invention for use in the manufacture of a medicament for use in the prophylaxis and/or treatment of dermatological disorders. In a particular embodiment, the dermatological disease is selected from atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, or Sjogren-Larsso Syndrome.

In additional method of treatment aspects, this invention provides methods of prophylaxis and/or treatment of a mammal afflicted with dermatological disorders, which methods comprise the administration of an effective amount of a compound of the invention or one or more of the pharmaceutical compositions herein described for the treatment or prophylaxis of said condition. In a particular embodiment, the dermatological disease is selected from atopic dermatitis, bullous disorders, collagenoses, psoriasis, psoriatic lesions, dermatitis, contact dermatitis, eczema, pruritus, urticaria, rosacea, scleroderma, wound healing, scarring, hypertrophic scarring, keloids, Kawasaki Disease, rosacea, or Sjogren-Larsso Syndrome.

In one embodiment, the present invention provides compounds of the invention or pharmaceutical compositions comprising a compound of the invention, for use in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma.

In another embodiment, the present invention provides compounds of the invention, or pharmaceutical compositions comprising a compound of the invention for use in the manufacture of a medicament for use in the prophylaxis and/or treatment of abnormal angiogenesis associated diseases. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma.

In additional method of treatment aspects, this invention provides methods of prophylaxis and/or treatment of a mammal afflicted with abnormal angiogenesis associated diseases, which methods comprise the administration of an effective amount of a compound of the invention or one or more of the pharmaceutical compositions herein described for the treatment or prophylaxis of said condition. In a particular embodiment, the abnormal angiogenesis associated disease is selected from atherosclerosis, hypertension, tumor growth, inflammation, rheumatoid arthritis, wet-form macular degeneration, choroidal neovascularization, retinal neovascularization, diabetic retinopathy, and glioblastoma multiforma.

Injection dose levels range from about 0.1 mg/kg/h to at least 10 mg/kg/h, all for from about 1 to about 120 h and especially 24 to 96 h. A preloading bolus of from about 0.1 mg/kg to about 10 mg/kg or more may also be administered to achieve adequate steady state levels. The maximum total dose is not expected to exceed about 1 g/day for a 40 to 80 kg human patient.

For the prophylaxis and/or treatment of long-term conditions, such as degenerative conditions, the regimen for treatment usually stretches over many months or years so oral dosing is preferred for patient convenience and tolerance. With oral dosing, one to four (1-4) regular doses daily, especially one to three (1-3) regular doses daily, typically one to two (1-2) regular doses daily, and most typically one (1) regular dose daily are representative regimens. Alternatively for long lasting effect drugs, with oral dosing, once every other week, once weekly, and once a day are representative regimens. In particular, dosage regimen can be every 1-14 days, more particularly 1-10 days, even more particularly 1-7 days, and most particularly 1-3 days.

Using these dosing patterns, each dose provides from about 1 to about 1000 mg of a compound of the invention, with particular doses each providing from about 10 to about 500 mg and especially about 30 to about 250 mg.

Transdermal doses are generally selected to provide similar or lower blood levels than are achieved using injection doses.

When used to prevent the onset of a condition, a compound of the invention will be administered to a patient at risk for developing the condition, typically on the advice and under the supervision of a physician, at the dosage levels described above. Patients at risk for developing a particular condition generally include those that have a family history of the condition, or those who have been identified by genetic testing or screening to be particularly susceptible to developing the condition.

A compound of the invention can be administered as the sole active agent or it can be administered in combination with other therapeutic agents, including other compound of the inventions that demonstrate the same or a similar therapeutic activity and that are determined to be safe and efficacious for such combined administration. In a specific embodiment, co-administration of two (or more) agents allows for significantly lower doses of each to be used, thereby reducing the side effects seen.

In one embodiment, a compound of the invention or a pharmaceutical composition comprising a compound of the invention is administered as a medicament. In a specific embodiment, said pharmaceutical composition additionally comprises a further active ingredient.

In one embodiment, a compound of the invention is co-administered with another therapeutic agent for the treatment and/or prophylaxis of a disease involving inflammation, particular agents include, but are not limited to, immunoregulatory agents e.g. azathioprine, corticosteroids (e.g. prednisolone or dexamethasone), cyclophosphamide, cyclosporin A, tacrolimus, mycophenolate, mofetil, muromonab-CD3 (OKT3, e.g. Orthocolone®), ATG, aspirin, acetaminophen, ibuprofen, naproxen, and piroxicam.

In one embodiment, a compound of the invention is co-administered with another therapeutic agent for the treatment and/or prophylaxis of arthritis (e.g. rheumatoid arthritis), particular agents include but are not limited to analgesics, non-steroidal anti-inflammatory drugs (NSAIDS), steroids, synthetic DMARDS (for example but without limitation methotrexate, leflunomide, sulfasalazine, auranofin, sodium aurothiomalate, penicillamine, chloroquine, hydroxychloroquine, azathioprine, tofacitinib, baricitinib, fostamatinib, and cyclosporin), and biological DMARDS (for example but without limitation infliximab, etanercept, adalimumab, rituximab, and abatacept).

In one embodiment, a compound of the invention is co-administered with another therapeutic agent for the treatment and/or prophylaxis of proliferative disorders, particular agents include but are not limited to: methotrexate, leukovorin, adriamycin, prednisone, bleomycin, cyclophosphamide, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody (e.g. Herceptin™), capecitabine, raloxifene hydrochloride, EGFR inhibitors (e.g. Iressa®, Tarceva™, Erbitux™), VEGF inhibitors (e.g. Avastin™), proteasome inhibitors (e.g. Velcade™) Glivec® and hsp90 inhibitors (e.g. 17-AAG). Additionally, the compound of the invention according to Formula I may be administered in combination with other therapies including, but not limited to, radiotherapy or surgery. In a specific embodiment the proliferative disorder is selected from cancer, myeloproliferative disease or leukaemia.

In one embodiment, a compound of the invention is co-administered with another therapeutic agent for the treatment and/or prophylaxis of autoimmune diseases, particular agents include but are not limited to: glucocorticoids, cytostatic agents (e.g. purine analogs), alkylating agents, (e.g. nitrogen mustards (cyclophosphamide), nitrosoureas, platinum compound of the inventions, and others), antimetabolites (e.g. methotrexate, azathioprine and mercaptopurine), cytotoxic antibiotics (e.g. dactinomycin anthracyclines, mitomycin C, bleomycin, and mithramycin), antibodies (e.g. anti-CD20, anti-CD25 or anti-CD3 (OTK3) monoclonal antibodies, Atgam® and Thymoglobuline®), cyclosporin, tacrolimus, rapamycin (sirolimus), interferons (e.g. IFN-(3), TNF binding proteins (e.g. infliximab, etanercept, or adalimumab), mycophenolate, fingolimod and myriocin.

In one embodiment, a compound of the invention is co-administered with another therapeutic agent for the treatment and/or prophylaxis of transplant rejection, particular agents include but are not limited to: calcineurin inhibitors (e.g. cyclosporin or tacrolimus (FK506)), mTOR inhibitors (e.g. sirolimus, everolimus), anti-proliferatives (e.g. azathioprine, mycophenolic acid), corticosteroids (e.g. prednisolone, hydrocortisone), antibodies (e.g. monoclonal anti-IL-2Rα receptor antibodies, basiliximab, daclizumab), polyclonal anti-T-cell antibodies (e.g. anti-thymocyte globulin (ATG), anti-lymphocyte globulin (ALG)).

In one embodiment, a compound of the invention is co-administered with another therapeutic agent for the treatment and/or prophylaxis of asthma and/or rhinitis and/or COPD, particular agents include but are not limited to: beta2-adrenoceptor agonists (e.g. salbutamol, levalbuterol, terbutaline and bitolterol), epinephrine (inhaled or tablets), anticholinergics (e.g. ipratropium bromide), glucocorticoids (oral or inhaled). Long-acting 02-agonists (e.g. salmeterol, formoterol, bambuterol, and sustained-release oral albuterol), combinations of inhaled steroids and long-acting bronchodilators (e.g. fluticasone/salmeterol, budesonide/formoterol), leukotriene antagonists and synthesis inhibitors (e.g. montelukast, zafirlukast and zileuton), inhibitors of mediator release (e.g. cromoglycate and ketotifen), biological regulators of IgE response (e.g. omalizumab), antihistamines (e.g. ceterizine, cinnarizine, fexofenadine) and vasoconstrictors (e.g. oxymethazoline, xylomethazoline, nafazoline and tramazoline).

Additionally, a compound of the invention may be administered in combination with emergency therapies for asthma and/or COPD, such therapies include oxygen or heliox administration, nebulized salbutamol or terbutaline (optionally combined with an anticholinergic (e.g. ipratropium), systemic steroids (oral or intravenous, e.g. prednisone, prednisolone, methylprednisolone, dexamethasone, or hydrocortisone), intravenous salbutamol, non-specific beta-agonists, injected or inhaled (e.g. epinephrine, isoetharine, isoproterenol, metaproterenol), anticholinergics (IV or nebulized, e.g. glycopyrrolate, atropine, ipratropium), methylxanthines (theophylline, aminophylline, bamiphylline), inhalation anesthetics that have a bronchodilatory effect (e.g. isoflurane, halothane, enflurane), ketamine and intravenous magnesium sulfate.

In one embodiment, a compound of the invention is co-administered with another therapeutic agent for the treatment and/or prophylaxis of inflammatory bowel disease (IBD), particular agents include but are not limited to: glucocorticoids (e.g. prednisone, budesonide) synthetic disease modifying, immunomodulatory agents (e.g. methotrexate, leflunomide, sulfasalazine, mesalazine, azathioprine, 6-mercaptopurine and cyclosporin) and biological disease modifying, immunomodulatory agents (infliximab, adalimumab, rituximab, and abatacept).

In one embodiment, a compound of the invention is co-administered with another therapeutic agent for the treatment and/or prophylaxis of SLE, particular agents include but are not limited to: human monoclonal antibodies (belimumab (Benlysta)), Disease-modifying antirheumatic drugs (DMARDs) such as antimalarials (e.g. plaquenil, hydroxychloroquine), immunosuppressants (e.g. methotrexate and azathioprine), cyclophosphamide and mycophenolic acid, immunosuppressive drugs and analgesics, such as nonsteroidal anti-inflammatory drugs, opiates (e.g. dextropropoxyphene and co-codamol), opioids (e.g. hydrocodone, oxycodone, MS Contin, or methadone) and the fentanyl duragesic transdermal patch.

In one embodiment, a compound of the invention is co-administered with another therapeutic agent for the treatment and/or prophylaxis of psoriasis, particular agents include but are not limited to: topical treatments such as bath solutions, moisturizers, medicated creams and ointments containing coal tar, dithranol (anthralin), corticosteroids like desoximetasone (Topicort™), fluocinonide, vitamin D3 analogues (for example, calcipotriol), argan oil and retinoids (etretinate, acitretin, tazarotene), systemic treatments such as methotrexate, cyclosporine, retinoids, tioguanine, hydroxyurea, sulfasalazine, mycophenolate mofetil, azathioprine, tacrolimus, fumaric acid esters or biologics such as Amevive™, Enbrel™, Humira™, Remicade™, Raptiva™ and ustekinumab (a IL-12 and IL-23 blocker). Additionally, a compound of the invention may be administered in combination with other therapies including, but not limited to phototherapy, or photochemotherapy (e.g. psoralen and ultraviolet A phototherapy (PUVA)).

In one embodiment, a compound of the invention is co-administered with another therapeutic agent for the treatment and/or prophylaxis of allergic reaction, particular agents include but are not limited to: antihistamines (e.g. cetirizine, diphenhydramine, fexofenadine, levocetirizine), glucocorticoids (e.g. prednisone, betamethasone, beclomethasone, dexamethasone), epinephrine, theophylline or anti-leukotrienes (e.g. montelukast or zafirlukast), anti-cholinergics and decongestants.

By co-administration is included any means of delivering two or more therapeutic agents to the patient as part of the same treatment regime, as will be apparent to the skilled person. Whilst the two or more agents may be administered simultaneously in a single formulation, i.e. as a single pharmaceutical composition, this is not essential. The agents may be administered in different formulations and at different times.

Chemical Synthetic Procedures

General

The compound of the invention can be prepared from readily available starting materials using the following general methods and procedures. It will be appreciated that where typical or preferred process conditions (i.e. reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art (Wuts and Greene 2012).

The following methods are presented with details as to the preparation of a compound of the invention as defined hereinabove and the comparative examples. A compound of the invention may be prepared from known or commercially available starting materials and reagents by one skilled in the art of organic synthesis.

All reagents are of commercial grade and are used as received without further purification, unless otherwise stated. Commercially available anhydrous solvents are used for reactions conducted under inert atmosphere. Reagent grade solvents are used in all other cases, unless otherwise specified. Column chromatography is performed on silica gel 60 (35-70 µm). Thin layer chromatography is carried out using pre-coated silica gel F-254 plates (thickness 0.25 mm). $^1$H NMR spectra are recorded on a Bruker DPX 400 NMR spectrometer (400 MHz or a Bruker Advance 300 NMR spectrometer (300 MHz). Chemical shifts ($\delta$) for $^1$H NMR spectra are reported in parts per million (ppm) relative to tetramethylsilane ($\delta$ 0.00) or the appropriate residual solvent peak, i.e. CHCl$_3$ ($\delta$ 7.27), as internal reference. Multiplicities are given as singlet (s), doublet (d), triplet (t), quartet (q), quintuplet (quin), multiplet (m) and broad (br). Electrospray MS spectra are obtained on a Waters platform LC/MS spectrometer or with Waters Acquity UPLC with Waters Acquity PDA detector and SQD mass spectrometer. Columns used: UPLC BEH C18 1.7 µm 2.1×5 mm VanGuard Pre-column with Acquity UPLC BEH C18 1.7 µm 2.1×30 mm Column or Acquity UPLC BEH C18 1.7 µm 2.1×50 mm Column. All the methods are using MeCN/H$_2$O gradients. MeCN and H$_2$O contain either 0.1% Formic Acid or NH$_3$ (10 mM). Preparative LC-MS: column used, Waters XBridge Prep C18 5 µm ODB 30 mm ID×100 mm L (preparative column) and Waters XBridge BEH C18 5 µm 4.6 mm ID×100 mm L (analytical column). All the methods are using either MeOH/H₂O or MeCN/H₂O gradients. MeOH, MeCN and H₂O contain either 0.1% Formic Acid or 0.1% Diethylamine. Microwave heating is performed with a Biotage Initiator. Celpure® P65 is a filter agent, commercial product (CAS number 61790-53-2).

List of abbreviations used in the experimental section:

| | |
|---|---|
| μL | microliter |
| APMA | 4-aminophenylmercuric acetate |
| app t | Apparent triplet |
| AUC | Area Under the Curve |
| BAL | Broncho-alveolar lavage |
| BALF | Broncho-alveolar lavage fluid |
| br d | Broad doublet |
| Boc | tert-Butyloxy-carbonyl |
| br s | Broad singlet |
| BSA | Bovine serum albumine |
| br t | Broad triplet |
| Cat. | Catalytic amount |
| cDNA | copy deoxyribonucleic acid |
| Cpd | Compound |
| d | doublet |
| DavePhos | 2-Dicyclohexylphosphino-2'-(N,N-dimethylamino)biphenyl |
| DCE | Dichloroethane |
| DCM | Dichloromethane |
| DDQ | 2,3-Dichloro-5,6-dicyano-1,4-benzoquinone |
| DEAD | diethyl azodicarboxylate |
| Desc'd | Described in details |
| DIAD | Diisopropyl azodicarboxylate |
| DIPE | Diisopropylether |
| DIPEA | N,N-diisopropylethylamine |
| DMA | Dimethylacetamide |
| DMF | N,N-dimethylformamide |
| DMSO | Dimethylsulfoxide |
| dppf | 1,1'-Bis( diphenylphosphino)ferrocene |
| EDC | 1-ethyl-3-(3-dimethylaminopropyl)carbodiimide) |
| EDC.HCl | N-(3-Dimethylaminopropyl)-N'-ethylcarbodiimide hydrochloride |
| eq. | Equivalent |
| Et₂O | Diethyl ether |
| EtOAc | Ethyl acetate |
| EtOH | Ethanol |
| FBS | Fetal bovine serum |
| FITC | Fluorescein Isothiocyanate |
| Fmoc | 9-Fluorenylmethoxycarbonyl |
| g | gram |
| h | hour |
| HATU | O-(7-azabenzotriazol-1-yl)-N,N,N',N'-tetramethyluronium hexafluorophosphate |
| HOBt | Hydroxybenzotriazole |
| HPLC | High pressure liquid chromatography |
| HRP | horseradish peroxydase |
| Int | Intermediate |
| JohnPhos | (2-Biphenyl)di-tert-butylphosphine |
| kg | kilogram |
| L | liter |
| LC-MS | Liquid Chromatography-Mass Spectrometry |
| LPC | lysophosphatidylcholine |
| LPA | Lysophosphatidic acid |
| m | multiplet |
| m-CPBA | 3-Chloroperbenzoic acid |
| MeCN | Acetonitrile |
| MeOH | Methanol |
| mg | milligram |
| min | minute |
| mL | millilitre |
| mmol | millimoles |
| MMP | Matrix Metallo Proteinase |
| MS Ms'd | Mass measured by LC-MS |
| MW | Molecular weight |
| N.A. | Not available |
| NBS | N-Bromosuccinimide |
| nBuOH | n-Butanol |
| NMR | Nuclear Magnetic Resonance |
| PBF | phosphate buffered formalin |
| PBS | Phosphate buffered saline |
| PCR | Polymerase chain reaction |
| Pd(amphos)Cl₂ | Bis(di-tert-butyl(4-dimethylaminophenyl) phosphine) dichloropalladium(II) |
| Pd(PPh₃)₄ | Tetrakis(triphenylphosphine) palladium(0) |
| Pd/C | Palladium on Carbon 10% |
| Pd₂(dba)₃ | Tris(dibenzylideneacetone) dipalladium(0) |
| PdCl₂dppf | [1,1'-Bis(diphenylphosphino)ferrocene]dichloropalladium(II) |
| Pd(OAc)₂ | Palladium(II) acetate |
| PEG | Polyethylene glycol |
| ppm | part-per-million |
| q | quadruplet |
| QrtPCR | quantitative real-time PCR |
| QTL | quantitative trait loci |
| r.t. | Room temperature |
| RNA | Ribonucleic acid |
| Rt | retention time |
| s | singlet |
| sept | septuplet |
| Sphos | 2-Dicyclohexylphosphino-2',6'-dimethoxybiphenyl |
| t | triplet |
| TBAF | Tetra-n-butylammonium fluoride |
| t-BuOH | Tert-butanol |
| TBDPSCl | Tert-butyldiphenylsilyl chloride |
| TBSCl | Tert-butyldimethylsilyl chloride |
| TEA | Triethylamine |
| TFA | Trifluoroacetic acid |
| THF | Tetrahydrofuran |
| TOOS | (N-ethyl-N-(2-hydroxy-3-sulfopropyl)-3-methylaniline, sodium salt dihydrate |
| TS | Tobacco smoke |
| XantPhos | 4'5-Bis(diphenylphosphino)-9,9-dimethylxanthene |

Synthetic Preparation of the Compounds of the Invention

Example 1. General Synthetic Methods 1.1. Synthetic Methods Overview

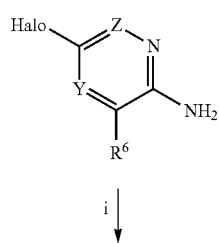

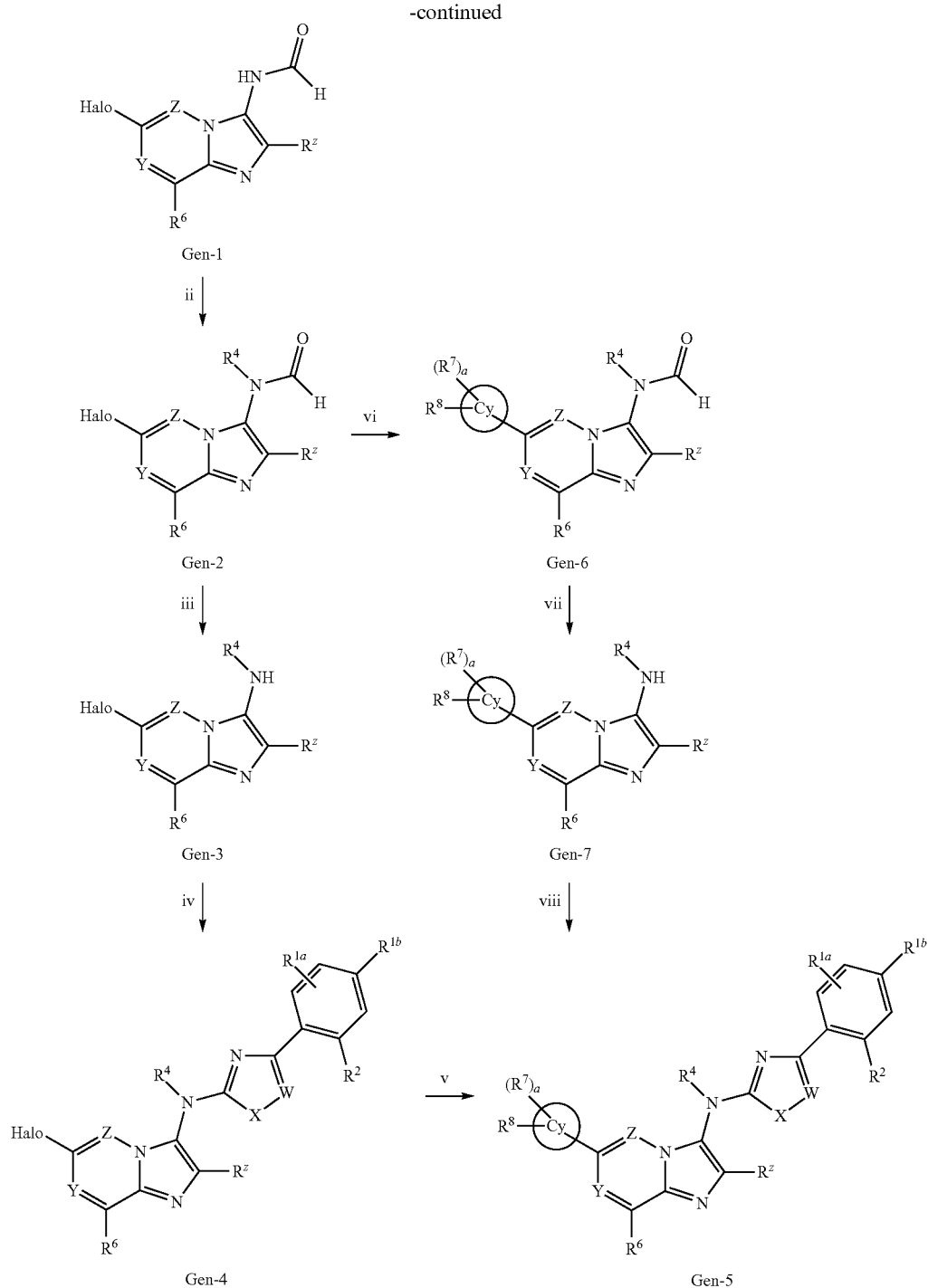

Where R$^z$ is R$^5$ or an alkyl, alkenyl or carbonyl group optionally substituted, and halo is F, Cl, Br or I.

Step i: method A

A1 (2 steps): Route using isonitrile reagent then reaction with HCOOH

A2 (2 steps): Route using KCN then reaction with HCOOH

Step ii: consists in one of the following methods

B1: Alkylation with NaH as base in DMF

B2: Alkylation with K$_2$CO$_3$ as base in acetone

Step iii: consists in one of the following methods

C1: Deformylation under acidic conditions

C2: Deformylation under basic conditions

Step iv: consists in one of the following methods

D1 (2 steps): formation of thiourea then cyclisation to give thiazole derivative D2: heteroaromatic nucleophilic substitution Step v: consists in one or several of the following methods E1a or E1b: Buchwald coupling E2: Suzuki coupling E3: Negishi coupling E4a or E4b: SNAr
E5a or E5b: Boc deprotection
E6: Reduction with $H_2$ in presence of transition metal catalyst
E7: Dess-Martin oxidation
E8: Alkylation
E9a, E9b or E9c: Amide bond forming reaction
E10: Reductive amination
E11: Sulfonylation
E12: Nucleophilic substitution
E13: Saponification
E14: Introduction of hydroxymethyl group
E15: Introduction of trifluoroacetyl group
E16: Halogenation
E17: Copper mediated cyanation
E18: Silyl protection
E19: Silyl deprotection
Step vi: consists in one or several of the methods E
Step vii: consists in one of the methods C
Step viii: consists in one of the methods D and one or several of the methods E
D3 (2 steps): heteroaromatic nucleophilic substitution then suzuki coupling 1.2. General Methods 1.2.1. General method A1 and A2: Synthesis of Intermediate Gen-1

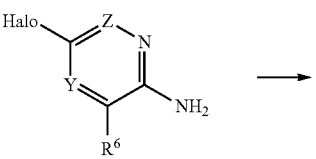

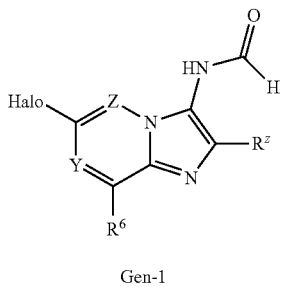

Gen-1

1.2.1.1. General Method A1

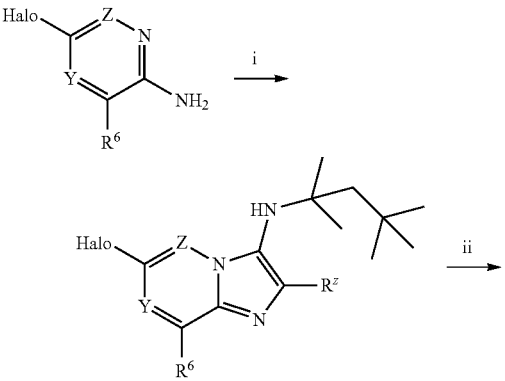

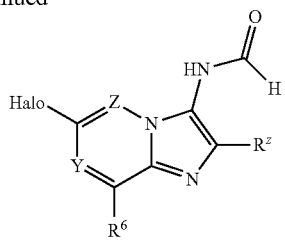

Step i)

To a solution of amino-heterocycle derivative (1 eq.) in nBuOH under argon are added successively the aldehyde $R^zCHO$ (2.5 eq.), $MgCl_2$ (0.04 eq.) and 1,1,3,3-tetramethylbutyl isocyanide (1.15 eq.). The reaction mixture is heated at 130° C. from between 3.5 h to overnight, and then concentrated in vacuo. The residue is partitioned between heptane and water, stirred for 15 to 40 min, the biphasic solution is filtered on Celpure® P65, and the cake is washed with heptane. The two layers of the filtrate are separated, the organic layer is washed successively with water, an aqueous 1M NaOH and brine, then dried over $Na_2SO_4$ and concentrated in vacuo to afford the expected amine which is used directly in the next step.

Step ii)

A solution of the above prepared compound (1 eq.) in formic acid is heated at 80° C. for 1 to 4 h. The reaction mixture is concentrated in vacuo. The residue is then triturated in $Et_2O$. The formed precipitate is filtered, rinsed and dried to afford Intermediate Gen-1.

1.2.1.2. Illustrative Synthesis of Intermediate Gen-1-b: N-(6-Bromo-2-ethyl-imidazo[1,2-a]pyrazin-3-yl)-formamide

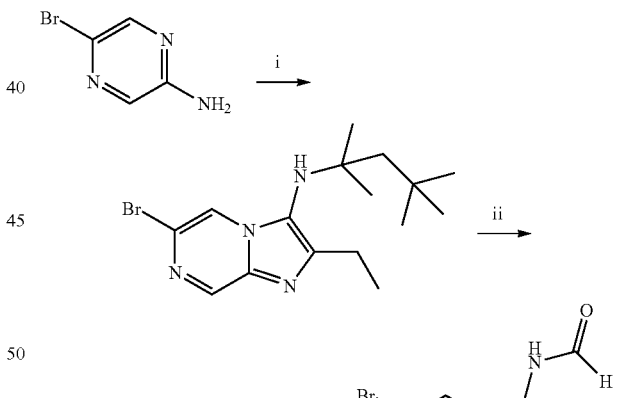

Step i)

To a solution of 5-Bromo-pyrazin-2-ylamine (10 g, 57.47 mmol, 1 eq.) in nBuOH (58 mL) under argon are added successively propanal (10.37 mL, 143.6 mmol, 2.5 eq.), $MgCl_2$ (219 mg, 2.29 mmol, 0.04 eq.) and 1,1,3,3-tetramethylbutyl isocyanide (11.6 mL, 66.1 mmol, 1.15 eq.). The reaction mixture is heated at 130° C. overnight, and then concentrated in vacuo. The residue is partitioned between heptane (100 mL) and water (100 mL), stirred for 20 min and the biphasic suspension is filtered on Celpure® P65, the cake is washed with heptane (100 mL). The two layers of the biphasic filtrate are separated, the organic layer is successively washed with water, an aqueous 1M NaOH solution, then brine, dried over Na$_2$SO$_4$ and concentrated in vacuo to afford the expected amine. (NB: A solid remaining on the celite pad is collected, then re-dissolved with DCM, dried over Na$_2$SO$_4$, filtered and concentrated in vacuo to afford first batch of the expected amine). The two batches are combined and used directly in the next step.

LC-MS: MW (calcd): 352 ($^{79}$Br), 354 ($^{81}$Br); m/z MW (obsd): 353 ($^{79}$Br M+H), 355 ($^{81}$Br M+H)

Step ii)

A solution of the above prepared compound (11.64 g, 32.9 mmol, 1 eq.) in formic acid (93.12 mL) is heated at 80° C. for 4 h. The reaction mixture is concentrated in vacuo. The residue is then triturated in Et$_2$O; the resulting precipitate is filtered, rinsed and dried to afford Intermediate Gen-1-b.

LC-MS: MW (calcd): 268 ($^{79}$Br), 270 ($^{81}$Br); m/z MW (obsd): 269 ($^{79}$Br M+H), 271 ($^{81}$Br M+H)

1.2.1.3. General method A2

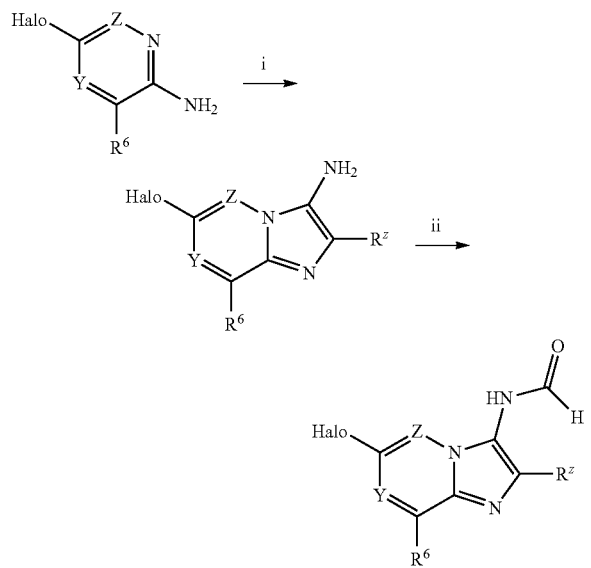

Step i)

To a suspension of amino-heterocycle derivative (1 eq.) in toluene are added the aldehyde R$^z$CHO (1 eq.) and benzotriazole (1.1 eq.). The mixture is stirred at r.t. overnight, then additional aldehyde reagent (0.5 eq.) is added. After 2 h to 4 h stirring at r.t., potassium cyanide (1.0 to 1.2 eq.) is added, followed by EtOH. The reaction mixture is stirred at r.t. for 1 to 5 days (another addition of aldehyde reagent and of potassium cyanide might be required). The crude product mixture is then quenched with a 1 M or 3 M NaOH solution. Solvents are evaporated carefully in vacuo. The residue is diluted with water and EtOAc. The aqueous layer is extracted with EtOAc, and the combined organic layers are washed with water, brine, dried over Na$_2$SO$_4$ and concentrated in vacuo. A solution of acetyl chloride (2 to 2.1 eq.) in EtOH at 0° C. is added dropwise carefully to a solution of the crude product mixture in EtOH at 0° C. The resulting reaction mixture is stirred at r.t. overnight and then concentrated to dryness to afford the expected amine as hydrochloride salt.

Step ii)

A solution of the above prepared amine hydrochloride salt (1 eq.) in formic acid is heated at 90° C. for 2 h. Solvents are evaporated in vacuo. The residue is dissolved in water. The mixture is carefully basified with a saturated NaHCO$_3$ solution until pH 8-9 is reached. The formed solid is filtered, washed with water and DIPE and dried to afford Intermediate Gen-1. Alternatively EtOAc is added to the basic aqueous layer and the layers are separated. The aqueous layer is further extracted with EtOAc. The combined organic layers are then washed with brine, dried over Na$_2$SO$_4$, filtered and concentrated in vacuo. The residue is triturated with DIPE at r.t. for 1 h, the resulting solid is separated by filtration and dried to afford Intermediate Gen-1.

1.2.1.4. Illustrative Synthesis of Intermediate Gen-1-a: N-(6-Bromo-2-ethyl-imidazo[1,2-b]pyridazin-3-yl)-formamide

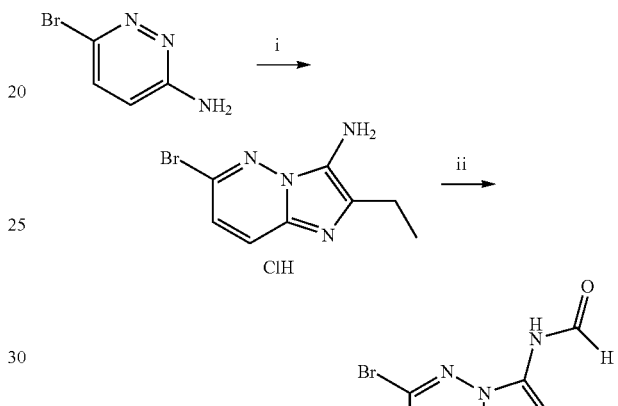

Step i)

To a suspension of 6-bromopyridazin-3-amine (26.28 g, 151 mmol, 1 eq.) in toluene (450 mL) are added propanal (11.12 mL, 151 mmol, 1 eq.) and benzotriazole (19.79 g, 166 mmol, 1.1 eq.). The mixture is stirred at r.t. overnight. Additional propanal (5.56 mL, 75.5 mmol 0.5 eq.) is added. After 2 h stirring at r.t., potassium cyanide (9.83 g, 151 mmol, 1 eq.) is added, followed by EtOH (1200 mL). The reaction mixture is stirred at r.t. overnight. Propanal (11.12 mL, 151 mmol, 1 eq.) and potassium cyanide (4.91 g, 75.5 mmol, 0.5 eq.) are added and the reaction is stirred at r.t. for 2 days. The crude product mixture is then quenched with an aqueous 1 M NaOH solution (1000 mL). Solvents are evaporated carefully in vacuo. The residue is diluted with water and EtOAc. The aqueous layer is extracted with EtOAc. The combined organic layers are washed with water and brine, dried over Na$_2$SO$_4$ and concentrated in vacuo. A solution of acetyl chloride (21.2 mL, 300.5 mmol, 2 eq.) in EtOH (600 mL) at 0° C. is added carefully dropwise to a solution of the crude product mixture in EtOH (750 mL) at 0° C. The resulting reaction mixture is stirred at r.t. overnight and then concentrated to dryness to afford the corresponding 6-Bromo-2-ethyl-imidazo[1,2-b]pyridazin-3-ylamine as hydrochloride salt.

LC-MS MW (calcd): 240 ($^{79}$Br), 242 ($^{81}$Br); m/z MW (obsd): 241 ($^{79}$Br M+H), 243 ($^{81}$Br M+H)

Step ii)

A solution of the above prepared imidazo[1,2-b]pyridazin-3-ylamine hydrochloride salt (27.0 g, 97.0 mmol, 1 eq.) in formic acid (150 mL) is heated at 90° C. for 2 h. Solvents are evaporated in vacuo. The residue is dissolved in water. The mixture is carefully basified with a saturated NaHCO₃ solution until pH 8-9 is reached. EtOAc is added and the layers are separated. The aqueous layer is extracted with EtOAc five times. The combined organic layers are then washed with brine, dried over Na₂SO₄, filtered and concentrated in vacuo. The residue is triturated with DIPE at r.t. for 1 h, the resulting solid is separated by filtration and dried to afford Intermediate Gen-1-a.

LC-MS MW (calcd): 268 ($^{79}$Br), 270 ($^{81}$Br); m/z MW (obsd): 269 ($^{79}$Br M+H), 271 ($^{81}$Br M+H)

1.2.2. General methods B1 and B2: Synthesis of Intermediate Gen-2

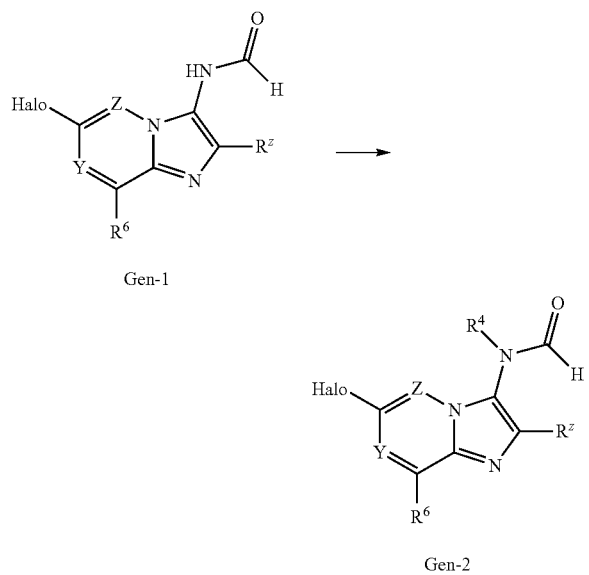

Gen-1

Gen-2

1.2.2.1. General Method B1

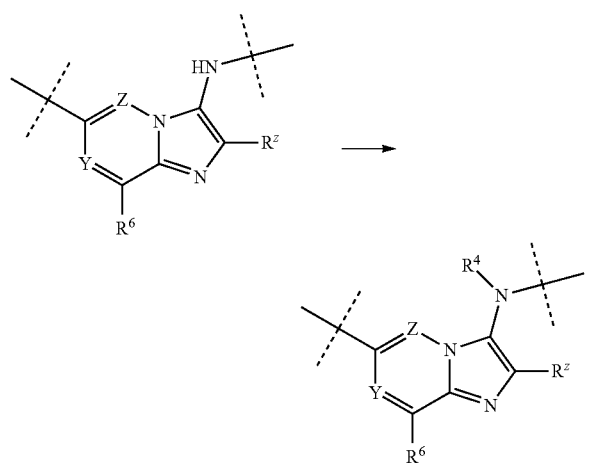

NaH (60% in oil suspension, 1.05 eq.) is slurried in dry DMF and cooled to −5° C. A suspension of imidazo[1,2-b]pyridazin-3-ylamine or imidazo[1,2-a]pyrazin-3-ylamine derivative (1 eq.) in dry DMF is added, and is stirred for 40 min at −5° C. to allow anion formation. Then alkyl iodide (1.5 eq.) is added to the reaction mixture which is stirred at −5° C. and then at 0° C. or 40° C. until completion. The reaction mixture is quenched with an aqueous 1 M HCl solution, and diluted with DCM, the layers are separated, the aqueous layer is extracted twice with DCM. The combined organic layers are dried over Na₂SO₄ and concentrated in vacuo. The expected product is obtained by chromatography on silica gel or crystallization.

1.2.2.2. Illustrative Synthesis of Intermediate Gen-2-c: N-[6-Bromo-2-((E)-styryl)-imidazo[1,2-b]pyridazin-3-yl]-N-methyl-formamide

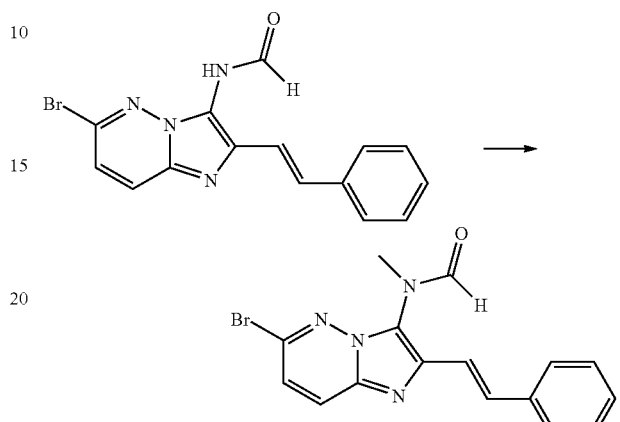

NaH (60% in oil suspension, 4.37 g, 109 mmol, 1.05 eq.) is slurried in dry DMF (100 mL) and cooled to −5° C. A suspension of Gen-1-c (35.7 g, 104 mmol, 1 eq.) in dry DMF (200 mL) is added, and is stirred for 40 min at −5° C. to allow anion formation. Then methyl iodide (9.71 mL, 156 mmol, 1.5 eq.) is added to the reaction mixture which is stirred at −5° C. for 30 min and then at 40° C. for 45 min. The reaction mixture is quenched with an aqueous 1 M HCl solution (1000 mL), and diluted with DCM (1000 mL), the layers are separated, the aqueous layer is extracted twice with DCM (300 mL). The combined organic layers are dried over Na₂SO₄ and concentrated in vacuo. The residue is triturated with EtOAc (500 mL) and stirred at r.t. overnight, the resulting solid is separated by filtration and dried to afford the expected Intermediate Gen-2-c.

LC-MS: MW (calcd): 356 ($^{79}$Br), 358 ($^{81}$Br); m/z MW (obsd): 357 ($^{79}$Br M+H), 359 ($^{81}$Br M+H)

1.2.2.3. General Method B2

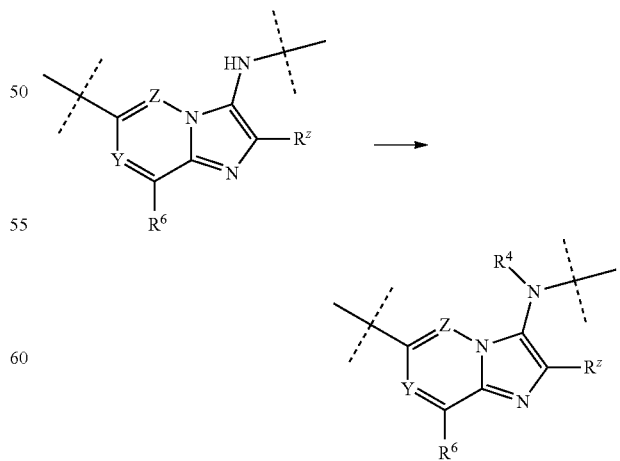

To a suspension of imidazo[1,2-b]pyridazin-3-ylamine or imidazo[1,2-a]pyrazin-3-ylamine derivative (1 eq.) in acetone are added potassium carbonate (3 eq.) and alkyl iodide (1.2 eq to 1.9 eq.). The reaction mixture is stirred at a temperature comprised between r.t. and refluxing temperature until completion. (NB: additional alkyl iodide may be introduced and stirring continued as needed to reach completion). The reaction mixture is then filtered and washed with acetone then DCM, the filtrate is concentrated in vacuo; alternatively, the reaction mixture is directly concentrated in vacuo. The residue is partitioned between DCM and water. The organic layer is separated, and the aqueous layer is further extracted with DCM. The combined organic layers are then washed with brine, dried over $Na_2SO_4$, filtered and concentrated in vacuo. The residue is triturated with $Et_2O$ at r.t. for 1 h, the resulting solid is separated by filtration and dried to afford the expected Intermediate.

1.2.2.4. Illustrative Synthesis of Intermediate Gen-2-a: N-(6-Bromo-2-ethyl-imidazo[1,2-b]pyridazin-3-yl)-N-methyl-formamide

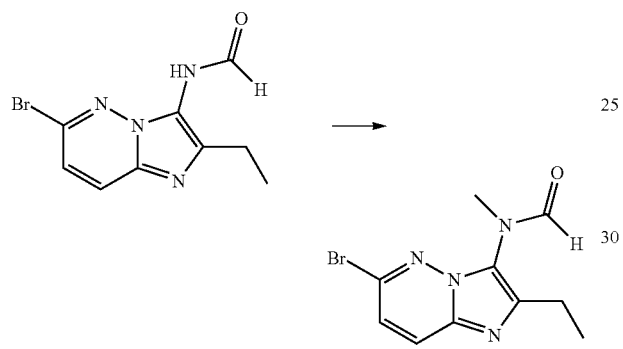

To a solution of N-(6-Bromo-2-ethyl-imidazo[1,2-b]pyridazin-3-yl)-formamide (Gen-1-a) (7.0 g, 26.0 mmol, 1 eq.) in acetone (300 mL) is added potassium carbonate (10.79 g, 78.0 mmol, 3 eq.) and methyl iodide (1.95 mL, 31.2 mmol, 1.2 eq). The reaction mixture is refluxed for 2 h, then more methyl iodide (0.97 mL, 15.75 mmol, 0.5 eq.) is introduced and stirring is continued for 2 h (this operation is repeated once more). The reaction mixture is concentrated in vacuo, the residue is partitioned between DCM and water. The aqueous layer is further extracted with DCM three times. The combined organic layers are then washed with brine, dried over $Na_2SO_4$, filtered and concentrated in vacuo. The residue is triturated with $Et_2O$ at r.t. for 1 h, the resulting solid is separated by filtration and dried to afford Intermediate Gen-2-a.

LC-MS: MW (calcd): 282 ($^{79}$Br), 284 ($^{81}$Br); m/z MW (obsd): 283 ($^{79}$Br M+H), 285 ($^{81}$Br M+H)

1.2.3. General Methods C1 and C2: Synthesis of Intermediate Gen-3

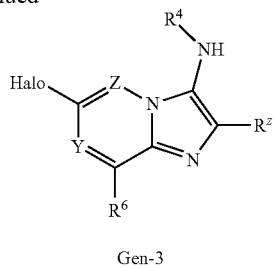

Gen-2

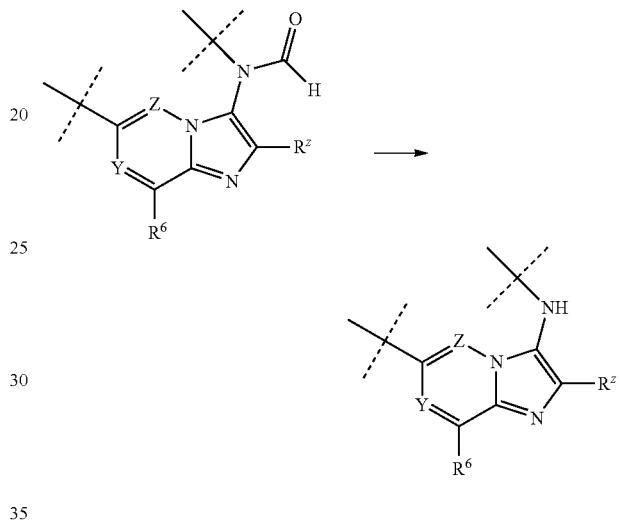

Gen-3

1.2.3.1. General Method C1

A 4 M HCl solution in dioxane or 1.25 M HCl solution in MeOH (4 to 12 eq.) is added to a solution of imidazo[1,2-b]pyridazin-3-yl formamide or imidazo[1,2-a]pyrazin-3-yl formamide derivative (1 eq.) in MeOH. The reaction mixture is stirred at a r.t. or refluxed for 3 h. If the reaction is not complete, additional 4 M HCl solution (1.5 eq.) is added and stirring is continued until completion. The reaction mixture is then concentrated in vacuo to afford the expected intermediate.

1.2.3.2. Illustrative Synthesis of Intermediate Gen-3-a: (6-Bromo-2-ethyl-imidazo[1,2-b]pyridazin-3-yl)-methyl-amine

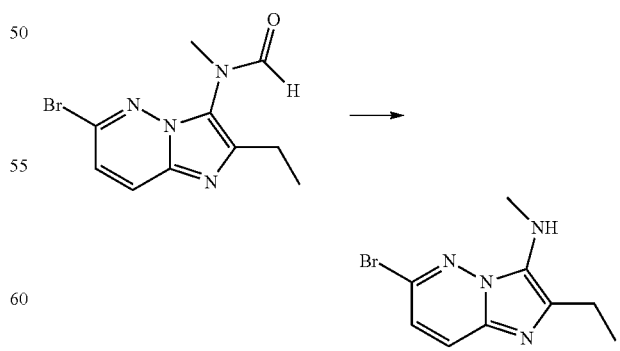

An aqueous 4 M HCl solution in dioxane (229.0 mL, 915.0 mmol, 12 eq.) is added to a solution of N-(6-Bromo-2-ethyl-imidazo[1,2-b]pyridazin-3-yl)-N-methyl-formamide (Gen-2-a) (21.6 g, 76.0 mmol, 1 eq.) in MeOH (600 mL). The reaction mixture is stirred at r.t. for 3 h. The reaction mixture is then concentrated in vacuo to afford Intermediate Gen-3-a as dihydrochloride salt.

LC-MS: MW (calcd): 254 ($^{79}$Br), 256 ($^{81}$Br); m/z MW (obsd): 255 ($^{79}$Br M+H), 257 ($^{81}$Br M+H)

1.2.3.3. General Method C2

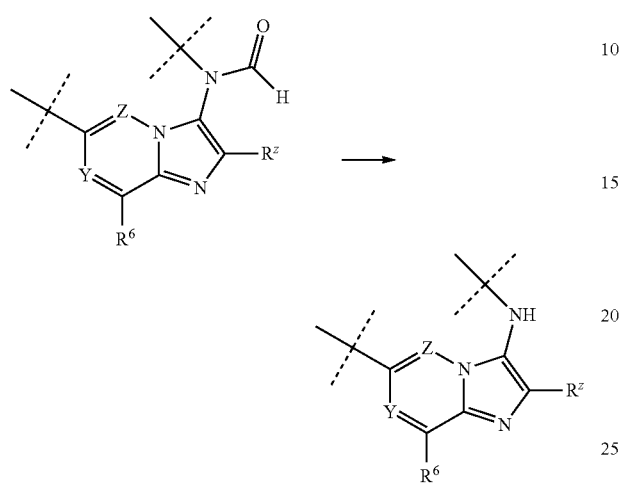

An aqueous 10 M aqueous KOH solution (15 eq.) is added to a solution of imidazo[1,2-b]pyridazin-3-yl formamide or imidazo[1,2-a]pyrazin-3-yl formamide derivative (1 eq.) in MeOH. The reaction mixture is stirred at r.t. until completion, then quenched with brine and MeOH is removed in vacuo. The remaining aqueous phase is extracted with DCM three times. The combined organic layers are washed with brine, dried over MgSO$_4$, filtered and concentrated in vacuo to afford the expected intermediate. If the product is precipitated after addition of brine, the following work up is used: the reaction mixture is filtered. The solid is washed with water and dried in vacuo to afford the expected intermediate.

1.2.3.4. Illustrative Synthesis of Intermediate Gen-3-b: (6-Bromo-2-ethyl-imidazo[1,2-a]pyrazin-3-yl)-methyl-amine

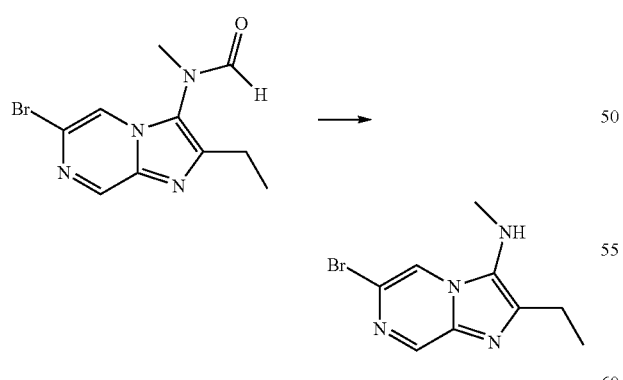

An aqueous 10 M aqueous KOH solution (28.92 mL, 289.2 mmol, 15 eq.) is added to a solution of Intermediate Gen-2-b (5.46 g, 19.2 mmol, 1 eq.) in MeOH (27.5 mL). The reaction mixture is stirred at r.t. for 1 h, then quenched with brine (100 mL). The reaction mixture is filtered. The solid is washed with water and dried in vacuo to afford Intermediate Gen-3-b.

LC-MS: MW (calcd): 254 ($^{79}$Br), 256 ($^{81}$Br); m/z (obsd): 255 ($^{79}$Br M+H), 257 ($^{81}$Br M+H)

1.2.4. General Methods D1, D2: Synthesis of Intermediate Gen-4

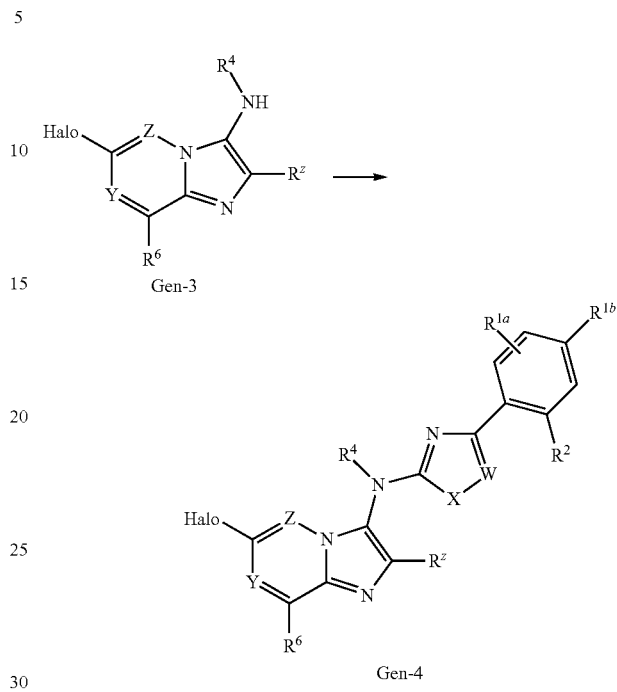

1.2.4.1. General Method D1

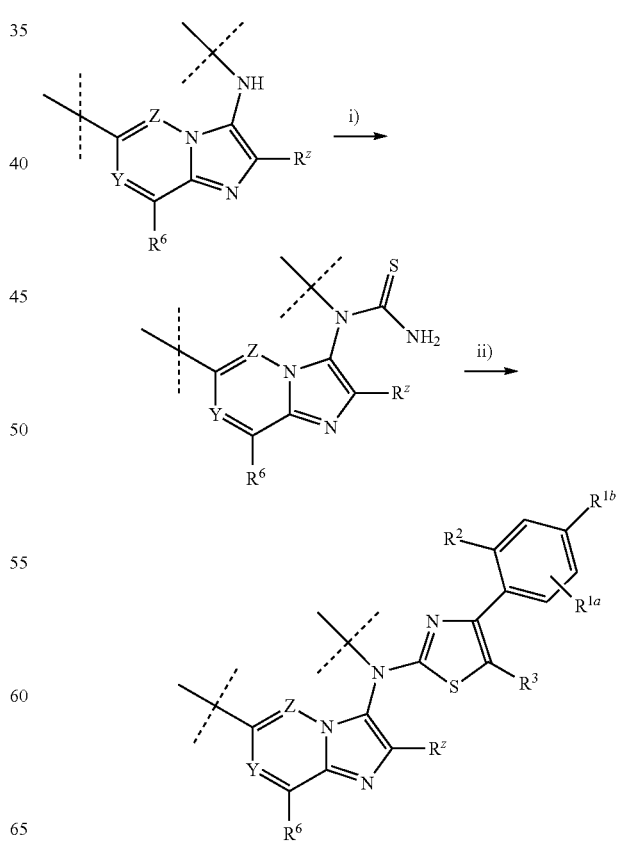

Step i)

To a suspension of imidazo[1,2-b]pyridazin-3-ylamine or imidazo[1,2-a]pyrazin-3-ylamine derivative (1 eq.) in DCM is added TEA (4.5 eq.). The mixture is stirred for 20 to 30 min at r.t. then Fmoc-isothiocyanate (1.12 to 2.2 eq.) is added. The resulting solution is stirred at r.t. for 3 h to overnight. If after stirring overnight the reaction is not complete, additional Fmoc-isothiocyanate (0.3 to 0.5 eq.) is then introduced and stirring is continued for 3 h to 4 h. Piperidine (3 to 3.2 eq.) is then introduced and the reaction mixture is stirred at r.t. until completion. Water is added to the solution and the layers are separated. The aqueous layer is extracted with DCM, the combined organic layers are washed with brine, dried over $Na_2SO_4$ and concentrated in vacuo. The expected product is obtained either by chromatography on silica gel or crystallization to afford the corresponding thiourea.

Step ii)

The above prepared thiourea (1 eq.) is added to a solution of the corresponding bromo acetophenone derivative Gen-8 (or commercially available products) (1.3 eq.) in EtOH. The reaction mixture is stirred at reflux for 1 h to 3 h then concentrated in vacuo. The expected product is obtained either by chromatography on silica gel or crystallization to afford the Intermediate Gen-4.

1.2.4.2. Illustrative Synthesis of Intermediate Gen-4-a: (6-Bromo-2-ethyl-imidazo[1,2-b]pyridazin-3-yl)-[4-(4-fluoro-phenyl)-thiazol-2-yl]-methyl-amine

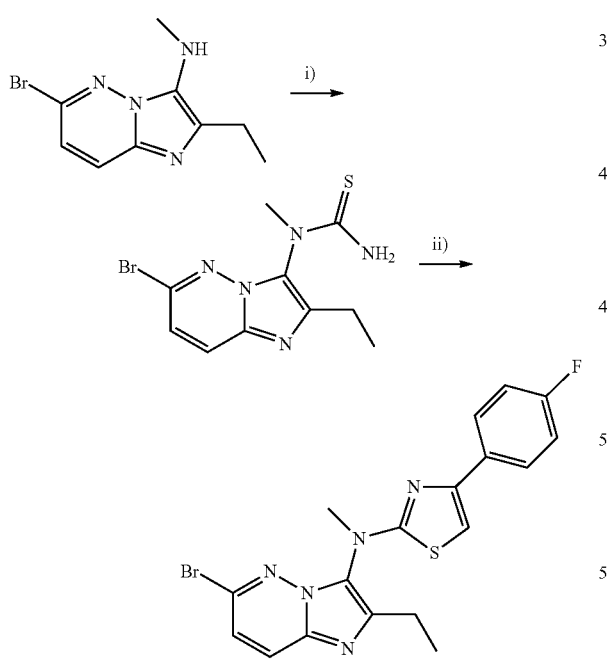

Step i)

To a suspension of (6-Bromo-2-ethyl-imidazo[1,2-b]pyridazin-3-yl)-methyl-amine (Gen-3-a) (17.28 g, 52.7 mmol, 1 eq.) in DCM (400 mL) is added TEA (30.5 mL, 219 mmol, 4.5 eq.). The mixture is stirred for 30 min at r.t. then Fmoc-isothiocyanate (32.6 g, 116 mmol, 2.2 eq.) is added. The resulting solution is stirred at r.t. overnight. The reaction is not complete, additional Fmoc-isothiocyanate (3.99 g, 14.17 mmol, 0.5 eq.) is then introduced and stirring is continued for 3 h. Piperidine (15.65 mL, 158 mmol, 3 eq.) is then introduced and the reaction mixture is stirred at r.t. for 3 h. Water is added to the solution and the layers are separated. The aqueous layer is extracted with DCM. The combined organic layers are washed with brine, dried over $Na_2SO_4$ and concentrated in vacuo. DIPE is added to the residue and stirred at r.t. overnight, the formed crystals are filtered off to afford the corresponding thiourea.

LC-MS: MW (calcd): 313 ($^{79}$Br), 315 ($^{81}$Br); m/z MW (obsd): 314 ($^{79}$Br M+H), 316 ($^{81}$Br M+H)

Step ii)

The above prepared thiourea (14.15 g, 45 mmol, 1 eq.) is added to a solution of 2-bromo-4'-fluoroacetophenone (12.71 g, 58.5 mmol, 1.3 eq.) in EtOH (300 mL). The reaction mixture is stirred at reflux for 1 h then concentrated in vacuo. The crude product is stirred at r.t. in DIPE overnight, the resulting solid is separated by filtration to afford Intermediate Gen-4-a as hydrobromide salt.

LC-MS: MW (calcd): 431 ($^{79}$Br), 433 ($^{81}$Br); m/z MW (obsd): 432 ($^{79}$Br M+H), 434 ($^{81}$Br M+H)

1.2.4.3. General Method D2

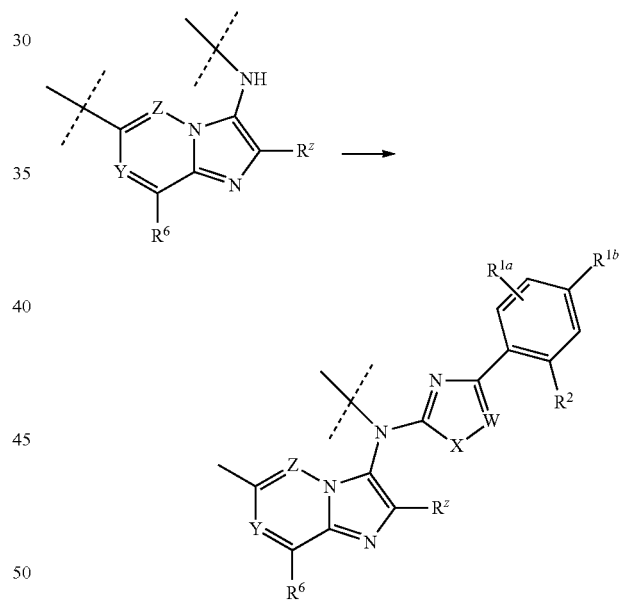

To a solution of imidazo[1,2-b]pyridazin-3-ylamine or imidazo[1,2-a]pyrazin-3-ylamine derivative (1 eq.) and the halogeno heteroaryl derivative Gen-9 (or commercially available products) (1.1 to 1.2 eq.) in THF under argon is added NaH (60% in oil suspension, 3 eq.). The reaction mixture is heated at 90° C. until completion then cooled to r.t. After cooling to r.t. the mixture is slowly quenched by addition of water and then diluted with EtOAc. The organic layer is separated and the aqueous layer is extracted with EtOAc. The combined organic layers are washed with water and brine, dried over $Na_2SO_4$, filtered and concentrated in vacuo. The residue is purified by chromatography on silica gel or by crystallization to deliver the expected intermediate.

1.2.4.4. Illustrative Synthesis of Intermediate Gen-4-d: 2-[(6-Bromo-2-ethyl-imidazo[1,2-a]pyrazin-3-yl)-methyl-amino]-4-(4-fluoro-phenyl)-thiazole-5-carbonitrile

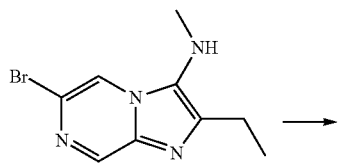

added NaH (60% in oil suspension, 658 mg, 16.4 mmol, 3 eq.). The reaction mixture is heated at 90° C. for 3 h. After cooling to r.t. the mixture is slowly quenched by addition of water (10 mL) and then diluted with EtOAc. The organic layer is separated and the aqueous layer is extracted with EtOAc. The combined organic layers are washed with water and brine, dried over $Na_2SO_4$, filtered and concentrated in vacuo. The solid is triturated for 1 h in EtOH (14 mL), filtered off, washed with EtOH (7 mL) twice, heptane (7 mL) and dried in vacuo to afford Intermediate Gen-4-d.

LC-MS: MW (calcd): 456 ($^{79}$Br), 458 ($^{81}$Br); m/z MW (obsd): 457 ($^{79}$Br M+H), 459 ($^{81}$Br M+H)

1.2.5. General Methods E, D1, D2 and D3: Synthesis of Intermediate Gen-5

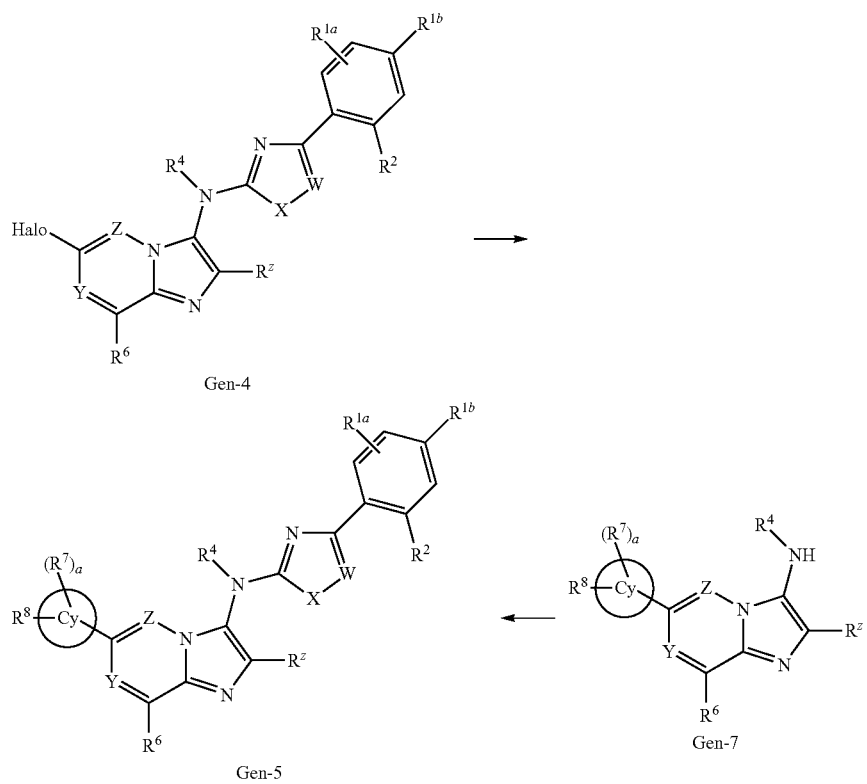

-continued

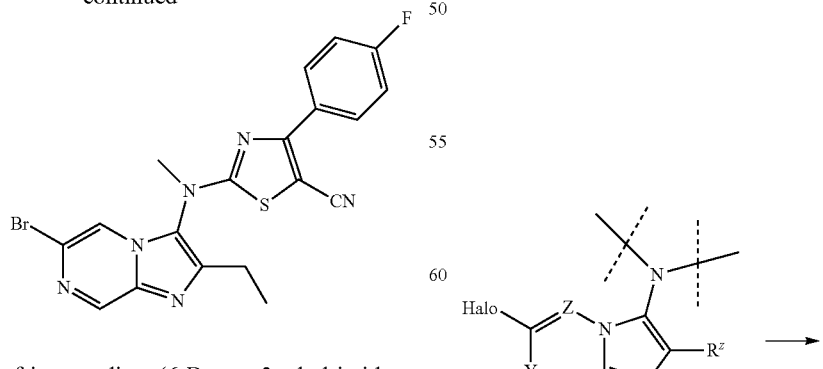

To a solution of intermediate (6-Bromo-2-ethyl-imidazo[1,2-a]pyrazin-3-yl)-methyl-amine (Gen-3-b) (1.4 g, 255.12 mmol, 1 eq.) and the chlorothiazole Gen-12-a (1.57 g, 238.67 mmol, 1.2 eq.) in THF (17.5 mL) under argon is 1.2.5.1. General Methods E1

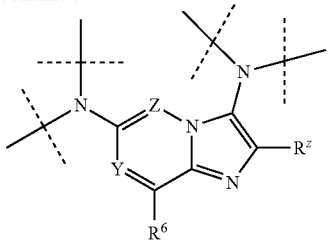

1.2.5.1.1. General Method E1a

To a solution of the 6-halo-imidazo[1,2-b]pyridazin-3-ylamine or 6-halo-imidazo[1,2-a]pyrazin-3-ylamine derivative (1 eq.) in toluene under argon are successively added the corresponding amine (5 eq.), sodium tert-butoxide (2 eq.), and then JohnPhos (0.13 eq.) and Pd$_2$(dba)$_3$ (0.1 eq.). The reaction mixture is heated at 115° C. until completion. After cooling to r.t., the crude product is filtered on Celpure® P65, the cake is washed with EtOAc. Alternatively, the filtrate is washed with brine, dried over Na$_2$SO$_4$, filtered and concentrated in vacuo, or the filtrate is concentrated in vacuo. The crude product is purified by chromatography on silica gel to afford the expected intermediate.

1.2.5.1.2. Illustrative Synthesis of Compound 1: 2-((2-ethyl-6-(piperazin-1-yl)imidazo[1,2-a]pyrazin-3-yl)(methyl)amino)-4-(4-fluorophenyl)thiazole-5-carbonitrile

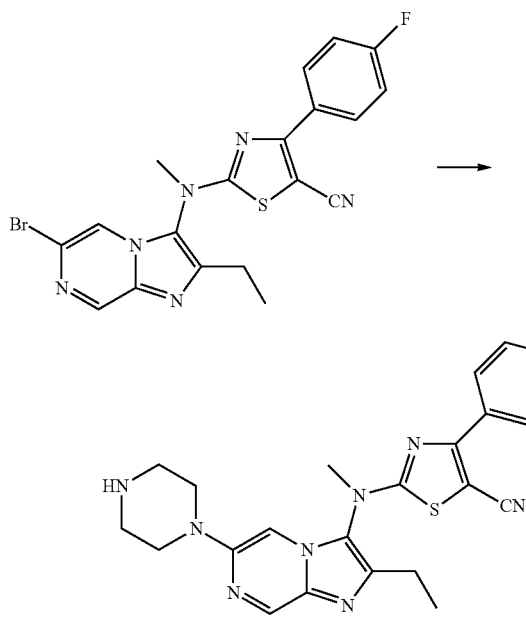

To a solution of the Intermediate Gen-4-d (1.73 g, 3.79 mmol, 1 eq.) in toluene (35 mL) under argon are successively added piperazine (1.63 g, 18.9 mmol, 5 eq.), sodium tert-butoxide (729 mg, 7.58 mmol, 2 eq.), and then JohnPhos (147 mg, 0.49 mmol, 0.13 eq.) and Pd$_2$(dba)$_3$ (348 mg, 0.38 mmol, 0.1 eq.). The reaction mixture is heated at 115° C. for 2 h. After cooling to r.t., the crude product is filtered on Celpure® P65, the cake is washed with EtOAc, and the filtrate is concentrated in vacuo. The crude product is purified by chromatography on silica gel (elution DCM/MeOH/NH$_3$: 100/0/0 to 100/7/1) to afford Compound 1.

LC-MS: MW (calcd): 462; m/z MW (obsd): 463 (M+H)

1.2.5.1.3. General Method E1b

To a solution of the 6-halo-imidazo[1,2-b]pyridazin-3-ylamine or 6-halo-imidazo[1,2-a]pyrazin-3-ylamine derivative (1 eq.) in toluene under argon are successively added the corresponding amine (1.1 to 1.6 eq.), sodium tert-butoxide (1.18 to 2 eq.), and then XantPhos or DavePhos (0.1 to 0.15 eq.) and Pd$_2$(dba)$_3$ or PdCl$_2$(dppf)$_2$ (0.05 to 0.056 eq.). The reaction mixture is heated at 90° C. until completion. After cooling to r.t., the crude product is filtered on Celite, the residue is washed with EtOAc and the filtrate is concentrated in vacuo. Water and EtOAc are added to the residue, the layers are separated, and the aqueous layer is extracted with EtOAc, the combined organic layers are washed with brine, dried over Na$_2$SO$_4$ and concentrated in vacuo. The crude product is purified by chromatography on silica gel or preparative LC-MS to afford the expected intermediate.

1.2.5.1.4. Illustrative Synthesis of Compound 79: [6-(1,1-Dioxothiomorpholin-4-yl)-2-ethyl-imidazo[1,2-b]pyridazin-3-yl]-[4-(4-fluoro-phenyl)-thiazol-2-yl]-methylamine

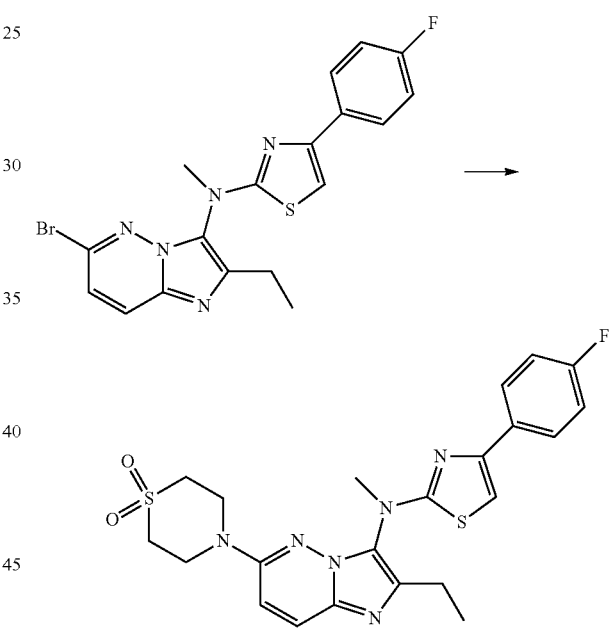

To a solution of intermediate (6-Bromo-2-ethyl-imidazo[1,2-b]pyridazin-3-yl)-[4-(4-fluoro-phenyl)-thiazol-2-yl]-methyl-amine (Gen-4-a) (100 mg, 0.231 mmol, 1 eq.) in toluene (2 mL) under argon are successively added thiomorpholine 1,1-dioxide (47 mg, 0.347 mmol, 1.5 eq.), sodium tert-butoxide (33 mg, 0.347 mmol, 1.5 eq.), and then DavePhos (14 mg, 0.035 mmol, 0.15 eq.) and Pd$_2$(dba)$_3$ (11 mg, 0.012 mmol, 0.05 eq.). The reaction mixture is heated at 90° C. for 1.75 h. After cooling to r.t., the crude product is filtered on Celite, the residue is washed with EtOAc and the filtrate is concentrated in vacuo. To the residue water and EtOAc are added, the layers are separated, and the aqueous layer is extracted with EtOAc, the combined organic layers are washed with brine, dried over Na$_2$SO$_4$ and concentrated in vacuo. The crude product is purified by preparative LC-MS to afford Compound 79.

LC-MS: MW (calcd): 486; m/z MW (obsd): 487 (M+H)

1.2.5.2. General Method E2

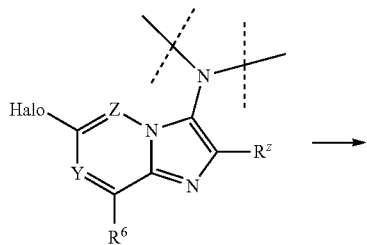

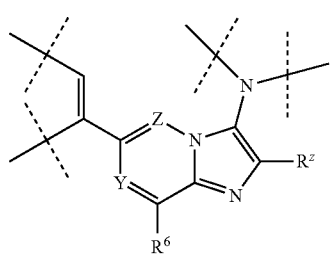

To a solution of 6-halo-imidazo[1,2-b]pyridazin-3-ylamine or 6-halo-imidazo[1,2-a]pyrazin-3-ylamine derivative (1 eq.) in a mixture dioxane/water 9/1 under argon are successively added sodium carbonate or cesium fluoride (2 to 4 eq.), the corresponding boronic ester (1.2 to 1.5 eq.), and then Pd(PPh$_3$)$_4$ or Pd(amphos)Cl$_2$ or PdCl$_2$dppf (0.05 to 0.08 eq.). The reaction mixture is heated between 85° C. and 95° C. until completion. After cooling to r.t., the crude product is filtered on Clarcel and the filtrate is concentrated in vacuo. Alternatively water and EtOAc are added to the reaction mixture, the layers are separated, and the aqueous layer is extracted again with EtOAc. The combined organic layers are washed with brine, dried over Na$_2$SO$_4$ and concentrated in vacuo. The residue is purified by chromatography on silica gel to afford the expected intermediate.

1.2.5.3. Illustrative Synthesis of Compound 193: tert-butyl 4-(2-ethyl-3-((4-(4-fluorophenyl)thiazol-2-yl)(methyl)amino)imidazo[1,2-b]pyridazin-6-yl)-5,6-dihydropyridine-1(2H)-carboxylate

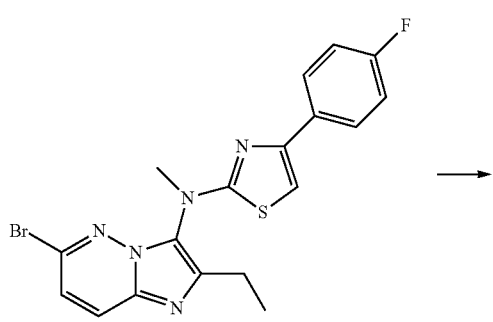

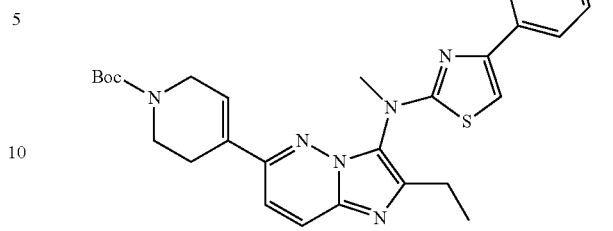

To a solution of the (6-Bromo-2-ethyl-imidazo[1,2-b]pyridazin-3-yl)-[4-(4-fluoro-phenyl)-thiazol-2-yl]-methyl-amine (Gen-4-a) (150.0 mg, 0.35 mmol, 1 eq.) in a mixture dioxane/water 9/1 (3.6 mL/0.4 mL) under argon are successively added sodium carbonate (265 mg, 1.39 mmol, 4 eq.), 4-(4,4,5,5-Tetramethyl-[1,3,2]dioxaborolan-2-yl)-3,6-dihydro-2H-pyridine-1-carboxylic acid tert-butyl ester (161 mg, 0.52 mmol, 1.5 eq.), and then Pd(PPh$_3$)$_4$ (20 mg, 0.02 mmol, 0.05 eq.). The reaction mixture is heated at 90° C. for 3 h. After cooling to r.t., water and EtOAc are added and the layers are separated, the aqueous layer is further extracted with EtOAc. The combined organic layers are washed with brine, dried over Na$_2$SO$_4$ and concentrated in vacuo. The residue is purified by chromatography on silica gel (elution with Heptane/EtOAc: 100/0 to 40/60) to afford Compound 193.

LC-MS: MW (calcd): 534; m/z MW (obsd): 535 (M+H)

1.2.5.4. General Method E3

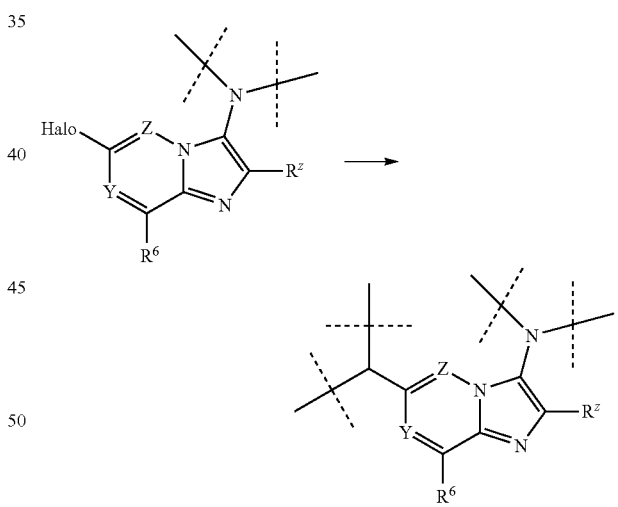

To a solution of 6-halo-imidazo[1,2-b]pyridazin-3-ylamine or 6-halo-imidazo[1,2-a]pyrazin-3-ylamine derivative (1 eq.) in DMA under argon are successively added the copper (I) iodide (0.25 eq.), PdCl$_2$dppf (0.1 eq.), and a solution of the corresponding organozinc compound (1.3 to 1.4 eq.) in DMA. The reaction mixture is heated at 80° C. for 1 h to 3 h. After cooling to r.t., the crude product is filtered on Celpure® P65, the cake is washed with EtOAc. The filtrate is washed with water and brine, dried over Na$_2$SO$_4$, filtered and concentrated in vacuo. The crude product is purified by chromatography on silica gel to afford the expected intermediate.

1.2.5.5. Illustrative Synthesis of Intermediate Gen-5-ai: 4-(3-{[5-Cyano-4-(4-fluoro-phenyl)-thiazol-2-yl]-methyl-amino}-2-ethyl-imidazo[1,2-a]pyrazin-6-yl)-piperidine-1-carboxylic acid tert-butyl ester

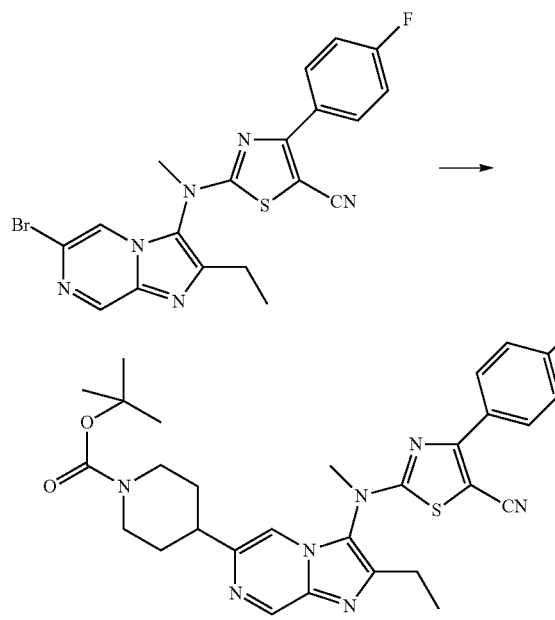

To a solution of 2-[(6-Bromo-2-ethyl-imidazo[1,2-a]pyrazin-3-yl)-methyl-amino]-4-(4-fluoro-phenyl)-thiazole-5-carbonitrile (Gen-4-d) (650 mg, 1.42 mmol, 1 eq.) in DMA (2 mL) under argon are successively added the copper (I) iodide (68 mg, 0.355 mmol, 0.25 eq.), PdCl$_2$dppf (104 mg, 0.142 mmol, 0.1 eq.), and a solution of 1-(tert-butoxy-carbonyl)piperidin-4-yl)zinc(II) iodide (prepared from 4-iodo-Boc-piperidine (Corley et al. 2004)) in DMA (1M in DMA, 1.99 mL, 1.99 mmol, 1.4 eq.). The reaction mixture is heated at 80° C. for 2 h. After cooling to r.t., the crude product is filtered on Celpure® P65, the residue is washed with EtOAc and the filtrate is washed with water and brine, dried over Na$_2$SO$_4$, filtered and concentrated in vacuo. The crude product is purified by chromatography on silica gel (elution DCM/MeOH: 100/0 to 70/30) to afford the expected Intermediate Gen-5-ai.

LC-MS: MW (calcd): 561; m/z MW (obsd): 562 (M+H)

1.2.5.6. General Method E4

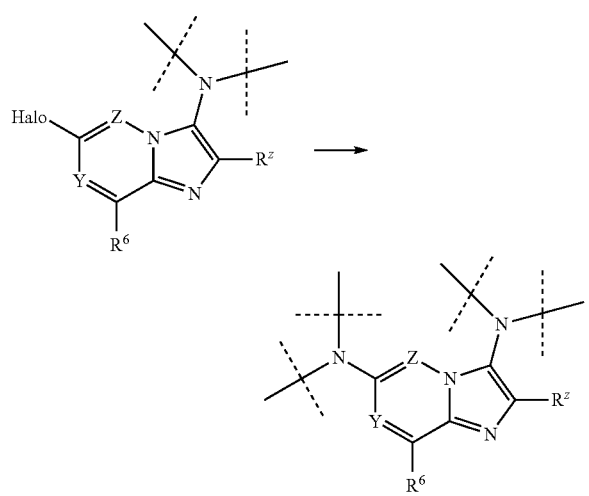

1.2.5.6.1. General Method E4a

To a solution of 6-halo-imidazo[1,2-b]pyridazin-3-ylamine or 6-halo-imidazo[1,2-a]pyrazin-3-ylamine derivative (1 eq.) in MeCN are successively added the corresponding amine Gen-10 (or commercially available products) (1.1 to 3 eq.), and DIPEA or TEA (0 to 6 eq). The reaction mixture is heated between 85° C. and 190° C. under microwave irradiation or under conventional heating until completion. After cooling to r.t., the crude product is concentrated in vacuo. The residue is directly purified by chromatography on silica gel or by preparative HPLC to afford the expected intermediate. Alternatively, the residue may be partitioned with DCM or EtOAc and water, the organic layer is separated, the aqueous layer is further extracted with DCM or EtOAc twice. The combined organic layers are washed with water and brine, dried over Na$_2$SO$_4$ and concentrated in vacuo. The crude product is purified by chromatography on silica gel or by preparative HPLC to afford the expected product.

1.2.5.6.2. Illustrative Synthesis of Compound 95: ethyl 1-(2-ethyl-3-((4-(4-fluorophenyl)thiazol-2-yl)(methyl)amino)imidazo[1,2-b]pyridazin-6-yl)piperidine-4-carboxylate

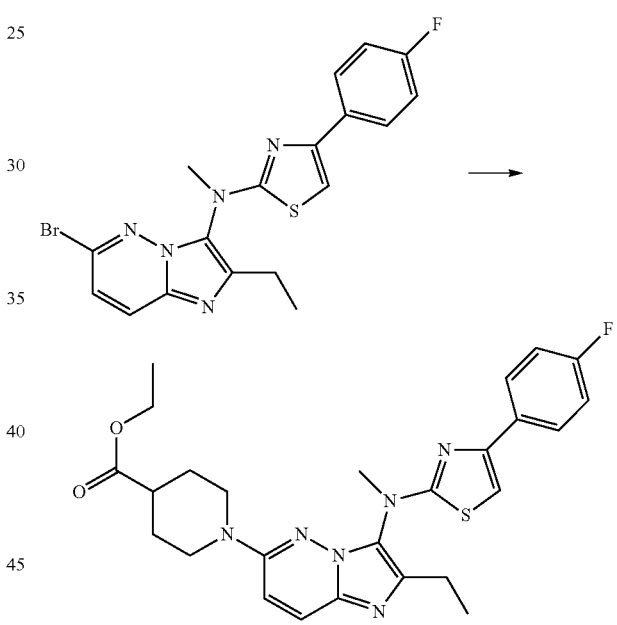

To a solution of (6-Bromo-2-ethyl-imidazo[1,2-b]pyridazin-3-yl)-[4-(4-fluoro-phenyl)-thiazol-2-yl]-methyl-amine (Gen-4-a) (70 mg, 0.160 mmol, 1 eq.) in MeCN (0.7 mL) are successively added piperidine-4-carboxylic acid ethyl ester (51 mg, 0.320 mmol, 2 eq.), and TEA (70 µL, 0.480 mmol, 3 eq). The reaction mixture is heated at 150° C. under microwave irradiation for 3 h. After cooling to r.t., the crude product is concentrated in vacuo. The residue is purified by chromatography on silica gel (elution DCM/MeOH: 100/0 to 98/2) to afford Compound 95.

LC-MS: MW (calcd): 508; m/z MW (obsd): 509 (M+H)

1.2.5.6.3. General Method E4b

To a solution of 6-halo-imidazo[1,2-b]pyridazin-3-ylamine or 6-halo-imidazo[1,2-a]pyrazin-3-ylamine derivative (1 eq.) in nBuOH are successively added the corresponding amine Gen-10 (or commercially available products) (1.1 to 4 eq.), and DIPEA or TEA (1.5 to 5 eq). The reaction mixture is heated between 120° C. and 140° C. under microwave irradiation or under conventional thermal conditions until completion. After cooling to r.t., the crude product is concentrated in vacuo. The residue is directly purified by chromatography on silica gel or by preparative HPLC to afford the expected intermediate. Alternatively, the residue is partioned with DCM or EtOAc and water, the organic layer is separated, the aqueous layer is extracted with DCM or EtOAc twice. The combined organic layers are washed with water and brine, dried over Na$_2$SO$_4$ and concentrated in vacuo. The crude product is purified by chromatography on silica gel or by preparative HPLC to afford the expected intermediate 1.2.5.6.4. Illustrative Synthesis of Compound 178: 2-((6-(3-((2S,6R)-2,6-dimethylmorpholino)pyrrolidin-1-yl)-2-ethyl-imidazo[1,2-b]pyridazin-3-yl)(methyl)amino)-4-(4-fluoro-phenyl)thiazole-5-carbonitrile

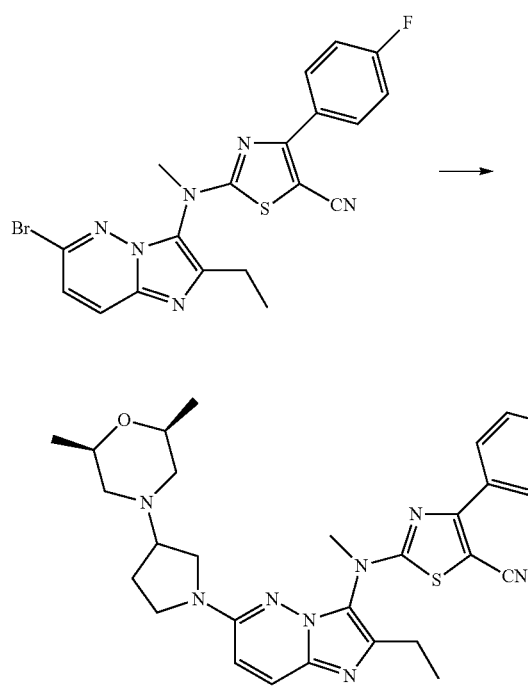

To a solution of intermediate 2-[(6-Bromo-2-ethyl-imidazo[1,2-b]pyridazin-3-yl)-methyl-amino]-4-(4-fluoro-phenyl)-thiazole-5-carbonitrile (Gen-4-b) (64.3 mg, 0.141 mmol, 1 eq.) in nBuOH (0.5 mL) are successively added the intermediate (2S,6R)-2,6-Dimethyl-4-pyrrolidin-3-yl-morpholine (Gen-10-u) (77.8 mg, 0.422 mmol, 3 eq.), and DIPEA (74 μL, 0.422 mmol, 3 eq). The reaction mixture is heated at 140° C. overnight. After cooling to r.t., the crude product is concentrated in vacuo, the residue is partitioned with DCM and water. The organic layer is separated, the aqueous layer is extracted with DCM twice. The combined organic layers are washed with water and brine, dried over Na$_2$SO$_4$ and concentrated in vacuo. The crude product is purified by chromatography on silica gel (elution DCM/MeOH: 100/0 to 94/6) to afford Compound 178.

LC-MS: MW (calcd): 560; m/z MW (obsd): 561 (M+H)

1.2.5.7. General Method E5

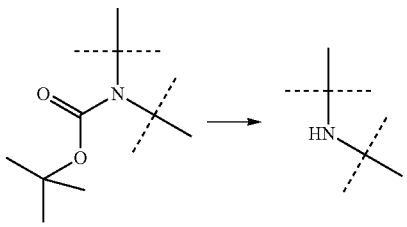

1.2.5.7.1. General Method E5a

To a solution of the boc protected amine (1 eq.) in DCM is added TFA (in excess). The reaction mixture is stirred at r.t. until completion. Then the reaction mixture is partitioned between DCM and water. The aqueous layer is washed twice with DCM. A saturated Na$_2$CO$_3$ solution is added to the aqueous layer until pH reached 8-9 and is extracted with DCM twice. The combined organic layers are then washed with brine, dried over Na$_2$SO$_4$, filtered and concentrated in vacuo to afford the expected intermediate 1.2.5.7.2. Illustrative Synthesis of Intermediate Gen-5-aa: [6-(3-Amino-azetidin-1-yl)-2-ethyl-imidazo[1,2-b]pyridazin-3-yl]-[4-(4-fluoro-phenyl)-thiazol-2-yl]-methyl-amine

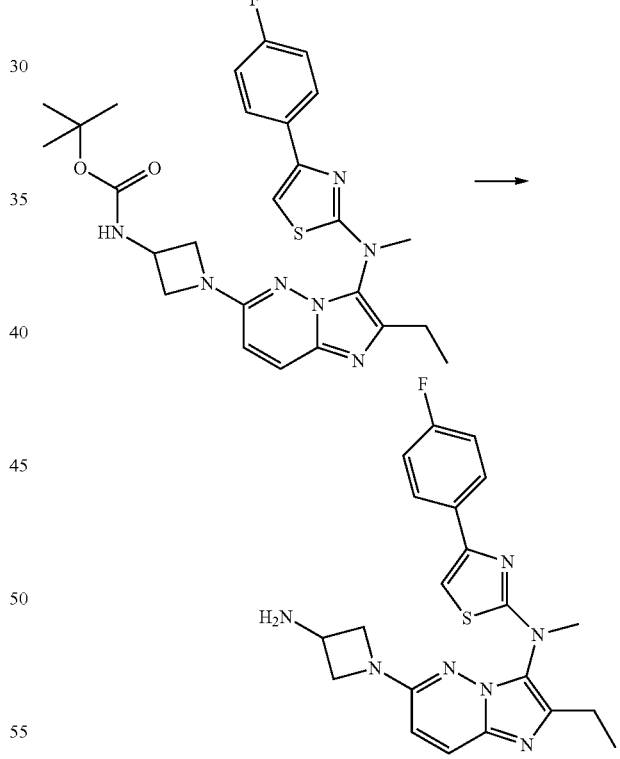

To a solution of compound 154 (428 mg, 0.780 mmol, 1 eq.) in DCM (5 mL) is added TFA (593 μL, 0.780 mmol, 10 eq.). The reaction mixture is stirred at r.t. overnight. Then the reaction mixture is partitioned between DCM and water. The aqueous layer is washed twice with DCM. A saturated Na$_2$CO$_3$ solution is added to the aqueous layer until pH reached 8-9 and is extracted with DCM twice. The combined organic layers are then washed with brine, dried over Na$_2$SO$_4$, filtered and concentrated in vacuo to afford the Intermediate Gen-5-aa.

LC-MS: MW (calcd): 423; m/z MW (obsd): 424 (M+H)

1.2.5.7.3. General Method E5b

To a solution of the boc protected amine (1 eq.) in MeOH or dioxane is added a HCl solution in Et$_2$O (2 M) or dioxane (4 M) or MeOH (1.25 M) or water (12 M) (in excess). The reaction mixture is stirred at r.t. until completion then concentrated in vacuo to afford the expected intermediate which is used directly in the next step without further purification. Alternatively, the residue is partitioned between EtOAc and a saturated Na$_2$CO$_3$ solution (until pH reached 8-9) and further extraction with EtOAc is performed. The combined organic layers are then washed with brine, dried over Na$_2$SO$_4$, filtered and concentrated in vacuo to afford the expected intermediate.

1.2.5.7.4. Illustrative Synthesis of Intermediate Gen-5-f: {6-[4-(2-Amino-ethyl)-piperazin-1-yl]-2-ethyl-imidazo[1,2-b]pyridazin-3-yl}-[4-(4-fluoro-phenyl)-thiazol-2-yl]-methyl-amine

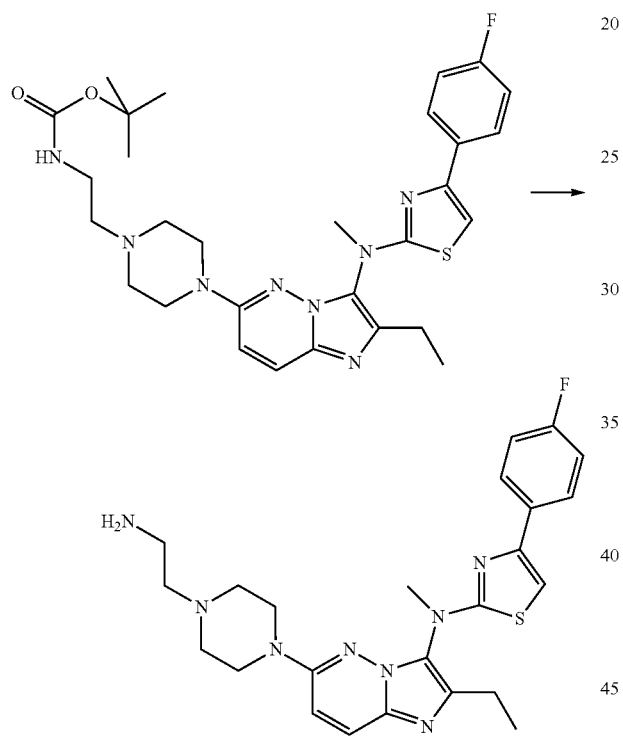

To a solution of compound 56 (190 mg, 0.327 mmol, 1 eq.) in MeOH (3 mL) is added a 4 M HCl solution in dioxane (2 mL). The reaction mixture is stirred at r.t. for 20 h then concentrated in vacuo to afford Intermediate Gen-5-f as a hydrochloride salt.

LC-MS: MW (calcd): 480; m/z MW (obsd): 481 (M+H)

1.2.5.8. General Method E6

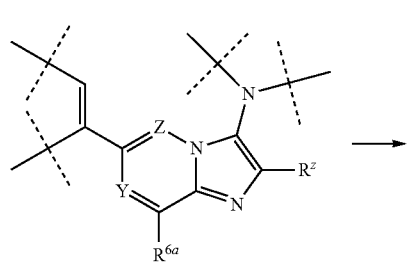

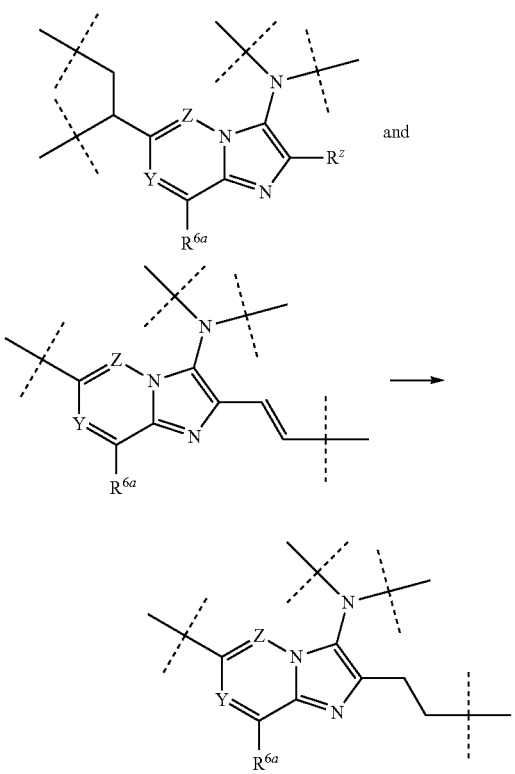

To a solution of imidazo[1,2-b]pyridazin-3-ylamine or imidazo[1,2-a]pyrazin-3-ylamine derivative (1 eq.) in a mixture THF/MeOH or EtOH/EtOAc with AcOH (0 to 0.05 eq.) is added PtO$_2$ (15 to 40%) or Pd/C (10 to 20%). The flask is evacuated and backfilled with argon. Then the reaction is evacuated and backfilled with H$_2$ and stirred at r.t. under atmospheric pressure until completion, several addition of catalyst might be required to get complete conversion. The crude product is filtered through a pad of Clarcel and washed with MeOH or EtOH/EtOAc. The filtrate is concentrated under reduced pressure. The residue is purified to chromatography on silica gel to afford the expected compound or the residue is partitioned between DCM, a saturated Na$_2$CO$_3$ solution and water and further extraction with DCM is performed. The combined organic layers are then washed with brine, dried over Na$_2$SO$_4$, filtered and concentrated in vacuo to afford the expected intermediate.

1.2.5.9. Illustrative Synthesis of Intermediate Gen-5-k: (2-Ethyl-6-piperidin-4-yl-imidazo[1,2-b]pyridazin-3-yl)-[4-(4-fluoro-phenyl)-thiazol-2-yl]-methyl-amine

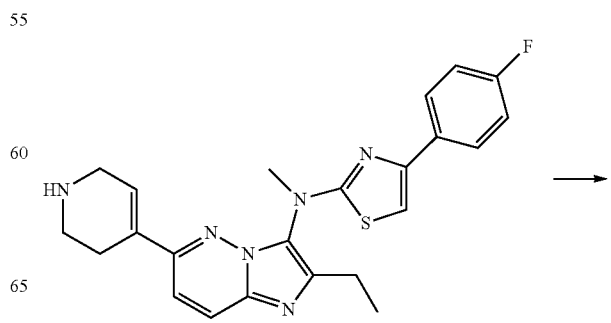

-continued

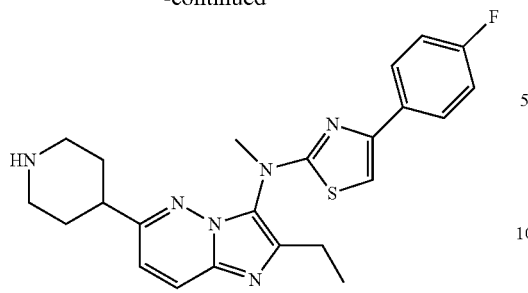

To a solution of the intermediate [2-Ethyl-6-(1,2,3,6-tetrahydro-pyridin-4-yl)-imidazo[1,2-b]pyridazin-3-yl]-[4-(4-fluoro-phenyl)-thiazol-2-yl]-methyl-amine (Gen-5-a) (300 mg, 0.637 mmol, 1 eq.) in a mixture THF/MeOH (10 mL/6 mL) is added $PtO_2$ (60 mg, 0.264 mmol, 40%). The flask is evacuated and backfilled with argon, then the reaction is evacuated and backfilled with $H_2$ and stirred at r.t. under atmospheric pressure for 18 h. Then $PtO_2$ (15 mg, 0.066 mmol, 10%) is added, the flask is evacuated and backfilled with argon, then the reaction is evacuated and backfilled with $H_2$ and stirred at r.t. under atmospheric pressure for 24 h. Then $PtO_2$ (7.5 mg, 0.033 mmol, 5%) is added, the flask is evacuated and backfilled with argon, then the reaction is evacuated and backfilled with $H_2$ and stirred at r.t. under atmospheric pressure for 7 h. Then $PtO_2$ (7.5 mg, 0.033 mmol, 5%) is added, the flask is evacuated and backfilled with argon, then the reaction is evacuated and backfilled with $H_2$ and stirred at r.t. under atmospheric pressure overnight. The crude product is filtered through a pad of Clarcel, washed with MeOH and the filtrate is concentrated under reduced pressure. The residue is partitioned between DCM, a saturated $Na_2CO_3$ solution and water and further extraction with DCM is performed. The combined organic layers are then washed with brine, dried over $Na_2SO_4$, filtered and concentrated in vacuo to afford Intermediate Gen-5-k.

LC-MS: MW (calcd): 436; m/z MW (obsd): 437 (M+H)

1.2.5.10. General Method E7

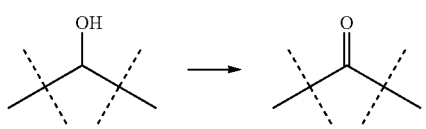

To a solution of the alcohol (1 eq.) in DCM is added Dess-Martin periodinane (1.5 to 4 eq.), the reaction mixture is stirred at r.t. overnight. Then the solid is filtered and the filtrate is concentrated in vacuo, the crude is purified by chromatography on silica gel to afford the expected compound. Alternatively the reaction mixture is quenched with water and a saturated $NaHCO_3$ solution then diluted with DCM, the aqueous layer is extracted with a mixture of DCM twice, the combined organic layers are washed with a saturated $NaHCO_3$ solution, a 10% $Na_2S_2O_3$ solution and brine, dried over $Na_2SO_4$, filtered and concentrated in vacuo. The residue is purified by chromatography on silica gel to afford the expected compound.

1.2.5.11. Illustrative Synthesis of Compound 172: 2-((2-ethyl-6-(3-oxopyrrolidin-1-yl)imidazo[1,2-b]pyridazin-3-yl)(methyl)amino)-4-(4-fluorophenyl)thiazole-5-carbonitrile

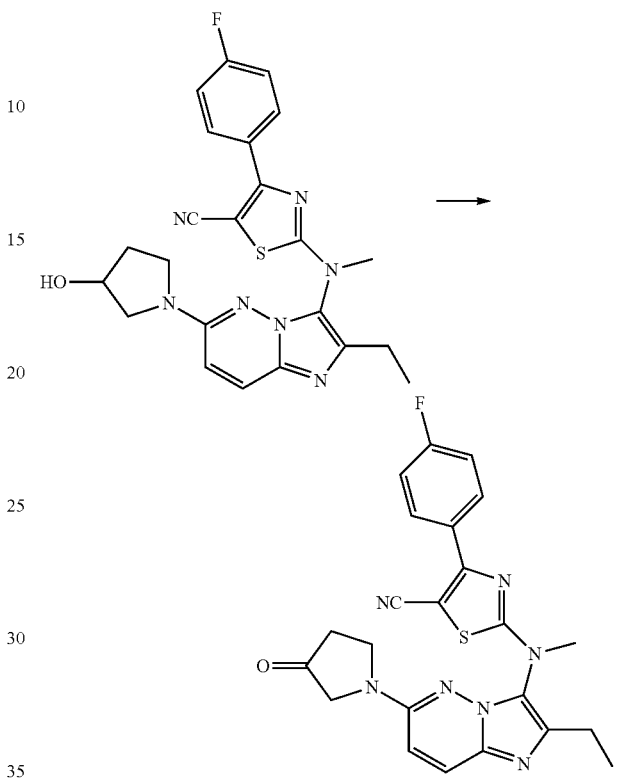

To a solution of compound 171 (40 mg, 0.086 mmol, 1 eq.) in DCM (3 mL) is added Dess-Martin periodinane (146 mg, 0.345 mmol, 4 eq.), the reaction mixture is stirred at r.t. overnight. The reaction mixture is quenched with water and a saturated $NaHCO_3$ solution then diluted with DCM, the aqueous layer is extracted with a mixture of DCM twice, the combined organic layers are washed with a saturated $NaHCO_3$ solution, a 10% $Na_2S_2O_3$ solution and brine, dried over $Na_2SO_4$, filtered and concentrated in vacuo. The residue is purified by chromatography on silica gel (elution DCM/MeOH: 100/0 to 96/4) to afford the expected Compound 172.

LC-MS: MW (calcd): 461; m/z MW (obsd): 462 (M+H)

1.2.5.12. General Method E8

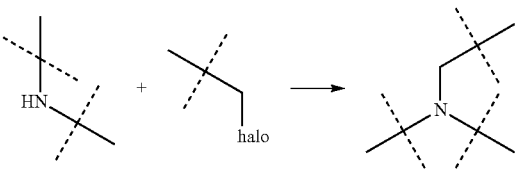

To a solution of amino derivative (1 eq.) in MeCN or DMF or n-BuOH are added potassium carbonate (2 to 3 eq.) or TEA (5 eq.) or DIPEA (2 eq.), halogenated derivative Gen-11 (or commercially available products) (1.5 to 4 eq.) and NaI (0 to 0.1 eq.). The reaction mixture is heated in thermic or microwave conditions between 70° C. to 170° C. for 1.5 h to 12 h then cooled to r.t. The reaction mixture is quenched with water and diluted with EtOAc. The aqueous layer is extracted with EtOAc. The combined organic layers are washed with water and brine, dried over Na$_2$SO$_4$ and concentrated in vacuo. The residue is purified by chromatography on silica gel to deliver the expected compound. If the product is precipitated in the reaction mixture the following work up is used: after cooling to r.t., the reaction mixture is filtered. The solid is washed with MeCN, water and dried in vacuo to afford the expected product.

1.2.5.13. Illustrative Synthesis of Compound 34: (S)-2-(4-(2-ethyl-3-((4-(4-fluorophenyl)thiazol-2-yl)(methyl)amino)imidazo[1,2-b]pyridazin-6-yl)piperazin-1-yl)-1-(3-hydroxypyrrolidin-1-yl)ethanone

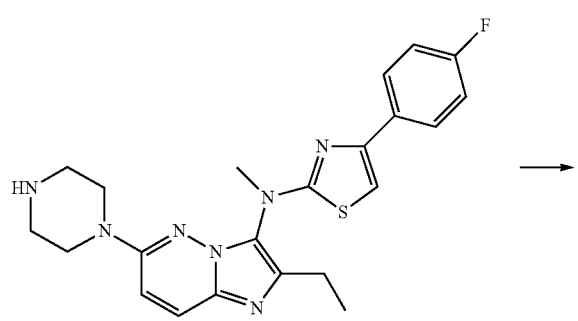

To a solution of Intermediate Gen-5-j (100 mg, 0.229 mmol, 1 eq.) in MeCN (5 mL) are added potassium carbonate (63 mg, 0.457 mmol, 2 eq), and intermediate (S)-2-Chloro-1-(3-hydroxy-pyrrolidin-1-yl)-ethanone (Gen-11-e) (75 mg, 0.457 mmol, 2 eq.). The reaction mixture is heated at 90° C. for 1.5 h then cooled to r.t, and stirred overnight. The reaction mixture is quenched with water and diluted with EtOAc. The aqueous layer is extracted with EtOAc. The combined organic layers are washed with water and brine, dried over Na$_2$SO$_4$ and concentrated in vacuo. The residue is purified by chromatography on silica gel (elution with DCM/MeOH: 100/0 to 93/7) to deliver the expected Compound 34.

LC-MS: MW (calcd): 564; m/z MW (obsd): 565 (M+H)

1.2.5.14. General Methods E9
1.2.5.14.1. General Method E9a

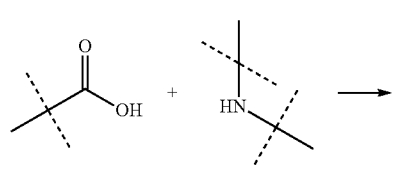 + 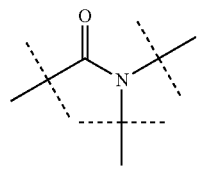 →

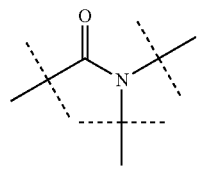

To a solution of acid (1 to 1.1 eq.) in DCM or DMF are added HOBT (1.2 eq.) and EDC.HCl (1.1 to 1.2 eq.). The reaction mixture is stirred at r.t. for 30 to 45 min then a prepared solution of amine (1 to 1.1 eq.) in DCM or DMF with TEA (3 eq.) is added. The reaction mixture is stirred at r.t. until completion, then water and a 1 M HCl solution are added, the aqueous layer is extracted with DCM or EtOAc, the organic layer is washed with a saturated Na$_2$CO$_3$ solution or water, and brine, dried over Na$_2$SO$_4$, filtered and concentrated in vacuo. The residue is purified by chromatography on silica gel or preparative LC-MS to afford the expected compound.

1.2.5.14.2. Illustrative Synthesis of Compound 97: 1-(2-ethyl-3-((4-(4-fluorophenyl)thiazol-2-yl)(methyl)amino)imidazo[1,2-b]pyridazin-6-yl)-N-(2-hydroxyethyl)piperidine-4-carboxamide

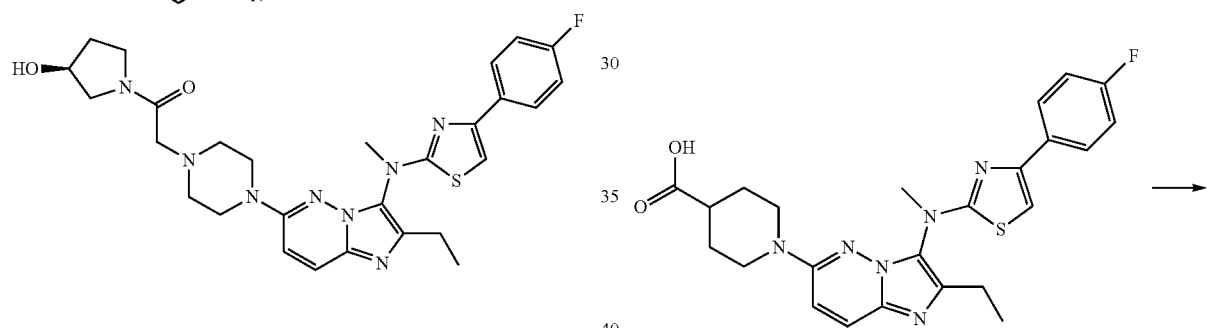

To a solution of Compound 96 (40 mg, 0.08 mmol, 1 eq.) in DMF (0.5 mL) are added HOBT (14 mg, 0.1 mmol, 1.2 eq.) and EDC.HCl (17 mg, 0.09 mmol, 1.1 eq.). The reaction mixture is stirred at r.t. for 30 min then a prepared solution of ethanolamine (15 mg, 0.09 mmol, 1.1 eq.) in DMF with TEA (35 L, 0.25 mmol, 3 eq.) is added. The reaction mixture is stirred at r.t. overnight, then water and a 1 M HCl solution are added, the aqueous layer is extracted with EtOAc, the organic layer is washed with water three times, dried over Na$_2$SO$_4$, filtered and concentrated in vacuo. The residue is purified by preparative LC-MS to afford Compound 97.

LC-MS: MW (calcd): 523; m/z MW (obsd): 524 (M+H)

1.2.5.14.3. General Method E9b

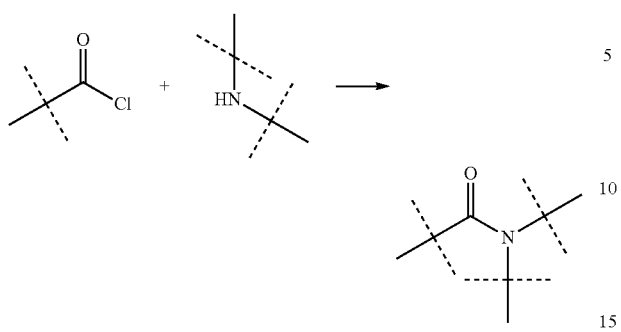

To a solution of amine (1 eq.) in DCM are added TEA (3 to 5 eq.) followed by acyl chloride derivative (1 to 2 eq.). The reaction mixture is stirred at r.t. until completion, then quenched with water and the aqueous layer is extracted with DCM twice. The organic layer is washed with water, and brine, dried over $Na_2SO_4$, filtered and concentrated in vacuo. The residue is purified by chromatography on silica gel to afford the expected compound.

1.2.5.14.4. Illustrative Synthesis of Compound 124: 1-(5-(2-ethyl-3-((4-(4-fluorophenyl)thiazol-2-yl)(methyl)amino)imidazo[1,2-b]pyridazin-6-yl)hexahydropyrrolo[3,4-c]pyrrol-2(1H)-yl)ethanone

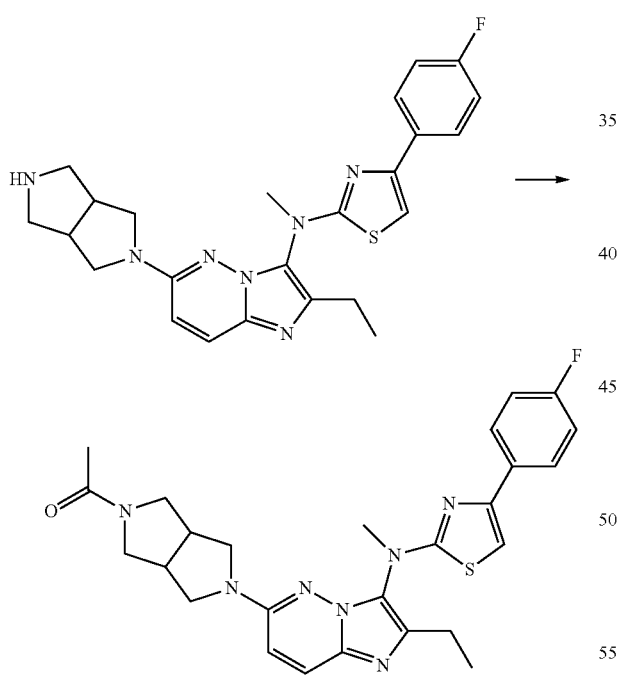

To a solution of intermediate [2-Ethyl-6-(hexahydro-pyrrolo[3,4-c]pyrrol-2-yl)-imidazo[1,2-b]pyridazin-3-yl]-[4-(4-fluoro-phenyl)-thiazol-2-yl]-methyl-amine (Gen-5-d) (100 mg, 0.2 mmol, 1 eq.) in DCM (4 mL) are added TEA (139 µL, 0.8 mmol, 4 eq.) followed by acetyl chloride (19 µL; 0.260 mmol, 1.3 eq.). The reaction mixture is stirred at r.t. overnight, then quenched with water and the aqueous layer is extracted with DCM twice. The organic layer is washed with water, and brine, dried over $Na_2SO_4$, filtered and concentrated in vacuo. The residue is purified by chromatography on silica gel (elution with DCM/MeOH: 100/0 to 98/2) to afford Compound 124.

LC-MS: MW (calcd): 505; m/z MW (obsd): 506 (M+H)

1.2.5.14.5. General Method E9c

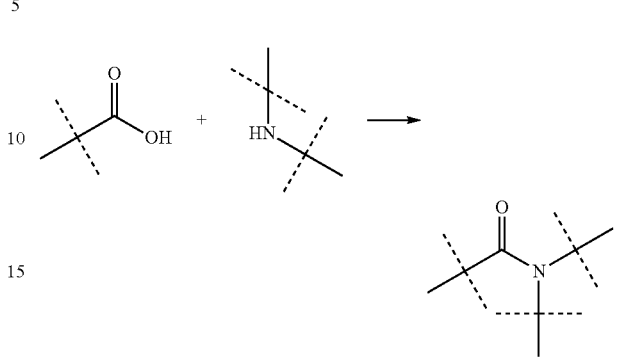

To a solution of acid (1.1 to 1.6 eq.) in DCM or DMF are added HATU (1.1 to 1.6 eq.) and DIPEA (2.2 to 4 eq.). The reaction mixture is stirred at r.t. for 15 min, then amine derivative (1 eq.) is added. The reaction mixture is stirred at r.t. until completion, then water is added, the aqueous layer is extracted with DCM or EtOAc, the organic layer is washed with brine, dried over $Na_2SO_4$, filtered and concentrated in vacuo. The residue is purified by chromatography on silica gel or preparative LC-MS to afford the expected compound.

1.2.5.14.6. Illustrative Synthesis of Compound 136: N-(1-(2-ethyl-3-((4-(4-fluorophenyl)thiazol-2-yl)(methyl)amino)imidazo[1,2-b]pyridazin-6-yl)pyrrolidin-3-yl)-2-hydroxyacetamide

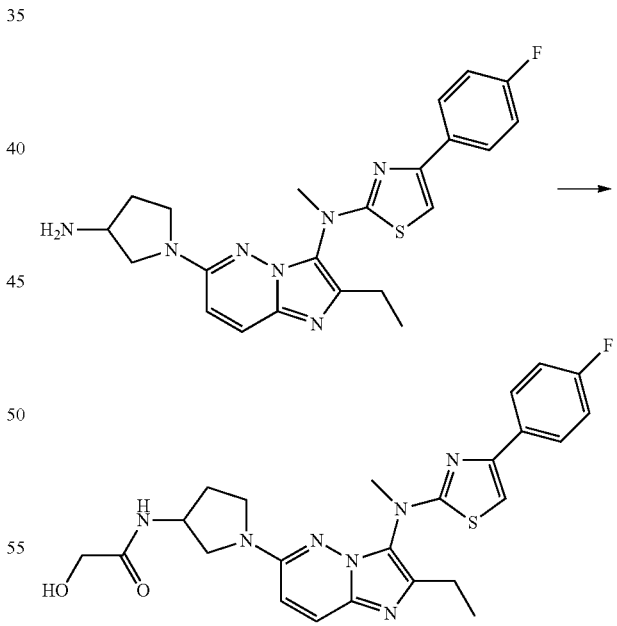

To a solution of hydroxy-acetic acid (26 mg, 0.34 mmol, 1.6 eq.) in DCM (2 mL) are added HATU (129 mg, 0.34 mmol, 1.6 eq.) and DIPEA (80 µL, 0.46 mmol, 2.2 eq.). The reaction mixture is stirred at r.t. for 15 min, then Compound 134 (90 mg, 0.21 mmol, 1 eq.) is added. The reaction mixture is stirred at r.t. overnight, then water is added, the aqueous layer is extracted with DCM. The organic layer is washed with brine, dried over $Na_2SO_4$, filtered and concentrated in vacuo. The residue is purified by chromatography on silica gel (elution with DCM/MeOH: 100/0 to 95/5) then by preparative LC-MS to afford Compound 136.

LC-MS: MW (calcd): 495; m/z MW (obsd): 496 (M+H)

1.2.5.15. General Method E10

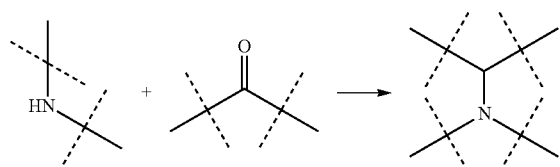

To a solution of the appropriate amine (1.0 eq.) in MeOH are added TEA (0 to 3 eq.), acetic acid if needed (0 to 3 eq) and the aldehyde or ketone (1.5 to 2 eq.). The reaction mixture is stirred at r.t. for 1 h to overnight then NaBH$_3$CN (1.5 to 3 eq.) is added. The reaction mixture is stirred at r.t. for 8 h to 16 h, then concentrated in vacuo. The residue is dissolved in a mixture of DCM and water or a saturated NaHCO$_3$ solution, the two phases are separated and the aqueous phase is extracted with DCM. The combined organic layers are washed with water and brine, dried over Na$_2$SO$_4$, filtered and concentrated in vacuo. The residue is purified by chromatography on silica gel to afford the expected product.

1.2.5.16. Illustrative Synthesis of Compound 38: N-(2-ethyl-6-(4-(oxetan-3-yl)piperazin-1-yl)imidazo[1,2-b]pyridazin-3-yl)-4-(4-fluorophenyl)-N-methylthiazol-2-amine

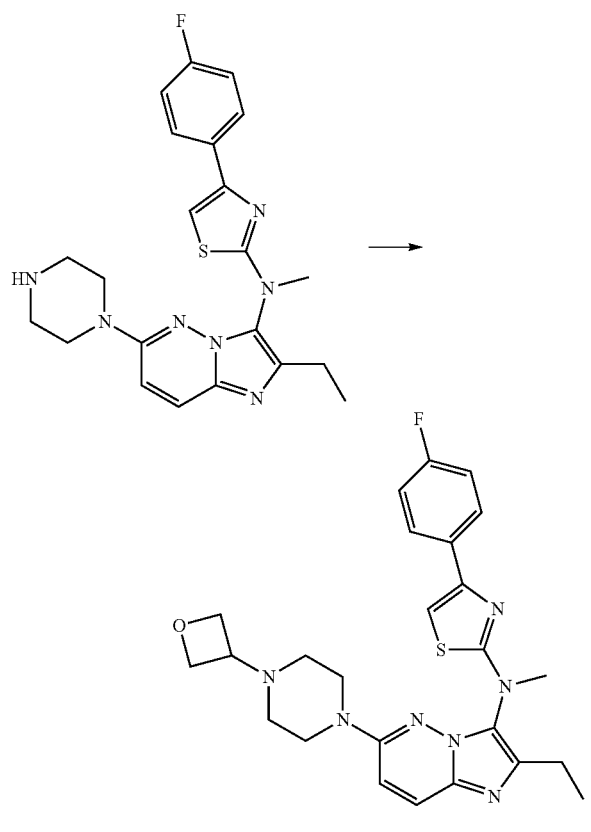

To a solution of Intermediate (2-Ethyl-6-piperazin-1-yl-imidazo[1,2-b]pyridazin-3-yl)-[4-(4-fluoro-phenyl)-thiazol-2-yl]-methyl-amine (Gen-5-j) (50 mg, 0.09 mmol, 1.0 eq.) in MeOH (2 mL) are added TEA (35 µL, 0.27 mmol, 3 eq) and oxetan-3-one (7.9 µL, 0.135 mmol, 1.5 eq.). The reaction mixture is stirred at r.t. for 14 h then NaBH$_3$CN (17 mg, 0.27 mmol, 3 eq.) is added. The reaction mixture is stirred at r.t. 8 h, then concentrated in vacuo. The residue is dissolved in a mixture of DCM and a saturated NaHCO$_3$ solution, the two phases are separated and the aqueous phase is extracted with DCM. The combined organic layers are washed with water and brine, dried over Na$_2$SO$_4$, filtered and concentrated in vacuo. The residue is purified by chromatography on silica gel (elution DCM/MeOH: 100/0 to 90/10) to afford Compound 38.

LC-MS: MW (calcd): 493; m/z MW (obsd): 494 (M+H)

1.2.5.17. General Method E11

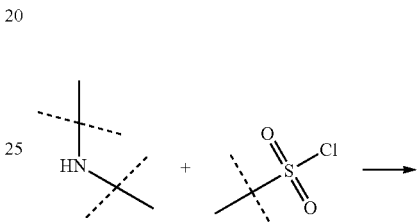

To a solution of the appropriate amine (1 eq.) in DCM or a mixture of DCM/MeCN (3/1) at 0° C. are added TEA (2.5 to 5 eq.) and sulfonyl chloride (1.1 to 2 eq.). The reaction mixture is stirred at r.t. until completion. The crude product is quenched with water and diluted with DCM, the aqueous layer is extracted with DCM. The combined organic layers are washed with water and brine, dried over Na$_2$SO$_4$, filtered and concentrated in vacuo. The residue is purified by chromatography on silica gel to afford the expected compound.

1.2.5.18. Illustrative synthesis of Compound 123: N-(2-ethyl-6-(5-(methylsulfonyl)hexahydropyrrolo[3,4-c]pyrrol-2(1H)-yl)imidazo[1,2-b]pyridazin-3-yl)-4-(4-fluorophenyl)-N-methylthiazol-2-amine

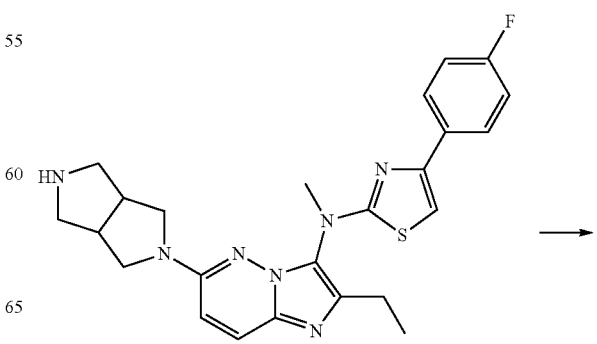

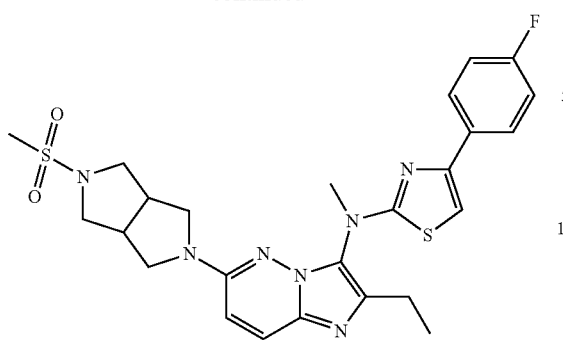

To a solution of intermediate [2-Ethyl-6-(hexahydro-pyrrolo[3,4-c]pyrrol-2-yl)-imidazo[1,2-b]pyridazin-3-yl]-[4-(4-fluoro-phenyl)-thiazol-2-yl]-methyl-amine (Gen-5-d) (100 mg, 0.2 mmol, 1 eq.) in DCM (6 mL) at 0° C. are added TEA (139 µL, 0.8 mmol, 4 eq.) and mesyl chloride (20 µL, 0.26 mmol, 1.3 eq.). The reaction mixture is stirred at r.t. for 2.5 h. The crude product is quenched with water and diluted with DCM, the aqueous layer is extracted with DCM. The combined organic layers are washed with water and brine, dried over Na$_2$SO$_4$, filtered and concentrated in vacuo. The residue is purified by chromatography on silica gel (elution with DCM/MeOH: 100/0 to 100/1) to afford the expected compound 123.

LC-MS: MW (calcd): 541; m/z MW (obsd): 542 (M+H)

1.2.5.19. General Methods E12

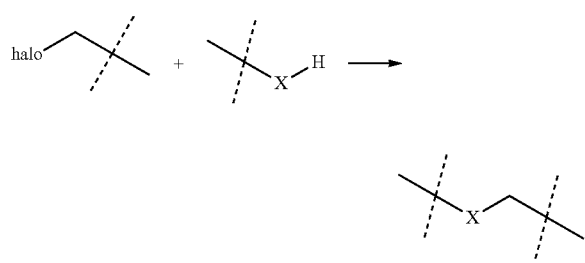

X = NR, O, S

To a solution of the corresponding nucleophile (2 to 6 eq.) in THF or a mixture of THF/MeCN (3/2) are added NaI (0.15 to 0.17 eq.) and halogenalkyl group containing imidazo[1,2-b]pyridazin-3-ylamine or imidazo[1,2-a]pyrazin-3-ylamine derivative (1 eq.). The reaction mixture is heated between 150° C. and 180° C. under microwave irradiation for 1.5 h to 2 h. After cooling, the reaction mixture is concentrated in vacuo, then the crude product is purified by preparative LC-MS to afford the expected compound. Alternatively the crude product is partitioned between water and DCM, the aqueous layer is extracted with DCM three times. The combined organic layers are washed with a saturated NaHCO$_3$ solution and brine, dried over Na$_2$SO$_4$, filtered and concentrated in vacuo. The residue is purified by chromatography on silica gel to afford the expected compound.

1.2.5.20. Illustrative Synthesis of Compound 127: N-(2-ethyl-6-(5-(3-morpholinopropylsulfonyl)hexahydropyrrolo[3, 4-c]pyrrol-2(1H)-yl)imidazo[1,2-b]pyridazin-3-yl)-4-(4-fluorophenyl)-N-methylthiazol-2-amine

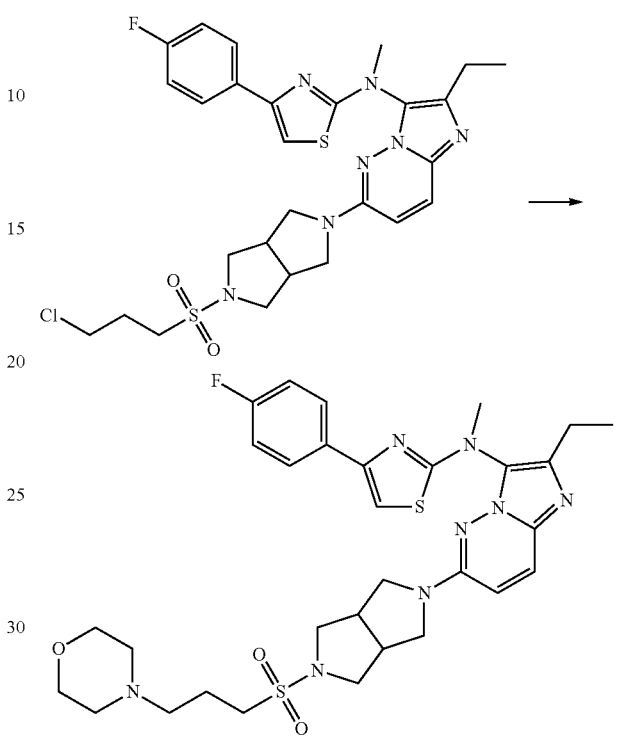

To a solution of morpholine (39 µL, 0.447 mmol, 6 eq.) in THF (3 mL) are added NaI (2 mg, 0.012 mmol, 0.17 eq.) and Compound 125 (45 mg, 0.074 mmol, 1 eq.). The reaction mixture is heated at 180° C. under microwave irradiation for 1.5 h. After cooling, the reaction mixture is concentrated in vacuo, then the crude product is purified by preparative LC-MS to afford Compound 127.

LC-MS: MW (calcd): 654; m/z MW (obsd): 655 (M+H)

1.2.5.21. General Method E13

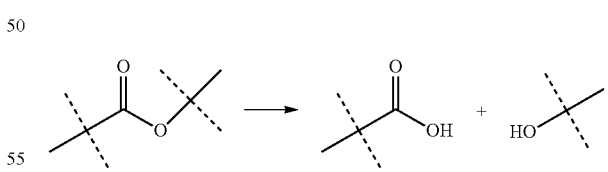

To a solution of the corresponding ester (1 eq.) in a mixture of THF/water (2/1) is added LiOH (4 to 5 eq.). The reaction mixture is stirred at r.t. until completion, then the reaction mixture is acidified with a 1M HCl solution. The aqueous layer is extracted with a mixture of Et$_2$O/EtOAc twice, the combined organic layers are washed with water and brine, dried over Na$_2$SO$_4$, filtered and concentrated in vacuo. The residue is purified by chromatography on silica gel to afford the expected product.

1.2.5.22. Illustrative Synthesis of Compound 96: 1-(2-ethyl-3-((4-(4-fluorophenyl)thiazol-2-yl)(methyl)amino)imidazo[1,2-b]pyridazin-6-yl)piperidine-4-carboxylic acid

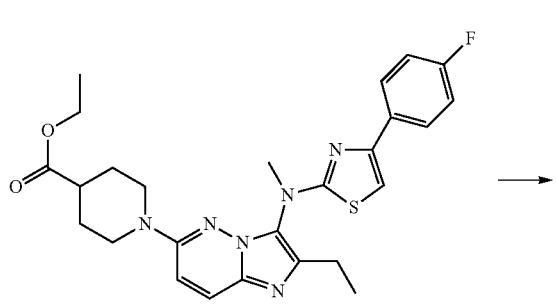

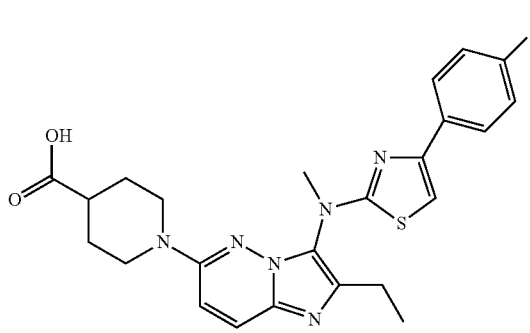

To a solution of compound 95 (70 mg, 0.14 mmol, 1 eq.) in a mixture of THF/water (2 mL/1 mL) is added LiOH (13 mg, 0.55 mmol, 5 eq.). The reaction mixture is stirred at r.t. for 3 days, then the reaction mixture is acidified with a 1 M HCl solution. The aqueous layer is extracted with a mixture of Et₂O/EtOAc twice, the combined organic layers are washed with water and brine, dried over Na₂SO₄, filtered and concentrated in vacuo. The residue is purified by chromatography on silica gel (elution with DCM/MeOH: 98/2 to 92/8) to afford Compound 96.

LC-MS: MW (calcd): 480; m/z MW (obsd): 481 (M+H)

1.2.5.23. General Method E14

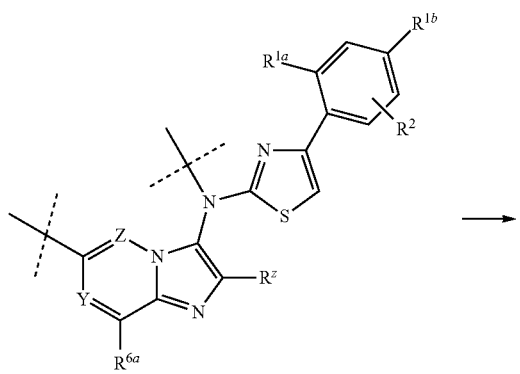

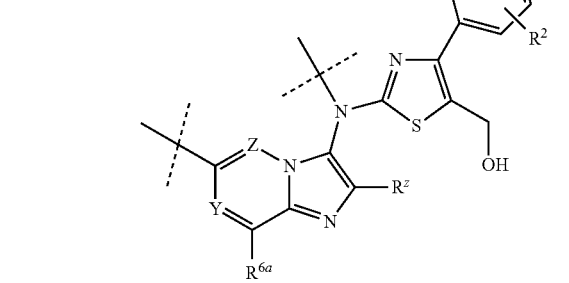

To a solution of thiazole derivative (1 eq.) in THF are added formaldehyde (in excess.), TEA (in excess) and water. The reaction mixture is heated to 140° C. under microwave irradiation for 40 min to 16 h. The crude product mixture is quenched with water and an aqueous NH₃ solution. The aqueous layer is extracted with EtOAc. The combined organic layers are washed with water and brine, dried over Na₂SO₄, filtered and concentrated in vacuo. The residue is purified by chromatography on silica gel or preparative HPLC to deliver the expected product.

1.2.5.24. Illustrative Synthesis of Compound 144: (1-(2-ethyl-3-((4-(4-fluorophenyl)-5-(hydroxymethyl)thiazol-2-yl)(methyl)amino)imidazo[, 2-b]pyridazin-6-yl)pyrrolidin-3-yl)methanol

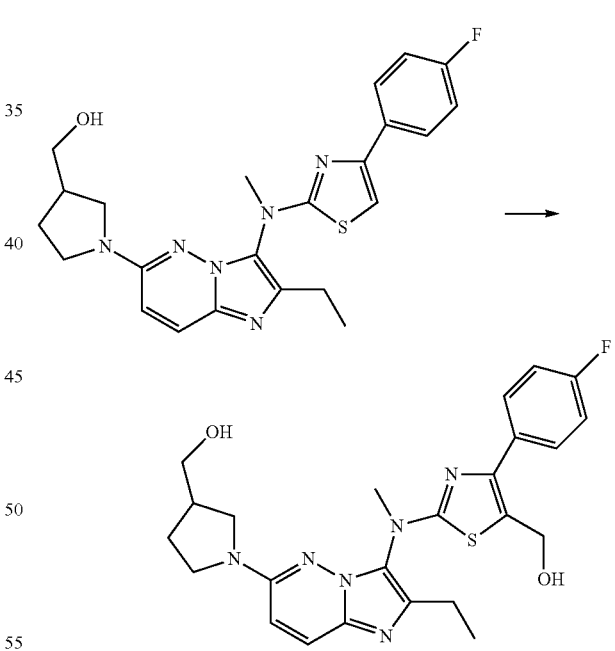

To a solution of compound 143 (100 mg, 0.22 mmol, 1 eq.) in THF (1 mL) are added aqueous formaldehyde (1.2 mL), TEA (250 µL) and water (1 mL). The reaction mixture is heated at 140° C. under microwave irradiation for 1 h. The crude product mixture is quenched with water and a aqueous NH₃ solution. The aqueous layer is extracted with EtOAc twice. The combined organic layers are washed with water and brine, dried over Na₂SO₄, filtered and concentrated in vacuo. The residue is purified by chromatography on silica gel (elution DCM/MeOH: 100/0 to 95/5) to afford Compound 144.

LC-MS: MW (calcd): 482; m/z MW (obsd): 483 (M+H)

1.2.5.25. General Method E15

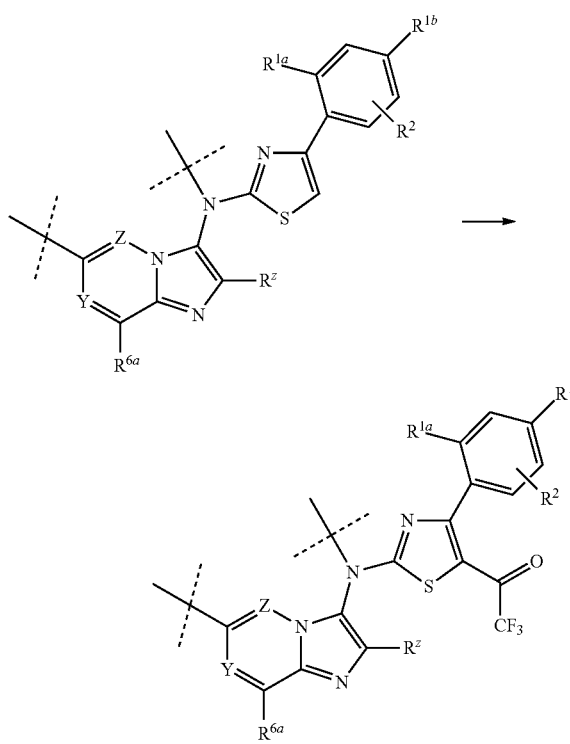

To a solution of thiazole derivative (1 eq.) in pyridine at 0° C. is slowly added trifluoroacetic anhydride (5 to 6 eq.). The reaction mixture is stirred at 0° C. for 1 h then partitioned between DCM or EtOAc and water or brine. The organic phase is separated. The aqueous layer is extracted with DCM. The combined organic layers are washed with water and brine, dried over MgSO$_4$, filtered and concentrated in vacuo. The residue is purified by chromatography on silica gel to afford the expected product.

1.2.5.26. Illustrative Synthesis of Intermediate Gen-5-af: 4-(2-Ethyl-3-{[4-(4-fluoro-phenyl)-5-(2,2,2-trifluoro-acetyl)-thiazol-2-yl]-methyl-amino}-imidazo[1,2-b]pyridazin-6-yl)-piperazine-1-carboxylic acid tert-butyl ester

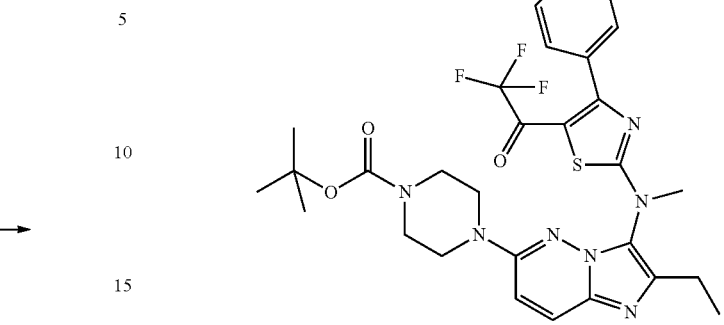

To a solution of intermediate 4-(2-Ethyl-3-{[4-(4-fluoro-phenyl)-thiazol-2-yl]-methyl-amino}-imidazo[1,2-b]pyridazin-6-yl)-piperazine-1-carboxylic acid tert-butyl ester (Gen-5-i) (250 mg, 0.47 mmol, 1 eq.) in pyridine (5 mL) at 0° C. is slowly added trifluoroacetic anhydride (328 µL, 2.33 mmol, 5 eq.). The reaction mixture is stirred at 0° C. for 1 h then partitioned between EtOAc and brine, the organic phase is separated. The aqueous layer is extracted with EtOAc twice. The combined organic layers are washed with water and brine, dried over MgSO$_4$, filtered and concentrated in vacuo. The crude product is purified by chromatography on silica gel (elution with DCM/MeOH: 100/01 to 90/10). The residue is dissolved in DCM, washed with a saturated NaHCO$_3$ solution and brine, dried over MgSO$_4$, filtered and concentrated in vacuo to afford Intermediate Gen-5-af.

LC-MS: MW (calcd): 633; m/z MW (obsd): 634 (M+H)

1.2.5.27. General Methods E16

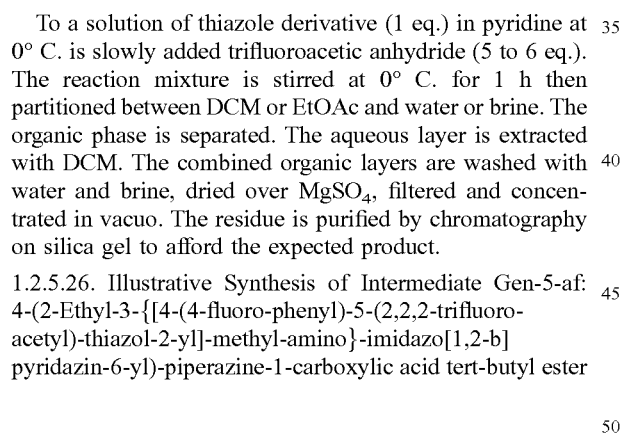

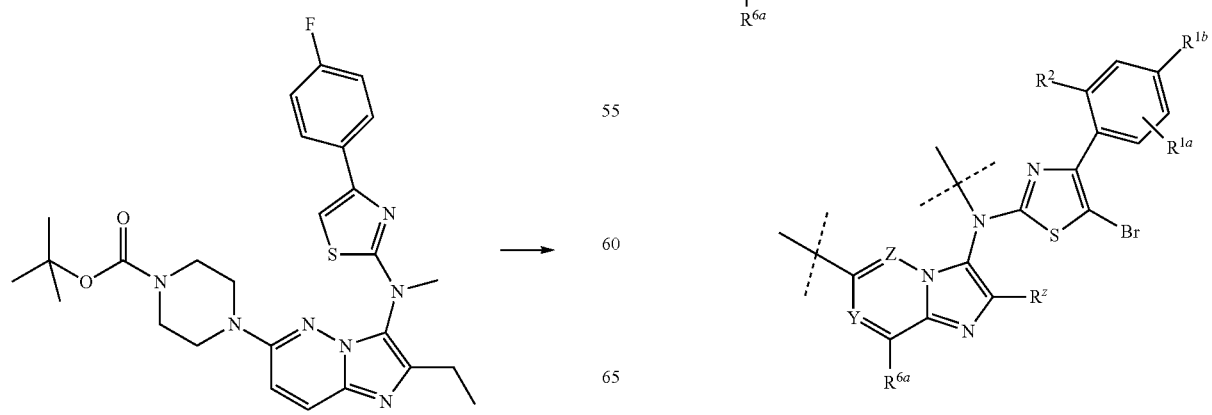

To a solution of thiazole derivative (1 eq.) in DCM is added polymer-supported bromide (1.1 eq.). The mixture is stirred vigorously at r.t. for 4 h to overnight. The crude mixture is filtered, the residue is washed with DCM and MeOH. The filtrate is concentrated in vacuo to afford the expected product.

1.2.5.28. Illustrative Synthesis of Intermediate Gen-5-m: 2-[4-(3-{[5-Bromo-4-(4-fluoro-phenyl)-thiazol-2-yl]-methyl-amino}-2-ethyl-imidazo[1,2-b]pyridazin-6-yl)-piperazin-1-yl]-N,N-dimethyl-acetamide

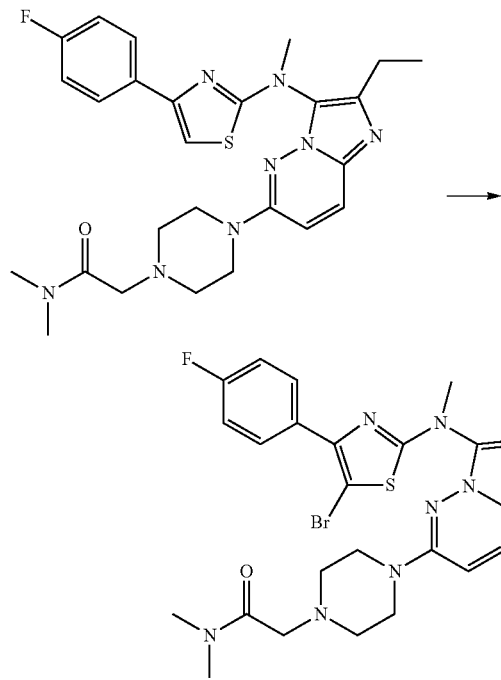

To a solution of Compound 42 (195 mg, 0.373 mmol, 1 eq.) in DCM (10 mL) is added polymer-supported bromide (274 mg, 0.410 mmol, 1.1 eq.). The mixture is stirred vigorously at r.t. overnight. The crude mixture is filtered, the residue is washed with DCM and MeOH. The filtrate is concentrated in vacuo to afford Intermediate Gen-5-m.

LC-MS: MW (calcd): 600 ($^{79}$Br), 602 ($^{81}$Br); m/z MW (obsd): 601 ($^{79}$Br M+H), 603 ($^{81}$Br M+H)

1.2.5.29. General Method E17

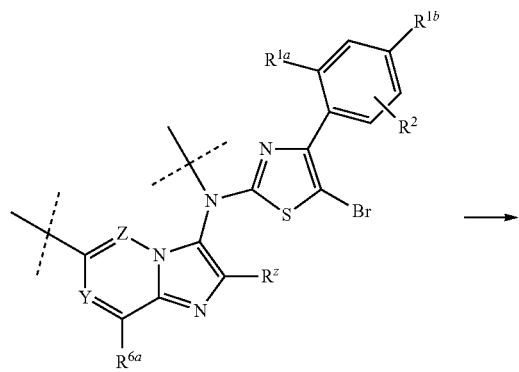

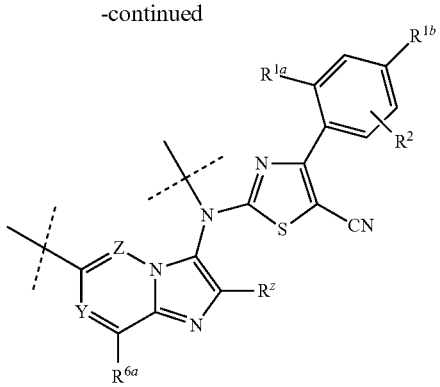

To a solution of the above prepared bromide (1 eq.) in pyridine is added copper (I) cyanide (5 eq.). The mixture is heated at 160° C. under microwave irradiation for 2 h. The crude mixture is quenched with water, and diluted in EtOAc. The organic layer is separated, the aqueous layer is extracted with EtOAc. The combined organic layers are washed with water and brine, dried over Na$_2$SO$_4$ and concentrated in vacuo. The residue is purified by chromatography on silica gel or preparative LC-MS to afford the expected product.

1.2.5.30. Illustrative Synthesis of Compound 44: 2-(4-(3-((5-cyano-4-(4-fluorophenyl)thiazol-2-yl)(methyl)amino)-2-ethylimidazo[1,2-b]pyridazin-6-yl)piperazin-1-yl)-N,N-dimethylacetamide

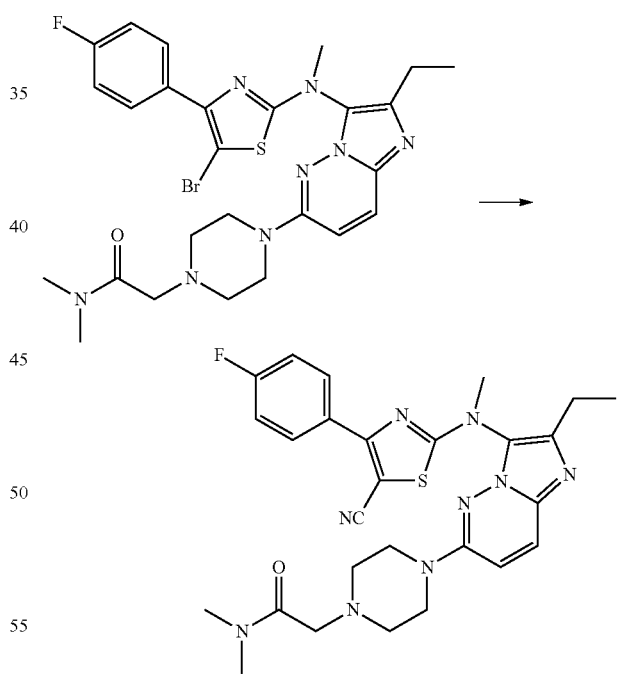

To a solution of intermediate 2-[4-(3-{[5-Bromo-4-(4-fluoro-phenyl)-thiazol-2-yl]-methyl-amino}-2-ethyl-imidazo[1,2-b]pyridazin-6-yl)-piperazin-1-yl]-N,N-dimethyl-acetamide (Gen-5-m) (95 mg, 0.158 mmol, 1 eq.) in pyridine (1 mL) is added copper cyanide (71 mg, 0.790 mmol, 5 eq.). The mixture is heated at 160° C. under microwave irradiation for 2 h. The crude mixture is quenched with water, and diluted in EtOAc. The organic layer is separated, the aqueous layer is extracted with EtOAc. The combined organic layers are washed with water and brine, dried over Na₂SO₄ and concentrated in vacuo. The residue is purified by chromatography on silica gel (elution DCM/MeOH: 100/0 to 90/10) and by preparative LC-MS to afford Compound 44.

LC-MS: MW (calcd): 547; m/z MW (obsd): 548 (M+H)

1.2.5.31. General Method E18

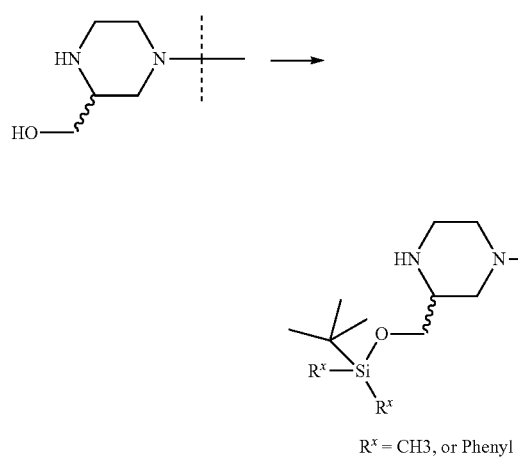

R$^x$ = CH3, or Phenyl

To a solution of hydroxy derivative (1 eq.) in DCM or DMF are added imidazole (2 to 3 eq.) and a solution of TBSCl or TBDPSCl (1.1 to 2 eq.) in DCM or DMF. The reaction mixture is stirred at r.t. until completion. Then the reaction mixture is quenched with a saturated Na₂CO₃ solution or water and diluted in DCM or EtOAc. The organic layer is separated, the aqueous layer is extracted with DCM or EtOAc twice. The combined organic layers are washed with brine, dried over Na₂SO₄ and concentrated in vacuo. The residue is purified by chromatography on silica gel to afford the expected product. Alternatively, the residue is used directly in the next step without purification.

1.2.5.32. Illustrative Synthesis of Intermediate Gen-5-ae: {6-[(S)-3-(tert-Butyl-diphenyl-silanyloxymethyl)-piperazin-1-yl]-2-ethyl-imidazo[1,2-b]pyridazin-3-yl}-[4-(4-fluoro-phenyl)-thiazol-2-yl]-methyl-amine

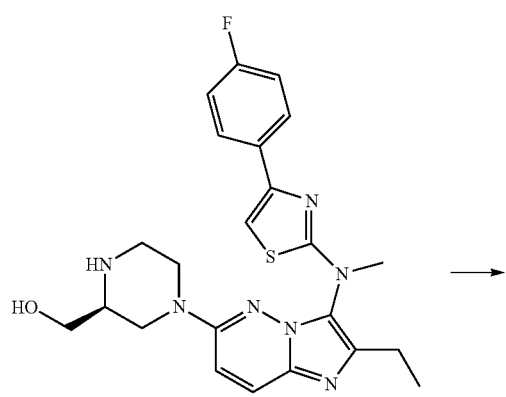

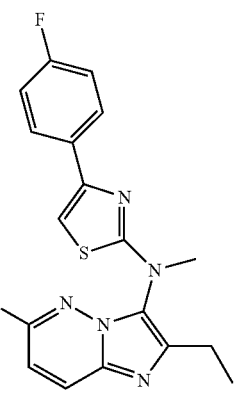

To a solution of compound 60 (90 mg, 0.19 mmol, 1 eq.) in DCM (2 mL) are added imidazole (26 mg, 0.38 mmol, 2 eq.) and a solution of TBDPSCl (59 μL, 0.23 mmol, 1.2 eq.) in DCM (0.4 mL). The reaction mixture is stirred at r.t. overnight. Then the reaction mixture is quenched with a saturated Na₂CO₃ solution and diluted in DCM. The organic layer is separated, the aqueous layer is extracted with DCM twice. The combined organic layers are washed with brine, dried over Na₂SO₄ and concentrated in vacuo. The residue is purified by chromatography on silica gel (elution with DCM/MeOH: 100/0 to 90/10) to afford Intermediate Gen-5-ae.

LC-MS: MW (calcd): 705; m/z (obsd): 706 (M+H)

1.2.5.33. General Method E19

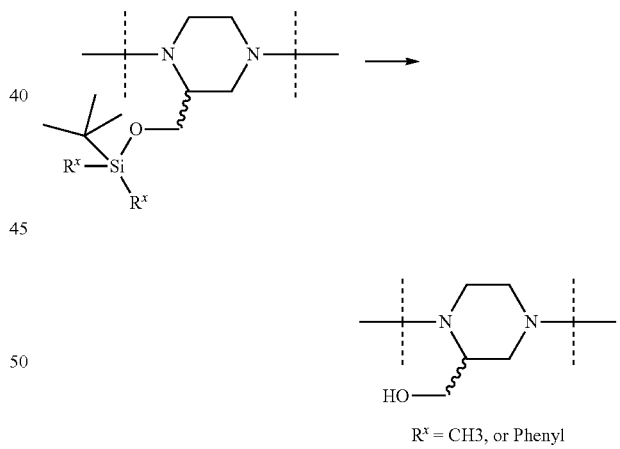

R$^x$ = CH3, or Phenyl

To a solution of protected hydroxy derivative (1 eq.) in THF is added a 1M TBAF solution in THF (1 to 2 eq.), the reaction mixture is stirred at r.t. until completion. Then the reaction mixture is quenched with a saturated Na₂CO₃ solution or water and diluted in EtOAc. The organic layer is separated, the aqueous layer is extracted with EtOAc three times. To the combined organic layers is added heptane, and are washed with water twice and brine, dried over Na₂SO₄ and concentrated in vacuo. The residue is purified by chromatography on silica gel or preparative LC-MS to afford the expected product.

119

1.2.5.34. Illustrative synthesis of compound 64: (S)-2-(4-(2-ethyl-3-((4-(4-fluorophenyl)thiazol-2-yl)(methyl)amino)imidazo[1,2-b]pyridazin-6-yl)-2-(hydroxymethyl)piperazin-1-yl)-1-(pyrrolidin-1-yl)ethanone

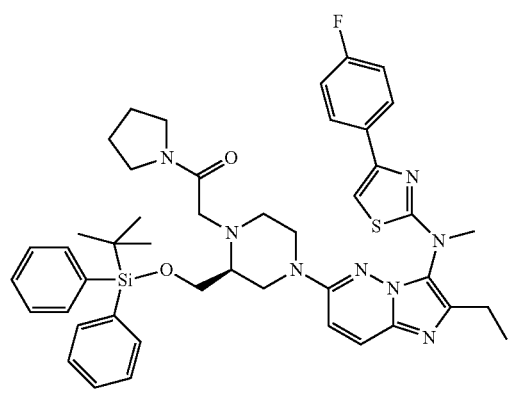

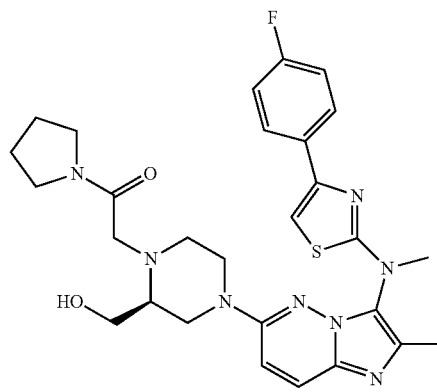

To a solution of 2-[2-(tert-Butyl-diphenyl-silanyloxymethyl)-4-(2-ethyl-3-{[4-(4-fluoro-phenyl)-thiazol-2-yl]-methyl-amino}-imidazo[1,2-b]pyridazin-6-yl)-piperazin-1-yl]-1-pyrrolidin-1-yl-ethanone (100 mg, 0.13 mmol, 1 eq.) in THF (1.5 mL) is added a 1M TBAF solution in THF (134 μL, 0.13 mmol, 1), the reaction mixture is stirred at r.t. for 1 h. Then the reaction mixture is quenched with a saturated Na$_2$CO$_3$ solution and diluted in EtOAc. The organic layer is separated, the aqueous layer is extracted with EtOAc three time. To the combined organic layers is added heptane, and are washed with water twice and brine, dried over Na$_2$SO$_4$ and concentrated in vacuo. The residue is purified by chromatography on silica gel (elution with DCM/MeOH: 100/0 to 93/7) to afford Compound 64.

LC-MS: MW (calcd): 578; m/z (obsd): 579 (M+H)

1.2.5.35. General Method D1

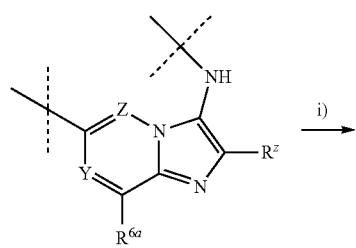

120

-continued

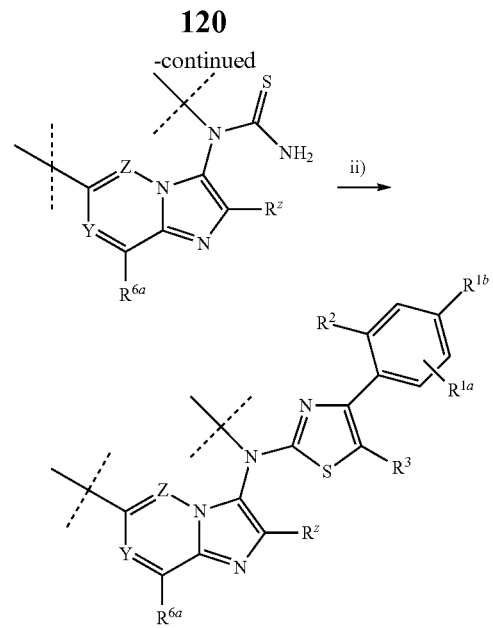

Intermediates Gen-5 are prepared from intermediates Gen-7 according to general method D1 described previously.

1.2.5.36. General Method D2

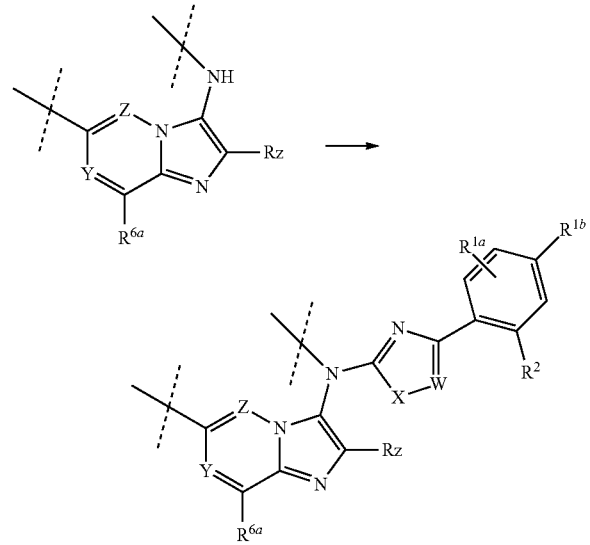

Intermediates Gen-5 are prepared from intermediates Gen-7 according to general method D2 described previously.

1.2.5.37. General Method D3

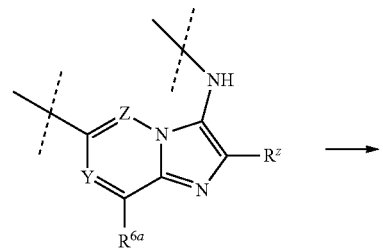

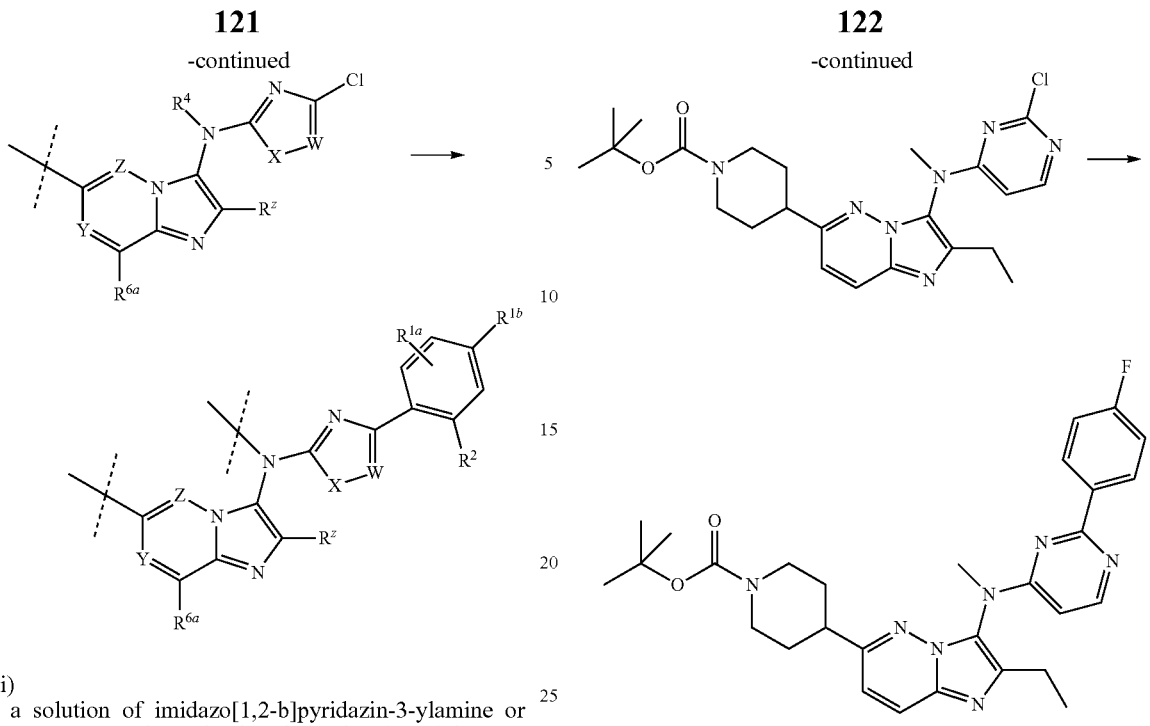

Step i)

To a solution of imidazo[1,2-b]pyridazin-3-ylamine or imidazo[1,2-a]pyrazin-3-ylamine derivative (1 eq.) in THF under argon is slowly added NaH (60% in oil suspension, 3 eq.). The reaction mixture is refluxed for 30 min then cooled to 40° C. before adding the halogeno heteroaryl derivative (1.2 eq.) in THF, the reaction mixture is refluxed until completion. After cooling to r.t. the mixture is slowly quenched by addition of water and then diluted with EtOAc. The organic layer is separated and the aqueous layer extracted with EtOAc. The combined organic layers are washed with water and brine, dried over $Na_2SO_4$, filtered and concentrated in vacuo. The residue is purified by chromatography on silica gel to deliver the corresponding halogeno derivative.

Step ii)

To a solution of the above prepared halogeno derivative (1 eq.) in a mixture of dioxane and water under argon are successively added CsF or LiOH (2.1 to 4 eq.), the corresponding boronic ester (1.2 to 1.5 eq.), and then Pd(amphos)$Cl_2$ (0.05 to 0.1 eq.) or Pd(OAc)$_2$ (0.01 eq.) with Sphos (0.02 eq.). The reaction mixture is heated between 80° C. and 110° C. until completion. After cooling to r.t., the crude product is partitioned with water and EtOAc and the layers are separated. The aqueous layer is extracted with EtOAc twice, the combined organic layers are washed with brine, dried over $Na_2SO_4$ and concentrated in vacuo. The residue is purified by chromatography on silica gel to afford the expected intermediate.

1.2.5.38. Illustrative Synthesis of Intermediate Gen-5-aad: 4-(2-Ethyl-3-{[2-(4-fluoro-phenyl)-pyrimidin-4-yl]-methyl-amino}-imidazo[1,2-b]pyridazin-6-yl)-piperidine-1-carboxylic acid tert-butyl ester

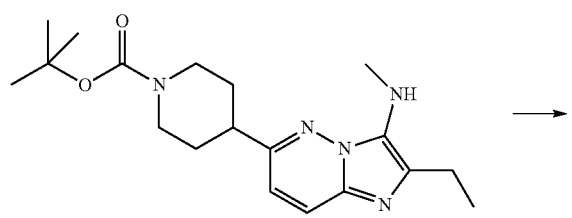

Step i)

To a solution of intermediate 4-(2-Ethyl-3-methylamino-imidazo[1,2-b]pyridazin-6-yl)-piperidine-1-carboxylic acid tert-butyl ester (Gen-7-a) (200 mg, 0.556 mmol, 1 eq.) in THF (2.6 mL) under argon is slowly added NaH (60% in oil suspension, 66.8 mg, 1.669 mmol, 3 eq.). The reaction mixture is refluxed for 30 min then cooled to 40° C. then 2,4-dichloropyrimidine (99.5 mg, 0.667 mmol, 1.2 eq.) in THF (1.2 mL) is added, the reaction mixture is refluxed for 1.5 h. After cooling to r.t. the mixture is slowly quenched by addition of water and then diluted with EtOAc. The organic layer is separated and the aqueous layer is extracted with EtOAc. The combined organic layers are washed with brine, dried over $Na_2SO_4$, filtered and concentrated in vacuo. The residue is purified by chromatography on silica gel (elution DCM/MeOH: 100/0 to 95/5) to deliver 4-{3-[(2-Chloro-pyrimidin-4-yl)-methyl-amino]-2-ethyl-imidazo[1,2-b]pyridazin-6-yl}-piperidine-1-carboxylic acid tert-butyl ester.

LC-MS: MW (calcd): 471 ($^{35}$Cl), 473 ($^{37}$Cl); m/z MW (obsd): 472 ($^{35}$Cl M+H), 474 ($^{37}$Cl M+H)

Step ii)

To a solution of the above prepared halogeno derivative (50 mg, 0.106 mmol, 1 eq.) in dioxane (850 μL) under argon are successively added LiOH (10.1 mg, 0.424 mmol, 4 eq.) in water (212 μL), 4-fluorophenylboronic acid (17.8 mg, 0.127 mmol, 1.2 eq.), Pd(OAc)$_2$ (0.3 mg, 0.001 mmol, 0.01 eq.) and Sphos (0.9 mg, 0.002 mmol, 0.02 eq.). The reaction mixture is heated at 80° C. for 4 h. After cooling to r.t., the crude product is partitioned with water and EtOAc and the layers are separated. The aqueous layer is extracted with EtOAc twice, the combined organic layers are washed with brine, dried over $Na_2SO_4$ and concentrated in vacuo. The residue is purified by chromatography on silica gel (elution DCM/MeOH: 100/0 to 90/10) to afford Intermediate Gen-5-aad.

LC-MS: MW (calcd): 531; m/z MW (obsd): 532 (M+H)

1.2.6. General Methods E: Synthesis of Intermediate Gen-6

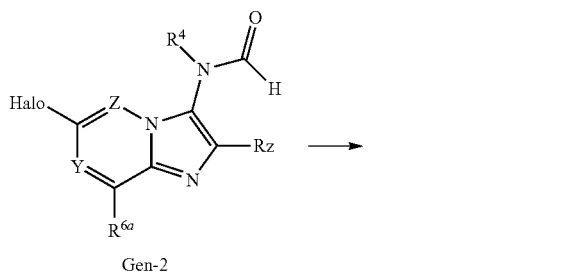

Gen-2

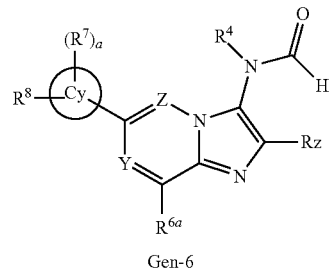

Gen-6

Intermediates Gen-6 are prepared from Intermediates Gen-2 according to one or several general methods E described previously.

1.2.7. General Methods C2: Synthesis of Intermediate Gen-7

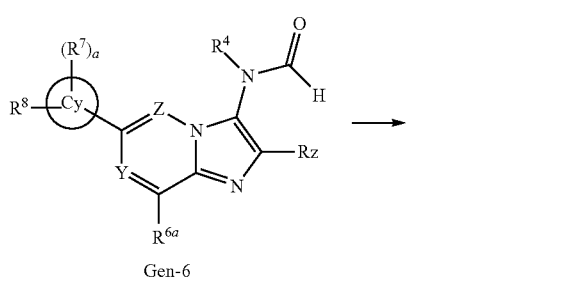

Gen-6

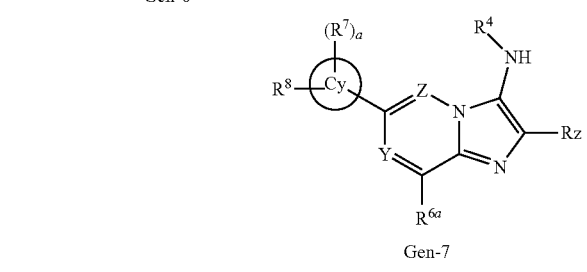

Gen-7

Intermediates Gen-7 are prepared from Intermediates Gen-6 according to general method C2 described previously.

1.2.8. General Method G1: General Synthesis of a Halogenoketones Gen-8

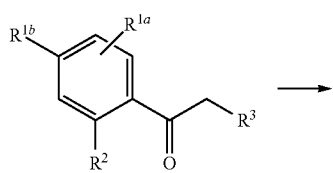

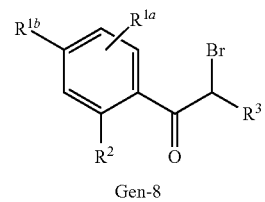

Gen-8

To a solution of ketone (1 eq.) in MeCN is added phenyltrimethylammonium tribromide (1 eq.). The resulting mixture is stirred at r.t. for 3 h, and then is concentrated in vacuo. The organic residue is dissolved in EtOAc and the organic layer is washed with water, with brine, dried over $Na_2SO_4$, filtered and concentrated in vacuo to give the Intermediate Gen-8. The crude product is used directly in the next step without purification

1.2.9. Illustrative Synthesis of Intermediate Gen-8-a: 2-(2-Bromo-acetyl)-5-fluoro-benzonitrile

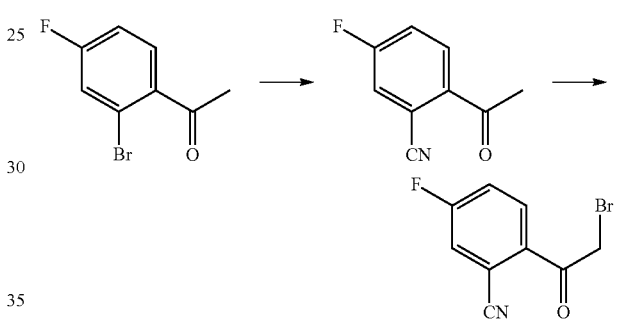

Step i)

To a solution of 1-(2-Bromo-4-fluoro-phenyl)-ethanone (3.0 g, 13.82 mmol, 1 eq.) in DMA (150 mL) under argon is added $Zn(CN)_2$ (1.6 g, 13.82 mmol, 1 eq.), $Pd_2(dba)_3$ (1.26 g, 1.38 mmol, 0.1 eq.), dppf (1.53 g, 2.76 mmol, 0.2 eq.) and Zn dust (107.8 mg, 1.65 mmol, 0.12 eq.). The reaction mixture is heated at 100° C. for 1.4 h, after cooling to r.t. the mixture is slowly quenched by addition of water and then diluted with EtOAc. The organic layer is separated and the aqueous layer extracted with EtOAc twice. The combined organic layers are washed with water, dried over $Na_2SO_4$, filtered and concentrated in vacuo. The residue is purified either by chromatography on silica gel to afford the expected product.

LC-MS: MW (calcd): 163; m/z MW (obsd): 164 (M+H)

Step ii)

To a solution of 2-acetyl-5-fluoro-benzonitrile (1.52 g, 9.33 mmol, 1 eq.) in MeCN (40 mL) is added phenyltrimethylammonium tribromide (3.51 g, 1 eq.). The resulting mixture is stirred at r.t. for 3 h, and then is concentrated in vacuo. The organic residue is dissolved in EtOAc and the organic layer is washed with water, with brine, dried over $Na_2SO_4$, filtered and concentrated in vacuo to give the Intermediate Gen-8-a. The crude is used directly in the next step without purification LC-MS: MW (calcd): 241 ($^{79}$Br), 243 ($^{81}$Br); m/z MW (obsd): 242 ($^{79}$Br M+H), 244 ($^{81}$Br M+H)

1.2.10. General Method G2: General Synthesis of Intermediates Gen-9

1.2.10.1. General Method G2a

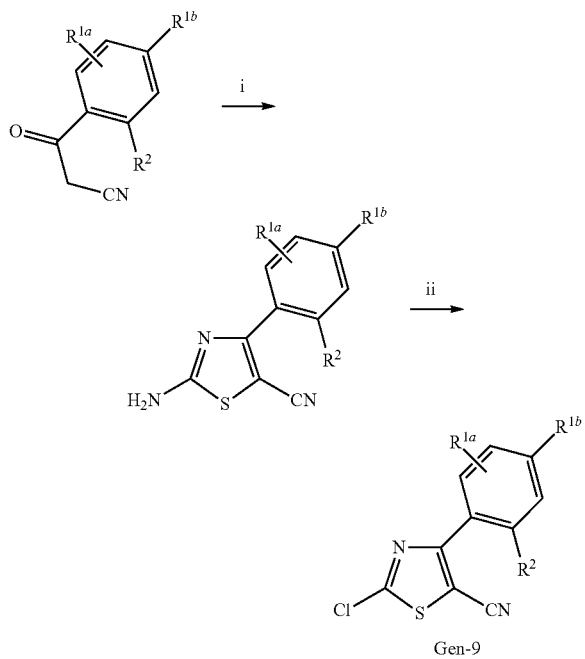

Gen-9

Step i)

To a solution of benzoylacetonitrile derivative (1 eq.) in EtOH is added pyridine (1 eq.). The resulting mixture is stirred at 70° C. for 15 min then cooled at r.t. A previously stirred suspension of thiourea (2 eq.) and iodine (1 eq.) in EtOH is then slowly added. After 1 h at r.t. a cold 1 M $Na_2S_2O_3$ solution is added under stirring. The resulting precipitate is filtered, washed with water, and finally dried under vacuo to afford the amino-4-phenyl-thiazole-5-carbonitrile derivative.

Step ii)

To a solution of copper (II) chloride (1.2 eq.) in MeCN is added dropwise tert-butyl nitrite (1.5 eq). After stirring at r.t. for 30 min, the amino-4-phenyl-thiazole-5-carbonitrile (1 eq.) is introduced portionwise and stirring is continued for 1 h. The reaction mixture is then carefully quenched by addition of a 1 M HCl solution. After 15 min stirring, the organic phase is separated; the aqueous phase is further extracted with EtOAc. The combined organic layers are washed with brine, dried over $Na_2SO_4$, filtered and concentrated in vacuo. The crude product product is filtered on a silica plug and eluted with DCM. Solvents are evaporated and the residue is finally triturated in heptane, filtered and dried to give Intermediate Gen-9.

1.2.10.2. Illustrative Synthesis of Intermediate Gen-9-a: 2-Chloro-4-(4-fluoro-phenyl)-thiazole-5-carbonitrile

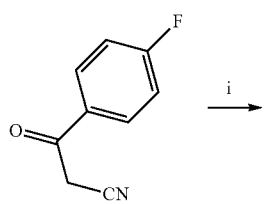

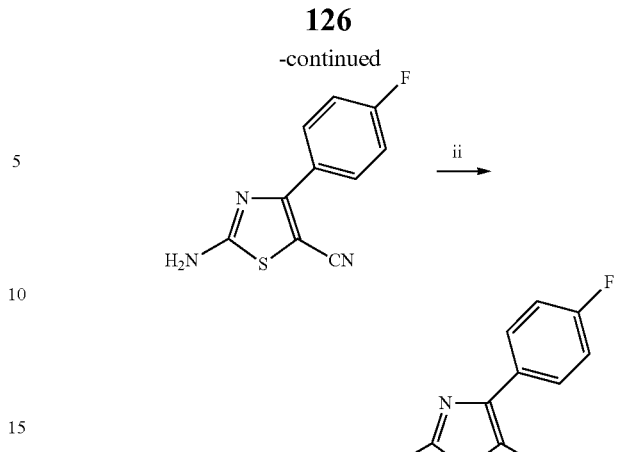

Step i)

To a solution of 4-fluorobenzoylacetonitrile (50 g, 306 mmol, 1 eq.) in EtOH (600 mL) is added pyridine (24.7 mL, 306 mmol, 1 eq.). The resulting mixture is stirred at 70° C. for 15 min then cooled to r.t. A previously stirred suspension of thiourea (46.7 g, 613 mmol, 2 eq.) and iodine (77.8 g, 306 mmol, 1 eq.) in EtOH (300 mL) is then slowly added. After 1 h at r.t. a cold 1 M $Na_2S_2O_3$ solution (360 mL) is added under stirring. The resulting precipitate is filtered, washed with water, and finally dried under vacuo to afford 2-Amino-4-(4-fluoro-phenyl)-thiazole-5-carbonitrile.

$^1$H NMR δ (ppm) (400 MHz, DMSO): 8.26 (2H, s), 7.97 (2H, dd), 7.36 (2H, t)

Step ii)

To a solution of copper (II) chloride (36.8 g, 273 mmol, 1.2 eq.) in MeCN (500 mL) is added dropwise tert-butyl nitrite (40.7 mL, 342 mmol, 1.5 eq). After stirring at r.t. for 30 min, amine previously obtained in step i (50 g, 228 mmol, 1 eq.) is introduced portionwise and stirring is continued for 1 h. The reaction mixture is then carefully quenched by addition of a 1 M HCl solution (750 mL). After 15 min stirring, the organic phase is separated, the aqueous phase is further extracted with EtOAc. The combined organic layers are washed with brine, dried over $Na_2SO_4$, filtered and concentrated in vacuo. The crude product product is filtered on a silica plug (250 g) and eluted with DCM. Solvents are evaporated and the residue is finally triturated in heptane, filtered and dried to afford Intermediate Gen-9-a.

$^1$H NMR δ (ppm) (400 MHz, DMSO): 8.06 (2H, dd), 7.46 (2H, dd)

1.2.10.3. General Method G2b

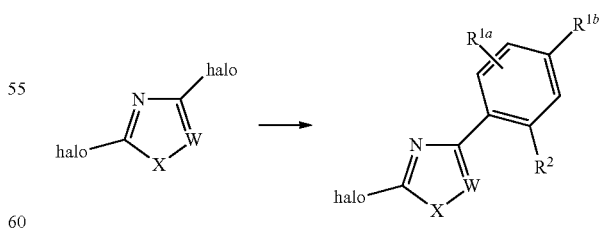

To a solution of the halogenoheterocycle derivative (1 eq.) in a mixture of dioxane/water (9/1) or MeCN/water (3/1) under argon are successively added the corresponding boronic ester (1 to 1.2 eq.), CsF (2.1 eq.) and Pd(amphos)Cl$_2$ (0.05 eq.) or Na$_2$CO$_3$ (3 eq.), and Pd(PPh$_3$)$_4$ (0.1 eq.). The reaction mixture is heated between 90° C. and 110° C. until completion. After cooling to r.t., the crude product is partitioned between water and EtOAc and the layers are separated. The aqueous layer is extracted with EtOAc twice, the combined organic layers are washed with brine, dried over Na$_2$SO$_4$ and concentrated in vacuo. The residue is purified by chromatography on silica gel to afford the expected intermediate.

1.2.10.4. Illustrative Synthesis of Intermediate Gen-9-d: 5-Fluoro-2-(6-fluoro-pyridin-2-yl)-benzonitrile

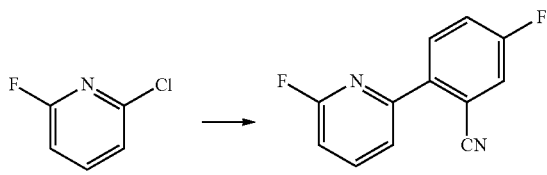 [SMILES: Fc1cccc(Cl)n1 ; N#Cc1cc(F)ccc1-c1cccc(F)n1]

To a solution of the 2-chloro-6-fluoropyridine (400 mg, 3.041 mmol, 1 eq.) in a mixture of dioxane (9 mL)/water (1 mL) under argon are successively added 5-Fluoro-2-(4,4,5,5-tetramethyl-[1,3,2]dioxaborolan-2-yl)-benzonitrile (901.6 mg, 3.649 mmol, 1.2 eq.), CsF (970 mg, 3.041 mmol, 2.1 eq.) and Pd(amphos)Cl$_2$ (107.7 mg, 0.152 mmol, 0.05 eq.). The reaction mixture is heated at 110° C. for 2.5 h. After cooling to r.t., the crude product is partitioned between water and EtOAc and the layers are separated. The aqueous layer is extracted with EtOAc twice, the combined organic layers are washed with brine, dried over Na$_2$SO$_4$ and concentrated in vacuo. The residue is purified by chromatography on silica gel (elution heptanes/EtOAc (100/0 to 80/20) to afford Intermediate Gen-9-d.

LC-MS: MW (calcd): 216; m/z MW (obsd): 217 (M+H)

1.2.11. General Method G3: General Synthesis of Intermediate Gen-10

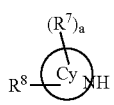

1.2.11.1. General Method G3a

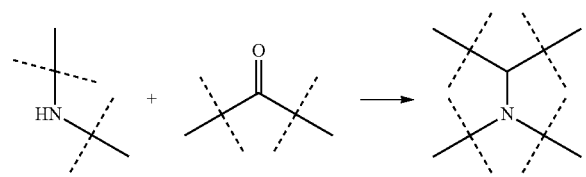

Step i)

To a solution of the appropriate amine (2.0 to 3.3 eq.) in MeOH or DCE are added acetic acid if needed (0 to 3 eq) and the aldehyde or ketone (1 eq.). The reaction mixture is stirred at r.t. for 1 h to overnight then NaBH$_3$CN (1.5 to 4 eq.) or NaBH(OAc)$_3$ (5 eq.) is added. The reaction mixture is stirred at r.t. for 8 h to 16 h, then concentrated in vacuo. The residue is dissolved in a mixture of DCM and a 1 M NaOH solution or a saturated NaHCO$_3$ solution, the two phases are separated and the aqueous phase is extracted with DCM. The combined organic layers are washed with water and brine, dried over Na$_2$SO$_4$, filtered and concentrated in vacuo. The residue is purified by chromatography on silica gel to afford the expected product.

Step ii)

To a solution of the boc protected amine (1 eq.) in MeOH or dioxane is added a HCl solution in Et$_2$O (2 M) or dioxane (4 M) or MeOH (1.25 M) or water (12 M) (in excess). Alternatively, to a solution of the boc protected amine (1 eq.) in DCM is added TFA (in excess). The reaction mixture is stirred at r.t. until completion then concentrated in vacuo. The residue is partitioned between EtOAc or DCM and a saturated Na$_2$CO$_3$ solution (until pH reached 8-9) and further extraction with EtOAc is performed. The combined organic layers are then washed with brine, dried over Na$_2$SO$_4$, filtered and concentrated in vacuo to afford the expected intermediate. Alternatively, the reaction mixture is concentrated in vacuo, and the crude product is used directly in the next step as hydrochloride salt without purification.

1.2.11.2. Illustrative Synthesis of Intermediate Gen-10-u: (2S,6R)-2,6-Dimethyl-4-pyrrolidin-3-yl-morpholine

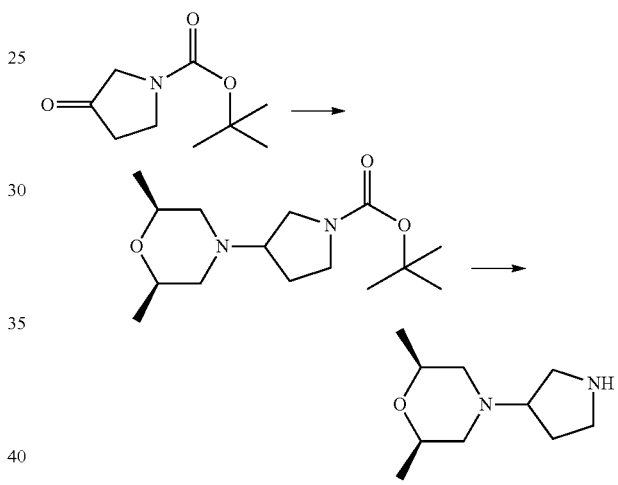

Step i)

To a solution of cis-2,6-dimethylmorpholine (0.22 mL, 1.782 mmol, 3.3 eq.) in DCE (9 mL) is added N-boc-3-pyrrolidinone (100 mg, 0.539 mmol, 1 eq.). The reaction mixture is stirred at r.t. then NaBH(OAc)$_3$ (572.1 mg, 2.699 mmol, 5 eq.) is added. The reaction mixture is stirred at r.t. overnight, then concentrated in vacuo. The residue is partitioned between DCM and a saturated NaHCO$_3$ solution, the two phases are separated and the aqueous phase is extracted with DCM twice. The combined organic layers are washed with brine, dried over Na$_2$SO$_4$, filtered and concentrated in vacuo. The residue is purified by chromatography on silica gel (elution Heptane/EtOAc: 50/50 to 0/100) to afford the expected product.

LC-MS: MW (calcd): 284; m/z MW (obsd): 285 (M+H)

Step ii)

To a solution of the above boc protected amine (120 mg, 0.422 mmol, 1 eq.) in dioxane (1 mL) is added a 4 M HCl solution in dioxane (0.85 mL). The reaction mixture is stirred at r.t. overnight then concentrated in vacuo, to afford Intermediate Gen-10-u as hydrochloride salt which used directly in the next step without purification.

LC-MS: MW (calcd): 184; m/z MW (obsd): 185 (M+H)

1.2.11.3. General Method G3b

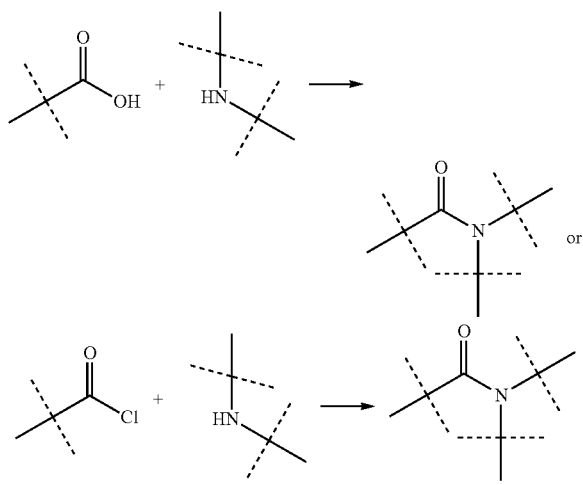

Step i)

To a solution of acid (1 to 1.1 eq.) in DCM or THF or a mixture THF/DCM are added HOBT (1.2 to 1.5 eq.) and EDC.HCl (1.2 to 1.5 eq.) or TBTU (1.1 eq.). The reaction mixture is stirred at r.t. for 30 to 45 min then a prepared solution of amine (1 to 1.1 eq.) in DCM or DMF with TEA (3 eq.) is added. The reaction mixture is stirred at r.t. until completion, then water and a 1 M HCl solution are added, the aqueous layer is extracted with DCM or EtOAc, the organic layer is washed with a saturated $Na_2CO_3$ solution or water, and brine, dried over $Na_2SO_4$, filtered and concentrated in vacuo. The residue is purified by chromatography on silica gel or preparative LC-MS to afford the expected product.

Or to a solution of amine (1 eq.) in DCM or MeCN are added TEA (0 to 2 eq.) followed by acyl chloride derivative (1 to 1.11 eq.). The reaction mixture is stirred at r.t. until completion, then is quenched with water and the aqueous layer is extracted with DCM or EtOAc twice. The organic layer is washed with water, and brine, dried over $Na_2SO_4$, filtered and concentrated in vacuo. The residue is purified by chromatography on silica gel to afford the expected product.

Step ii)

Intermediates Gen-10 are prepared from the above boc protected amine in step i according to step ii of general method G3a.

1.2.11.4. Illustrative Synthesis of Intermediate Gen-10-f: Pyrrolidine-3-carboxylic acid (2-hydroxy-ethyl)-amide

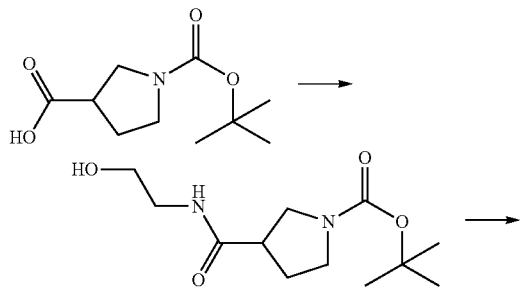

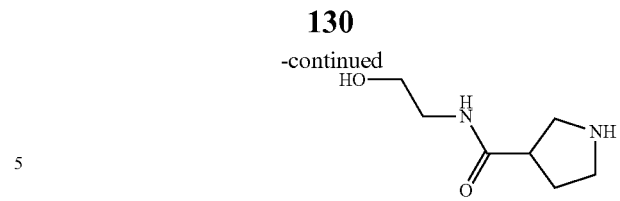

Step i)

To a solution of pyrrolidine-1,3-dicarboxylic acid 1-tert-butyl ester (200 mg, 0.929 mmol, 1 eq.) in THF/DCM (2 mL/3 mL) are added HOBT (188 mg, 0.394 mmol, 1.5 eq.) and EDC.HCl (267 mg, 1.394 mmol, 1.5 eq.). The reaction mixture is stirred at r.t. for 45 min then a prepared solution of ethanolamine (84 µL, 1.394 mmol, 1.5 eq.) in DCM is added. The reaction mixture is stirred at r.t. for 2 h, then water and a 1 M HCl solution are added, the aqueous layer is extracted with DCM, the organic layer is washed with a saturated $Na_2CO_3$ solution or water, and brine, dried over $Na_2SO_4$, filtered and concentrated in vacuo to afford the expected product.

Step ii)

To a solution of the above boc protected amine (150 mg, 0.437 mmol, 1 eq.) in MeOH (2 mL) is added a 4 M HCl solution in dioxane (2 mL). The reaction mixture is stirred at r.t. overnight then concentrated in vacuo, to afford Intermediate Gen-10-f as hydrochloride salt which used directly in the next step without purification.

1.2.11.5. Illustrative Synthesis of Intermediate Gen-10-r: (3-Hydroxy-pyrrolidin-3-ylmethyl)-carbamic acid methyl ester

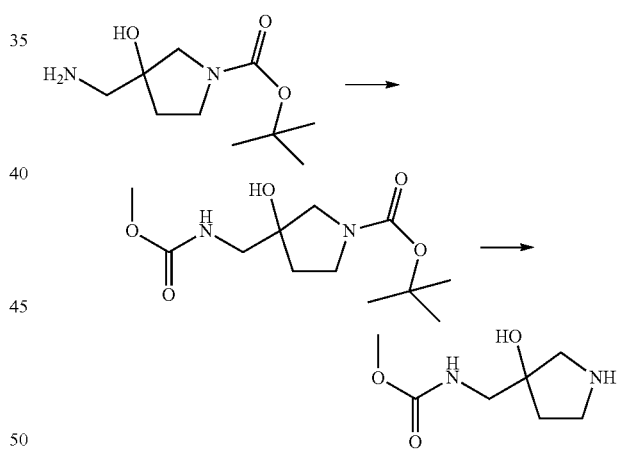

Step i

To a solution of 3-Aminomethyl-3-hydroxy-pyrrolidine-1-carboxylic acid tert-butyl ester (120 mg, 0.56 mmol, 1 eq.) in MeCN (1 mL) are added TEA (156 µL, 1.12 mmol, 2 eq.) followed by methyl chloroformate (42.7 µL, 0.56 mmol, 1 eq.). The reaction mixture is stirred at r.t. overnight, then is quenched with water and the aqueous layer is extracted with EtOAc twice. The organic layer is washed with brine, dried over $Na_2SO_4$, filtered and concentrated in vacuo. The residue is purified by chromatography on silica gel (elution DCM/MeOH: 100/01 to 94/6) to afford the expected product.

Step ii)

To a solution of the boc protected amine (94 mg, 0.34 mmol, 1 eq.) in dioxane (2 mL) is added an aqueous 12 M HCl solution (12M) (144 μL). The reaction mixture is stirred at r.t. for 4.5 days then concentrated in vacuo, to afford Intermediate Gen-10-r.

1.2.12. General Method G4: General Synthesis of Intermediaire Gen-11

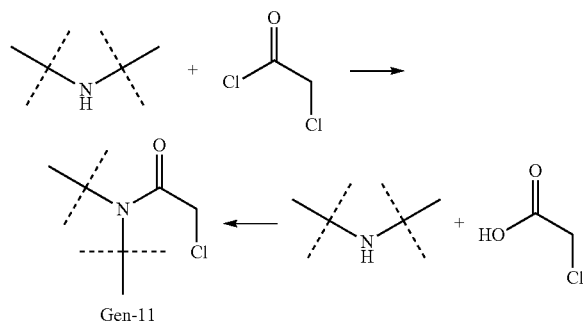

Gen-11

1.2.12.1. General Method G4a

To a suspension of potassium carbonate (2.2 eq.) in water is added the amine derivative (1 eq.). The reaction mixture is stirred at r.t. until complete dissolution, then diluted with DCM and cooled to 0° C. prior to the dropwise introduction of chloroacetyl chloride (1.2 eq.) over 30 min. After 2 h stirring at r.t., the reaction mixture is filtered, the organic layer and the aqueous phase are separated, and the aqueous phase is extracted either with DCM or with a mixture of EtOAc/nBuOH 1:1. The combined organic layers are dried over $Na_2SO_4$, filtered and concentrated in vacuo. The residue is suspended in acetone and stirred vigorously for 20 min, filtered and the filtrate is concentrated in vacuo to afford Intermediate Gen-11

1.2.12.2. Illustrative Synthesis of Intermediate Gen-11-a: 2-Chloro-1-(3-hydroxy-azetidin-1-yl)-ethanone

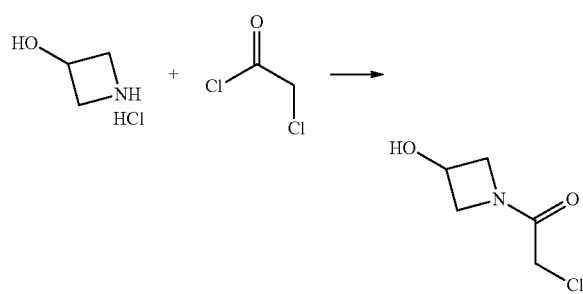

To a suspension of potassium carbonate (13.9 g, 100 mmol, 2.2 eq.) in water (33.5 mL) is added hydroxyazetidine hydrochloride (5 g, 45.6 mmol, 1 eq.). The reaction mixture is stirred at r.t. until complete dissolution, then diluted with 33.5 mL of DCM and cooled to 0° C. prior to the dropwise introduction of chloroacetyl chloride (4.4 mL, 54.8 mmol, 1.2 eq.) over 30 min. After 2 h stirring at r.t., the reaction mixture is filtered, the organic layer is separated, and the aqueous phase is extracted with a mixture EtOAc/nBuOH (1/1) (6×16 mL). The combined organic layers are dried over $Na_2SO_4$, filtered and concentrated in vacuo. The residue is suspended in acetone (48 mL) and stirred vigorously for 20 min, filtered and the filtrate is concentrated in vacuo to afford Intermediate Gen-11-a.

$^1$H NMR δ (ppm) (400 MHz, $CDCl_3$): 4.77-4.68 (1H, m), 4.50 (1H, dd), 4.50 (1H, dd), 4.32 (1H, dd), 4.16 (1H, dd), 3.89 (2H, s), 2.55 (1H, d).

1.2.12.3. General Method G4b

To a solution of chloroacetyl chloride (1 eq) and TEA (1.2 to 2 eq) in DCM at 0° C. is added the amine derivative (1.1 to 1.2 eq.). The reaction mixture is stirred overnight at r.t., then concentrated in vacuo. The residue is suspended in acetone or THF and stirred vigorously for 20 min filtered and the filtrate is concentrated in vacuo to afford Intermediate Gen-11 which is used directly without further purification in the next step.

1.2.12.4. Illustrative Synthesis of Intermediate Gen-1-f: (R)-2-Chloro-1-(3-hydroxy-pyrrolidin-1-yl)-ethanone

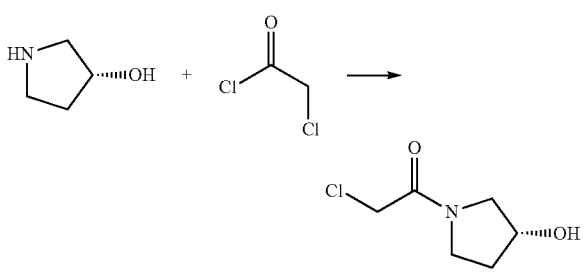

To a solution of chloroacetyl chloride (2 mL, 25.11 mmol, 1 eq) and TEA (4.19 mL, 30.13 mmol, 1.2 eq) in DCM (90 mL) at 0° C. is added (R)-pyrrolidin-3-ol (2.41 g, 27.62 mmol, 1.1 eq.). The reaction mixture is stirred overnight at r.t., then concentrated in vacuo. The residue is suspended in THF and stirred vigorously for 20 min, filtered, washed with THF and the filtrate is concentrated in vacuo to afford Intermediate Gen-11-f which is used directly in the next step without further purification.

LC-MS: MW (calcd): 163 ($^{35}$Cl), 165 ($^{37}$Cl); m/z MW (obsd): 164 ($^{35}$Cl M+H), 166 ($^{37}$Cl M+H)

1.2.12.5. General Method G4c

To a solution of chloroacetic acid (1 eq.) and the amine derivative (1 eq.) in DCM are added TEA (1.5 to 3 eq.) and Mukaiyama's resin (1.5 to 2 eq.). The reaction mixture is stirred at r.t. overnight, then filtered. The resin is washed with DCM and the filtrate is concentrated in vacuo. The residue is suspended in acetone, filtered and the filtrate is concentrated in vacuo to afford Intermediate Gen-11 which is used directly in the next step without further purification.

1.2.12.6. Illustrative Synthesis of Intermediate Gen-11-l: 2-Chloro-1-(2-methyl-pyrrolidin-1-yl)-ethanone

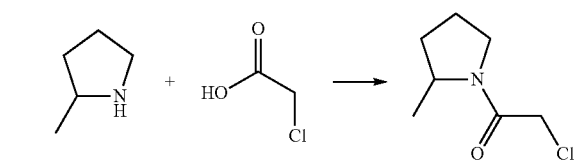

To a solution of chloroacetic acid (100 mg, 1.058 mmol, 1 eq.) and 2-methylpyrrolidine (102 mg, 1.058 mmol, 1 eq) in DCM (8 mL) are added TEA (441 μL, 3.175 mmol, 3 eq.) and Mukaiyama's resin (1.8 g, 2.12 mmol, 1.5 eq.). The reaction mixture is stirred at r.t. overnight, then filtered. The resin is washed with DCM and the filtrate is concentrated in vacuo. The residue is suspended in acetone, filtered and the filtrate is concentrated in vacuo to afford Intermediate Gen-11-l which used directly without further purification in the next step.

Example 2. Preparation of the Compounds of the Invention 2.1. Compound 52: 3-(4-(2-ethyl-3-((4-(4-fluorophenyl)thiazol-2-yl)(methyl)amino)imidazo[1,2-b]pyridazin-6-yl)piperazin-1-yl)propanamide

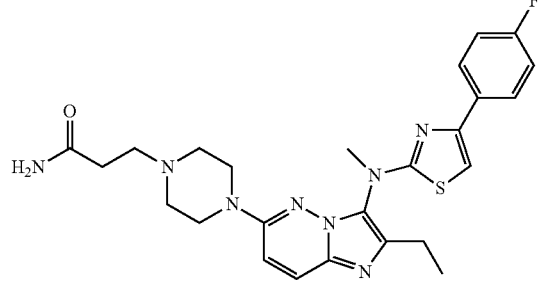

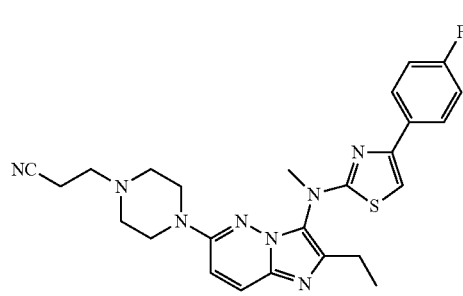

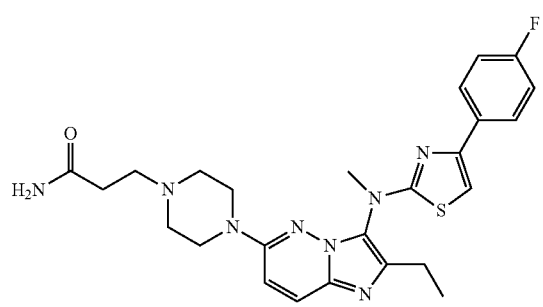

To Compound 51 (90 mg, 0.183 mmol, 1 eq.) is added H$_2$SO$_4$ (2 mL), the reaction mixture is heated at 80° C. for 1 h, then cooled to r.t. A saturated NaHCO$_3$ solution, and potassium carbonate are added until a basic pH is reached, then the reaction mixture is stirred at r.t. overnight. The reaction mixture is diluted with DCM and the aqueous layer is extracted three times with DCM. The combined organic layers are washed with brine, dried over Na$_2$SO$_4$, filtered and concentrated in vacuo. The crude product is purified by chromatography on silica gel (elution with DCM/MeOH: 100 to 95/5) to afford Compound 52.

LC-MS: MW (calcd): 508 m/z (obsd): 509 (M+H)

2.2. Compound 61: (S)-7-(2-ethyl-3-((4-(4-fluorophenyl)thiazol-2-yl)(methyl)amino)imidazo[1,2-b]pyridazin-6-yl)tetrahydro-1H-oxazolo[3,4-a]pyrazin-3 (5H)-one

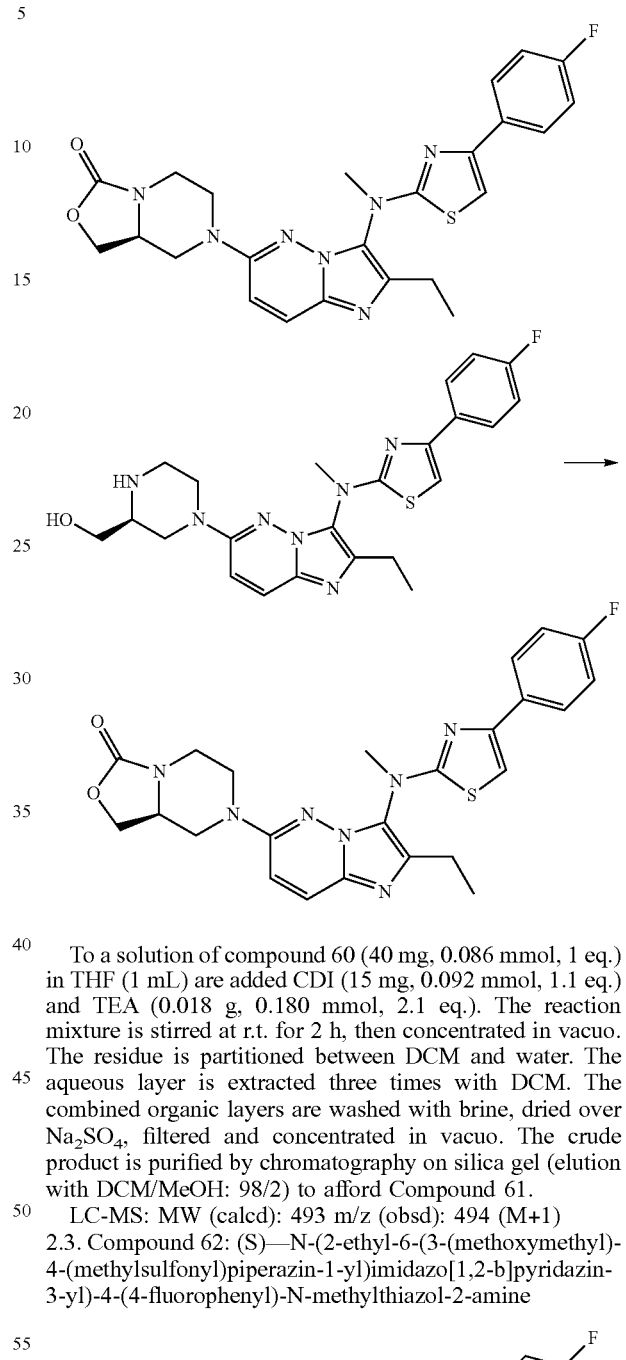

To a solution of compound 60 (40 mg, 0.086 mmol, 1 eq.) in THF (1 mL) are added CDI (15 mg, 0.092 mmol, 1.1 eq.) and TEA (0.018 g, 0.180 mmol, 2.1 eq.). The reaction mixture is stirred at r.t. for 2 h, then concentrated in vacuo. The residue is partitioned between DCM and water. The aqueous layer is extracted three times with DCM. The combined organic layers are washed with brine, dried over Na$_2$SO$_4$, filtered and concentrated in vacuo. The crude product is purified by chromatography on silica gel (elution with DCM/MeOH: 98/2) to afford Compound 61.

LC-MS: MW (calcd): 493 m/z (obsd): 494 (M+1)

2.3. Compound 62: (S)—N-(2-ethyl-6-(3-(methoxymethyl)-4-(methylsulfonyl)piperazin-1-yl)imidazo[1,2-b]pyridazin-3-yl)-4-(4-fluorophenyl)-N-methylthiazol-2-amine

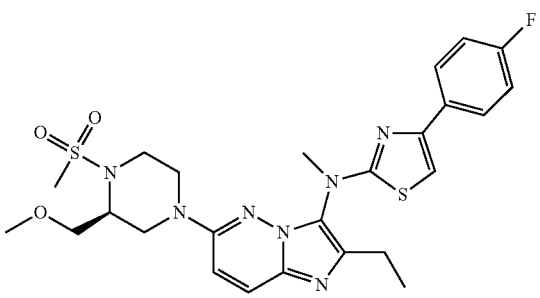 [SMILES: CCc1nc2ccc(N3CCN(S(C)(=O)=O)[C@H](COC)C3)nn2c1N(C)c1nc(-c2ccc(F)cc2)cs1]

Step i)

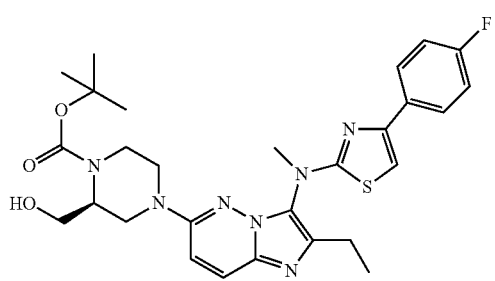

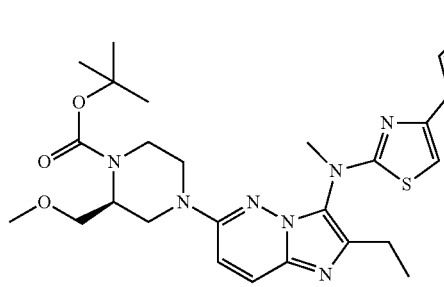

To a solution of Compound 59 (60 mg, 0.11 mmol, 1 eq.) in DMF (1 mL) at 0° C. is added NaH (60% in oil suspension, 6 mg, 0.16 mmol, 1.5 eq.), the reaction mixture is stirred at 0° C. for 45 min, then methyl iodide (14 μL, 0.22 mmol, 2 eq.) is added and stirred at r.t. for 2 h. Then quenched with water and diluted with EtOAc, the aqueous layer is extracted with EtOAc twice. The combined organic layers are washed with brine, dried over Na$_2$SO$_4$, filtered and concentrated in vacuo to afford Intermediate Gen-5-ac.

LC-MS: MW (calcd): 581 m/z (obsd): 582 (M+H)

Step ii)

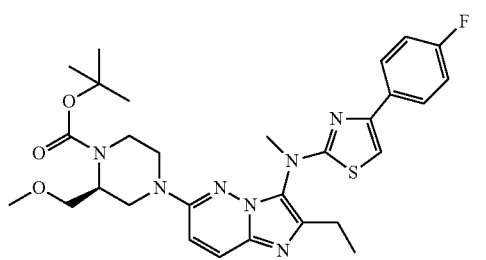

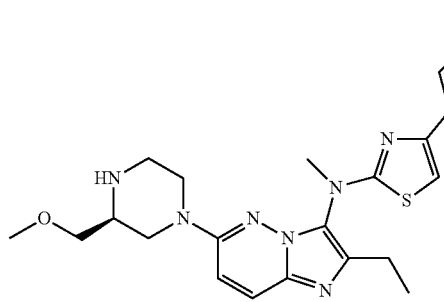

Boc deprotection of intermediate (S)-4-(2-Ethyl-3-{[4-(4-fluoro-phenyl)-thiazol-2-yl]-methyl-amino}-imidazo[1,2-b]pyridazin-6-yl)-2-methoxymethyl-piperazine-1-carboxylic acid tert-butyl ester (Gen-5-ac) is performed according to general method E5b to afford Intermediate Gen-5-ad.

LC-MS: MW (calcd): 481 m/z (obsd): 482 (M+H)

Step iii)

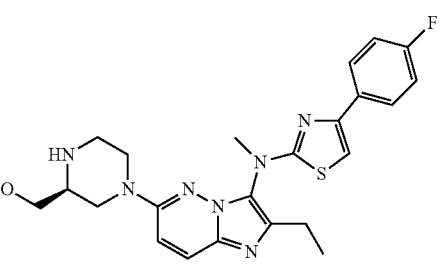

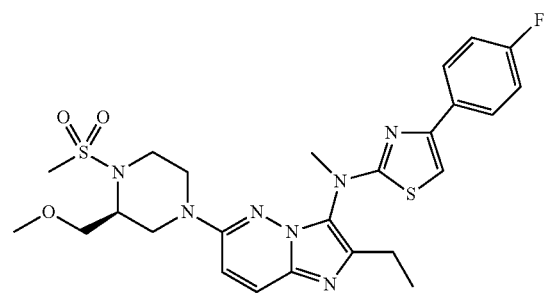

Intermediate [2-Ethyl-6-((S)-3-methoxymethyl-piperazin-1-yl)-imidazo[1,2-b]pyridazin-3-yl]-[4-(4-fluoro-phenyl)-thiazol-2-yl]-methyl-amine (Gen-5-ad) is sulfonylated with methanesulfonyl chloride using general method E11 to give Compound 62.

LC-MS: MW (calcd): 559 m/z (obsd): 560 (M+H)

2.4. Compound 66: (S)-8-(2-ethyl-3-((4-(4-fluorophenyl)thiazol-2-yl)(methyl)amino)imidazo[1,2-b]pyridazin-6-yl)hexahydropyrazino[2,1-c][1,4]oxazin-4(1H)-one

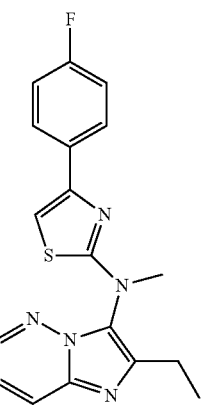

Step i)
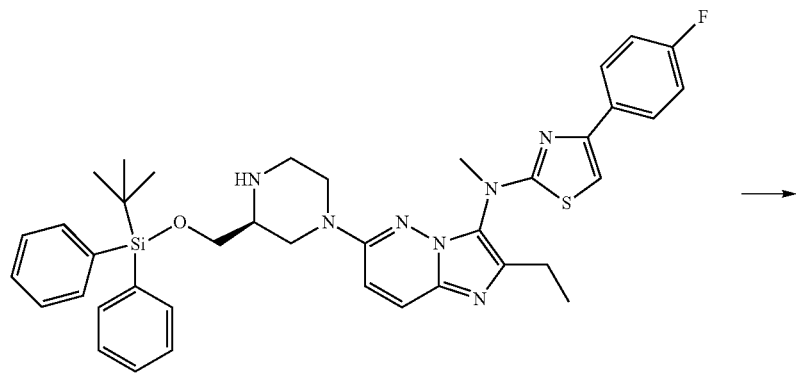
Intermediate Gen-5-ae is coupled with chloroacetyl chloride using general method E9b to give 1-[2-(tert-Butyl-diphenyl-silanyloxymethyl)-4-(2-ethyl-3-{[4-(4-fluoro-phenyl)-thiazol-2-yl]-methyl-amino}-imidazo[1,2-b]pyridazin-6-yl)-piperazin-1-yl]-2-chloro-ethanone.
Step ii)
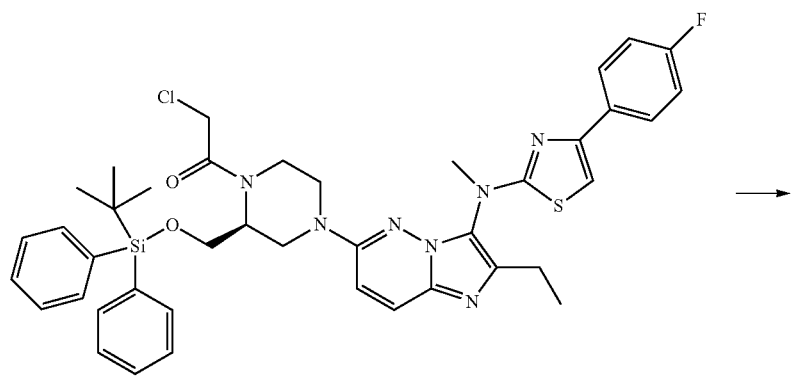
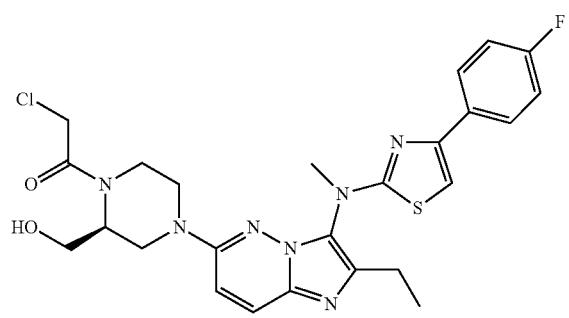

Silyl deprotection of 1-[2-(tert-Butyl-diphenyl-silanyloxymethyl)-4-(2-ethyl-3-{[4-(4-fluoro-phenyl)-thiazol-2-yl]-methyl-amino}-imidazo[1,2-b]pyridazin-6-yl)-piperazin-1-yl]-2-chloro-ethanone is performed according to general method E19 to afford 2-Chloro-1-[4-(2-ethyl-3-{[4-(4-fluoro-phenyl)-thiazol-2-yl]-methyl-amino}-imidazo[1,2-b]pyridazin-6-yl)-2-hydroxymethyl-piperazin-1-yl]-ethanone.

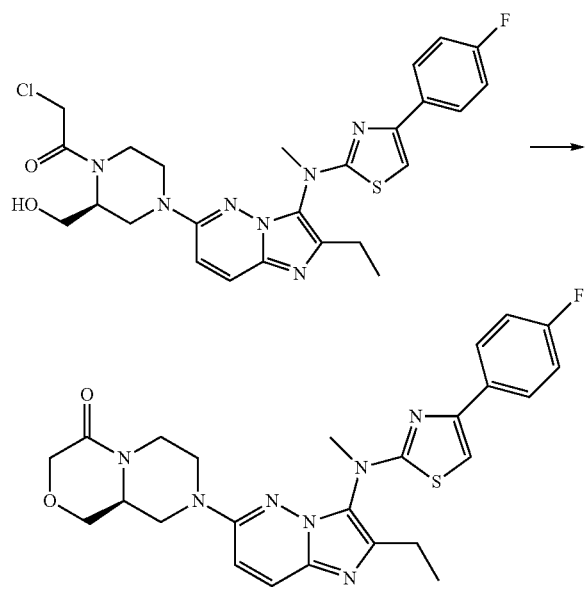

Step iii)
2-Chloro-1-[4-(2-ethyl-3-{[4-(4-fluoro-phenyl)-thiazol-2-yl]-methyl-amino}-imidazo[1,2-b]pyridazin-6-yl)-2-hydroxymethyl-piperazin-1-yl]-ethanone (27 mg, 0.050 mmol, 1 eq.) is dissolved in THF (1 mL). After cooling to 0° C., potassium tert-butoxide (7 mg, 0.06 mmol, 1.2 eq.) is added. The reaction mixture is stirred 15 min at 0° C. and 1 h at r.t., then quenched with one drop of acetic acid and diluted with a saturated $Na_2CO_3$ solution. The aqueous layer is extracted three times with EtOAc. The combined organic layers are washed with brine, dried over $Na_2SO_4$, filtered and concentrated in vacuo. Compound 66 is obtained by chromatography on silica gel (elution with DCM/MeOH: 100/0 to 95/5).

LC-MS: MW (calcd): 507 m/z (obsd): 508 (M+H)

2.5. Compound 89: N-(1-(2-ethyl-3-((4-(4-fluorophenyl)thiazol-2-yl)(methyl)amino)imidazo[1,2-b]pyridazin-6-yl)piperidin-4-yl)pyrrolidine-1-carboxamide

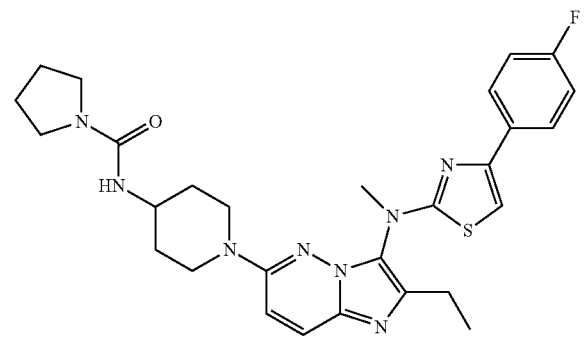 [SMILES: CCc1nc2ccc(N3CCC(NC(=O)N4CCCC4)CC3)nn2c1N(C)c1nc(-c2ccc(F)cc2)cs1]

Step i)

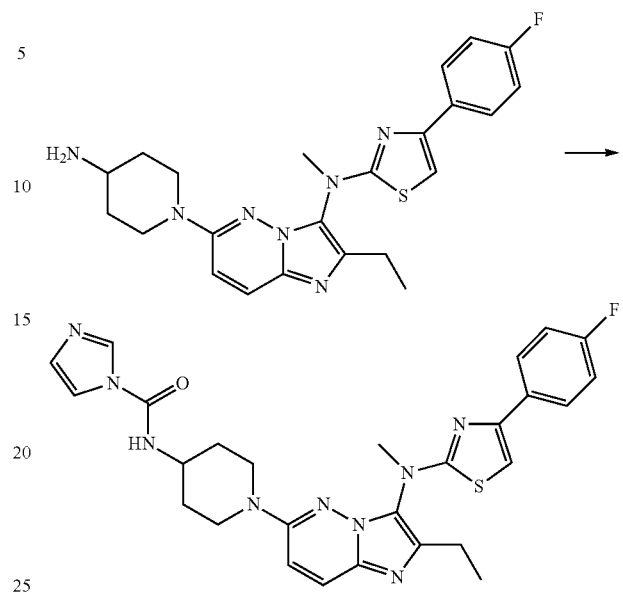

To a solution of Compound 82 (100 mg, 0.20 mmol, 1 eq.) in THF (0.5 mL) are successively added TEA (83 L, 0.60 mmol, 3 eq.) and 1,1'-Carbonyldiimidazole (0.133 g, 0.82 mmol, 4 eq.). The reaction mixture is heated at 50° C. for 6 h and stirred at r.t. overnight. Water is added to the solution and the aqueous layer is extracted with EtOAc three times. The combined organic layers are washed with water and brine, dried over $Na_2SO_4$, filtered and concentrated to afford Intermediate Gen-5-1.

LC-MS: MW (calcd): 545 m/z (obsd): 546 (M+H)

Step ii)

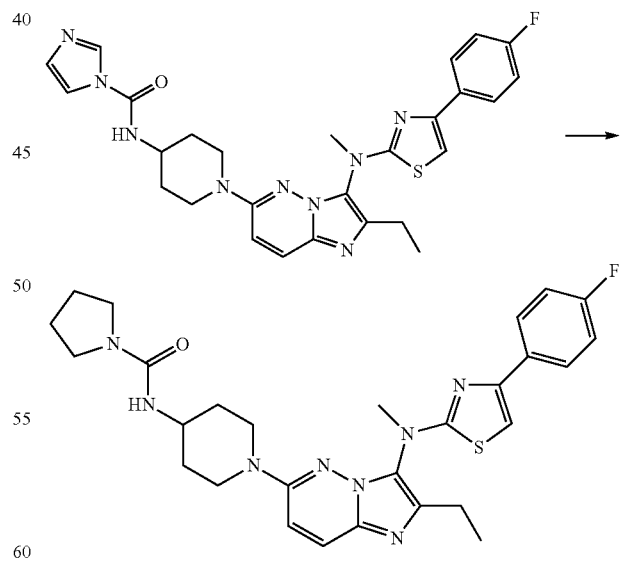

To a solution of Gen-5-1 (80 mg, 0.15 mmol, 1 eq.) in DMF (1 mL) is added pyrrolidine (25 L, 0.30 mmol, 2 eq.). The reaction mixture is stirred at r.t. for 3 h and quenched with a saturated $NaHCO_3$ solution. The aqueous layer is extracted with EtOAc three times. The organic layer is washed with water and brine, dried over $Na_2SO_4$, filtered and concentrated in vacuo. The crude product is purified by chromatography on silica gel (elution with DCM/MeOH: 100/0 to 97/3) to afford Compound 89.

LC-MS: MW (calcd): 548 m/z (obsd): 549 (M+H)

2.6. Compound 130: 1-(2-ethyl-3-((4-(4-fluorophenyl)thiazol-2-yl)(methyl)amino)imidazo[1,2-b]pyridazin-6-yl)pyrrolidin-3-yl formate

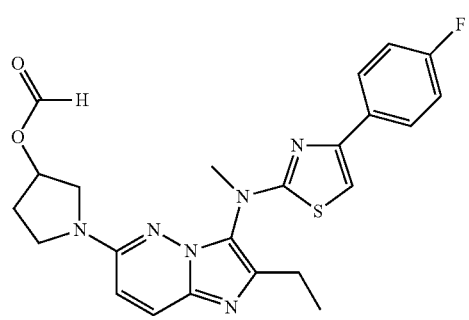 [SMILES: CCc1nc2ccc(N3CCC(OC=O)C3)nn2c1N(C)c1nc(-c2ccc(F)cc2)cs1]

Step i)

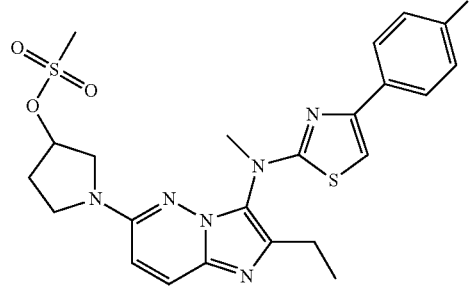

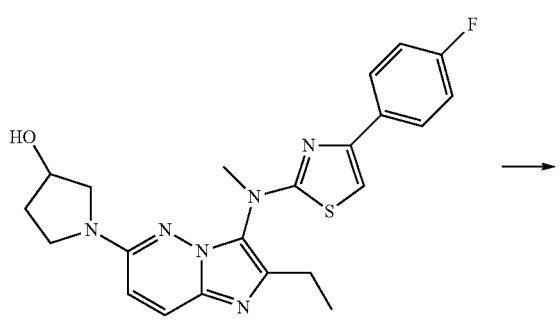

To a solution of Compound 129 (400 mg, 0.912 mmol, 1 eq.) in DCM (20 mL) are added TEA (380 µL, 2.736 mmol, 3 eq.) and sulfonyl chloride (141 µL, 1.824 mmol, 2 eq.). The reaction mixture is stirred at r.t. for 1.5 h, then quenched with water. The aqueous layer is extracted with EtOAc and the organic layer is washed with brine, dried over Na₂SO₄, filtered and concentrated in vacuo to afford Gen-5-ab.

LC-MS: MW (calcd): 516 m/z (obsd): 517 (M+H)

Step ii)

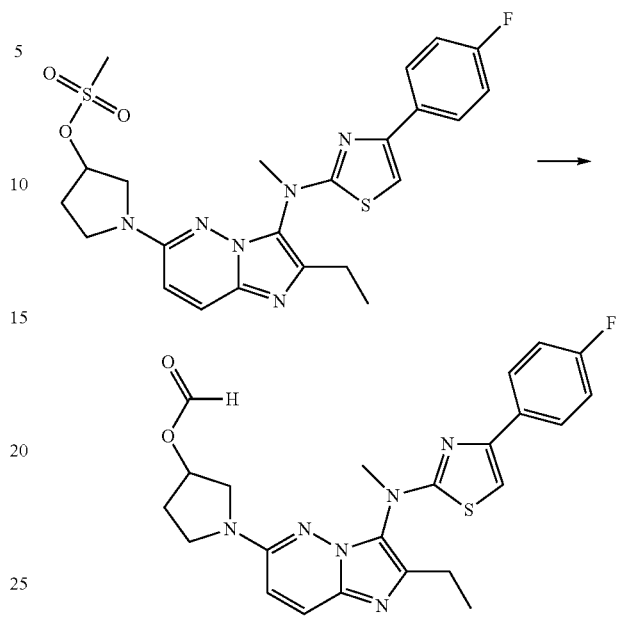

To a solution of Intermediate Gen-5-ab (50 mg, 0.097 mmol, 1 eq.) in DMF (4 mL) is added thiomorpholine (28 µL, 0.290 mmol, 3 eq.). The reaction mixture is irradiated at 200° C. for 15 min, then partitioned between EtOAc and water. The aqueous layer is extracted with EtOAc and the organic layer is washed with water and brine, dried over Na₂SO₄, filtered and concentrated in vacuo. The crude product is purified by column chromatography (elution with DCM/MeOH: 100/98 to 95/5) to afford Compound 130.

LC-MS: MW (calcd): 466 m/z (obsd): 467 (M+H)

2.7. Compound 132: 1-(3-((5-chloro-4-(4-fluorophenyl)thiazol-2-yl)(methyl)amino)-2-ethylimidazo[1,2-b]pyridazin-6-yl)pyrrolidin-3-one

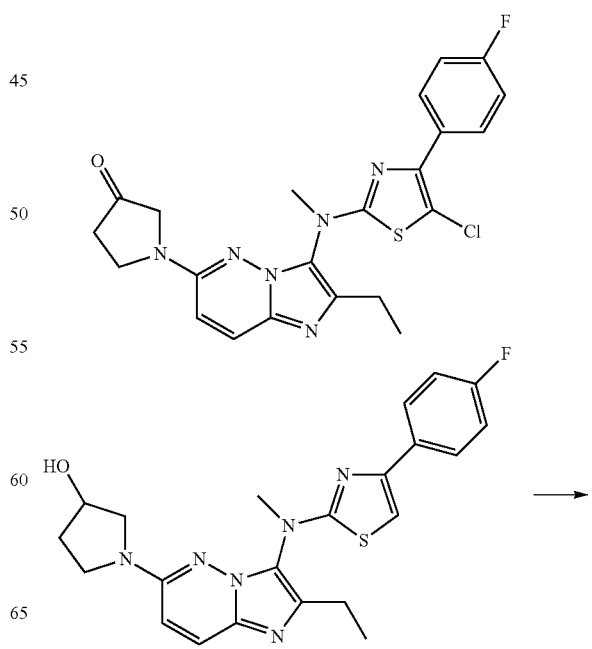

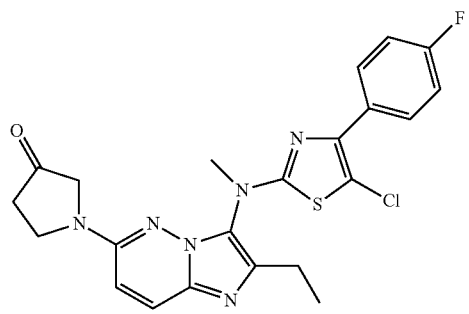

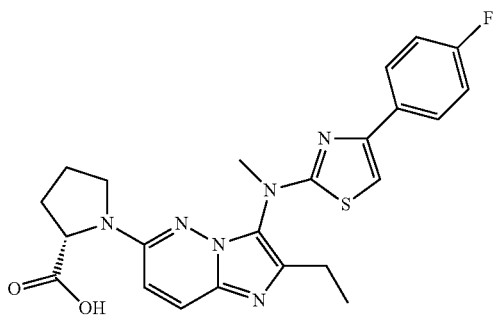

In a flask under nitrogen flow are introduced a solution of oxalyl chloride (91 µL, 0.953 mmol, 2.2 eq.) in DCM (7 mL), and DMSO (123 µL), the reaction mixture is cooled to −78° C. A solution of compound 129 (190 mg, 0.433 mmol, 1 eq.) in DCM (3 mL) is slowly introduced to the reaction mixture. The reaction mixture is stirred at −78° C. for 1.25 h, then TEA (361 L, 2.6 mmol, 6 eq.) is added and the solution is stirred for a further 1 h. After warming-up to r.t., the reaction mixture is partitioned between water and DCM. The aqueous layer is extracted with DCM, the organic layer is washed with water and brine, dried over $Na_2SO_4$, filtered and concentrated in vacuo to give Compound 132.

LC-MS: MW (calcd): 470 ($^{35}Cl$), 472 ($^{37}Cl$); m/z MW (obsd): 471 ($^{35}Cl$ M+H), 473 ($^{37}Cl$ M+H)

2.8. Compound 138: (S)-1-(2-ethyl-3-((4-(4-fluorophenyl)thiazol-2-yl)(methyl)amino)imidazo[1,2-b]pyridazin-6-yl)pyrrolidine-2-carboxylic acid To a solution of Intermediate Gen-4-a (100 mg, 0.231 mmol, 1 eq.), L-proline (11 mg, 0.092 mmol, 0.4 eq.), CuI (9 mg, 0.046 mmol, 0.2 eq.) and cesium carbonate (301 mg, 0.925 mmol, 4 eq.) in dry DMSO under argon is added 4-Ethoxy-3-oxo-butyric acid ethyl ester (43 µL, 0.277 mmol, 1.2 eq.). The reaction mixture is heated at 50° C. overnight and at r.t. for 4 days. The solution is quenched by a saturated $NH_4Cl$ solution, diluted with EtOAc and filtered. The solid is washed with EtOAc and dried in vacuo to afford Compound 138.

LC-MS: MW (calcd): 466 m/z (obsd): 467 (M+H)

2.9. Compound 195: (3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)methanol

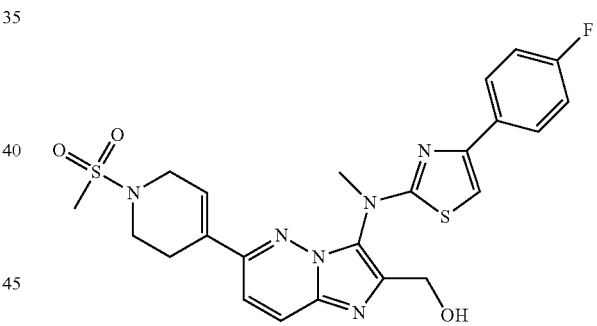

Step i)

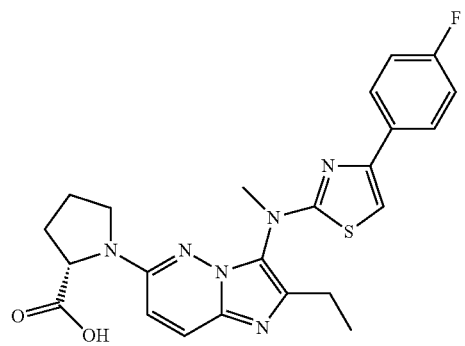

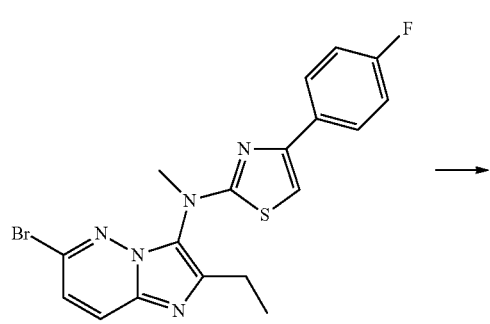

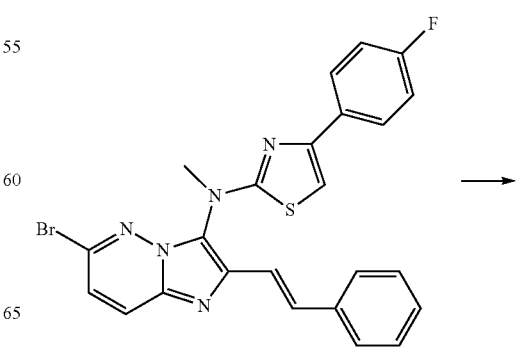

-continued

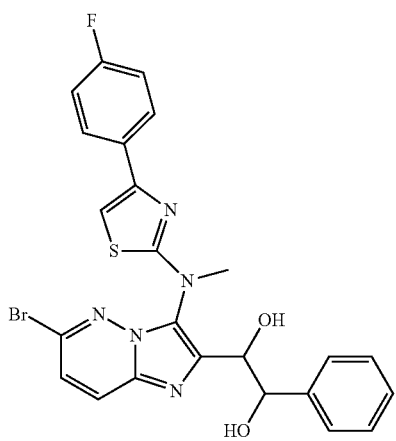

To a solution of Intermediate Gen-4-i (2.03 g, 4 mmol, 1 eq.) in DCM (150 mL) cooled at 3° C. are added osmium tetraoxide (in t-BuOH, 2.03 g, 0.2 mmol, 0.05 eq.), N-methylmorpholine-4-oxide (811 mg, 6 mmol, 1.5 eq.) and the reaction kept stirring. After 30 min an additional portion of N-methylmorpholine-4-oxide (541 mg, 4 mmol, 1 eq.) is added, this operation is performed seven times but with 0.5 eq. of N-methylmorpholine-4-oxide (until complete conversion of starting material is observed). The reaction is quenched by addition of water (500 mL). The two layers are separated and the aqueous layer is extracted with DCM (200 mL) twice. The combined organic layers are dried over $Na_2SO_4$, filtered and concentrated in vacuo. The crude product is purified by chromatography on silica gel (elution with DCM/MeOH: 100/0 to 97/3) to give Intermediate Gen-4-j.

LC-MS: MW (calcd): 539 ($^{79}$Br), 541 ($^{81}$Br); m/z (obsd): 540 ($^{79}$Br M+H), 542 ($^{81}$Br M+H)

Step ii)

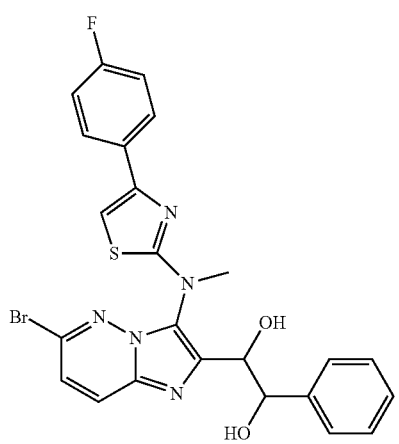

-continued

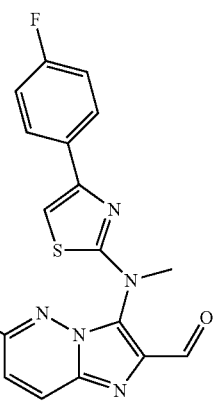

A solution of 1-(6-bromo-3-((4-(4-fluorophenyl)thiazol-2-yl)(methyl)amino)imidazo[1,2-b]pyridazin-2-yl)-2-phenylethane-1,2-diol (Gen-4-j) (4.70 g, 8.70 mmol, 1 eq.) in DCM (300 mL) is cooled to −4° C. Lead tetraacetate (dried before use, 5.79 g, 13.05 mmol, 1.5 eq.) is added and stirred at −11° C. for 20 min. The reaction is quenched by addition of water (500 mL) and brine (300 mL). The mixture is filtered and the two layers of the biphasic filtrate are separated. The aqueous layer is extracted with DCM (400 mL) twice. The combined organic layers are dried over $Na_2SO_4$, filtered and concentrated in vacuo. The crude product is purified by chromatography on silica gel (elution with heptane/EtOAc: 100/0 to 50/50) to give Intermediate Gen-4-k.

LC-MS: MW (calcd): 431 ($^{79}$Br), 433 ($^{81}$Br); m/z (obsd): 432 ($^{79}$Br M+H), 434 ($^{81}$Br M+H).

Step iii)

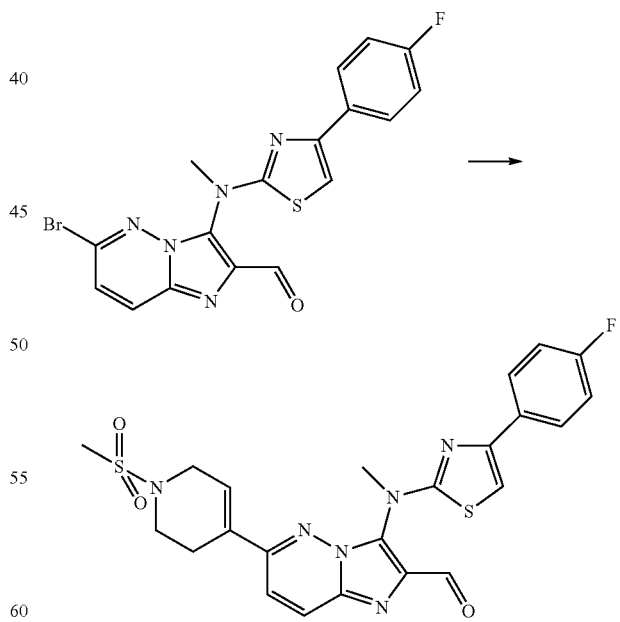

Suzuki coupling of Intermediate Gen-4-k with 1-(methylsulfonyl)-4-(4,4,5,5-tetramethyl-1,3,2-dioxaborolan-2-yl)-1,2,3,6-tetrahydropyridine according to general method E2 affords Intermediate Gen-5-aag.

LC-MS: MW (calcd): 512; MW (obsd): 513 (M+H)

Step iv

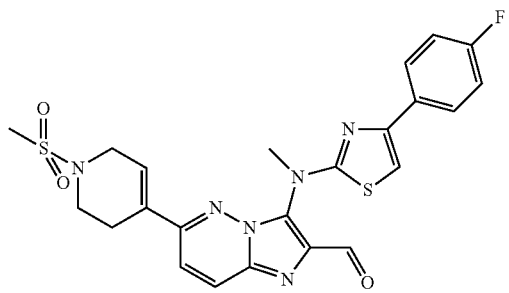

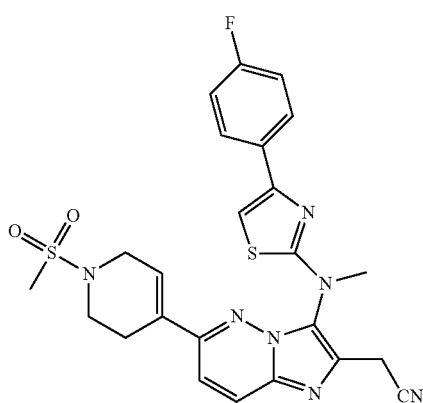 [SMILES: CN(c1nc(-c2ccc(F)cc2)cs1)c1c(CC#N)nc2ccc(C3=CCN(S(C)(=O)=O)CC3)nn12]

To a solution of intermediate 3-((4-(4-fluorophenyl)thiazol-2-yl)(methyl)amino)-6-(1-(methylsulfonyl)-1,2,3,6-tetrahydropyridin-4-yl)imidazo[1,2-b]pyridazine-2-carbaldehyde (Gen-5-aag) (50 mg, 0.098 mmol, 1 eq.) in DCM/MeOH (1 mL/1 mL) under nitrogen atmosphere at r.t. is added sodium borohydride (7.4 mg, 0.195 mmol, 2 eq.). The reaction is stirred at r.t. for 1 h, then quenched with excess of water, filtered off and concentrated in vacuo. The crude product is purified by chromatography on silica gel (elution with DCM/MeOH: 99/1 to 97/3) to afford Compound 195.

LC-MS: MW (calcd): 514; MW (obsd): 515 (M+H)

2.10. Compound 196: 2-(3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)acetonitrile Step i)

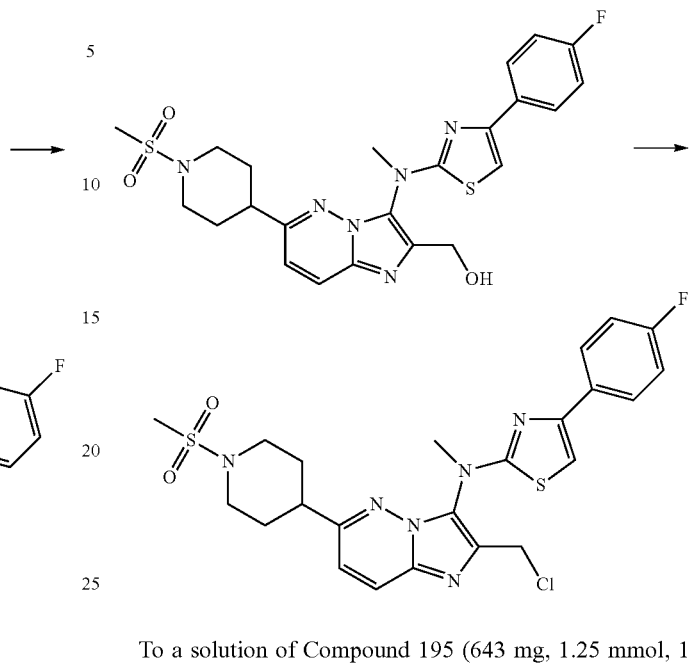

To a solution of Compound 195 (643 mg, 1.25 mmol, 1 eq.) in DCM (50 mL) is added thionyl chloride (297 mg, 2.5 mmol, 2 eq.), the reaction mixture is stirred at r.t. for 1 h. The mixture is diluted with a saturated NaHCO$_3$ solution (50 mL), then extracted with DCM (10 mL) three times. The combined, organic layers are dried over Na$_2$SO$_4$, filtered and concentrated in vacuo. The crude is purified by chromatography on silica gel (elution with DCM/MeOH: 100/0 to 97/3) to give Intermediate Gen-5-z.

LC-MS: MW (calcd): 532 ($^{35}$Cl), 534 ($^{37}$Cl); m/z (obsd): 533 ($^{35}$Cl M+H), 535 ($^{37}$Cl M+H).

Step ii)

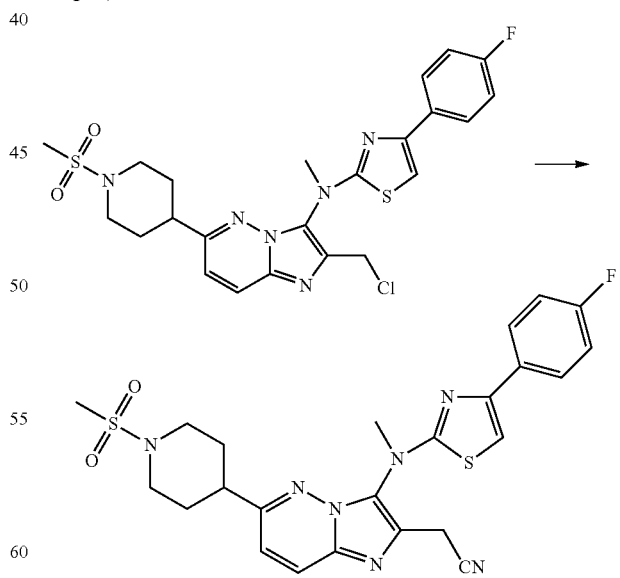

[2-Chloromethyl-6-(1-methanesulfonyl-piperidin-4-yl)-imidazo[1,2-b]pyridazin-3-yl]-[4-(4-fluoro-phenyl)-thiazol-2-yl]-methyl-amine (Gen-5-z) (560 mg, 1.05 mmol, 1 eq.) and potassium cyanide (103 mg, 1.575 mmol, 1.5 eq.) are dissolved in dry DMSO (6 mL). The reaction mixture is heated at 50° C. for 3.5 h, after cooling to r.t. the mixture is quenched by addition of a saturated NaHCO₃ solution (100 mL) and extracted with DCM (20 mL) three times. The combined organic layers are washed with water, dried over Na₂SO₄, filtered and concentrated in vacuo. The crude is purified by chromatography on silica gel (elution with DCM/MeOH: 100/0 to 97.5/2.5) to afford Compound 196.

LC-MS: MW (calcd): 523; MW (obsd): 524 (M+H)

2.11. Compound 197: 3-(3-((4-(4-fluorophenyl)thiazol-2-yl)(methyl)amino)-6-(1-(methylsulfonyl)piperidin-4-yl)imidazo[1,2-b]pyridazin-2-yl)propanamide

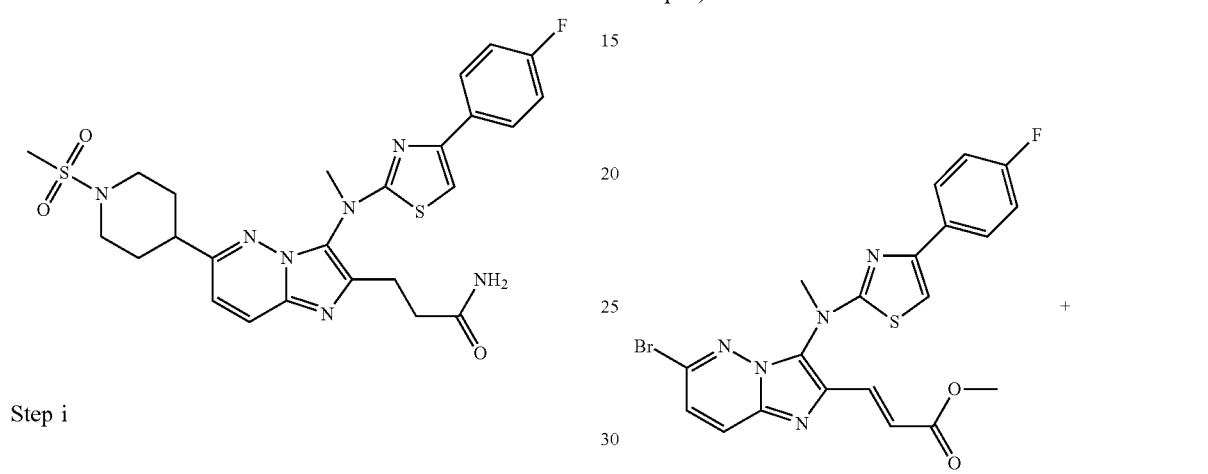

Step i

The mixture is stirred for 1 h at −78° C., allowed to warm to r.t. and stirred for 1 h. The mixture is diluted with water and DCM, the aqueous layer is extracted with DCM twice. The combined organic layers are washed twice with a saturated NaHCO₃ solution, dried over Na₂SO₄, filtered and concentrated in vacuo. The product is purified by column chromatography (elution with heptane./EtOAc: 90/10 to 0/100) to give Intermediate Gen-4-1.

LC-MS: MW (calcd): 487 ($^{79}$Br), 489 ($^{81}$Br); m/z (obsd): 488 ($^{79}$Br M+H), 490 ($^{81}$Br M+H).

Step ii)

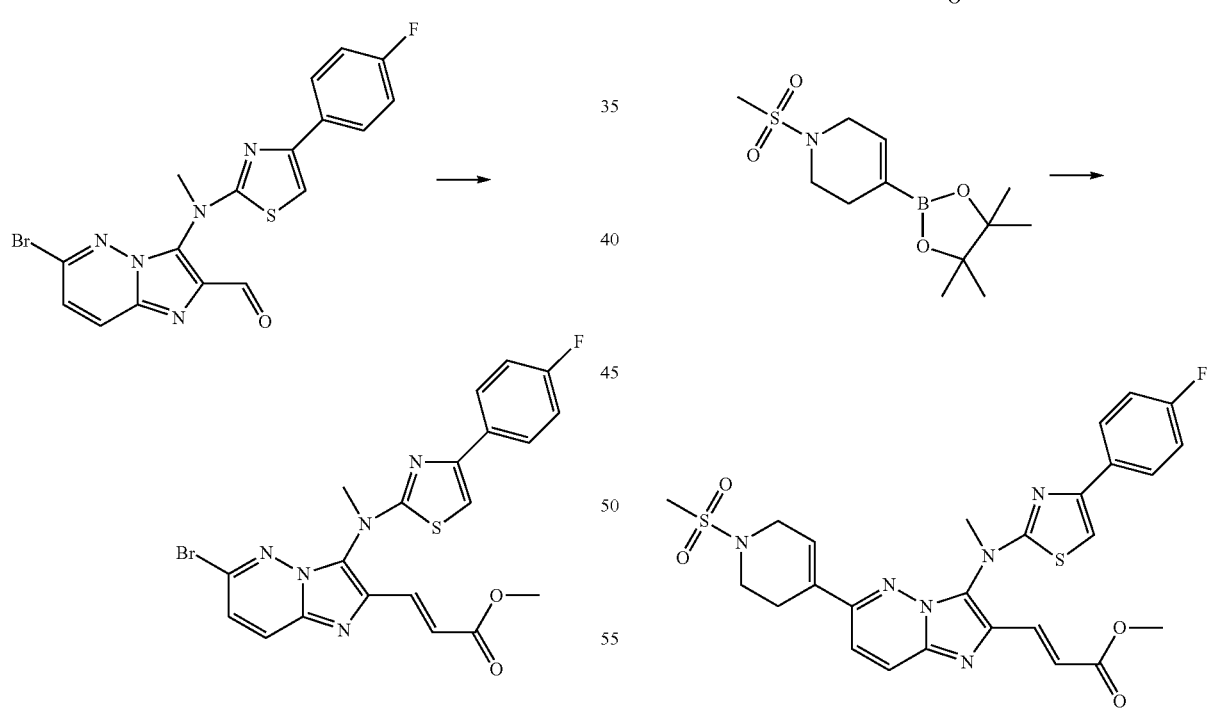

Trimethyl phosphonoacetate (206 μL, 1.272 mmol, 1.1 eq.) is dissolved in dry THF (20 mL). Sodium hydride is added (60% in oil suspension, 53 mg, 1.330 mmol, 1.15 eq.). The mixture is stirred at r.t. for 10 min, then cooled to −78° C. A solution of 6-bromo-3-((4-(4-fluorophenyl)thiazol-2-yl)(methyl)amino)imidazo[1,2-b]pyridazine-2-carbaldehyde (Gen-4-k), described in Compound 195, (500 mg, 1.157 mmol, 1 eq.) in dry THF (20 mL) is added dropwise.

Suzuki coupling of (E)-methyl-3-(6-bromo-3-((4-(4-fluorophenyl)thiazol-2-yl)(methyl)amino)imidazo[1,2-b]pyridazin-2-yl)acrylate (Gen-4-1) with 1-(methylsulfonyl)-4-(4,4,5,5-tetramethyl-1,3,2-dioxaborolan-2-yl)-1,2,3,6-tetrahydropyridine following general method E2 affords Intermediate Gen-5-aah.

LC-MS: MW (calcd): 568; MW (obsd): 569 (M+H).

Step iii)

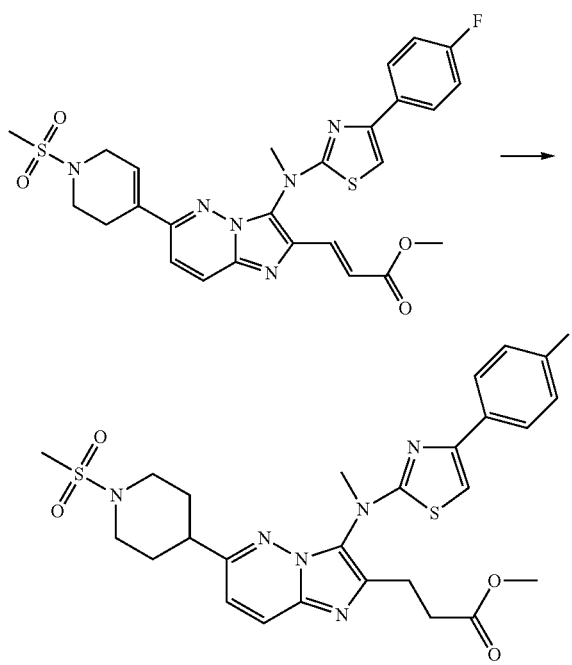

Reduction of Intermediate Gen-5-aah is performed according general method E6 to give Intermediate Gen-5-aai.

LC-MS: MW (calcd): 572; m/z (obsd): 573 (M+H). Step iv)

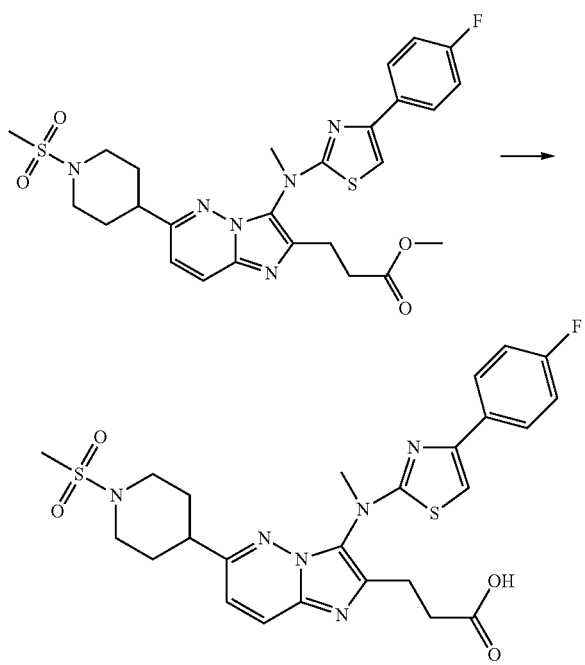

To a solution of methyl-3-(3-((4-(4-fluorophenyl)thiazol-2-yl)(methyl)amino)-6-(1-methylsulfonyl)piperidin-4-yl)imidazo[1,2-b]pyridazin-2-yl)propanoate. (Gen-5-aai) (256 mg, 0.447 mmol, 1 eq.) in THF (4 mL) are added MeOH (4 mL) and a 2 M NaOH solution (4 mL, 8.00 mmol, 17.9 eq.).

The mixture is stirred at r.t. for 2 h. Organic solvent are evaporated in vacuo. The aqueous layer is acidified with a 1 M HCl solution to slightly acid. The aqueous layer is extracted with DCM four times, the combined organic layers are dried over $Na_2SO_4$, filtered and concentrated in vacuo to afford Gen-5-aaj.

LC-MS: MW (calcd): 558; m/z (obsd): 559 (M+H).
Step iv)

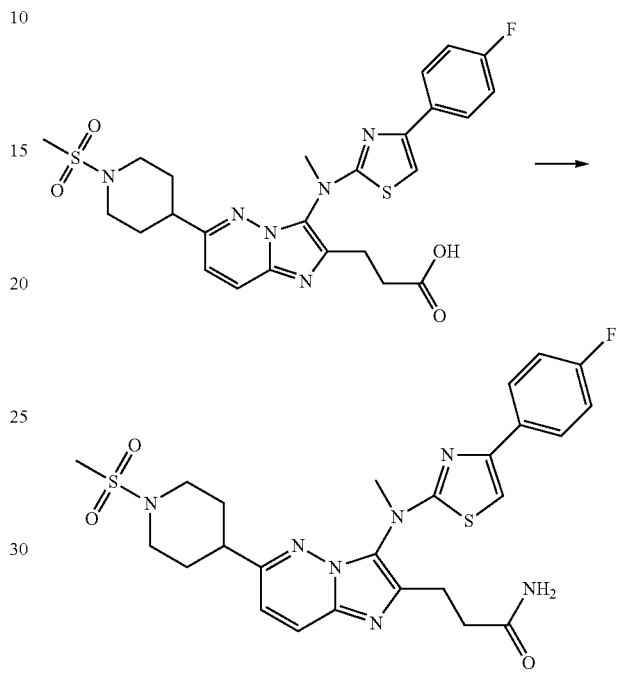

A solution of 3-(3-((4-(4-fluorophenyl)thiazol-2-yl)(methyl)amino)-6-(1-methylsulfonyl)piperidin-4-yl)imidazo[1,2-b]pyridazin-2-yl)propanoic acid (Gen-5-aaj) (50 mg, 0.090 mmol, 1 eq.) and TEA (50 µL, 0.358 mmol, 4 eq.) in dry DMF (2 mL). is stirred for 10 min. Ammonium chloride (9.58 mg, 0.179 mmol, 2 eq.) followed by propane phosphonic acid anhydride (114 m g, 0.179 mmol, 1.5 eq.) are added, and the resulting mixture is stirred at r.t. overnight. The reaction mixture is quenched with water and diluted with EtOAc, the aqueous layer is extracted with EtOAc. The combined organic layers are washed twice with a saturated $NaHCO_3$ solution and brine, dried over $Na_2SO_4$, filtered and concentrated in vacuo to afford the expected Compound 197.

LC-MS: MW (calcd): 557; m/z (obsd): 558 (M+H).

2.12. Compound 198: 3-(3-((4-(4-fluorophenyl)thiazol-2-yl)(methyl)amino)-6-(1-(methylsulfonyl)piperidin-4-yl)imidazo[1,2-b]pyridazin-2-yl)propanenitrile

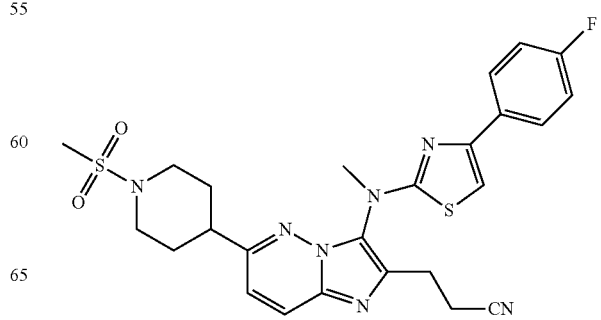

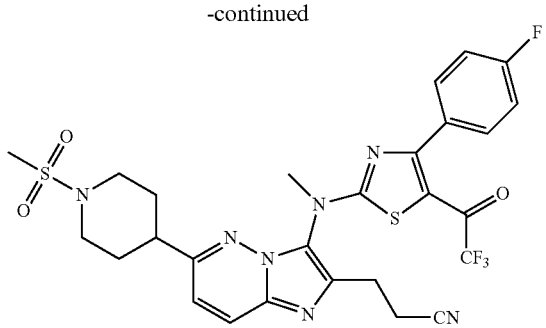

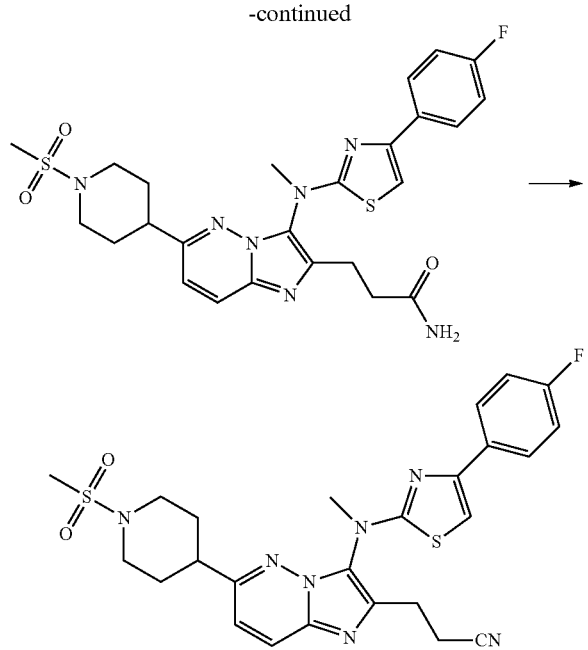

A diluted solution of Compound 197 (100 mg, 0.179 mmol, 1 eq.) in pyridine dried on molecular sieves (powder 4 angstrom) (15 mL) is stirred at −5° C. under nitrogen and treated dropwise with trifluoroacetic acid anhydride (250 µL, 1.79 mmol, 10 eq.) in 10 additions of 25 µL every 30 min. Solvent are evaporated in vacuo. The residue is diluted with water and DCM. The aqueous layer is extracted with DCM twice, the combined organic layers are washed three times with water and brine, is dried over $Na_2SO_4$, filtered and concentrated in vacuo to obtain Compound 198.

LC-MS: MW (calcd): 539; m/z (obsd): 540 (M+H).

2.13. Compound 199: 3-(3-((4-(4-fluorophenyl)-5-(2, 2, 2-trifluoroacetoyl)thiazol-2-yl)(methyl)amino)-6-(1-(methylsulfonyl)piperidin-4-yl)imidazo[1,2-b]pyridazin-2-yl)propanenitrile

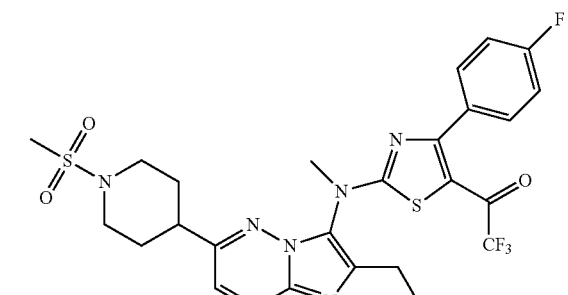

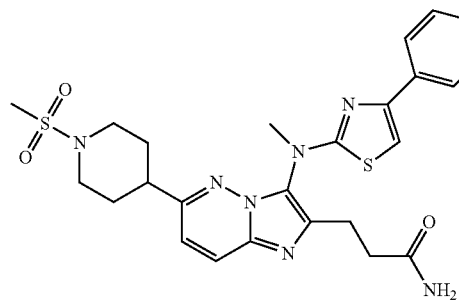

To a solution of Compound 197 (483 mg, 0.087 mmol, 1 eq.) in pyridine (2 mL) at 0° C., is added dropwise trifluoroacetic anhydride (73 µL, 0.520 mmol, 6 eq.). The reaction mixture is stirred at 0° C. for 1 h, then allowed to warm up to r.t. for 1 h, then concentrated in vacuo. The residue is partitioned between water and DCM, the aqueous layer is extracted with DCM twice, the combined organic layers are washed with water three times and brine, dried over $Na_2SO_4$, filtered and concentrated in vacuo. The crude is purified by chromatography on silica gel (DCM/MeOH: 99/1 to 90/10) to afford the expected Compound 199.

LC-MS: MW (calcd): 635; m/z (obsd): 636 (M+H).

2.14. Compound 200: 3-(3-((4-(4-fluorophenyl)thiazol-2-yl)(methyl)amino)-6-(1-(methylsulfonyl)piperidin-4-yl)imidazo[1,2-b]pyridazin-2-yl)propan-1-ol

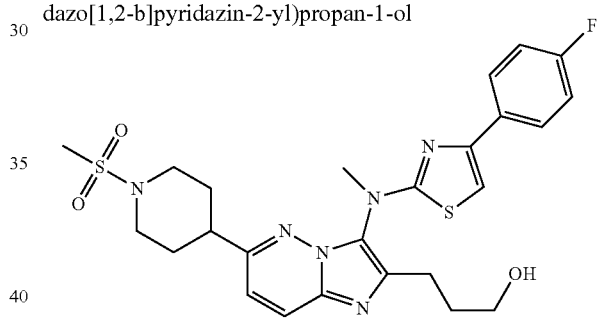

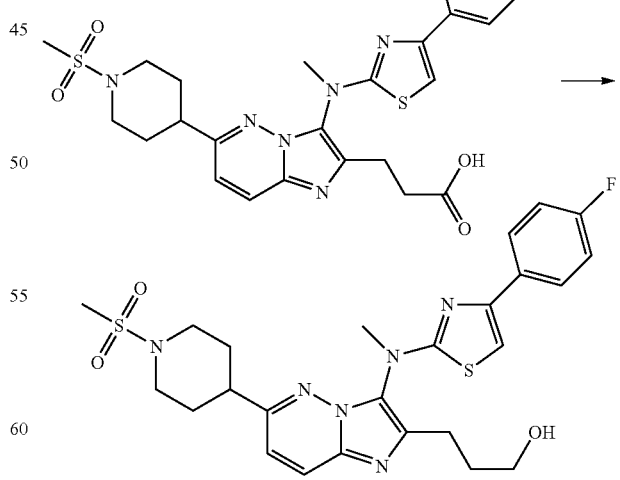

To a solution of intermediate 3-(3-((4-(4-fluorophenyl)thiazol-2-yl)(methyl)amino)-6-(1-methylsulfonyl)piperidin-4-yl)imidazo[1,2-b]pyridazin-2-yl)propanoic acid. (Gen-5-aaj) (50 mg, 0.090 mmol, 1 eq.) in dry THF (6 mL) are added TEA (15 μL, 0.107 mmol, 1.2 eq.) followed by isobutyl chloroformate (14 μL, 0.107 mmol, 1.2 eq.). The reaction mixture is stirred at r.t. for 1 h, then sodium borohydride (14 mg, 0.358 mmol, 4 eq.) is added followed by addition of absolute ethanol (1 mL). The reaction mixture is stirred at r.t. for 2 h, then quenched with a 1 M HCl solution, diluted with water and DCM. The aqueous layer is extracted with DCM twice, the combined organic layers are washed with water and brine, dried over Na$_2$SO$_4$, filtered and concentrated in vacuo. The crude is purified by preparative LC-MS to afford the expected Compound 200.

LC-MS: MW (calcd): 544; m/z (obsd): 545 (M+H)

2.15. Compound 219: 2-(5-((2-ethyl-6-(piperidin-4-yl)imidazo[1,2-b]pyridazin-3-yl)(methyl)amino)-1,2,4-thiadiazol-3-yl)-5-fluorobenzonitrile LC-MS: MW (calcd): 521 ($^{79}$Br), 523 ($^{81}$Br); m/z (obsd): 522 ($^{79}$Br M+H), 524 ($^{81}$Br M+H).

Step ii)

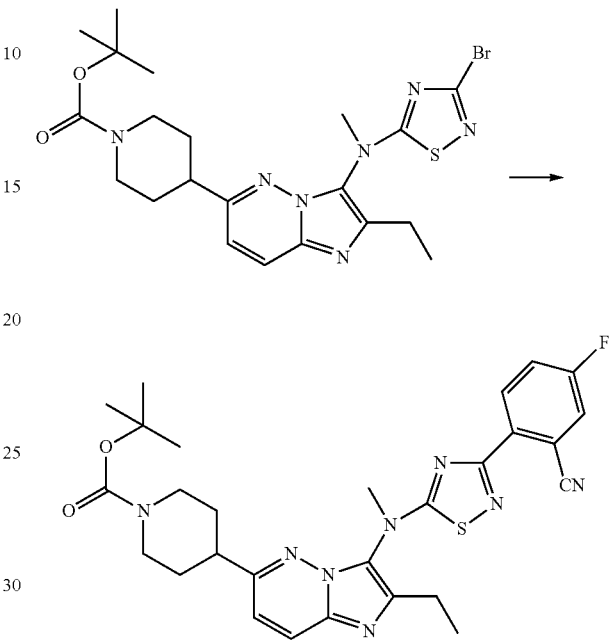

To a solution of intermediate 4-{3-[(3-Bromo-[1,2,4]thiadiazol-5-yl)-methyl-amino]-2-ethyl-imidazo[1,2-b]pyridazin-6-yl}-piperidine-1-carboxylic acid tert-butyl ester (Gen-5-an) (261.2 mg, 0.5 mmol, 1 eq.) in a mixture of dioxane (1.5 mL) and water (150 μL) under argon are successively added CsF (159.5 mg, 1.05 mmol, 2.1 eq.), 5-Fluoro-2-(4,4,5,5-tetramethyl-[1,3,2]dioxaborolan-2-yl)-benzonitrile (148.2 mg, 0.6 mmol, 1.2 eq.), and then Pd(amphos)Cl$_2$ (35.4 mg, 0.049 mmol, 0.1 eq.). The reaction mixture is heated at 80° C. for 4 days. After cooling to r.t., the crude product is partitioned between water and EtOAc and the layers are separated. The aqueous layer is extracted with a mixture of EtOAc and Et$_2$O twice, the combined organic layers are dried over Na$_2$SO$_4$ and concentrated in vacuo. The residue is purified by chromatography on silica gel (DCM/MeOH: 100/0 to 92/8) to afford Intermediate Gen-5-ao LC-MS: MW (calcd): 562; m/z MW (obsd): 563 (M+H)

Step iii)

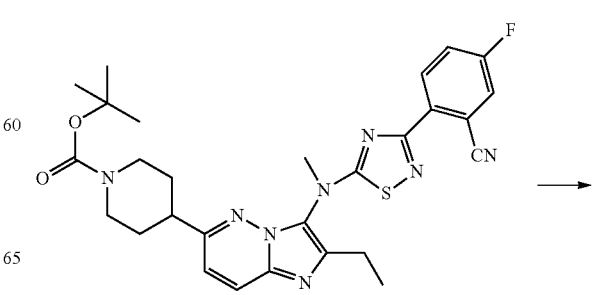

Step i)

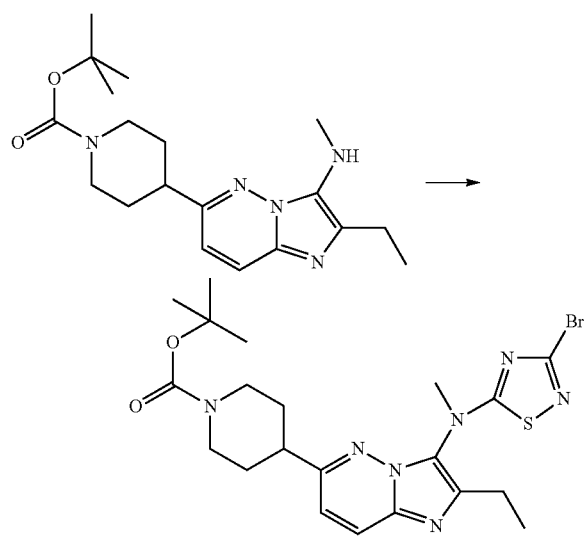

To a solution of intermediate 4-(2-Ethyl-3-methylamino-imidazo[1,2-b]pyridazin-6-yl)-piperidine-1-carboxylic acid tert-butyl ester (Gen-7-a) (1 g, 2.78 mmol, 1 eq.) in MeCN (5 mL) under argon are added 3-Bromo-5-chloro-[1,2,4]thiadiazole (1.66 g, 8.35 mmol, 3 eq.) followed by DIPEA (484 μL, 2.78 mmol, 1 eq.). The reaction mixture is heated at 90° C. for 20 h, then concentrated in vacuo. The crude is purified by chromatography on silica gel (DCM/MeOH: 100/0 to 98/2) to afford Intermediate Gen-5-an.

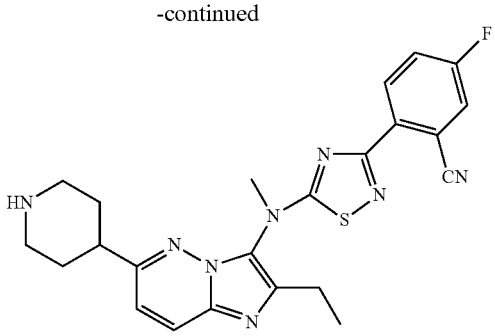

Boc deprotection of intermediate 4-(3-{[3-(2-Cyano-4-fluoro-phenyl)-[1,2,4]thiadiazol-5-yl]-methyl-amino}-2-ethyl-imidazo[1,2-b]pyridazin-6-yl)-piperidine-1-carboxylic acid tert-butyl ester (Gen-5-ao) is performed according to general method E5b to afford Compound 219.

LC-MS: MW (calcd): 462 m/z (obsd): 463 (M+H)

2.16. Intermediate Gen-9-e: 2-Chloro-4-(4-fluoro-phenyl)-pyrimidine-5-carbonitrile

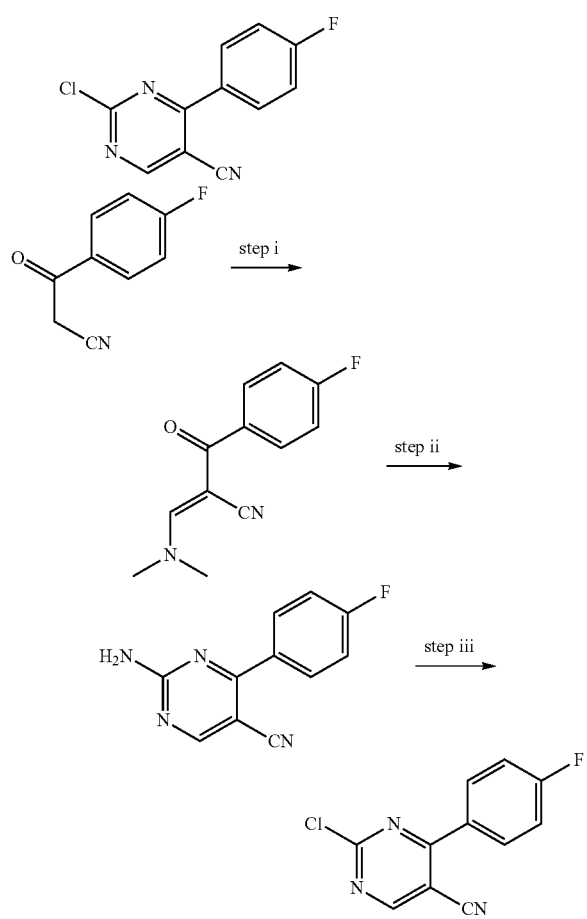

Step i)

To 3-(4-Fluoro-phenyl)-3-oxo-propionitrile (3 g, 18.3 mmol, 1 eq.) is added N,N-Dimethylformamide dimethyl acetal (7.32 mL, 55.163 mmol, 3 eq.). The reaction mixture is stirred at r.t. for 15 min. The reaction mixture is diluted with water, and the solid is filtered off, washed with water and dried in vacuo. The crude is purified by cake of silica gel (elution with DCM/MeOH: 100/3) to afford the expected product.

LC-MS: MW (calcd): 218; m/z MW (obsd): 219 (M+H)

Step ii)

To a solution of 3-Dimethylamino-2-(4-fluoro-benzoyl)-acrylonitrile (1.78 g, 8.15 mmol, 1 eq.) in EtOH (44.5 mL) at r.t. are added guanidine carbonate salt (5.87 g, 32.6 mmol, 4 eq.) and sodium acetate (6.02 g, 73.4 mmol, 9 eq.). The reaction mixture is refluxed for 3 h, then cooled to r.t., and diluted with DCM (45 mL). The crude product is filtered on Celpure® P65, washed with a mixture of DCM/EtOH (15 mL/15 mL) three times and the filtrate is concentrated in vacuo to afford the expected product.

LC-MS: MW (calcd): 214; m/z MW (obsd): 215 (M+H)

Step iii)

To a solution of 2-Amino-4-(4-fluoro-phenyl)-pyrimidine-5-carbonitrile (600 mg, 8.80 mmol, 1 eq.) and copper (II) chloride (451.9 mg, 3.36 mmol, 1.2 eq.) in dry MeCN (24 mL) under argon is added dropwise tert-butyl nitrite (0.5 mL, 4.20 mmol, 1.5 eq.). The reaction mixture is refluxed for 2 h, after cooling to r.t. the reaction mixture is diluted with $Et_2O$. The organic layer is washed with water three times, dried over $Na_2SO_4$, filtered and concentrated in vacuo. The crude is purified by chromatography on silica gel (elution heptane/EtOAc: 100/0 to 80/20) to afford the expected Intermediate Gen-9-e.

LC-MS: MW (calcd): 233 ($^{35}$Cl), 235 ($^{37}$Cl); m/z MW (obsd): 234 ($^{35}$Cl M+H), 236 ($^{37}$Cl M+H)

2.17. Intermediate Gen-10-a: Piperidine-4-sulfonic acid cyclopropylamide

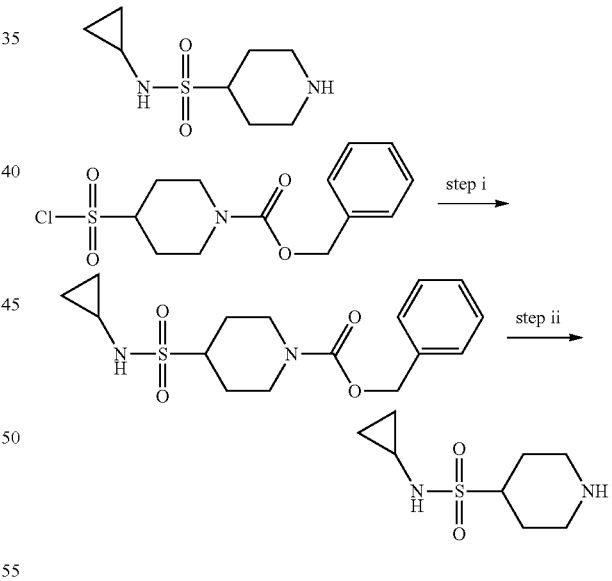

Step i)

To a solution of cyclopropylamine (39 μL, 0.566 mmol, 1.2 eq.) in DCM (2 mL) are added TEA (197 μL, 1.416 mmol, 3 eq.) and 4-Chlorosulfonyl-piperidine-1-carboxylic acid benzyl ester (150 mg, 0.472 mmol, 1 eq.). The reaction mixture is stirred at r.t. for 24 h. The crude product is quenched with water and diluted with DCM, the aqueous layer is extracted with DCM. The combined organic layers are washed with a saturated $NaHCO_3$ solution and brine, dried over $Na_2SO_4$, filtered and concentrated in vacuo. The residue is purified by chromatography on silica gel (elution DCM/MeOH: 100/0 to 95/5) to afford the expected product.

Step ii)

To a solution of 4-Cyclopropylsulfamoyl-piperidine-1-carboxylic acid benzyl ester (115 mg, 0.340 mmol, 1 eq.) in MeOH (2 mL) is added Pd/C (12 mg, 10%). The flask is evacuated and backfilled with argon. Then the reaction is evacuated and backfilled with $H_2$ and stirred at r.t. overnight. The crude product is filtered through a pad of Clarcel and washed with MeOH. The filtrate is concentrated in vacuo to afford Intermediate Gen-10-a.

2.18. Intermediate Gen-10-j: 1-(2-Piperazin-1-yl-ethyl)-pyrrolidin-2-one

Step i)

To a solution of 1-(2-Hydroxy-ethyl)-pyrrolidin-2-one (300 μL, 2.657 mmol, 1 eq.) in DCM (4 mL) is added 1-Chloro-N,N,2-trimethyl-1-propenylamine (527 μL, 3.986 mmol, 1.5 eq.). The reaction mixture is stirred at r.t. for 1 h. The crude product is quenched with water and diluted with DCM, the aqueous layer is extracted with DCM. The combined organic layers are washed with water and brine, dried over $Na_2SO_4$, filtered and concentrated in vacuo, to afford 1-(2-Chloro-ethyl)-pyrrolidin-2-one.

Step ii)

To a solution of Boc-piperazine (200 mg, 1.074 mmol, 1 eq.) in MeCN (5 mL) are added TEA (299 μL, 2.148 mmol, 2 eq.) and 1-(2-Chloro-ethyl)-pyrrolidin-2-one (238 mg, 1.611 mmol, 1.5 eq.). The reaction mixture is heated at 190° C. under microwave irradiation for 1.2 h. After cooling, the reaction mixture is concentrated in vacuo, then the crude product is partitioned between water and DCM, the aqueous layer is extracted with DCM three times. The combined organic layers are washed with water and brine, dried over $Na_2SO_4$, filtered and concentrated in vacuo. The residue is purified by chromatography on silica gel (elution DCM/MeOH: 100 to 95/5) to afford the expected intermediate.

Step iii)

To a solution of the above boc protected amine (149 mg, 0.501 mmol, 1 eq.) in MeOH (2 mL) is added a 4 M HCl solution in dioxane (3 mL). The reaction mixture is stirred at r.t. overnight then concentrated in vacuo, to afford the expected intermediate Gen-10-j as hydrochloride salt which used directly in the next step without purification.

2.19. Intermediate Gen-10-i: N,N-Dimethyl-2-piperazin-1-yl-acetamide

Step i)

To a solution of N-boc piperazine (150 mg, 0.81 mmol, 1 eq.) in MeCN (2 mL) are added TEA (224 μL, 1.61 mmol, 2 eq.) and 2-Chloro-N,N-dimethyl-acetamide (124 μL, 1.21 mmol, 1.5 eq.). The reaction mixture is stirred at r.t. for 4 h. The crude product is quenched with water and diluted with DCM, the aqueous layer is extracted with DCM. The combined organic layers are washed with brine, dried over $Na_2SO_4$, filtered and concentrated in vacuo to afford the expected product.

Step ii)

To a solution of the above boc protected amine (216 mg, 0.8 mmol, 1 eq.) in a mixture of MeOH (3 mL) and dioxane (3 mL) is added a 4 M HCl solution in dioxane (995 μL). The reaction mixture is stirred at r.t. for 2.5 days then concentrated in vacuo. The crude is triturated in $Et_2O$, filtered off and dried to afford the expected Intermediate Gen-10-l as hydrochloride salt which used directly in the next step without purification.

2.20. Intermediate Gen-10-o: 1-Oxa-3, 7-diaza-spiro[4.4]nonan-2-one

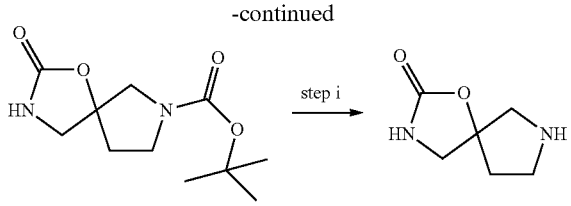

Step i)
To a solution of 3-Aminomethyl-3-hydroxy-pyrrolidine-1-carboxylic acid tert-butyl ester (200 mg, 0.93 mmol, 1 eq.) in MeCN (2 mL) are added TEA (130 μL, 0.93 mmol, 1 eq.) and 4-nitrophenyl chloroformate (186 mg, 0.93 mmol, 1 eq.). The reaction mixture is stirred at r.t. for 2.5 days, then heated at 75° C. overnight, and the crude product is concentrated in vacuo. The residue is purified by chromatography on silica gel (elution DCM/MeOH: 100/0 to 95/5) to afford the expected product.

Step ii)
To a solution of the boc protected amine (110 mg, 0.45 mmol, 1 eq.) in dioxane (2 mL) is added an aqueous 12 M HCl solution (152 μL). The reaction mixture is stirred at r.t. overnight then concentrated in vacuo, to afford Intermediate Gen-10-o.

2.21. Intermediate Gen-10-x: 4-Morpholin-4-yl-pyrrolidin-3-ol

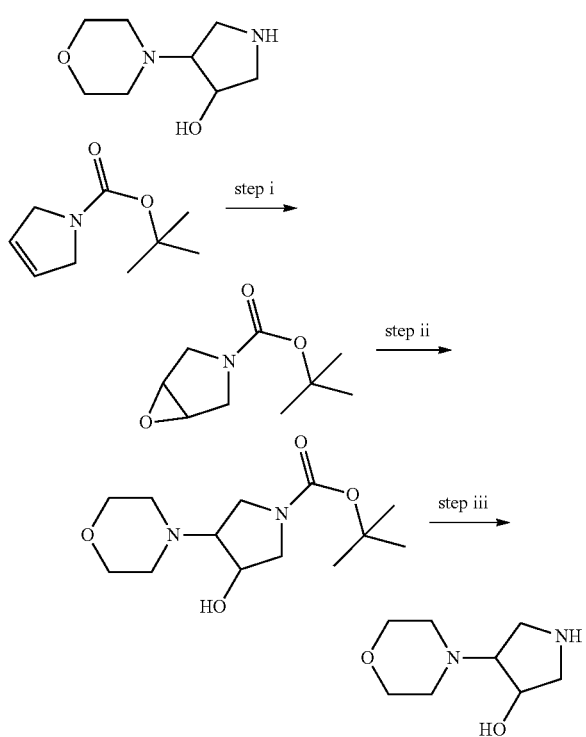

Step i)
To a solution of 2,5-dihydro-pyrrole-1-carboxylic acid tert-butyl ester (100 mg, 0.591 mmol, 1 eq.) in DCM (1.4 mL) is added m-CPBA (335.1 mg, 1.359 mmol, 2.3 eq.), the reaction mixture is stirred at r.t. overnight. The crude product is quenched with a 1 M NaOH solution and diluted with DCM, the aqueous layer is extracted with DCM twice. The combined organic layers are dried over Na₂SO₄, filtered and concentrated in vacuo, the residue is purified by chromatography on silica gel (elution heptane/EtOAc: 100/0 to 60/40) to afford the expected product.

LC-MS: MW (calcd): 185; m/z MW (obsd): 186 (M+H)

Step ii)
To a solution of 6-Oxa-3-aza-bicyclo[3.1.0]hexane-3-carboxylic acid tert-butyl ester (70 mg, 0.378 mmol, 1 eq.) in EtOH (0.4 mL) is added morpholine (36.6 μL, 0.416 mmol, 1.1 eq.). The reaction mixture is heated at 130° C. under microwave irradiation for 40 min, then morpholine (36.6 μL, 0.416 mmol, 1.1 eq.) is added and the reaction mixture is another heated at 130° C. under microwave irradiation for 40 min. The reaction mixture is concentrated in vacuo, the residue is purified by chromatography on silica gel (elution DCM/MeOH: 100/0 to 90/10) to afford the expected product.

LC-MS: MW (calcd): 272; m/z MW (obsd): 273 (M+H)

Step iii)
To a solution of the above boc protected amine (95 mg, 0.349 mmol, 1 eq.) in dioxane (0.75 mL) is added a 4 M HCl solution in dioxane (0.70 mL). The reaction mixture is stirred at r.t. for 6 h then concentrated in vacuo, to afford the expected Intermediate Gen-10-x as hydrochloride salt which used directly in the next step without purification.

LC-MS: MW (calcd): 172; m/z MW (obsd): 173 (M+H)

2.22. Intermediate Gen-10-aa: 4-Methoxy-1-pyrrolidin-3-yl-piperidine

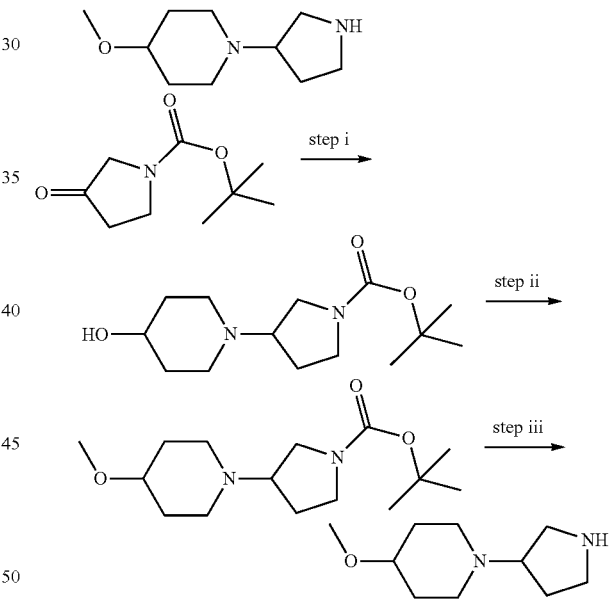

Step i)
To a solution of 4-hydroxypiperidine (901.1 mg, 8.909 mmol, 3.3 eq.) in DCE (20 mL) is added N-boc-3-pyrrolidinone (500 mg, 2.699 mmol, 1 eq.). The reaction mixture is stirred at r.t. then NaBH(OAc)₃ (2.86 g, 13.497 mmol, 5 eq.) is added. The reaction mixture is stirred at r.t. overnight, then concentrated in vacuo. The residue is dissolved in a mixture of DCM and a saturated NaHCO₃ solution, the two phases are separated and the aqueous phase is extracted with DCM twice. The combined organic layers are washed with brine, dried over Na₂SO₄, filtered and concentrated in vacuo. The residue is purified by chromatography on silica gel (elution DCM/MeOH: 100/0 to 90/10) to afford the expected product.

LC-MS: MW (calcd): 270; m/z MW (obsd): 271 (M+H)

Step ii)

To a solution of 3-(4-Hydroxy-piperidin-1-yl)-pyrrolidine-1-carboxylic acid tert-butyl ester (300 mg, 1.109 mmol, 1 eq.) in dry DMF (3 mL) are added NaH (60% in oil suspension, 66.6 mg, 1.664 mmol, 1.5 eq.) and methyl iodide (82.2 µL, 1.332 mmol, 1.2 eq.). The reaction mixture is stirred at r.t. overnight, then the reaction mixture is quenched with water, and diluted with AcOEt, the layers are separated, the aqueous layer is extracted with AcOEt. The combined organic layers are dried over $Na_2SO_4$ and concentrated in vacuo. The expected product is obtained by chromatography on silica gel (elution DCM/MeOH: 100/0 to 90/10).

LC-MS: MW (calcd): 284; m/z MW (obsd): 285 (M+H)

Step iii)

To a solution of the above boc protected amine (150 mg, 0.527 mmol, 1 eq.) in dioxane (1.1 mL) is added a 4 M HCl solution in dioxane (1.1 mL). The reaction mixture is stirred at r.t. for 7 h then concentrated in vacuo, to afford the expected intermediate Gen-10-aa as hydrochloride salt which used directly in the next step the next step without purification.

2.23. Intermediate Gen-10-ab: 2-(1-Methanesulfonyl-piperazin-2-yl)-ethanol

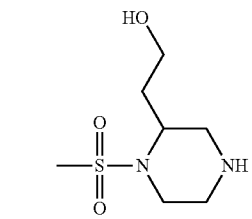

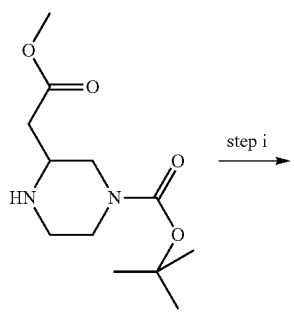

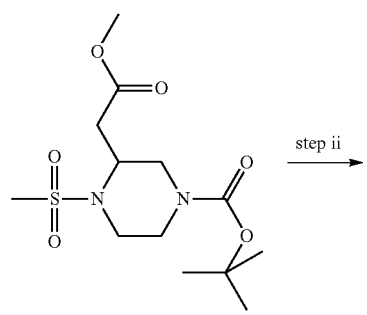

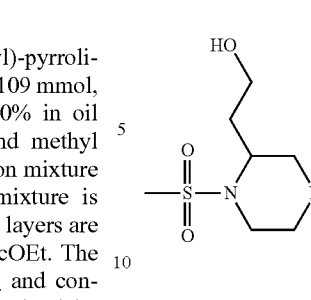 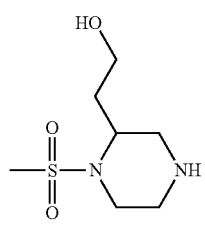

Step i)

To a solution of 3-Methoxycarbonylmethyl-piperazine-1-carboxylic acid tert-butyl ester (700 mg, 2.71 mmol, 1 eq.) in DCM (9 mL) are added TEA (1.13 mL, 8.13 mmol, 3 eq.) and mesyl chloride (231 µL, 2.98 mmol, 1.1 eq.). The reaction mixture is stirred at r.t. overnight. The crude product is quenched with water and a saturated $NaHCO_3$ solution and diluted with DCM, the aqueous layer is extracted with DCM three times. The combined organic layers are washed with brine, dried over $Na_2SO_4$, filtered and concentrated in vacuo. The residue is purified by chromatography on silica gel (elution with heptane/EtOAc: 70/30 to 50/50) to afford the expected product.

Step ii)

To a solution of 4-Methanesulfonyl-3-methoxycarbonyl-methyl-piperazine-1-carboxylic acid tert-butyl ester (150 mg, 0.45 mmol, 1 eq.) in dry THF (2 mL) at 0° C. is added dropwise a 1 M LiAlH$_4$ solution in THF (670 µL, 0.67 mmol, 1.5 eq.). The reaction mixture is stirred at 0° C. then at r.t. overnight. The crude product is filtered through a pad of Clarcel, washed with THF and DCM, and the filtrate is concentrated in vacuo. The crude is purified by chromatography on silica gel (elution DCM/MeOH: 98/2 to 96/4) to afford the expected product.

Step iii)

To a solution of the above boc protected amine (95 mg, 0.31 mmol, 1 eq.) in dioxane (2 mL) is added a 4 M HCl solution in dioxane (385 µL). The reaction mixture is stirred at r.t. overnight, then a 4 M HCl solution in dioxane (800 µL) is added again, and stirred at r.t. overnight, then concentrated in vacuo to afford the expected Intermediate Gen-10-ab as hydrochloride salt which used directly in the next step without purification.

2.24. Intermediate Gen-10-ac: 1-(4-Methoxy-benzyl)-3-piperazin-1-yl-pyrrolidin-2-one

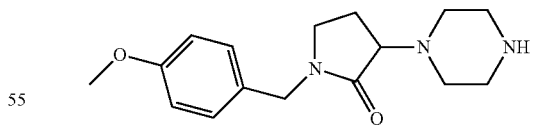

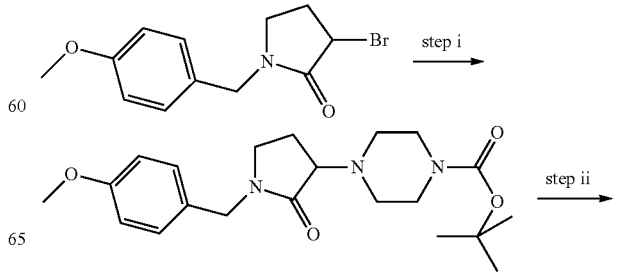

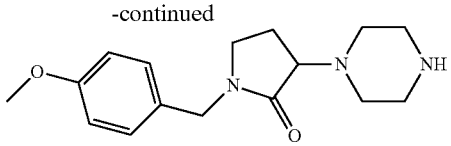

Step i)

To a solution of Boc-piperazine (204.5 mg, 1.1 mmol, 1.1 eq.) in dry DMF (8.3 mL) are added potassium carbonate (276.4 mg, 2.0 mmol, 2 eq.), 3-Bromo-1-(4-methoxy-benzyl)-pyrrolidin-2-one (284.2 mg, 1. mmol, 1 eq.) and NaI (149.9 mg, 1 mmol, 1 eq.). The reaction mixture is stirred at r.t. overnight, then Boc-piperazine (37.3 mg, 0.2 mmol, 0.2 eq.) and the reaction mixture is stirred at r.t. for 2 h. The reaction mixture is quenched with water and diluted with EtOAc, the aqueous layer is extracted with EtOAc twice. The combined organic layers are washed with water and brine, dried over $Na_2SO_4$, filtered and concentrated in vacuo. The residue is purified by chromatography on silica gel (elution DCM/MeOH: 98/2 to 95/5) to afford the expected intermediate.

LC-MS: MW (calcd): 389; m/z MW (obsd): 390 (M+H)

Step ii)

To a solution of the above boc protected amine (299.4 mg, 0.77 mmol, 1 eq.) in MeOH (2 mL) is added a 4 M HCl solution in dioxane (1.9 mL). The reaction mixture is stirred at r.t. for 4 h then concentrated in vacuo, to afford the expected Intermediate Gen-10-ac as hydrochloride salt which used directly for the next step without purification.

LC-MS: MW (calcd): 289; m/z MW (obsd): 290 (M+H)

2.25. Intermediate Gen-11-j: 2-Chloro-1-(2, 5-dimethyl-pyrrolidin-1-yl)-ethanone

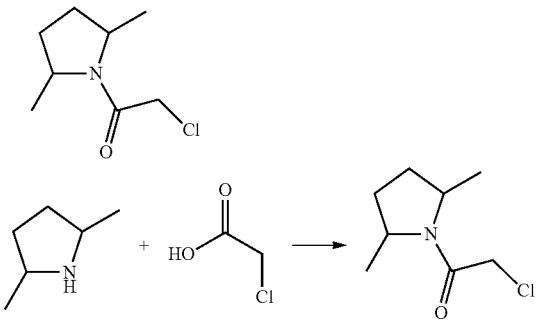

To a solution of chloroacetic acid (100 mg, 1.058 mmol, 1 eq.) and 2,5-Dimethyl-pyrrolidine (130 µL, 1.058 mmol, 1 eq.) in DCM (15 mL) is added DCC resin (14 mg, 2.116 mmol, 2 eq.). The reaction mixture is stirred at r.t. overnight then filtered. The resin is washed with MeOH and DCM, and the filtrate is concentrated in vacuo to afford Intermediate Gen-11-j which used without further purification in the next step.

TABLE 1

Intermediates used towards the compounds of the invention.

| Int | Structures | Name | Mtd | MW | MS Ms'd |
|---|---|---|---|---|---|
| Gen-1-a | (structure) | N-(6-Bromo-2-ethyl-imidazo[1,2-b]pyridazin-3-yl)-formamide | A2 | 268 ($^{79}$Br), 270 ($^{81}$Br) | 269 ($^{79}$Br M + H), 271 ($^{81}$Br M + H) |
| Gen-1-b | (structure) | N-(6-Bromo-2-ethyl-imidazo[1,2-a]pyrazin-3-yl)-formamide | A1 | 268 ($^{79}$Br), 270 ($^{81}$Br) | 269 ($^{79}$Br M + H), 271 ($^{81}$Br M + H) |
| Gen-1-c | (structure) | N-[6-Bromo-2-((E)-styryl)-imidazo[1,2-b]pyridazin-3-yl]-formamide | A1 | 342 ($^{79}$Br), 344 ($^{81}$Br) | 343 ($^{79}$Br M + H), 345 ($^{81}$Br M + H) |
| Gen-2-a | (structure) | N-(6-Bromo-2-ethyl-imidazo[1,2-b]pyridazin-3-yl)-N-methyl-formamide | Gen-1-a B2 | 282 ($^{79}$Br), 284 ($^{81}$Br) | 283 ($^{79}$Br M + H), 285 ($^{81}$Br M + H) |

TABLE 1-continued

Intermediates used towards the compounds of the invention.

| Int | Structures | Name | Mtd | MW | MS Ms'd |
|---|---|---|---|---|---|
| Gen-2-b | 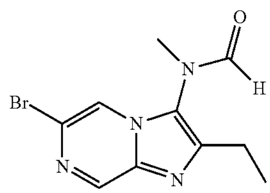 [SMILES: CCc1nc2cnc(Br)cn2c1N(C)C=O] | N-(6-Bromo-2-ethyl-imidazo[1,2-a]pyrazin-3-yl)-N-methyl-formamide | Gen-1-b B2 | 282 ($^{79}$Br), 284 ($^{81}$Br) | 283 ($^{79}$Br M + H), 285 ($^{81}$Br M + H) |
| Gen-2-c | 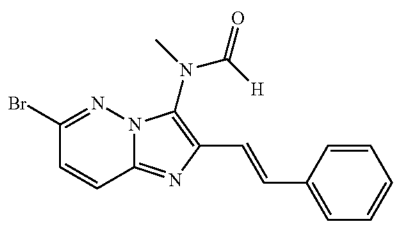 [SMILES: CN(C=O)c1c(/C=C/c2ccccc2)nc2ccc(Br)nn12] | N-[6-Bromo-2-((E)-styryl)-imidazo[1,2-b]pyridazin-3-yl]-N-methyl-formamide | Gen-1-c B1 | 356 ($^{79}$Br), 358 ($^{81}$Br) | 357 ($^{79}$Br M + H), 359 ($^{81}$Br M + H) |
| Gen-3-a | 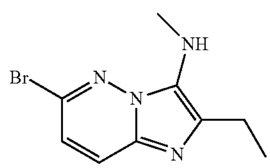 | (6-Bromo-2-ethyl-imidazo[1,2-b]pyridazin-3-yl)-methyl-amine | Gen-2-a C1 | 254 ($^{79}$Br), 256 ($^{81}$Br) | 255 ($^{79}$Br M + H), 257 ($^{81}$Br M + H) |
| Gen-3-b | 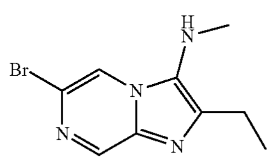 | (6-Bromo-2-ethyl-imidazo[1,2-a]pyrazin-3-yl)-methyl-amine | Gen-2-b C2 | 254 ($^{79}$Br), 256 ($^{81}$Br) | 255 ($^{79}$Br M + H), 257 ($^{81}$Br M + H) |
| Gen-3-c | 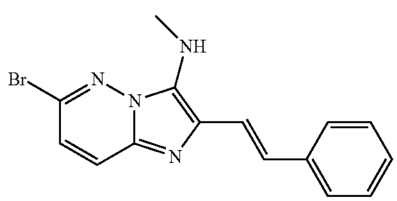 [SMILES: CNc1c(/C=C/c2ccccc2)nc2ccc(Br)nn12] | (E)-N-(6-bromo-2-styrylimidazo[1,2-b]pyridazin-3-yl)-N-methylamine | Gen-2-c C1 | 328 ($^{79}$Br), 330 ($^{81}$Br); | 329 ($^{79}$Br M + H), 331 ($^{81}$Br M + H) |
| Gen-4-a | 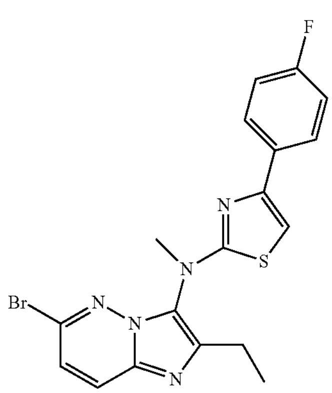 [SMILES: CCc1nc2ccc(Br)nn2c1N(C)c1nc(-c2ccc(F)cc2)cs1] | (6-Bromo-2-ethyl-imidazo[1,2-b]pyridazin-3-yl)-[4-(4-fluoro-phenyl)-thiazol-2-yl]-methyl-amine | Gen-3-a D1 | 431 ($^{79}$Br), 433 ($^{81}$Br) | 432 ($^{79}$Br M + H), 434 ($^{81}$Br M + H) |

TABLE 1-continued

Intermediates used towards the compounds of the invention.

| Int | Structures | Name | Mtd | MW | MS Ms'd |
|---|---|---|---|---|---|
| Gen-4-b | 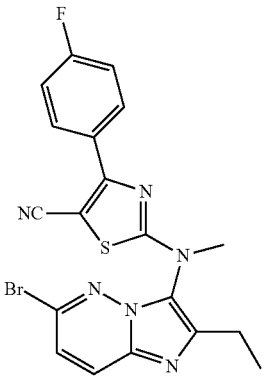 [SMILES: CCc1nc2ccc(Br)nn2c1N(C)c1nc(-c2ccc(F)cc2)c(C#N)s1] | 2-[(6-Bromo-2-ethyl-imidazo[1,2-b]pyridazin-3-yl)-methyl-amino]-4-(4-fluoro-phenyl)-thiazole-5-carbonitrile | Gen-3-a D2 | 456 ($^{79}$Br), 458 ($^{81}$Br) | 457 ($^{79}$Br M + H), 459 ($^{81}$Br M + H) |
| Gen-4-c | 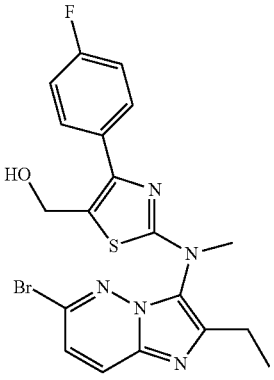 [SMILES: CCc1nc2ccc(Br)nn2c1N(C)c1nc(-c2ccc(F)cc2)c(CO)s1] | [2-[(6-Bromo-2-ethyl-imidazo[1,2-b]pyridazin-3-yl)-methyl-amino]-4-(4-fluoro-phenyl)-thiazol-5-yl]-methanol | Gen-4-a E14 | 461 ($^{79}$Br), 463 ($^{81}$Br) | 462 ($^{79}$Br M + H), 464 ($^{81}$Br M + H) |
| Gen-4-d | 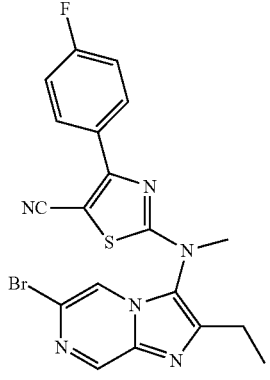 [SMILES: CCc1nc2cnc(Br)cn2c1N(C)c1nc(-c2ccc(F)cc2)c(C#N)s1] | 2-[(6-Bromo-2-ethyl-imidazo[1,2-a]pyrazin-3-yl)-methyl-amino]-4-(4-fluoro-phenyl)-thiazole-5-carbonitrile | Gen-3-b D2 | 456 ($^{79}$Br), 458 ($^{81}$Br) | 457 ($^{79}$Br M + H), 459 ($^{81}$Br M + H) |
| Gen-4-e | 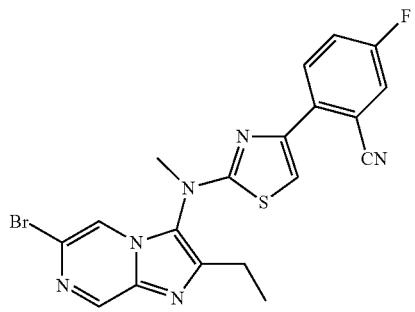 [SMILES: CCc1nc2cnc(Br)cn2c1N(C)c1nc(-c2ccc(F)cc2C#N)cs1] | 2-{2-[(6-Bromo-2-ethyl-imidazo[1,2-a]pyrazin-3-yl)-methyl-amino]-thiazol-4-yl}-5-fluoro-benzonitrile | Gen-3-b D1 | 456 ($^{79}$Br), 458 ($^{81}$Br) | 457 ($^{79}$Br M + H), 459 ($^{81}$Br M + H) |

TABLE 1-continued

Intermediates used towards the compounds of the invention.

| Int | Structures | Name | Mtd | MW | MS Ms'd |
|---|---|---|---|---|---|
| Gen-4-f | 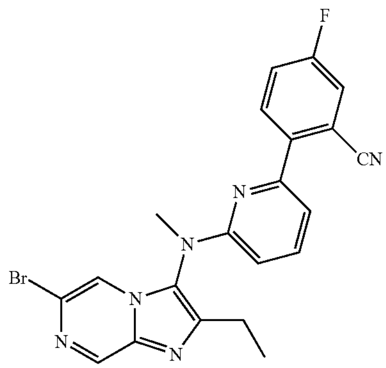 [SMILES: CCc1nc2cnc(Br)cn2c1N(C)c1cccc(-c2ccc(F)cc2C#N)n1] | 2-{6-[(6-Bromo-2-ethyl-imidazo[1,2-a]pyrazin-3-yl)-methyl-amino]-pyridin-2-yl}-5-fluoro-benzonitrile | Gen-3-b D2 | 450 ($^{79}$Br), 452 ($^{81}$Br) | 451 ($^{79}$Br M + H), 453 ($^{81}$Br, M + H) |
| Gen-4-g | 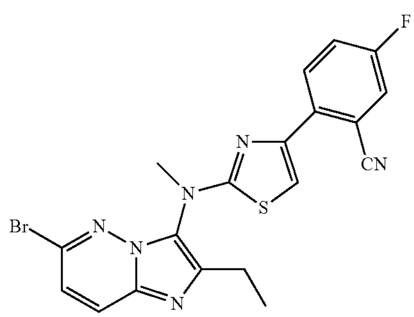 [SMILES: CCc1nc2ccc(Br)nn2c1N(C)c1nc(-c2ccc(F)cc2C#N)cs1] | 2-{2-[(6-Bromo-2-ethyl-imidazo[1,2-b]pyridazin-3-yl)-methyl-amino]-thiazol-4-yl}-5-fluoro-benzonitrile | Gen-3-a D1 | 456 ($^{79}$Br), 458 ($^{81}$Br) | 457 ($^{79}$Br M + H), 459 ($^{81}$Br M + H) |
| Gen-4-h | 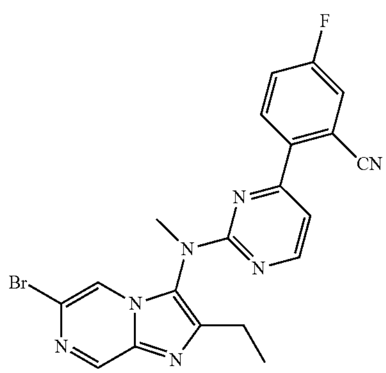 [SMILES: CCc1nc2cnc(Br)cn2c1N(C)c1nccc(-c2ccc(F)cc2C#N)n1] | 2-{2-[(6-Bromo-2-ethyl-imidazo[1,2-a]pyrazin-3-yl)-methyl-amino]-pyrimidin-4-yl}-5-fluoro-benzonitrile | Gen-3-b D2 | 451 ($^{79}$Br), 453 ($^{81}$Br) | 452 ($^{79}$Br M + H), 454 ($^{81}$Br M + H) |
| Gen-4-i | 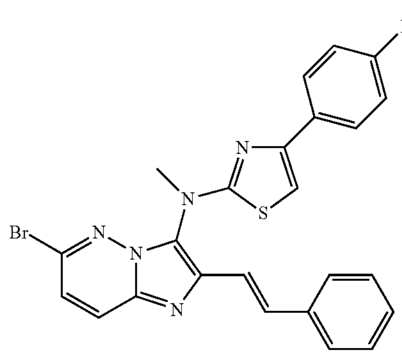 | [6-Bromo-2-((E)-styryl)-imidazo[1,2-b]pyridazin-3-yl)-[4-(4-fluoro-phenyl)-thiazol-2-yl]-methyl-amine | Gen-3-c D1 | 505 ($^{79}$Br), 507 ($^{81}$Br) | 506 ($^{79}$Br M + H), 508 ($^{81}$Br M + H) |

TABLE 1-continued

Intermediates used towards the compounds of the invention.

| Int | Structures | Name | Mtd | MW | MS Ms'd |
|---|---|---|---|---|---|
| Gen-4-j | 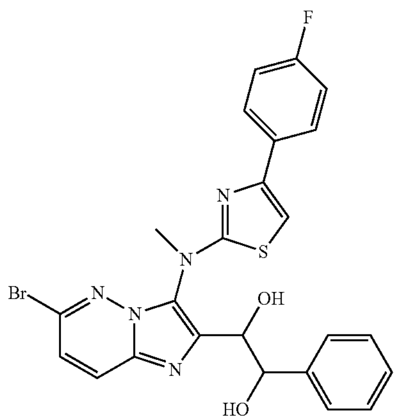 [SMILES: CN(c1nc(-c2ccc(F)cc2)cs1)c1c(C(O)C(O)c2ccccc2)nc2ccc(Br)nn12] | 1-(6-bromo-3-((4-(4-fluorophenyl)thiazol-2-yl)(methyl)amino)imidazo[1,2-b]pyridazin-2-yl)-2-phenylethane-1,2-diol | Gen-4-i See Cpd 195 | 539 ($^{79}$Br), 541 ($^{81}$Br) | 540 ($^{79}$Br M + H), 542 ($^{81}$Br M + H) |
| Gen-4-k | 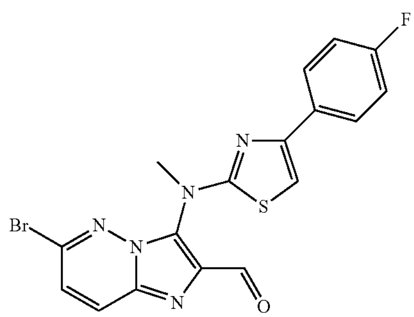 [SMILES: CN(c1nc(-c2ccc(F)cc2)cs1)c1c(C=O)nc2ccc(Br)nn12] | 6-bromo-3-((4-(4-fluorophenyl)thiazol-2-yl)(methyl)amino)imidazo[1,2-b]pyridazine-2-carbaldehyde | Gen-4-j See Cpd 195 | 431 ($^{79}$Br), 433 ($^{81}$Br) | 432 ($^{79}$Br M + H), 434 ($^{81}$Br M + H) |
| Gen-4-l | 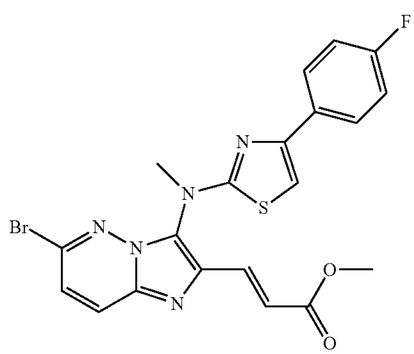 [SMILES: COC(=O)/C=C/c1nc2ccc(Br)nn2c1N(C)c1nc(-c2ccc(F)cc2)cs1] | (E)-methyl-3-(6-bromo-3-((4-(4-fluorophenyl)thiazol-2-yl)(methyl)amino)imidazo[1,2-b]pyridazin-2-yl)acrylate | Gen-4-k See cpd 197 | 487 ($^{79}$Br), 489 ($^{81}$Br) | 488 ($^{79}$Br M + H), 490 ($^{81}$Br M + H) |
| Gen-4-m | 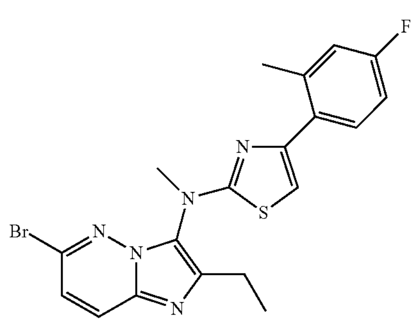 [SMILES: CCc1nc2ccc(Br)nn2c1N(C)c1nc(-c2ccc(F)cc2C)cs1] | N-(6-bromo-2-ethylimidazo[1,2-b]pyridazin-3-yl)-4-(4-fluoro-2-methylphenyl)-N-methylthiazol-2-amine | Gen-3-a D1 | 445 ($^{79}$Br), 447 ($^{81}$Br) | 446 ($^{79}$Br M + H), 448 ($^{81}$Br M + H) |

TABLE 1-continued

Intermediates used towards the compounds of the invention.

| Int | Structures | Name | Mtd | MW | MS Ms'd |
|---|---|---|---|---|---|
| Gen-4-n | 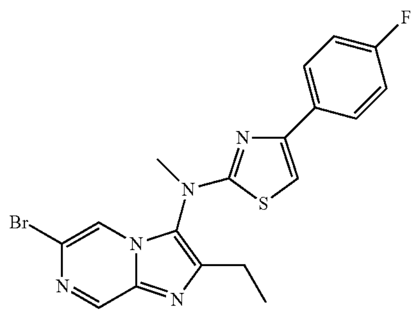 [SMILES: CCc1nc2cnc(Br)cn2c1N(C)c1nc(-c2ccc(F)cc2)cs1] | (6-Bromo-2-ethyl-imidazo[1,2-a]pyrazin-3-yl)-[4-(4-fluoro-phenyl)-thiazol-2-yl]-methyl-amine | Gen-3-b D1 | 431 ($^{79}$Br), 433 ($^{81}$Br) | 432 ($^{79}$Br M + H), 434 ($^{81}$Br M + H) |
| Gen-4-o | 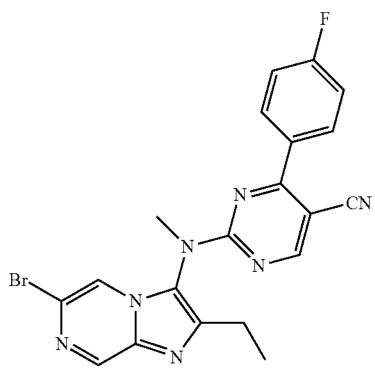 [SMILES: CCc1nc2cnc(Br)cn2c1N(C)c1ncc(C#N)c(-c2ccc(F)cc2)n1] | 2-[(6-Bromo-2-ethyl-imidazo[1,2-a]pyrazin-3-yl)-methyl-amino]-4-(4-fluoro-phenyl)-pyrimidine-5-carbonitrile | Gen-3-b D2 | 451 ($^{79}$Br), 453 ($^{81}$Br) | 452 ($^{79}$Br M + H), 454 ($^{81}$Br M + H) |
| Gen-5-a | 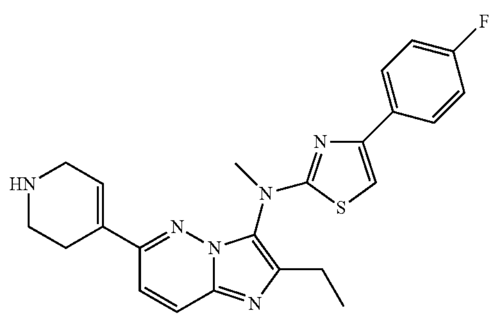 [SMILES: CCc1nc2ccc(C3=CCNCC3)nn2c1N(C)c1nc(-c2ccc(F)cc2)cs1] | [2-Ethyl-6-(1,2,3,6-tetrahydro-pyridin-4-yl)-imidazo[1,2-b]pyridazin-3-yl]-[4-(4-fluoro-phenyl)-thiazol-2-yl]-methyl-amine | Cpd 193 E5b | 434 | 435 (M + H) |
| Gen-5-b | 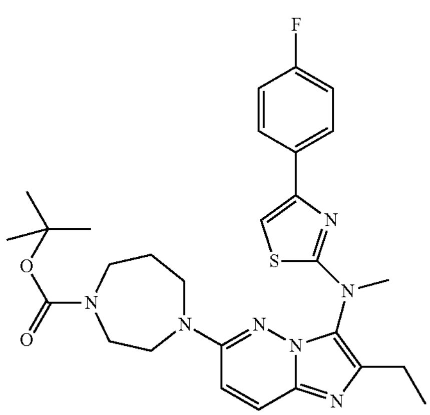 [SMILES: CCc1nc2ccc(N3CCCN(C(=O)OC(C)(C)C)CC3)nn2c1N(C)c1nc(-c2ccc(F)cc2)cs1] | 4-(2-Ethyl-3-{[4-(4-fluoro-phenyl)-thiazol-2-yl]-methyl-amino}-imidazo[1,2-b]pyridazin-6-yl)-[1,4]diazepane-1-carboxylic acid tert-butyl ester | Gen-4-a E4a | 551 | 552 (M + H) |

TABLE 1-continued

Intermediates used towards the compounds of the invention.

| Int | Structures | Name | Mtd | MW | MS Ms'd |
|---|---|---|---|---|---|
| Gen-5-c | 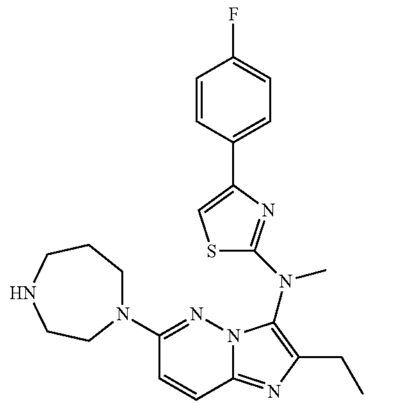 [SMILES: CCc1nc2ccc(N3CCCNCC3)nn2c1N(C)c1nc(-c2ccc(F)cc2)cs1] | (6-[1,4]Diazepan-1-yl-2-ethyl-imidazo[1,2-b]pyridazin-3-yl)-[4-(4-fluoro-phenyl)-thiazol-2-yl]-methyl-amine | Gen-5-b E5b | 451 | 452 (M + H) |
| Gen-5-d | 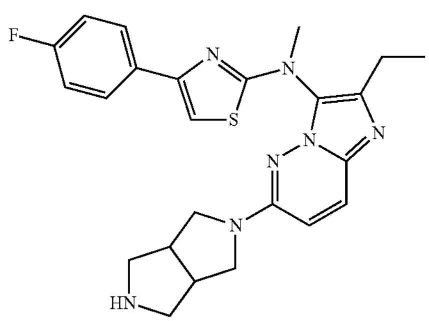 [SMILES: CCc1nc2ccc(N3CC4CNCC4C3)nn2c1N(C)c1nc(-c2ccc(F)cc2)cs1] | [2-Ethyl-6-(hexahydro-pyrrolo[3,4-c]pyrrol-2-yl)-imidazo[1,2-b]pyridazin-3-yl]-[4-(4-fluoro-phenyl)-thiazol-2-yl]-methyl-amine | Cpd 122 E5b | 463 | 464 (M + H) |
| Gen-5-e | 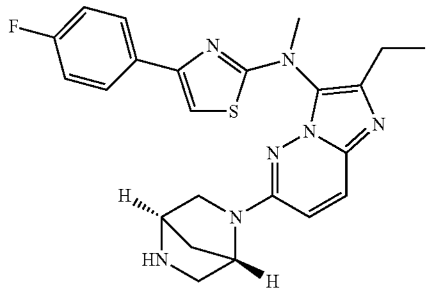 [SMILES: CCc1nc2ccc(N3C[C@H]4C[C@H]3CN4)nn2c1N(C)c1nc(-c2ccc(F)cc2)cs1] | (1R,4S)-[6-(2,5-Diaza-bicyclo[2.2.1]hept-2-yl)-2-ethyl-imidazo[1,2-b]pyridazin-3-yl]-[4-(4-fluoro-phenyl)-thiazol-2-yl]-methyl-amine | Cpd 74 E5b | 449 | 450 (M + H) |
| Gen-5-f | 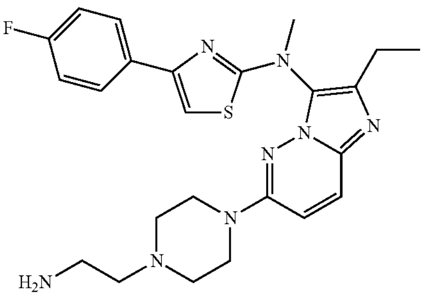 [SMILES: CCc1nc2ccc(N3CCN(CCN)CC3)nn2c1N(C)c1nc(-c2ccc(F)cc2)cs1] | {6-[4-(2-Amino-ethyl)-piperazin-1-yl]-2-ethyl-imidazo[1,2-b]pyridazin-3-yl}-[4-(4-fluoro-phenyl)-thiazol-2-yl]-methyl-amine | Cpd 56 E5b | 480 | 481 (M + H) |

TABLE 1-continued

Intermediates used towards the compounds of the invention.

| Int | Structures | Name | Mtd | MW | MS Ms'd |
|---|---|---|---|---|---|
| Gen-5-g | 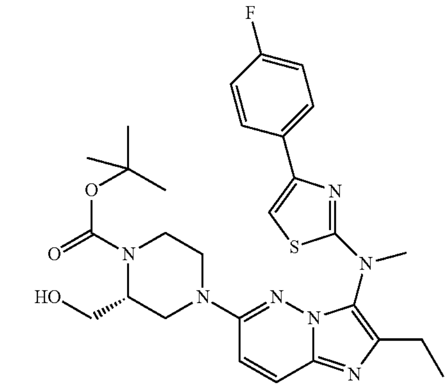 [SMILES: CCc1nc2ccc(N3CCN(C(=O)OC(C)(C)C)[C@@H](CO)C3)nn2c1N(C)c1nc(-c2ccc(F)cc2)cs1] | (R)-4-(2-Ethyl-3-{[4-(4-fluoro-phenyl)-thiazol-2-yl]-methyl-amino}-imidazo[1,2-b]pyridazin-6-yl)-2-hydroxymethyl-piperazine-1-carboxylic acid tert-butyl ester | Gen-4-a E4b | 567 | 568 (M + H) |
| Gen-5-h | 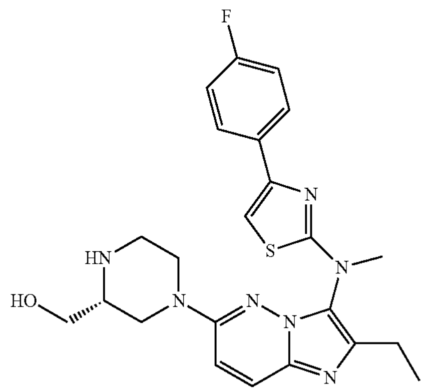 | (R)-[4-(2-Ethyl-3-{[4-(4-fluoro-phenyl)-thiazol-2-yl]-methyl-amino}-imidazo[1,2-b]pyridazin-6-yl)-piperazin-2-yl]-methanol | Gen-5-g E5a | 467 | 468 (M + H) |
| Gen-5-i | 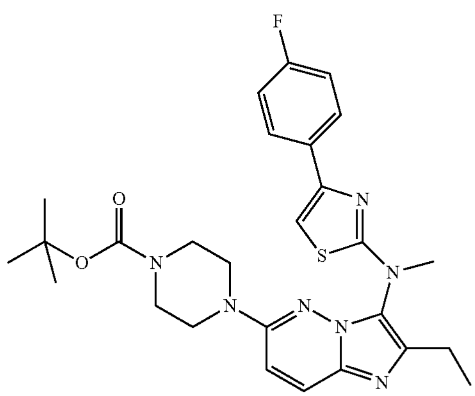 | 4-(2-Ethyl-3-{[4-(4-fluoro-phenyl)-thiazol-2-yl]-methyl-amino}-imidazo[1,2-b]pyridazin-6-yl)-piperazine-1-carboxylic acid tert-butyl ester | Gen-4-a E4a or E4b | 537 | 538 (M + H) |
| Gen-5-j | 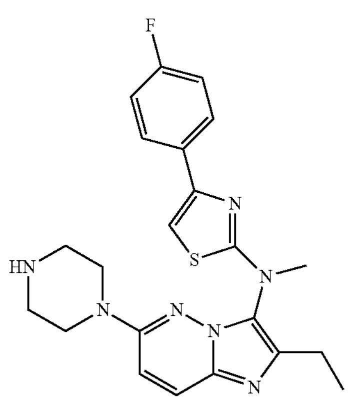 | (2-Ethyl-6-piperazin-1-yl-imidazo[1,2-b]pyridazin-3-yl)-[4-(4-fluoro-phenyl)-thiazol-2-yl]-methyl-amine | Gen-5-i E5b | 437 | 438 (M + H) |

TABLE 1-continued

Intermediates used towards the compounds of the invention.

| Int | Structures | Name | Mtd | MW | MS Ms'd |
|---|---|---|---|---|---|
| Gen-5-k | 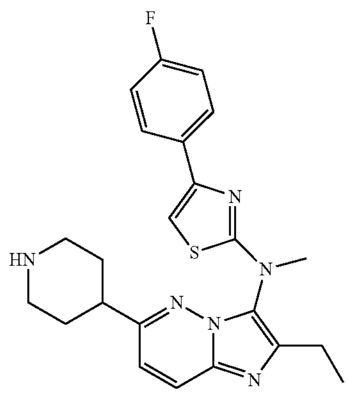 | (2-Ethyl-6-piperidin-4-yl-imidazo[1,2-b]pyridazin-3-yl)-[4-(4-fluoro-phenyl)-thiazol-2-yl]-methyl-amine | Gen-5-a E6 | 436 | 437 (M + H) |
| Gen-5-l | 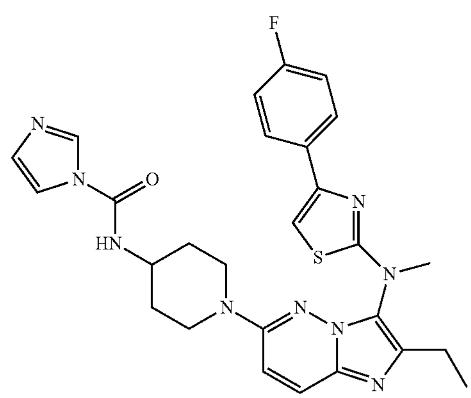 | Imidazole-1-carboxylic acid [1-(2-ethyl-3-{[4-(4-fluoro-phenyl)-thiazol-2-yl]-methyl-amino}-imidazo[1,2-b]pyridazin-6-yl)-piperidin-4-yl]-amide | Cpd 82 See Cpd 89 | 545 | 546 (M + H) |
| Gen-5-m | 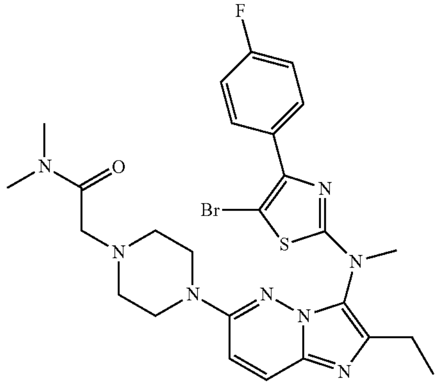 | 2-[4-(3-{[5-Bromo-4-(4-fluoro-phenyl)-thiazol-2-yl]-methyl-amino}-2-ethyl-imidazo[1,2-b]pyridazin-6-yl)-piperazin-1-yl]-N,N-dimethyl-acetamide | Cpd 42 E16 | 600 ($^{79}$Br), 602 ($^{81}$Br) | 601 ($^{79}$Br M + H), 603 ($^{81}$Br M + H) |

TABLE 1-continued

Intermediates used towards the compounds of the invention.

| Int | Name | Mtd | MW | MS Ms'd |
|---|---|---|---|---|
| Gen-5-n | 4-(3-{[5-Bromo-4-(4-fluoro-phenyl)-thiazol-2-yl]-methyl-amino}-2-ethyl-imidazo[1,2-b]pyridazin-6-yl)-piperazine-1-carboxylic acid tert-butyl ester | Gen-5-i E16 | 615 ($^{79}$Br), 617 ($^{81}$Br) | 616 ($^{79}$Br M + H), 618 ($^{81}$Br M + H) |
| Gen-5-o | 4-(3-{[5-Cyano-4-(4-fluoro-phenyl)-thiazol-2-yl]-methyl-amino}-2-ethyl-imidazo[1,2-b]pyridazin-6-yl)-piperazine-1-carboxylic acid tert-butyl ester | Gen-5-n E17 or Gen-4-b E4b | 562 | 563 (M + H) |
| Gen-5-p | 2-[(2-Ethyl-6-piperazin-1-yl-imidazo[1,2-b]pyridazin-3-yl)-methyl-amino]-4-(4-fluoro-phenyl)-thiazole-5-carbonitrile | Gen-5-o E5b | 462 | 463 (M + H) |
| Gen-5-q | [5-Bromo-4-(4-fluoro-phenyl)-thiazol-2-yl]-[2-ethyl-6-(3-morpholin-4-yl-pyrrolidin-1-yl)-imidazo[1,2-b]pyridazin-3-yl]-methyl-amine | Cpd 147 E16 | 585 ($^{79}$Br), 587 ($^{81}$Br) | 586 ($^{79}$Br M + H), 588 ($^{81}$Br M + H) |

TABLE 1-continued

Intermediates used towards the compounds of the invention.

| Int | Structures | Name | Mtd | MW | MS Ms'd |
|---|---|---|---|---|---|
| Gen-5-r | 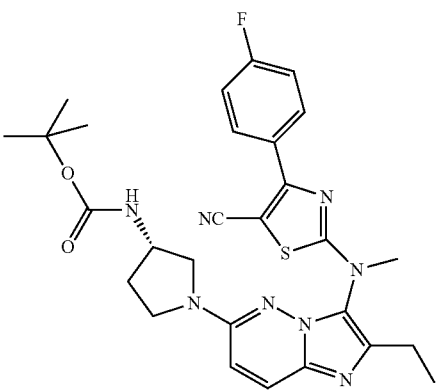 [SMILES: CCc1nc2ccc(N3CC[C@H](NC(=O)OC(C)(C)C)C3)nn2c1N(C)c1nc(-c2ccc(F)cc2)c(C#N)s1] | [(S)-1-(3-{[5-Cyano-4-(4-fluoro-phenyl)-thiazol-2-yl]-methyl-amino}-2-ethyl-imidazo[1,2-b]pyridazin-6-yl)-pyrrolidin-3-yl]-carbamic acid tert-butyl ester | Gen-4-b E4a | 562 | 563 (M + H) |
| Gen-5-s | 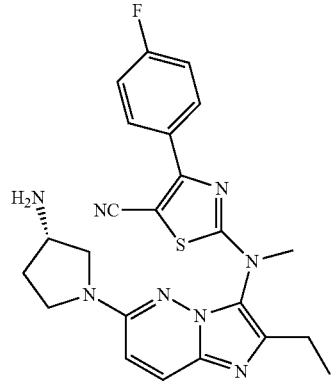 [SMILES: CCc1nc2ccc(N3CC[C@H](N)C3)nn2c1N(C)c1nc(-c2ccc(F)cc2)c(C#N)s1] | 2-{[6-((S)-3-Amino-pyrrolidin-1-yl)-2-ethyl-imidazo[1,2-b]pyridazin-3-yl]-methyl-amino}-4-(4-fluoro-phenyl)-thiazole-5-carbonitrile | Gen-5-r E5b | 462 | 463 (M + H) |
| Gen-5-t | 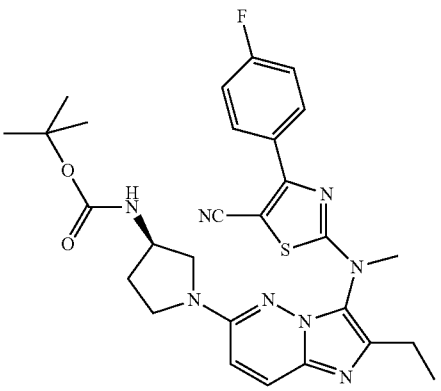 [SMILES: CCc1nc2ccc(N3CC[C@@H](NC(=O)OC(C)(C)C)C3)nn2c1N(C)c1nc(-c2ccc(F)cc2)c(C#N)s1] | [(R)-1-(3-{[5-Cyano-4-(4-fluoro-phenyl)-thiazol-2-yl]-methyl-amino}-2-ethyl-imidazo[1,2-b]pyridazin-6-yl)-pyrrolidin-3-yl]-carbamic acid tert-butyl ester | Gen-4-b E4a | 562 | 563 (M + H) |

TABLE 1-continued

Intermediates used towards the compounds of the invention.

| Int | Structures | Name | Mtd | MW | MS Ms'd |
|---|---|---|---|---|---|
| Gen-5-u | 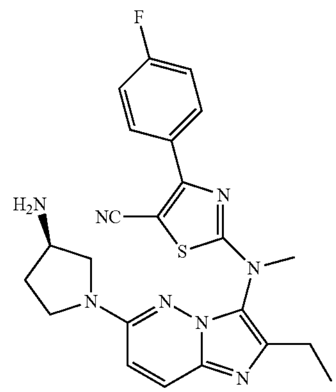 [SMILES: CCc1nc2ccc(N3CC[C@@H](N)C3)nn2c1N(C)c1nc(-c2ccc(F)cc2)c(C#N)s1] | 2-{[6-((R)-3-Amino-pyrrolidin-1-yl)-2-ethyl-imidazo[1,2-b]pyridazin-3-yl]-methyl-amino}-4-(4-fluoro-phenyl)-thiazole-5-carbonitrile | Gen-5-t E5b | 462 | 463 (M + H) |
| Gen-5-v | 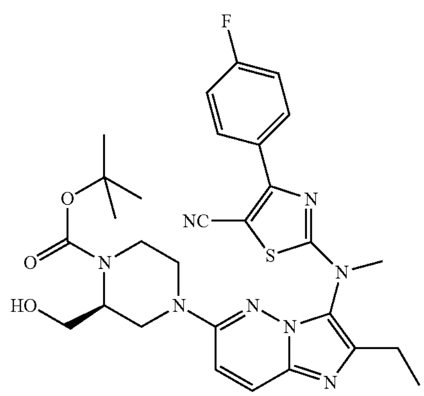 [SMILES: CCc1nc2ccc(N3CCN(C(=O)OC(C)(C)C)[C@H](CO)C3)nn2c1N(C)c1nc(-c2ccc(F)cc2)c(C#N)s1] | (S)-4-(3-{[5-Cyano-4-(4-fluoro-phenyl)-thiazol-2-yl]-methyl-amino}-2-ethyl-imidazo[1,2-b]pyridazin-6-yl)-2-hydroxymethyl-piperazine-1-carboxylic acid tert-butyl ester | Gen-4-b E4b | 592 | 593 (M + H) |
| Gen-5-w | 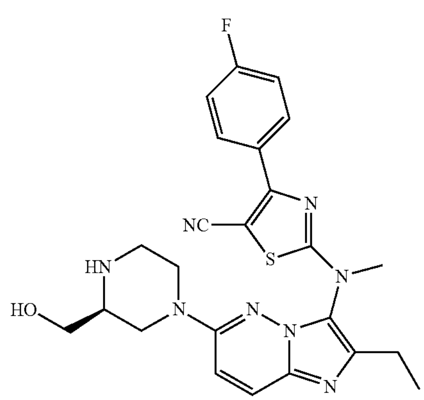 [SMILES: CCc1nc2ccc(N3CCN[C@H](CO)C3)nn2c1N(C)c1nc(-c2ccc(F)cc2)c(C#N)s1] | 2-{[2-Ethyl-6-((S)-3-hydroxymethyl-piperazin-1-yl)-imidazo[1,2-b]pyridazin-3-yl]-methyl-amino}-4-(4-fluoro-phenyl)-thiazole-5-carbonitrile | Gen-5-v E5b | 492 | 493 (M + H) |

TABLE 1-continued

Intermediates used towards the compounds of the invention.

| Int | Structures | Name | Mtd | MW | MS Ms'd |
|---|---|---|---|---|---|
| Gen-5-x | 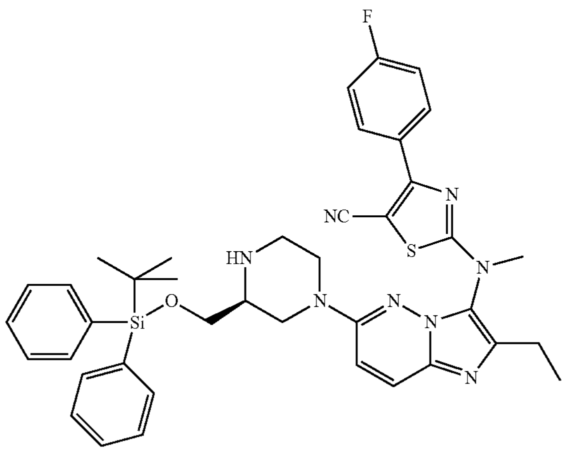 [SMILES: CCc1nc2ccc(N3CCN[C@H](CO[Si](c4ccccc4)(c4ccccc4)C(C)(C)C)C3)nn2c1N(C)c1nc(-c2ccc(F)cc2)c(C#N)s1] | 2-({6-[(S)-3-(tert-Butyl-diphenyl-silanyloxymethyl)-piperazin-1-yl]-2-ethyl-imidazo[1,2-b]pyridazin-3-yl}-methyl-amino)-4-(4-fluoro-phenyl)-thiazole-5-carbonitrile | Gen-5-w E18 | 730 | 731 (M + H) |
| Gen-5-y | 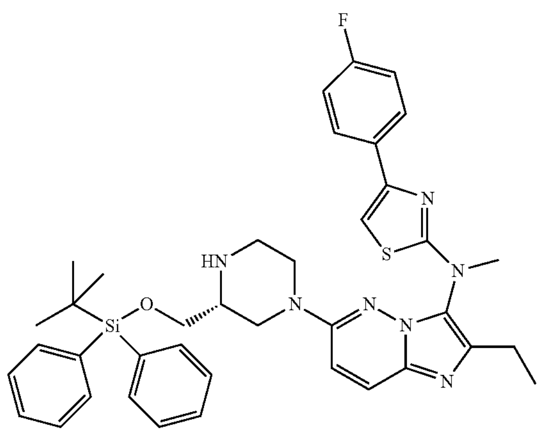 [SMILES: CCc1nc2ccc(N3CCN[C@@H](CO[Si](c4ccccc4)(c4ccccc4)C(C)(C)C)C3)nn2c1N(C)c1nc(-c2ccc(F)cc2)cs1] | {6-[(R)-3-(tert-Butyl-diphenyl-silanyloxymethyl)-piperazin-1-yl]-2-ethyl-imidazo[1,2-b]pyridazin-3-yl}-[4-(4-fluoro-phenyl)-thiazol-2-yl]-methyl-amine | Gen-5-h E18 | 705 | 706 (M + H) |
| Gen-5-z | 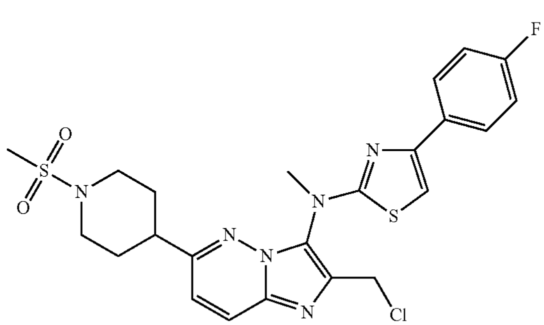 [SMILES: CN(c1nc(-c2ccc(F)cc2)cs1)c1c(CCl)nc2ccc(C3CCN(S(C)(=O)=O)CC3)nn12] | [2-Chloromethyl-6-(1-methanesulfonyl-piperidin-4-yl)-imidazo[1,2-b]pyridazin-3-yl]-[4-(4-fluoro-phenyl)-thiazol-2-yl]-methyl-amine | Cpd 195 See Cpd 196 | 532 ($^{35}$Cl), 534 ($^{37}$Cl) | 533 ($^{35}$Cl M + H), 535 ($^{37}$Cl M + H) |

TABLE 1-continued

Intermediates used towards the compounds of the invention.

| Int | Structures | Name | Mtd | MW | MS Ms'd |
|---|---|---|---|---|---|
| Gen-5-aa | 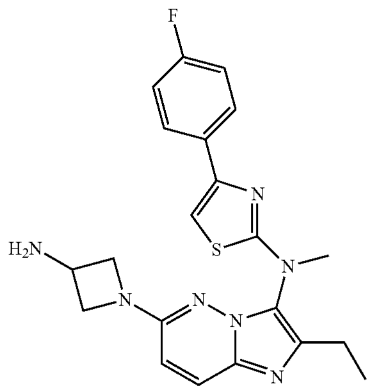 [SMILES: CCc1nc2ccc(N3CC(N)C3)nn2c1N(C)c1nc(-c2ccc(F)cc2)cs1] | [6-(3-Amino-azetidin-1-yl)-2-ethyl-imidazo[1,2-b]pyridazin-3-yl]-[4-(4-fluoro-phenyl)-thiazol-2-yl]-methyl-amine | Cpd 154 E5a | 423 | 424 (M + H) |
| Gen-5-ab | 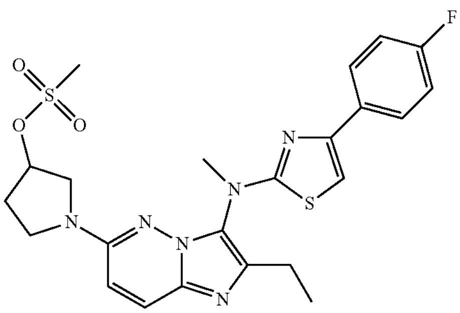 [SMILES: CCc1nc2ccc(N3CCC(OS(C)(=O)=O)C3)nn2c1N(C)c1nc(-c2ccc(F)cc2)cs1] | Methanesulfonic acid 1-(2-ethyl-3-{[4-(4-fluoro-phenyl)-thiazol-2-yl]-methyl-amino}-imidazo[1,2-b]pyridazin-6-yl)-pyrrolidin-3-yl ester | Cpd 129 See Cpd 130 | 516 | 517 (M + H) |
| Gen-5-ac | 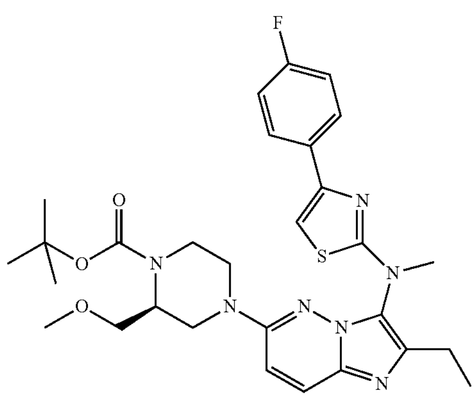 [SMILES: CCc1nc2ccc(N3CCN(C(=O)OC(C)(C)C)[C@H](COC)C3)nn2c1N(C)c1nc(-c2ccc(F)cc2)cs1] | (S)-4-(2-Ethyl-3-{[4-(4-fluoro-phenyl)-thiazol-2-yl]-methyl-amino}-imidazo[1,2-b]pyridazin-6-yl)-2-methoxymethyl-piperazine-1-carboxylic acid tert-butyl ester | Cpd 59 See Cpd 62 | 581 | 582 (M + H) |
| Gen-5-ad | 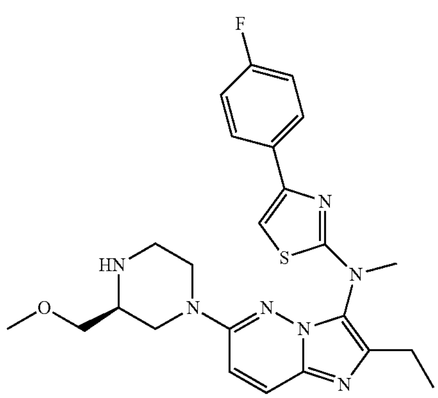 [SMILES: CCc1nc2ccc(N3CCN[C@H](COC)C3)nn2c1N(C)c1nc(-c2ccc(F)cc2)cs1] | [2-Ethyl-6-((S)-3-methoxymethyl-piperazin-1-yl)-imidazo[1,2-b]pyridazin-3-yl]-[4-(4-fluoro-phenyl)-thiazol-2-yl]-methyl-amine | Gen-5-ac E5b | 481 | 482 (M + H) |

TABLE 1-continued

Intermediates used towards the compounds of the invention.

| Int | Structures | Name | Mtd | MW | MS Ms'd |
|---|---|---|---|---|---|
| Gen-5-ae | 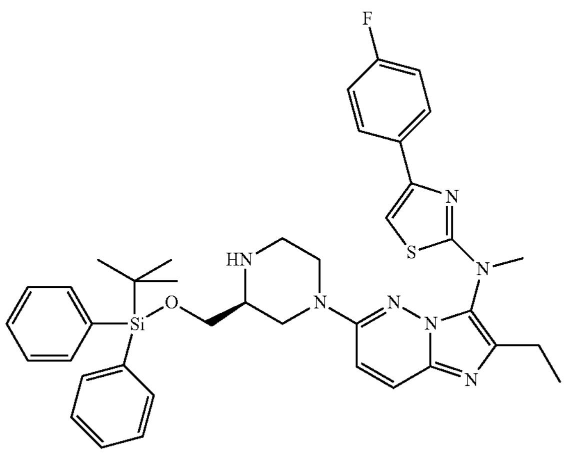 [SMILES: CCc1nc2ccc(N3CCN[C@H](CO[Si](c4ccccc4)(c4ccccc4)C(C)(C)C)C3)nn2c1N(C)c1nc(-c2ccc(F)cc2)cs1] | {6-[(S)-3-(tert-Butyl-diphenyl-silanyloxymethyl)-piperazin-1-yl]-2-ethyl-imidazo[1,2-b]pyridazin-3-yl}-[4-(4-fluoro-phenyl)-thiazol-2-yl]-methyl-amine | Cpd 60 E18 | 705 | 706 (M + H) |
| Gen-5-af | 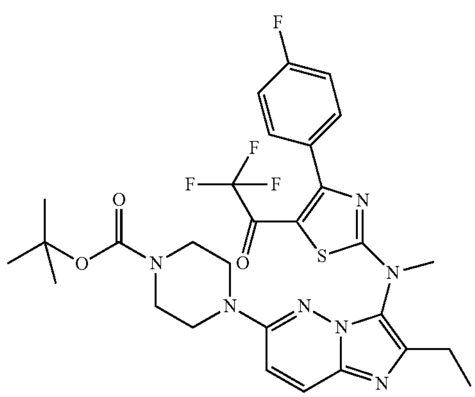 [SMILES: CCc1nc2ccc(N3CCN(C(=O)OC(C)(C)C)CC3)nn2c1N(C)c1nc(-c2ccc(F)cc2)c(C(=O)C(F)(F)F)s1] | 4-(2-Ethyl-3-{[4-(4-fluoro-phenyl)-5-(2,2,2-trifluoro-acetyl)-thiazol-2-yl]-methyl-amino}-imidazo[1,2-b]pyridazin-6-yl)-piperazine-1-carboxylic acid tert-butyl ester | Gen-5-i E15 | 633 | 634 (M + H) |
| Gen-5-ag | 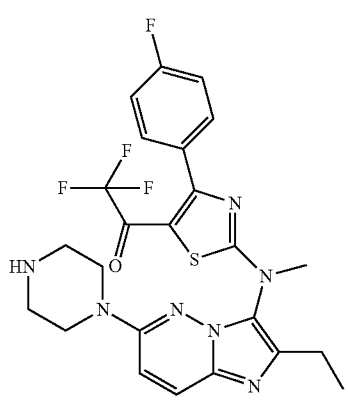 [SMILES: CCc1nc2ccc(N3CCNCC3)nn2c1N(C)c1nc(-c2ccc(F)cc2)c(C(=O)C(F)(F)F)s1] | 1-[2-[(2-Ethyl-6-piperazin-1-yl-imidazo[1,2-b]pyridazin-3-yl)-methyl-amino]-4-(4-fluoro-phenyl)-thiazol-5-yl]-2,2,2-trifluoro-ethanone | Gen-5-af E5a | 533 | 534 (M + H) |

TABLE 1-continued

Intermediates used towards the compounds of the invention.

| Int | Structures | Name | Mtd | MW | MS Ms'd |
|---|---|---|---|---|---|
| Gen-5-ah | 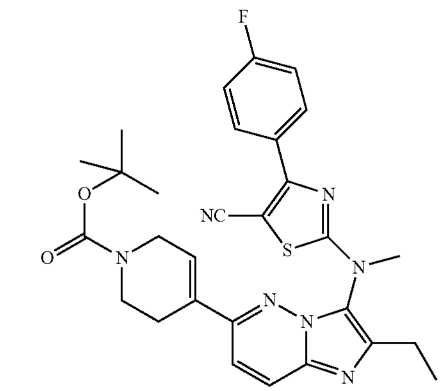 [SMILES: CCc1nc2ccc(C3=CCN(C(=O)OC(C)(C)C)CC3)nn2c1N(C)c1nc(-c2ccc(F)cc2)c(C#N)s1] | 4-(3-{[5-Cyano-4-(4-fluoro-phenyl)-thiazol-2-yl]-methyl-amino}-2-ethyl-imidazo[1,2-b]pyridazin-6-yl)-3,6-dihydro-2H-pyridine-1-carboxylic acid tert-butyl ester | Gen-4-b E2 | 459 | 460 (M + H) |
| Gen-5-ai | 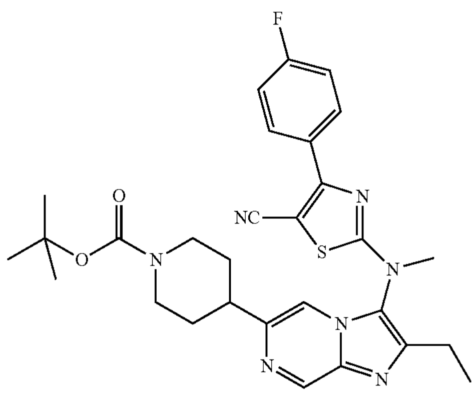 [SMILES: CCc1nc2cnc(C3CCN(C(=O)OC(C)(C)C)CC3)cn2c1N(C)c1nc(-c2ccc(F)cc2)c(C#N)s1] | 4-(3-{[5-Cyano-4-(4-fluoro-phenyl)-thiazol-2-yl]-methyl-amino]-2-ethyl-imidazo[1,2-a]pyrazin-6-yl)-piperidine-1-carboxylic acid tert-butyl ester | Gen-4-d E3 | 561 | 562 (M + H) |
| Gen-5-aj | 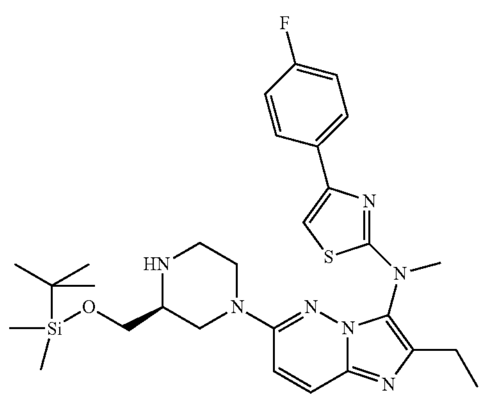 | {6-[(S)-3-(tert-Butyl-dimethyl-silanyloxymethyl)-piperazin-1-yl]-2-ethyl-imidazo[1,2-b]pyridazin-3-yl}-[4-(4-fluoro-phenyl)-thiazol-2-yl]-methyl-amine | Cpd 60 E18 | 705 | 706 (M + H) |
| Gen-5-ak | 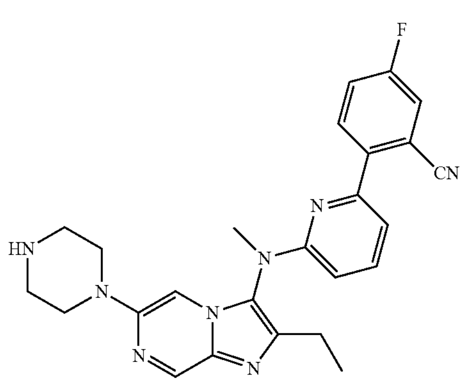 [SMILES: CCc1nc2cnc(N3CCNCC3)cn2c1N(C)c1cccc(-c2ccc(F)cc2C#N)n1] | 2-{6-[(2-Ethyl-6-piperazin-1-yl-imidazo[1,2-a]pyrazin-3-yl)-methyl-amino]-pyridin-2-yl}-5-fluoro-benzonitrile | Gen-4-f E1a | 456 | 457 (M + H) |

TABLE 1-continued

Intermediates used towards the compounds of the invention.

| Int | Structures | Name | Mtd | MW | MS Ms'd |
|---|---|---|---|---|---|
| Gen-5-al | 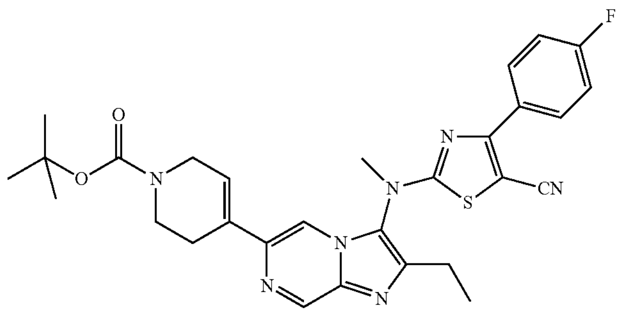 [SMILES: CCc1nc2cnc(C3=CCN(C(=O)OC(C)(C)C)CC3)cn2c1N(C)c1nc(-c2ccc(F)cc2)c(C#N)s1] | 4-(3-{[5-Cyano-4-(4-fluoro-phenyl)-thiazol-2-yl]-methyl-amino}-2-ethyl-imidazo[1,2-a]pyrazin-6-yl)-3,6-dihydro-2H-pyridine-1-carboxylic acid tert-butyl ester | Gen-4-d E2 | 559 | 560 (M + H) |
| Gen-5-am | 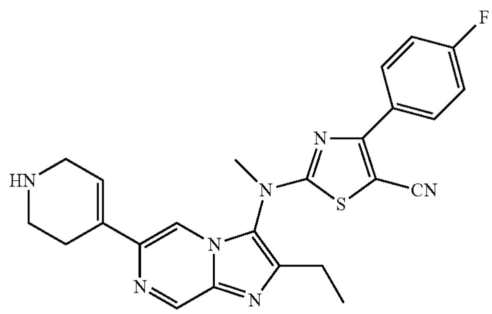 [SMILES: CCc1nc2cnc(C3=CCNCC3)cn2c1N(C)c1nc(-c2ccc(F)cc2)c(C#N)s1] | 2-{[2-Ethyl-6-(1,2,3,6-tetrahydro-pyridin-4-yl)-imidazo[1,2-a]pyrazin-3-yl]-methyl-amino}-4-(4-fluoro-phenyl)-thiazole-5-carbonitrile | Gen-5-al E5b | 459 | 460 (M + H) |
| Gen-5-an | 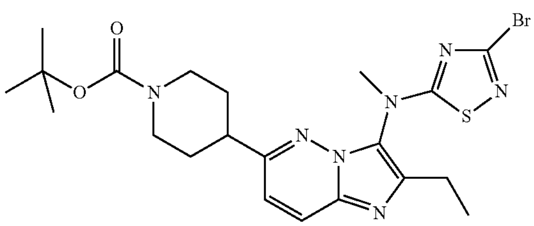 [SMILES: CCc1nc2ccc(C3CCN(C(=O)OC(C)(C)C)CC3)nn2c1N(C)c1nc(Br)ns1] | 4-{3-[(3-Bromo-[1,2,4]thiadiazol-5-yl)-methyl-amino]-2-ethyl-imidazo[1,2-b]pyridazin-6-yl}-piperidine-1-carboxylic acid tert-butyl ester | Gen-7-a See Cpd 219 | 521 ($^{79}$Br), 523 ($^{81}$Br) | 522 ($^{79}$Br), 524 ($^{81}$Br) |
| Gen-5-ao | 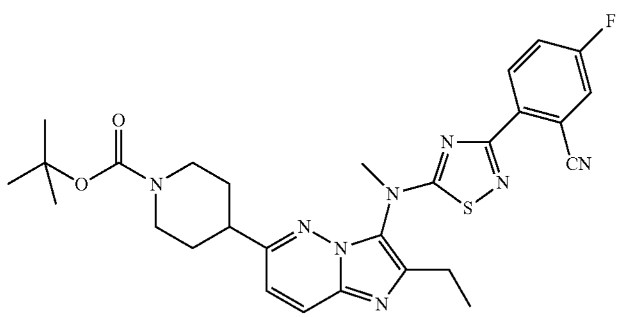 [SMILES: CCc1nc2ccc(C3CCN(C(=O)OC(C)(C)C)CC3)nn2c1N(C)c1nc(-c2ccc(F)cc2C#N)ns1] | 4-(3-{[3-(2-Cyano-4-fluoro-phenyl)-[1,2,4]thiadiazol-5-yl]-methyl-amino}-2-ethyl-imidazo[1,2-b]pyridazin-6-yl)-piperidine-1-carboxylic acid tert-butyl ester | Gen-5-an See Cpd 219 | 562 | 563 (M + H) |
| Gen-5-ap | 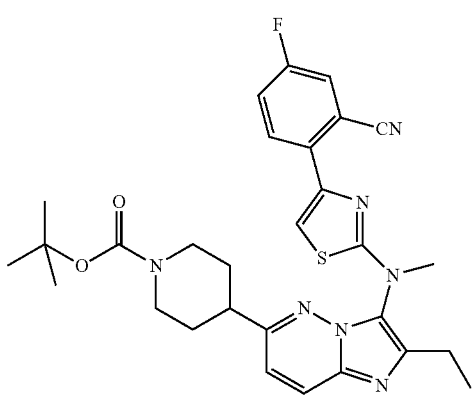 [SMILES: CCc1nc2ccc(C3CCN(C(=O)OC(C)(C)C)CC3)nn2c1N(C)c1nc(-c2ccc(F)cc2C#N)cs1] | 4-(3-{[4-(2-Cyano-4-fluoro-phenyl)-thiazol-2-yl]-methyl-amino}-2-ethyl-imidazo[1,2-b]pyridazin-6-yl)-piperidine-1-carboxylic acid tert-butyl ester | Gen-7-a D1 | 561 | 562 (M + H) |

TABLE 1-continued

Intermediates used towards the compounds of the invention.

| Int | Structures | Name | Mtd | MW | MS Ms'd |
|---|---|---|---|---|---|
| Gen-5-aq | 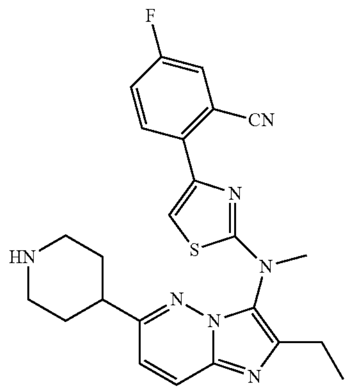 [SMILES: CCc1nc2ccc(C3CCNCC3)nn2c1N(C)c1nc(-c2ccc(F)cc2C#N)cs1] | 2-{2-[(2-Ethyl-6-piperidin-4-yl-imidazo[1,2-b]pyridazin-3-yl)-methyl-amino]-thiazol-4-yl}-5-fluoro-benzonitrile | Gen-5-ap E5b | 461 | 462 (M + H) |
| Gen-5-ar | 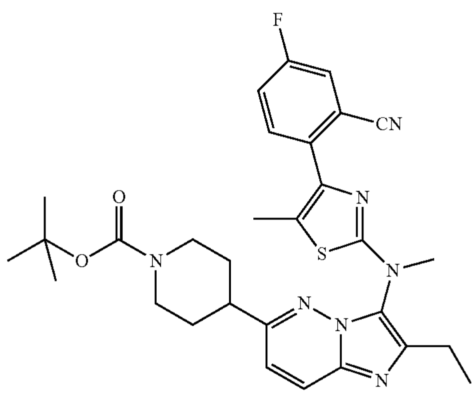 [SMILES: CCc1nc2ccc(C3CCN(C(=O)OC(C)(C)C)CC3)nn2c1N(C)c1nc(-c2ccc(F)cc2C#N)c(C)s1] | 4-(3-{[4-(2-Cyano-4-fluoro-phenyl)-5-methyl-thiazol-2-yl]-methyl-amino}-2-ethyl-imidazo[1,2-b]pyridazin-6-yl)-piperidine-1-carboxylic acid tert-butyl ester | Gen-7-a D1 | 575 | 576 (M + H) |
| Gen-5-as | 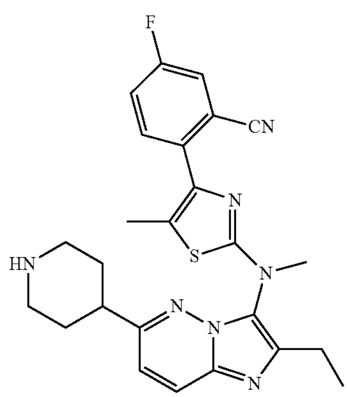 [SMILES: CCc1nc2ccc(C3CCNCC3)nn2c1N(C)c1nc(-c2ccc(F)cc2C#N)c(C)s1] | 2-{2-[(2-Ethyl-6-piperidin-4-yl-imidazo[1,2-b]pyridazin-3-yl)-methyl-amino]-5-methyl-thiazol-4-yl}-5-fluoro-benzonitrile | Gen-5-ar E5b | 475 | 476 (M + H) |
| Gen-5-at | 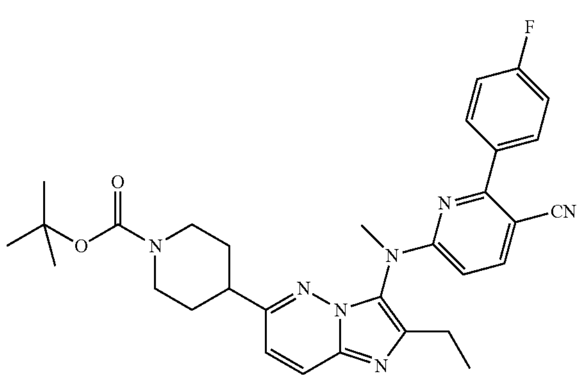 [SMILES: CCc1nc2ccc(C3CCN(C(=O)OC(C)(C)C)CC3)nn2c1N(C)c1ccc(C#N)c(-c2ccc(F)cc2)n1] | 4-(3-{[5-Cyano-6-(4-fluoro-phenyl)-pyridin-2-yl]-methyl-amino}-2-ethyl-imidazo[1,2-b]pyridazin-6-yl)-piperidine-1-carboxylic acid tert-butyl ester | Gen-7-a D3 | 555 | 556 (M + H) |

TABLE 1-continued

Intermediates used towards the compounds of the invention.

| Int | Structures | Name | Mtd | MW | MS Ms'd |
|---|---|---|---|---|---|
| Gen-5-au | 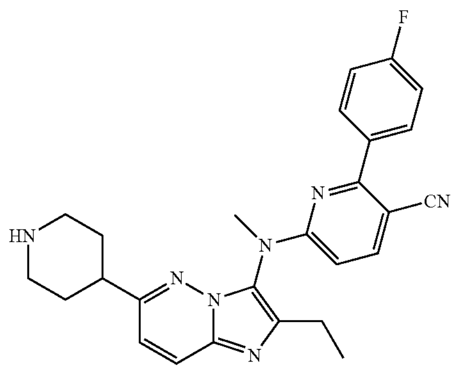 [SMILES: CCc1nc2ccc(C3CCNCC3)nn2c1N(C)c1ccc(C#N)c(-c2ccc(F)cc2)n1] | 6-[(2-Ethyl-6-piperidin-4-yl-imidazo[1,2-b]pyridazin-3-yl)-methyl-amino]-2-(4-fluoro-phenyl)-nicotinonitrile | Gen-5-at E5b | 455 | 456 (M + H) |
| Gen-5-av | 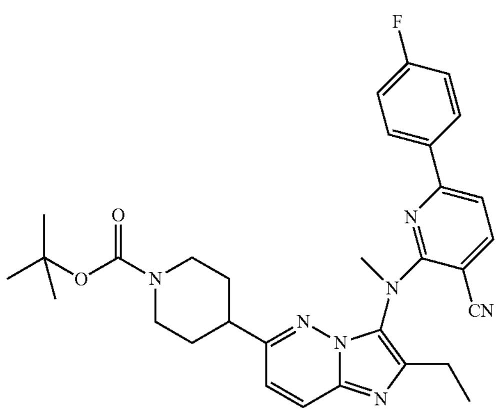 [SMILES: CCc1nc2ccc(C3CCN(C(=O)OC(C)(C)C)CC3)nn2c1N(C)c1nc(-c2ccc(F)cc2)ccc1C#N] | 4-(3-{[3-Cyano-6-(4-fluoro-phenyl)-pyridin-2-yl]-methyl-amino}-2-ethyl-imidazo[1,2-b]pyridazin-6-yl)-piperidine-1-carboxylic acid tert-butyl ester | Gen-7-a D3 | 555 | 556 (M + H) |
| Gen-5-aw | 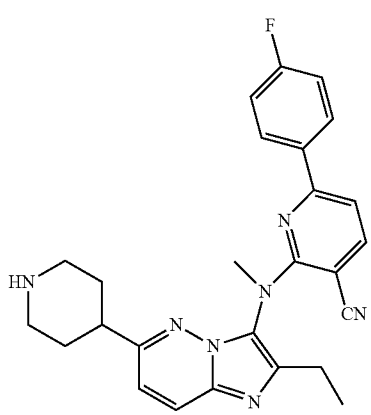 [SMILES: CCc1nc2ccc(C3CCNCC3)nn2c1N(C)c1nc(-c2ccc(F)cc2)ccc1C#N] | 2-[(2-Ethyl-6-piperidin-4-yl-imidazo[1,2-b]pyridazin-3-yl)-methyl-amino]-6-(4-fluoro-phenyl)-nicotinonitrile | Gen-5-av E5b | 455 | 456 (M + H) |

TABLE 1-continued

Intermediates used towards the compounds of the invention.

| Int | Structures | Name | Mtd | MW | MS Ms'd |
|---|---|---|---|---|---|
| Gen-5-ax | 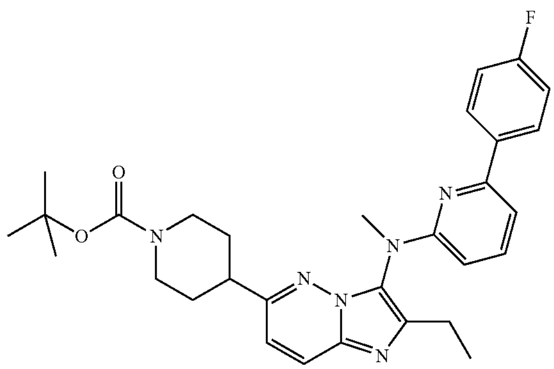 [SMILES: CCc1nc2ccc(C3CCN(C(=O)OC(C)(C)C)CC3)nn2c1N(C)c1cccc(-c2ccc(F)cc2)n1] | 4-(2-Ethyl-3-{[6-(4-fluoro-phenyl)-pyridin-2-yl]-methyl-amino}-imidazo[1,2-b]pyridazin-6-yl)-piperidine-1-carboxylic acid tert-butyl ester | Gen-7-a D2 | 530 | 531 (M + H) |
| Gen-5-ay | 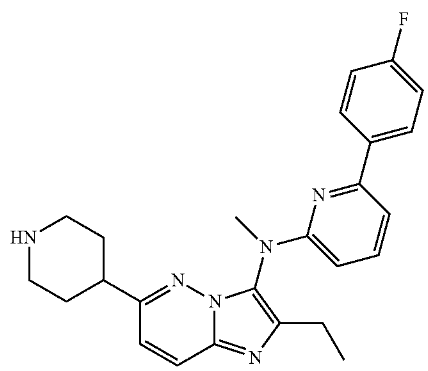 [SMILES: CCc1nc2ccc(C3CCNCC3)nn2c1N(C)c1cccc(-c2ccc(F)cc2)n1] | (2-Ethyl-6-piperidin-4-yl-imidazo[1,2-b]pyridazin-3-yl)-[6-(4-fluoro-phenyl)-pyridin-2-yl]-methyl-amine | Gen-5-ax E5b | 430 | 431 (M + H) |
| Gen-5-az | 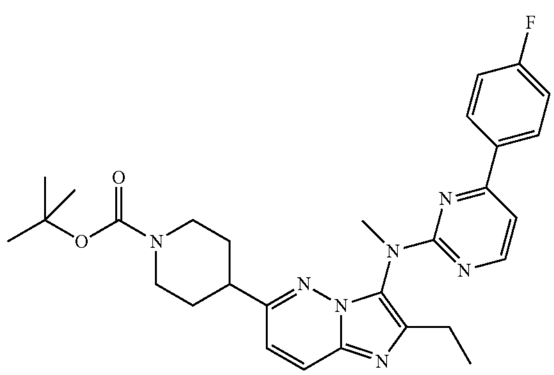 [SMILES: CCc1nc2ccc(C3CCN(C(=O)OC(C)(C)C)CC3)nn2c1N(C)c1nccc(-c2ccc(F)cc2)n1] | 4-(2-Ethyl-3-{[4-(4-fluoro-phenyl)-pyrimidin-2-yl]-methyl-amino}-imidazo[1,2-b]pyridazin-6-yl)-piperidine-1-carboxylic acid tert-butyl ester | Gen-7-a D2 | 531 | 532 (M + H) |
| Gen-5-aaa | 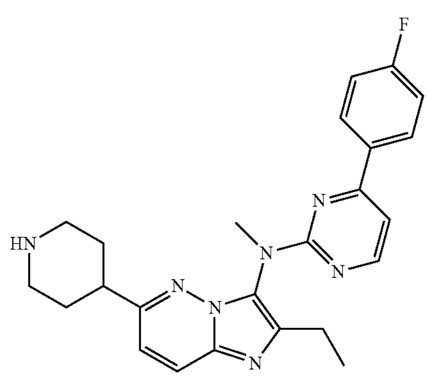 | (2-Ethyl-6-piperidin-4-yl-imidazo[1,2-b]pyridazin-3-yl)-[4-(4-fluoro-phenyl)-pyrimidin-2-yl]-methyl-amine | Gen-5-az E5b | 431 | 432 (M + H) |

TABLE 1-continued

Intermediates used towards the compounds of the invention.

| Int | Structures | Name | Mtd | MW | MS Ms'd |
|---|---|---|---|---|---|
| Gen-5-aab | 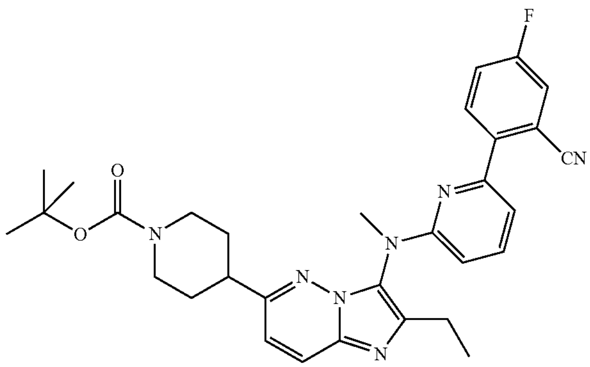 [SMILES: CCc1nc2ccc(C3CCN(C(=O)OC(C)(C)C)CC3)nn2c1N(C)c1cccc(-c2ccc(F)cc2C#N)n1] | 4-(3-{[6-(2-Cyano-4-fluoro-phenyl)-pyridin-2-yl]-methyl-amino}-2-ethyl-imidazo[1,2-b]pyridazin-6-yl)-piperidine-1-carboxylic acid tert-butyl ester | Gen-7-a D2 | 555 | 556 (M + H) |
| Gen-5-aac | 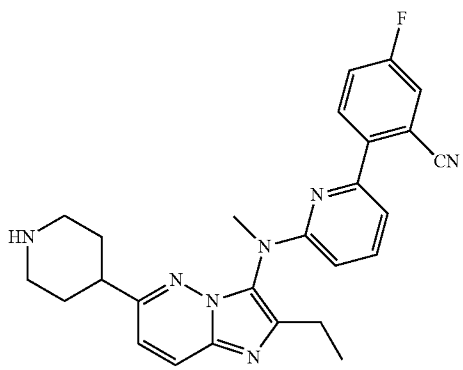 [SMILES: CCc1nc2ccc(C3CCNCC3)nn2c1N(C)c1cccc(-c2ccc(F)cc2C#N)n1] | 2-{6-[(2-Ethyl-6-piperidin-4-yl-imidazo[1,2-b]pyridazin-3-yl)-methyl-amino]-pyridin-2-yl}-5-fluoro-benzonitrile | Gen-5-aab E5b | 455 | 456 (M + H) |
| Gen-5-aad | 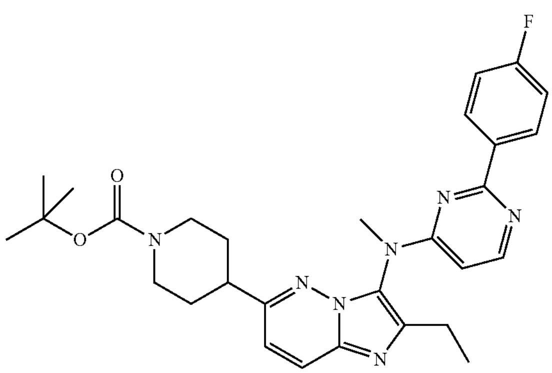 [SMILES: CCc1nc2ccc(C3CCN(C(=O)OC(C)(C)C)CC3)nn2c1N(C)c1ccnc(-c2ccc(F)cc2)n1] | 4-(2-Ethyl-3-{[2-(4-fluoro-phenyl)-pyrimidin-4-yl]-methyl-amino}-imidazo[1,2-b]pyridazin-6-yl)-piperidine-1-carboxylic acid tert-butyl ester | Gen-7-a D3 | 531 | 532 (M + H) |
| Gen-5-aae | 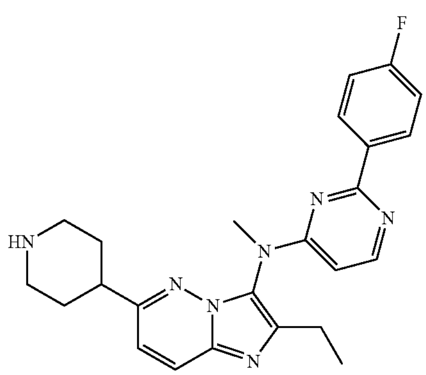 [SMILES: CCc1nc2ccc(C3CCNCC3)nn2c1N(C)c1ccnc(-c2ccc(F)cc2)n1] | (2-Ethyl-6-piperidin-4-yl-imidazo[1,2-b]pyridazin-3-yl)-[2-(4-fluoro-phenyl)-pyrimidin-4-yl]-methyl-amine | Gen-5-aad E5b | 431 | 432 (M + H) |

TABLE 1-continued

Intermediates used towards the compounds of the invention.

| Int | Structures | Name | Mtd | MW | MS Ms'd |
|---|---|---|---|---|---|
| Gen-5-aaf | 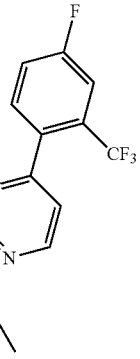 | 2-{2-[(2-Ethyl-6-piperazin-1-yl-imidazo[1,2-a]pyrazin-3-yl)-methyl-amino]-pyrimidin-4-yl}-5-fluoro-benzonitrile | Gen-4-h E1a | 457 | 458 (M + H) |
| Gen-5-aag | 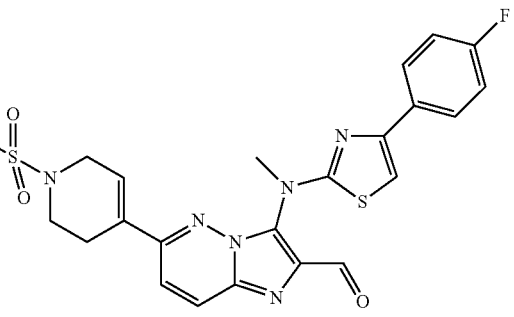 | 3-((4-(4-fluorophenyl)thiazol-2-yl)(methyl)amino)-6-(1-(methylsylfonyl)-1,2,3,6-tetrahydropyridin-4-yl)imidazo[1,2-b]pyridazine-2-carbaldehyde | Gen-4-k E2 | 512 | 513 (M + H) |
| Gen-5-aah | 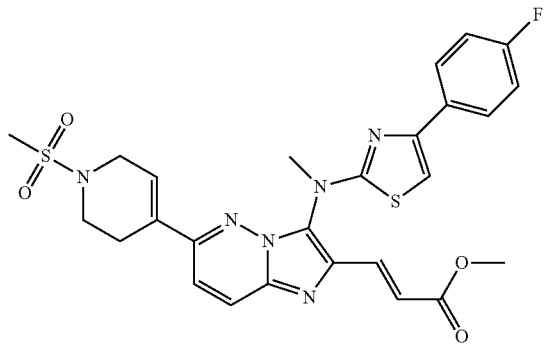 [SMILES: COC(=O)/C=C/c1nc2ccc(C3=CCN(S(C)(=O)=O)CC3)nn2c1N(C)c1nc(-c2ccc(F)cc2)cs1] | (E)-methyl-3-(3-((4-(4-fluorophenyl)thiazol-2-yl)(methyl)amino)-6-(1-methylsufonyl)-1,2,3,6-tetrahydropyridin-4-yl)imidazo[1,2-b]pyridazin-2-yl)acrylate | Gen-4-l E2 | 568 | 569 (M + H) |
| Gen-5-aai | 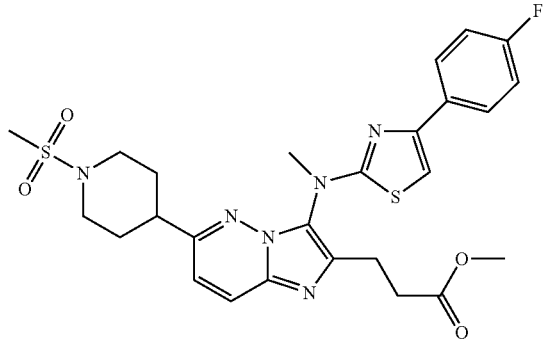 [SMILES: COC(=O)CCc1nc2ccc(C3CCN(S(C)(=O)=O)CC3)nn2c1N(C)c1nc(-c2ccc(F)cc2)cs1] | methyl-3-(3-((4-(4-fluorophenyl)thiazol-2-yl)(methyl)amino)-6-(1-methylsufonyl)piperidin-4-yl)imidazo[1,2-b]pyridazin-2-yl)propanoate. | Gen-5-aah E6 | 572 | 573 (M + H) |

TABLE 1-continued

Intermediates used towards the compounds of the invention.

| Int | Structures | Name | Mtd | MW | MS Ms'd |
|---|---|---|---|---|---|
| Gen-5-aaj | 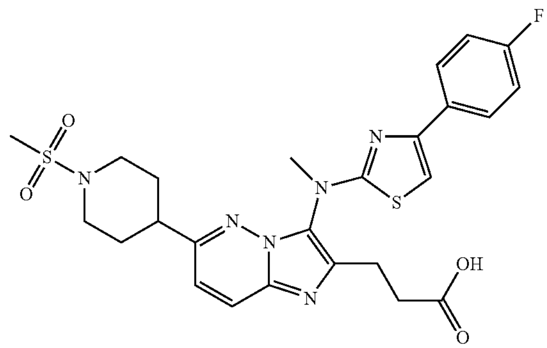 [SMILES: CN(c1nc(-c2ccc(F)cc2)cs1)c1c(CCC(=O)O)nc2ccc(C3CCN(S(C)(=O)=O)CC3)nn12] | 3-(3-((4-(4-fluorophenyl)thiazol-2-yl)(methyl)amino)-6-(1-methylsulfonyl)piperidin-4-yl)imidazo[1,2-b]pyridazin-2-yl)propanoic acid. | Gen-4-aai See Cpd 197 | 558 | 559 (M + H) |
| Gen-5-aak | 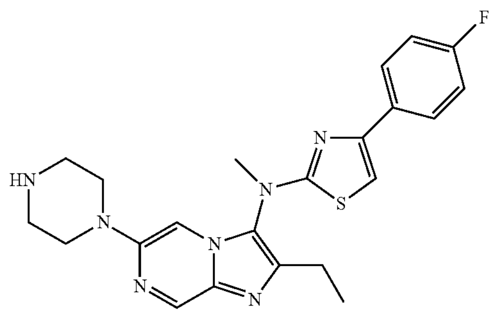 [SMILES: CCc1nc2cnc(N3CCNCC3)cn2c1N(C)c1nc(-c2ccc(F)cc2)cs1] | (2-Ethyl-6-piperazin-1-yl-imidazo[1,2-a]pyrazin-3-yl)-[4-(4-fluoro-phenyl)-thiazol-2-yl]-methyl-amine | Gen-4-n E1a | 437 | 438 (M + H) |
| Gen-5-aal | 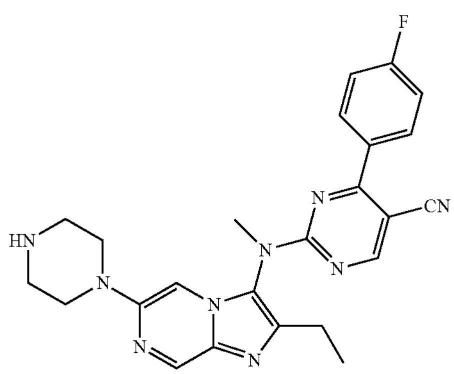 [SMILES: CCc1nc2cnc(N3CCNCC3)cn2c1N(C)c1ncc(C#N)c(-c2ccc(F)cc2)n1] | 2-[(2-Ethyl-6-piperazin-1-yl-imidazo[1,2-a]pyrazin-3-yl)-methyl-amino]-4-(4-fluoro-phenyl)-pyrimidine-5-carbonitrile | Gen-4-o E1a | 457 | 458 (M + H) |
| Cpd 15 | 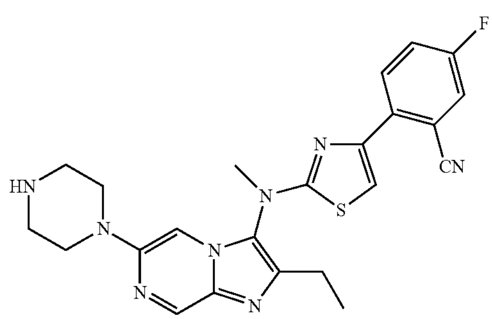 [SMILES: CCc1nc2cnc(N3CCNCC3)cn2c1N(C)c1nc(-c2ccc(F)cc2C#N)cs1] | 2-{2-[(2-Ethyl-6-piperazin-1-yl-imidazo[1,2-a]pyrazin-3-yl)-methyl-amino]-thiazol-4-yl}-5-fluoro-benzonitrile | Gen-4-e E1a | 462 | 463 (M + H) |

TABLE 1-continued

Intermediates used towards the compounds of the invention.

| Int | Structures | Name | Mtd | MW | MS Ms'd |
|---|---|---|---|---|---|
| Cpd 22 | 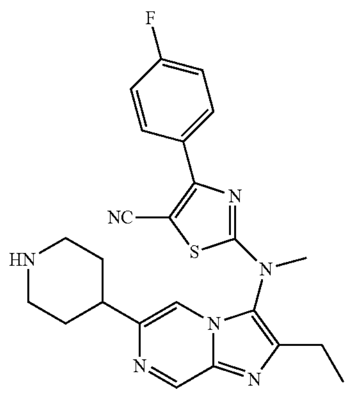 | 2-[(2-Ethyl-6-piperidin-4-yl-imidazo[1,2-a]pyrazin-3-yl)-methyl-amino]-4-(4-fluoro-phenyl)-thiazole-5-carbonitrile | Gen-5-ai E5b | 461 | 462 (M + H) |
| Cpd 42 | 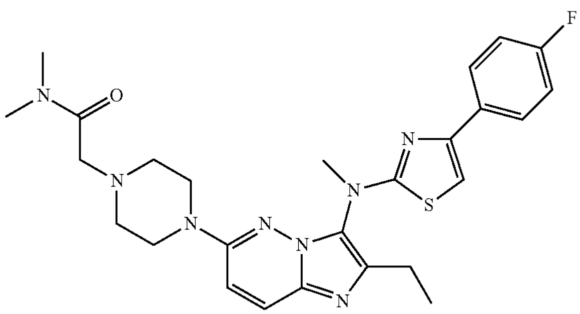 [SMILES: CCc1nc2ccc(N3CCN(CC(=O)N(C)C)CC3)nn2c1N(C)c1nc(-c2ccc(F)cc2)cs1] | 2-(4-(2-ethyl-3-((4-(4-fluorophenyl)thiazol-2-yl)(methyl)amino) imidazo[1,2-b] pyridazin-6-yl) piperazin-1-yl)-N,N-dimethylacetamide | Gen-5-j E8 | 522 | 523 (M + H) |
| Cpd 56 | 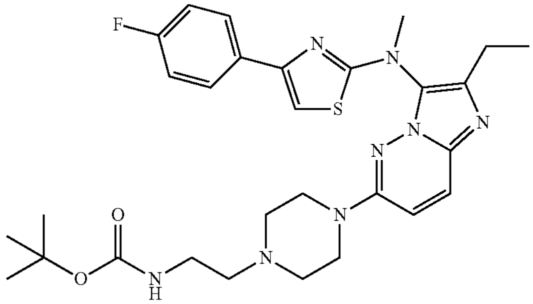 [SMILES: CCc1nc2ccc(N3CCN(CCNC(=O)OC(C)(C)C)CC3)nn2c1N(C)c1nc(-c2ccc(F)cc2)cs1] | tert-butyl 2-(4-(2-ethyl-3-((4-(4-fluorophenyl)thiazol-2-yl)(methyl)amino) imidazo[1,2-b] pyridazin-6-yl)piperazin-1-yl)ethylcarbamate | Gen-4-a E4a | 580 | 581 (M + H) |
| Cpd 59 | 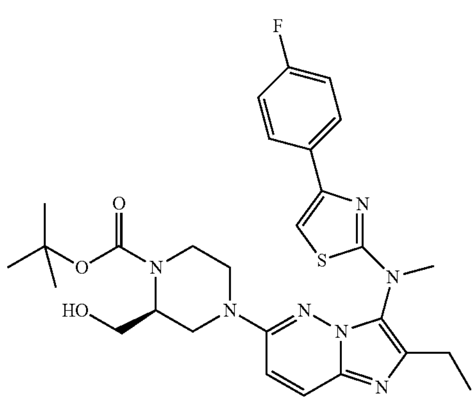 | (S)-tert-butyl 4-(2-ethyl-3-((4-(4-fluorophenyl)thiazol-2-yl)(methyl)amino) imidazo[1,2-b] pyridazin-6-yl)-2-(hydroxymethyl) piperazine-1-carboxylate | Gen-4-a E4a or E4b | 567 | 568 (M + H) |

TABLE 1-continued

Intermediates used towards the compounds of the invention.

| Int | Structures | Name | Mtd | MW | MS Ms'd |
|---|---|---|---|---|---|
| Cpd 60 | 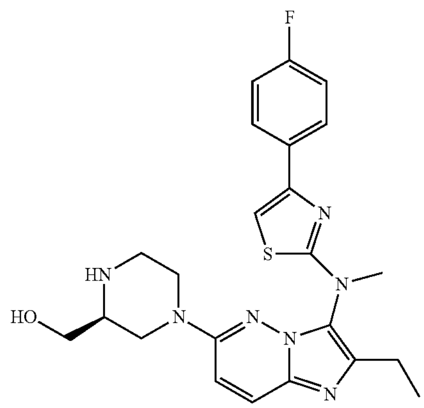 [SMILES: CCc1nc2ccc(N3CCN[C@H](CO)C3)nn2c1N(C)c1nc(-c2ccc(F)cc2)cs1] | (S)-(4-(2-ethyl-3-((4-(4-fluorophenyl)thiazol-2-yl)(methyl)amino)imidazo[1,2-b]pyridazin-6-yl)piperazin-2-yl)methanol | Cpd 59 E5a | 467 | 468 (M + H) |
| Cpd 74 | 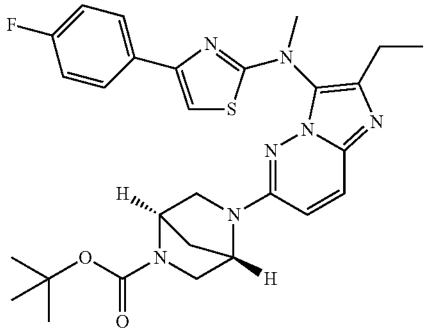 [SMILES: CCc1nc2ccc(N3C[C@H]4C[C@H]3CN4C(=O)OC(C)(C)C)nn2c1N(C)c1nc(-c2ccc(F)cc2)cs1] | tert-butyl-(1R,4S)-5-(2-ethyl-3-((4-(4-fluorophenyl)thiazol-2-yl)(methyl)amino)imidazo[1,2-b]pyridazin-6-yl)-2,5-diazabicyclo[2.2.1]heptane-2-carboxylate | Gen-4-a E4a | 549 | 550 (M + H) |
| Cpd 75 | 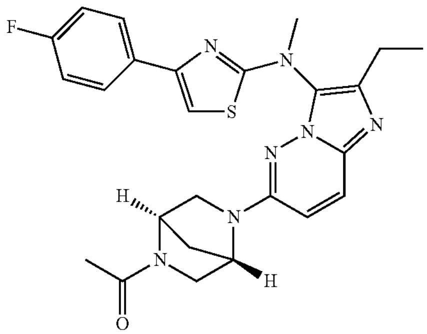 [SMILES: CCc1nc2ccc(N3C[C@H]4C[C@H]3CN4C(C)=O)nn2c1N(C)c1nc(-c2ccc(F)cc2)cs1] | 1-((1R,4S)-5-(2-ethyl-3-((4-(4-fluorophenyl)thiazol-2-yl)(methyl)amino)imidazo[1,2-b]pyridazin-6-yl)-2,5-diazabicyclo[2.2.1]heptan-2-yl)ethanone | Gen-4-a E4a | 491 | 492 (M + H) |
| Cpd 81 | 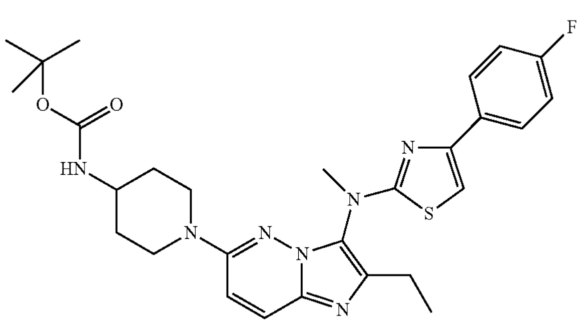 [SMILES: CCc1nc2ccc(N3CCC(NC(=O)OC(C)(C)C)CC3)nn2c1N(C)c1nc(-c2ccc(F)cc2)cs1] | tert-butyl 1-(2-ethyl-3-((4-(4-fluorophenyl)thiazol-2-yl)(methyl)amino)imidazo[1,2-b]pyridazin-6-yl)piperidin-4-ylcarbamate | Gen-4-a E4a or E4b | 551 | 552 (M + H) |

TABLE 1-continued

Intermediates used towards the compounds of the invention.

| Int | Structures | Name | Mtd | MW | MS Ms'd |
|---|---|---|---|---|---|
| Cpd 82 | 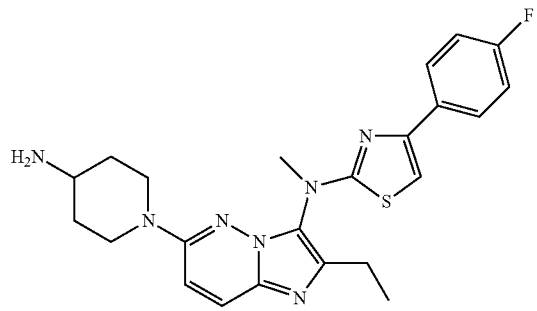 [SMILES: CCc1nc2ccc(N3CCC(N)CC3)nn2c1N(C)c1nc(-c2ccc(F)cc2)cs1] | N-(6-(4-aminopiperidin-1-yl)-2-ethylimidazo[1,2-b]pyridazin-3-yl)-4-(4-fluorophenyl)-N-methylthiazol-2-amine | Cpd 81 E5b | 451 | 452 (M + H) |
| Cpd 95 | 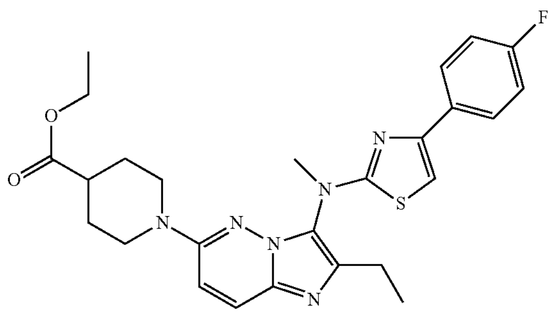 [SMILES: CCOC(=O)C1CCN(c2ccc3nc(CC)c(N(C)c4nc(-c5ccc(F)cc5)cs4)n3n2)CC1] | ethyl 1-(2-ethyl-3-((4-(4-fluorophenyl)thiazol-2-yl)(methyl)amino)imidazo[1,2-b]pyridazin-6-yl)piperidine-4-carboxylate | Gen-4-a E4a | 508 | 509 (M + H) |
| Cpd 96 | 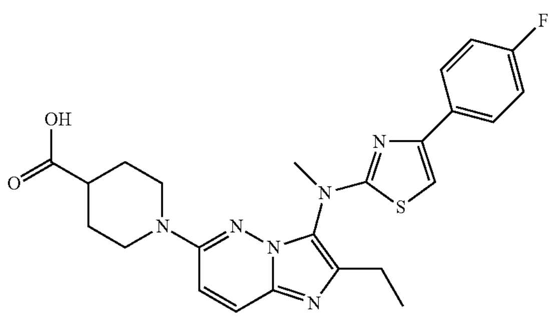 [SMILES: CCc1nc2ccc(N3CCC(C(=O)O)CC3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)piperidine-4-carboxylic acid | Cpd 95 E13 | 480 | 481 (M + H) |
| Cpd 100 | 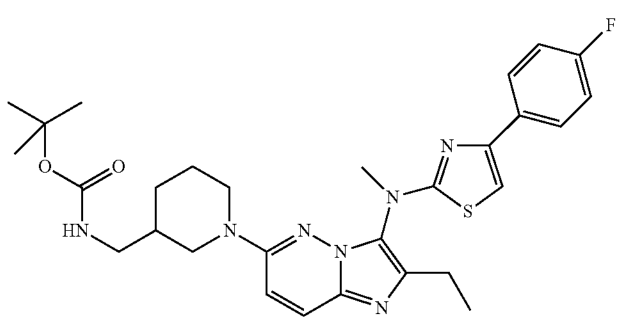 [SMILES: CCc1nc2ccc(N3CCCC(CNC(=O)OC(C)(C)C)C3)nn2c1N(C)c1nc(-c2ccc(F)cc2)cs1] | [1-(2-Ethyl-3-{[4-(4-fluoro-phenyl)-thiazol-2-yl]-methyl-amino}-imidazo[1,2-b]pyridazin-6-yl)-piperidin-3-ylmethyl]-carbamic acid tert-butyl ester | Gen-4-a E4a | 565 | 566 (M + H) |

TABLE 1-continued

Intermediates used towards the compounds of the invention.

| Int | Structures | Name | Mtd | MW | MS Ms'd |
|---|---|---|---|---|---|
| Cpd 101 | 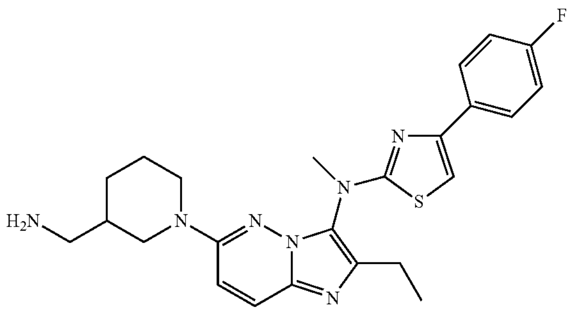 [SMILES: CCc1nc2ccc(N3CCCC(CN)C3)nn2c1N(C)c1nc(-c2ccc(F)cc2)cs1] | N-(6-(3-(aminomethyl)piperidin-1-yl)-2-ethylimidazo[1,2-b]pyridazin-3-yl)-4-(4-fluorophenyl)-N-methylthiazol-2-amine | Cpd 100 E5b | 465 | 466 (M + H) |
| Cpd 122 | 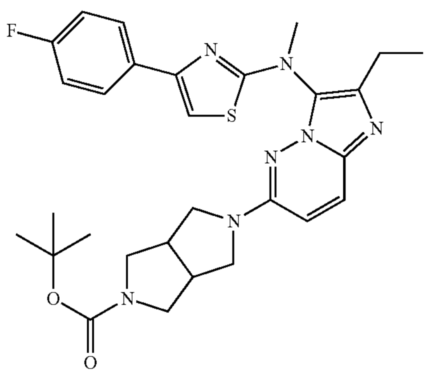 [SMILES: CCc1nc2ccc(N3CC4CN(C(=O)OC(C)(C)C)CC4C3)nn2c1N(C)c1nc(-c2ccc(F)cc2)cs1] | tert-butyl 5-(2-ethyl-3-((4-(4-fluorophenyl)thiazol-2-yl)(methyl)amino)imidazo[1,2-b]pyridazin-6-yl)hexahydropyrrolo[3,4-c]pyrrole-2(1H)-carboxylate | Gen-4-a E4a | 563 | 564 (M + H) |
| Cpd 125 | 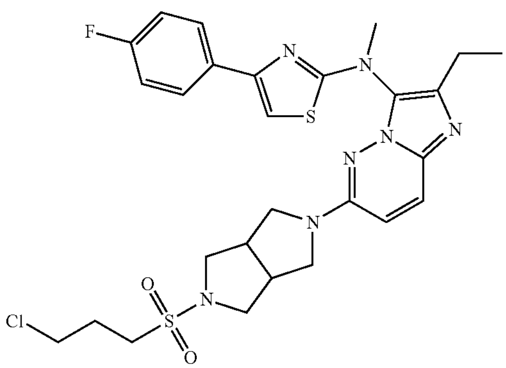 [SMILES: CCc1nc2ccc(N3CC4CN(S(=O)(=O)CCCCl)CC4C3)nn2c1N(C)c1nc(-c2ccc(F)cc2)cs1] | N-(6-(5-(3-chloropropylsulfonyl)hexahydropyrrolo[3,4-c]pyrrol-2(1H)-yl)-2-ethylimidazo[1,2-b]pyridazin-3-yl)-4-(4-fluorophenyl)-N-methylthiazol-2-amine | Gen-5-d E11 | 603 ($^{35}$Cl), 605 ($^{37}$Cl) | 604 ($^{35}$Cl M + H), 606 ($^{37}$Cl M + H) |
| Cpd 129 | 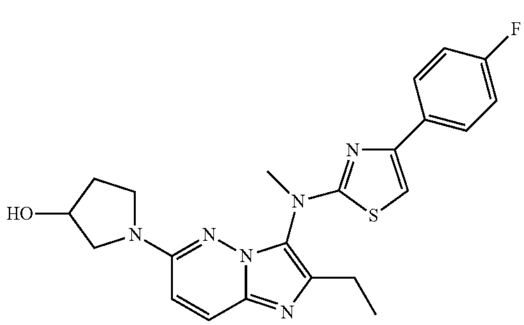 [SMILES: CCc1nc2ccc(N3CCC(O)C3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)pyrrolidin-3-ol | Gen-4-a E4a | 438 | 439 (M + H) |

TABLE 1-continued

Intermediates used towards the compounds of the invention.

| Int | Structures | Name | Mtd | MW | MS Ms'd |
|---|---|---|---|---|---|
| Cpd 133 | 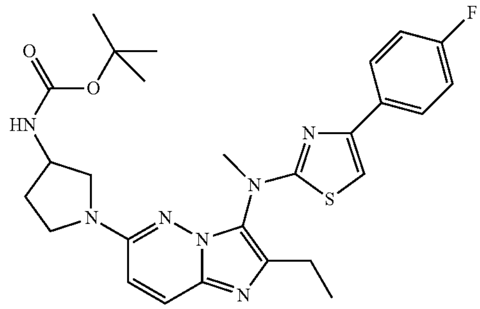 [SMILES: CCc1nc2ccc(N3CCC(NC(=O)OC(C)(C)C)C3)nn2c1N(C)c1nc(-c2ccc(F)cc2)cs1] | tert-butyl 1-(2-ethyl-3-((4-(4-fluorophenyl)thiazol-2-yl)(methyl)amino)imidazo[1,2-b]pyridazin-6-yl)pyrrolidin-3-ylcarbamate | Gen-4-a E4a | 537 | 538 (M + H) |
| Cpd 134 | 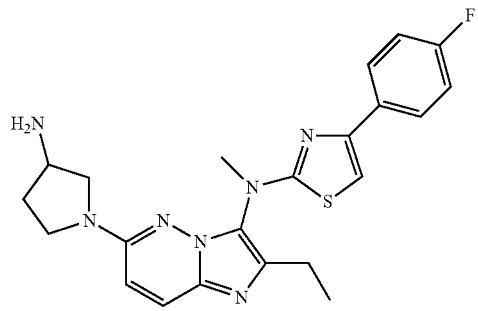 [SMILES: CCc1nc2ccc(N3CCC(N)C3)nn2c1N(C)c1nc(-c2ccc(F)cc2)cs1] | N-(6-(3-aminopyrrolidin-1-yl)-2-ethylimidazo[1,2-b]pyridazin-3-yl)-4-(4-fluorophenyl)-N-methylthiazol-2-amine | Cpd 133 E5b | 437 | 438 (M + H) |
| Cpd 147 | 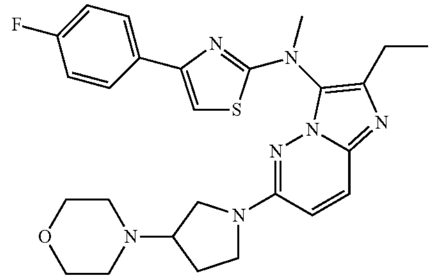 [SMILES: CCc1nc2ccc(N3CCC(N4CCOCC4)C3)nn2c1N(C)c1nc(-c2ccc(F)cc2)cs1] | N-(2-ethyl-6-(3-morpholinopyrrolidin-1-yl)imidazo[1,2-b]pyridazin-3-yl)-4-(4-fluorophenyl)-N-methylthiazol-2-amine | Gen-4-a E4a | 507 | 508 (M + H) |
| Cpd 154 | 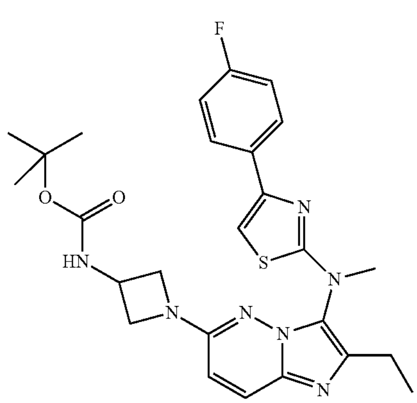 [SMILES: CCc1nc2ccc(N3CC(NC(=O)OC(C)(C)C)C3)nn2c1N(C)c1nc(-c2ccc(F)cc2)cs1] | [1-(2-Ethyl-3-{[4-(4-fluoro-phenyl)-thiazol-2-yl]-methyl-amino}-imidazo[1,2-b]pyridazin-6-yl)-azetidin-3-yl]-carbamic acid tert-butyl ester | Gen-4-a E4a or E1b | 523 | 524 (M + H) |

TABLE 1-continued

Intermediates used towards the compounds of the invention.

| Int | Structures | Name | Mtd | MW | MS Ms'd |
|---|---|---|---|---|---|
| Cpd 171 | 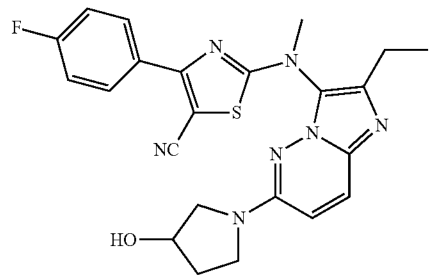 [SMILES: CCc1nc2ccc(N3CCC(O)C3)nn2c1N(C)c1nc(-c2ccc(F)cc2)c(C#N)s1] | 2-((2-ethyl-6-(3-hydroxypyrrolidin-1-yl)imidazo[1,2-b]pyridazin-3-yl)(methyl)amino)-4-(4-fluorophenyl)thiazole-5-carbonitrile | Gen-4-b E4a | 463 | 464 (M + H) |
| Cpd 193 | 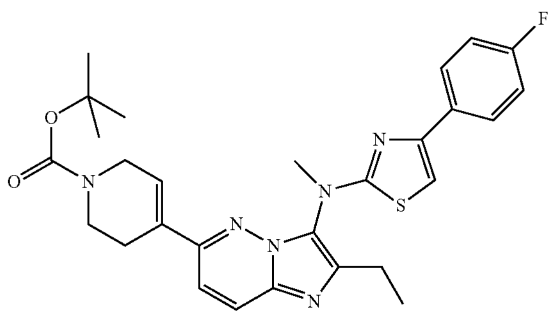 [SMILES: CCc1nc2ccc(C3=CCN(C(=O)OC(C)(C)C)CC3)nn2c1N(C)c1nc(-c2ccc(F)cc2)cs1] | tert-butyl 4-(2-ethyl-3-((4-(4-fluorophenyl)thiazol-2-yl)(methyl)amino)imidazo[1,2-b]pyridazin-6-yl)-5,6-dihydropyridine-1(2H)-carboxylate | Gen-4-a E2 | 534 | 535 (M + H) |
| Cpd 195 | 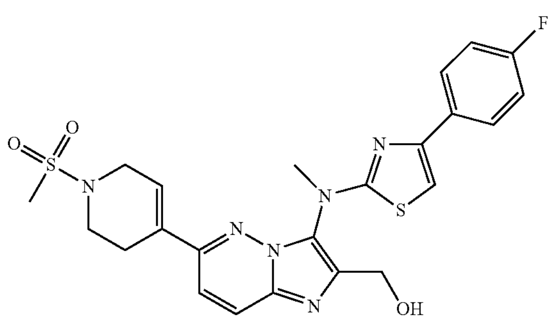 [SMILES: CN(c1nc(-c2ccc(F)cc2)cs1)c1c(CO)nc2ccc(C3=CCN(S(C)(=O)=O)CC3)nn12] | (3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)methanol | Gen-5-aag See Cpd 195 | 514 | 515 (M + H) |
| Gen-6-a | 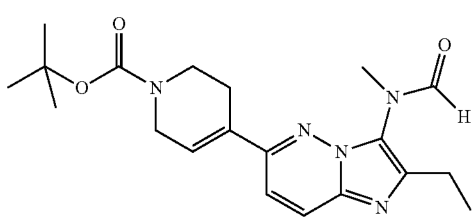 [SMILES: CCc1nc2ccc(C3=CCN(C(=O)OC(C)(C)C)CC3)nn2c1N(C)C=O] | 4-[2-Ethyl-3-(formyl-methyl-amino)-imidazo[1,2-b]pyridazin-6-yl]-3,6-dihydro-2H-pyridine-1-carboxylic acid tert-butyl ester | Gen-2-a E2 | 385 | 386 (M + H) |
| Gen-6-b | 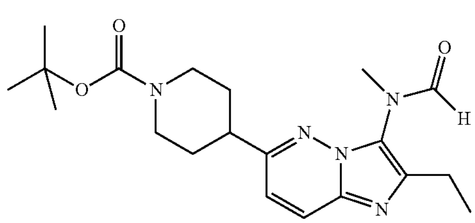 [SMILES: CCc1nc2ccc(C3CCN(C(=O)OC(C)(C)C)CC3)nn2c1N(C)C=O] | 4-[2-Ethyl-3-(formyl-methyl-amino)-imidazo[1,2-b]pyridazin-6-yl]-piperidine-1-carboxylic acid tert-butyl ester | Gen-6-a E6 | 387 | 388 (M + H) |

TABLE 1-continued

Intermediates used towards the compounds of the invention.

| Int | Structures | Name | Mtd | MW | MS Ms'd |
|---|---|---|---|---|---|
| Gen-7-a | 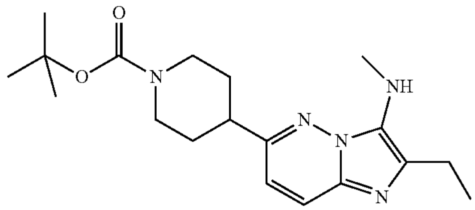 [SMILES: CCc1nc2ccc(C3CCN(C(=O)OC(C)(C)C)CC3)nn2c1NC] | 4-(2-Ethyl-3-methylamino-imidazo[1,2-b]pyridazin-6-yl)-piperidine-1-carboxylic acid tert-butyl ester | Gen-6-b C2 | 359 | 360 (M + H) |
| Gen-8-a | 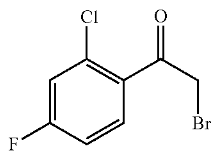 | 2-(2-Bromo-acetyl)-5-fluoro-benzonitrile | G1 | 241 ($^{79}$Br), 243 ($^{81}$Br) | 242 ($^{79}$Br M + H), 244 ($^{81}$Br M + H) |
| Gen-8-b | 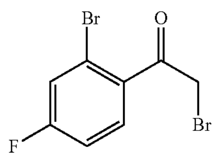 | 2-Bromo-1-(2-bromo-4-fluoro-phenyl)-ethanone | G1 | 294 296 298 | N.A |
| Gen-8-c | 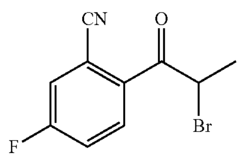 | 2-(2-Bromo-propionyl)-5-fluoro-benzonitrile | G1 | 255 ($^{79}$Br), 257 ($^{81}$Br) | N.A |
| Gen-9-a | 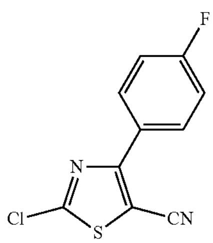 [SMILES: N#Cc1sc(Cl)nc1-c1ccc(F)cc1] | 2-Chloro-4-(4-fluoro-phenyl)-thiazole-5-carbonitrile | G2a | 238 ($^{35}$Cl), 240 ($^{37}$Cl) | 239 ($^{35}$Cl M + H), 241 ($^{37}$Cl M + H) |
| Gen-9-b | 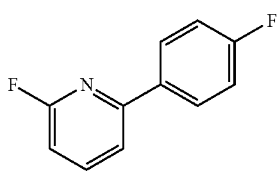 [SMILES: Fc1ccc(-c2cccc(F)n2)cc1] | 2-Fluoro-6-(4-fluoro-phenyl)-pyridine | G2b | 191 | 192 (M + H) |
| Gen-9-c | 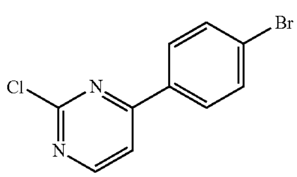 [SMILES: Clc1nccc(-c2ccc(Br)cc2)n1] | 2-Chloro-4-(4-fluoro-phenyl)-pyrimidine | G2b | 208 ($^{35}$Cl), 210 ($^{37}$Cl) | 209 ($^{35}$Cl M + H), 211 ($^{37}$Cl M + H) |
| Gen-9-d | 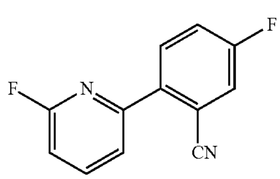 [SMILES: N#Cc1cc(F)ccc1-c1cccc(F)n1] | 5-Fluoro-2-(6-fluoro-pyridin-2-yl)-benzonitrile | G2b | 216 | 217 (M + H) |

TABLE 1-continued

Intermediates used towards the compounds of the invention.

| Int | Structures | Name | Mtd | MW | MS Ms'd |
|---|---|---|---|---|---|
| Gen-9-e | 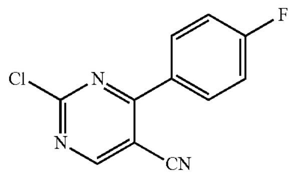 [SMILES: N#Cc1cnc(Cl)nc1-c1ccc(F)cc1] | 2-Chloro-4-(4-fluoro-phenyl)-pyrimidine-5-carbonitrile | See Gen-9-e | 233 ($^{35}$Cl), 235 ($^{37}$Cl) | 234 ($^{35}$Cl M + H), 236 ($^{37}$Cl M + H) |
| Gen-10-a | 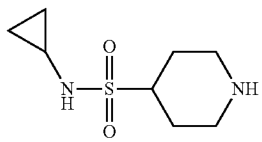 [SMILES: O=S(=O)(NC1CC1)C1CCNCC1] | Piperidine-4-sulfonic acid cyclopropylamide | See Gen-10-a | 204 | N.A |
| Gen-10-b | 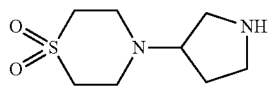 [SMILES: O=S1(=O)CCN(C2CCNC2)CC1] | 4-Pyrrolidin-3-yl-thiomorpholine 1,1-dioxide | G3a | 204 | N.A |
| Gen-10-c | 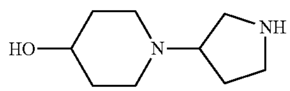 [SMILES: OC1CCN(C2CCNC2)CC1] | 1-Pyrrolidin-3-yl-piperidin-4-ol | G3a | 170 | N.A |
| Gen-10-d | 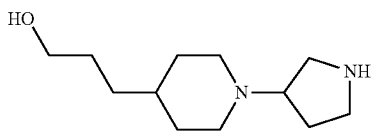 [SMILES: OCCCC1CCN(C2CCNC2)CC1] | 3-(1-Pyrrolidin-3-yl-piperidin-4-yl)-propan-1-ol | G3a | 212 | N.A |
| Gen-10-e | 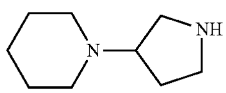 | 1-Pyrrolidin-3-yl-piperidine | G3a | 154 | N.A |
| Gen-10-f | 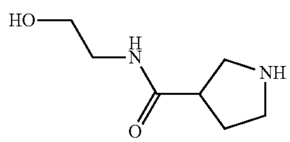 [SMILES: O=C(NCCO)C1CCNC1] | Pyrrolidine-3-carboxylic acid (2-hydroxy-ethyl)-amide | G3b | 158 | N.A |
| Gen-10-g | 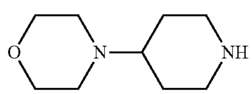 [SMILES: C1CC(N2CCOCC2)CCN1] | 4-Piperidin-4-yl-morpholine | G3a | 170 | N.A |
| Gen-10-h | 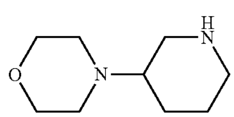 [SMILES: C1CNCC(N2CCOCC2)C1] | 4-Piperidin-3-yl-morpholine | G3a | 170 | N.A |
| Gen-10-i | 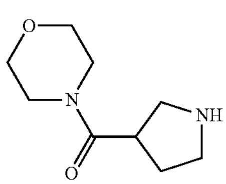 [SMILES: O=C(C1CCNC1)N1CCOCC1] | Morpholin-4-yl-pyrrolidin-3-yl-methanone | G3b | 184 | N.A |
| Gen-10-j | 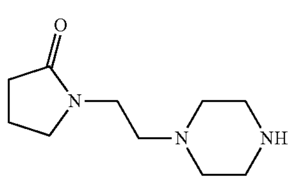 [SMILES: O=C1CCCN1CCN1CCNCC1] | 1-(2-Piperazin-1-yl-ethyl)-pyrrolidin-2-one | See Gen-10-j | 197 | N.A |

TABLE 1-continued

Intermediates used towards the compounds of the invention.

| Int | Structures | Name | Mtd | MW | MS Ms'd |
|---|---|---|---|---|---|
| Gen-10-k | 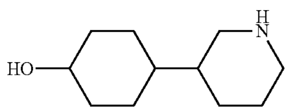 [SMILES: OC1CCC(C2CCCNC2)CC1] | 4-Piperidin-3-yl-cyclohexanol | G3a | 101 | N.A |
| Gen-10-l | 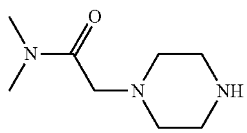 | N,N-Dimethyl-2-piperazin-1-yl-acetamide | See Gen-10-l | 171 | N.A |
| Gen-10-m | 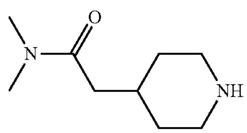 | N,N-Dimethyl-2-piperidin-4-yl-acetamide | G3b | 170 | N.A |
| Gen-10-n | 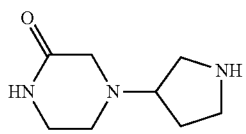 [SMILES: O=C1CN(C2CCNC2)CCN1] | 4-Pyrrolidin-3-yl-piperazin-2-one | G3a | 169 | N.A |
| Gen-10-o | 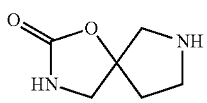 | 1-Oxa-3,7-diaza-spiro[4.4]nonan-2-one | See Gen-10-o | 142 | N.A |
| Gen-10-p | 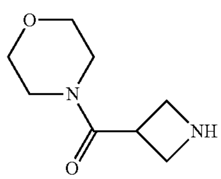 [SMILES: O=C(C1CNC1)N1CCOCC1] | Azetidin-3-yl-morpholin-4-yl-methanone | G3b | 170 | N.A |
| Gen-10-q | 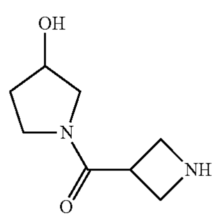 [SMILES: O=C(C1CNC1)N1CCC(O)C1] | Azetidin-3-yl-(3-hydroxy-pyrrolidin-1-yl)-methanone | G3b | 170 | N.A |
| Gen-10-r | 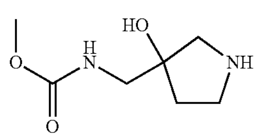 | (3-Hydroxy-pyrrolidin-3-ylmethyl)-carbamic acid methyl ester | G3b | 174 | N.A |
| Gen-10-s | 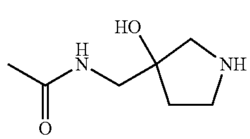 | N-(3-Hydroxy-pyrrolidin-3-ylmethyl)-acetamide | G3b | 158 | N.A |
| Gen-10-t | 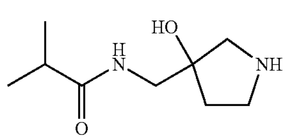 | N-(3-Hydroxy-pyrrolidin-3-ylmethyl)-isobutyramide | G3b | 186 | N.A |

TABLE 1-continued

Intermediates used towards the compounds of the invention.

| Int | Structures | Name | Mtd | MW | MS Ms'd |
|---|---|---|---|---|---|
| Gen-10-u | 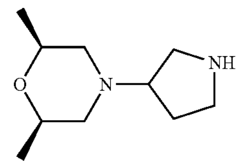 | (2S,6R)-2,6-Dimethyl-4-pyrrolidin-3-yl-morpholine | G3a | 184 | 185 (M + H) |
| Gen-10-v | 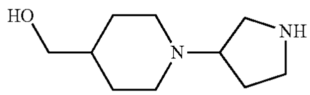 | (1-Pyrrolidin-3-yl-piperidin-4-yl)-methanol | G3a | 184 | 185 (M + H) |
| Gen-10-w | 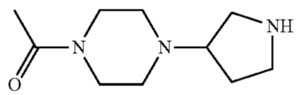 | 1-(4-Pyrrolidin-3-yl-piperazin-1-yl)-ethanone | G3a | 197 | 198 (M + H) |
| Gen-10-x | 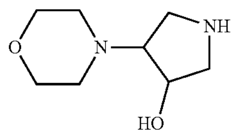 [SMILES: OC1CNCC1N1CCOCC1] | 4-Morpholin-4-yl-pyrrolidin-3-ol | See Gen-10-x | 172 | 173 (M + H) |
| Gen-10-y | 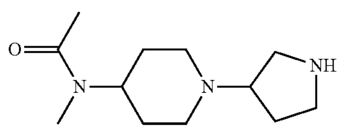 [SMILES: CC(=O)N(C)C1CCN(C2CCNC2)CC1] | N-Methyl-N-(1-pyrrolidin-3-yl-piperidin-4-yl)-acetamide | G3b + G3a | 225 | N.A |
| Gen-10-z | 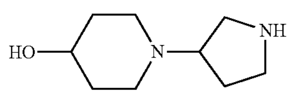 [SMILES: OC1CCN(C2CCNC2)CC1] | 1-Pyrrolidin-3-yl-piperidin-4-ol | G3a | 170 | N.A |
| Gen-10-aa | 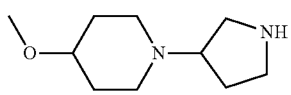 | 4-Methoxy-1-pyrrolidin-3-yl-piperidine | See Gen-10-aa | 184 | N.A |
| Gen-10-ab | 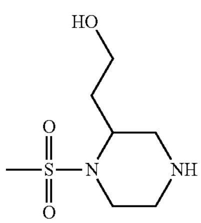 | 2-(1-Methanesulfonyl-piperazin-2-yl)-ethanol | See Gen-10-ab | 208 | N.A |
| Gen-10-ac | 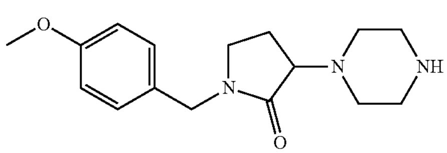 [SMILES: COc1ccc(CN2CCC(N3CCNCC3)C2=O)cc1] | 1-(4-Methoxy-benzyl)-3-piperazin-1-yl-pyrrolidin-2-one | See Gen-10-ac | 289 | 290 (M + H |
| Gen-11-a | 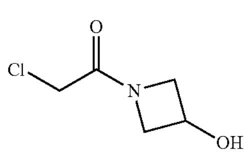 | 2-Chloro-1-(3-hydroxy-azetidin-1-yl)-ethanone | G3a | 149 ($^{35}$Cl), 151 ($^{37}$Cl) | N.A |
| Gen-11-b | 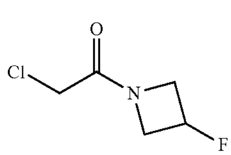 | 2-Chloro-1-(3-fluoro-azetidin-1-yl)-ethanone | G3a | 151 ($^{35}$Cl), 153 ($^{37}$Cl) | N.A |

TABLE 1-continued

Intermediates used towards the compounds of the invention.

| Int | Structures | Name | Mtd | MW | MS Ms'd |
|---|---|---|---|---|---|
| Gen-11-c | 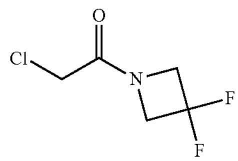 | 2-Chloro-1-(3,3-difluoro-azetidin-1-yl)-ethanone | G3a | 169 ($^{35}$Cl), 170 ($^{37}$Cl) | 170 ($^{35}$Cl M + H) 172 ($^{37}$Cl M + H) |
| Gen-11-d | 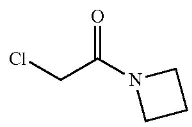 | 1-Azetidin-1-yl-2-chloro-ethanone | G3a | 133 ($^{35}$Cl), 135 ($^{37}$Cl) | N.A |
| Gen-11-e | 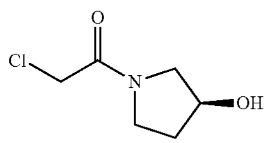 | (S)-2-Chloro-1-(3-hydroxy-pyrrolidin-1-yl)-ethanone | G3a | 163 ($^{35}$Cl), 165 ($^{37}$Cl) | 164 ($^{35}$Cl M + H), 166 ($^{37}$Cl M + H) |
| Gen-11-f | 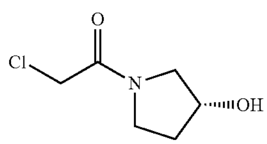 | (R)-2-Chloro-1-(3-hydroxy-pyrrolidin-1-yl)-ethanone | G3b | 163 ($^{35}$Cl), 165 ($^{37}$Cl) | 164 ($^{35}$Cl M + H), 166 ($^{37}$Cl M + H) |
| Gen-11-g | 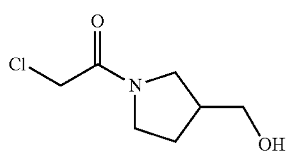 [SMILES: O=C(CCl)N1CCC(CO)C1] | 2-Chloro-1-(3-hydroxymethyl-pyrrolidin-1-yl)-ethanone | G3c | 177 ($^{35}$Cl), 178 ($^{37}$Cl) | N.A |
| Gen-11-h | 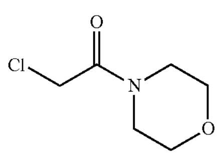 | 2-Chloro-1-morpholin-4-yl-ethanone | G3b | 163 ($^{35}$Cl), 165 ($^{37}$Cl)) | N.A |
| Gen-11-i | 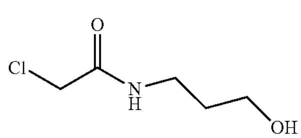 | 2-Chloro-N-(3-hydroxy-propyl)-acetamide | G3b | 151 ($^{35}$Cl), 153 ($^{37}$Cl) | N.A |
| Gen-11-j | 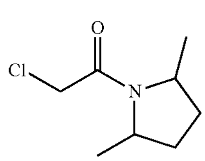 | 2-Chloro-1-(2,5-dimethyl-pyrrolidin-1-yl)-ethanone | See Gen-11-j | 174 ($^{35}$Cl), 176 ($^{37}$Cl) | N.A |
| Gen-11-k | 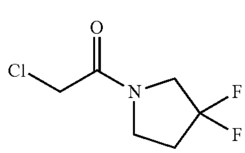 [SMILES: O=C(CCl)N1CCC(F)(F)C1] | 2-Chloro-1-(3,3-difluoro-pyrrolidin-1-yl)-ethanone | G3c | 182 ($^{35}$Cl), 184 ($^{37}$Cl) | N.A |

TABLE 1-continued

Intermediates used towards the compounds of the invention.

| Int | Structures | Name | Mtd | MW | MS Ms'd |
|---|---|---|---|---|---|
| Gen-11-1 | | 2-Chloro-1-(2-methyl-pyrrolidin-1-yl)-ethanone | G3c | 160 ($^{35}$Cl), 162 ($^{37}$Cl) | N.A |

TABLE II

Illustrative compounds of the invention.

| Cpd | Structures | Name | Mtd | MW | MS Ms'd |
|---|---|---|---|---|---|
| 1 | 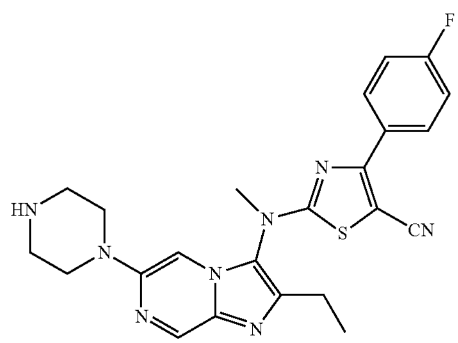 [SMILES: CCc1nc2cnc(N3CCNCC3)cn2c1N(C)c1nc(-c2ccc(F)cc2)c(C#N)s1] | 2-((2-ethyl-6-(piperazin-1-yl)imidazo[1,2-a]pyrazin-3-yl)(methyl)amino)-4-(4-fluorophenyl)thiazole-5-carbonitrile | Gen-4-d A1-B2-C2-D2-E1a | 462 | 463 (M + H) |
| 2 | 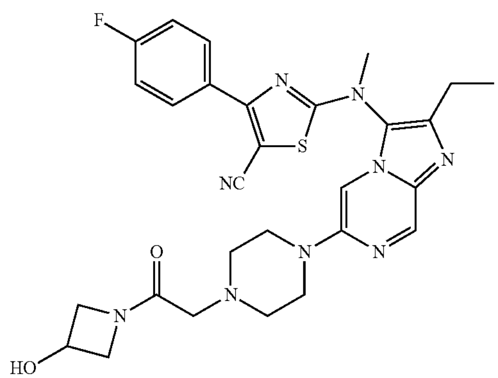 | 2-((2-ethyl-6-(4-(2-(3-hydroxyazetidin-1-yl)-2-oxoethyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E8 | 575 | 576 (M + H) |
| 3 | 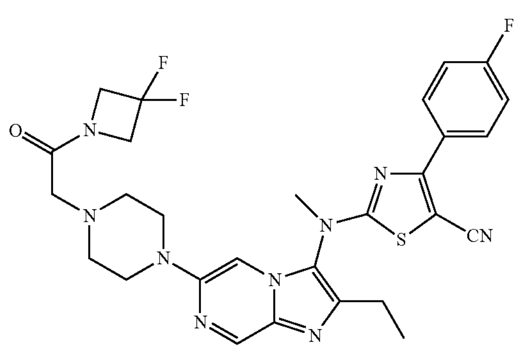 [SMILES: CCc1nc2cnc(N3CCN(CC(=O)N4CC(F)(F)C4)CC3)cn2c1N(C)c1nc(-c2ccc(F)cc2)c(C#N)s1] | 2-((6-(4-(2-(3,3-difluoroazetidin-1-yl)-2-oxoethyl)piperazin-1-yl)-2-ethylimidazo[1,2-a]pyrazin-3-yl)(methyl)amino)-4-(4-fluorophenyl)thiazole-5-carbonitrile | Cpd 1 A1-B2-C2-D2-E1a-E8 | 595 | 596 (M + H) |

TABLE II-continued

Illustrative compounds of the invention.

| Cpd | Structures | Name | Mtd | MW | MS Ms'd |
|---|---|---|---|---|---|
| 4 | 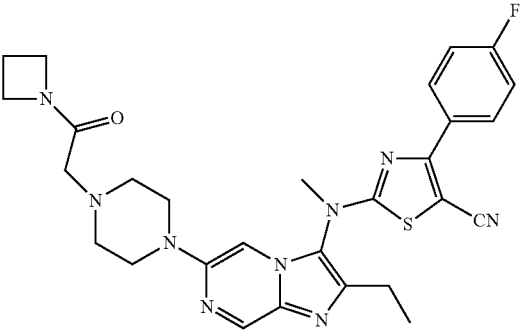 [SMILES: CCc1nc2cnc(N3CCN(CC(=O)N4CCC4)CC3)cn2c1N(C)c1nc(-c2ccc(F)cc2)c(C#N)s1] | 2-((6-(4-(2-(azetidin-1-yl)-2-oxoethyl)piperazin-1-yl)-2-ethylimidazo[1,2-a]pyrazin-3-yl)(methyl)amino)-4-(4-fluorophenyl)thiazole-5-carbonitrile | Cpd 1 A1-B2-C2-D2-E1a-E8 | 559 | 560 (M + H) |
| 5 | 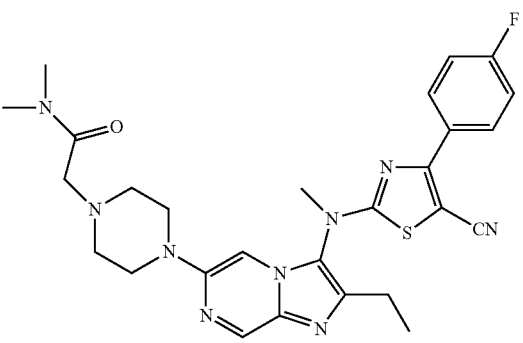 [SMILES: CCc1nc2cnc(N3CCN(CC(=O)N(C)C)CC3)cn2c1N(C)c1nc(-c2ccc(F)cc2)c(C#N)s1] | 2-(4-(3-((5-cyano-4-(4-fluorophenyl)thiazol-2-yl)(methyl)amino)-2-ethylimidazo[1,2-a]pyrazin-6-yl)piperazin-1-yl)-N,N-dimethylacetamide | Cpd 1 A1-B2-C2-D2-E1a-E8 | 547 | 548 (M + H) |
| 6 | 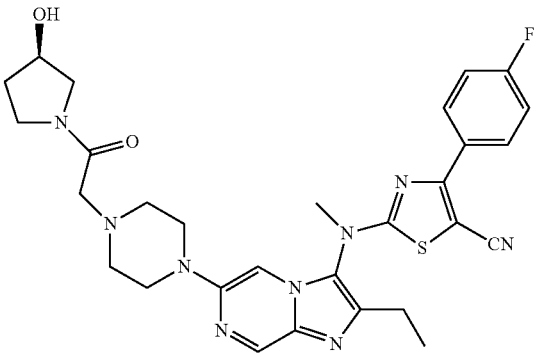 [SMILES: CCc1nc2cnc(N3CCN(CC(=O)N4CC[C@H](O)C4)CC3)cn2c1N(C)c1nc(-c2ccc(F)cc2)c(C#N)s1] | (R)-2-((2-ethyl-6-(4-(2-(3-hydroxypyrrolidin-1-yl)-2-oxoethyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E8 | 589 | 590 (M + H) |
| 7 | 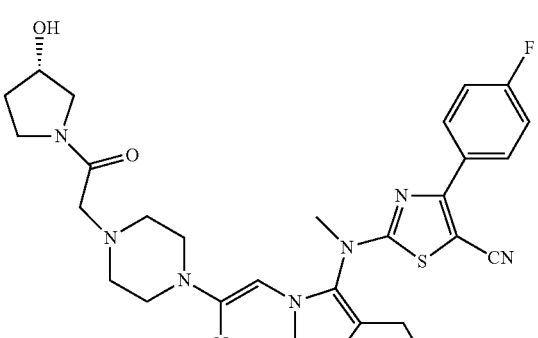 | (S)-2-((2-ethyl-6-(4-(2-(3-hydroxypyrrolidin-1-yl)-2-oxoethyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E8 | 589 | 590 (M + H) |

TABLE II-continued

Illustrative compounds of the invention.

| Cpd | Structures | Name | Mtd | MW | MS Ms'd |
|---|---|---|---|---|---|
| 8 | 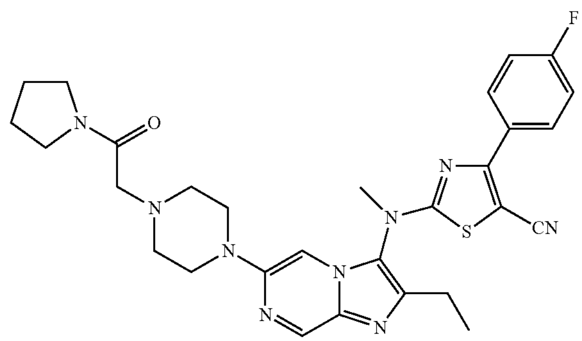 [SMILES: CCc1nc2cnc(N3CCN(CC(=O)N4CCCC4)CC3)cn2c1N(C)c1nc(-c2ccc(F)cc2)c(C#N)s1] | 2-((2-ethyl-6-(4-(2-oxo-2-(pyrrolidin-1-yl)ethyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E8 | 573 | 574 (M + H) |
| 9 | 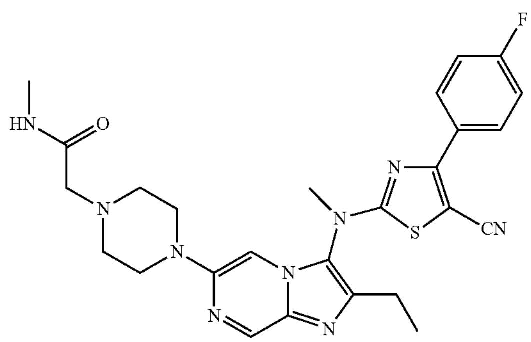 [SMILES: CCc1nc2cnc(N3CCN(CC(=O)NC)CC3)cn2c1N(C)c1nc(-c2ccc(F)cc2)c(C#N)s1] | 2-(4-(3-((5-cyano-4-(4-fluorophenyl)thiazol-2-yl)(methyl)amino)-2-ethylimidazo[1,2-a]pyrazin-6-yl)piperazin-1-yl)-N-methylacetamide | Cpd 1 A1-B2-C2-D2-E1a-E8 | 533 | 534 (M + H) |
| 10 | 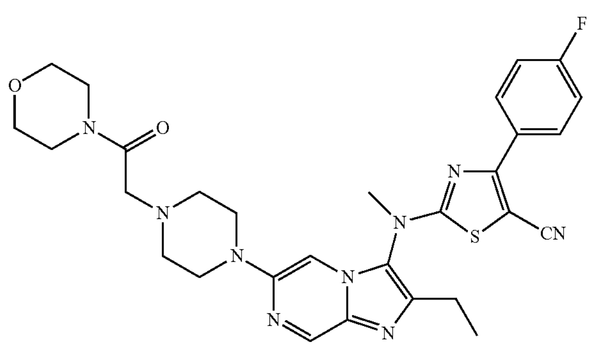 [SMILES: CCc1nc2cnc(N3CCN(CC(=O)N4CCOCC4)CC3)cn2c1N(C)c1nc(-c2ccc(F)cc2)c(C#N)s1] | 2-((2-ethyl-6-(4-(2-morpholino-2-oxoethyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E8 | 589 | 590 (M + H) |
| 11 | 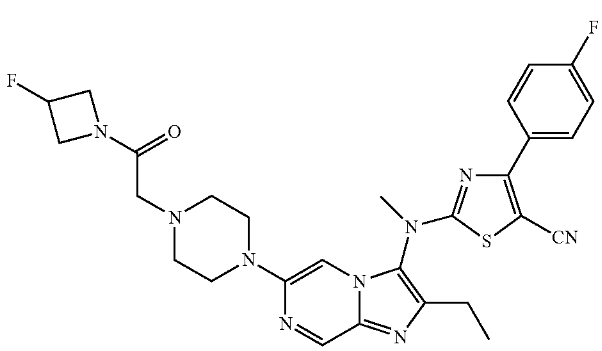 [SMILES: CCc1nc2cnc(N3CCN(CC(=O)N4CC(F)C4)CC3)cn2c1N(C)c1nc(-c2ccc(F)cc2)c(C#N)s1] | 2-((2-ethyl-6-(4-(2-(3-fluoroazetidin-1-yl)-2-oxoethyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E8 | 577 | 578 (M + H) |

TABLE II-continued

Illustrative compounds of the invention.

| Cpd | Structures | Name | Mtd | MW | MS Ms'd |
|---|---|---|---|---|---|
| 12 | 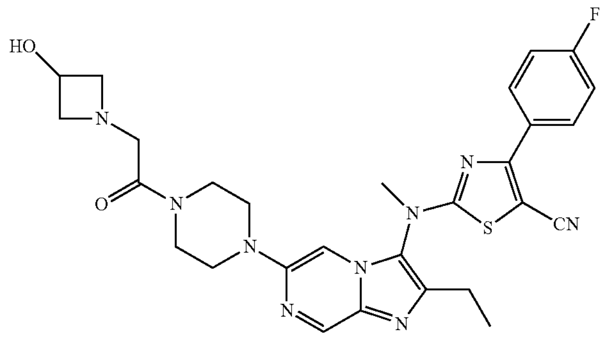 [SMILES: CCc1nc2cnc(N3CCN(C(=O)CN4CC(O)C4)CC3)cn2c1N(C)c1nc(-c2ccc(F)cc2)c(C#N)s1] | 2-((2-ethyl-6-(4-(2-(3-hydroxyazetidin-1-yl)acetoyl)piperazin-1-yl)imidazo[1,2-a]pyrazin-3-yl)(methyl)amino)-4-(4-fluorophenyl)thiazole-5-carbonitrile | Cpd 1 A1-B2-C2-D2-E1a-E9b-E8 | 575 | 576 (M + H) |
| 13 | 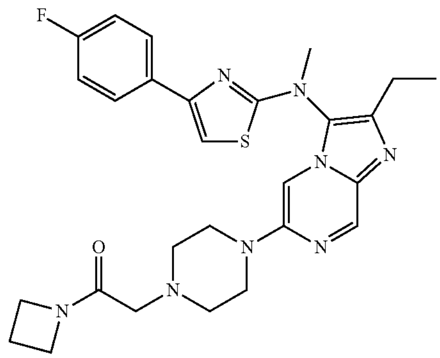 [SMILES: CCc1nc2cnc(N3CCN(CC(=O)N4CCC4)CC3)cn2c1N(C)c1nc(-c2ccc(F)cc2)cs1] | 1-(azetidin-1-yl)-2-(4-(2-ethyl-3-((4-(4-fluorophenyl)thiazol-2-yl)(methyl)amino)imidazo[1,2-a]pyrazin-6-yl)piperazin-1-yl)ethanone | Gen-5-aak A1-B2-C2-D1-E1a-E8 | 534 | 535 (M + H) |
| 14 | 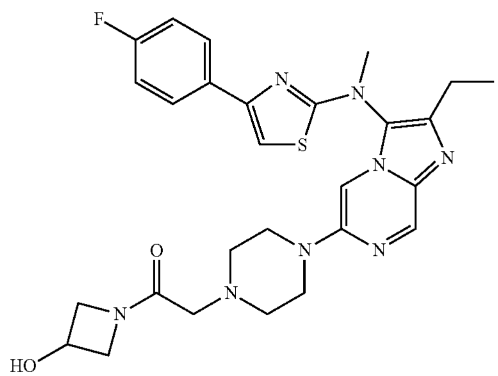 [SMILES: CCc1nc2cnc(N3CCN(CC(=O)N4CC(O)C4)CC3)cn2c1N(C)c1nc(-c2ccc(F)cc2)cs1] | 2-(4-(2-ethyl-3-((4-(4-fluorophenyl)thiazol-2-yl)(methyl)amino)imidazo[1,2-a]pyrazin-6-yl)piperazin-1-yl)-1-(3-hydroxyazetidin-1-yl)ethanone | Gen-5-aak A1-B2-C2-D1-E1a-E8 | 550 | 551 (M + H) |
| 15 | 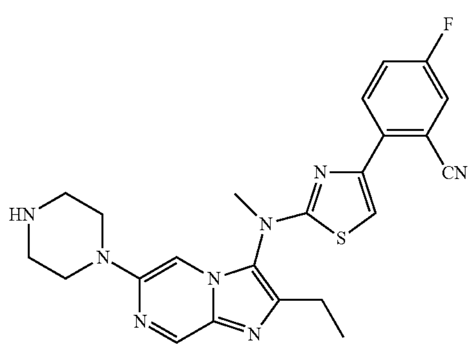 [SMILES: CCc1nc2cnc(N3CCNCC3)cn2c1N(C)c1nc(-c2ccc(F)cc2C#N)cs1] | 2-(2-((2-ethyl-6-(piperazin-1-yl)imidazo[1,2-a]pyrazin-3-yl)(methyl)amino)thiazol-4-yl)-5-fluorobenzonitrile | Gen-4-c A1-B2-C2-D1-E1a | 462 | 563 (M + H) |

TABLE II-continued

Illustrative compounds of the invention.

| Cpd | Structures | Name | Mtd | MW | MS Ms'd |
|---|---|---|---|---|---|
| 16 | 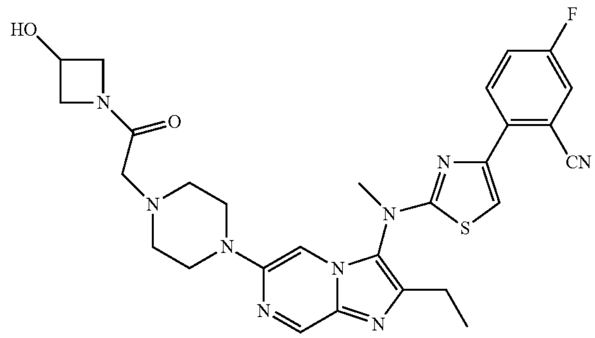 [SMILES: CCc1nc2cnc(N3CCN(CC(=O)N4CC(O)C4)CC3)cn2c1N(C)c1nc(-c2ccc(F)cc2C#N)cs1] | 2-(2-((2-ethyl-6-(4-(2-(3-hydroxyazetidin-1-yl)-2-oxoethyl)piperazin-1-yl)imidazo[1,2-a]pyrazin-3-yl)(methyl)amino)thiazol-4-yl)-5-fluorobenzonitrile | Cpd 15 A1-B2-C2-D1-E1a-E8 | 575 | 576 (M + H) |
| 15 | 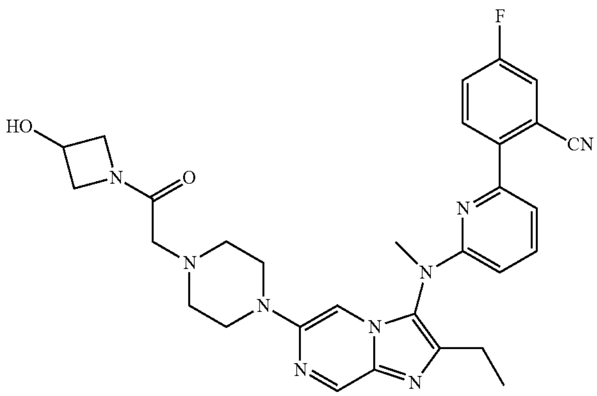 [SMILES: CCc1nc2cnc(N3CCN(CC(=O)N4CC(O)C4)CC3)cn2c1N(C)c1cccc(-c2ccc(F)cc2C#N)n1] | 2-(6-((2-ethyl-6-(4-(2-(3-hydroxyazetidin-1-yl)-2-oxoethyl)piperazin-1-yl)imidazo[1,2-a]pyrazin-3-yl)(methyl)amino)pyridin-2-yl)-5-fluorobenzonitrile | Gen-5-ak A1-B2-C2-D2-E1a-E8 | 569 | 570 (M + H) |
| 18 | 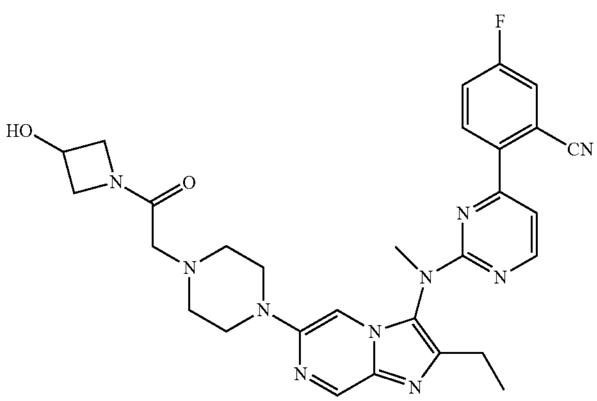 [SMILES: CCc1nc2cnc(N3CCN(CC(=O)N4CC(O)C4)CC3)cn2c1N(C)c1nccc(-c2ccc(F)cc2C#N)n1] | 2-(2-((2-ethyl-6-(4-(2-(3-hydroxyazetidin-1-yl)-2-oxoethyl)piperazin-1-yl)imidazo[1,2-a]pyrazin-3-yl)(methyl)amino)pyrimidin-4-yl)-5-fluorobenzonitrile | Gen-5-aaf A1-B2-C2-D2-E1a-E8 | 570 | 571 (M + H) |
| 19 | 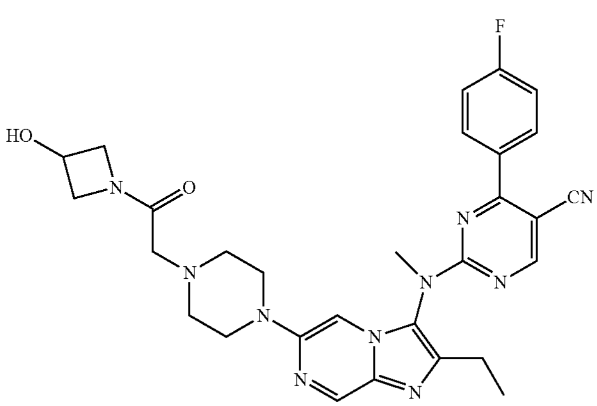 [SMILES: CCc1nc2cnc(N3CCN(CC(=O)N4CC(O)C4)CC3)cn2c1N(C)c1ncc(C#N)c(-c2ccc(F)cc2)n1] | 2-((2-ethyl-6-(4-(2-(3-hydroxyazetidin-1-yl)-2-oxoethyl)piperazin-1-yl)imidazo[1,2-a]pyrazin-3-yl)(methyl)amino)-4-(4-fluorophenyl)pyrimidine-5-carbonitrile | Gen-5-aal A1-B2-C2-D2-E1a-E8 | 570 | 571 (M + H) |

TABLE II-continued

Illustrative compounds of the invention.

| Cpd | Structures | Name | Mtd | MW | MS Ms'd |
|---|---|---|---|---|---|
| 20 | 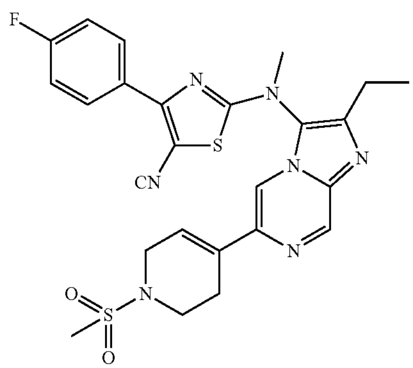 | 2-((2-ethyl-6-(1-(methylsulfonyl)-1,2,3,6-tetrahydropyridin-4-yl)imidazo[1,2-a]pyrazin-3-yl)(methyl)amino)-4-(4-fluorophenyl)thiazole-5-carbonitrile | Gen-4-d A1-B2-C2-D2-E2 | 537 | 538 (M + H) |
| 21 | 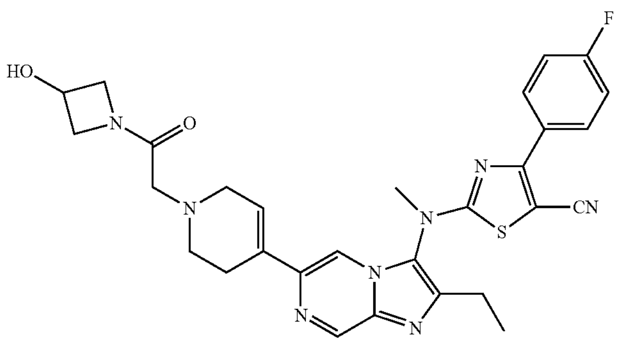 [SMILES: CCc1nc2cnc(C3=CCN(CC(=O)N4CC(O)C4)CC3)cn2c1N(C)c1nc(-c2ccc(F)cc2)c(C#N)s1] | 2-((2-ethyl-6-(1-(2-(3-hydroxyazetidin-1-yl)-2-oxoethyl)-1,2,3,6-tetrahydropyridin-4-yl)imidazo[1,2-a]pyrazin-3-yl)(methyl)amino)-4-(4-fluorophenyl)thiazole-5-carbonitrile | Gen-5-am A1-B2-C2-D2-E2-E5b-E8 | 572 | 573 (M + H) |
| 22 | 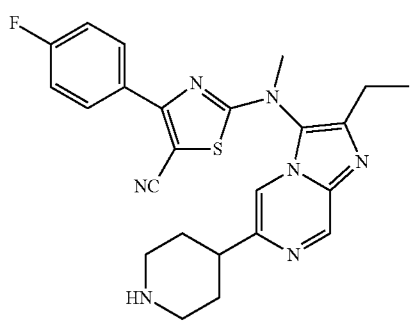 [SMILES: CCc1nc2cnc(C3CCNCC3)cn2c1N(C)c1nc(-c2ccc(F)cc2)c(C#N)s1] | 2-((2-ethyl-6-(piperidin-4-yl)imidazo[1,2-a]pyrazin-3-yl)(methyl)amino)-4-(4-fluorophenyl)thiazole-5-carbonitrile | Gen-5-ai A1-B2-C2-D2-E3-E5b | 461 | 462 (M + H) |
| 23 | 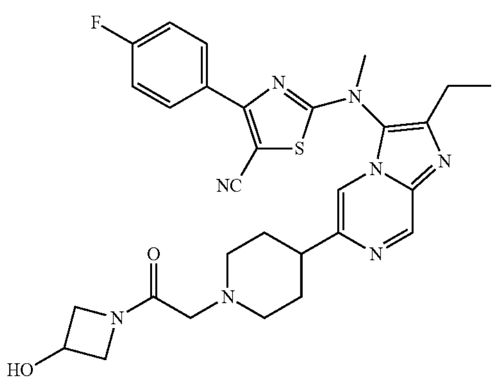 [SMILES: CCc1nc2cnc(C3CCN(CC(=O)N4CC(O)C4)CC3)cn2c1N(C)c1nc(-c2ccc(F)cc2)c(C#N)s1] | 2-((2-ethyl-6-(1-(2-(3-hydroxyazetidin-1-yl)-2-oxoethyl)piperidin-4-yl)imidazo[1,2-a]pyrazin-3-yl)(methyl)amino)-4-(4-fluorophenyl)thiazole-5-carbonitrile | Cpd 22 A1-B2-C2-D2-E3-E5b-E8 | 574 | 575 (M + H) |

TABLE II-continued

Illustrative compounds of the invention.

| Cpd | Structures | Name | Mtd | MW | MS Ms'd |
|---|---|---|---|---|---|
| 24 | 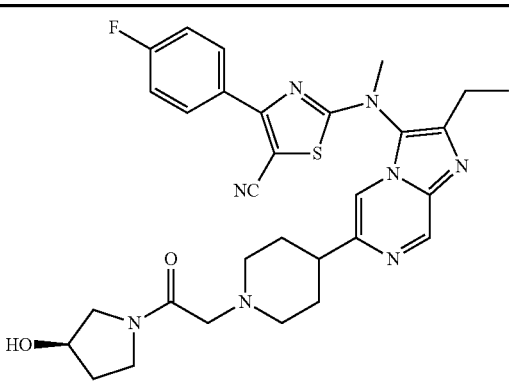 | (R)-2-((2-ethyl-6-(1-(2-(3-hydroxypyrrolidin-1-yl)-2-oxoethyl)piperidin-4-yl)imidazo[1,2-a]pyrazin-3-yl)(methyl)amino)-4-(4-fluorophenyl)thiazole-5-carbonitrile | Cpd 22 A1-B2-C2-D2-E3-E5b-E8 | 588 | 589 (M + H) |
| 25 | 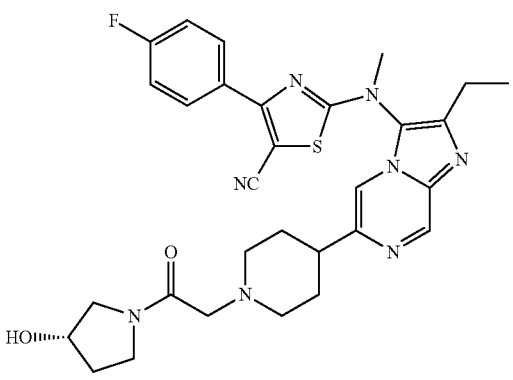 [SMILES: CCc1nc2cnc(C3CCN(CC(=O)N4CC[C@H](O)C4)CC3)cn2c1N(C)c1nc(-c2ccc(F)cc2)c(C#N)s1] | (S)-2-((2-ethyl-6-(1-(2-(3-hydroxypyrrolidin-1-yl)-2-oxoethyl)piperidin-4-yl)imidazo[1,2-a]pyrazin-3-yl)(methyl)amino)-4-(4-fluorophenyl)thiazole-5-carbonitrile | Cpd 22 A1-B2-C2-D2-E3-E5b-E8 | 588 | 589 (M + H) |
| 26 | 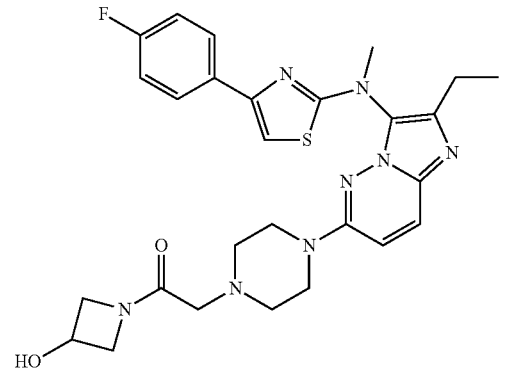 | 2-(4-(2-ethyl-3-((4-(4-fluorophenl)thiazol-2-yl)(methyl)amino)imidazo[1,2-b]pyridazin-6-yl)piperazin-1-yl)-1-(3-hydroxyazetidin-1-yl)ethanone | Gen-5-j A2-B2-C1-D1-E4b-E5b-E8 | 550 | 551 (M + H) |
| 27 | 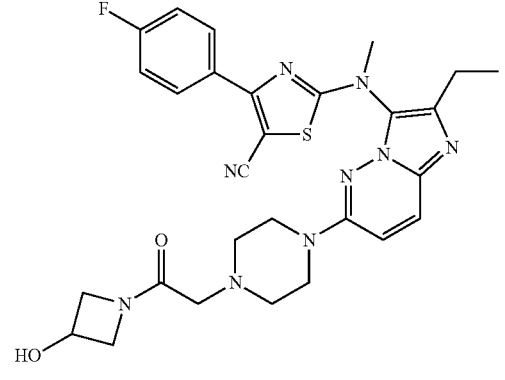 | 2-((2-ethyl-6-(4-(2-(3-hydroxyazetidin-1-yl)-2-oxoethyl)piperazin-1-yl)imidazo[1,2-b]pyridazin-3-yl)(methyl)amino)-4-(4-fluorophenyl)thiazole-5-carbonitrile | Gen-5-o A2-B2-C1-D1-E4b-E16-E17-E5b-E8 | 575 | 576 (M + H) |

TABLE II-continued

Illustrative compounds of the invention.

| Cpd | Structures | Name | Mtd | MW | MS Ms'd |
|---|---|---|---|---|---|
| 28 | 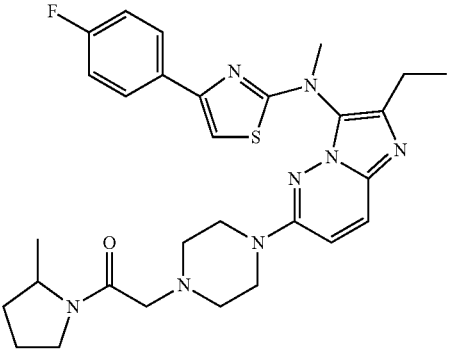 [SMILES: CCc1nc2ccc(N3CCN(CC(=O)N4CCCC4C)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-1-(2-methylpyrrolidin-1-yl)ethanone | Gen-5-j A2-B2-C1-D1-E4b-E5b-E8 | 562 | 563 (M + H) |
| 29 | 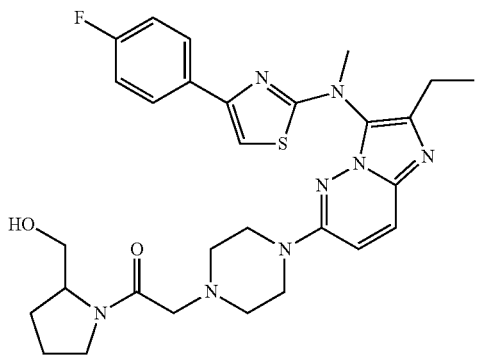 [SMILES: CCc1nc2ccc(N3CCN(CC(=O)N4CCCC4CO)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-(2-(hydroxymethyl)pyrrolidin-1-yl)ethanone | Gen-5-j A2-B2-C1-D1-E4b-E5b-E8 | 578 | 579 (M + H) |
| 30 | 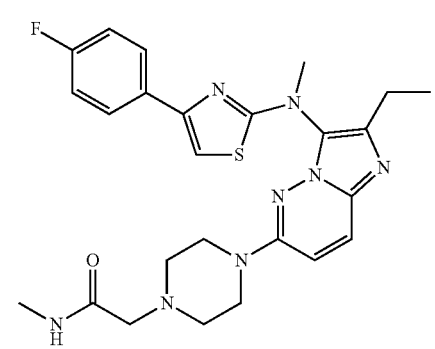 [SMILES: CCc1nc2ccc(N3CCN(CC(=O)NC)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-N-methylacetamide | Gen-5-j A2-B2-C1-D1-E4b-E5b-E8 | 508 | 509 (M + H) |
| 31 | 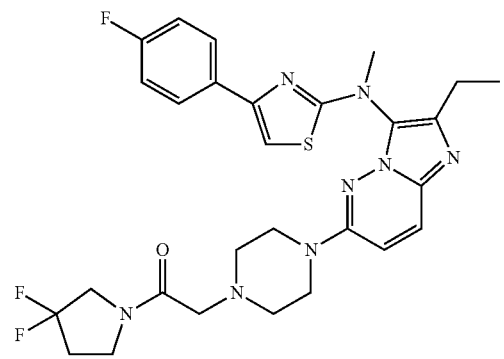 [SMILES: CCc1nc2ccc(N3CCN(CC(=O)N4CCC(F)(F)C4)CC3)nn2c1N(C)c1nc(-c2ccc(F)cc2)cs1] | 1-(3,3-difluoropyrrolidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone | Gen-5-j A2-B2-C1-D1-E4b-E5b-E8 | 584 | 585 (M + H) |

TABLE II-continued

Illustrative compounds of the invention.

| Cpd | Structures | Name | Mtd | MW | MS Ms'd |
|---|---|---|---|---|---|
| 32 | 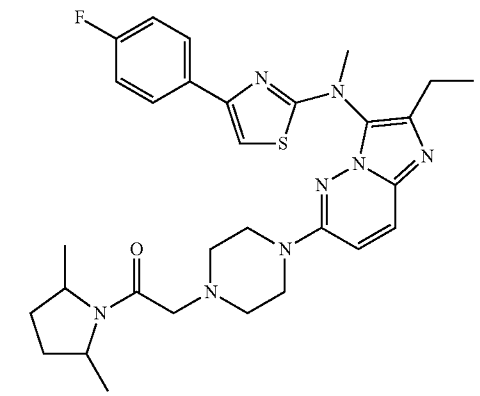 [SMILES: CCc1nc2ccc(N3CCN(CC(=O)N4C(C)CCC4C)CC3)nn2c1N(C)c1nc(-c2ccc(F)cc2)cs1] | 1-(2,5-dimethylpyrrolidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone | Gen-5-j A2-B2-C1-D1-E4b-E5b-E8 | 576 | 577 (M + H) |
| 33 | 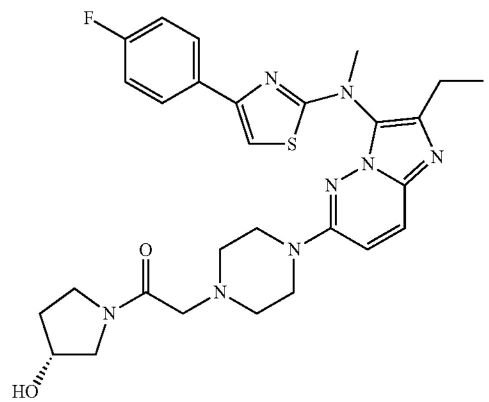 [SMILES: CCc1nc2ccc(N3CCN(CC(=O)N4CC[C@@H](O)C4)CC3)nn2c1N(C)c1nc(-c2ccc(F)cc2)cs1] | (R)-2-(4-(2-ethyl-3-((4-(4-fluorophenyl)thiazol-2-yl)(methyl)amino)imidazo[1,2-b]pyridazin-6-yl)piperazin-1-yl)-1-(3-hydroxypyrrolidin-1-yl)ethanone | Gen-5-j A2-B2-C1-D1-E4b-E5b-E8 | 564 | 565 (M + H) |
| 34 | 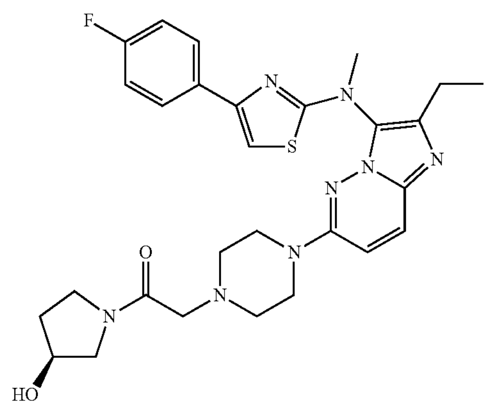 [SMILES: CCc1nc2ccc(N3CCN(CC(=O)N4CC[C@H](O)C4)CC3)nn2c1N(C)c1nc(-c2ccc(F)cc2)cs1] | (S)-2-(4-(2-ethyl-3-((4-(4-fluorophenyl)thiazol-2-yl)(methyl)amino)imidazo[1,2-b]pyridazin-6-yl)piperazin-1-yl)-1-(3-hydroxypyrrolidin-1-yl)ethanone | Gen-5-j A2-B2-C1-D1-E4b-E5b-E8 | 564 | 565 (M + H) |
| 35 | 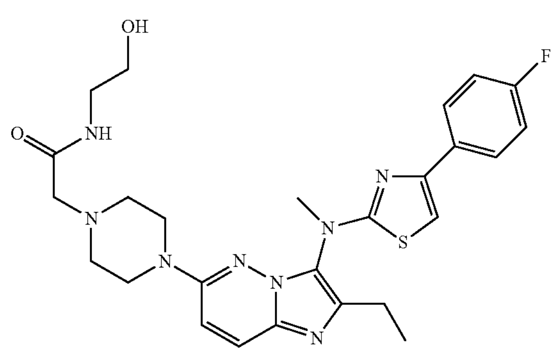 [SMILES: CCc1nc2ccc(N3CCN(CC(=O)NCCO)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-N-(2-hydroxyethyl)acetamide | Gen-5-j A2-B2-C1-D1-E4b-E5b-E8 | 538 | 539 (M + H) |

TABLE II-continued

Illustrative compounds of the invention.

| Cpd | Structures | Name | Mtd | MW | MS Ms'd |
|---|---|---|---|---|---|
| 36 | 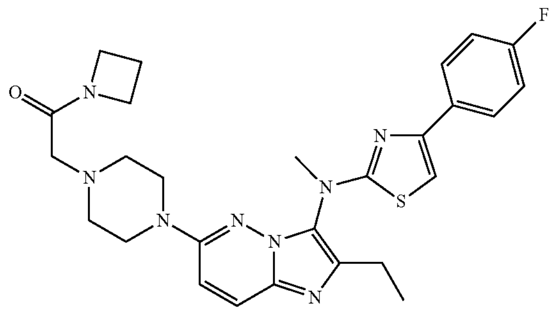 [SMILES: CCc1nc2ccc(N3CCN(CC(=O)N4CCC4)CC3)nn2c1N(C)c1nc(-c2ccc(F)cc2)cs1] | 1-(azetidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone | Gen-5-j A2-B2-C1-D1-E4b-E5b-E8 | 534 | 535 (M + H) |
| 37 | 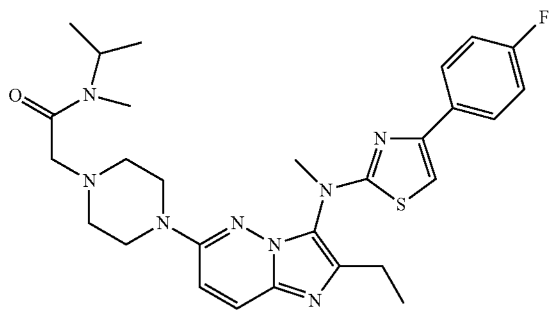 [SMILES: CCc1nc2ccc(N3CCN(CC(=O)N(C)C(C)C)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-N-isopropyl-N-methylacetamide | Gen-5-j A2-B2-C1-D1-E4b-E5b-E8 | 550 | 551 (M + H) |
| 38 | 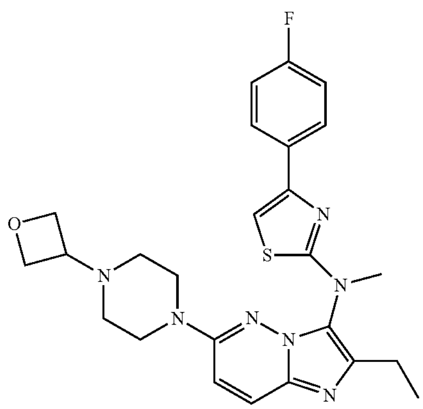 [SMILES: CCc1nc2ccc(N3CCN(C4COC4)CC3)nn2c1N(C)c1nc(-c2ccc(F)cc2)cs1] | N-(2-ethyl-6-(4-(oxetan-3-yl)piperazin-1-yl)imidazo[1,2-b]pyridazin-3-yl)-4-(4-fluorophenyl)-N-methylthiazol-2-amine | Gen-5-j A2-B2-C1-D1-E4a-E5b-E10 | 493 | 494 (M + H) |
| 39 | 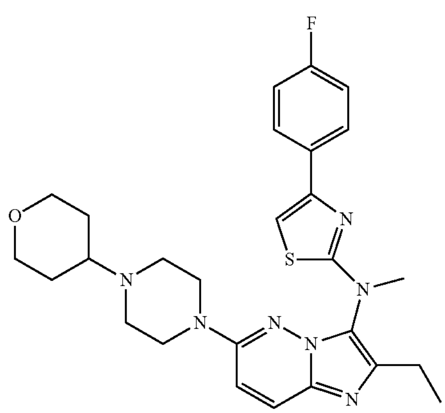 [SMILES: CCc1nc2ccc(N3CCN(C4CCOCC4)CC3)nn2c1N(C)c1nc(-c2ccc(F)cc2)cs1] | N-(2-ethyl-6-(4-(tetrahydro-2H-pyran-4-yl)piperazin-1-yl)imidazo[1,2-b]pyridazin-3-yl)-4-(4-fluorophenyl)-N-methylthiazol-2-amine | Gen-5-j A2-B2-C1-D1-E4a-E5b-E10 | 521 | 522 (M + H) |

TABLE II-continued

Illustrative compounds of the invention.

| Cpd | Structures | Name | Mtd | MW | MS Ms'd |
|---|---|---|---|---|---|
| 40 | 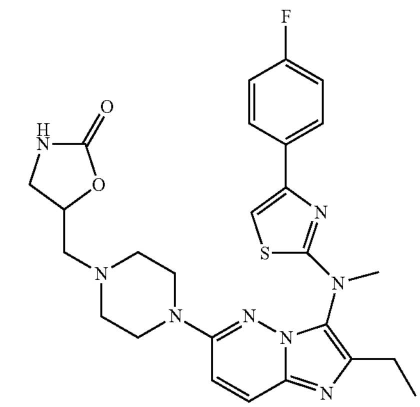 [SMILES: CCc1nc2ccc(N3CCN(CC4CNC(=O)O4)CC3)nn2c1N(C)c1nc(-c2ccc(F)cc2)cs1] | 5-((4-(2-ethyl-3-((4-(4-fluorophenyl)thiazol-2-yl)(methyl)amino)imidazo[1,2-b]pyridazin-6-yl)piperazin-1-yl)methyl)oxazolidin-2-one | Gen-5-j A2-B2-C1-D1-E4b-E5b-E8 | 536 | 537 (M + H) |
| 41 | 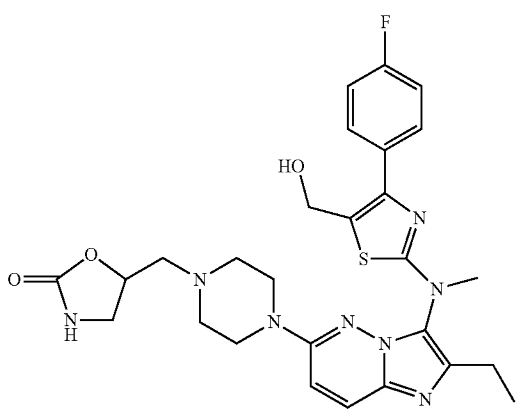 [SMILES: CCc1nc2ccc(N3CCN(CC4CNC(=O)O4)CC3)nn2c1N(C)c1nc(-c2ccc(F)cc2)c(CO)s1] | 5-((4-(2-ethyl-3-((4-(4-fluorophenyl)-5-(hydroxymethyl)thiazol-2-yl)(methyl)amino)imidazo[1,2-b]pyridazin-6-yl)piperazin-1-yl)methyl)oxazolidin-2-one | Cpd 40 A2-B2-C1-D1-E4b-E5b-E8-E14 | 566 | 567 (M + H) |
| 42 | 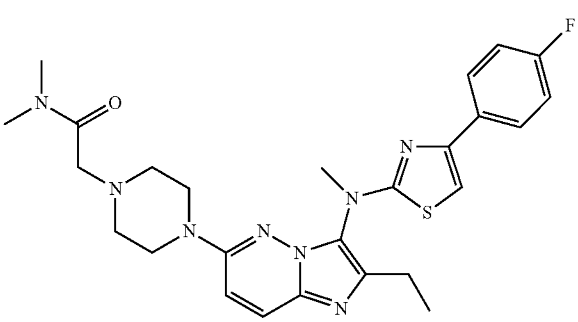 [SMILES: CCc1nc2ccc(N3CCN(CC(=O)N(C)C)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-N,N-dimethylacetamide | Gen-5-j A2-B2-C1-D1-E4b-E5b-E8 | 522 | 523 (M + H) |
| 43 | 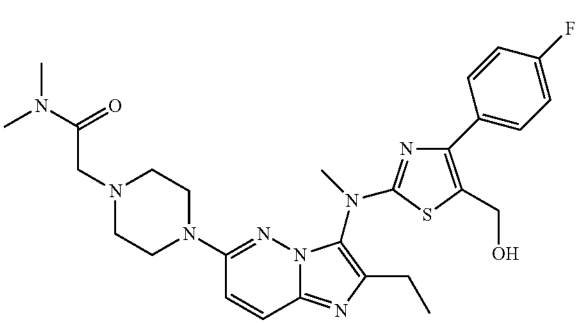 [SMILES: CCc1nc2ccc(N3CCN(CC(=O)N(C)C)CC3)nn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-b]pyridazin-6-yl)piperazin-1-yl)-N,N-dimethylacetamide | Cpd 42 A2-B2-C1-D1-E4b-E14 | 552 | 553 (M + H) |

TABLE II-continued

Illustrative compounds of the invention.

| Cpd | Structures | Name | Mtd | MW | MS Ms'd |
|---|---|---|---|---|---|
| 44 | 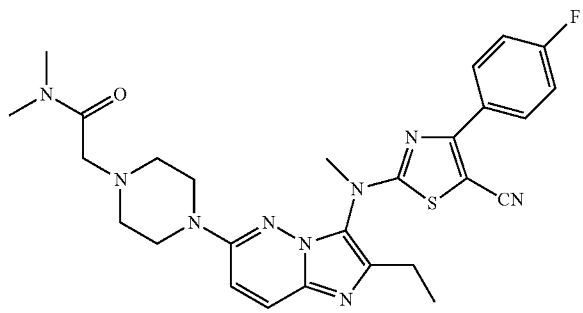 [SMILES: CCc1nc2ccc(N3CCN(CC(=O)N(C)C)CC3)nn2c1N(C)c1nc(-c2ccc(F)cc2)c(C#N)s1] | 2-(4-(3-((5-cyano-4-(4-fluorophenyl)thiazol-2-yl)(methyl)amino)-2-ethylimidazo[1,2-b]pyridazin-6-yl)piperazin-1-yl)-N,N-dimethylacetamide | Gen-5-m A2-B2-C1-D1-E4b-E5b-E8-E16-E17 | 547 | 548 (M + H) |
| 45 | 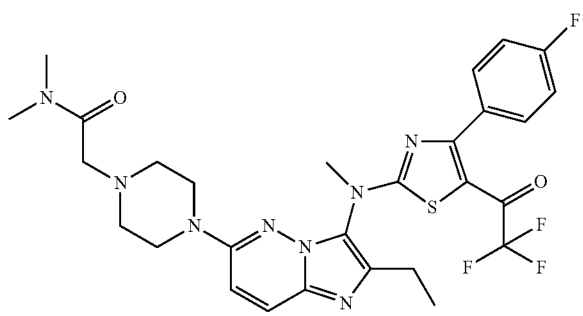 [SMILES: CCc1nc2ccc(N3CCN(CC(=O)N(C)C)CC3)nn2c1N(C)c1nc(-c2ccc(F)cc2)c(C(=O)C(F)(F)F)s1] | 2-(4-(2-ethyl-3-((4-(4-fluorophenyl)-5-(2,2,2-trifluoroacetoyl)thiazol-2-yl)(methyl)amino)imidazo[1,2-b]pyridazin-6-yl)piperazin-1-yl)-N,N-dimethylacetamide | Gen-5-ag A2-B2-C1-D1-E4b-E15-E5b-E8 | 618 | 619 (M + H) |
| 46 | 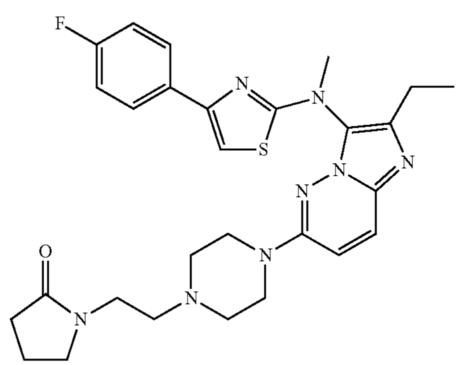 [SMILES: CCc1nc2ccc(N3CCN(CCN4CCCC4=O)CC3)nn2c1N(C)c1nc(-c2ccc(F)cc2)cs1] | 1-(2-(4-(2-ethyl-3-((4-(4-fluorophenyl)thiazol-2-yl)(methyl)amino)imidazo[1,2-b]pyridazin-6-yl)piperazin-1-yl)ethyl)pyrrolidin-2-one | Gen-4-a A2-B2-C1-D1-E4a | 548 | 549 (M + H) |
| 47 | 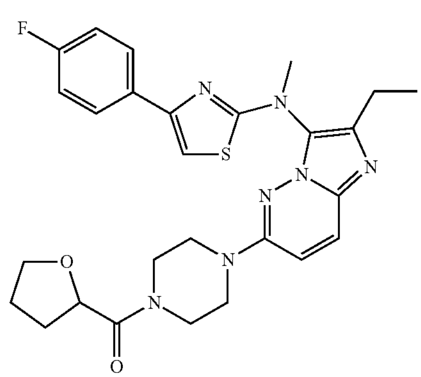 [SMILES: CCc1nc2ccc(N3CCN(C(=O)C4CCCO4)CC3)nn2c1N(C)c1nc(-c2ccc(F)cc2)cs1] | (4-(2-ethyl-3-((4-(4-fluorophenyl)thiazol-2-yl)(methyl)amino)imidazo[1,2-b]pyridazin-6-yl)piperazin-1-yl)(tetrahydrofuran-2-yl)methanone | Gen-4-a A2-B2-C1-D1-E4a | 435 | 436 (M + H) |

TABLE II-continued

Illustrative compounds of the invention.

| Cpd | Structures | Name | Mtd | MW | MS Ms'd |
|---|---|---|---|---|---|
| 48 | 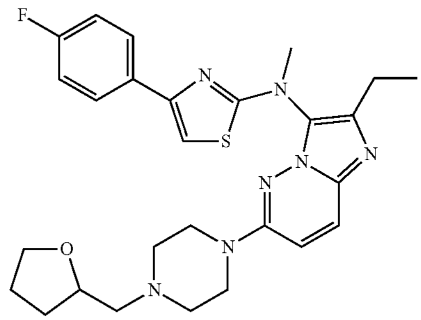 [SMILES: CCc1nc2ccc(N3CCN(CC4CCCO4)CC3)nn2c1N(C)c1nc(-c2ccc(F)cc2)cs1] | N-(2-ethyl-6-(4-((tetrahydrofuran-2-yl)methyl)piperazin-1-yl)imidazo[1,2-b]pyridazin-3-yl)-4-(4-fluorophenyl)-N-methylthiazol-2-amine | Gen-4-a A2-B2-C1-D1-E4a | 521 | 522 (M + H) |
| 49 | 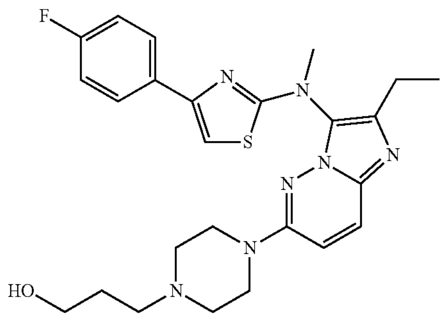 [SMILES: CCc1nc2ccc(N3CCN(CCCO)CC3)nn2c1N(C)c1nc(-c2ccc(F)cc2)cs1] | 3-(4-(2-ethyl-3-((4-(4-fluorophenyl)thiazol-2-yl)(methyl)amino)imidazo[1,2-b]pyridazin-6-yl)piperazin-1-yl)propan-1-ol | Gen-4-a A2-B2-C1-D1-E4a | 495 | 496 (M + H) |
| 50 | 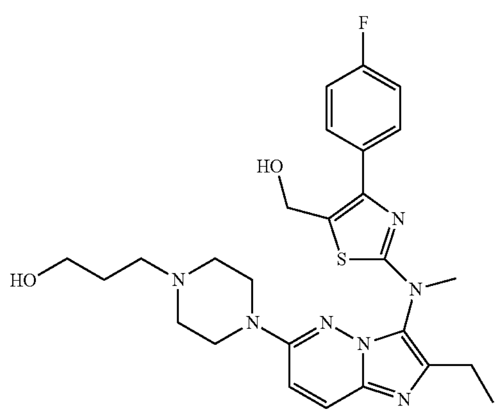 [SMILES: CCc1nc2ccc(N3CCN(CCCO)CC3)nn2c1N(C)c1nc(-c2ccc(F)cc2)c(CO)s1] | 3-(4-(2-ethyl-3-((4-(4-fluorophenyl)-5-(hydroxymethyl)thiazol-2-yl)(methyl)amino)imidazo[1,2-b]pyridazin-6-yl)piperazin-1-yl)propan-1-ol | Cdp 49 A2-B2-C1-D1-E4a-E14 | 525 | 526 (M + H) |
| 51 | 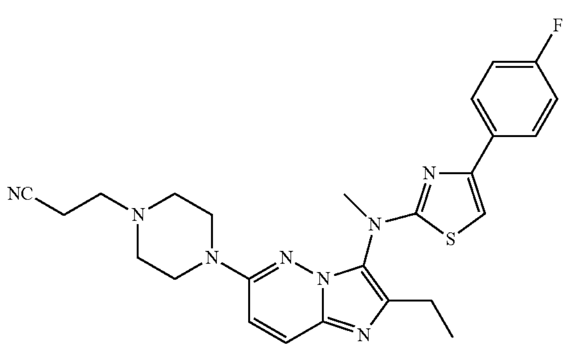 [SMILES: CCc1nc2ccc(N3CCN(CCC#N)CC3)nn2c1N(C)c1nc(-c2ccc(F)cc2)cs1] | 3-(4-(2-ethyl-3-((4-(4-fluorophenyl)thiazol-2-yl)(methyl)amino)imidazo[1,2-b]pyridazin-6-yl)piperazin-1-yl)propanenitrile | Gen-4-a A2-B2-C1-D1-E4a | 490 | 491 (M + H) |

TABLE II-continued

Illustrative compounds of the invention.

| Cpd | Structures | Name | Mtd | MW | MS Ms'd |
|---|---|---|---|---|---|
| 52 | 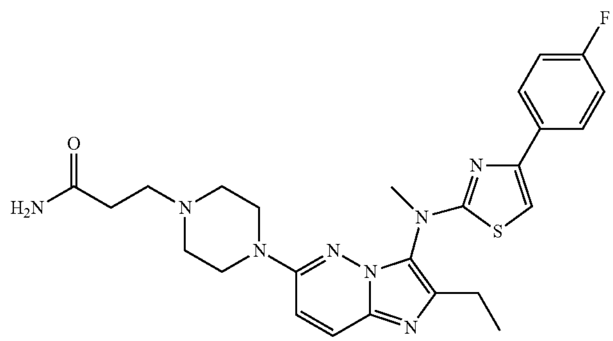 [SMILES: CCc1nc2ccc(N3CCN(CCC(N)=O)CC3)nn2c1N(C)c1nc(-c2ccc(F)cc2)cs1] | 3-(4-(2-ethyl-3-((4-(4-fluorophenyl)thiazol-2-yl)(methyl)amino)imidazo[1,2-b]pyridazin-6-yl)piperazin-1-yl)propanamide | Cpd 51 A2-B2-C1-D1-E4a-see Cpd 52 | 508 | 509 (M + H) |
| 53 | 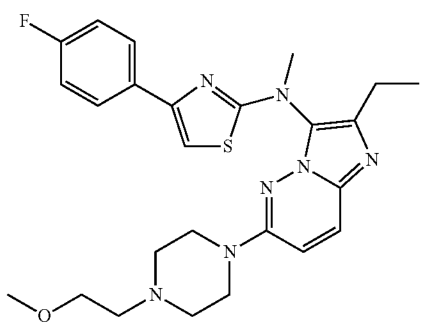 [SMILES: CCc1nc2ccc(N3CCN(CCOC)CC3)nn2c1N(C)c1nc(-c2ccc(F)cc2)cs1] | N-(2-ethyl-6-(4-(2-methoxyethyl)piperazin-1-yl)imidazo[1,2-b]pyridazin-3-yl)-4-(4-fluorophenyl)-N-methylthiazol-2-amine | Gen-4-a A2-B2-C1-D1-E4a | 495 | 496 (M + H) |
| 54 | 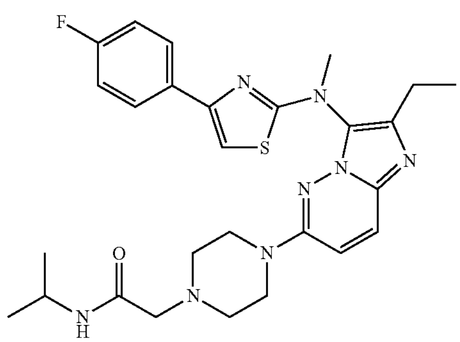 [SMILES: CCc1nc2ccc(N3CCN(CC(=O)NC(C)C)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-N-isopropylacetamide | Gen-4-a A2-B2-C1-D1-E4a | 536 | 537 (M + H) |
| 55 | 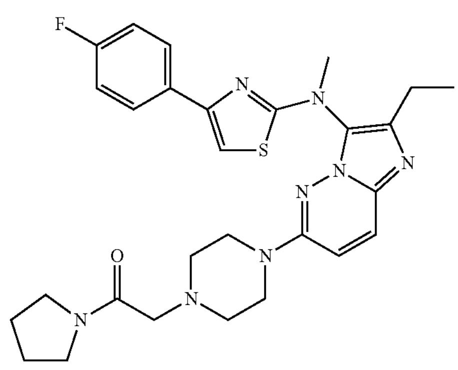 [SMILES: CCc1nc2ccc(N3CCN(CC(=O)N4CCCC4)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperazin-1-yl)-1-(pyrrolidin-1-yl)ethanone | Gen-4-a A2-B2-C1-D1-E4a | 548 | 549 (M + H) |

TABLE II-continued

Illustrative compounds of the invention.

| Cpd | Structures | Name | Mtd | MW | MS Ms'd |
|---|---|---|---|---|---|
| 56 | 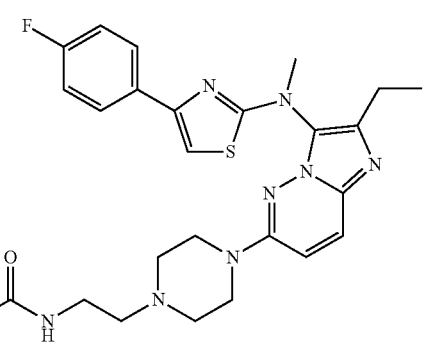 | tert-butyl 2-(4-(2-ethyl-3-((4-(4-fluorophenyl)thiazol-2-yl)(methyl)amino)imidazo[1,2-b]pyridazin-6-yl)piperazin-1-yl)ethylcarbamate | Gen-4-a A2-B2-C1-D1-E4a | 580 | 581 (M + H) |
| 57 | 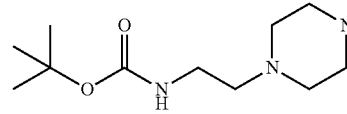 | N-(2-(4-(2-ethyl-3-((4-(4-fluorophenyl)thiazol-2-yl)(methyl)amino)imidazo[1,2-b]pyridazin-6-yl)piperazin-1-yl)ethyl)acetamide | Gen-5-f A2-B2-C1-D1-E4a-E5b-E9b | 522 | 523 (M + H) |
| 58 | 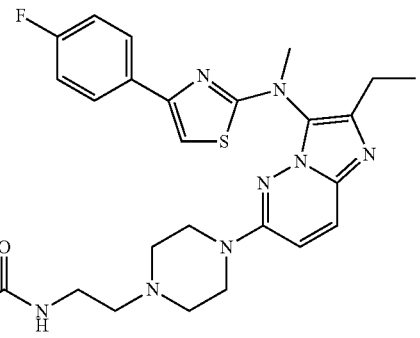 | ethyl 2-(4-(2-ethyl-3-((4-(4-fluorophenyl)thiazol-2-yl)(methyl)amino)imidazo[1,2-b]pyridazin-6-yl)piperazin-1-yl)ethylcarbamate | Gen-5-f A2-B2-C1-D1-E4a-E5b-E9b | 552 | 553 (M + H) |
| 59 | 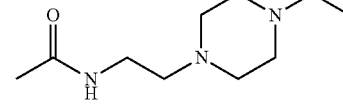 | (S)-tert-butyl 4-(2-ethyl-3-((4-(4-fluorophenyl)thiazol-2-yl)(methyl)amino)imidazo[1,2-b]pyridazin-6-yl)-2-(hydroxymethyl)piperazine-1-carboxylate | Gen-4-a A2-B2-C1-D1-E4a | 567 | 568 (M + H) |

TABLE II-continued

Illustrative compounds of the invention.

| Cpd | Structures | Name | Mtd | MW | MS Ms'd |
|---|---|---|---|---|---|
| 60 | 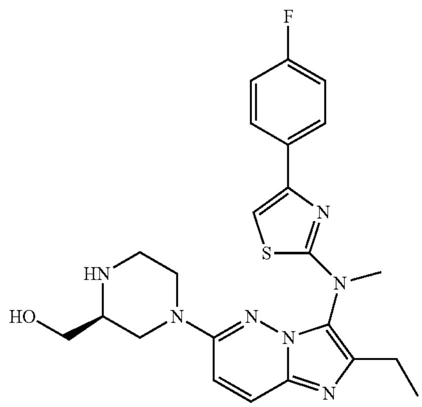 [SMILES: CCc1nc2ccc(N3CCN[C@H](CO)C3)nn2c1N(C)c1nc(-c2ccc(F)cc2)cs1] | (S)-(4-(2-ethyl-3-((4-(4-fluorophenyl)thiazol-2-yl)(methyl)amino)imidazo[1,2-b]pyridazin-6-yl)piperazin-2-yl)methanol | Cpd 59 A2-B2-C1-D1-E4a-E5a | 467 | 568 (M + H) |
| 61 | 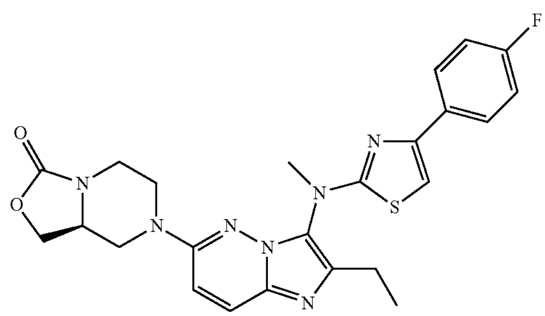 [SMILES: CCc1nc2ccc(N3CCN4C(=O)OC[C@@H]4C3)nn2c1N(C)c1nc(-c2ccc(F)cc2)cs1] | (S)-7-(2-ethyl-3-((4-(4-fluorophenyl)thiazol-2-yl)(methyl)amino)imidazo[1,2-b]pyridazin-6-yl)tetrahydro-1H-oxazolo[3,4-a]pyrazin-3(5H)-one | Cpd 60 A2-B2-C1-D1-E4a-E5a-see Cpd 61 | 493 | 494 (M + H) |
| 62 | 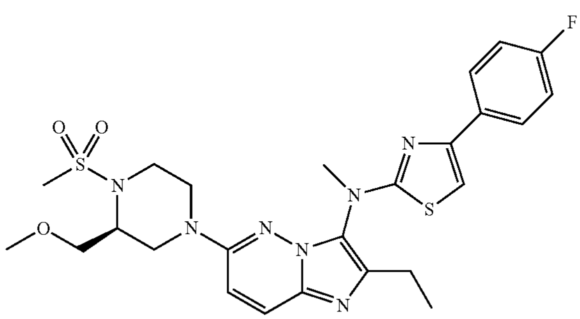 [SMILES: CCc1nc2ccc(N3CCN(S(C)(=O)=O)[C@H](COC)C3)nn2c1N(C)c1nc(-c2ccc(F)cc2)cs1] | (S)-N-(2-ethyl-6-(3-(methoxymethyl)-4-(methylsulfonyl)piperazin-1-yl)imidazo[1,2-b]pyridazin-3-yl)-4-(4-fluorophenyl)-N-methylthiazol-2-amine | Gen-5-ad A2-B2-C1-D1-E4b-see Cpd 62-E5b-E11 | 559 | 560 (M + H) |
| 63 | 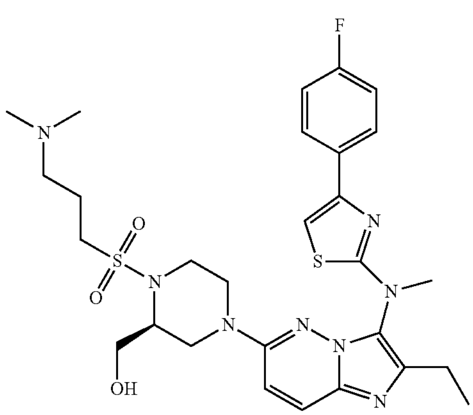 [SMILES: CCc1nc2ccc(N3CCN(S(=O)(=O)CCCN(C)C)[C@H](CO)C3)nn2c1N(C)c1nc(-c2ccc(F)cc2)cs1] | (S)-(1-(3-(dimethylamino)propylsulfonyl)-4-(2-ethyl-3-((4-(4-fluorophenyl)thiazol-2-yl)(methyl)amino)imidazo[1,2-b]pyridazin-6-yl)piperazin-2-yl)methanol | Gen-5-ae A2-B2-C1-D1-E4b-E2-E5b-E18-E11-E12-E19 | 616 | 617 (M + H) |

TABLE II-continued

Illustrative compounds of the invention.

| Cpd | Structures | Name | Mtd | MW | MS Ms'd |
|---|---|---|---|---|---|
| 64 | 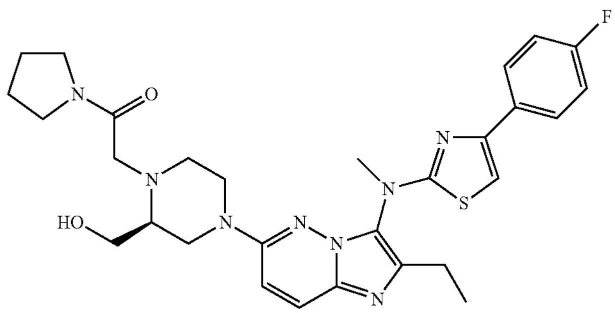 [SMILES: CCc1nc2ccc(N3CCN(CC(=O)N4CCCC4)[C@H](CO)C3)nn2c1N(C)c1nc(-c2ccc(F)cc2)cs1] | (S)-2-(4-(2-ethyl-3-((4-(4-fluorophenyl)thiazol-2-yl)(methyl)amino)imidazo[1,2-b]pyridazin-6-yl)-2-(hydroxymethyl)piperazin-1-yl)-1-(pyrrolidin-1-yl)ethanone | Gen-5-ac A2-B2-C1-D1-E4b-E5b-E18-E8-E19 | 578 | 579 (M + H) |
| 65 | 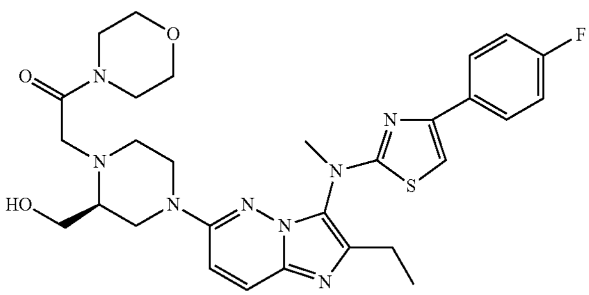 [SMILES: CCc1nc2ccc(N3CCN(CC(=O)N4CCOCC4)[C@H](CO)C3)nn2c1N(C)c1nc(-c2ccc(F)cc2)cs1] | (S)-2-(4-(2-ethyl-3-((4-(4-fluorophenyl)thiazol-2-yl)(methyl)amino)imidazo[1,2-b]pyridazin-6-yl)-2-(hydroxymethyl)piperazin-1-yl)-1-morpholinoethanone | Gen-5-ae A2-B2-C1-D1-E4b-E5b-E18-E8-E19 | 594 | 595 (M + H) |
| 66 | 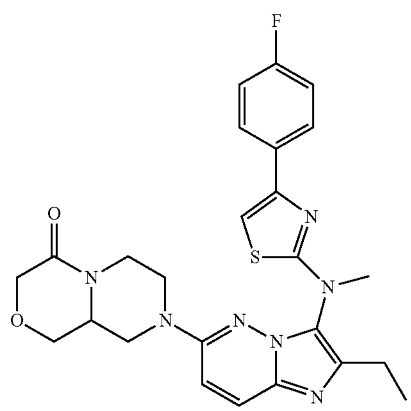 [SMILES: CCc1nc2ccc(N3CCN4C(=O)COCC4C3)nn2c1N(C)c1nc(-c2ccc(F)cc2)cs1] | (S)-8-(2-ethyl-3-((4-(4-fluorophenyl)thiazol-2-yl)(methyl)amino)imidazo[1,2-b]pyridazin-6-yl)hexahydropyrazino[2,1-c][1,4]oxazin-4(1H)-one | Gen-5-ae A2-B2-C1-D1-E4b-E5b-E18-E9b-E19-See Cpd 66 | 507 | 508 (M + H) |
| 67 | 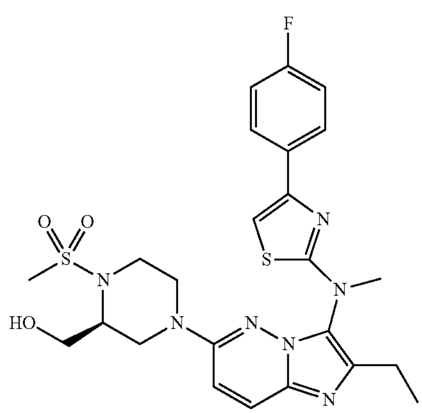 [SMILES: CCc1nc2ccc(N3CCN(S(C)(=O)=O)[C@H](CO)C3)nn2c1N(C)c1nc(-c2ccc(F)cc2)cs1] | (S)-(4-(2-ethyl-3-((4-(4-fluorophenyl)thiazol-2-yl)(methyl)amino)imidazo[1,2-b]pyridazin-6-yl)-1-(methylsulfonyl)piperazin-2-yl)methanol | Gen-5-aj A2-B2-C1-D1-E4a-E5a-E18-E11-E19 | 545 | 546 (M + H) |

TABLE II-continued

Illustrative compounds of the invention.

| Cpd | Structures | Name | Mtd | MW | MS Ms'd |
|---|---|---|---|---|---|
| 68 | 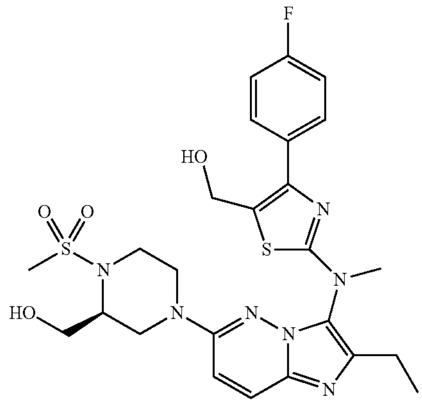 [SMILES: CCc1nc2ccc(N3CCN(S(C)(=O)=O)[C@H](CO)C3)nn2c1N(C)c1nc(-c2ccc(F)cc2)c(CO)s1] | (S)-(4-(2-ethyl-3-((4-(4-fluorophenyl)-5-(hydroxymethyl)thiazol-2-yl)(methyl)amino)imidazo[1,2-b]pyridazin-6-yl)-1-(methylsulfonyl)piperazin-2-yl)methanol | Cdp 67 A2-B2-C1-D1-E4a-E5a-E18-E11-E19-E14 | 575 | 576 (M + H) |
| 69 | 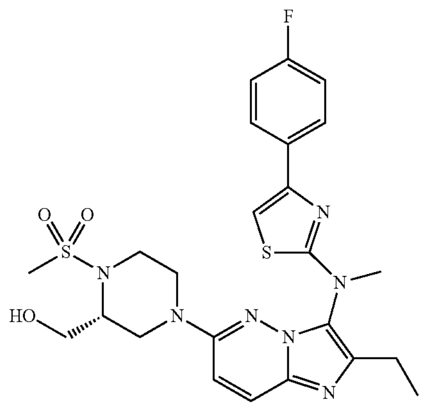 [SMILES: CCc1nc2ccc(N3CCN(S(C)(=O)=O)[C@@H](CO)C3)nn2c1N(C)c1nc(-c2ccc(F)cc2)cs1] | (R)-(4-(2-ethyl-3-((4-(4-fluorophenyl)thiazol-2-yl)(methyl)amino)imidazo[1,2-b]pyridazin-6-yl)-1-(methylsulfonyl)piperazin-2-yl)methanol | Gen-5-y A2-B2-C1-D1-E4b-E5a-E18-E11-E19 | 545 | 546 (M + H) |
| 70 | 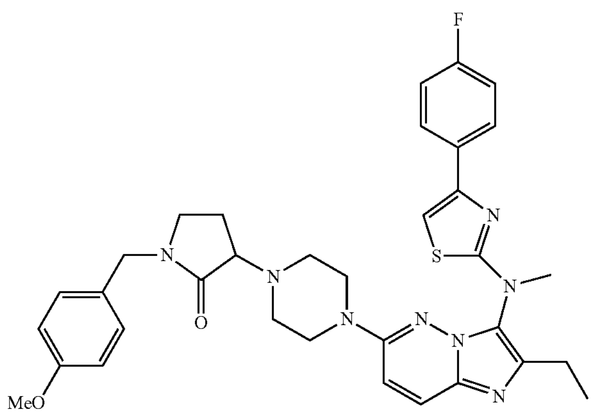 [SMILES: CCc1nc2ccc(N3CCN(C4CCN(Cc5ccc(OC)cc5)C4=O)CC3)nn2c1N(C)c1nc(-c2ccc(F)cc2)cs1] | 3-(4-(2-ethyl-3-((4-(4-fluorophenyl)thiazol-2-yl)(methyl)amino)imidazo[1,2-b]pyridazin-6-yl)piperazin-1-yl)-1-(4-methoxybenzyl)pyrrolidin-2-one | Gen-4-a A2-B2-C1-D1-E4b | 640 | 641 (M + H) |
| 71 | 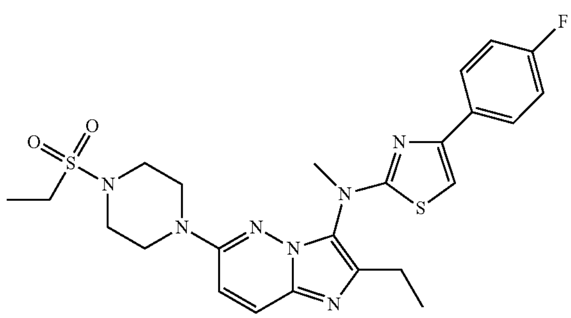 [SMILES: CCc1nc2ccc(N3CCN(S(=O)(=O)CC)CC3)nn2c1N(C)c1nc(-c2ccc(F)cc2)cs1] | N-(2-ethyl-6-(4-(ethylsulfonyl)piperazin-1-yl)imidazo[1,2-b]pyridazin-3-yl)-4-(4-fluorophenyl)-N-methylthiazol-2-amine | Gen-4-a A2-B2-C1-D1-E4b | 529 | 530 (M + H) |

TABLE II-continued

Illustrative compounds of the invention.

| Cpd | Structures | Name | Mtd | MW | MS Ms'd |
|---|---|---|---|---|---|
| 72 | 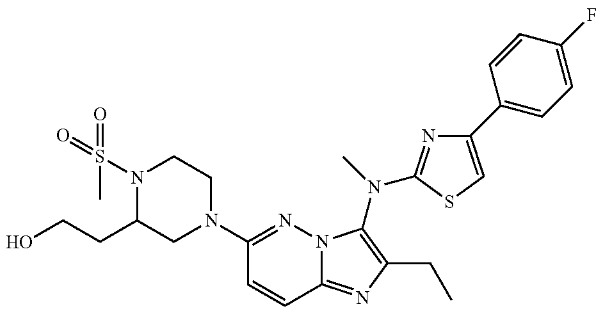 [SMILES: CCc1nc2ccc(N3CCN(S(C)(=O)=O)C(CCO)C3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)-1-(methylsulfonyl)piperazin-2-yl)ethanol | Gen-4-a A2-B2-C1-D1-E4b | 559 | 560 (M + H) |
| 73 | 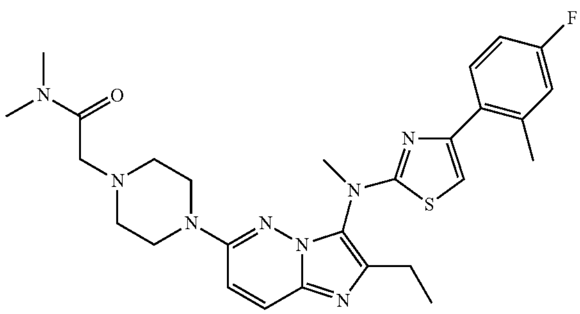 [SMILES: CCc1nc2ccc(N3CCN(CC(=O)N(C)C)CC3)nn2c1N(C)c1nc(-c2ccc(F)cc2C)cs1] | 2-(4-(2-ethyl-3-((4-(4-fluoro-2-methylphenyl)thiazol-2-yl)(methyl)amino)imidazo[1,2-b]pyridazin-6-yl)piperazin-1-yl)-N,N-dimethylacetamide | Gen-4-m A2-B2-C1-D1-E4b | 536 | 537 (M + H) |
| 74 | 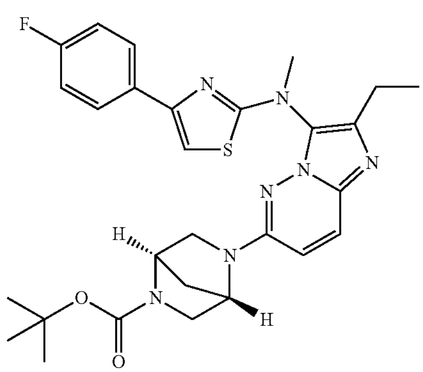 [SMILES: CCc1nc2ccc(N3C[C@H]4C[C@H]3CN4C(=O)OC(C)(C)C)nn2c1N(C)c1nc(-c2ccc(F)cc2)cs1] | tert-butyl-(1R,4S)-5-(2-ethyl-3-((4-(4-fluorophenyl)thiazol-2-yl)(methyl)amino)imidazo[1,2-b]pyridazin-6-yl)-2,5-diazabicyclo[2.2.1]heptane-2-carboxylate | Gen-4-a A2-B2-C1-D1-E4a | 549 | 550 (M + H) |
| 75 | 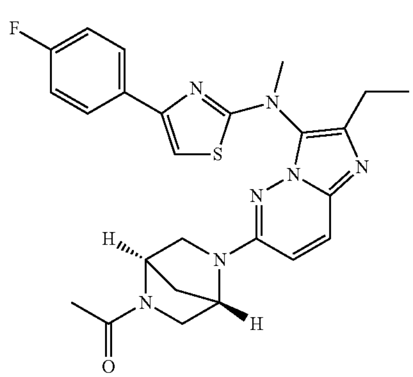 [SMILES: CCc1nc2ccc(N3C[C@H]4C[C@H]3CN4C(C)=O)nn2c1N(C)c1nc(-c2ccc(F)cc2)cs1] | 1-((1R,4S)-5-(2-ethyl-3-((4-(4-fluorophenyl)thiazol-2-yl)(methyl)amino)imidazo[1,2-b]pyridazin-6-yl)-2,5-diazabicyclo[2.2.1]heptan-2-yl)ethanone | Gen-5-e A2-B2-C1-D1-E4a-E5b-E9b | 491 | 492 (M + H) |

TABLE II-continued

Illustrative compounds of the invention.

| Cpd | Structures | Name | Mtd | MW | MS Ms'd |
|---|---|---|---|---|---|
| 76 | 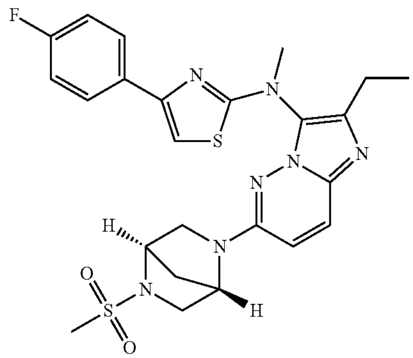 [SMILES: CCc1nc2ccc(N3C[C@H]4C[C@H]3CN4S(C)(=O)=O)nn2c1N(C)c1nc(-c2ccc(F)cc2)cs1] | N-(2-ethyl-6-((1S,4R)-5-(methylsulfonyl)-2,5-diazabicyclo[2.2.1]heptan-2-yl)imidazo[1,2-b]pyridazin-3-yl)-4-(4-fluorophenyl)-N-methylthiazol-2-amine | Gen-5-e A2-B2-C1-D1-E4a-E5b-E11 | 527 | 528 (M + H) |
| 77 | 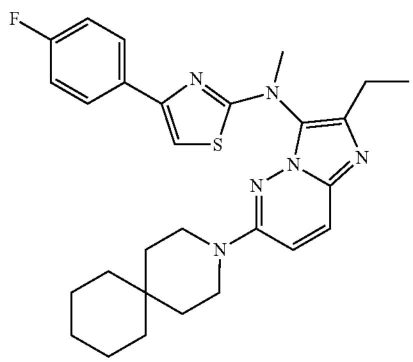 [SMILES: CCc1nc2ccc(N3CCC4(CCCCC4)CC3)nn2c1N(C)c1nc(-c2ccc(F)cc2)cs1] | N-(2-ethyl-6-(3-azaspiro[5.5]undecan-3-yl)imidazo[1,2-b]pyridazin-3-yl)-4-(4-fluorophenyl)-N-methylthiazol-2-amine | Gen-4-a A2-B2-C1-D1-E4a | 504 | 505 (M + H) |
| 78 | 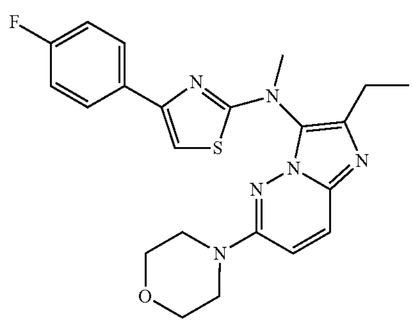 [SMILES: CCc1nc2ccc(N3CCOCC3)nn2c1N(C)c1nc(-c2ccc(F)cc2)cs1] | N-(2-ethyl-6-morpholinoimidazo[1,2-b]pyridazin-3-yl)-4-(4-fluorophenyl)-N-methylthiazol-2-amine | Gen-4-a A2-B2-C1-D1-E4a | 438 | 439 (M + H) |
| 79 | 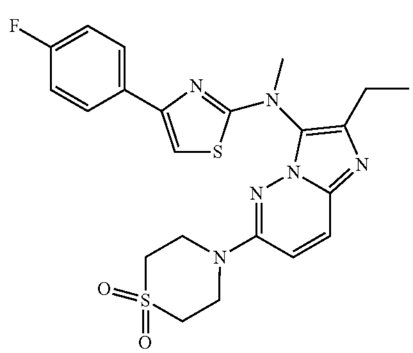 [SMILES: CCc1nc2ccc(N3CCS(=O)(=O)CC3)nn2c1N(C)c1nc(-c2ccc(F)cc2)cs1] | 6-(1,1-Dioxo-thiomorpholin-4-yl)-2-ethyl-imidazo[1,2-b]pyridazin-3-yl]-[4-(4-fluoro-phenyl)-thiazol-2-yl]-methyl-amine | Gen-4-a A2-B2-C1-D1-E1b | 486 | 487 (M + H) |

TABLE II-continued

Illustrative compounds of the invention.

| Cpd | Structures | Name | Mtd | MW | MS Ms'd |
|---|---|---|---|---|---|
| 80 | 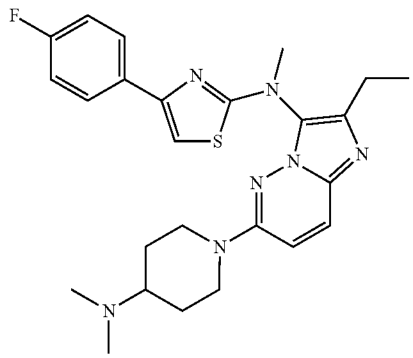 [SMILES: CCc1nc2ccc(N3CCC(N(C)C)CC3)nn2c1N(C)c1nc(-c2ccc(F)cc2)cs1] | N-(6-(4-(dimethylamino)piperidin-1-yl)-2-ethylimidazo[1,2-b]pyridazin-3-yl)-4-(4-fluorophenyl)-N-methylthiazol-2-amine | Gen-4-a A2-B2-C1-D1-E4a | 479 | 480 (M + H) |
| 81 | 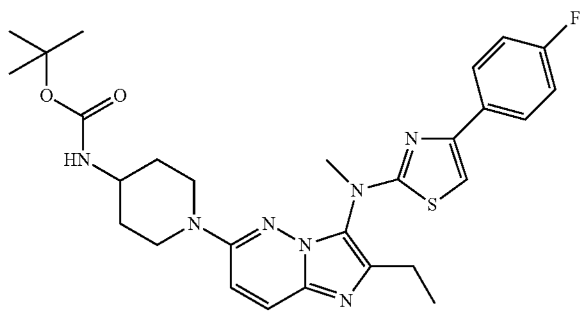 [SMILES: CCc1nc2ccc(N3CCC(NC(=O)OC(C)(C)C)CC3)nn2c1N(C)c1nc(-c2ccc(F)cc2)cs1] | tert-butyl 1-(2-ethyl-3-((4-(4-fluorophenyl)thiazol-2-yl)(methyl)amino)imidazo[1,2-b]pyridazin-6-yl)piperidin-4-ylcarbamate | Gen-4-a A2-B2-C1-D1-E4a | 551 | 552 (M + H) |
| 82 | 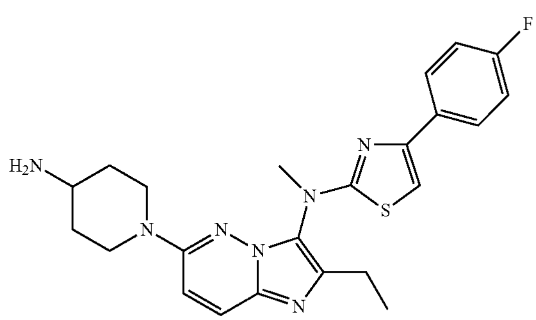 [SMILES: CCc1nc2ccc(N3CCC(N)CC3)nn2c1N(C)c1nc(-c2ccc(F)cc2)cs1] | N-(6-(4-aminopiperidin-1-yl)-2-ethylimidazo[1,2-b]pyridazin-3-yl)-4-(4-fluorophenyl)-N-methylthiazol-2-amine | Cpd 81 A2-B2-C1-D1-E4a-E5b | 451 | 452 (M + H) |
| 83 | 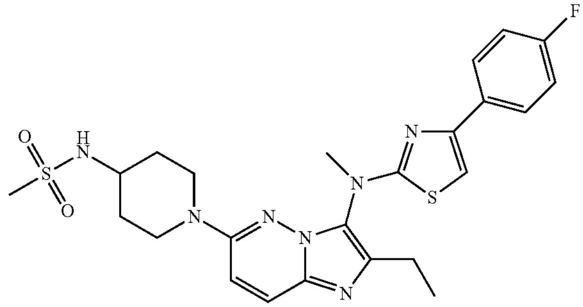 [SMILES: CCc1nc2ccc(N3CCC(NS(C)(=O)=O)CC3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)piperidin-4-yl)methanesulfonamide | Cpd 82 A2-B2-C1-D1-E4a-E5b-E11 | 529 | 452 (M + H) |

TABLE II-continued

Illustrative compounds of the invention.

| Cpd | Structures | Name | Mtd | MW | MS Ms'd |
|---|---|---|---|---|---|
| 84 | 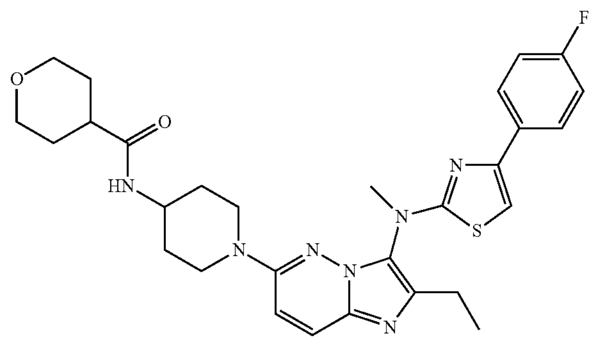 [SMILES: CCc1nc2ccc(N3CCC(NC(=O)C4CCOCC4)CC3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)piperidin-4-yl)tetrahydro-2H-pyran-4-carboxamide | Cpd 82 A2-B2-C1-D1-E4b-E5b-E9b | 563 | 452 (M + H) |
| 85 | 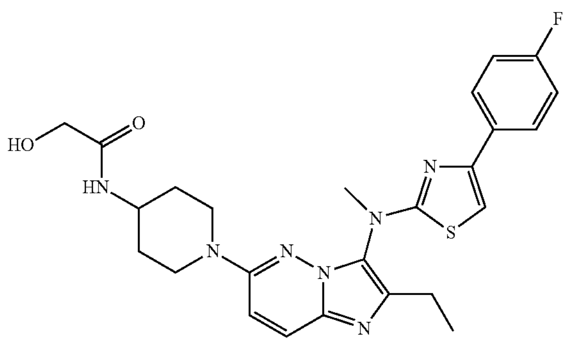 [SMILES: CCc1nc2ccc(N3CCC(NC(=O)CO)CC3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)piperidin-4-yl)-2-hydroxyacetamide | Cpd 82 A2-B2-C1-D1-E4b-E5b-E9c | 509 | 510 (M + H) |
| 86 | 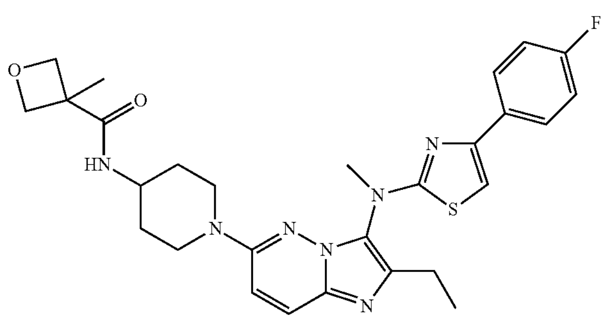 [SMILES: CCc1nc2ccc(N3CCC(NC(=O)C4(C)COC4)CC3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)piperidin-4-yl)-3-methyloxetane-3-carboxamide | Cpd 82 A2-B2-C1-D1-E4b-E5b-E9c | 549 | 550 (M + H) |
| 87 | 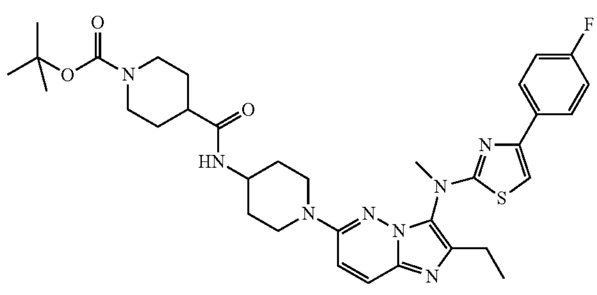 [SMILES: CCc1nc2ccc(N3CCC(NC(=O)C4CCN(C(=O)OC(C)(C)C)CC4)CC3)nn2c1N(C)c1nc(-c2ccc(F)cc2)cs1] | tert-butyl 4-(1-(2-ethyl-3-((4-(4-fluorophenyl)thiazol-2-yl)(methyl)amino)imidazo[1,2-b]pyridazin-6-yl)piperidin-4-ylcarbamoyl)piperidine-1-carboxylate | Cpd 82 A2-B2-C1-D1-E4b-E5b-E9c | 662 | 663 (M + H) |

TABLE II-continued

Illustrative compounds of the invention.

| Cpd | Structures | Name | Mtd | MW | MS Ms'd |
|---|---|---|---|---|---|
| 88 | 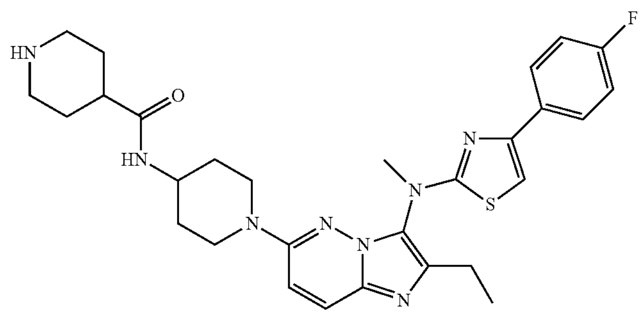 [SMILES: CCc1nc2ccc(N3CCC(NC(=O)C4CCNCC4)CC3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)piperidin-4-yl)piperidine-4-carboxamide | Cpd 87 A2-B2-C1-D1-E4b-E5b-E9c-E5b | 562 | 463 (M + H) |
| 89 | 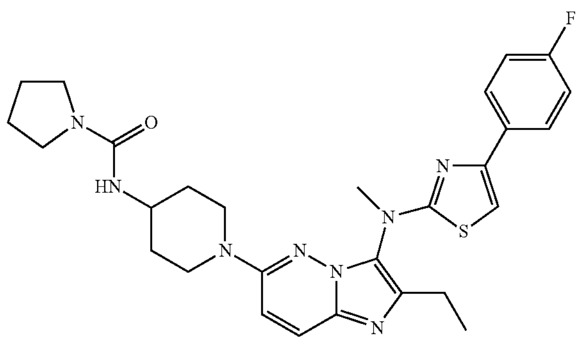 [SMILES: CCc1nc2ccc(N3CCC(NC(=O)N4CCCC4)CC3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)piperidin-4-yl)pyrrolidine-1-carboxamide | Gen-5-1 A2-B2-C1-D1-E4b-see Cpd 89 | 548 | 549 (M + H) |
| 90 | 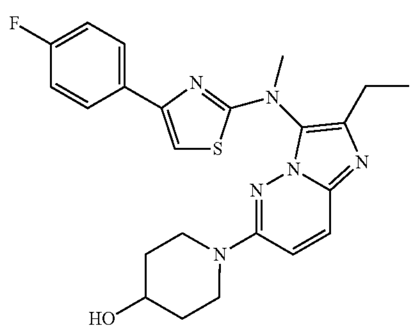 [SMILES: CCc1nc2ccc(N3CCC(O)CC3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)piperidin-4-ol | Gen-4-a A2-B2-C1-D1-E4a | 452 | 453 (M + H) |
| 91 | 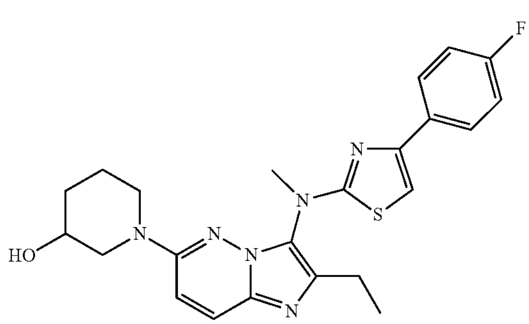 [SMILES: CCc1nc2ccc(N3CCCC(O)C3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)piperidin-3-ol | Gen-4-a A2-B2-C1-D1-E4a | 452 | 453 (M + H) |

TABLE II-continued

Illustrative compounds of the invention.

| Cpd | Structures | Name | Mtd | MW | MS Ms'd |
|---|---|---|---|---|---|
| 92 | 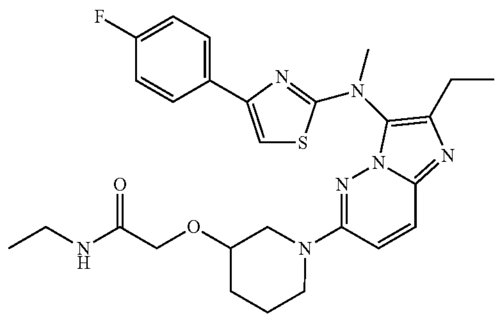 [SMILES: CCNC(=O)COC1CCCN(c2ccc3nc(CC)c(N(C)c4nc(-c5ccc(F)cc5)cs4)n3n2)C1] | N-ethyl-2-(1-(2-ethyl-3-((4-(4-fluorophenyl)thiazol-2-yl)(methyl)amino)imidazo[1,2-b]pyridazin-6-yl)piperidin-3-yloxy)acetamide | Gen-4-a A2-B2-C1-D1-E4a | 537 | 538 (M + H) |
| 93 | 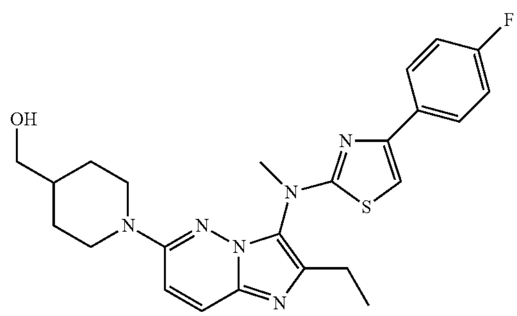 [SMILES: CCc1nc2ccc(N3CCC(CO)CC3)nn2c1N(C)c1nc(-c2ccc(F)cc2)cs1] | (1-(2-ethyl-3-((4-(4-fluorophenyl)thiazol-2-yl)(methyl)amino)imidazo[1,2-b]pyridazin-6-yl)piperidin-4-yl)methanol | Gen-4-a A2-B2-C1-D1-E4a | 466 | 467 (M + H) |
| 94 | 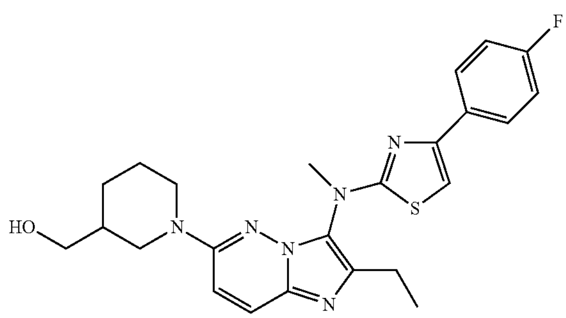 [SMILES: CCc1nc2ccc(N3CCCC(CO)C3)nn2c1N(C)c1nc(-c2ccc(F)cc2)cs1] | (1-(2-ethyl-3-((4-(4-fluorophenyl)thiazol-2-yl)(methyl)amino)imidazo[1,2-b]pyridazin-6-yl)piperidin-3-yl)methanol | Gen-4-a A2-B2-C1-D1-E4a | 466 | 467 (M + H) |
| 95 | 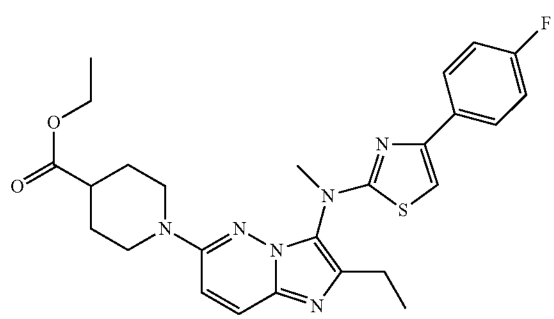 [SMILES: CCOC(=O)C1CCN(c2ccc3nc(CC)c(N(C)c4nc(-c5ccc(F)cc5)cs4)n3n2)CC1] | 1-(2-Ethyl-3-{[4-(4-fluoro-phenyl)-thiazol-2-yl]-methyl-amino}-imidazo[1,2-b]pyridazin-6-yl)-piperidine-4-carboxylic acid ethyl ester | Gen-4-a A2-B2-C1-D1-E4a | 508 | 509 (M + H) |

TABLE II-continued

Illustrative compounds of the invention.

| Cpd | Structures | Name | Mtd | MW | MS Ms'd |
|---|---|---|---|---|---|
| 96 | 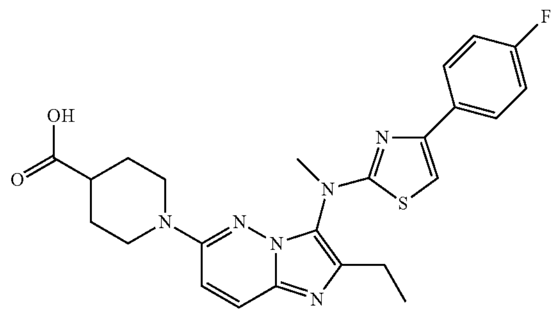 [SMILES: CCc1nc2ccc(N3CCC(C(=O)O)CC3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)piperidine-4-carboxylic acid | Cpd 95 A2-B2-C1-D1-E4a-E13 | 480 | 481 (M + H) |
| 97 | 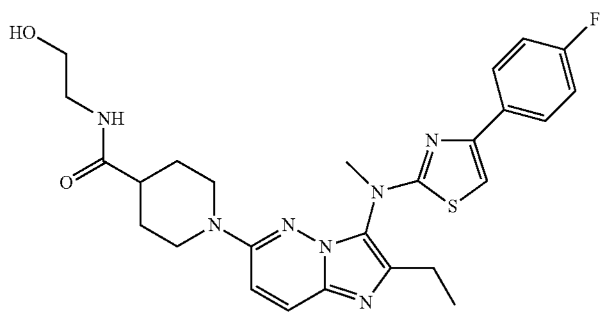 [SMILES: CCc1nc2ccc(N3CCC(C(=O)NCCO)CC3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)-N-(2-hydroxyethyl)piperidine-4-carboxamide | Cpd 96 A2-B2-C1-D1-E4a-E13-E9a | 523 | 524 (M + H) |
| 98 | 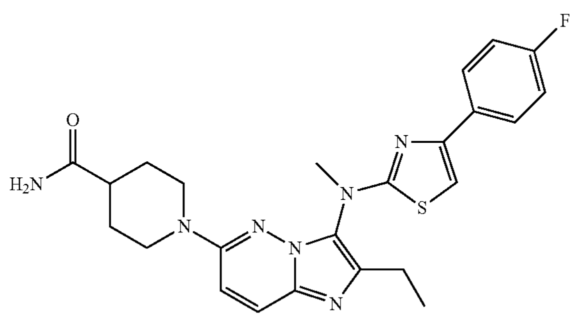 [SMILES: CCc1nc2ccc(N3CCC(C(N)=O)CC3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)piperidine-4-carboxamide | Gen-4-a A2-B2-C1-D1-E4a | 479 | 480 (M + H) |
| 99 | 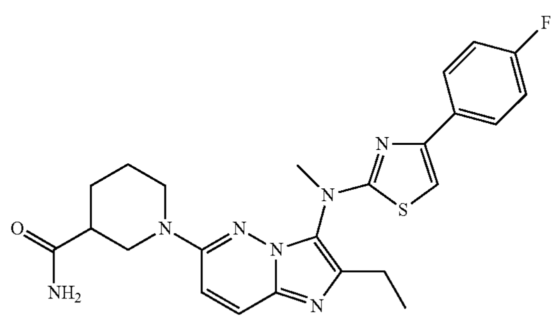 [SMILES: CCc1nc2ccc(N3CCCC(C(N)=O)C3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)piperidine-3-carboxamide | Gen-4-a A2-B2-C1-D1-E4a | 479 | 480 (M + H) |

TABLE II-continued

Illustrative compounds of the invention.

| Cpd | Structures | Name | Mtd | MW | MS Ms'd |
|---|---|---|---|---|---|
| 100 | 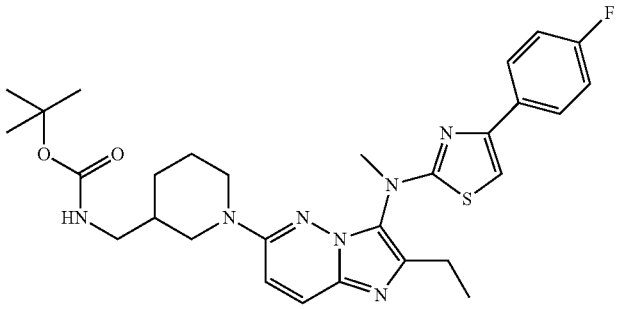 [SMILES: CCc1nc2ccc(N3CCCC(CNC(=O)OC(C)(C)C)C3)nn2c1N(C)c1nc(-c2ccc(F)cc2)cs1] | [1-(2-Ethyl-3-{[4-(4-fluoro-phenyl)-thiazol-2-yl]-methyl-amino}-imidazo[1,2-b]pyridazin-6-yl)-piperidin-3-ylmethyl]-carbamic acid tert-butyl ester | Gen-4-a A2-B2-C1-D1-E4a | 565 | 566 (M + H) |
| 101 | 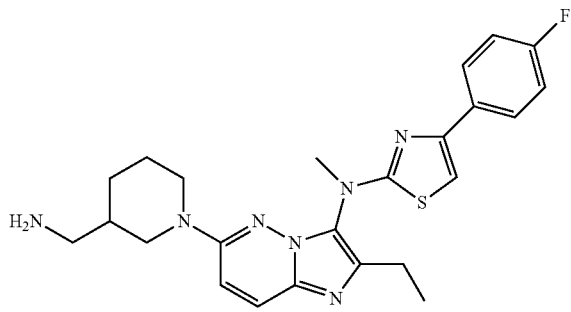 [SMILES: CCc1nc2ccc(N3CCCC(CN)C3)nn2c1N(C)c1nc(-c2ccc(F)cc2)cs1] | N-(6-(3-(aminomethyl) piperidin-1-yl)-2-ethylimidazo[1,2-b]pyridazin-3-yl)-4-(4-fluorophenyl)-N-methylthiazol-2-amine | Cpd 100 A2-B2-C1-D1-E4a-E5b | 465 | 466 (M + H) |
| 102 | 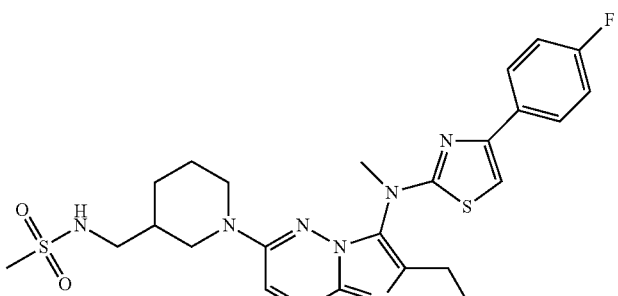 | N-((1-(2-ethyl-3-((4-(4-fluorophenyl) thiazol-2-yl)(methyl)amino) imidazo[1,2-b]pyridazin-6-yl)piperidin-3-yl)methyl) methanesulfonamide | Cpd 101 A2-B2-C1-D1-E4a-E5b-E11 | 543 | 544 (M + H) |
| 103 | 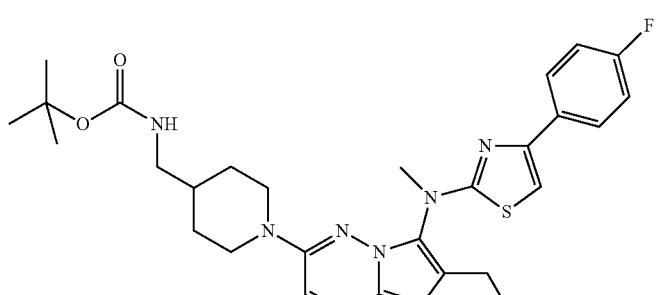 | [1-(2-Ethyl-3-{[4-(4-fluoro-phenyl)-thiazol-2-yl]-methyl-amino}-imidazo[1,2-b]pyridazin-6-yl)-piperidin-4-ylmethyl]-carbamic acid tert-butyl ester | Gen-4-a A2-B2-C1-D1-E4b | 565 | 566 (M + H) |

TABLE II-continued

Illustrative compounds of the invention.

| Cpd | Structures | Name | Mtd | MW | MS Ms'd |
|---|---|---|---|---|---|
| 104 | 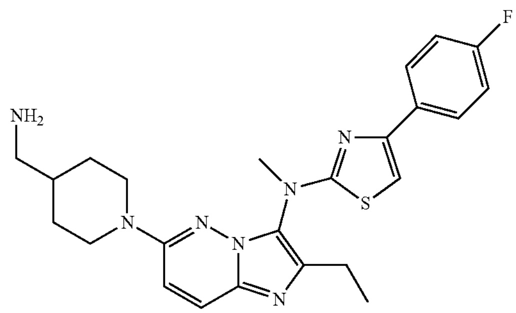 [SMILES: CCc1nc2ccc(N3CCC(CN)CC3)nn2c1N(C)c1nc(-c2ccc(F)cc2)cs1] | N-(6-(4-(aminomethyl)piperidin-1-yl)-2-ethylimidazo[1,2-b]pyridazin-3-yl)-4-(4-fluorophenyl)-N-methylthiazol-2-amine | Cpd 103 A2-B2-C1-D1-E4b-E5b | 465 | 466 (M + H) |
| 105 | 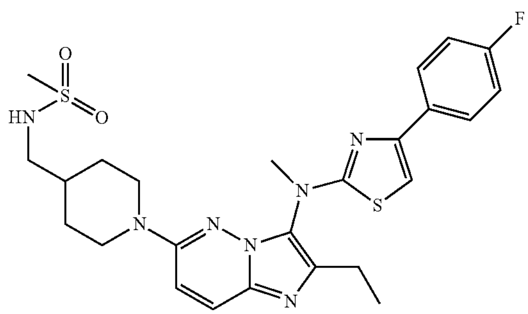 [SMILES: CCc1nc2ccc(N3CCC(CNS(C)(=O)=O)CC3)nn2c1N(C)c1nc(-c2ccc(F)cc2)cs1] | N-((1-(2-ethyl-3-((4-(4-fluorophenyl)thiazol-2-yl)(methyl)amino)imidazo[1,2-b]pyridazin-6-yl)piperidin-4-yl)methyl)methanesulfonamide | Cpd 104 A2-B2-C1-D1-E4b-E5b-E11 | 543 | 544 (M + H) |
| 106 | 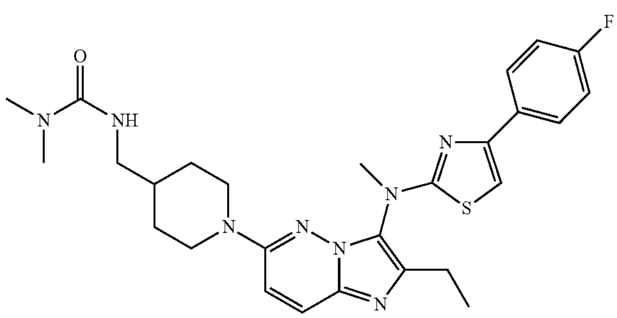 [SMILES: CCc1nc2ccc(N3CCC(CNC(=O)N(C)C)CC3)nn2c1N(C)c1nc(-c2ccc(F)cc2)cs1] | 3-((1-(2-ethyl-3-((4-(4-fluorophenyl)thiazol-2-yl)(methyl)amino)imidazo[1,2-b]pyridazin-6-yl)piperidin-4-yl)methyl)-1,1-dimethylurea | Cpd 104 A2-B2-C1-D1-E4b-E5b-E9b | 536 | 537 (M + H) |
| 107 | 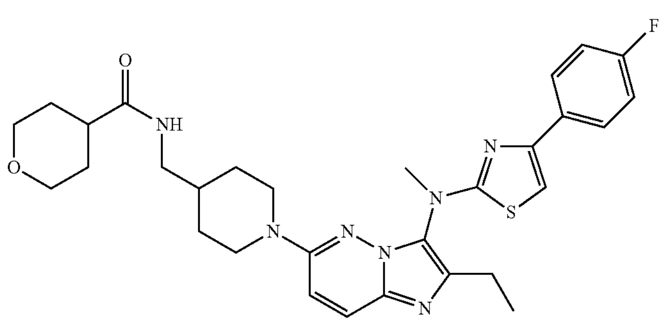 [SMILES: CCc1nc2ccc(N3CCC(CNC(=O)C4CCOCC4)CC3)nn2c1N(C)c1nc(-c2ccc(F)cc2)cs1] | N-((1-(2-ethyl-3-((4-(4-fluorophenyl)thiazol-2-yl)(methyl)amino)imidazo[1,2-b]pyridazin-6-yl)piperidin-4-yl)methyl)tetrahydro-2H-pyran-4-carboxamide | Cpd 104 A2-B2-C1-D1-E4b-E5b-E9b | 577 | 578 (M + H) |

TABLE II-continued

Illustrative compounds of the invention.

| Cpd | Structures | Name | Mtd | MW | MS Ms'd |
|---|---|---|---|---|---|
| 108 | 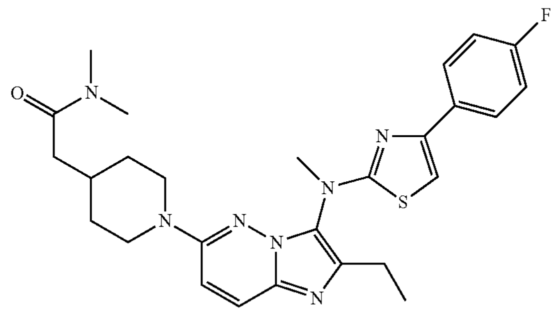 [SMILES: CCc1nc2ccc(N3CCC(CC(=O)N(C)C)CC3)nn2c1N(C)c1nc(-c2ccc(F)cc2)cs1] | 2-(1-(2-ethyl-3-((4-(4-fluorophenyl)thiazol-2-yl)(methyl)amino)imidazo[1,2-b]pyridazin-6-yl)piperidin-4-yl)-N,N-dimethylacetamide | Gen-4-a A2-B2-C1-D1-E4b | 521 | 522 (M + H) |
| 109 | 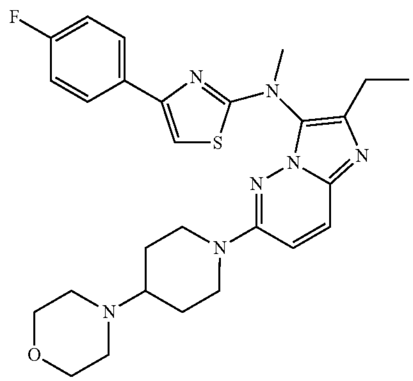 [SMILES: CCc1nc2ccc(N3CCC(N4CCOCC4)CC3)nn2c1N(C)c1nc(-c2ccc(F)cc2)cs1] | N-(2-ethyl-6-(4-morpholino-piperidin-1-yl)imidazo[1,2-b]pyridazin-3-yl)-4-(4-fluorophenyl)-N-methylthiazol-2-amine | Gen-4-a A2-B2-C1-D1-E4a | 521 | 522 (M + H) |
| 110 | 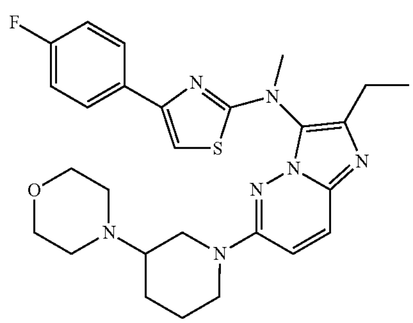 [SMILES: CCc1nc2ccc(N3CCCC(N4CCOCC4)C3)nn2c1N(C)c1nc(-c2ccc(F)cc2)cs1] | N-(2-ethyl-6-(3-morpholino-piperidin-1-yl)imidazo[1,2-b]pyridazin-3-yl)-4-(4-fluorophenyl)-N-methylthiazol-2-amine | Gen-4-a A2-B2-C1-D1-E4a | 521 | 522 (M + H) |
| 111 | 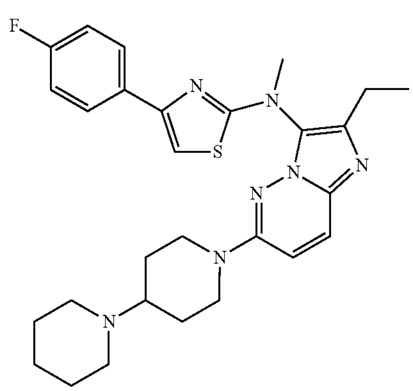 [SMILES: CCc1nc2ccc(N3CCC(N4CCCCC4)CC3)nn2c1N(C)c1nc(-c2ccc(F)cc2)cs1] | N-(6-(1,4'-bipiperidin-1'-yl)-2-ethylimidazo[1,2-b]pyridazin-3-yl)-4-(4-fluorophenyl)-N-methylthiazol-2-amine | Gen-4-a A2-B2-C1-D1-E4a | 519 | 520 (M + H) |

TABLE II-continued

Illustrative compounds of the invention.

| Cpd | Structures | Name | Mtd | MW | MS Ms'd |
|-----|------------|------|-----|-----|---------|
| 112 | 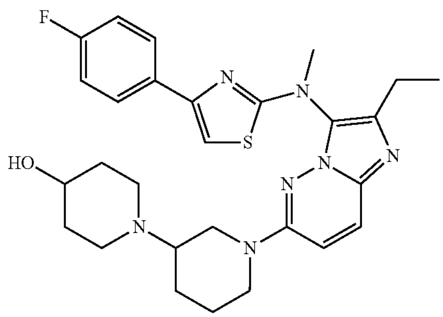 [SMILES: CCc1nc2ccc(N3CCCC(N4CCC(O)CC4)C3)nn2c1N(C)c1nc(-c2ccc(F)cc2)cs1] | 1'-(2-ethyl-3-((4-(4-fluorophenyl)thiazol-2-yl)(methyl)amino)imidazo[1,2-b]pyridazin-6-yl)-1,3'-bipiperidin-4-ol | Gen-4-a A2-B2-C1-D1-E4a | 535 | 536 (M + H) |
| 113 | 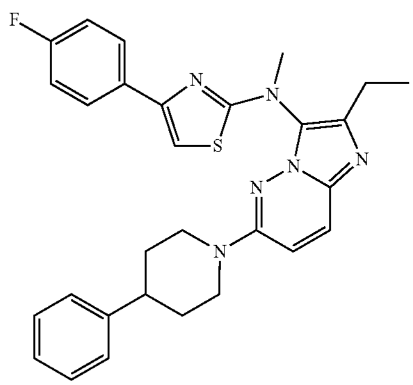 [SMILES: CCc1nc2ccc(N3CCC(c4ccccc4)CC3)nn2c1N(C)c1nc(-c2ccc(F)cc2)cs1] | N-(2-ethyl-6-(4-phenylpiperidin-1-yl)imidazo[1,2-b]pyridazin-3-yl)-4-(4-fluorophenyl)-N-methylthiazol-2-amine | Gen-4-a A2-B2-C1-D1-E4a | 512 | 513 (M + H) |
| 114 | 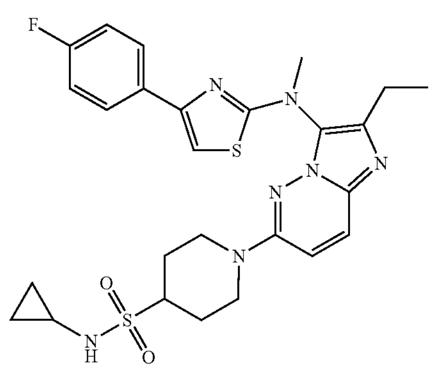 [SMILES: CCc1nc2ccc(N3CCC(S(=O)(=O)NC4CC4)CC3)nn2c1N(C)c1nc(-c2ccc(F)cc2)cs1] | N-cyclopropyl-1-(2-ethyl-3-((4-(4-fluorophenyl)thiazol-2-yl)(methyl)amino)imidazo[1,2-b]pyridazin-6-yl)piperidine-4-sulfonamide | Gen-4-a A2-B2-C1-D1-E4a | 555 | 556 (M + H) |
| 115 | 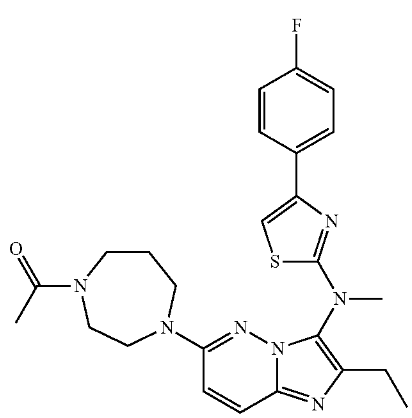 [SMILES: CCc1nc2ccc(N3CCCN(C(C)=O)CC3)nn2c1N(C)c1nc(-c2ccc(F)cc2)cs1] | 1-(4-(2-ethyl-3-((4-(4-fluorophenyl)thiazol-2-yl)(methyl)amino)imidazo[1,2-b]pyridazin-6-yl)-1,4-diazepan-1-yl)ethanone | Gen-4-a A2-B2-C1-D1-E4a | 493 | 494 (M + H) |

| Cpd | Structures | Name | Mtd | MW | MS Ms'd |
|---|---|---|---|---|---|
| 116 | 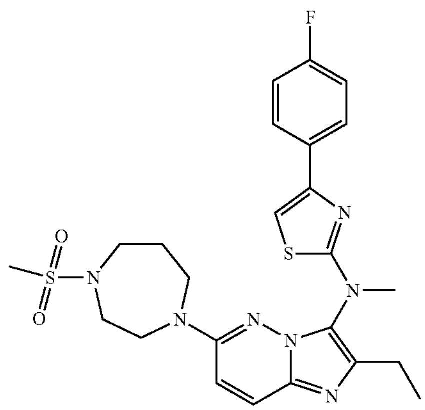 [SMILES: CCc1nc2ccc(N3CCCN(S(C)(=O)=O)CC3)nn2c1N(C)c1nc(-c2ccc(F)cc2)cs1] | N-(2-ethyl-6-(4-(methylsulfonyl)-1,4-diazepan-1-yl)imidazo[1,2-b]pyridazin-3-yl)-4-(4-fluorophenyl)-N-methylthiazol-2-amine | Gen-5-c A2-B2-C1-D1-E4a-E5b-E11 | 529 | 530 (M + H) |
| 117 | 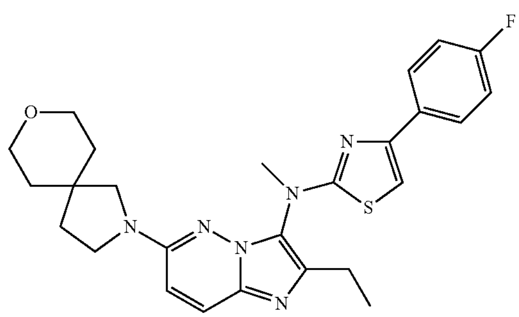 [SMILES: CCc1nc2ccc(N3CCC4(CCOCC4)C3)nn2c1N(C)c1nc(-c2ccc(F)cc2)cs1] | N-(2-ethyl-6-(8-oxa-2-azaspiro[4.5]decan-2-yl)imidazo[1,2-b]pyridazin-3-yl)-4-(4-fluorophenyl)-N-methylthiazol-2-amine | Gen-4-a A2-B2-C1-D1-E1b | 492 | 493 (M + H) |
| 118 | 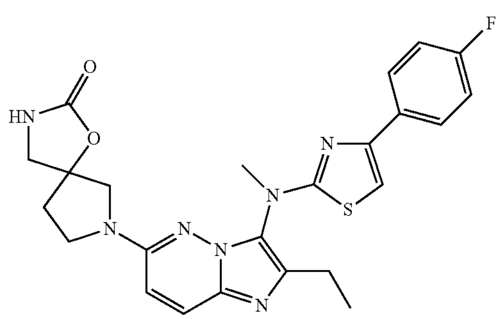 [SMILES: CCc1nc2ccc(N3CCC4(CNC(=O)O4)C3)nn2c1N(C)c1nc(-c2ccc(F)cc2)cs1] | 7-(2-ethyl-3-((4-(4-fluorophenyl)thiazol-2-yl)(methyl)amino)imidazo[1,2-b]pyridazin-6-yl)-1-oxa-3,7-diazaspiro[4.4]nonan-2-one | Gen-4-a A2-B2-C1-D1-E4a | 493 | 494 (M + H) |
| 119 | 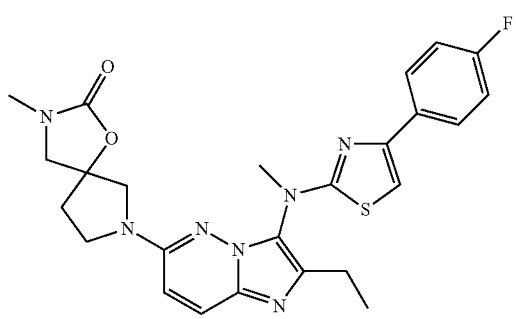 [SMILES: CCc1nc2ccc(N3CCC4(CN(C)C(=O)O4)C3)nn2c1N(C)c1nc(-c2ccc(F)cc2)cs1] | 7-(2-ethyl-3-((4-(4-fluorophenyl)thiazol-2-yl)(methyl)amino)imidazo[1,2-b]pyridazin-6-yl)-3-methyl-1-oxa-3,7-diazaspiro[4.4]nonan-2-one | Gen-4-a A2-B2-C1-D1-E4a | 507 | 508 (M + H) |

TABLE II-continued

Illustrative compounds of the invention.

| Cpd | Structures | Name | Mtd | MW | MS Ms'd |
|---|---|---|---|---|---|
| 120 | 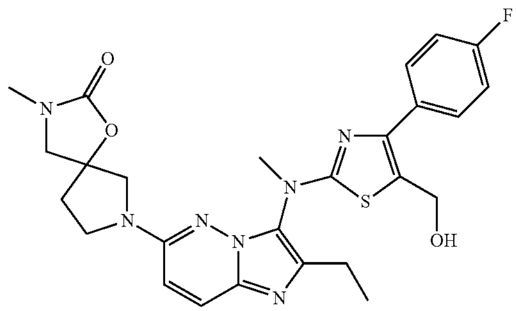 [SMILES: CCc1nc2ccc(N3CCC4(CN(C)C(=O)O4)C3)nn2c1N(C)c1nc(-c2ccc(F)cc2)c(CO)s1] | 7-(2-ethyl-3-((4-(4-fluorophenyl)-5-(hydroxymethyl)thiazol-2-yl)(methyl)amino)imidazo[1,2-b]pyridazin-6-yl)-3-methyl-1-oxa-3,7-diazaspiro[4.4]nonan-2-one | Cpd 119 A2-B2-C1-D1-E4a-E14 | 537 | 538 (M + H) |
| 121 | 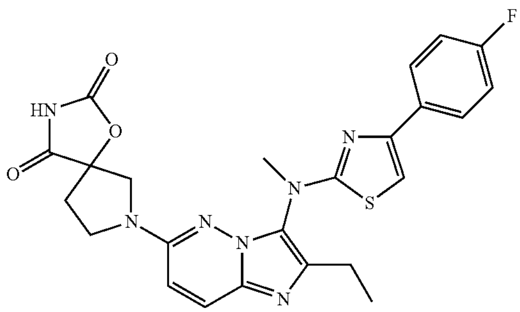 [SMILES: CCc1nc2ccc(N3CCC4(C3)OC(=O)NC4=O)nn2c1N(C)c1nc(-c2ccc(F)cc2)cs1] | 7-(2-ethyl-3-((4-(4-fluorophenyl)thiazol-2-yl)(methyl)amino)imidazo[1,2-b]pyridazin-6-yl)-2,7-diazaspiro[4.4]nonane-1,3-dione | Gen-4-a A2-B2-C1-D1-E4a | 505 | 506 (M + H) |
| 122 | 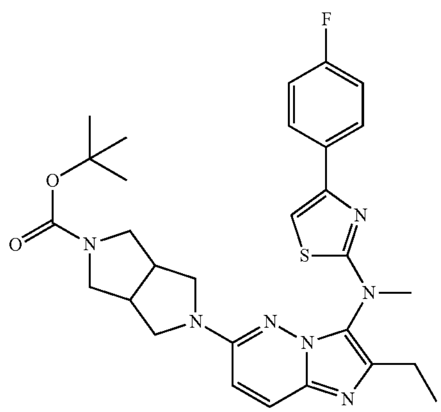 [SMILES: CCc1nc2ccc(N3CC4CN(C(=O)OC(C)(C)C)CC4C3)nn2c1N(C)c1nc(-c2ccc(F)cc2)cs1] | tert-butyl 5-(2-ethyl-3-((4-(4-fluorophenyl)thiazol-2-yl)(methyl)amino)imidazo[1,2-b]pyridazin-6-yl)hexahydropyrrolo[3,4-c]pyrrole-2(1H)-carboxylate | Gen-4-a A2-B2-C1-D1-E4a | 563 | 564 (M + H) |
| 123 | 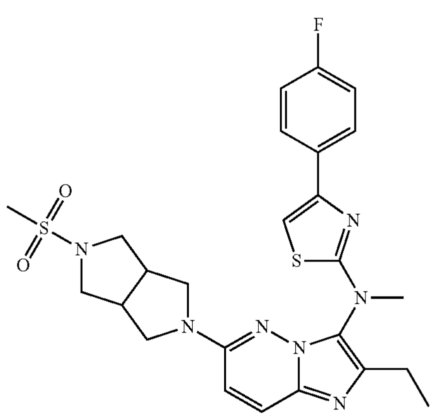 [SMILES: CCc1nc2ccc(N3CC4CN(S(C)(=O)=O)CC4C3)nn2c1N(C)c1nc(-c2ccc(F)cc2)cs1] | N-(2-ethyl-6-(5-(methylsulfonyl)hexahydropyrrolo[3,4-c]pyrrol-2(1H)-yl)imidazo[1,2-b]pyridazin-3-yl)-4-(4-fluorophenyl)-N-methylthiazol-2-amine | Gen-5-d A2-B2-C1-D1-E4a-E5b-E11 | 541 | 542 (M + H) |

TABLE II-continued

Illustrative compounds of the invention.

| Cpd | Structures | Name | Mtd | MW | MS Ms'd |
|---|---|---|---|---|---|
| 124 | 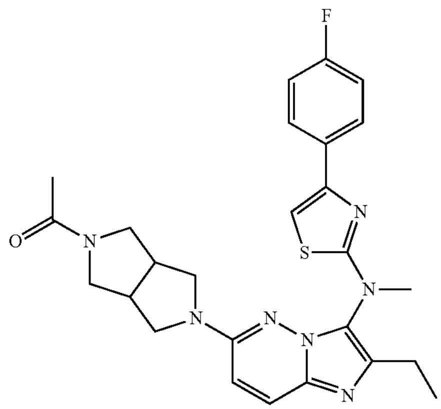 [SMILES: CCc1nc2ccc(N3CC4CN(C(C)=O)CC4C3)nn2c1N(C)c1nc(-c2ccc(F)cc2)cs1] | 1-(5-(2-ethyl-3-((4-(4-fluorophenyl)thiazol-2-yl)(methyl)amino)imidazo[1,2-b]pyridazin-6-yl)hexahydro-pyrrolo[3,4-c]pyrrol-2(1H)-yl)ethanone | Gen-5-d A2-B2-C1-D1-E4a-E5b-E9b | 505 | 506 (M + H) |
| 125 | 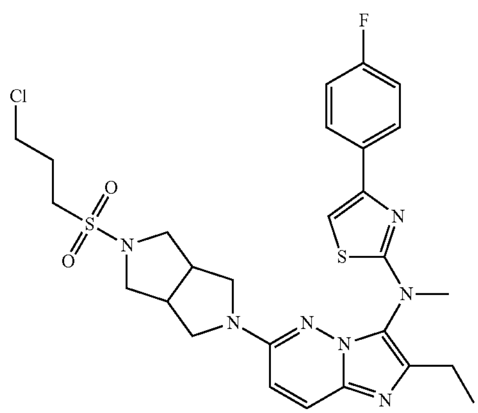 [SMILES: CCc1nc2ccc(N3CC4CN(S(=O)(=O)CCCCl)CC4C3)nn2c1N(C)c1nc(-c2ccc(F)cc2)cs1] | N-(6-(5-(3-chloropropyl-sulfonyl)-hexahydropyrrolo[3,4-c]pyrrol-2(1H)-yl)-2-ethylimidazo[1,2-b]pyridazin-3-yl)-4-(4-fluorophenyl)-N-methylthiazol-2-amine | Gen-5-d A2-B2-C1-D1-E4a-E5b-E11 | 603 ($^{35}$Cl), 605 ($^{37}$Cl) | 604 ($^{35}$Cl M + H), 606 ($^{37}$Cl M + H) |
| 126 | 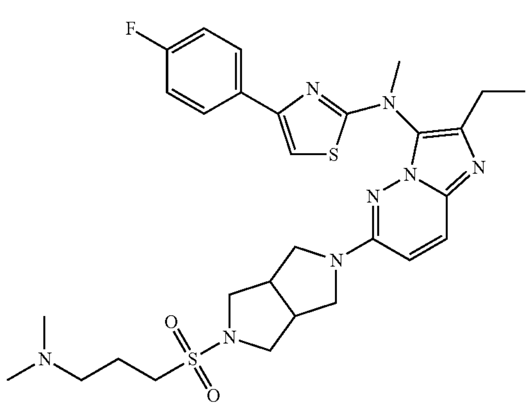 [SMILES: CCc1nc2ccc(N3CC4CN(S(=O)(=O)CCCN(C)C)CC4C3)nn2c1N(C)c1nc(-c2ccc(F)cc2)cs1] | N-(6-(5-(3-(dimethylamino)propylsulfonyl)hexahydropyrrolo[3,4-c]pyrrol-2(1H)-yl)-2-ethylimidazo[1,2-b]pyridazin-3-yl)-4-(4-fluorophenyl)-N-methylthiazol-2-amine | Cpd 125 A2-B2-C1-D1-E4a-E5b-E11-E12 | 612 | 613 (M + H) |

TABLE II-continued

Illustrative compounds of the invention.

| Cpd | Structures | Name | Mtd | MW | MS Ms'd |
|---|---|---|---|---|---|
| 127 | 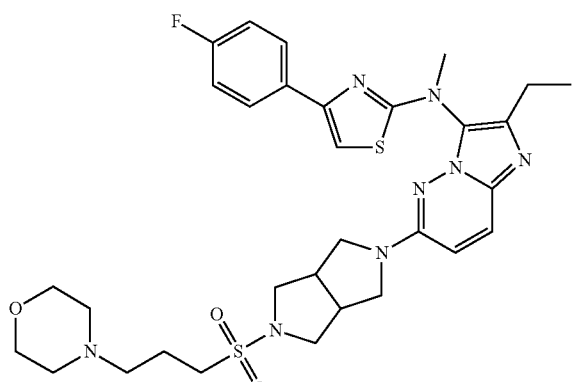 | N-(2-ethyl-6-(5-(3-morpholinopropyl-sulfonyl)hexahydro-pyrrolo[3,4-c]pyrrol-2(1H)-yl)imidazo[1,2-b]pyridazin-3-yl)-4-(4-fluorophenyl)-N-methylthiazol-2-amine | Cpd 125 A2-B2-C1-D1-E4a-E5b-E11-E12 | 654 | 655 (M + H) |
| 128 | 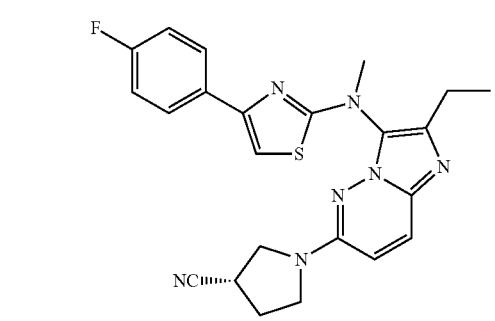 [SMILES: CCc1nc2ccc(N3CC[C@H](C#N)C3)nn2c1N(C)c1nc(-c2ccc(F)cc2)cs1] | (S)-1-(2-ethyl-3-((4-(4-fluorophenyl)thiazol-2-yl)(methyl)amino)imidazo[1,2-b]pyridazin-6-yl)pyrrolidine-3-carbonitrile | Gen-4-a A2-B2-C1-D1-E4a | 447 | 448 (M + H) |
| 129 | 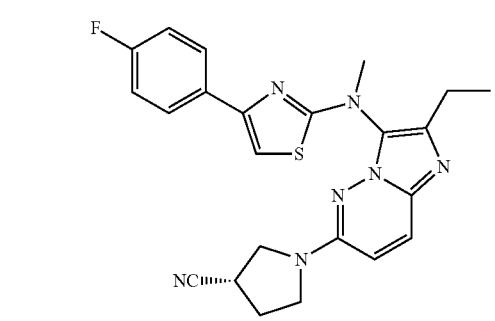 | 1-(2-ethyl-3-((4-(4-fluorophenyl)thiazol-2-yl)(methyl)amino)imidazo[1,2-b]pyridazin-6-yl)pyrrolidin-3-ol | Gen-4-a A2-B2-C1-Dl-E4a | 438 | 439 (M + H) |
| 130 | 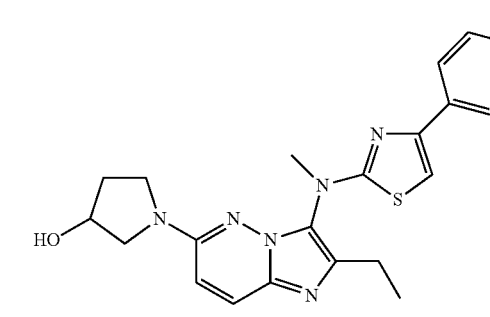 | 1-(2-ethyl-3-((4-(4-fluorophenyl)thiazol-2-yl)(methyl)amino)imidazo[1,2-b]pyridazin-6-yl)pyrrolidin-3-yl formate | Cpd 129 A2-B2-C1-D1-E4a-see Cpd 130 | 466 | 467 (M + H) |

TABLE II-continued

Illustrative compounds of the invention.

| Cpd | Structures | Name | Mtd | MW | MS Ms'd |
|---|---|---|---|---|---|
| 131 | 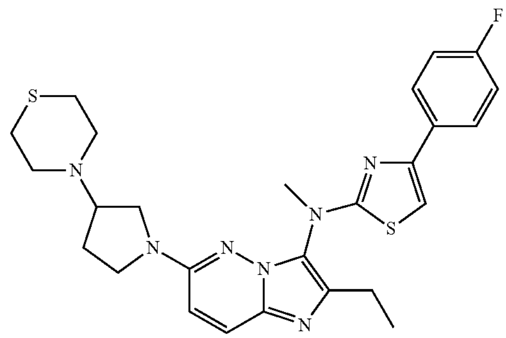 [SMILES: CCc1nc2ccc(N3CCC(N4CCSCC4)C3)nn2c1N(C)c1nc(-c2ccc(F)cc2)cs1] | N-(2-ethyl-6-(3-thiomorpholino-pyrrolidin-1-yl)imidazo[1,2-b]pyridazin-3-yl)-4-(4-fluorophenyl)-N-methylthiazol-2-amine | Cpd 129 A2-B2-C1-D1-E4a-E7-E10 | 523 | 524 (M + H) |
| 132 | 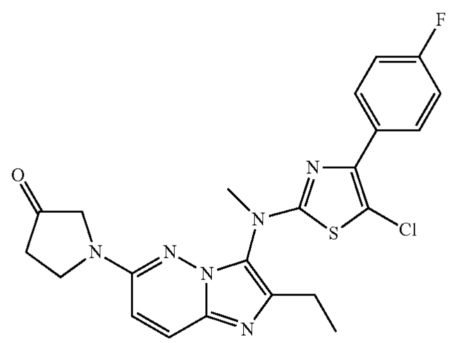 [SMILES: CCc1nc2ccc(N3CCC(=O)C3)nn2c1N(C)c1nc(-c2ccc(F)cc2)c(Cl)s1] | 1-(3-((5-chloro-4-(4-fluorophenyl)thiazol-2-yl)(methyl)amino)-2-ethylimidazo[1,2-b]pyridazin-6-yl)pyrrolidin-3-one | Cpd 129 A2-B2-C1-D1-E4a-see Cpd 132 | 470 ($^{35}$Cl), 472 ($^{37}$Cl) | 471 ($^{35}$Cl M + H), 473 ($^{37}$Cl M + H) |
| 133 | 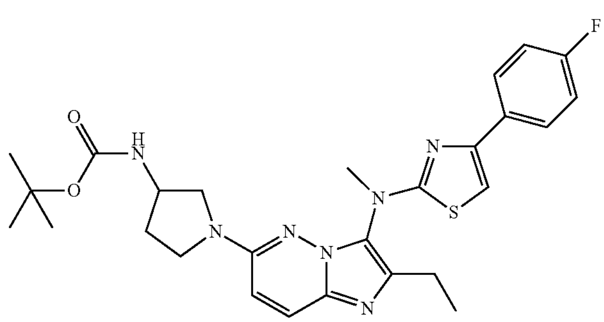 [SMILES: CCc1nc2ccc(N3CCC(NC(=O)OC(C)(C)C)C3)nn2c1N(C)c1nc(-c2ccc(F)cc2)cs1] | tert-butyl 1-(2-ethyl-3-((4-(4-fluorophenyl)thiazol-2-yl)(methyl)amino)imidazo[1,2-b]pyridazin-6-yl)pyrrolidin-3-ylcarbamate | Gen-4-a A2-B2-C1-D1-E4a | 537 | 538 (M + H) |
| 134 | 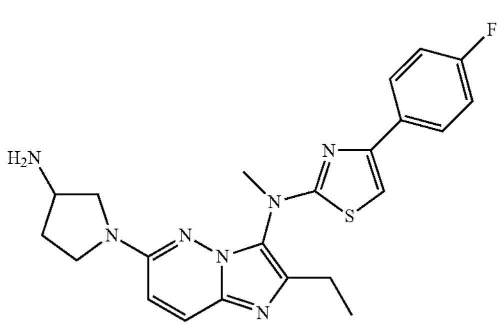 [SMILES: CCc1nc2ccc(N3CCC(N)C3)nn2c1N(C)c1nc(-c2ccc(F)cc2)cs1] | N-(6-(3-aminopyrrolidin-1-yl)-2-ethylimidazo[1,2-b]pyridazin-3-yl)-4-(4-fluorophenyl)-N-methylthiazol-2-amine | Cpd 133 A2-B2-C1-D1-E4a-E5b | 437 | 438 (M + H) |

TABLE II-continued

Illustrative compounds of the invention.

| Cpd | Structures | Name | Mtd | MW | MS Ms'd |
|---|---|---|---|---|---|
| 135 | 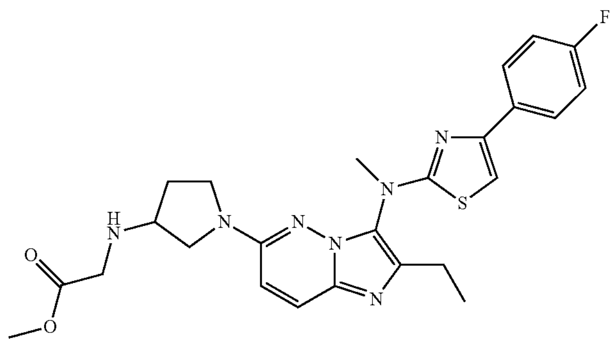 [SMILES: CCc1nc2ccc(N3CCC(NCC(=O)OC)C3)nn2c1N(C)c1nc(-c2ccc(F)cc2)cs1] | methyl 2-(1-(2-ethyl-3-((4-(4-fluorophenyl)thiazol-2-yl)(methyl)amino)imidazo[1,2-b]pyridazin-6-yl)pyrrolidin-3-ylamino)acetate | Cpd 134 A2-B2-C1-D1-E4a-E5b-E8 | 509 | 510 (M + H) |
| 136 | 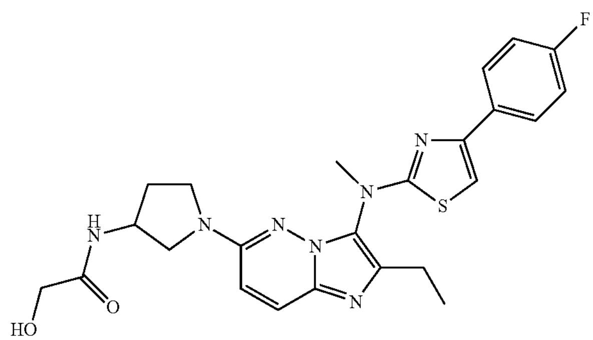 [SMILES: CCc1nc2ccc(N3CCC(NC(=O)CO)C3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)pyrrolidin-3-yl)-2-hydroxyacetamide | Cpd 134 A2-B2-C1-D1-E4a-E5b-E9c | 495 | 496 (M + H) |
| 137 | 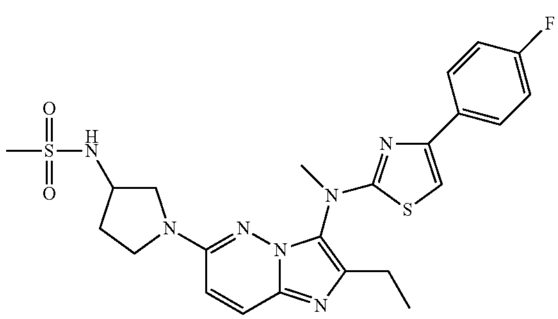 [SMILES: CCc1nc2ccc(N3CCC(NS(C)(=O)=O)C3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)pyrrolidin-3-yl)methanesulfonamide | Cpd 134 A2-B2-C1-D1-E4a-E5b-E11 | 515 | 516 (M + H) |
| 138 | 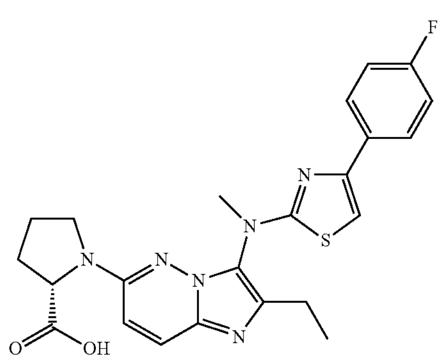 [SMILES: CCc1nc2ccc(N3CCC[C@H]3C(=O)O)nn2c1N(C)c1nc(-c2ccc(F)cc2)cs1] | (S)-1-(2-ethyl-3-((4-(4-fluorophenyl)thiazol-2-yl)(methyl)amino)imidazo[1,2-b]pyridazin-6-yl)pyrrolidine-2-carboxylic acid | Gen-4-a A2-B2-C1-D1-see Cpd 138 | 466 | 467 (M + H) |

TABLE II-continued

Illustrative compounds of the invention.

| Cpd | Structures | Name | Mtd | MW | MS Ms'd |
|---|---|---|---|---|---|
| 139 | 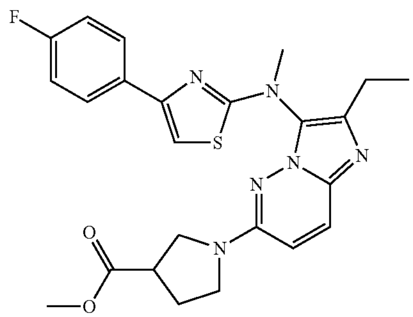 [SMILES: CCc1nc2ccc(N3CCC(C(=O)OC)C3)nn2c1N(C)c1nc(-c2ccc(F)cc2)cs1] | 1-(2-Ethyl-3-{[4-(4-fluoro-phenyl)-thiazol-2-yl]-methyl-amino}-imidazo[1,2-b]pyridazin-6-yl)-pyrrolidine-3-carboxylic acid methyl ester | Gen-4-a A2-B2-C1-D1-E4a | 480 | 481 (M + H) |
| 140 | 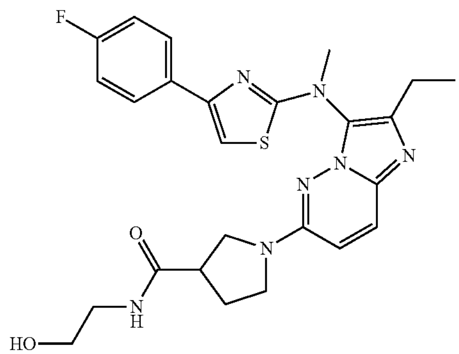 [SMILES: CCc1nc2ccc(N3CCC(C(=O)NCCO)C3)nn2c1N(C)c1nc(-c2ccc(F)cc2)cs1] | 1-(2-ethyl-3-((4-(4-fluorophenyl)thiazol-2-yl)(methyl)amino)imidazo[1,2-b]pyridazin-6-yl)-N-(2-hydroxyethyl)pyrrolidine-3-carboxamide | Gen-4-a A2-B2-C1-D1-E4a | 509 | 510 (M + H) |
| 141 | 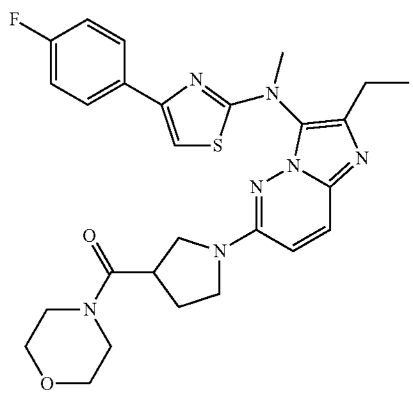 [SMILES: CCc1nc2ccc(N3CCC(C(=O)N4CCOCC4)C3)nn2c1N(C)c1nc(-c2ccc(F)cc2)cs1] | (1-(2-ethyl-3-((4-(4-fluorophenyl)thiazol-2-yl)(methyl)amino)imidazo[1,2-b]pyridazin-6-yl)pyrrolidin-3-yl)(morpholino)methanone | Gen-4-a A2-B2-C1-D1-E4a | 535 | 536 (M + H) |
| 142 | 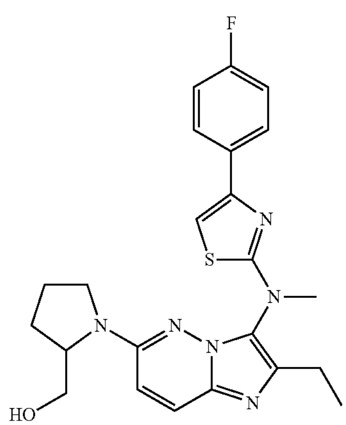 [SMILES: CCc1nc2ccc(N3CCCC3CO)nn2c1N(C)c1nc(-c2ccc(F)cc2)cs1] | (1-(2-ethyl-3-((4-(4-fluorophenyl)thiazol-2-yl)(methyl)amino)imidazo[1,2-b]pyridazin-6-yl)pyrrolidin-2-yl)methanol | Gen-4-a A2-B2-C1-D1-E4a | 452 | 453 (M + H) |

TABLE II-continued

Illustrative compounds of the invention.

| Cpd | Structures | Name | Mtd | MW | MS Ms'd |
|---|---|---|---|---|---|
| 143 | 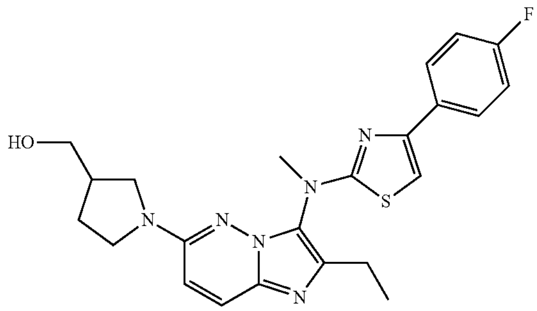 [SMILES: CCc1nc2ccc(N3CCC(CO)C3)nn2c1N(C)c1nc(-c2ccc(F)cc2)cs1] | (1-(2-ethyl-3-((4-(4-fluorophenyl)thiazol-2-yl)(methyl)amino)imidazo[1,2-b]pyridazin-6-yl)pyrrolidin-3-yl)methanol | Gen-4-a A2-B2-C1-D1-E4a | 452 | 453 (M + H) |
| 144 | 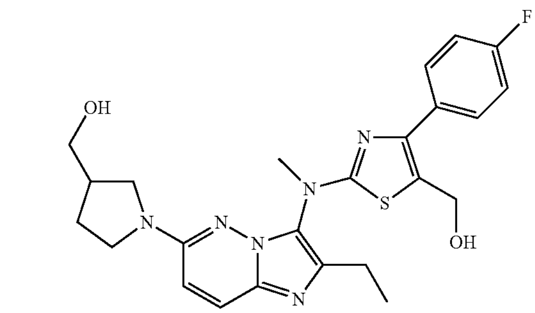 [SMILES: CCc1nc2ccc(N3CCC(CO)C3)nn2c1N(C)c1nc(-c2ccc(F)cc2)c(CO)s1] | (1-(2-ethyl-3-((4-(4-fluorophenyl)-5-(hydroxymethyl)thiazol-2-yl)(methyl)amino)imidazo[1,2-b]pyridazin-6-yl)pyrrolidin-3-yl)methanol | Cpd 143 A2-B2-C1-D1-E4a-E14 | 482 | 483 (M + H) |
| 145 | 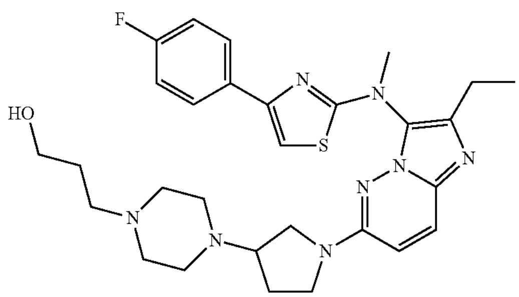 [SMILES: CCc1nc2ccc(N3CCC(N4CCN(CCCO)CC4)C3)nn2c1N(C)c1nc(-c2ccc(F)cc2)cs1] | 3-(4-(1-(2-ethyl-3-((4-(4-fluorophenyl)thiazol-2-yl)(methyl)amino)imidazo[1,2-b]pyridazin-6-yl)pyrrolidin-3-yl)piperazin-1-yl)propan-1-ol | Gen-4-a A2-B2-C1-D1-E4a | 564 | 565 (M + H) |
| 146 | 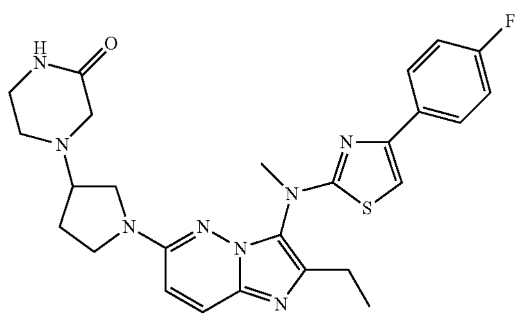 [SMILES: CCc1nc2ccc(N3CCC(N4CCNC(=O)C4)C3)nn2c1N(C)c1nc(-c2ccc(F)cc2)cs1] | 4-(1-(2-ethyl-3-((4-(4-fluorophenyl)thiazol-2-yl)(methyl)amino)imidazo[1,2-b]pyridazin-6-yl)pyrrolidin-3-yl)piperazin-2-one | Gen-4-a A2-B2-C1-D1-E4a | 520 | 521 (M + H) |
| 147 | 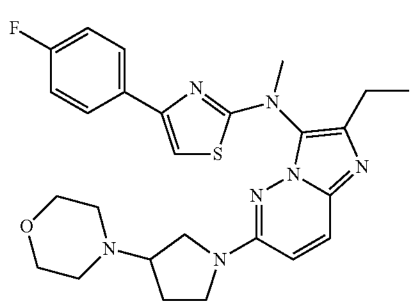 [SMILES: CCc1nc2ccc(N3CCC(N4CCOCC4)C3)nn2c1N(C)c1nc(-c2ccc(F)cc2)cs1] | N-(2-ethyl-6-(3-morpholinopyrrolidin-1-yl)imidazo[1,2-b]pyridazin-3-yl)-4-(4-fluorophenyl)-N-methylthiazol-2-amine | Gen-4-a A2-B2-C1-D1-E4a | 507 | 508 (M + H) |

TABLE II-continued

Illustrative compounds of the invention.

| Cpd | Structures | Name | Mtd | MW | MS Ms'd |
|---|---|---|---|---|---|
| 148 | 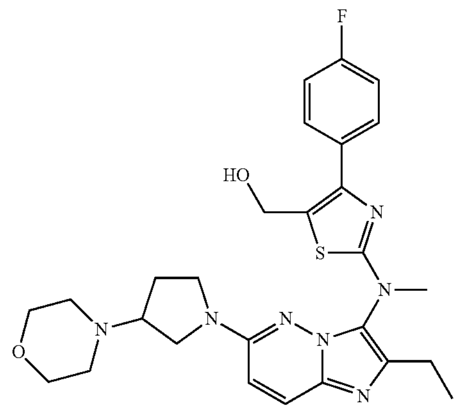 [SMILES: CCc1nc2ccc(N3CCC(N4CCOCC4)C3)nn2c1N(C)c1nc(-c2ccc(F)cc2)c(CO)s1] | (2-((2-ethyl-6-(3-morpholino-pyrrolidin-1-yl)imidazo[1,2-b]pyridazin-3-yl)(methyl)amino)-4-(4-fluorophenyl)thiazol-5-yl)methanol | Cpd 147 A2-B2-C1-D1-E4a-E14 | 537 | 538 (M + H) |
| 149 | 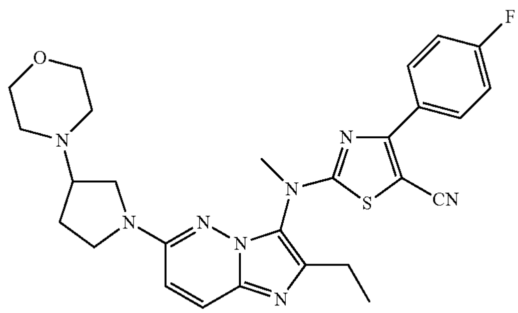 [SMILES: CCc1nc2ccc(N3CCC(N4CCOCC4)C3)nn2c1N(C)c1nc(-c2ccc(F)cc2)c(C#N)s1] | 2-((2-ethyl-6-(3-morpholino-pyrrolidin-1-yl)imidazo[1,2-b]pyridazin-3-yl)(methyl)amino)-4-(4-fluorophenyl)thiazole-5-carbonitrile | Gen-5-q A2-B2-C1-D1-E4a-E16-E17 | 532 | 533 (M + H) |
| 150 | 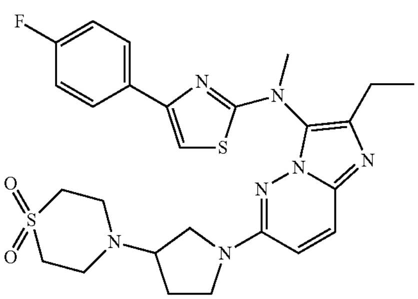 [SMILES: CCc1nc2ccc(N3CCC(N4CCS(=O)(=O)CC4)C3)nn2c1N(C)c1nc(-c2ccc(F)cc2)cs1] | {6-[3-(1,1-Dioxo-thiomorpholin-4-yl)-pyrrolidin-1-yl]-2-ethyl-imidazo[1,2-b]pyridazin-3-yl}-[4-(4-fluoro-phenyl)-thiazol-2-yl]-methyl-amine | Gen-4-a A2-B2-C1-D1-E4a | 555 | 556 (M + H) |
| 151 | 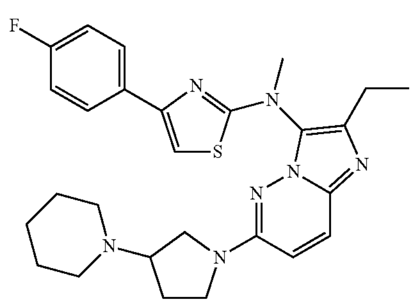 [SMILES: CCc1nc2ccc(N3CCC(N4CCCCC4)C3)nn2c1N(C)c1nc(-c2ccc(F)cc2)cs1] | N-(2-ethyl-6-(3-(piperidin-1-yl)pyrrolidin-1-yl)imidazo[1,2-b]pyridazin-3-yl)-4-(4-fluorophenyl)-N-methylthiazol-2-amine | Gen-4-a A2-B2-C1-D1-E4a | 505 | 506 (M + H) |

TABLE II-continued

Illustrative compounds of the invention.

| Cpd | Structures | Name | Mtd | MW | MS Ms'd |
|---|---|---|---|---|---|
| 152 | 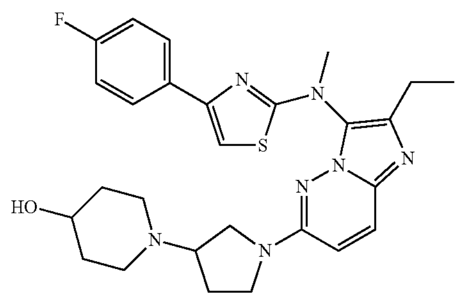 [SMILES: CCc1nc2ccc(N3CCC(N4CCC(O)CC4)C3)nn2c1N(C)c1nc(-c2ccc(F)cc2)cs1] | 1-(1-(2-ethyl-3-((4-(4-fluorophenyl)thiazol-2-yl)(methyl)amino)imidazo[1,2-b]pyridazin-6-yl)pyrrolidin-3-yl)piperidin-4-ol | Gen-4-a A2-B2-C1-D1-E4a | 521 | 522 (M + H) |
| 153 | 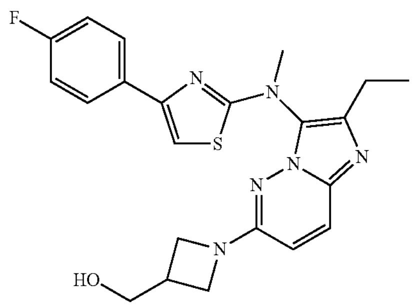 [SMILES: CCc1nc2ccc(N3CC(CO)C3)nn2c1N(C)c1nc(-c2ccc(F)cc2)cs1] | (1-(2-ethyl-3-((4-(4-fluorophenyl)thiazol-2-yl)(methyl)amino)imidazo[1,2-b]pyridazin-6-yl)azetidin-3-yl)methanol | Gen-4-a A2-B2-C1-D1-E4a | 438 | 439 (M + H) |
| 154 | 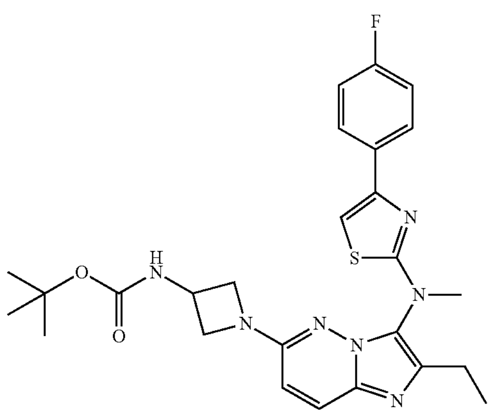 [SMILES: CCc1nc2ccc(N3CC(NC(=O)OC(C)(C)C)C3)nn2c1N(C)c1nc(-c2ccc(F)cc2)cs1] | [1-(2-Ethyl-3-{[4-(4-fluoro-phenyl)-thiazol-2-yl]-methyl-amino}-imidazo[1,2-b]pyridazin-6-yl)-azetidin-3-yl]-carbamic acid tert-butyl ester | Gen-4-a A2-B2-C1-D1-E4a | 523 | 524 (M + H) |
| 155 | 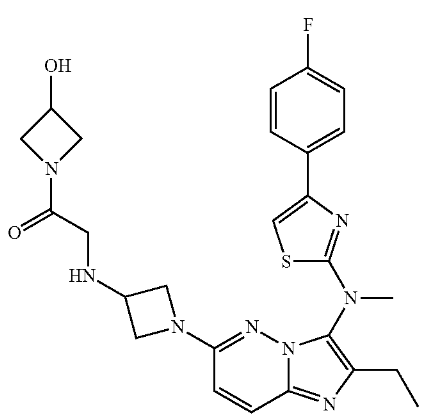 [SMILES: CCc1nc2ccc(N3CC(NCC(=O)N4CC(O)C4)C3)nn2c1N(C)c1nc(-c2ccc(F)cc2)cs1] | 2-(1-(2-ethyl-3-((4-(4-fluorophenyl)thiazol-2-yl)(methyl)amino)imidazo[1,2-b]pyridazin-6-yl)azetidin-3-ylamino)-1-(3-hydroxyazetidin-1-yl)ethanone | Gen-5-aa A2-B2-C1-D1-E4a E5a-E8 | 536 | 537 (M + H) |

TABLE II-continued

Illustrative compounds of the invention.

| Cpd | Structures | Name | Mtd | MW | MS Ms'd |
|---|---|---|---|---|---|
| 156 | 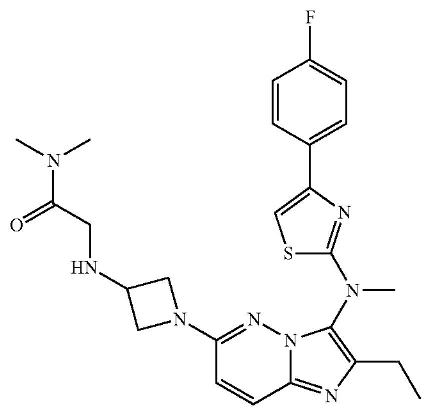 [SMILES: CCc1nc2ccc(N3CC(NCC(=O)N(C)C)C3)nn2c1N(C)c1nc(-c2ccc(F)cc2)cs1] | 2-(1-(2-ethyl-3-((4-(4-fluorophenyl)thiazol-2-yl)(methyl)amino)imidazo[1,2-b]pyridazin-6-yl)azetidin-3-ylamino)-N,N-dimethylacetamide | Gen-5-aa A2-B2-C1-D1-E1b-E5a-E8 | 508 | 509 (M + H) |
| 157 | 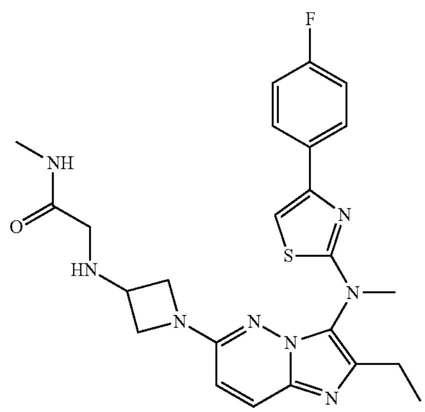 [SMILES: CCc1nc2ccc(N3CC(NCC(=O)NC)C3)nn2c1N(C)c1nc(-c2ccc(F)cc2)cs1] | 2-(1-(2-ethyl-3-((4-(4-fluorophenyl)thiazol-2-yl)(methyl)amino)imidazo[1,2-b]pyridazin-6-yl)azetidin-3-ylamino)-N-methylacetamide | Gen-5-aa A2-B2-C1-D1-E1b-E5a-E8 | 494 | 495 (M + H) |
| 158 | 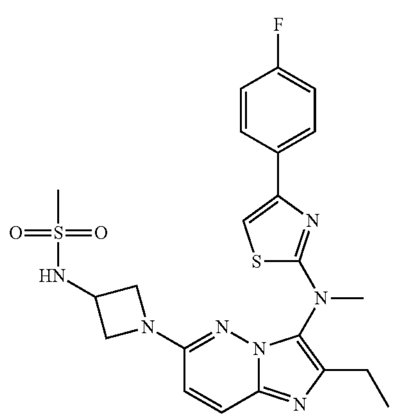 [SMILES: CCc1nc2ccc(N3CC(NS(C)(=O)=O)C3)nn2c1N(C)c1nc(-c2ccc(F)cc2)cs1] | N-(1-(2-ethyl-3-((4-(4-fluorophenyl)thiazol-2-yl)(methyl)amino)imidazo[1,2-b]pyridazin-6-yl)azetidin-3-yl)methanesulfonamide | Gen-5-aa A2-B2-C1-D1-E4a-E5a-E11 | 501 | 502 (M + H) |

US 9,796,719 B2

313                                                                   314

TABLE II-continued

Illustrative compounds of the invention.

| Cpd | Structures | Name | Mtd | MW | MS Ms'd |
|---|---|---|---|---|---|
| 159 | 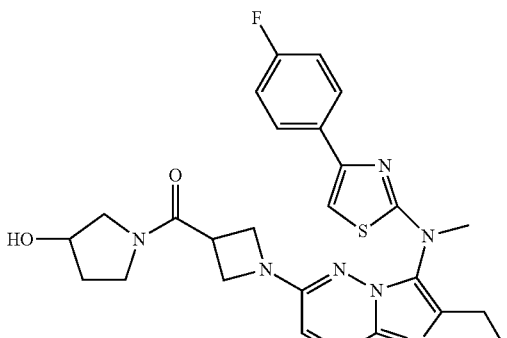 | (1-(2-ethyl-3-((4-(4-fluorophenyl)thiazol-2-yl)(methyl)amino)imidazo[1,2-b]pyridazin-6-yl)azetidin-3-yl)(3-hydroxypyrrolidin-1-yl)methanone | Gen-4-a A2-B2-C1-D1-E4b | 521 | 522 (M + H) |
| 160 | 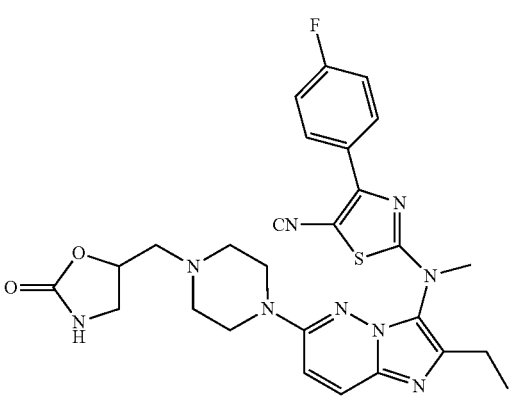 | 2-((2-ethyl-6-(4-((2-oxooxazolidin-5-yl)methyl)piperazin-1-yl)imidazo[1,2-b]pyridazin-3-yl)(methyl)amino)-4-(4-fluorophenyl)thiazole-5-carbonitrile | Gen-5-p A2-B2-C1-D2-E4b-E5b-E8 | 561 | 562 (M + H) |
| 161 | 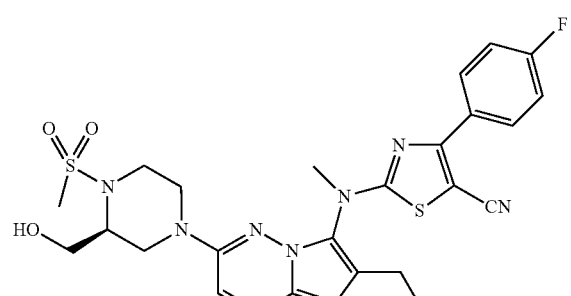 | (S)-2-((2-ethyl-6-(3-(hydroxymethyl)-4-(methylsulfonyl)piperazin-1-yl)imidazo[1,2-b]pyridazin-3-yl)(methyl)amino)-4-(4-fluorophenyl)thiazole-5-carbonitrile | Gen-5-x A2-B2-C1-D2-E4b-E5b-E18-E11-E19 | 570 | 571 (M + H) |
| 162 | 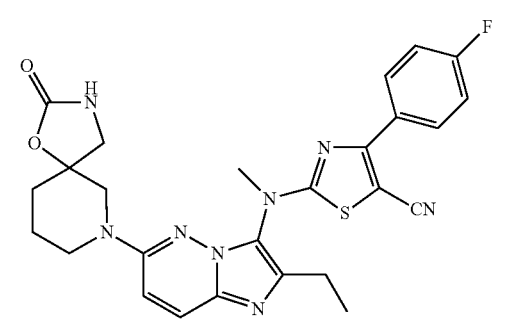 [SMILES: CCc1nc2ccc(N3CCCC4(CNC(=O)O4)C3)nn2c1N(C)c1nc(-c2ccc(F)cc2)c(C#N)s1] | 2-((2-ethyl-6-(2-oxo-1-oxa-3,7-diazaspiro[4.5]decan-7-yl)imidazo[1,2-b]pyridazin-3-yl)(methyl)amino)-4-(4-fluorophenyl)thiazole-5-carbonitrile | Gen-4-b A2-B2-C1-D2-E4a | 532 | 533 (M + H) |

TABLE II-continued

Illustrative compounds of the invention.

| Cpd | Structures | Name | Mtd | MW | MS Ms'd |
|---|---|---|---|---|---|
| 163 | 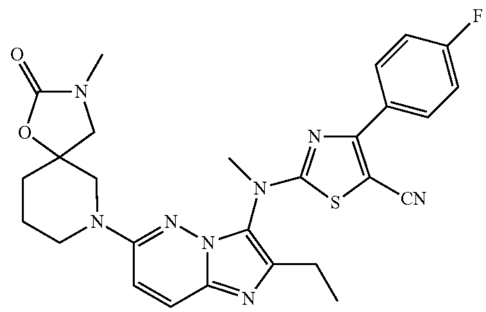 [SMILES: CCc1nc2ccc(N3CCCC4(CN(C)C(=O)O4)C3)nn2c1N(C)c1nc(-c2ccc(F)cc2)c(C#N)s1] | 2-((2-ethyl-6-(3-methyl-2-oxo-1-oxa-3,7-diazaspiro[4.5]decan-7-yl)imidazo[1,2-b]pyridazin-3-yl)(methyl)amino)-4-(4-fluorophenyl)thiazole-5-carbonitrile | Gen-4-b A2-B2-C1-D2-E4a | 546 | 547 (M + H) |
| 164 | 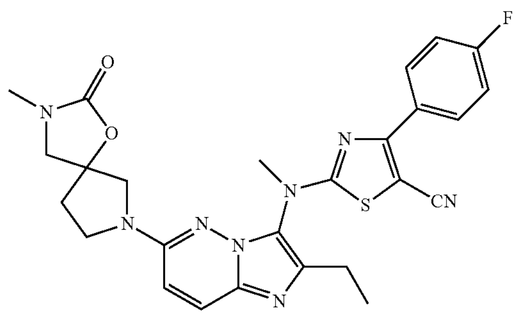 [SMILES: CCc1nc2ccc(N3CCC4(CN(C)C(=O)O4)C3)nn2c1N(C)c1nc(-c2ccc(F)cc2)c(C#N)s1] | 2-((2-ethyl-6-(3-methyl-2-oxo-1-oxa-3,7-diazaspiro[4.4]nonan-7-yl)imidazo[1,2-b]pyridazin-3-yl)(methyl)amino)-4-(4-fluorophenyl)thiazole-5-carbonitrile | Gen-4-b A2-B2-C1-D2-E4a | 532 | 533 (M + H) |
| 165 | 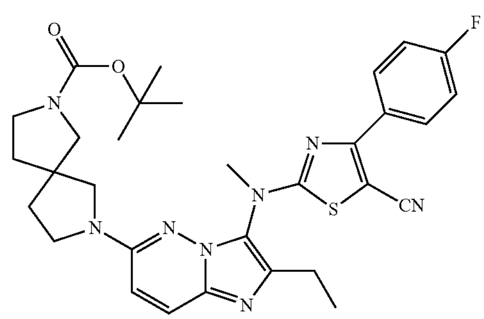 [SMILES: CCc1nc2ccc(N3CCC4(CCN(C(=O)OC(C)(C)C)C4)C3)nn2c1N(C)c1nc(-c2ccc(F)cc2)c(C#N)s1] | tert-butyl 7-(3-((5-cyano-4-(4-fluorophenyl)thiazol-2-yl)(methyl)amino)-2-ethylimidazo[1,2-b]pyridazin-6-yl)-2,7-diazaspiro[4.4]nonane-2-carboxylate | Gen-4-b A2-B2-C1-D2-E4a | 602 | 603 (M + H) |
| 166 | 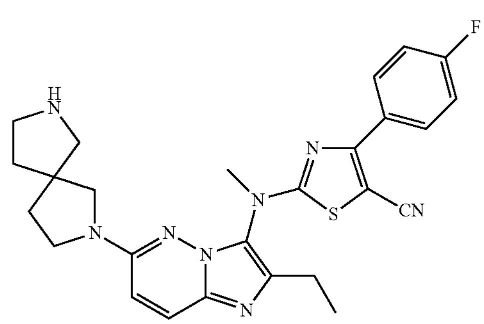 [SMILES: CCc1nc2ccc(N3CCC4(CCNC4)C3)nn2c1N(C)c1nc(-c2ccc(F)cc2)c(C#N)s1] | 2-((2-ethyl-6-(2,7-diazaspiro[4.4]nonan-2-yl)imidazo[1,2-b]pyridazin-3-yl)(methyl)amino)-4-(4-fluorophenyl)thiazole-5-carbonitrile | Cpd 165 A2-B2-C1-D2-E4a-E5b | 502 | 503 (M + H) |

TABLE II-continued

Illustrative compounds of the invention.

| Cpd | Structures | Name | Mtd | MW | MS Ms'd |
|---|---|---|---|---|---|
| 167 | 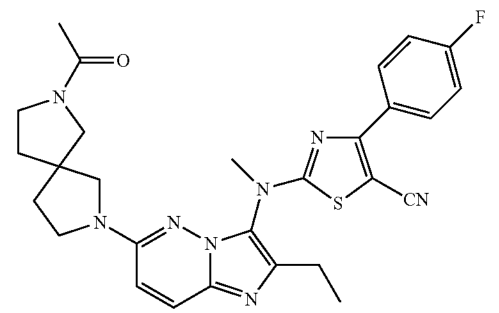 [SMILES: CCc1nc2ccc(N3CCC4(CCN(C(C)=O)C4)C3)nn2c1N(C)c1nc(-c2ccc(F)cc2)c(C#N)s1] | 2-((6-(7-acetoyl-2,7-diazaspiro[4.4]nonan-2-yl)-2-ethylimidazo[1,2-b]pyridazin-3-yl)(methyl)amino)-4-(4-fluorophenyl)thiazole-5-carbonitrile | Cpd 166 A2-B2-C1-D2-E4a-E5b-E9b | 544 | 545 (M + H) |
| 168 | 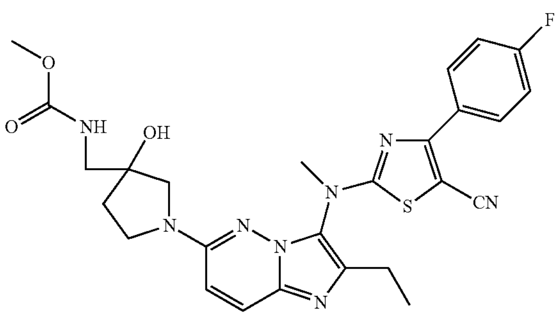 [SMILES: CCc1nc2ccc(N3CCC(O)(CNC(=O)OC)C3)nn2c1N(C)c1nc(-c2ccc(F)cc2)c(C#N)s1] | methyl (1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl) | Gen-4-b A2-B2-C1-D2-E4a | 550 | 551 (M + H) |
| 169 | 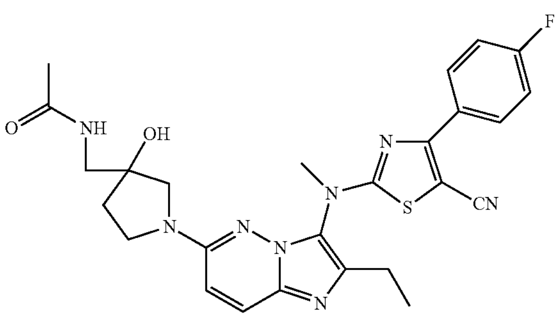 [SMILES: CCc1nc2ccc(N3CCC(O)(CNC(C)=O)C3)nn2c1N(C)c1nc(-c2ccc(F)cc2)c(C#N)s1] | N-((1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl)methyl)acetamide | Gen-4-b A2-B2-C1-D2-E4a | 534 | 535 (M + H) |
| 170 | 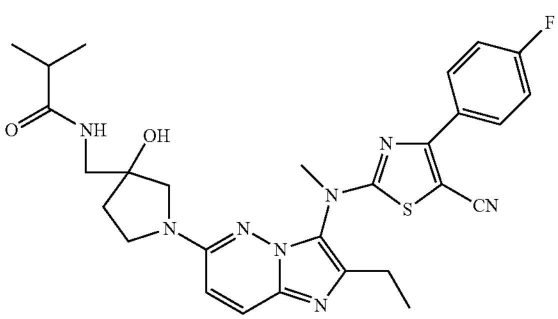 [SMILES: CCc1nc2ccc(N3CCC(O)(CNC(=O)C(C)C)C3)nn2c1N(C)c1nc(-c2ccc(F)cc2)c(C#N)s1] | N-((1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl)methyl)isobutyramide | Gen-4-b A2-B2-C1-D2-E4a | 562 | 563 (M + H) |

TABLE II-continued

Illustrative compounds of the invention.

| Cpd | Structures | Name | Mtd | MW | MS Ms'd |
|---|---|---|---|---|---|
| 171 | 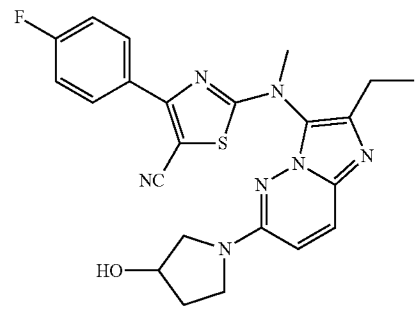 [SMILES: CCc1nc2ccc(N3CCC(O)C3)nn2c1N(C)c1nc(-c2ccc(F)cc2)c(C#N)s1] | 2-((2-ethyl-6-(3-hydroxypyrrolidin-1-yl)imidazo[1,2-b]pyridazin-3-yl)(methyl)amino)-4-(4-fluorophenyl)thiazole-5-carbonitrile | Gen-4-b A2-B2-C1-D2-E4a | 463 | 464 (M + H) |
| 172 | 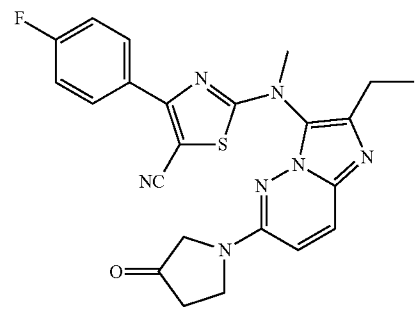 [SMILES: CCc1nc2ccc(N3CCC(=O)C3)nn2c1N(C)c1nc(-c2ccc(F)cc2)c(C#N)s1] | 2-((2-ethyl-6-(3-oxopyrrolidin-1-yl)imidazo[1,2-b]pyridazin-3-yl)(methyl)amino)-4-(4-fluorophenyl)thiazole-5-carbonitrile | Cpd 171 A2-B2-C1-D2-E4a-E7 | 461 | 462 (M + H) |
| 173 | 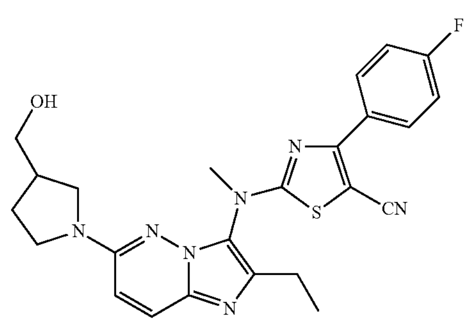 [SMILES: CCc1nc2ccc(N3CCC(CO)C3)nn2c1N(C)c1nc(-c2ccc(F)cc2)c(C#N)s1] | 2-((2-ethyl-6-(3-(hydroxymethyl)pyrrolidin-1-yl)imidazo[1,2-b]pyridazin-3-yl)(methyl)amino)-4-(4-fluorophenyl)thiazole-5-carbonitrile | Gen-4-b A2-B2-C1-D2-E4a | 477 | 478 (M + H) |
| 174 | 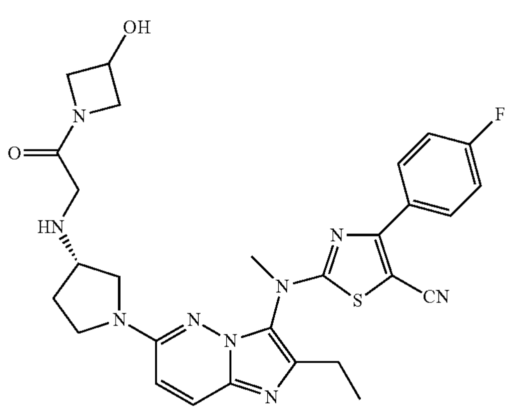 [SMILES: CCc1nc2ccc(N3CC[C@H](NCC(=O)N4CC(O)C4)C3)nn2c1N(C)c1nc(-c2ccc(F)cc2)c(C#N)s1] | (S)-2-((2-ethyl-6-(3-(2-(3-hydroxyazetidin-1-yl)-2-oxoethylamino)pyrrolidin-1-yl)imidazo[1,2-b]pyridazin-3-yl)(methyl)amino)-4-(4-fluorophenyl)thiazole-5-carbonitrile | Gen-5-s A2-B2-C1-D2-E4a-E5b-E8 | 575 | 576 (M + H) |

TABLE II-continued

Illustrative compounds of the invention.

| Cpd | Structures | Name | Mtd | MW | MS Ms'd |
|---|---|---|---|---|---|
| 175 | 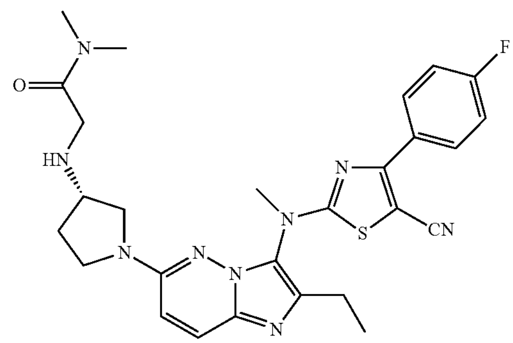 [SMILES: CCc1nc2ccc(N3CC[C@H](NCC(=O)N(C)C)C3)nn2c1N(C)c1nc(-c2ccc(F)cc2)c(C#N)s1] | (S)-2-(1-(3-((5-cyano-4-(4-fluorophenyl)thiazol-2-yl)(methyl)amino)-2-ethylimidazo[1,2-b]pyridazin-6-yl)pyrrolidin-3-ylamino)-N,N-dimethylacetamide | Gen-5-s A2-B2-C1-D2-E4a-E5b-E8 | 547 | 548 (M + H) |
| 176 | 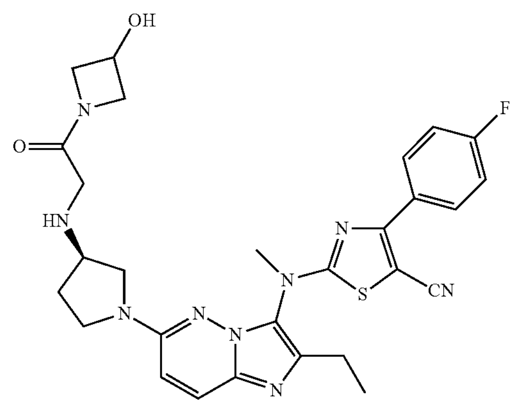 [SMILES: CCc1nc2ccc(N3CC[C@@H](NCC(=O)N4CC(O)C4)C3)nn2c1N(C)c1nc(-c2ccc(F)cc2)c(C#N)s1] | (R)-2-((2-ethyl-6-(3-(2-(3-hydroxyazetidin-1-yl)-2-oxoethylamino)pyrrolidin-1-yl)imidazo[1,2-b]pyridazin-3-yl)(methyl)amino)-4-(4-fluorophenyl)thiazole-5-carbonitrile | Gen-5-u A2-B2-C1-D2-E4a-E5b-E8 | 575 | 576 (M + H) |
| 177 | 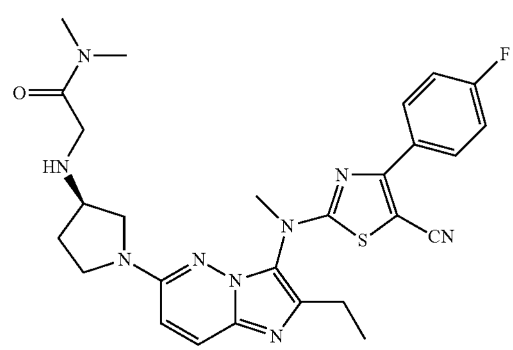 [SMILES: CCc1nc2ccc(N3CC[C@@H](NCC(=O)N(C)C)C3)nn2c1N(C)c1nc(-c2ccc(F)cc2)c(C#N)s1] | (R)-2-(1(3-((5-cyano-4-(4-fluorophenyl)thiazol-2-yl)(methyl)amino)-2-ethylimidazo[1,2-b]pyridazin-6-yl)pyrrolidin-3-ylamino)-N,N-dimethylacetamide | Gen-5-u A2-B2-C1-D2-E4a-E5b-E8 | 547 | 548 (M + H) |
| 178 | 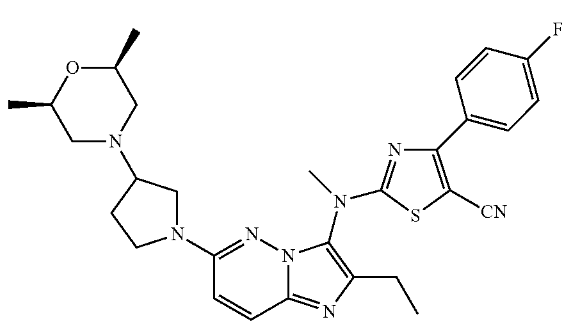 [SMILES: CCc1nc2ccc(N3CCC(N4C[C@@H](C)O[C@@H](C)C4)C3)nn2c1N(C)c1nc(-c2ccc(F)cc2)c(C#N)s1] | 2-((6-(3-((2S,6R)-2,6-dimethylmorpholino)pyrrolidin-1-yl)-2-ethylimidazo[1,2-b]pyridazin-3-yl)(methyl)amino)-4-(4-fluorophenyl)thiazole-5-carbonitrile | Gen-4-b A2-B2-C1-D2-E4b | 560 | 561 (M + H) |

TABLE II-continued

Illustrative compounds of the invention.

| Cpd | Structures | Name | Mtd | MW | MS Ms'd |
|---|---|---|---|---|---|
| 179 | 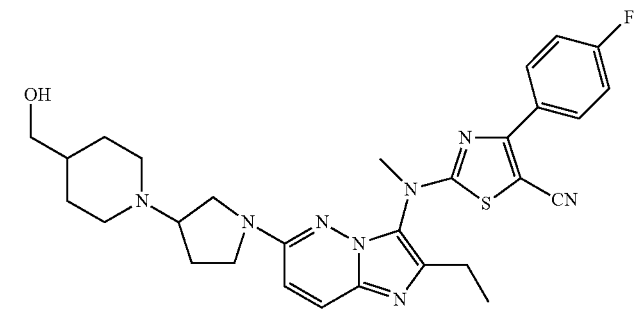 [SMILES: CCc1nc2ccc(N3CCC(N4CCC(CO)CC4)C3)nn2c1N(C)c1nc(-c2ccc(F)cc2)c(C#N)s1] | 2-((2-ethyl-6-(3-(4-(hydroxymethyl)piperidin-1-yl)pyrrolidin-1-yl)imidazo[1,2-b]pyridazin-3-yl)(methyl)amino)-4-(4-fluorophenyl)thiazole-5-carbonitrile | Gen-4-b A2-B2-C1-D2-E4b | 560 | 561 (M + H) |
| 180 | 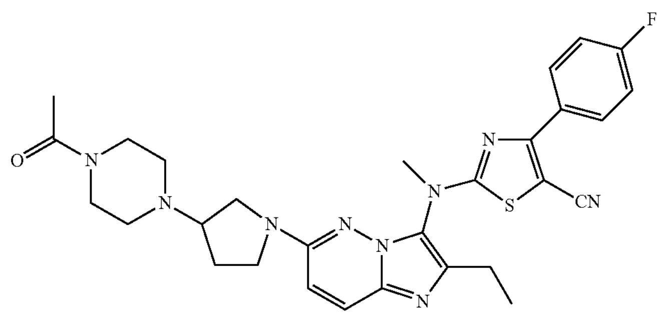 [SMILES: CCc1nc2ccc(N3CCC(N4CCN(C(C)=O)CC4)C3)nn2c1N(C)c1nc(-c2ccc(F)cc2)c(C#N)s1] | 2-((6-(3-(4-acetoylpiperazin-1-yl)pyrrolidin-1-yl)-2-ethylimidazo[1,2-b]pyridazin-3-yl)(methyl)amino)-4-(4-fluorophenyl)thiazole-5-carbonitrile | Gen-4-b A2-B2-C1-D2-E4b | 573 | 574 (M + H) |
| 181 | 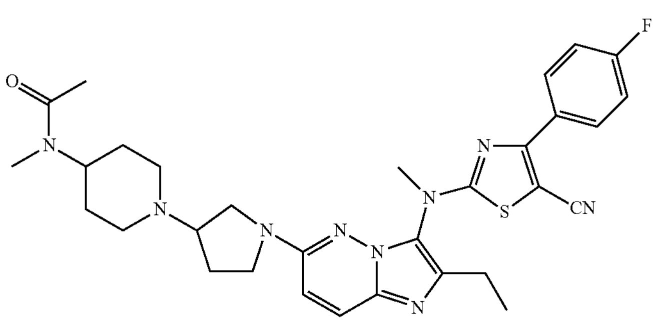 [SMILES: CCc1nc2ccc(N3CCC(N4CCC(N(C)C(C)=O)CC4)C3)nn2c1N(C)c1nc(-c2ccc(F)cc2)c(C#N)s1] | N-(1-(1-(3-((5-cyano-4-(4-fluorophenyl)thiazol-2-yl)(methyl)amino)-2-ethylimidazo[1,2-b]pyridazin-6-yl)pyrrolidin-3-yl)piperidin-4-yl)-N-methylacetamide | Gen-4-b A2-B2-C1-D2-E4b | 601 | 602 (M + H) |
| 182 | 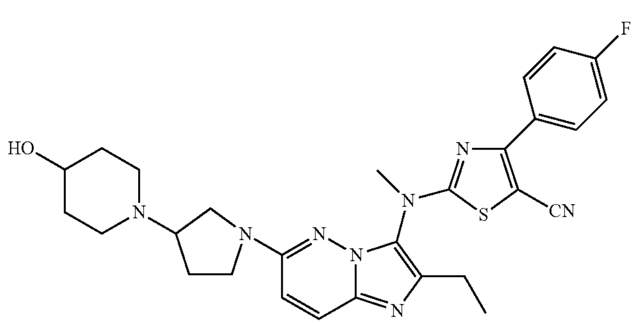 [SMILES: CCc1nc2ccc(N3CCC(N4CCC(O)CC4)C3)nn2c1N(C)c1nc(-c2ccc(F)cc2)c(C#N)s1] | 2-((2-ethyl-6-(3-(4-hydroxypiperidin-1-yl)pyrrolidin-1-yl)imidazo[1,2-b]pyridazin-3-yl)(methyl)amino)-4-(4-fluorophenyl)thiazole-5-carbonitrile | Gen-4-b A2-B2-C1-D2-E4b | 546 | 547 (M + H) |

TABLE II-continued

Illustrative compounds of the invention.

| Cpd | Structures | Name | Mtd | MW | MS Ms'd |
|---|---|---|---|---|---|
| 183 | 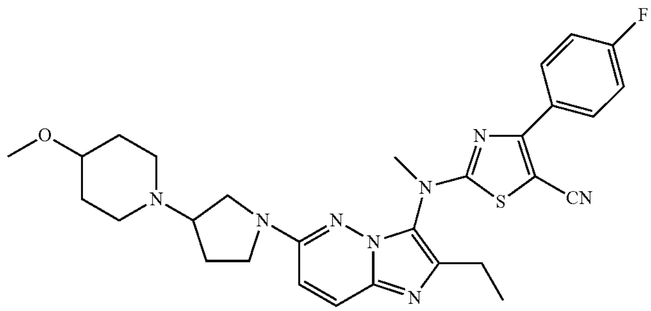 [SMILES: CCc1nc2ccc(N3CCC(N4CCC(OC)CC4)C3)nn2c1N(C)c1nc(-c2ccc(F)cc2)c(C#N)s1] | 2-((2-ethyl-6-(3-(4-methoxypiperidin-1-yl)pyrrolidin-1-yl)imidazo[1,2-b]pyridazin-3-yl)(methyl)amino)-4-(4-fluorophenyl)thiazole-5-carbonitrile | Gen-4-b A2-B2-C1-D2-E4b | 560 | 561 (M + H) |
| 184 | 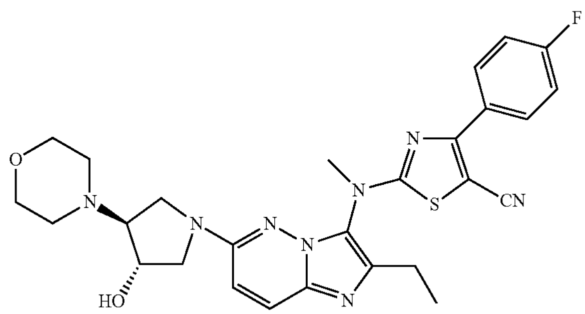 [SMILES: CCc1nc2ccc(N3C[C@H](O)[C@@H](N4CCOCC4)C3)nn2c1N(C)c1nc(-c2ccc(F)cc2)c(C#N)s1] | 2-((2-ethyl-6-((3S,4S)-3-hydroxy-4-morpholino-pyrrolidin-1-yl)imidazo[1,2-b]pyridazin-3-yl)(methyl)amino)-4-(4-fluorophenyl)thiazole-5-carbonitrile | Gen-4-b A2-B2-C1-D2-E4b | 548 | 549 (M + H) |
| 185 | 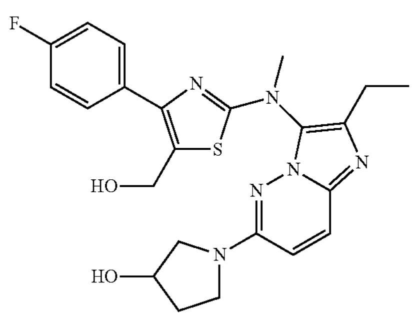 [SMILES: CCc1nc2ccc(N3CCC(O)C3)nn2c1N(C)c1nc(-c2ccc(F)cc2)c(CO)s1] | 1-(2-ethyl-3-((4-(4-fluorophenyl)-5-(hydroxymethyl)thiazol-2-yl)(methyl)amino)imidazo[1,2-b]pyridazin-6-yl)pyrrolidin-3-ol | Gen-4-c A2-B2-C1-D2-E14-E4a | 468 | 469 (M + H) |
| 186 | 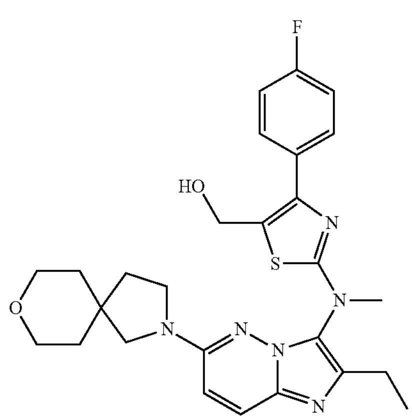 [SMILES: CCc1nc2ccc(N3CCC4(CCOCC4)C3)nn2c1N(C)c1nc(-c2ccc(F)cc2)c(CO)s1] | (2-((2-ethyl-6-(8-oxa-2-azaspiro[4.5]decan-2-yl)[1,2-b]pyridazin-3-yl)(methyl)amino)-4-(4-fluorophenyl)thiazol-5-yl)methanol | Gen-4-c A2-B2-C1-D1-E14-E4a | 522 | 523 (M + H) |

TABLE II-continued

Illustrative compounds of the invention.

| Cpd | Structures | Name | Mtd | MW | MS Ms'd |
|---|---|---|---|---|---|
| 187 | 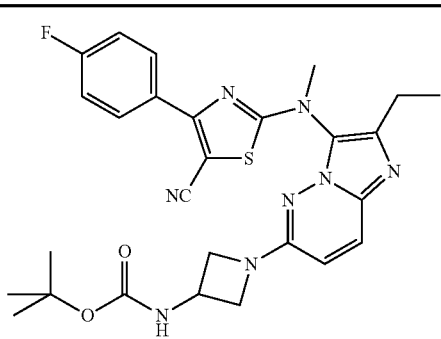 | [1-(3-{[5-Cyano-4-(4-fluoro-phenyl)-thiazol-2-yl]-methyl-amino}-2-ethyl-imidazo[1,2-b]pyridazin-6-yl)-azetidin-3-yl]-carbamic acid tert-butyl ester | Gen-4-b A2-B2-C1-D2-E1b | 548 | 549 (M + H) |
| 188 | 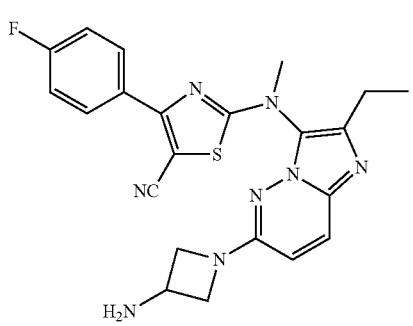 [SMILES: CCc1nc2ccc(N3CC(N)C3)nn2c1N(C)c1nc(-c2ccc(F)cc2)c(C#N)s1] | 2-((6-(3-aminoazetidin-1-yl)-2-ethylimidazo[1,2-b]pyridazin-3-yl)(methyl)amino)-4-(4-fluorophenyl)thiazole-5-carbonitrile | Cpd 187 A2-B2-C1-D2-E1b-E5a | 448 | 449 (M + H) |
| 189 | 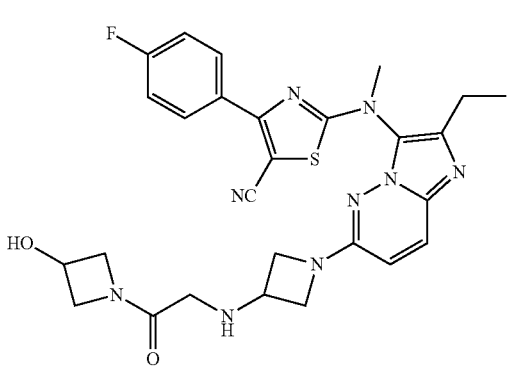 [SMILES: CCc1nc2ccc(N3CC(NCC(=O)N4CC(O)C4)C3)nn2c1N(C)c1nc(-c2ccc(F)cc2)c(C#N)s1] | 2-((2-ethyl-6-(3-(2-(3-hydroxyazetidin-1-yl)-2-oxoethylamino)azetidin-1-yl)imidazo[1,2-b]pyridazin-3-yl)(methyl)amino)-4-(4-fluorophenyl)thiazole-5-carbonitrile | Cpd 188 A2-B2-C1-D2-E1b-E5a-E8 | 561 | 562 (M + H) |
| 190 | 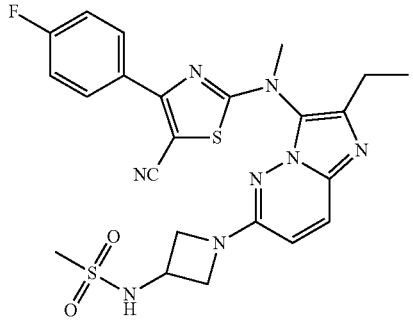 [SMILES: CCc1nc2ccc(N3CC(NS(C)(=O)=O)C3)nn2c1N(C)c1nc(-c2ccc(F)cc2)c(C#N)s1] | N-(1-(3-((5-cyano-4-(4-fluorophenyl)thiazol-2-yl)(methyl)amino)-2-ethylimidazo[1,2-b]pyridazin-6-yl)azetidin-3-yl)methanesulfonamide | Cpd 188 A2-B2-C1-D2-E1b-E5a-E11 | 526 | 527 (M + H) |

TABLE II-continued

Illustrative compounds of the invention.

| Cpd | Structures | Name | Mtd | MW | MS Ms'd |
|---|---|---|---|---|---|
| 191 | 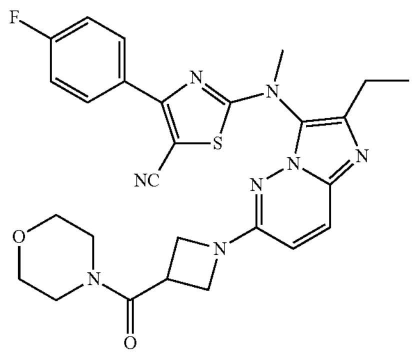 [SMILES: CCc1nc2ccc(N3CC(C(=O)N4CCOCC4)C3)nn2c1N(C)c1nc(-c2ccc(F)cc2)c(C#N)s1] | 2-((2-ethyl-6-(3-(morpholine-4-carbonyl)azetidin-1-yl)imidazo[1,2-b]pyridazin-3-yl)(methyl)amino)-4-(4-fluorophenyl)thiazole-5-carbonitrile | Gen-4-b A2-B2-C1-D2-E4a | 546 | 547 (M + H) |
| 192 | 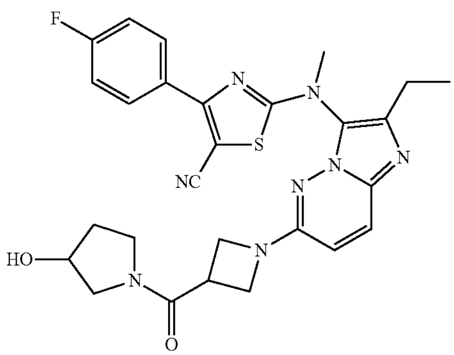 [SMILES: CCc1nc2ccc(N3CC(C(=O)N4CCC(O)C4)C3)nn2c1N(C)c1nc(-c2ccc(F)cc2)c(C#N)s1] | 2-((2-ethyl-6-(3-(3-hydroxy-pyrrolidine-1-carbonyl)azetidin-1-yl)imidazo[1,2-b]pyridazin-3-yl)(methyl)amino)-4-(4-fluorophenyl)thiazole-5-carbonitrile | Gen-4-b A2-B2-C1-D2-E4a | 546 | 547 (M + H) |
| 193 | 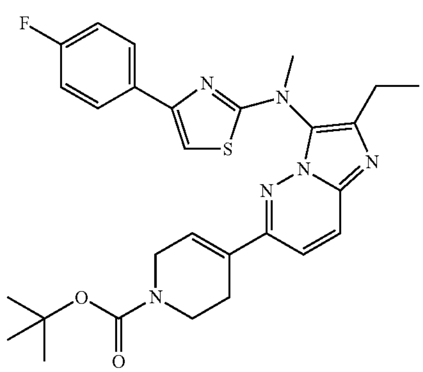 [SMILES: CCc1nc2ccc(C3=CCN(C(=O)OC(C)(C)C)CC3)nn2c1N(C)c1nc(-c2ccc(F)cc2)cs1] | 4-(2-Ethyl-3-{[4-(4-fluoro-phenyl)-thiazol-2-yl]-methyl-amino}-imidazo[1,2-b]pyridazin-6-yl)-3,6-dihydro-2H-pyridine-1-carboxylic acid tert-butyl ester | Gen-4-a A2-B2-C1-D1-E2 | 534 | 535 (M + H) |
| 194 | 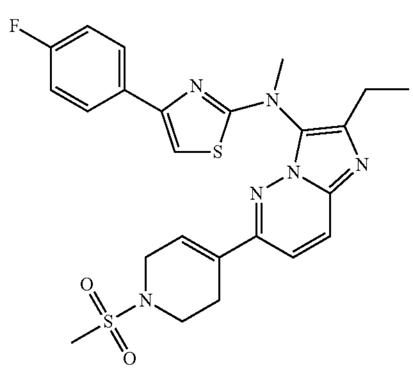 [SMILES: CCc1nc2ccc(C3=CCN(S(C)(=O)=O)CC3)nn2c1N(C)c1nc(-c2ccc(F)cc2)cs1] | N-(2-ethyl-6-(1-(methylsulfonyl)-1,2,3,6-tetrahydropyridin-4-yl)imidazo[1,2-b]pyridazin-3-yl)-4-(4-fluorophenyl)-N-methylthiazol-2-amine | Gen-5-a A2-B2-C1-D1-E2-E5b-E11 | 512 | 513 (M + H) |

TABLE II-continued

Illustrative compounds of the invention.

| Cpd | Structures | Name | Mtd | MW | MS Ms'd |
|---|---|---|---|---|---|
| 195 | 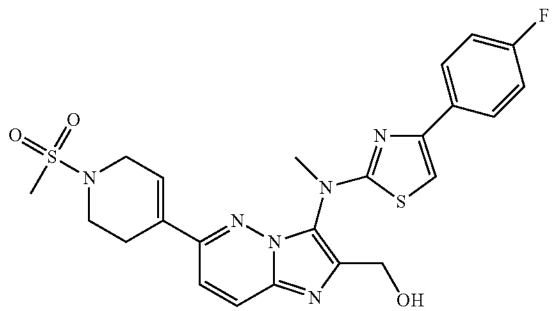 [SMILES: CN(c1nc(-c2ccc(F)cc2)cs1)c1c(CO)nc2ccc(C3=CCN(S(C)(=O)=O)CC3)nn12] | (3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)methanol | Gen-5-aag A1-B1-C1-D1-see Cpd 195-E2-see Cpd 195 | 514 | 515 (M + H) |
| 196 | 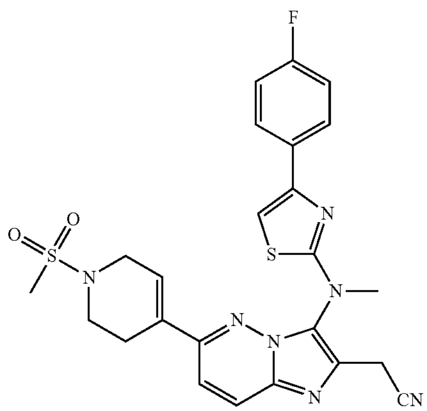 [SMILES: CN(c1nc(-c2ccc(F)cc2)cs1)c1c(CC#N)nc2ccc(C3=CCN(S(C)(=O)=O)CC3)nn12] | 2-(3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)acetonitrile | Gen-5-z A1-B1-C1-D1-see Cpd 195-E2-See Cpd 196 | 523 | 524 (M + H) |
| 197 | 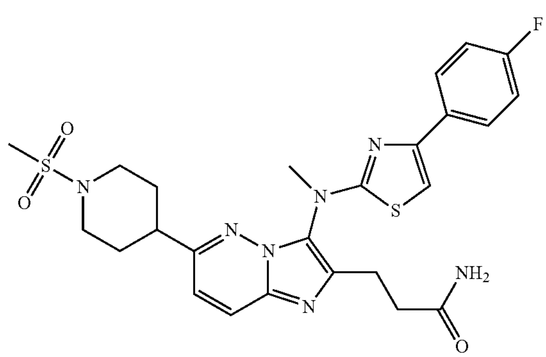 [SMILES: CN(c1nc(-c2ccc(F)cc2)cs1)c1c(CCC(N)=O)nc2ccc(C3CCN(S(C)(=O)=O)CC3)nn12] | 3-(3-((4-(4-fluorophenyl)thiazol-2-yl)(methyl)amino)-6-(1-(methylsulfonyl)piperidin-4-yl)imidazo[1,2-b]pyridazin-2-yl)propanamide | Gen-5-aaj A1-B1-C1-D1-See Cpd 197-E2-E6- See Cpd 197 | 557 | 558 (M + H) |
| 198 | 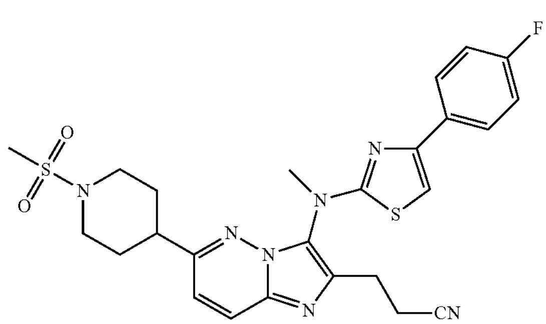 [SMILES: CN(c1nc(-c2ccc(F)cc2)cs1)c1c(CCC#N)nc2ccc(C3CCN(S(C)(=O)=O)CC3)nn12] | 3-(3-((4-(4-fluorophenyl)thiazol-2-yl)(methyl)amino)-6-(1-(methylsulfonyl)piperidin-4-yl)imidazo[1,2-b]pyridazin-2-yl)propanenitrile | Cpd 197 A1-B1-C1-D1-See Cpd 197-E2-E6-See Cpd 197-See Cpd 198 | 539 | 540 (M + H) |

TABLE II-continued

Illustrative compounds of the invention.

| Cpd | Structures | Name | Mtd | MW | MS Ms'd |
|---|---|---|---|---|---|
| 199 | 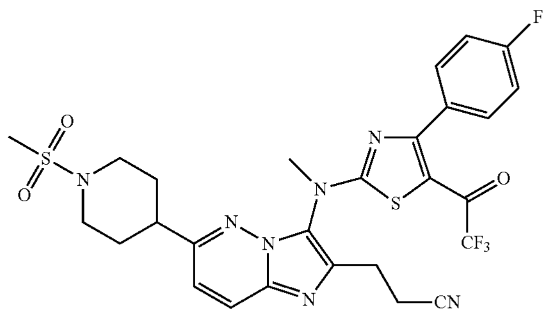 [SMILES: CN(c1nc(-c2ccc(F)cc2)c(C(=O)C(F)(F)F)s1)c1c(CCC#N)nc2ccc(C3CCN(S(C)(=O)=O)CC3)nn12] | 3-(3-((4-(4-fluorophenyl)-5-(2,2,2-trifluoroacetoyl)thiazol-2-yl)(methyl)amino)-6-(1-(methylsulfonyl)piperidin-4-yl)imidazo[1,2-b]pyridazin-2-yl)propanenitrile | Cpd 197 A1-B1-C1-D1-see Cpd 199-E2-E6-see Cpd 199 | 635 | 636 (M + H) |
| 200 | 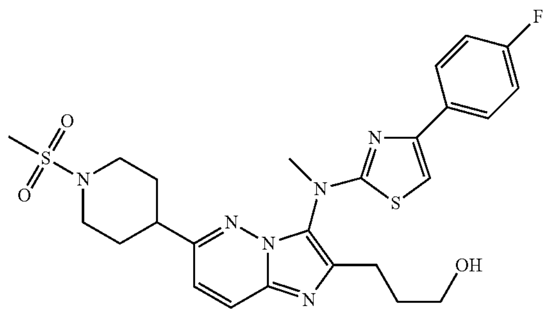 [SMILES: CN(c1nc(-c2ccc(F)cc2)cs1)c1c(CCCO)nc2ccc(C3CCN(S(C)(=O)=O)CC3)nn12] | 3-(3-((4-(4-fluorophenyl)thiazol-2-yl)(methyl)amino)-6-(1-(methylsulfonyl)piperidin-4-yl)imidazo[1,2-b]pyridazin-2-yl)propan-1-ol | Gen-5-aaj A1-B1-C1-D1-See Cpd 197-E2-E6-see Cpd 197-See Cpd 200 | 544 | 545 (M + H) |
| 201 | 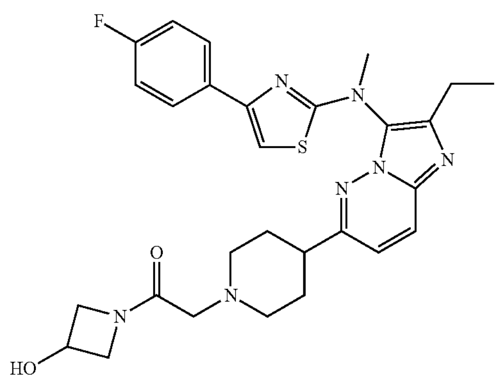 [SMILES: CCc1nc2ccc(C3CCN(CC(=O)N4CC(O)C4)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperidin-1-yl)-1-(3-hydroxyazetidin-1-yl)ethanone | Gen-5-k A2-B2-C1-D1-E2-E5b-E6-E8 | 549 | 550 (M + H) |
| 202 | 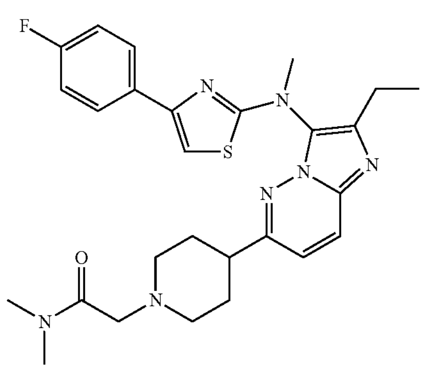 [SMILES: CCc1nc2ccc(C3CCN(CC(=O)N(C)C)CC3)nn2c1N(C)c1nc(-c2ccc(F)cc2)cs1] | 2-(4-(2-ethyl-3-((4-(4-fluorophenyl)thiazol-2-yl)(methyl)amino)imidazo[1,2-b]pyridazin-6-yl)piperidin-1-yl)-N,N-dimethylacetamide | Gen-5-k A2-B2-C1-D1-E2-E5b-E6-E8 | 521 | 522 (M + H) |

TABLE II-continued

Illustrative compounds of the invention.

| Cpd | Structures | Name | Mtd | MW | MS Ms'd |
|---|---|---|---|---|---|
| 203 | 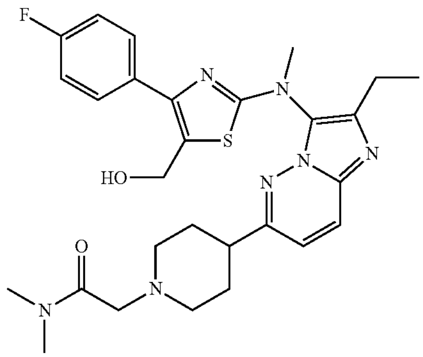 [SMILES: CCc1nc2ccc(C3CCN(CC(=O)N(C)C)CC3)nn2c1N(C)c1nc(-c2ccc(F)cc2)c(CO)s1] | 2-(4-(2-ethyl-3-((4-(4-fluorophenyl)-5-(hydroxymethyl)thiazol-2-yl)(methyl)amino)imidazo[1,2-b]pyridazin-6-yl)piperidin-1-yl)-N,N-dimethylacetamide | Cpd 202 A2-B2-C1-D1-E2-E5b-E6-E8-E14 | 551 | 552 (M + H) |
| 204 | 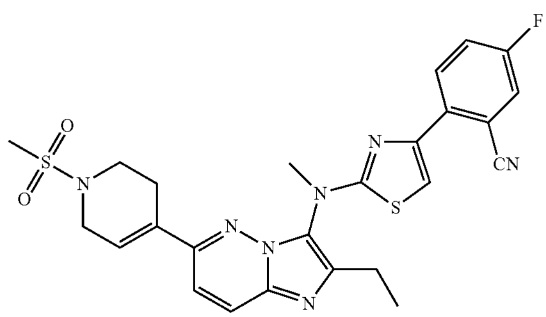 [SMILES: CCc1nc2ccc(C3=CCN(S(C)(=O)=O)CC3)nn2c1N(C)c1nc(-c2ccc(F)cc2C#N)cs1] | 2-(2-((2-ethyl-6-(1-(methylsulfonyl)-1,2,3,6-tetrahydropyridin-4-yl)imidazo[1,2-b]pyridazin-3-yl)(methyl)amino)thiazol-4-yl)-5-fluorobenzonitrile | Gen-4-g A2-B2-C1-D1-E2 | 537 | 538 (M + H) |
| 205 | 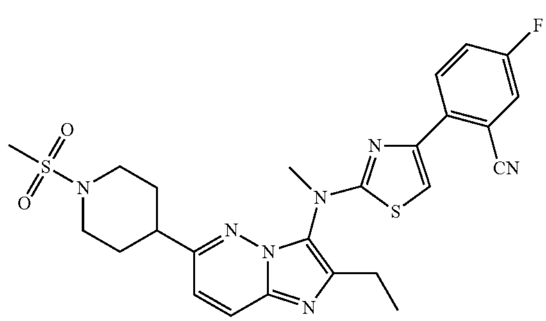 [SMILES: CCc1nc2ccc(C3CCN(S(C)(=O)=O)CC3)nn2c1N(C)c1nc(-c2ccc(F)cc2C#N)cs1] | 2-(2-((2-ethyl-6-(1-(methylsulfonyl)piperidin-4-yl)imidazo[1,2-b]pyridazin-3-yl)(methyl)amino)thiazol-4-yl)-5-fluorobenzonitrile | Cpd 204 A2-B2-C1-D1-E2-E6 | 539 | 540 (M + H) |
| 206 | 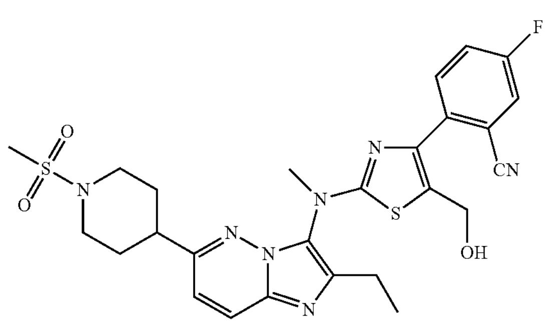 [SMILES: CCc1nc2ccc(C3CCN(S(C)(=O)=O)CC3)nn2c1N(C)c1nc(-c2ccc(F)cc2C#N)c(CO)s1] | 2-(2-((2-ethyl-6-(1-(methylsulfonyl)piperidin-4-yl)imidazo[1,2-b]pyridazin-3-yl)(methyl)amino)-5-(hydroxymethyl)thiazol-4-yl)-5-fluorobenzonitrile | Cpd 205 A2-B2-C1-D1-E2-E6-E14 | 569 | 570 (M + H) |

TABLE II-continued

Illustrative compounds of the invention.

| Cpd | Structures | Name | Mtd | MW | MS Ms'd |
|---|---|---|---|---|---|
| 207 | 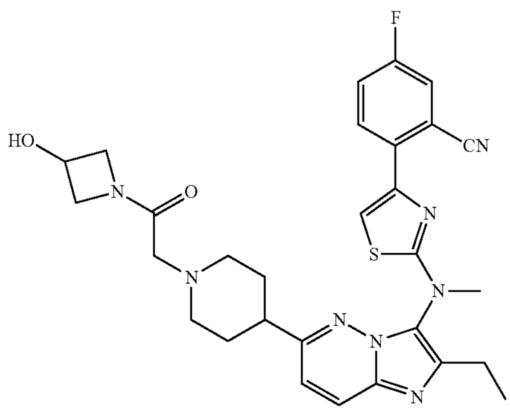 [SMILES: CCc1nc2ccc(C3CCN(CC(=O)N4CC(O)C4)CC3)nn2c1N(C)c1nc(-c2ccc(F)cc2C#N)cs1] | 2-(2-((2-ethyl-6-(1-(2-(3-hydroxyazetidin-1-yl)-2-oxoethyl)piperidin-4-yl)imidazo[1,2-b]pyridazin-3-yl)(methyl)amino)thiazol-4-yl)-5-fluorobenzonitrile | Gen-5-aq A2-B2-E2-E6-C2-D1-E5b-E8 | 574 | 575 (M + H) |
| 208 | 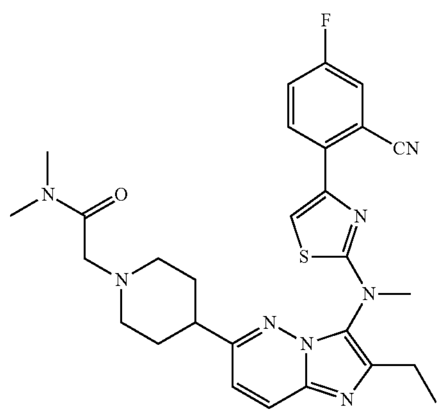 [SMILES: CCc1nc2ccc(C3CCN(CC(=O)N(C)C)CC3)nn2c1N(C)c1nc(-c2ccc(F)cc2C#N)cs1] | 2-(4-(3-((4-(2-cyano-4-fluorophenyl)thiazol-2-yl)(methyl)amino)-2-ethylimidazo[1,2-b]pyridazin-6-yl)piperidin-1-yl)-N,N-dimethylacetamide | Gen-5-aq A2-B2-E2-E6-C2-D1-E5b-E8 | 546 | 547 (M + H) |
| 209 | 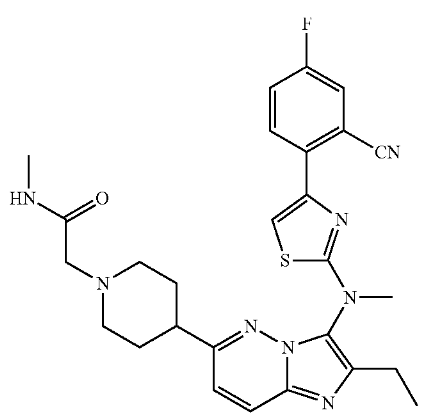 [SMILES: CCc1nc2ccc(C3CCN(CC(=O)NC)CC3)nn2c1N(C)c1nc(-c2ccc(F)cc2C#N)cs1] | 2-(4-(3-((4-(2-cyano-4-fluorophenyl)thiazol-2-yl)(methyl)amino)-2-ethylimidazo[1,2-b]pyridazin-6-yl)piperidin-1-yl)-N-methylacetamide | Gen-5-aq A2-B2-E2-E6-C2-D1-E5b-E8 | 532 | 533 (M + H) |

TABLE II-continued

Illustrative compounds of the invention.

| Cpd | Structures | Name | Mtd | MW | MS Ms'd |
|---|---|---|---|---|---|
| 210 | 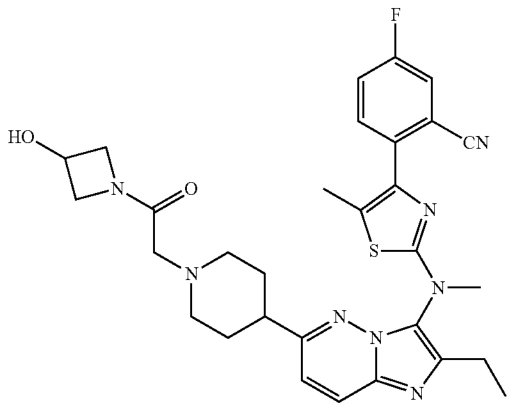 [SMILES: CCc1nc2ccc(C3CCN(CC(=O)N4CC(O)C4)CC3)nn2c1N(C)c1nc(-c2ccc(F)cc2C#N)c(C)s1] | 2-(2-((2-ethyl-6-(1-(2-(3-hydroxyazetidin-1-yl)-2-oxoethyl)piperidin-4-yl)imidazo[1,2-b]pyridazin-3-yl)(methyl)amino)-5-methylthiazol-4-yl)-5-fluorobenzonitrile | Gen-5-as A2-B2-E2-E6-C2-D1-E5b-E8 | 588 | 589 (M + H) |
| 211 | 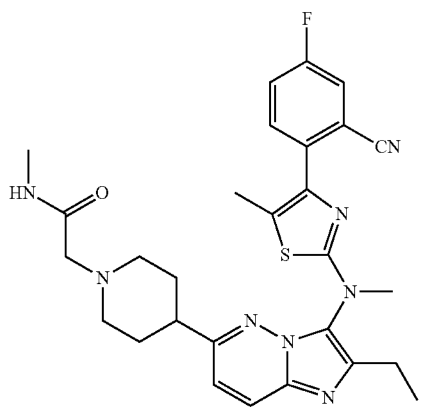 [SMILES: CCc1nc2ccc(C3CCN(CC(=O)NC)CC3)nn2c1N(C)c1nc(-c2ccc(F)cc2C#N)c(C)s1] | 2-(4-(3-((4-(2-cyano-4-fluorophenyl)-5-methylthiazol-2-yl)(methyl)amino)-2-ethylimidazo[1,2-b]pyridazin-6-yl)piperidin-l-yl)-N-methylacetamide | Gen-5-as A2-B2-E2-E6-C2-D1-E5b-E8 | 546 | 547 (M + H) |
| 212 | 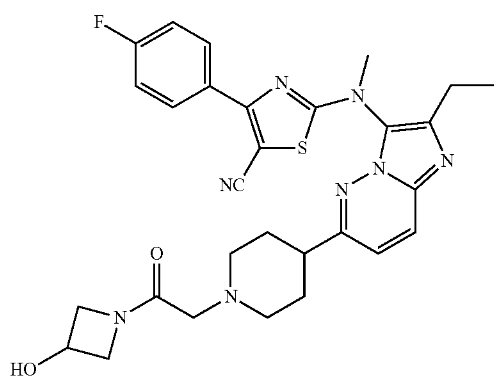 [SMILES: CCc1nc2ccc(C3CCN(CC(=O)N4CC(O)C4)CC3)nn2c1N(C)c1nc(-c2ccc(F)cc2)c(C#N)s1] | 2-((2-ethyl-6-(1-(2-(3-hydroxyazetidin-1-yl)-2-oxoethyl)piperidin-4-yl)imidazo[1,2-b]pyridazin-3-yl)(methyl)amino)-4-(4-fluorophenyl)thiazole-5-carbonitrile | Gen-5-ah A2-B2-C1-D2-E2-E6-E5b-E8 | 574 | 575 (M + H) |
| 213 | 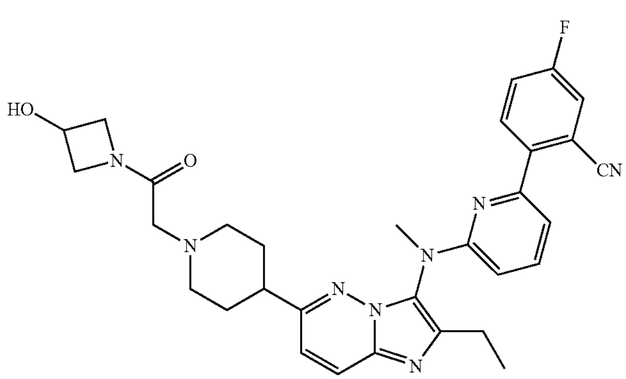 [SMILES: CCc1nc2ccc(C3CCN(CC(=O)N4CC(O)C4)CC3)nn2c1N(C)c1cccc(-c2ccc(F)cc2C#N)n1] | 2-(6-((2-ethyl-6-(1-(2-(3-hydroxyazetidin-1-yl)-2-oxoethyl)piperidin-4-yl)imidazo[1,2-b]pyridazin-3-yl)(methyl)amino)pyridin-2-yl)-5-fluorobenzonitrile | Gen-5-aac A2-B2-E2-E6-C2-D2-E5b-E8 | 568 | 569 (M + H) |

TABLE II-continued

Illustrative compounds of the invention.

| Cpd | Structures | Name | Mtd | MW | MS Ms'd |
|---|---|---|---|---|---|
| 214 | 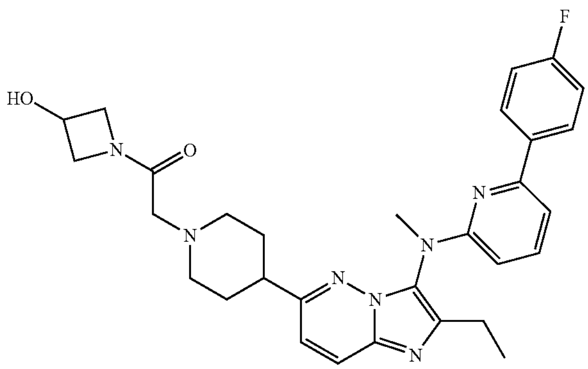 [SMILES: CCc1nc2ccc(C3CCN(CC(=O)N4CC(O)C4)CC3)nn2c1N(C)c1cccc(-c2ccc(F)cc2)n1] | 2-(4-(2-ethyl-3-((6-(4-fluorophenyl)pyridin-2-yl)(methyl)amino)imidazo[1,2-b]pyridazin-6-yl)piperidin-1-yl)-1-(3-hydroxyazetidin-1-yl)ethanone | Gen-5-ay A2-B2-E2-E6-C2-D2-E5b-E8 | 543 | 544 (M + H) |
| 215 | 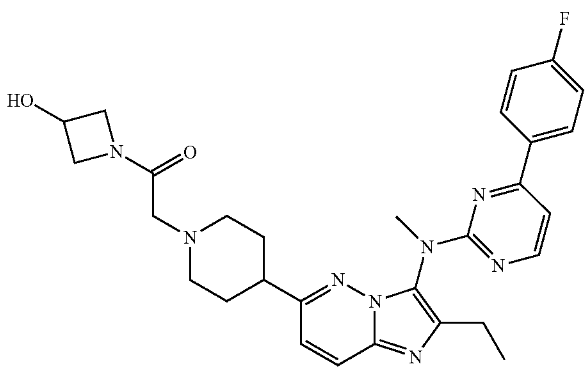 [SMILES: CCc1nc2ccc(C3CCN(CC(=O)N4CC(O)C4)CC3)nn2c1N(C)c1nccc(-c2ccc(F)cc2)n1] | 2-(4-(2-ethyl-3-((4-(4-fluorophenyl)pyrimidin-2-yl)(methyl)amino)imidazo[1,2-b]pyridazin-6-yl)piperidin-1-yl)-1-(3-hydroxyazetidin-1-yl)ethanone | Gen-5-aaa A2-B2-E2-E6-C2-D2-E5b-E8 | 544 | 545 (M + H) |
| 216 | 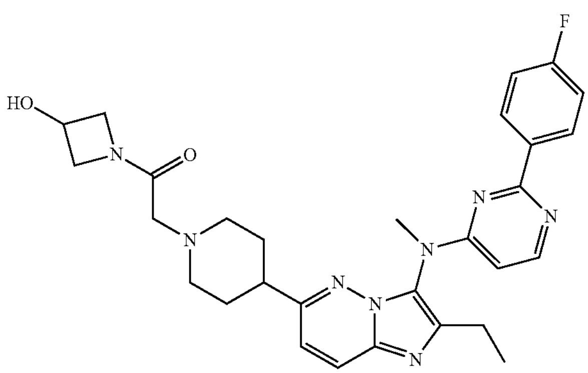 [SMILES: CCc1nc2ccc(C3CCN(CC(=O)N4CC(O)C4)CC3)nn2c1N(C)c1ccnc(-c2ccc(F)cc2)n1] | 2-(4-(2-ethyl-3-((2-(4-fluorophenyl)pyrimidin-4-yl)(methyl)amino)imidazo[1,2-b]pyridazin-6-yl)piperidin-1-yl)-1-(3-hydroxyazetidin-1-yl)ethanone | Gen-5-aae A2-B2-E2-E6-C2-D3-E5b-E8 | 544 | 545 (M + H) |
| 217 | 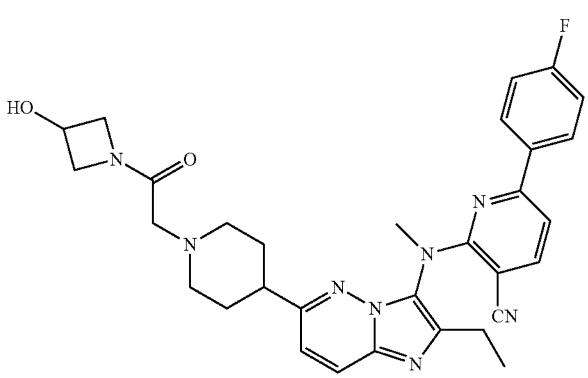 [SMILES: CCc1nc2ccc(C3CCN(CC(=O)N4CC(O)C4)CC3)nn2c1N(C)c1nc(-c2ccc(F)cc2)ccc1C#N] | 2-((2-ethyl-6-(1-(2-(3-hydroxyazetidin-1-yl)-2-oxoethyl)piperidin-4-yl)imidazo[1,2-b]pyridazin-3-yl)(methyl)amino)-6-(4-fluorophenyl)nicotinonitrile | Gen-5-aw A2-B2-E2-E6-C2-D3-E5b-E8 | 568 | 569 (M + H) |

TABLE II-continued

Illustrative compounds of the invention.

| Cpd | Structures | Name | Mtd | MW | MS Ms'd |
|-----|------------|------|-----|-----|---------|
| 218 | 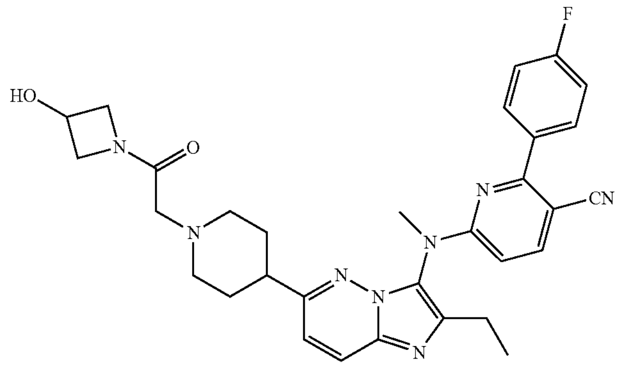 [SMILES: CCc1nc2ccc(C3CCN(CC(=O)N4CC(O)C4)CC3)nn2c1N(C)c1ccc(C#N)c(-c2ccc(F)cc2)n1] | 6-((2-ethyl-6-(1-(2-(3-hydroxyazetidin-1-yl)-2-oxoethyl)piperidin-4-yl)imidazo[1,2-b]pyridazin-3-yl)(methyl)amino)-2-(4-fluorophenyl)nicotinonitrile | Gen-5-au A2-B2-E2-E6-C2-D3-E5b-E8 | 568 | 569 (M + H) |
| 219 | 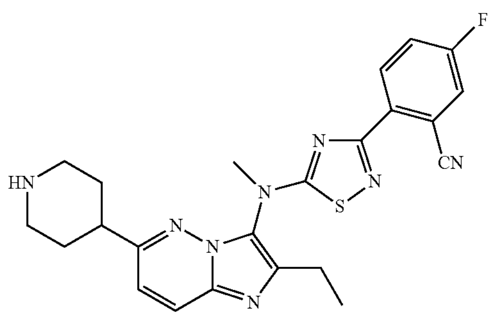 [SMILES: CCc1nc2ccc(C3CCNCC3)nn2c1N(C)c1nc(-c2ccc(F)cc2C#N)ns1] | 2-(5-((2-ethyl-6-(piperidin-4-yl)imidazo[1,2-b]pyridazin-3-yl)(methyl)amino)-1,2,4-thiadiazol-3-yl)-5-fluorobenzonitrile | Gen-5-ao A2-B2-E2-E6-C2-See Cpd 219 | 462 | 463 (M + H) |
| 220 | 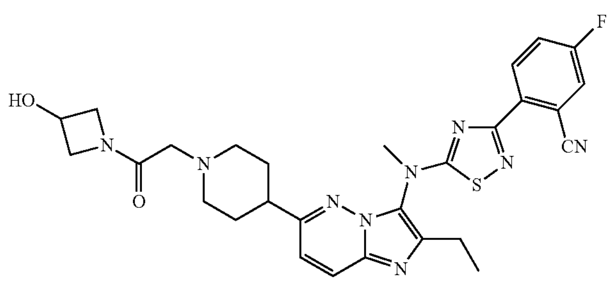 [SMILES: CCc1nc2ccc(C3CCN(CC(=O)N4CC(O)C4)CC3)nn2c1N(C)c1nc(-c2ccc(F)cc2C#N)ns1] | 2-(5-((2-ethyl-6-(1-(2-(3-hydroxyazetidin-1-yl)-2-oxoethyl)piperidin-4-yl)imidazo[1,2-b]pyridazin-3-yl)(methyl)amino)-1,2,4-thiadiazol-3-yl)-5-fluorobenzonitrile | Cpd 219 A2-B2-E2-E6-C2-See Cpd 219-E5b-E8 | 575 | 576 (M + H) |

TABLE III

NMR data of illustrative compounds of the invention.

Cpd  NMR data (δ)

2   $^1$H NMR (300 MHz, CDCl$_3$-d) δ ppm 8.84 (1 H, d), 8.21-8.11 (2 H, m), 7.19 (2 H, t), 6.92 (1 H, d), 4.69 (1 H, br. s), 4.51-4.42 (1 H, m), 4.30 (1 H, dd), 4.18-4.10 (1 H, m), 3.92 (1 H, dd), 3.63 (3 H, s), 3.45 (4 H, br. s), 3.26-3.09 (2 H, m), 2.86-2.72 (6 H, m), 1.36 (3 H, t)

23  $^1$H NMR (300 MHz, CDCl$_3$-d) δ ppm 9.05 (1 H, d), 8.20-8.08 (2 H, m), 7.59 (1 H, d), 7.18 (2 H, t), 4.73-4.60 (1 H, m), 4.53-4.41 (1 H, m), 4.32-4.16 (2 H, m), 4.03-3.90 (1 H, m), 3.65 (3 H, s), 3.50-3.20 (4 H, m), 2.91-2.60 (3 H, m), 2.75-2.62 (2 H, m), 2.18-2.00 (4 H, m), 1.38 (3 H, t)

24  $^1$H NMR (300 MHz, CDCl$_3$-d) δ ppm 9.05 (1 H, s), 8.14 (2 H, dd), 7.61 (1 H, br. s), 7.23-7.12 (2 H, m), 4.52 (1 H, dd), 3.79-3.56 (7 H, m), 3.56-3.42 (2 H, m), 3.42-3.25 (2 H, m), 2.91-2.74 (6 H, m), 2.20-2.01 (4 H, m), 2.02-1.89 (1 H, m), 1.38 (3 H, t)

25  $^1$H NMR (300 MHz, CDCl$_3$-d) δ ppm 9.04 (1 H, s), 8.19-8.07 (2 H, m), 7.58 (1 H, br. s), 7.17 (2 H, t), 4.60-4.44 (1 H, m), 3.78-3.56 (6 H, m), 3.54-3.26 (3 H, m), 3.25-3.12 (2 H, m), 2.89-2.70 (3 H, m), 2.66-2.35 (3 H, m), 2.15-1.88 (5 H, m), 1.38 (3 H, t)

27  $^1$H NMR (400 MHz, CDCl$_3$-d) δ ppm 8.16 (2 H, dd), 7.70 (1 H, d), 7.17 (2 H, t), 6.89 (1 H, d), 4.73-4.62 (1 H, m), 4.48-4.39 (1 H, m), 4.33-4.23 (1 H, m), 4.08 (1 H, dd), 3.89 (1 H, dd), 3.61 (3 H, s), 3.49 (4 H, br. s), 3.07 (2 H, s), 2.74 (2 H, q), 2.61 (4 H, br. s), 1.35 (3 H, t)

30  $^1$H NMR (400 MHz, CDCl$_3$-d) δ ppm 7.89-7.81 (2 H, m), 7.70 (1 H, d), 7.08 (2 H, t), 7.05-7.01 (1 H, m), 6.83 (1 H, d), 6.64 (1 H, s), 3.61 (3 H, s), 3.50-3.42 (4 H, m), 3.04 (2 H, s), 2.84 (3 H, d), 2.76 (2 H, q), 2.65-2.57 (4 H, m), 1.34 (3 H, t)

TABLE III-continued

NMR data of illustrative compounds of the invention.

| Cpd | NMR data (δ) |
|---|---|
| 40 | $^1$H NMR (400 MHz, CDCl$_3$-d) δ ppm 7.89-7.82 (2 H, m), 7.69 (1 H, d), 7.08 (2 H, t), 6.82 (1 H, d), 6.64 (1 H, s), 5.55 (1 H, br. s), 4.83-4.73 (1 H, m), 3.66 (1 H, t), 3.60 (3 H, s), 3.50-3.41 (4 H, m), 3.40-3.34 (1 H, m), 2.75 (2 H, q), 2.71-2.65 (4 H, m), 2.64-2.57 (2 H, m), 1.34 (3 H, t) |
| 43 | $^1$H NMR (400 MHz, CDCl$_3$-d) δ ppm 7.80-7.73 (2 H, m), 7.61 (1 H, d), 7.10 (2 H, t), 6.80 (1 H, d), 4.68-4.59 (2 H, m), 3.52 (3 H, s), 3.51-3.43 (4 H, m), 3.22-3.13 (2 H, m), 3.06 (3 H, s), 2.93 (3 H, s), 2.67 (2 H, q), 2.61-2.51 (4 H, m), 1.28 (3 H, t) |
| 45 | $^1$H NMR (400 MHz, MeOD-d$_4$) δ ppm 7.79-7.68 (2 H, m), 7.61 (1 H, dd), 7.25 (1 H, d), 7.22-7.13 (1 H, m), 7.07 (1 H, t), 3.64-3.48 (7 H, m) 3.26 (2 H, d), 3.08 (3 H, d), 2.93 (3 H, d), 2.80-2.69 (2 H, m), 2.58-2.65 (4 H, m), 1.33 (3 H, td) |
| 63 | $^1$H NMR (400 MHz, CDCl$_3$-d) δ ppm 7.89-7.82 (2 H, m), 7.71 (1 H, d), 7.09 (2 H, t), 6.80 (1 H, d), 6.66 (1 H, s), 4.15-4.00 (2 H, m), 4.00-3.92 (1 H, m), 3.88-3.77 (2 H, m), 3.60 (4 H, s), 3.38-3.26 (2 H, m), 3.26-2.99 (3 H, m), 2.76 (2 H, q), 2.54-2.42 (1 H, m), 2.41-2.32 (1 H, m), 2.24 (6 H, s), 2.05-1.91 (2 H, m), 1.34 (3 H, t) |
| 67 | $^1$H NMR (400 MHz, CDCl$_3$-d) δ ppm 7.89-7.81 (2 H, m), 7.72 (1 H, d), 7.08 (2 H, t), 6.82 (1 H, d), 6.66 (1 H, s), 4.23-4.09 (1 H, m), 4.09-4.01 (1 H, m), 3.96 (1 H, br. d), 3.84-3.63 (3 H, m), 3.60 (3 H, s), 3.32-3.08 (3 H, m), 2.94 (3 H, s), 2.76 (2 H, q), 1.34 (3 H, t) |
| 119 | $^1$H NMR (400 MHz, MeOD-d$_4$) δ ppm 7.91-7.83 (2 H, m), 7.70 (1 H, d), 7.10 (2 H, t), 6.92-6.87 (2 H, m), 3.81 (1 H, d), 3.75-3.66 (2 H, m), 3.64-3.53 (6 H, m), 2.84 (3 H, s), 2.70 (2 H, q), 2.44-2.31 (1 H, m), 2.28-2.14 (1 H, m), 1.31 (3 H, t) |
| 143 | $^1$H NMR (400 MHz, CDCl$_3$-d) δ ppm 7.86 (2 H, dd), 7.65 (1 H, d), 7.08 (2 H, t), 6.63 (1 H, s), 6.60 (1 H, d), 3.73-3.64 (2 H, m), 3.62 (3 H, s), 3.61-3.57 (1 H, m), 3.57-3.50 (1 H, m), 3.47-3.39 (1 H, m), 3.24 (1 H, dd), 2.75 (2 H, q), 2.61-2.49 (1 H, m), 2.18-2.08 (1 H, m), 1.88-1.77 (1 H, m), 1.34 (3 H, t) |
| 147 | $^1$H NMR (400 MHz, CDCl$_3$-d) δ ppm 7.91-7.80 (2 H, m), 7.64 (1 H, d), 7.07 (2 H, t), 6.63 (1 H, s), 6.57 (1 H, d), 3.76-3.63 (5 H, m), 3.62-3.57 (4 H, m), 3.45-3.35 (1 H, m), 3.23 (1 H, dd), 2.98-2.87 (1 H, m), 2.74 (2 H, q), 2.58 - 2.46 (4 H, m), 2.25-2.15 (1 H, m), 1.96-1.84 (1 H, m), 1.33 (3 H, t) |
| 161 | $^1$H NMR (400 MHz, CDCl$_3$-d) δ ppm 8.24-8.08 (2 H, m), 7.76 (1 H, d), 7.18 (2 H, t), 6.89 (1 H, d), 4.22-4.06 (2 H, m), 4.03-3.93 (1 H, m), 3.92-3.65 (3 H, m), 3.63 (3 H, s), 3.36-3.08 (3 H, m), 2.98 (3 H, s), 2.76 (2 H, q), 2.32-2.13 (1 H, m), 1.36 (3 H, t) |
| 172 | $^1$H NMR (400 MHz, CDCl$_3$-d) δ ppm 8.20-8.12 (2 H, m), 7.80 (1 H, d), 7.17 (2 H, t), 6.73 (1 H, d), 3.94-3.84 (4 H, m), 3.64 (3 H, s), 2.82-2.72 (4 H, m), 1.37 (3 H, t) |
| 189 | $^1$H NMR (300 MHz, CDCl$_3$-d) δ ppm 8.21-8.11 (2 H, m), 7.69 (1 H, d), 7.17 (2 H, t), 6.47 (1 H, d), 4.73-4.63 (1 H, m), 4.36-4.15 (4 H, m), 4.00 (1 H, dd), 3.94-3.78 (4 H, m), 3.61 (3 H, s), 3.28 (2 H, d), 2.74 (2 H, q), 1.35 (3 H, t) |
| 190 | $^1$H NMR (400 MHz, CDCl$_3$-d) δ ppm 8.20-8.11 (2 H, m), 7.84 (1 H, d), 7.17 (2 H, t), 6.53 (1 H, d), 5.11 (1 H, br. d), 4.51-4.35 (3 H, m), 3.98 (2 H, dd), 3.61 (3 H, s), 3.00 (3 H, s), 2.84-2.71 (2 H, m), 1.38 (3 H, t) |
| 198 | $^1$H NMR (400 MHz, DMSO-d$_6$) δ ppm 8.16 (1 H, d), 7.95-7.89 (2 H, m), 7.42 (1 H, d), 7.24 (3 H, t), 3.61-3.48 (5 H, m), 3.06-2.77 (10 H, m), 2.05-1.95 (2 H, m), 1.83-1.69 (2 H, m) |
| 213 | $^1$H NMR (300 MHz, CDCl$_3$-d) δ ppm 7.90 (1 H, dd), 7.83 (1 H, d), 7.53 (1 H, dd), 7.48-7.35 (2 H, m), 7.11 (1 H, d), 6.97 (1 H, d), 6.13 (1 H, d), 4.69-4.61 (1 H, m), 4.50-4.41 (1 H, m), 4.26 (1 H, dd), 4.13 (1 H, dd), 3.91 (1 H, dd), 3.63 (3 H, s), 3.05 (2 H, d), 3.02-2.89 (2 H, m), 2.81-2.58 (3 H, m), 2.26-2.13 (2 H, m), 1.96-1.80 (4 H, m), 1.32 (3 H, t) |
| 214 | $^1$H NMR (400 MHz, CDCl$_3$-d) δ ppm 8.12-8.02 (2 H, m), 7.82 (1 H, d), 7.39 (1 H, t), 7.20-7.08 (3 H, m), 6.96 (1 H, d), 6.06 (1 H, d), 4.70-4.59 (1 H, m), 4.47-4.38 (1 H, m), 4.32-4.19 (1 H, m), 4.07 (1 H, dd), 3.88 (1 H, dd), 3.60 (3 H, s), 3.01 (2 H, s), 2.99-2.92 (2 H, m), 2.78-2.66 (3 H, m), 2.26-2.10 (2 H, m), 1.92-1.81 (4 H, m), 1.30 (3 H, t) |
| 215 | $^1$H NMR (400 MHz, CDCl$_3$-d) δ ppm 8.50-7.40 (4 H, m), 7.24-6.87 (4 H, m), 4.71-4.54 (1 H, m), 4.46-4.34 (1 H, m), 4.23 (1 H, dd), 4.06 (1 H, dd), 4.02-3.92 (1 H, m), 3.87 (1 H, dd), 3.61 (3 H, s), 3.07-2.88 (4 H, m), 2.85-2.61 (3 H, m), 2.24-2.06 (2 H, m), 1.90-1.74 (4 H, m), 1.31 (3 H, t) |
| 218 | $^1$H NMR (400 MHz, CDCl$_3$-d) δ ppm 8.07 (2 H, br. s.), 7.85 (1 H, d), 7.60 (1 H, d), 7.21 (2 H, t), 7.02 (1 H, d), 6.16-6.03 (1 H, m), 4.68 -4.61 (1 H, m), 4.45-4.37 (1 H, m), 4.31-4.23 (1 H, m), 4.07 (1 H, dd), 3.88 (1 H, dd), 3.60 (3 H, s), 3.06 - 2.93 (4 H, m), 2.83-2.67 (5 H, m), 2.25-2.12 (2 H, m), 1.91-1.81 (2 H, m), 1.32 (3 H, t) |
| 220 | $^1$H NMR (400 MHz, CDCl$_3$-d) δ ppm 8.35 (1 H, dd), 7.88 (1 H, d), 7.51 (1 H, dd), 7.42-7.35 (1 H, m), 7.10 (1 H, d), 4.67-4.60 (1 H, m), 4.50-4.38 (1 H, m), 4.32-4.23 (1 H, m), 4.19-4.10 (1 H, m), 3.92 (1 H, dd), 3.73 (3 H, s), 3.29-3.12 (4 H, m), 2.93-2.85 (1 H, m), 2.82 (2 H, q), 2.64-2.46 (2 H, br. m), 2.12-1.95 (4 H, br. m), 1.38 (3 H, t) |

BIOLOGICAL EXAMPLES

Example 3. In Vitro Assays 3.1. Principle

The principle of the assay consists in quantifying the released choline with an enzymatic method using choline oxidase and peroxidase. Choline oxydation by choline oxydase releases betaine and peroxide. The latter is quantified in presence of HRP that converts the peroxide detection agent TOOS and 4-aminoantipyrine into quinoneimine dye. The appearance of quinoneimine dye is measured spectrophotometrically at 555 nm and is proportional to the amount of choline released by ENPP2. Inhibition of ENPP2 will result in a decrease of the signal.

3.2. Human ENPP2 (hENPP2) Assay 3.2.1. LPC as Substrate

Compound IC$_{50}$ values are determined in a hENPP2 (UniProtKB/SwissProt Sequence ref Q13822) biochemical assay using LPC as substrate.

5 μL of a dilution series of compound, starting from 20 μM highest concentration, 1/5 dilution, is added to the wells. hENPP2 is used at a final concentration of 1 μg/mL or 3 μg/mL (it will be appreciated by the skilled person that the potency read out is independent of the enzyme concentration). The enzyme is diluted in 50 mM Tris-HCl pH 8.5, 500 mM NaCl, 5 mM KCl, 10 mM CaCl$_2$, 0.1% fatty acid free BSA in a total volume of 10 μL. the reaction is started by the addition of 10 μL of 150 μM LPC (palmitoyl 16:0) diluted in the same buffer as described above and the mixture is incubated at 37° C. for 30 min. The reaction is terminated and choline quantified by the addition of a 25 μL of a mixture containing 0.6 U/mL of choline oxidase, 0.6 U/mL of peroxydase, 1.8 mM TOOS, 1.2 mM amino-antipyrine, 20 mM EGTA (stop-developer solution) diluted in the buffer described above. Luminescence is read on the Envision after an incubation of 30 min at room temperature (Excitation 555 nm, excitation light=70%).

TABLE IV

LPC hENPP2 assay IC$_{50}$ of the compounds of the invention.

| Cpd # | LPC – IC$_{50}$ |
|---|---|
| 1 | * |
| 2 | *** |
| 3 | * |
| 4 | *** |
| 5 | *** |
| 6 | *** |
| 7 | *** |
| 8 | *** |
| 9 | ** |
| 10 | *** |
| 11 | *** |
| 12 | * |
| 13 | * |
| 14 | * |
| 15 | * |
| 16 | * |
| 15 | * |
| 18 | * |
| 19 | * |
| 20 | * |
| 21 | *** |
| 22 | * |
| 23 | *** |
| 24 | *** |
| 25 | *** |
| 26 | *** |
| 27 | **** |
| 28 | *** |
| 29 | *** |
| 30 | ** |
| 31 | *** |
| 32 | * |
| 33 | *** |
| 34 | *** |
| 35 | * |
| 36 | *** |
| 37 | *** |
| 38 | * |
| 39 | * |
| 40 | *** |
| 41 | ** |
| 42 | *** |
| 43 | *** |
| 44 | **** |
| 45 | **** |
| 46 | *** |
| 47 | * |
| 48 | *** |
| 49 | ** |
| 50 | * |
| 51 | * |
| 52 | ** |
| 53 | * |
| 54 | * |
| 55 | *** |
| 56 | * |
| 57 | *** |
| 58 | * |
| 59 | * |
| 60 | * |
| 61 | * |
| 62 | * |
| 63 | **** |
| 64 | *** |
| 65 | *** |
| 66 | * |
| 67 | *** |
| 68 | *** |
| 69 | * |
| 70 | ** |
| 71 | * |
| 72 | ** |
| 73 | *** |
| 74 | * |
| 75 | * |
| 76 | * |
| 77 | * |
| 78 | * |
| 79 | * |
| 80 | * |
| 81 | * |
| 82 | * |
| 83 | * |
| 84 | *** |
| 85 | * |
| 86 | * |
| 87 | * |
| 88 | ** |
| 89 | ** |
| 90 | * |
| 91 | * |
| 92 | * |
| 93 | * |
| 94 | * |
| 95 | * |
| 96 | * |
| 97 | ** |
| 98 | * |
| 99 | * |
| 100 | * |
| 101 | * |
| 102 | * |
| 103 | * |
| 104 | * |
| 105 | * |
| 106 | * |
| 107 | ** |
| 108 | ** |
| 109 | ** |
| 110 | * |
| 111 | * |
| 112 | * |
| 113 | * |
| 114 | * |
| 115 | * |
| 116 | * |
| 117 | * |
| 118 | ** |
| 119 | *** |
| 120 | *** |
| 121 | * |
| 122 | * |
| 123 | * |
| 124 | * |
| 125 | * |
| 126 | ** |
| 127 | * |
| 128 | * |
| 129 | * |

TABLE IV-continued

LPC hENPP2 assay IC$_{50}$ of the compounds of the invention.

| Cpd # | LPC – IC$_{50}$ |
|---|---|
| 130 | * |
| 131 | * |
| 132 | * |
| 133 | * |
| 134 | * |
| 135 | ** |
| 136 | * |
| 137 | * |
| 138 | * |
| 139 | * |
| 140 | * |
| 141 | * |
| 142 | * |
| 143 | * |
| 144 | ** |
| 145 | ** |
| 146 | ** |
| 147 | *** |
| 148 | ** |
| 149 | **** |
| 150 | * |
| 151 | * |
| 152 | ** |
| 153 | * |
| 154 | * |
| 155 | *** |
| 156 | ** |
| 157 | ** |
| 158 | ** |
| 159 | * |
| 160 | **** |
| 161 | *** |
| 162 | *** |
| 163 | * |
| 164 | *** |
| 165 | *** |
| 166 | *** |
| 167 | **** |
| 168 | **** |
| 169 | **** |
| 170 | *** |
| 171 | *** |
| 172 | *** |
| 173 | *** |
| 174 | **** |
| 175 | **** |
| 176 | **** |
| 177 | **** |
| 178 | ** |
| 179 | **** |
| 180 | **** |
| 181 | **** |
| 182 | **** |
| 183 | **** |
| 184 | **** |
| 185 | * |
| 186 | *** |
| 187 | *** |
| 188 | **** |
| 189 | **** |
| 190 | **** |
| 191 | *** |
| 192 | *** |
| 194 | * |
| 195 | * |
| 196 | * |
| 197 | ** |
| 198 | *** |
| 199 | * |
| 200 | * |
| 201 | *** |
| 202 | ** |
| 203 | ** |
| 204 | *** |
| 205 | *** |
| 206 | ** |
| 207 | *** |
| 208 | *** |
| 209 | *** |
| 210 | * |
| 211 | * |
| 212 | **** |
| 213 | **** |
| 214 | ** |
| 215 | *** |
| 216 | ** |
| 217 | * |
| 218 | *** |
| 219 | * |
| 220 | *** |

****: 0.01-100 nM
***: >100-500 nM
**: >500-1000 nM
*: >1000 nM

3.2.2. FS-3 as Substrate

Compound IC$_{50}$ values are determined in a fluorescent hENPP2 (UniProtKB/SwissProt Sequence ref Q13822) biochemical assay using the fluorogenic autotaxin substrate FS-3 as substrate. FS-3 is a doubly labeled analog of LPC wherein the fluorophore is quenched through intramolecular energy transfer. Without hENPP2, the emission of the probe is quenched. If the substrate is hydrolyzed by hENPP2, the emission of the probe is not quenched anymore resulting in a fluorescence increase. Inhibition of hENPP2 by compounds will result in a decrease of the signal.

10 µL of a dilution series of compound, starting from 20 µM highest concentration, ⅕ dilution, is added to the wells. hENPP2 is used at a final concentration of 0.4 µg/mL or 0.64 µg/mL (it will be appreciated by the skilled person that the potency read out is independent of the enzyme concentration). The enzyme is diluted in 50 mM Tris-HCl pH 8.0, 250 mM NaCl, 5 mM KCl, 1 mM MgCl$_2$, 1 mM CaCl$_2$, 0.1% fatty acid free BSA in a total volume of 20 µL. Enzyme mixture is added to compounds and the resulting mixture is incubated for 30 min at room temperature under shaking. The reaction is started by the addition of 20 µL of 0.75 µM FS-3 diluted in the same buffer as described above and the mixture is incubated at 30° C. for 30 min. Fluorescence is read on the Envision (Excitation 485 nm, emission 520 nM).

TABLE V

FS3 hENPP2 assay IC$_{50}$ of the compounds of the invention.

| Cpd # | FS3 – IC$_{50}$ |
|---|---|
| 4 | **** |
| 5 | **** |
| 6 | **** |
| 7 | **** |
| 8 | **** |
| 9 | **** |
| 10 | **** |
| 11 | **** |
| 12 | **** |
| 16 | ** |
| 19 | * |

TABLE V-continued

FS3 hENPP2 assay
$IC_{50}$ of the compounds
of the invention.

| Cpd # | FS3 – $IC_{50}$ |
|---|---|
| 21 | **** |
| 22 | *** |
| 23 | **** |
| 24 | **** |
| 25 | **** |
| 26 | **** |
| 27 | **** |
| 29 | **** |
| 33 | **** |
| 34 | **** |
| 40 | **** |
| 42 | **** |
| 43 | **** |
| 45 | **** |
| 46 | **** |
| 47 | **** |
| 48 | **** |
| 49 | **** |
| 51 | **** |
| 52 | **** |
| 53 | **** |
| 54 | **** |
| 55 | **** |
| 57 | **** |
| 60 | **** |
| 61 | **** |
| 63 | **** |
| 64 | **** |
| 65 | **** |
| 67 | **** |
| 71 | **** |
| 72 | **** |
| 78 | **** |
| 79 | *** |
| 81 | **** |
| 82 | **** |
| 83 | **** |
| 91 | *** |
| 93 | **** |
| 94 | **** |
| 95 | **** |
| 96 | **** |
| 97 | **** |
| 98 | **** |
| 99 | **** |
| 100 | **** |
| 101 | *** |
| 102 | **** |
| 108 | **** |
| 109 | **** |
| 114 | ** |
| 115 | **** |
| 116 | **** |
| 122 | **** |
| 123 | **** |
| 124 | **** |
| 125 | **** |
| 126 | **** |
| 127 | **** |
| 129 | **** |
| 131 | **** |
| 133 | **** |
| 134 | **** |
| 137 | **** |
| 142 | **** |
| 143 | **** |
| 145 | **** |
| 147 | **** |
| 150 | **** |
| 151 | **** |
| 152 | **** |
| 154 | **** |
| 171 | **** |
| 172 | **** |
| 193 | **** |
| 194 | **** |
| 195 | **** |
| 196 | **** |
| 197 | **** |
| 198 | **** |
| 199 | **** |
| 200 | **** |
| 201 | **** |
| 202 | **** |
| 212 | **** |
| 213 | **** |
| 214 | **** |
| 215 | **** |
| 216 | **** |
| 217 | ** |
| 218 | **** |

****: 0.01-25 nM
***: >25-50 nM
**: >50-100 nM
*: >100 nM 3.3. Mouse ENPP2 (mENPP2)

3.3.1. LPC as Substrate

Compound $IC_{50}$ values are determined in a mENPP2 (UniProtKB/SwissProt Sequence ref Q9R1E6) biochemical assay using LPC as substrate.

Five μL of a dilution series of compound, starting from 20 μM highest concentration, ⅕ dilution, is added to the wells. mENPP2 is used at a final concentration of 1 μg/mL. The enzyme is diluted in 50 mM Tris-HCl pH 8.5, 500 mM NaCl, 5 mM KCl, 10 mM $CaCl_2$, 0.1% fatty acid free BSA in a total volume of 10 μL. the reaction is started by the addition of 10 μL of 150 μM LPC (palmitoyl 16:0) diluted in the same buffer as described above and the mixture is incubated at 37° C. for 30 min. The reaction is terminated and choline quantified by the addition of a 25 μL of a mixture containing 0.6 U/mL of choline oxidase, 0.6 U/mL of peroxydase, 1.8 mM TOOS, 1.2 mM amino-antipyrine, 20 mM EGTA (stop-developer solution) diluted in the buffer described above. Luminescence is read on the Envision after an incubation of 30 min at room temperature (Excitation 555 nm, excitation light=70%).

3.3.2. FS-3 as Substrate

Compound $IC_{50}$ values are determined in a fluorescent mENPP2 (UniProtKB/SwissProt Sequence ref Q9R1E6) biochemical assay using the fluorogenic autotaxin substrate FS-3 as substrate. FS-3 is a doubly labeled analog of LPC wherein the fluorophore is quenched through intramolecular energy transfer. Without mENPP2, the emission of the probe is quenched. If the substrate is hydrolyzed by mENPP2, the emission of the probe is not quenched anymore resulting in a fluorescence increase. Inhibition of mENPP2 by compounds will result in a decrease of the signal.

Ten μL of a dilution series of compound, starting from 20 μM highest concentration, ⅕ dilution, is added to the wells. mENPP2 is used at a final concentration of 0.4 μg/mL. The enzyme is diluted in 50 mM Tris-HCl pH 8.0, 250 mM NaCl, 5 mM KCl, 1 mM $MgCl_2$, 1 mM $CaCl_2$, 0.1% fatty acid free BSA in a total volume of 20 μL. Enzyme mixture is added to compounds and the resulting mixture is incubated for 30 min at room temperature under shaking. The reaction is started by the addition of 20 μL of 0.75 μM FS-3 diluted in the same buffer as described above and the mixture is incubated at 30° C. for 30 min. Fluorescence is read on the Envision (Excitation 485 nm, emission 520 nM).

Example 4. Whole Blood Assay 4.1. Human LPA Assay

Blood is collected from healthy volunteers who gave informed consent into sodium heparin tubes by venipuncture, then gently inverted several times to prevent clotting. Tubes are centrifuged at 3000 rpm for 15 min at 4° C. then plasma is stored at −80° C. Compounds are diluted in DMSO in concentration dependent manner then 0.5 μL are dispensed into 96-wells plate placed in ice. Plasma is defrosted on ice then 49.5 μL of plasma are added into the well containing 0.5 μL of compound (1% DMSO final). Plates are covered with a lid in polypropylene and incubated at +37° C., 5% $CO_2$, for 2 h under gentle shaking (except controls which are stored at −20° C.).

At the end of the incubation, controls are defrosted in ice and transferred in the incubated plates for LC-MS/MS analysis with a non GLP-validated method. For the analysis, plasma proteins from a 10 μL incubated plates are precipitated with an excess of methanol containing the internal standard, LPA 17:0. After centrifugation, the corresponding supernatant is injected on a C18 column. Analytes are eluted out of the column under isocratic conditions. An API5500 QTRAP mass spectrometer (ABSciex™) is used for the detection of LPA 18:2. No calibration curve is prepared for LPA 18:2, however relative quantities are evaluated based on the peak area.

4.2. Rat or Mouse LPA Assay

Whole blood is collected from rats or mouse by exsanguinations on sodium heparin tube, then after centrifugation at 3000 rpm for 15 min at 4° C., plasma is stored at −80° C. Compounds are diluted in DMSO in concentration dependent manner then 0.5 μL are dispensed into 96-wells plate placed in ice. Plasma is defrosted on ice then 49.5 μL of plasma are added into the well containing 0.5 μL of compound (1% DMSO final). Plates are covered with a lid in polypropylene and incubated at +37° C., 5% $CO_2$, for 2 h under gentle shaking (except controls which are stored at −20° C.).

At the end of the incubation, controls are defrosted in ice and transferred in the incubated plates for LC-MS/MS analysis with a non GLP-validated method. For the analysis, plasma proteins from a 10 μL incubated plates are precipitated with an excess of methanol containing the internal standard, LPA 17:0. After centrifugation, the corresponding supernatant is injected on a C18 column. Analytes are eluted out of the column under isocratic conditions. An API5500 QTRAP mass spectrometer (ABSciex™) is used for the detection of LPA 18:2. No calibration curve is prepared for LPA 18:2, however relative quantities are evaluated based on the peak area.

TABLE VI

Rat/Mouse whole blood assay $IC_{50}$ of the compounds of the invention.

| Cpd # | $IC_{50}$ | Species |
|---|---|---|
| 2 | * | Rat |
| 5 | * | Rat |
| 6 | *** | Rat |
| 7 | *** | Rat |
| 10 | * | Rat |
| 12 | * | Rat |
| 14 | * | Rat |
| 16 | * | Rat |
| 19 | * | Rat |
| 21 | * | Mouse |
| 23 | *** | Rat |
| 24 | **** | Rat |
| 25 | **** | Rat |
| 40 | *** | Rat |
| 42 | *** | Rat |
| 63 | **** | Rat |
| 118 | * | Rat |
| 149 | **** | Rat |
| 198 | **** | Rat |
| 205 | *** | Rat |
| 206 | *** | Rat |
| 213 | *** | Rat |
| 216 | * | Rat |
| 218 | *** | Rat |

****: 0.01-100 nM
***: >100-500 nM
**: >500-1000 nM
*: >1000 nM

Example 5. In Vivo Models 5.1. Tobacco Smoke (TS) Model
5.1.1. Lungs Inflammatory Cells Recruitment Evaluation
5.1.1.1. Overview The aim of this experiment is to evaluate the efficacy and potency of a test compound administered p.o., once or twice daily on days 6 to 11, vs reference compounds, on pulmonary inflammation induced by 11 days of TS-exposure in female C57BL/6J mice, by assessing the effect of a test compound on the tobacco smoke induced recruitment of inflammatory cells to the lungs.

5.1.1.2. Protocol

The test compounds are formulated in PEG200/0.5% methylcellulose (25/75, v/v) and are given at a dose volume of 10 mL/kg. Roflumilast and Dexamethasone are included as positive and negative control, respectively. Each treatment group consists of 10 mice.

A first group of mice is subjected to daily TS-exposure for 5 consecutive days and sacrificed on the day 6, 24 h after the final TS-exposure.

A second group is exposed to air for 5 consecutive days (sham exposure) and sacrificed on the day 6, 24 h after the final air-exposure.

Compound and reference-treated groups are subjected to daily TS-exposure for 11 consecutive days and sacrificed on the day 12, 24 h after the final TS-exposure. Mice are dosed p.o. on days 6 to 11, twice daily, 1 h prior to and 6 h after each TS-exposure, with either vehicle, or the test compound at 3, 5, 10 or 30 mg/kg. Another group is dosed p.o. on days 6 to 11, once daily, 1 h prior to each TS-exposure, with either vehicle, or the test compound at a selected dose, for example 10 mg/kg.

An additional group is dosed p.o., once daily, on days 6 to 11, with roflumilast at 5 mg/kg, 1 h prior to each TS-exposure. Dexamethasone is dosed p.o., twice daily, on days 6 to 11, at 0.3 mg/kg, 1 h prior to and 6 h after each TS-exposure.

For each mouse, a BAL is performed using 0.4 mL of PBS. The lavage fluid is centrifuged, the supernatant removed and the resulting cell pellet re-suspended for total cell counts and cytospin slide preparation. The remaining cells are re-pelleted and frozen. The supernatants are stored at −40° C. for possible future analysis.

The lungs are dissected out and the left lobes are removed, snap-frozen and stored at −80° C. The right lobes are inflated with 10% phosphate buffered formalin (PBF) to a pressure of 18 cm PBF for 20 min and then immersed in PBF. After 24 h, the right lobe samples are transferred to 70% ethanol and stored at room temperature. Cell data are presented as individual data points for each animal and the mean value calculated for each group.

Data are subjected to an unpaired Students "t" test. Data from other groups are initially subjected to a one-way analysis of variance test (ANOVA), followed by a Bonferroni correction for multiple comparisons in order to test for differences between treatment groups. A "p" value of <0.05 is considered to be statistically significant.

Percentage inhibitions for the cell data are calculated using the formula below:

$$\% \text{ inhibition} = \left(1 - \left(\frac{\text{treatment group result} - \text{sham group result}}{\text{TS vehicule group result} - \text{sham group result}}\right)\right) * 100$$

5.1.1.3. Results

For example, when tested in this protocol, Compound 2 and 12 significantly inhibited the number of cells recovered in the BALF, in particular macrophage cells, epithelial cells, and neutrophils at 10 mg/kg twice daily p.o. (Compound 2 & 12) and 3 mg/kg twice daily p.o. (Compound 2).

5.1.2. Compound Efficacy and Potency Evaluation 5.1.2.1. Overview

A second tobacco smoke (TS) experiment is carried out, aimed at evaluating the efficacy and potency of a test compound administered p.o., twice daily on days 6 to 11, vs a reference compound, on pulmonary inflammation induced by 11 days of TS-exposure, reading out the effects on gene expression in the lungs. This second experiment consisted of 4 groups of mice.

5.1.2.2. Protocols

Three groups of mice are subjected to daily TS-exposure for 11 consecutive days and sacrificed on the day 12, 24 h after the final TS-exposure. Two groups are dosed, p.o., on days 6 to 11, twice daily (b.i.d.), 1 h prior to and 6 h after each TS-exposure, with either vehicle or the test compound at 10 mg/kg. The third group is dosed p.o., on days 6 to 11, once daily (q.d.) with Roflumilast at 5 mg/kg, 1 h prior to each TS-exposure. This group receives vehicle 6 h after each TS-exposure. One further group is exposed to air for 11 consecutive days and receive vehicle 1 h prior to and 6 h after exposure on days 6 to 11. This group is also sacrificed on the day 12, 24 h after the final exposure.

All groups receive a final dose, of the relevant treatment, 2 h prior to sacrifice on day 12. One final group is exposed to air for 11 consecutive days and received vehicle 1 h prior to and 6 h after exposure on days 6 to 11. This group is also sacrificed on the day 12, 24 h after the final exposure. Mice receive a dose volume of 10 mL/kg. Each group consists in 10 subjects.

Mice are euthanized, by intra-peritoneal barbiturate anaesthetic overdose, on day 12, 24 h after the final air or TS-exposure. All mice receive a final dose of the relevant treatment, 2 h prior to sacrifice. The lungs are dissected out and placed in RNAse-free 15 mL tubes containing ~5 mL of RNAlater solution, ensuring the tissue is completely submerged. The lungs are stored overnight at 4° C. Following overnight incubation, the lungs are removed from RNAlater, the left and right lobes are separated, placed in individual tubes and stored at −80° C.

RNA extractions are performed for 5 mice per group using Qiagen RNeasy Mini Kit according to the manufacturer's specifications (Animal tissue protocol). Total RNA are then eluted in RNase-free water (30 µl for four reference samples and 50 µL for the twenty-four test samples). Quality of the samples is assessed by measurement of their concentration in RNA using a NanoDrop ND-1000 spectrophotometer and by the measurement of RNA integrity using an 2100 Bioanalyzer (Agilent Technologies).

RNA preparations are of good quality (RIN value lies between 7.6 and 9.2) and subjected to quantitative real-time PCR (QrtPCR), which involved a first cDNA synthesis step. To this end, 300 ng of total RNA are reverse transcribed using the High capacity cDNA synthesis Kit (Applied Biosystems™) with random hexamers. Quantitative PCR reactions are performed using Quanti-Fast SYBR® Green PCR Master Mix (Qiagen™) and gene-specific primer pairs for β-actin (Eurogentech™) and QuantiTect primer assays for all other tested genes (Qiagen™). For the genes of interest, the following Quantitect primer pairs are used: CCL2 (QT00167832); CDK1 (QT00167734); SAA3 QT00249823), TIMP1 (QT00996282); Slc26a4 (QT00131908); LCN2 (QT00113407); CXCL5 (QT01658146), MMP12 (QT00098945); PLAla (QT00161448); TNFsF11 (QT00147385). Reactions are carried out with a denaturation step at 95° C. for 5 min, followed by 40 cycles (95° C. for 10 sec, 60° C. for 1 min) in a ViiATM7 Real-Time PCR System (Applied Biosystems™).

Real-time PCR data for each target gene are expressed as $2^{-\Delta\Delta ct}$ relative quantification versus endogenous β-actin. For statistical analysis, a 2-way analysis of variance (ANOVA) followed by a Dunnett's post-hoc test versus the TS-vehicle group is performed.

The relevance of CCL2, CDK1, SAA3, TIMP1, Slc26a4, LCN2, CXCL5, MMP12, PLAla, and TNFsF11 towards COPD is well-established through literature data based on patient specimen. A reference towards the relevant paper for each gene is provided in Table VII below.

5.1.2.3. Results

The increase in relative expression levels caused by the tobacco smoke treatment is measured, and increase in the expression of this relevant gene set upon tobacco smoke treatment further validates the relevance of the model applied. Roflumilast, an approved treatment for COPD, is taken along as positive control in the experiment.

The inhibition of ENPP2 in a therapeutic setting strongly suppresses the increase in expression of disease-relevant genes in lungs of tobacco smoke-treated mice, providing a strong support for key a role of ENPP2 in the pathogenesis of COPD.

TABLE VII

| TS induced relative expression levels in selected genes | |
|---|---|
| Gene Name | Literature reference |
| CCL2 | Llinàs et al. 2011) |
| SAA3 | (Bozinovski et al. 2008) |
| TIMP1 | (Tilley et al. 2011) |
| SLC26A4 | (Nakao et al. 2008) |

TABLE VII-continued

TS induced relative expression
levels in selected genes

| Gene Name | Literature reference |
|---|---|
| LCN2 | (Eagan et al. 2010) |
| MMP12 | (Demedts et al. 2006) |

5.2. CIA Model 5.2.1. Materials

Completed Freund's adjuvant (CFA) and incomplete Freund's adjuvant (IFA) are purchased from Difco. Bovine collagen type II (CII), lipopolysaccharide (LPS), and Enbrel is obtained from Chondrex (Isle d'Abeau, France); Sigma (P4252, L'Isle d'Abeau, France), Whyett (25 mg injectable syringe, France) Acros Organics (Palo Alto, Calif.), respectively. All other reagents used are of reagent grade and all solvents are of analytical grade.

5.2.2. Animals

Dark Agouti rats (male, 7-8 weeks old) are obtained from Harlan Laboratories (Maison-Alfort, France). Rats are kept on a 12 h light/dark cycle (0700-1900). Temperature is maintained at 22° C., and food and water are provided ad libitum.

5.2.3. Collagen Induced Arthritis (CIA)

One day before the experiment, CII solution (2 mg/mL) is prepared with 0.05 M acetic acid and stored at 4° C. Just before the immunization, equal volumes of adjuvant (IFA) and CII are mixed by a homogenizer in a pre-cooled glass bottle in an ice water bath. Extra adjuvant and prolonged homogenization may be required if an emulsion is not formed. 0.2 mL of the emulsion is injected intradermally at the base of the tail of each rat on day 1, a second booster intradermal injection (CII solution at 2 mg/mL in CFA 0.1 mL saline) is performed on day 9. This immunization method is modified from published methods (Sims et al. 2004; Jou et al. 2005).

5.2.4. Study Design

The therapeutic effects of the compounds are tested in the rat CIA model. Rats are randomly divided into equal groups and each group contains 10 rats. All rats are immunized on day 1 and boosted on day 9. Therapeutic dosing lasted from day 16 to day 30. The negative control group is treated with vehicle and the positive control group with Enbrel (10 mg/kg, 3× week. s.c.). A compound of interest is typically tested at 4 doses, e.g. 0.3, 1, 3, and 10 mg/kg, p.o.

5.2.5. Clinical Assessment of Arthritis

Arthritis is scored according to literature-described method (Khachigian 2006; H.-S. Lin et al. 2007; Nishida et al. 2004, 20). The swelling of each of the four paws is ranked with the arthritic score as follows: 0-no symptoms; 1-mild, but definite redness and swelling of one type of joint such as the ankle or wrist, or apparent redness and swelling limited to individual digits, regardless of the number of affected digits; 2-moderate redness and swelling of two or more types of joints; 3-severe redness and swelling of the entire paw including digits; 4-maximally inflamed limb with involvement of multiple joints (maximum cumulative clinical arthritis score 16 per animal) (Nishida et al. 2004).

To permit the meta-analysis of multiple studies the clinical score values are normalised as follows:

AUC of Clinical Score (AUC Score):

The area under the curve (AUC) from day 1 to day 14 is calculated for each individual rat. The AUC of each animal is divided by the average AUC obtained for the vehicle in the study from which the data on that animal is obtained and multiplied by 100 (i.e. the AUC is expressed as a percentage of the average vehicle AUC per study).

Clinical Score Increase from Day 1 to Day 14 (End Point Score):

The clinical score difference for each animal is divided by the average clinical score difference obtained for the vehicle in the study from which the data on that animal is obtained and multiplied by 100 (i.e. the difference is expressed as a percentage of the average clinical score difference for the vehicle per study).

5.2.6. Change in Body Weight (%) after Onset of Arthritis

Clinically, body weight loss is associated with arthritis (Shelton et al. 2005; Rall and Roubenoff 2004; Walsmith et al. 2004). Hence, changes in body weight after onset of arthritis can be used as a non-specific endpoint to evaluate the effect of therapeutics in the rat model. The change in body weight (%) after onset of arthritis is calculated as follows:

$$\text{Mice: } \frac{\text{Body Weight (week 6)} - \text{Body Weight (Week 5)}}{\text{Body Weight (Week 5)}} * 100\%$$

$$\text{Rats: } \frac{\text{Body Weight (week 4)} - \text{Body Weight (Week 3)}}{\text{Body Weight (Week 3)}} * 100\%$$

5.2.7. Radiology

X-ray photos are taken of the hind paws of each individual animal. A random blind identity number is assigned to each of the photos, and the severity of bone erosion is ranked by two independent scorers with the radiological Larsen's score system as follows: 0—normal with intact bony outlines and normal joint space; 1—slight abnormality with any one or two of the exterior metatarsal bones showing slight bone erosion; 2—definite early abnormality with any three to five of the exterior metatarsal bones showing bone erosion; 3—medium destructive abnormality with all the exterior metatarsal bones as well as any one or two of the interior metatarsal bones showing definite bone erosions; 4—severe destructive abnormality with all the metatarsal bones showing definite bone erosion and at least one of the inner metatarsal joints completely eroded leaving some bony joint outlines partly preserved; 5—mutilating abnormality without bony outlines. This scoring system is a modification from literature protocols (Salvemini et al. 2001; Bush et al. 2002; Sims et al. 2004; Jou et al. 2005).

5.2.8. Histology

After radiological analysis, the hind paws of mice are fixed in 10% phosphate-buffered formalin (pH 7.4), decalcified with rapid bone decalcifiant for fine histology (Laboratories Eurobio) and embedded in paraffin. To ensure extensive evaluation of the arthritic joints, at least four serial sections (5 µm thick) are cut and each series of sections are 100 µm in between. The sections are stained with hematoxylin and eosin (H&E). Histologic examinations for synovial inflammation and bone and cartilage damage are performed double blind. In each paw, four parameters are assessed using a four-point scale. The parameters are cell infiltration, pannus severity, cartilage erosion and bone erosion. Scoring is performed according as follows: 1-normal, 2-mild, 3-moderate, 4-marked. These four scores are summed together and represented as an additional score, namely the 'RA total score'.

5.2.9. Micro-Computed Tomography (CT) Analysis of Calcaneus (Heel Bone)

Bone degradation observed in RA occurs especially at the cortical bone and can be revealed by µCT analysis (Sims et al. 2004; Oste et al. 2007). After scanning and 3D volume reconstruction of the calcaneus bone, bone degradation is measured as the number of discrete objects present per slide, isolated in silico perpendicular to the longitudinal axis of the bone. The more the bone is degraded, the more discrete objects are measured. 1000 slices, evenly distributed along the calcaneus (spaced by about 10.8 µm), are analyzed.

5.2.10. Steady State PK

At day 7 or later, blood samples are collected at the retro-orbital sinus with lithium heparin as anti-coagulant at the following time points: predose, 1, 3 and 6 h. Whole blood samples are centrifuged and the resulting plasma samples are stored at –20° C. pending analysis. Plasma concentrations of each test compound are determined by an LC-MS/MS method in which the mass spectrometer is operated in positive electrospray mode. Pharmacokinetic parameters are calculated using Winnonlin® (Pharsight®, United States) and it is assumed that the predose plasma levels are equal to the 24 h plasma levels.

5.3. Idiopathic Pulmonary Fibrosis Assay

5.3.1. Overview

The mouse bleomycin-induced fibrosis model mimics the main characteristics of human lung fibrosis and is used to test potential new therapies for lung fibrosis (Walters and Kleeberger 2001).

5.3.2. Protocol

In vivo efficacy of a compound of the invention is assessed in a 10-days mouse preventive bleomycin-induced pulmonary fibrosis model by oral route. Mice (20-25 g female C57BL/6; n=10-15 per group) are treated with bleomycin sulfate (1.5 U/kg) via intratracheal instillation at day 0 under isoflurane anesthesia, and then treated with the compounds accordingly to the study protocol from day 1 to day 10. Mice are kept on a 12 hr light/dark cycle (07:00-19:00). The temperature is maintained at 22° C., and food and water are provided ad libitum. At sacrifice, broncho alveolar lavage fluid (BALF; 2×0.75 mL PBS) is collected from lungs.

This material is used to determine:
the amount of infiltrated inflammatory cells:
All the BALF cells (for example macrophage, eosinophil, neutrophil and epithelial cells) are pelleted, resuspended in PBS and counted
the total amount of proteins using a Bradford dosing:
this readout reflects the vascular leakage occurring, leading to the formation of an exudates in the lungs
the amount of collagen using a Sircol™ dosing (Available from Biocolor Ltd., 8 Meadowbank Road, Carrickfergus, BT38 8YF, County Antrim, UK)
This readout reflects the level of extra-cellular matrix degradation and tissue remodeling occurring in the lungs.

One lung of each mouse is also collected and prepared for histological analysis using 10% neutral buffered formalin.

5.4. Septic Shock Model

Injection of lipopolysaccharide (LPS) induces a rapid release of soluble tumour necrosis factor (TNF-alpha) into the periphery. This model is used to analyse prospective blockers of TNF release in vivo.

Six BALB/cJ female mice (20 g) per group are treated at the intended dosing once, po.

Thirty min later, LPS (15 µg/kg; *E. Coli* serotype 0111: B4) is injected ip. Ninety min later, mice are euthanized and blood is collected. Circulating TNF alpha levels are determined using commercially available ELISA kits. Dexamethasone (5 µg/kg) is used as a reference anti-inflammatory compound.

5.5. MAB Model

The MAB model allows a rapid assessment of the modulation of an RA-like inflammatory response by therapeutics (Khachigian 2006). DBA/J mice are injected i.v. with a cocktail of mAbs directed against collagen II. One day later, compound treatment is initiated. Three days later, mice receive an i.p. LPS injection (50 µg/mouse), resulting in a fast onset of inflammation. Compound treatment is continued until 10 days after the mAb injection. Inflammation is read by measuring paw swelling and recording the clinical score of each paw. The cumulative clinical arthritis score of four limbs is presented to show the severity of inflammation. A scoring system is applied to each limb using a scale of 0-4, with 4 being the most severe inflammation.

0 Symptom free
1 Mild, but definite redness and swelling of one type of joint such as the ankle or wrist, or apparent redness and swelling limited to individual digits, regardless of the number of affected digits
2 Moderate redness and swelling of two or more types of joints
3 Severe redness and swelling of the entire paw including digits
4 Maximally inflamed limb with involvement of multiple joints

5.6. Mouse IBD Model

The mouse chronic dextran sodium sulphate (DSS)-induced inflammatory bowel disease (IBD) model is a well validated disease model for inflammatory bowel disease (Sina et al. 2009; Wirtz and Neurath 2007).

To induce a chronic colitis, female BALB/c mice are fed with 4% DSS dissolved in drinking water for 4 days, followed by 3 days of regular drinking water. This cycle is repeated three times. This protocol induces a strong colitis while avoiding high mortality rates. Animals are divided into several groups:

a. intact (water; vehicle alone, n=10),
b. diseased (DSS; vehicle alone, n=10),
c. sulfazalazine used as reference (DSS; 20 mg/kg/day sulfazalazine, p.o., n=10) and
d. the tested compound (DSS; 1, 3, 10 and 30 mg/kg/day test compound, p.o., n=10/dose).

Clinical parameters are measured daily. The disease activity index (DAI) is a combination of the individual scores for weight loss, stool consistency and rectal bleeding. At necropsy, the complete colons are removed and rinsed with sterile PBS. Segments of the distal colon are dissected for histological analysis, gene expression and protein level measurement.

5.7. Mouse Asthma Model

In vitro and in vivo models to validate efficacy of small molecules towards asthma are described by (Alba et al. 2010; Nials and Uddin 2008; Park et al. 2013; Kudlacz et al. 2008).

5.8. LPS Induced Lung Inflammation Model

5.8.1. Overview

The aim of the assay is to assess the effect of a test compound in a mouse model of acute lung inflammation induced by intranasal instillation of LPS. The impact on the induced cells recruitment in lung is evaluated by measurement of white cells count in broncho-alveolar lavage (BAL) fluid with VetABC device (medical solution gmbh, Rothusstrasse 23, 6331 Hunenberg, Switzerland).

5.8.2. Protocol

The animals (BALB/c J mice, 18-20 g) are obtained from Harlan Laboratories (Maison-Alfort, France). The animals are maintained on 12 hours light/dark cycle at 22° C. with ad libitum access to tap water and food. Litters are changed twice a week. For each tested compound, a group of 10 subjects is used. In addition to the test compound-treated groups, a vehicle+LPS control group (inLPS), a non-treated group (intact), and a positive control dexamethasone treated group (DEX) are used.

LPS is dissolved in saline solution in order to obtain a final 10 µg/50 µL solution for intranasal instillation, and administered at 50 µL/mouse by intranasal instillation.

The test compounds are prepared in 15 mL PEG200 (9 mL)/H$_2$O (6 mL) to be dosed in a range of 0.3, 1, 3, 10, and 30 mg/kg, and then kept at room temperature in the dark, and are administered once (qd) or twice daily (bid) over 2 days.

Dexamethasone (10 mg/kg, bid, po) is used as a positive control.

On day 1, mice are anaesthetized by isoflurane inhalation. During breathing, LPS solution is instilled intra-nasally and mice are monitored until complete recovery from anaesthesia.

On day 2, mice are anaesthetized by intra-peritoneal injection (under a volume of 10 mL/kg) of anaesthetic solution (18 mL NaCl 0.9%+0.5 mL xylazine (5 mg/kg)+1.5 mL ketamine (75 mg/kg)).

The trachea is canulated with a catheter, and BAL is performed by 2×0.75 mL sterile PBS. The BAL fluid removed is shaked gently at room temperature before centrifugation at 1500 r.p.m. during 10 min at 4° C.

The supernatant is removed and the cell pellet is suspended in 200 µL of PBS, kept on ice and total cell count is processed with VetABC device. Finally, mice are sacrificed under anaesthesia.

5.8.3. Data Analysis

For each readout, mean and sem are calculated. A difference statistically significant between intact or treated groups and inLPS Vehicle group is evaluated with Prism® software using a one-way ANOVA (for treatment groups) followed by a Student test. *: $p<0.05$; : $p<0.01$; *: $p<0.001$ versus inLPS Vehicle group.

Illustrative compounds tested according to this protocol are reported in the table below.

TABLE VIII in-LPS test results

| Cpd# | Dose (bid po mg/kg) | Effect significance on recruited BALF cells |
|---|---|---|
| 42 | 30 | *** |
|  | 3 | *** |
|  | 10 | *** |
|  | 10 | ** |
| 33 | 10 | ** |
| 34 | 10 | * |
| 44 | 3 | ** |
| 201 | 10 | ** |

5.9. Pharmakokinetic Studies in Rodents and Dogs 5.9.1. Animals

Male Sprague-Dawley rats (180-200 g) and female C57BL/6Rj mice (18-22 g) are obtained from Janvier (France). Non-naïve male Beagle dogs (8-13 kg) are obtained from Marshall BioResources (Italy). Two days before administration of compound, rats undergo surgery to place a catheter in the jugular vein under isoflurane anesthesia. Before oral dosing, animals are deprived of food for at least 16 h before dosing until 4 h after. Water is provided ad libitum. All in vivo experiments are carried out in a dedicated pathogen free facility (22° C.).

5.9.2. Pharmacokinetic Study

Compounds are formulated in PEG200/water for injection (25/75, v/v) for the intravenous route and in PEG200/0.5% methylcellulose (25/75, v/v) for the oral route.

5.9.2.1. Rodents

Compounds are orally dosed as a single esophageal gavage at 5 mg/kg (dosing volume of 5 mL/kg) and intravenously dosed as a bolus via the caudal vein at 1 mg/kg (dosing volume of 5 mL/kg). In the rat studies, each group consists of three rats and blood samples are collected via the jugular vein. In the mouse studies, each group consists of 21 mice (n=3/time point) and blood samples are collected by intra-cardiac puncture under isoflurane anesthesia. Li-heparin is used as anti-coagulant and blood is taken at 0.05, 0.25, 0.5, 1, 3, 5, 8 and 24 h (i.v. route) and 0.25, 0.5, 1, 3, 5, 8 and 24 h (p.o. route).

5.9.2.2. Dogs

Compounds are dosed to three animals i.v. via a 10 min infusion in the cephalic vein with a dose level of 1 mg/kg (dose volume of 2 mL/kg) and after a washout of minimally 3 days, dosed orally as a single gavage with a dose level of 5 mg/kg (dose volume of 2 mL/kg). Blood samples are taken from the jugular vein using vacutainers and Li-heparin as anticoagulant at 0.083, 0.167, 0.5, 1, 2, 4, 6, 8, 10 and 24 h (i.v.) and at 0.25, 0.5, 1, 2, 3, 4, 6, 8, 10 and 24 h (p.o.).

5.9.3. Quantification of Compound Levels in Plasma

Whole blood samples are centrifuged at 5000 rpm for 10 min and the resulting plasma samples are stored at −20° C. pending analysis. Plasma concentrations of each test compound are determined by an LC-MS/MS method 5.9.4. Determination of Pharmacokinetic Parameters Pharmacokinetic parameters are calculated using Winnonlin® (Pharsight®, United States).

5.9.5. 5-Day Rat Toxicity Study

A 5-day oral toxicity study with test compounds is performed in Sprague-Dawley male rats to assess their toxic potential and toxicokinetics, at daily doses of 100, 300 and 600 mg/kg/day, by gavage, at the constant dosage-volume of 20 mL/kg/day.

The test compounds are formulated in PEG200/0.5% methylcellulose (25/75, v/v). Each group included 6 principal male rats as well as 3 satellite animals for toxicokinetics. A fourth group is given PEG200/0.5% methylcellulose (25/75, v/v) only, at the same frequency, dosage volume and by the same route of administration, and acted as the vehicle control group.

The goal of the study is to determine the lowest dose that resulted in no adverse events (no observable adverse effect level—NOAEL).

5.9.6. Hepatocyte Stability

Models to evaluate metabolic clearance in hepatocyte are described by (McGinnity et al. 2004).

5.9.7. Liability for QT Prolongation

Potential for QT prolongation is assessed in the hERG patch clamp assay.

Whole-cell patch-clamp recordings are performed using an EPC10 amplifier controlled by Pulse v8.77 software (HEKA). Series resistance is typically less than 10 MS2 and compensated by greater than 60%, recordings are not leak subtracted. Electrodes are manufactured from GC150TF pipette glass (Harvard).

The external bathing solution contains: 135 mM NaCl, 5 mM KCl, 1.8 mM CaCl$_2$, 5 mM Glucose, 10 mM HEPES, pH 7.4.

The internal patch pipette solution contains: 100 mM Kgluconate, 20 mM KCl, 1 mM CaCl$_2$, 1 mM MgCl$_2$, 5 mM Na$_2$ATP, 2 mM Glutathione, 11 mM EGTA, 10 mM HEPES, pH 7.2.

Drugs are perfused using a Biologic MEV-9/EVH-9 rapid perfusion system.

All recordings are performed on HEK293 cells stably expressing hERG channels. Cells are cultured on 12 mm round coverslips (German glass, Bellco) anchored in the recording chamber using two platinum rods (Goodfellow). hERG currents are evoked using an activating pulse to +40 mV for 1000 ms followed by a tail current pulse to −50 mV for 2000 ms, holding potential is −80 mV. Pulses are applied every 20 s and all experiments are performed at rt.

Example 6. ADME 6.1. Kinetic Solubility

Starting from a 10 mM stock in DMSO, a serial dilution of the compound is prepared in DMSO. The dilution series is transferred to a 96 NUNC Maxisorb plate F-bottom (Cat no. 442404) and 0.1M phosphate buffer pH7.4 or 0.1M citrate buffer pH3.0 at room temperature is added.

The final concentration will range from 300 µM to 18.75 µM in 5 equal dilution steps. The final DMSO concentration does not exceed 3%. 200 µM Pyrene is added to the corner points of each 96 well plate and serves as a reference point for calibration of Z-axis on the microscope.

The assay plates are sealed and incubated for 1 h at 37° C. while shaking at 230 rpm. The plates are then scanned under a white light microscope, yielding individual pictures of the precipitate per concentration. The precipitate is analyzed and converted into a number with a software tool which can be plotted onto a graph. The first concentration at which the compound appears completely dissolved is the concentration reported; however the true concentration lies somewhere between this concentration and one dilution step higher.

Solubility values measured according to this protocol are reported in µM and µg/mL.

6.2. Plasma Protein Binding (Equilibrium Dialysis)

A 10 mM stock solution of the compound in DMSO is diluted with a factor 5 in DMSO. This solution is further diluted in freshly thawed human, rat, mouse or dog plasma (BioReclamation INC) with a final concentration of 5 µM and final DMSO concentration of 0.5% (5.5 µL in 1094.5 µL plasma in a PP-Masterblock 96well (Greiner, Cat no. 780285))

A Pierce Red Device plate with inserts (ThermoScientific, Cat no. 89809) is prepared and filled with 750 µL PBS in the buffer chamber and 500 µL of the spiked plasma in the plasma chamber. The plate is incubated for 4 h at 37° C. while shaking at 230 rpm. After incubation, 120 µL of both chambers is transferred to 360 µL acetonitrile in a 96-well round bottom, PP deep-well plates (Nunc, Cat no. 278743) and sealed with an aluminum foil lid. The samples are mixed and placed on ice for 30 min. This plate is then centrifuged 30 min at 1200rcf at 4° C. and the supernatant is transferred to a 96 v-bottom PP plate (Greiner, 651201) for analysis on LC-MS.

The plate is sealed with sealing mats (MA96RD-04S) of Kinesis, Cambs, PE19 8YX, UK and samples are measured at room temperature on LC-MS (ZQ 1525 from Waters) under optimized conditions using Quanoptimize to determine the appropriate mass of the molecule.

The samples are analyzed by LC-MS. Peak area from the compound in the buffer chamber and the plasma chamber are considered to be 100% compound. The percentage bound to plasma is derived from these results and is repor$_{te}$d as percentage bound to plasma.

The solubility of the compound in the final test concentration in PBS is inspected by microscope to indicate whether precipitation is observed or not.

6.3. Microsomal Stability

A 10 mM stock solution of compound in DMSO is diluted to 6 µM in a 105 mM phosphate buffer, pH 7.4 in a 96 deep well plate (Greiner, Cat no. 780285) and pre-warmed at 37° C.

A Glucose-6-phosphate-dehydrogenase (G6PDH, Roche, 10127671001) working stock solution of 700 U/mL is diluted with a factor 1:700 in a 105 mM phosphate buffer, pH7.4. A co-factor mix containing 0.528M MgCl$_2$.6H$_2$O (Sigma, M2670), 0.528M glucose-6-phosphate (Sigma, G-7879) and 0.208M NADP+ (Sigma, N-0505) is diluted with a factor 1:8 in a 105 mM phosphate buffer, pH7.4.

A working solution is made containing 1 mg/mL liver microsomes (Provider, Xenotech) of the species of interest (human, mouse, rat, dog, . . . ), 0.8 U/mL G6PDH and co-factor mix (6.6 mM MgCl$_2$, 6.6 mM glucose-6-phosphate, 2.6 mM NADP+). This mix is pre-incubated for 15 min, but never more than 20 min, at room temperature.

After pre-incubation, compound dilution and the mix containing the microsomes, are added together in equal amount and incubated for 30 min at 300 rpm. For the time point of 0 min, two volumes of methanol are added to the compound dilution before the microsome mix is added. The final concentration during incubation are: 3 µM test compound or control compound, 0.5 mg/mL microsomes, 0.4 U/mL G6PDH, 3.3 mM MgCl$_2$, 3.3 mM glucose-6-phosphate and 1.3 mM NaDP+.

After 30 min of incubation, the reaction is stopped with 2 volumes of methanol.

Of both time points, samples are mixed, centrifuged and the supernatant is harvested for analysis on LC-MS/MS. The instrument responses (i.e. peak heights) are referenced to the zero time-point samples (as 100%) in order to determine the percentage of compound remaining. Standard compounds Propanolol and Verapamil are included in the assay design.

The data on microsomal stability are expressed as a percentage of the total amount of compound remaining after 30 min.

6.4. CYP inhibition 6.4.1. Direct CYP inhibition

The in vitro direct inhibitory potential (IC50) of the compounds on cytochrome P450 isoenzymes in pooled human liver microsomes (HLM) is determined based on the draft FDA Guidance for Industry (Drug Interaction Studies—Study Design, Data Analysis, Implications for Dosing, and Labeling Recommendations), 2006, http://www.fda.gov/cder/guidance/index.htm.

The following probe substrates are used: phenacetin for CYP1A2, diclofenac for CYP2C9, S(+)-mephenytoin for CYP2C19, bufuralol for CYP2D6 and testosterone for CYP3A4. The following positive control inhibitors are used: α-naphtoflavone for CYP1A2, sulfaphenazole for CYP2C9, tranylcypromine for CYP2C19, quinidine for CYP2D6 and ketoconazole for CYP3A4.

6.4.2. Time-Dependent CYP3A4 Inhibition

Time-dependent CYP3A4 inhibition by the compounds, assessed in pooled HLM, is determined via IC$_{50}$ determination according to Grimm et al. Drug Metabolism and Disposition 2009, 37, 1355-1370 and the draft FDA Guidance for Industry (Drug Interaction Studies—Study Design, Data Analysis, Implications for Dosing, and Labeling Recommendations), 2006, http://www.fda.gov/cder/guidance/index.htm. Testosterone is used as probe substrate and troleandomycin is used as positive control.

6.5. Caco2 Permeability

Bi-directional Caco-2 assays are performed as described below. Caco-2 cells are obtained from European Collection of Cell Cultures (ECACC, cat 86010202) and used after a 21 day cell culture in 24-well Transwell plates (Fisher TKT-545-020B).

2×105 cells/well are seeded in plating medium consisting of DMEM+GlutaMAXI+1% NEAA+10% FBS (FetalClone II)+1% Pen/Strep. The medium is changed every 2-3 days.

Test and reference compounds (propranolol and rhodamine 123 or vinblastine, all purchased from Sigma) are prepared in Hanks' Balanced Salt Solution containing 25 mM HEPES (pH7.4) and added to either the apical (125 µL) or basolateral (600 µL) chambers of the Transwell plate assembly at a concentration of 10 µM with a final DMSO concentration of 0.25%.

50 µM Lucifer Yellow (Sigma) is added to the donor buffer in all wells to assess integrity of the cell layers by monitoring Lucifer Yellow permeation. As Lucifer Yellow (LY) cannot freely permeate lipophilic barriers, a high degree of LY transport indicates poor integrity of the cell layer.

After a 1 hr incubation at 37° C. while shaking at an orbital shaker at 150 rpm, 70 µL aliquots are taken from both apical (A) and basal (B) chambers and added to 100 µL 50:50 acetonitrile:water solution containing analytical internal standard (0.5 µM carbamazepine) in a 96 well plate.

Lucifer yellow is measured with a Spectramax Gemini XS (Ex 426 nm and Em 538 nm) in a clean 96 well plate containing 150 µL of liquid from basolateral and apical side.

Concentrations of compound in the samples are measured by high performance liquid-chromatography/mass spectroscopy (LC-MS/MS).

Apparent permeability (Papp) values are calculated from the relationship:

$$Papp=[compound]acceptor\ final \times Vacceptor/([compound]donor\ initial \times Vdonor)/Tinc \times Vdonor/surface\ area \times 60 \times 10^{-6}\ cm/s$$

V=chamber volume
Tinc=incubation time.
Surface area=0.33 cm$^2$

The Efflux ratios, as an indication of active efflux from the apical cell surface, are calculated using the ratio of Papp B>A/Papp A>B.

The following assay acceptance criteria are used:
Propranolol: Papp (A>B) value ≥20(×10$^{-6}$ cm/s)
Rhodamine 123 or Vinblastine: Papp (A>B) value <5 (×10$^{-6}$ cm/s) with Efflux ratio ≥5.
Lucifer yellow permeability: ≤100 nm/s

REFERENCES

Alba, J. De, K. Raemdonck, A. Dekkak, M. Collins, S. Wong, A. T. Nials, R. G. Knowles, M. G. Belvisi, and M. A. Birrell. 2010. "House Dust Mite Induces Direct Airway Inflammation in Vivo: Implications for Future Disease Therapy?" *European Respiratory Journal* 35 (6): 1377-87. doi: 10.1183/09031936.00022908.

Bandoh, K, J Aoki, A Taira, M Tsujimoto, H Arai, and K Inoue. 2000. "Lysophosphatidic Acid (LPA) Receptors of the EDG Family Are Differentially Activated by LPA Species. Structure-Activity Relationship of Cloned LPA Receptors." *FEBS Letters* 478 (1-2): 159-65.

Baumforth, Karl R N, Joanne R Flavell, Gary M Reynolds, Gillian Davies, Trevor R Pettit, Wenbin Wei, Susan Morgan, et al. 2005. "Induction of Autotaxin by the Epstein-Barr Virus Promotes the Growth and Survival of Hodgkin Lymphoma Cells." *Blood* 106 (6): 2138-46. doi: 10.1182/blood-2005-02-0471.

Bozinovski, Steven, Anastasia Hutchinson, Michelle Thompson, Lochlan Macgregor, James Black, Eleni Giannakis, Anne-Sophie Karlsson, et al. 2008. "Serum Amyloid a Is a Biomarker of Acute Exacerbations of Chronic Obstructive Pulmonary Disease." *American Journal of Respiratory and Critical Care Medicine* 177 (3): 269-78. doi: 10.1164/rccm.200705-678OC.

Braddock, Demetrios T. 2010. "Autotaxin and Lipid Signaling Pathways as Anticancer Targets." *Current Opinion in Investigational Drugs (London, England:* 2000) 11 (6): 629-37.

Bundgaard, Hans. 1992. "(C) Means to Enhance Penetration: (1) Prodrugs as a Means to Improve the Delivery of Peptide Drugs." *Advanced Drug Delivery Reviews* 8 (1): 1-38. doi:10.1016/0169-409X(92)90014-H.

Bush, Katherine A., Katherine M. Farmer, Judith S. Walker, and Bruce W. Kirkham. 2002. "Reduction of Joint Inflammation and Bone Erosion in Rat Adjuvant Arthritis by Treatment with Interleukin-17 Receptor IgG1 Fc Fusion Protein." *Arthritis & Rheumatism* 46 (3): 802-5. doi: 10.1002/art. 10173.

Castelino, Flavia V., Jon Seiders, Gretchen Bain, Sarah F. Brooks, Chris King, James S. Swaney, Daniel S. Lorrain, Jerold Chun, Andrew D. Luster, and Andrew M. Tager. 2011. "Genetic Deletion or Pharmacologic Antagonism of LPA1 Ameliorates Dermal Fibrosis in a Scleroderma Mouse Model." *Arthritis and Rheumatism* 63 (5): 1405-15. doi: 10.1002/art.30262.

Corley, Edward G., Karen Conrad, Jerry A. Murry, Cecile Savarin, Justin Holko, and Genevieve Boice. 2004. "Direct Synthesis of 4-Arylpiperidines via Palladium/Copper(I)-Cocatalyzed Negishi Coupling of a 4-Piperidylzinc Iodide with Aromatic Halides and Triflates." *The Journal of Organic Chemistry* 69 (15): 5120-23. doi: 10.1021/jo049647i.

David, Marion, Estelle Wannecq, Francoise Descotes, Silvia Jansen, Blandine Deux, Johnny Ribeiro, Claire-Marie Serre, et al. 2010. "Cancer Cell Expression of Autotaxin Controls Bone Metastasis Formation in Mouse through Lysophosphatidic Acid-Dependent Activation of Osteoclasts." *PLoS ONE* 5 (3). doi: 10.1371/journal-.pone.0009741. http://www.ncbi.nlm.nih.gov/pmc/articles/PMC2840030/.

Demedts, I K, A Morel-Montero, S Lebecque, Y Pacheco, D Cataldo, G F Joos, R A Pauwels, and G G Brusselle. 2006. "Elevated MMP-12 Protein Levels in Induced Sputum from Patients with COPD." *Thorax* 61 (3): 196-201. doi: 10.1136/thx.2005.042432.

Eagan, Tomas M., Jan K. Damas, Thor Ueland, Marianne Voll-Aanerud, Tom E. Mollnes, Jon A. Hardie, Per S. Bakke, and Pal Aukrust. 2010. "Neutrophil Gelatinase-Associated Lipocalin: A Biomarker in Copd." *CHEST Journal* 138 (4): 888-95. doi:10.1378/chest.09-2718.

Emo, Jason, Nida Meednu, Timothy J. Chapman, Fariba Rezaee, Marlene Balys, Troy Randall, Tirumalai Rangasamy, and Steve N. Georas. 2012. "Lpa2 Is a Negative Regulator of Dendritic Cell Activation and Murine Models of Allergic Lung Inflammation." *Journal of Immunology* (Baltimore, Md.: 1950) 188 (8): 3784-90. doi: 10.4049/jimmunol. 1102956.

Federico, Lorenzo, Hongmei Ren, Paul A. Mueller, Tao Wu, Shuying Liu, Jelena Popovic, Eric M. Blalock, et al. 2012. "Autotaxin and Its Product Lysophosphatidic Acid Suppress Brown Adipose Differentiation and Promote Diet-Induced Obesity in Mice." *Molecular Endocrinology* 26 (5): 786-97. doi:10.1210/me.2011-1229.

Ferry, Gilles, Edwige Tellier, Anne Try, Sandra Gres, Isabelle Naime, Marie Francoise Simon, Marianne Rodriguez, et al. 2003. "Autotaxin Is Released from Adipocytes, Catalyzes Lysophosphatidic Acid Synthesis, and Activates Preadipocyte Proliferation UP-REGULATED EXPRESSION WITH ADIPOCYTE DIFFERENTIATION AND OBESITY." *Journal of Biological Chemistry* 278 (20): 18162-69.

Gaetano, Cristoforo G., Nasser Samadi, Jose L. Tomsig, Timothy L. Macdonald, Kevin R. Lynch, and David N. Brindley. 2009. "Inhibition of Autotaxin Production or Activity Blocks Lysophosphatidylcholine-Induced Migration of Human Breast Cancer and Melanoma Cells." *Molecular Carcinogenesis* 48 (9): 801-9. doi: 10.1002/mc.20524.

Ganguly, Koustav, Tobias Stoeger, Scott C. Wesselkamper, Claudia Reinhard, Maureen A. Sartor, Mario Medvedovic, Craig R. Tomlinson, et al. 2007. "Candidate Genes Controlling Pulmonary Function in Mice: Transcript Profiling and Predicted Protein Structure." *Physiological Genomics* 31 (3): 410-21. doi:10.1152/physiolgenomics.00260.2006.

Gardell, Shannon E., Adrienne E. Dubin, and Jerold Chun. 2006. "Emerging Medicinal Roles for Lysophospholipid Signaling." *Trends in Molecular Medicine* 12 (2): 65-75. doi: 10.1016/j.molmed.2005.12.001.

Gennero, Isabelle, Sara Laurencin-Dalicieux, Francoise Conte-Auriol, Fabienne Briand-Mesange, Danielle Laurencin, Jackie Rue, Nicolas Beton, et al. 2011. "Absence of the Lysophosphatidic Acid Receptor LPA1 Results in Abnormal Bone Development and Decreased Bone Mass." *Bone* 49 (3): 395-403. doi:10.1016/j.bone.2011.04.018.

Georas, S. N., E. Berdyshev, W. Hubbard, I. A. Gorshkova, P. V. Usatyuk, B. Saatian, A. C. Myers, et al. 2007. "Lysophosphatidic Acid Is Detectable in Human Bronchoalveolar Lavage Fluids at Baseline and Increased after Segmental Allergen Challenge." *Clinical & Experimental Allergy* 37 (3): 311-22. doi:10.1111/j.1365-2222.2006.02626.x.

Gierse, James, Atli Thorarensen, Konstantine Beltey, Erica Bradshaw-Pierce, Luz Cortes-Burgos, Troii Hall, Amy Johnston, et al. 2010. "A Novel Autotaxin Inhibitor Reduces Lysophosphatidic Acid Levels in Plasma and the Site of Inflammation." *Journal of Pharmacology and Experimental Therapeutics* 334 (1): 310-17. doi:10.1124/jpet.110.165845.

Hausmann, Jens, Satwik Kamtekar, Evangelos Christodoulou, Jacqueline E. Day, Tao Wu, Zachary Fulkerson, Harald M. H. G. Albers, et al. 2011. "Structural Basis for Substrate Discrimination and Integrin Binding by Autotaxin." *Nature Structural & Molecular Biology* 18 (2): 198-204. doi:10.1038/nsmb.1980.

Inoue, M., W. Xie, Y. Matsushita, J. Chun, J. Aoki, and H. Ueda. 2008. "Lysophosphatidylcholine Induces Neuropathic Pain through an Action of Autotaxin to Generate Lysophosphatidic Acid." *Neuroscience* 152 (2): 296-98. doi:10.1016/j.neuroscience.2007.12.041.

Iyer, Padma, Robert Lalane, Corey Morris, Pratap Challa, Robin Vann, and Ponugoti Vasantha Rao. 2012. "Autotaxin-Lysophosphatidic Acid Axis Is a Novel Molecular Target for Lowering Intraocular Pressure." *PLoS ONE* 7 (8). doi:10.1371/journal.pone.0042627. http://www.ncbi.nlm.nih.gov/pmc/articles/PMC3423407/.

Jou, I-Ming, Ai-Li Shiau, Shih-Yao Chen, Chrong-Reen Wang, Dar-Bin Shieh, Ching-Shan Tsai, and Chao-Liang Wu. 2005. "Thrombospondin 1 as an Effective Gene Therapeutic Strategy in Collagen-Induced Arthritis." *Arthritis & Rheumatism* 52 (1): 339-44. doi: 10.1002/art.20746.

Kanda, Hidenobu, Rebecca Newton, Russell Klein, Yuka Morita, Michael D. Gunn, and Steven D. Rosen. 2008. "Autotaxin, a Lysophosphatidic Acid-Producing Ectoenzyme, Promotes Lymphocyte Entry into Secondary Lymphoid Organs." *Nature Immunology* 9 (4): 415-23. doi: 10.1038/ni 1573.

Khachigian, Levon M. 2006. "Collagen Antibody-Induced Arthritis." *Nature Protocols* 1 (5): 2512-16. doi: 10.1038/nprot.2006.393.

Kishi, Yasuhiro, Shinichi Okudaira, Masayuki Tanaka, Kotaro Hama, Dai Shida, Joji Kitayama, Takao Yamori, Junken Aoki, Takamitsu Fujimaki, and Hiroyuki Arai. 2006. "Autotaxin Is Overexpressed in Glioblastoma Multiforme and Contributes to Cell Motility of Glioblastoma by Converting Lysophosphatidylcholine TO Lysophosphatidic Acid." *Journal of Biological Chemistry* 281 (25): 17492-500. doi:10.1074/jbc.M601803200.

Kremer, Andreas E., Job J. W. W. Martens, Wim Kulik, Franziska Rueff, Edith M. M. Kuiper, Henk R. van Buuren, Karel J. van Erpecum, et al. 2010. "Lysophosphatidic Acid Is a Potential Mediator of Cholestatic Pruritus." *Gastroenterology* 139 (3): 1008-1018.e1. doi: 10.1053/j.gastro.2010.05.009.

Kudlacz, Elizabeth, Maryrose Conklyn, Catharine Andresen, Carrie Whitney-Pickett, and Paul Changelian. 2008. "The JAK-3 Inhibitor CP-690550 Is a Potent Anti-Inflammatory Agent in a Murine Model of Pulmonary Eosinophilia." *European Journal of Pharmacology* 582 (1-3): 154-61. doi: 10.1016/j.ejphar.2007.12.024.

Lin, H—S, C—Y Hu, H-Y Chan, Y-Y Liew, H-P Huang, L Lepescheux, E Bastianelli, R Baron, G Rawadi, and P Clément-Lacroix. 2007. "Anti-Rheumatic Activities of Histone Deacetylase (HDAC) Inhibitors in Vivo in Collagen-Induced Arthritis in Rodents." *British Journal of Pharmacology* 150 (7): 862-72. doi: 10.1038/sj.bjp.0707165.

Lin, Mu-En, Deron R. Herr, and Jerold Chun. 2010. "Lysophosphatidic Acid (LPA) Receptors: Signaling Properties and Disease Relevance." *Prostaglandins & Other Lipid Mediators* 91 (3-4): 130-38. doi: 10.1016/j.prostaglandins.2009.02.002.

Llinás, Laia, Victor I. Peinado, J. Ramon Gofii, Roberto Rabinovich, Sandra Pizarro, Robert Rodriguez-Roisin, Joan Albert Barberà, and Ricardo Bastos. 2011. "Similar Gene Expression Profiles in Smokers and Patients with Moderate COPD." *Pulmonary Pharmacology & Therapeutics* 24 (1): 32-41. doi: 10.1016/j.pupt.2010.10.010.

Matas-Rico, Elisa, Beatriz Garcia-Diaz, Pedro Llebrez-Zayas, Diana Lopez-Barroso, Luis Santin, Carmen Pedraza, Anibal Smith-Fernandez, et al. 2008. "Deletion of Lysophosphatidic Acid Receptor LPA1 Reduces Neurogenesis in the Mouse Dentate Gyrus." *Molecular and Cellular Neurosciences* 39 (3): 342-55. doi:10.1016/j.mcn.2008.07.014.

McGinnity, Dermot F., Matthew G. Soars, Richard A. Urbanowicz, and Robert J. Riley. 2004. "Evaluation of Fresh and Cryopreserved Hepatocytes as in Vitro Drug Metabolism Tools for the Prediction of Metabolic Clearance." *Drug Metabolism and Disposition* 32 (11): 1247-53. doi: 10.1124/dmd. 104.000026.

Murph, Mandi, Giang Nguyen, Harish Radhakrishna, and Gordon B. Mills. 2008. "Sharpening the Edges of Understanding the Structure/function of the LPA1 Receptor." *Biochimica et Biophysica Acta* 1781 (9): 547-57. doi: 10.1016/j.bbalip.2008.04.007.

Nakao, Isao, Sachiko Kanaji, Shoichiro Ohta, Hidetomo Matsushita, Kazuhiko Arima, Noriko Yuyama, Mutsuo Yamaya, et al. 2008. "Identification of Pendrin as a Common Mediator for Mucus Production in Bronchial Asthma and Chronic Obstructive Pulmonary Disease." *The Journal of Immunology* 180 (9): 6262-69.

Nakasaki, Tae, Toshiyuki Tanaka, Shinichi Okudaira, Michi Hirosawa, Eiji Umemoto, Kazuhiro Otani, Soojung Jin, et al. 2008. "Involvement of the Lysophosphatidic Acid-Generating Enzyme Autotaxin in Lymphocyte-Endothelial Cell Interactions." *The American Journal of Pathology* 173 (5): 1566-76. doi: 10.2353/ajpath.2008.071153.

Nials, Anthony T., and Sorif Uddin. 2008. "Mouse Models of Allergic Asthma: Acute and Chronic Allergen Challenge." *Disease Models & Mechanisms* 1 (4-5): 213-20. doi:10.1242/dmm.000323.

Nikitopoulou, Ioanna, Nikos Oikonomou, Emmanuel Karouzakis, loanna Sevastou, Nefeli Nikolaidou-Katsaridou, Zhenwen Zhao, Vassilis Mersinias, et al. 2012. "Autotaxin Expression from Synovial Fibroblasts Is Essential for the Pathogenesis of Modeled Arthritis." *The Journal of Experimental Medicine* 209 (5): 925-33. doi: 10.1084/jem.20112012.

Nishida, Keiichiro, Takamitsu Komiyama, Shin-ichi Miyazawa, Zheng-Nan Shen, Takayuki Furumatsu, Hideyuki Doi, Aki Yoshida, et al. 2004. "Histone Deacetylase Inhibitor Suppression of Autoantibody-Mediated Arthritis in Mice via Regulation of p16INK4a and p21WAF1/Cip1 Expression." *Arthritis & Rheumatism* 50 (10): 3365-76. doi:10.1002/art.20709.

Nouh, Mohammed Ahmed Abdel Muneem, Xiu-Xian Wu, Homare Okazoe, Hiroyuki Tsunemori, Reiji Haba, Abdel Muneem Mohammed Abou-Zeid, Mohammed Diaa Saleem, et al. 2009. "Expression of Autotaxin and Acylglycerol Kinase in Prostate Cancer: Association with Cancer Development and Progression." *Cancer Science* 100 (9): 1631-38. doi:10.1111/j.1349-7006.2009.01234.x.

Oikonomou, Nikos, Marios-Angelos Mouratis, Argyris Tzouvelekis, Eleanna Kaffe, Christos Valavanis, George Vilaras, Andreas Karameris, Glenn D. Prestwich, Demosthenes Bouros, and Vassilis Aidinis. 2012. "Pulmonary Autotaxin Expression Contributes to the Pathogenesis of Pulmonary Fibrosis." *American Journal of Respiratory Cell and Molecular Biology* 47 (5): 566-74. doi:10.1165/rcmb.2012-00040C.

Oste, Line, Phil Salmon, Graham Dixon, and Luc van Rompaey. 2007. "A High Throughput Method of Measuring Bone Architectural Disturbance in a Murine CIA Model by Micro-CT Morphometry". Poster presented at the European Calcified Tissue Society, May 8, Copenhagen. http://www.ectsoc.org/copenhagen2007/.

Panupinthu, N, H Y Lee, and G B Mills. 2010. "Lysophosphatidic Acid Production and Action: Critical New Players in Breast Cancer Initiation and Progression." *British Journal of Cancer* 102 (6): 941-46. doi: 10.1038/sj.bjc.6605588.

Park, Gye Young, Yong Gyu Lee, Evgeny Berdyshev, Sharmilee Nyenhuis, Jian Du, Panfeng Fu, Irina A. Gorshkova, et al. 2013. "Autotaxin Production of Lysophosphatidic Acid Mediates Allergic Asthmatic Inflammation." *American Journal of Respiratory and Critical Care Medicine* 188 (8): 928-40. doi: 10.1164/rccm.201306-1014OC.

Pradére, Jean-Philippe, Julie Klein, Sandra Gres, Charlotte Guigne, Eric Neau, Philippe Valet, Denis Calise, et al. 2007. "LPA1 Receptor Activation Promotes Renal Interstitial Fibrosis." *Journal of the American Society of Nephrology* 18 (12): 3110-18. doi:10.1681/ASN.2007020196.

Rall, L. C., and R. Roubenoff 2004. "Rheumatoid Cachexia: Metabolic Abnormalities, Mechanisms and Interventions." *Rheumatology* 43 (10): 1219-23. doi:10.1093/rheumatology/keh321.

Salvemini, D, E Mazzon, L Dugo, I Serraino, A De Sarro, A P Caputi, and S Cuzzocrea. 2001. "Amelioration of Joint Disease in a Rat Model of Collagen-Induced Arthritis by M40403, a Superoxide Dismutase Mimetic." *Arthritis and Rheumatism* 44 (12): 2909-21.

Shelton, David L., Jörg Zeller, Wei-Hsien Ho, Jaume Pons, and Amrnon Rosenthal. 2005. "Nerve Growth Factor Mediates Hyperalgesia and Cachexia in Auto-Immune Arthritis." *Pain* 116 (1-2): 8-16. doi: 10.1016/j.pain.2005.03.039.

Sims, Natalie A., Jonathan R. Green, Markus Glatt, Stephen Schlict, T. John Martin, Matthew T. Gillespie, and Evan Romas. 2004. "Targeting Osteoclasts with Zoledronic Acid Prevents Bone Destruction in Collagen-Induced Arthritis." *Arthritis & Rheumatism* 50 (7): 2338-46. doi: 10.1002/art.20382.

Sina, Christian, Olga Gavrilova, Matti Förster, Andreas Till, Stefanie Derer, Friederike Hildebrand, Bjorn Raabe, et al. 2009. "G Protein-Coupled Receptor 43 Is Essential for Neutrophil Recruitment during Intestinal Inflammation." *The Journal of Immunology* 183 (11): 7514-22. doi: 10.4049/jimmunol.0900063.

Stassar, M J J G, G Devitt, M Brosius, L Rinnab, J Prang, T Schradin, J Simon, S Petersen, A Kopp-Schneider, and M Zoller. 2001. "Identification of Human Renal Cell Carcinoma Associated Genes by Suppression Subtractive Hybridization." *British Journal of Cancer* 85 (9): 1372-82. doi:10.1054/bjoc.2001.2074.

Sumida, Hayakazu, Kyoko Noguchi, Yasuyuki Kihara, Manabu Abe, Keisuke Yanagida, Fumie Hamano, Shinichi Sato, et al. 2010. "LPA4 Regulates Blood and Lymphatic Vessel Formation during Mouse Embryogenesis." *Blood* 116 (23): 5060-70. doi: 10.1182/blood-2010-03-272443.

Tager, Andrew M., Peter LaCamera, Barry S. Shea, Gabriele S. Campanella, Moises Selman, Zhenwen Zhao, Vasiliy Polosukhin, et al. 2008. "The Lysophosphatidic Acid Receptor LPA1 Links Pulmonary Fibrosis to Lung Injury by Mediating Fibroblast Recruitment and Vascular Leak." *Nature Medicine* 14 (1): 45-54. doi:10.1038/nm1685.

Tanaka, Masayuki, Shinichi Okudaira, Yasuhiro Kishi, Ryunosuke Ohkawa, Sachiko Iseki, Masato Ota, Sumihare Noji, Yutaka Yatomi, Junken Aoki, and Hiroyuki Arai. 2006. "Autotaxin Stabilizes Blood Vessels and Is Required for Embryonic Vasculature by Producing Lysophosphatidic Acid." *Journal of Biological Chemistry* 281 (35): 25822-30. doi: 10.1074/jbc.M605142200.

Tania, Mousumi, Md. Asaduzzaman Khan, Huaiyuan Zhang, Jinhua Li, and Yuanda Song. 2010. "Autotaxin: A Protein with Two Faces." *Biochemical and Biophysical Research Communications* 401 (4): 493-97. doi: 10.1016/j.bbrc.2010.09.114.

Tilley, Ann E., Timothy P. O'Connor, Neil R. Hackett, Yael Strulovici-Barel, Jacqueline Salit, Nancy Amoroso, Xi Kathy Zhou, et al. 2011. "Biologic Phenotyping of the Human Small Airway Epithelial Response to Cigarette Smoking." *PLoS ONE* 6 (7). doi:10.1371/journal.pone.0022798. http://www.ncbi.nlm.nih.gov/pmc/articles/PMC3145669/.

Van Meeteren, Laurens A., Paula Ruurs, Catelijne Stortelers, Peter Bouwman, Marga A. van Rooijen, Jean Philippe Pradere, Trevor R. Pettit, et al. 2006. "Autotaxin, a Secreted Lysophospholipase D, Is Essential for Blood Vessel Formation during Development." *Molecular and Cellular Biology* 26 (13): 5015-22. doi: 10.1128/MCB.02419-05.

Vidot, Susanne, James Witham, Roshan Agarwal, Sebastian Greenhough, Harnoor S. Bamrah, Gabor J. Tigyi, Stanley B. Kaye, and Alan Richardson. 2010. "Autotaxin Delays Apoptosis Induced by Carboplatin in Ovarian Cancer Cells." *Cellular Signalling* 22 (6): 926-35. doi: 10.1016/j.cellsig.2010.01.017.

Walsmith, Joseph, Leslie Abad, Joseph Kehayias, and Ronenn Roubenoff. 2004. "Tumor Necrosis Factor-Alpha Production Is Associated with Less Body Cell Mass in Women with Rheumatoid Arthritis." *The Journal of Rheumatology* 31 (1): 23-29.

Walters, Dianne M., and Steven R. Kleeberger. 2001. "Mouse Models of Bleomycin-Induced Pulmonary Fibrosis." In *Current Protocols in Pharmacology*. John Wiley & Sons, Inc. http://onlinelibrary.wiley.com/doi/10.1002/0471141755.ph0546s40/abstract.

Wirtz, Stefan, and Markus F. Neurath. 2007. "Mouse Models of Inflammatory Bowel Disease." *Advanced Drug Delivery Reviews* 59 (11): 1073-83. doi: 10.1016/j.addr.2007.07.003.

Wu, Jian-Min, Yan Xu, Nicholas J Skill, Hongmiao Sheng, Zhenwen Zhao, Menggang Yu, Romil Saxena, and Mary A Maluccio. 2010. "Autotaxin Expression and Its Connection with the TNF-Alpha-NF-?B Axis in Human Hepatocellular Carcinoma." *Molecular Cancer* 9 (March): 71. doi: 10.1186/1476-4598-9-71.

Wuts, Peter G. M., and Theodora W. Greene. 2012. *Greene's Protective Groups in Organic Synthesis*. 4 edition. Wiley-Interscience.

Xu, Ming Yan, Joanne Porte, Alan J. Knox, Paul H. Weinreb, Toby M. Maher, Shelia M. Violette, Robin J. McAnulty, Dean Sheppard, and Gisli Jenkins. 2009. "Lysophosphatidic Acid Induces αvβ6 Integrin-Mediated TGF-B Activation via the LPA2 Receptor and the Small G Protein Gaq." *The American Journal of Pathology* 174 (4): 1264-79. doi: 10.2353/ajpath.2009.080160.

Xu, Xiaoyu, and Glenn D Prestwich. 2010. "Inhibition of Tumor Growth and Angiogenesis by a Lysophosphatidic Acid Antagonist in a Engineered Three-Dimensional Lung Cancer Xenograft Model." *Cancer* 116 (7): 1739-50. doi:10.1002/cncr.24907.

Ye, Xiaoqin, Kotaro Hama, James J. A. Contos, Brigitte Anliker, Aska Inoue, Michael K. Skinner, Hiroshi Suzuki, et al. 2005. "LPA3-Mediated Lysophosphatidic Acid Signalling in Implantation and Embryo Spacing." *Nature* 435 (7038): 104-8. doi:10.1038/nature03505.

Zhang, Honglu, Xiaoyu Xu, Joanna Gajewiak, Ryoko Tsukahara, *Yuko* Fujiwara, Jianxiong Liu, James I. Fells, et al. 2009. "Dual Activity Lysophosphatidic Acid Receptor Pan-Antagonist/Autotaxin Inhibitor Reduces Breast Cancer Cell Migration In Vitro and Causes Tumor Regression In Vivo." *Cancer Research* 69 (13): 5441-49. doi: 10.1158/0008-5472.CAN-09-0302.

Zhao, Jing, Donghong He, Evgeny Berdyshev, Mintao Zhong, Ravi Salgia, Andrew J. Morris, Susan S. Smyth, Viswanathan Natarajan, and Yutong Zhao. 2011. "Autotaxin Induces Lung Epithelial Cell Migration through lysoPLD Activity-Dependent and -Independent Pathways." *The Biochemical Journal* 439 (1): 45-55. doi: 10.1042/BJ20110274.

Zhao, Yutong, and Viswanathan Natarajan. 2013. "Lysophosphatidic Acid (LPA) and Its Receptors: Role in Airway Inflammation and Remodeling." *Biochimica et Biophysica Acta* 1831 (1): 86-92. doi: 10.1016/j.bbalip.2012.06.014.

Zhao, Yutong, Jiankun Tong, Donghong He, Srikanth Pendyala, Berdyshev Evgeny, Jerold Chun, Anne I Sperling, and Viswanathan Natarajan. 2009. "Role of Lysophosphatidic Acid Receptor LPA2 in the Development of Allergic Airway Inflammation in a Murine Model of Asthma." *Respiratory Research* 10 (1): 114. doi:10.1186/1465-9921-10-114.

FINAL REMARKS

It will be appreciated by those skilled in the art that the foregoing descriptions are exemplary and explanatory in nature, and intended to illustrate the invention and its preferred embodiments. Through routine experimentation, an artisan will recognize apparent modifications and variations that may be made without departing from the spirit of the invention. All such modifications coming within the scope of the appended claims are intended to be included therein. Thus, the invention is intended to be defined not by the above description, but by the following claims and their equivalents.

All publications, including but not limited to patents and patent applications, cited in this specification are herein incorporated by reference as if each individual publication are specifically and individually indicated to be incorporated by reference herein as though fully set forth.

It should be understood that factors such as the differential cell penetration capacity of the various compounds can contribute to discrepancies between the activity of the compounds in the in vitro biochemical and cellular assays.

At least some of the chemical names of compound of the invention as given and set forth in this application, may have been generated on an automated basis by use of a commercially available chemical naming software program, and have not been independently verified. Representative programs performing this function include the Lexichem naming tool sold by Open Eye Software, Inc. and the Autonom Software tool sold by MDL, Inc. In the instance where the indicated chemical name and the depicted structure differ, the depicted structure will control.

The invention claimed is:
1. A compound according to Formula I:

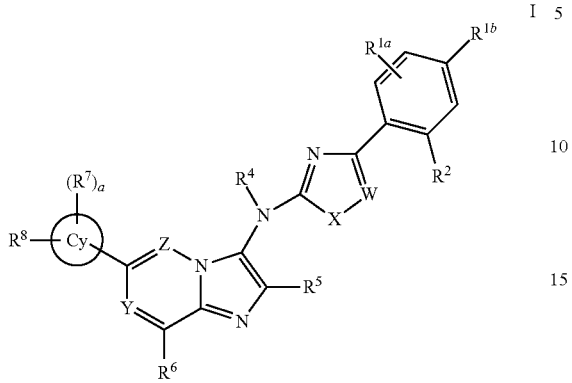

wherein
$R^{1a}$ is H, halo or $C_{1-4}$ alkyl;
$R^{1b}$ is:
  halo,
  $C_{1-4}$ alkyl (which alkyl is optionally substituted with one or more independently selected halo), or
  $C_{1-4}$ alkoxy (which alkoxy is optionally substituted with one or more independently selected halo);
X is —S—, —O—, —N=CH—, —CH=N— or —CH=CH—;
W is N, or $CR^3$
when W is N, $R^2$ is:
  H,
  —CN,
  halo,
  $C_{1-4}$ alkyl (which alkyl is optionally substituted with one or more independently selected OH, or CN),
  —C(=O)CH$_3$,
  —C(=O)CF$_3$,
  —C(=O)OCH$_3$,
  —C(=O)NH$_2$,
  —NHC(=O)CH$_3$, or
when W is $CR^3$, one of $R^2$ or $R^3$ is:
  H,
  —CN,
  halo,
  $C_{1-4}$ alkyl (which alkyl is optionally substituted with one or more independently selected OH, or CN),
  —C(=O)CH$_3$,
  —C(=O)CF$_3$,
  —C(=O)OCH$_3$,
  —C(=O)NH$_2$,
  —NHC(=O)CH$_3$,
  and the other is H, or $C_{1-4}$ alkyl;
$R^4$ is $C_{1-4}$ alkyl;
$R^5$ is $C_{1-4}$ alkyl optionally substituted with one or more independently selected CN, OH, halo, or —C(=O)NH$_2$;
one of Y and Z is CH and the other is N;
$R^6$ is selected from H, —CH$_3$ and halo;
Cy is:
  $C_{4-10}$ cycloalkyl,
  4-10 membered mono or bicyclic heterocycloalkyl containing one or more heteroatoms independently selected from O, N, and S, or
  4-7 membered heterocycloalkenyl containing 1 double bond, containing one or more heteroatoms independently selected from O, N, and S;
each $R^7$ is independently selected from:
  OH,
  oxo,
  halo, and
  $C_{1-4}$ alkyl (which alkyl is optionally substituted with one or more independently selected OH, or $C_{1-4}$ alkoxy);
the subscript a is 0, 1 or 2;
$R^8$ is -($L_1$-$W_1$)$_m$-$L_2$-$G_1$,
wherein
$L_1$ is absent, or is —O—, —C(=O)—, —NR$^i$, —NR$^h$C(=O)—, or —SO$_2$;
$W_1$ is $C_{1-4}$ alkylene;
the subscript m is 0, or 1;
$L_2$ is absent, or is —O—, —C(=O)—, —C(=O)O—, —OC(=O)—, —C(=O)—C(=O)—, —C(=O)C(=O)NR$^a$—, —NR$^b$—, —C(=O)NR$^c$—, —NR$^d$C(=O)—, —NR$^d$C(=O)O—, —SO$_2$—, —SO$_2$NR$^e$— or —NR$^f$SO$_2$—;
$G_1$ is
  H,
  —CN,
  $C_{1-4}$ alkyl (which alkyl is optionally substituted with one or more independently selected —CN, OH, halo or phenyl),
  $C_{3-7}$ cycloalkyl (which cycloalkyl is optionally substituted with —NH$_2$),
  5-6 membered heterocycloalkenyl containing 1 double bond containing one or more heteroatoms independently selected from O, N, and S, (which heterocycloalkenyl is optionally substituted with one or more independently selected $R^9$ groups),
  4-10 membered mono, bi or spirocyclic heterocycloalkyl containing one or more heteroatoms independently selected from O, N, and S, (which heterocycloalkyl is optionally substituted with one or more independently selected $R^9$ groups), or
  5-6 membered heteroaryl containing one or more heteroatoms independently selected from O, N, and S, (which heteroaryl is optionally substituted with one or more independently selected $R^{10}$ groups), or
each $R^9$ is oxo, or $R^{10}$;
each $R^{10}$ is:
  —OH,
  halo,
  —CN,
  $C_{1-4}$ alkyl (which alkyl is optionally substituted with one or more independently selected OH, halo, or phenyl),
  $C_{1-4}$ alkoxy,
  $C_{3-7}$ cycloalkyl,
  phenyl,
  —SO$_2$CH$_3$,
  —C(=O)C$_{1-4}$ alkoxy,
  —C(=O)C$_{1-4}$ alkyl, or
  —NR$^g$C(=O)C$_{1-4}$ alkyl; and
each $R^a$, $R^b$, $R^c$, $R^d$, $R^e$, $R^f$, $R^g$, $R^h$, $R^i$, and $R^j$ is independently selected from H, and $C_{1-4}$ alkyl;
or a pharmaceutically acceptable salt, or a solvate, or a pharmaceutically acceptable salt of a solvate thereof, or a biologically active metabolite thereof.

2. A compound or pharmaceutically acceptable salt thereof, according to claim 1, wherein $R^{1a}$ is F, Cl, —CH$_3$ or —C$_2$H$_5$.

3. A compound or pharmaceutically acceptable salt thereof, according to claim 1, wherein $R^{1b}$ is F, Cl, —CH$_3$, —C$_2$H$_5$, —CF$_3$, —OCH$_3$, or —OCF$_3$.

4. A compound or pharmaceutically acceptable salt thereof, according to claim 1, wherein Cy is oxetanyl, azetidinyl, tetrahydrofuranyl, pyrolidinyl, tetrahydropyranyl, piperidinyl, piperazinyl, morpholinyl, or thiomorpholinyl.

5. A compound or pharmaceutically acceptable salt thereof, according to claim 1, wherein the subscript a is 1 or 2, and $R^7$ is OH, oxo, F, Cl, or —CH$_3$.

6. A compound or pharmaceutically acceptable salt thereof, according to claim 1, wherein the compound is according to Formula IVa, IVb, IVc or IVd:

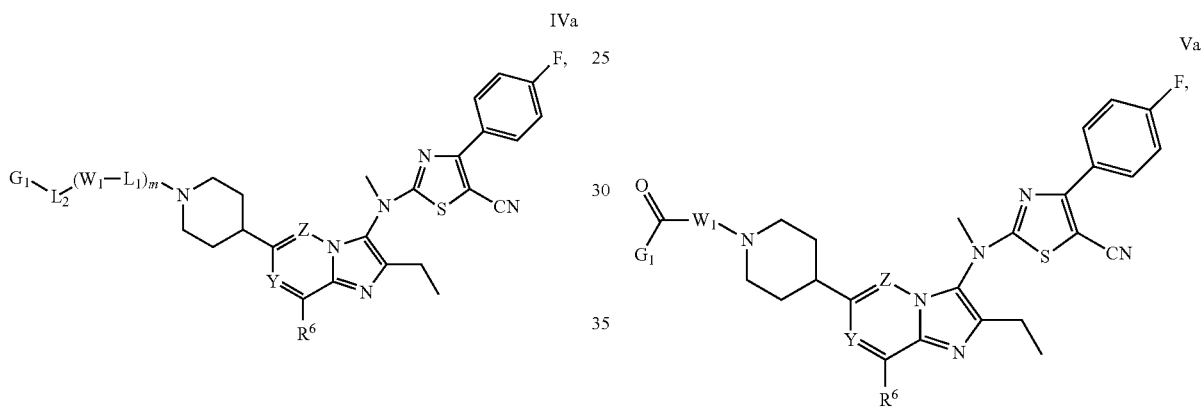

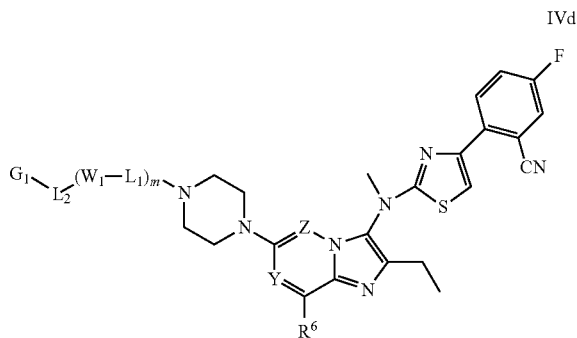

wherein Y, Z, $R^6$, $L_1$, $W_1$, $L_2$, $G_1$ and the subscript m are according to claim 1.

7. A compound or pharmaceutically acceptable salt thereof, according to claim 1, wherein the compound is according to Formula Va, Vb, Vc, or Vd:

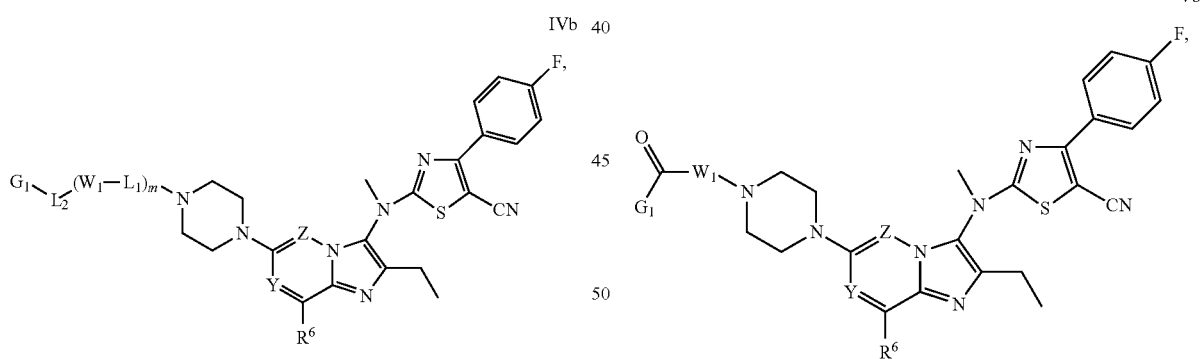

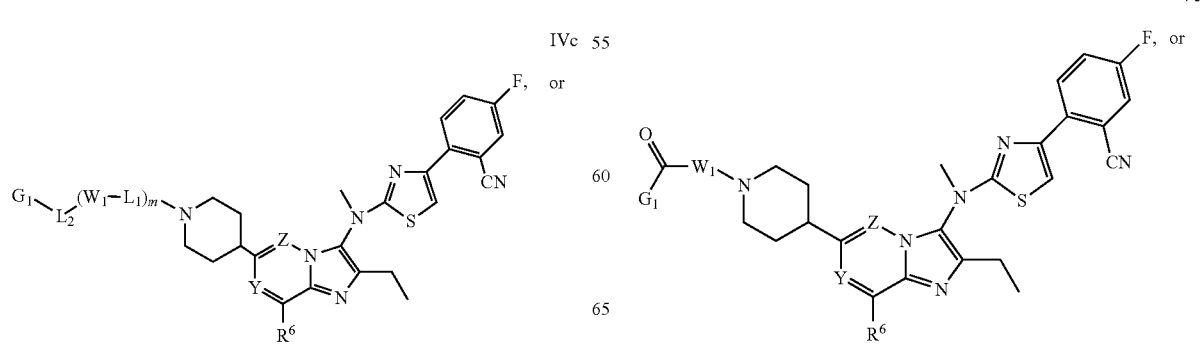

-continued

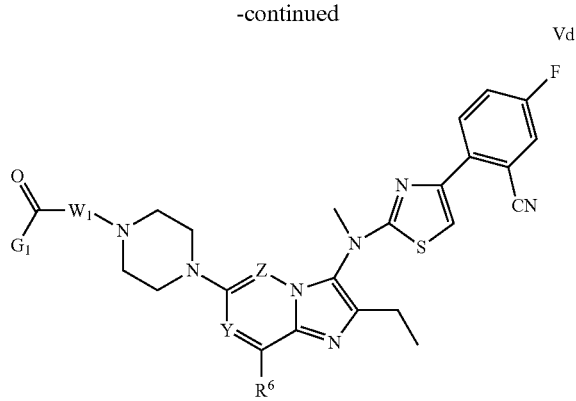

Vd wherein Y, Z, $R^6$, $W_1$, and $G_1$ are according to claim 1.

8. A compound or pharmaceutically acceptable salt thereof, according to claim 1, wherein $W_f$ is —CH$_2$—, —CH$_2$—CH$_2$—, —C(CH$_3$)H—, —CH$_2$—CH$_2$—CH$_2$— or —CH$_2$—C(CH$_3$)H—.

9. A compound or pharmaceutically acceptable salt thereof, according to claim 1, wherein $G_1$ is oxetanyl, azetidinyl, tetrahydrofuranyl, pyrolidinyl, tetrahydropyranyl, piperidinyl, piperazinyl, morpholinyl, or thiomorpholinyl, each of which is substituted with one or two independently selected $R^9$ groups.

10. A compound or pharmaceutically acceptable salt thereof, according to claim 9, wherein $R^9$ is $R^{10}$ and $R^{10}$ is selected from OH, F, Cl, and —CN.

11. A compound or pharmaceutically acceptable salt thereof, according to claim 1, wherein $R^6$ is H, —CH$_3$ or F.

12. A compound or pharmaceutically acceptable salt thereof, according to claim 1, wherein Y is N and Z is CH.

13. A compound or pharmaceutically acceptable salt thereof, according to claim 1, wherein the compound is selected from:
- 2-((2-ethyl-6-(piperazin-1-yl)imidazo[1,2-a]pyrazin-3-yl)(methyl)amino)-4-(4-fluorophenyl)thiazole-5-carbonitrile,
- 2-((2-ethyl-6-(4-(2-(3-hydroxyazetidin-1-yl)-2-oxoethyl)piperazin-1-yl)imidazo[1,2-a]pyrazin-3-yl)(methyl)amino)-4-(4-fluorophenyl)thiazole-5-carbonitrile,
- 2-((6-(4-(2-(3,3-difluoroazetidin-1-yl)-2-oxoethyl)piperazin-1-yl)-2-ethylimidazo[1,2-a]pyrazin-3-yl)(methyl)amino)-4-(4-fluorophenyl)thiazole-5-carbonitrile,
- 2-((6-(4-(2-(azetidin-1-yl)-2-oxoethyl)piperazin-1-yl)-2-ethylimidazo[1,2-a]pyrazin-3-yl)(methyl)amino)-4-(4-fluorophenyl)thiazole-5-carbonitrile,
- 2-(4-(3-((5-cyano-4-(4-fluorophenyl)thiazol-2-yl)(methyl)amino)-2-ethylimidazo[1,2-a]pyrazin-6-yl)piperazin-1-yl)-N,N-dimethylacetamide,
- (R)-2-((2-ethyl-6-(4-(2-(3-hydroxypyrrolidin-1-yl)-2-oxoethyl)piperazin-1-yl)imidazo[1,2-a]pyrazin-3-yl)(methyl)amino)-4-(4-fluorophenyl)thiazole-5-carbonitrile,
- (S)-2-((2-ethyl-6-(4-(2-(3-hydroxypyrrolidin-1-yl)-2-oxoethyl)piperazin-1-yl)imidazo[1,2-a]pyrazin-3-yl)(methyl)amino)-4-(4-fluorophenyl)thiazole-5-carbonitrile,
- 2-((2-ethyl-6-(4-(2-oxo-2-(pyrrolidin-1-yl)ethyl)piperazin-1-yl)imidazo[1,2-a]pyrazin-3-yl)(methyl)amino)-4-(4-fluorophenyl)thiazole-5-carbonitrile,
- 2-(4-(3-((5-cyano-4-(4-fluorophenyl)thiazol-2-yl)(methyl)amino)-2-ethylimidazo[1,2-a]pyrazin-6-yl)piperazin-1-yl)-N-methylacetamide,
- 2-((2-ethyl-6-(4-(2-morpholino-2-oxoethyl)piperazin-1-yl)imidazo[1,2-a]pyrazin-3-yl)(methyl)amino)-4-(4-fluorophenyl)thiazole-5-carbonitrile,
- 2-((2-ethyl-6-(4-(2-(3-fluoroazetidin-1-yl)-2-oxoethyl)piperazin-1-yl)imidazo[1,2-a]pyrazin-3-yl)(methyl)amino)-4-(4-fluorophenyl)thiazole-5-carbonitrile,
- 2-((2-ethyl-6-(4-(2-(3-hydroxyazetidin-1-yl)acetoyl)piperazin-1-yl)imidazo[1,2-a]pyrazin-3-yl)(methyl)amino)-4-(4-fluorophenyl)thiazole-5-carbonitrile,
- 1-(azetidin-1-yl)-2-(4-(2-ethyl-3-((4-(4-fluorophenyl)thiazol-2-yl)(methyl)amino)imidazo[1,2-a]pyrazin-6-yl)piperazin-1-yl)ethanone,
- 2-(4-(2-ethyl-3-((4-(4-fluorophenyl)thiazol-2-yl)(methyl)amino)imidazo[1,2-a]pyrazin-6-yl)piperazin-1-yl)-1-(3-hydroxyazetidin-1-yl)ethanone,
- 2-(2-((2-ethyl-6-(piperazin-1-yl)imidazo[1,2-a]pyrazin-3-yl)(methyl)amino)thiazol-4-yl)-5-fluorobenzonitrile,
- 2-(2-((2-ethyl-6-(4-(2-(3-hydroxyazetidin-1-yl)-2-oxoethyl)piperazin-1-yl)imidazo[1,2-a]pyrazin-3-yl)(methyl)amino)thiazol-4-yl)-5-fluorobenzonitrile,
- 2-(6-((2-ethyl-6-(4-(2-(3-hydroxyazetidin-1-yl)-2-oxoethyl)piperazin-1-yl)imidazo[1,2-a]pyrazin-3-yl)(methyl)amino)pyridin-2-yl)-5-fluorobenzonitrile,
- 2-(2-((2-ethyl-6-(4-(2-(3-hydroxyazetidin-1-yl)-2-oxoethyl)piperazin-1-yl)imidazo[1,2-a]pyrazin-3-yl)(methyl)amino)pyrimidin-4-yl)-5-fluorobenzonitrile,
- 2-((2-ethyl-6-(4-(2-(3-hydroxyazetidin-1-yl)-2-oxoethyl)piperazin-1-yl)imidazo[1,2-a]pyrazin-3-yl)(methyl)amino)-4-(4-fluorophenyl)pyrimidine-5-carbonitrile,
- 2-((2-ethyl-6-(1-(methylsulfonyl)-1,2,3,6-tetrahydropyridin-4-yl)imidazo[1,2-a]pyrazin-3-yl)(methyl)amino)-4-(4-fluorophenyl)thiazole-5-carbonitrile,
- 2-((2-ethyl-6-(1-(2-(3-hydroxyazetidin-1-yl)-2-oxoethyl)-1,2,3,6-tetrahydropyridin-4-yl)imidazo[1,2-a]pyrazin-3-yl)(methyl)amino)-4-(4-fluorophenyl)thiazole-5-carbonitrile,
- 2-((2-ethyl-6-(piperidin-4-yl)imidazo[1,2-a]pyrazin-3-yl)(methyl)amino)-4-(4-fluorophenyl)thiazole-5-carbonitrile,
- 2-((2-ethyl-6-(1-(2-(3-hydroxyazetidin-1-yl)-2-oxoethyl)piperidin-4-yl)imidazo[1,2-a]pyrazin-3-yl)(methyl)amino)-4-(4-fluorophenyl)thiazole-5-carbonitrile,
- (R)-2-((2-ethyl-6-(1-(2-(3-hydroxypyrrolidin-1-yl)-2-oxoethyl)piperidin-4-yl)imidazo[1,2-a]pyrazin-3-yl)(methyl)amino)-4-(4-fluorophenyl)thiazole-5-carbonitrile,
- (S)-2-((2-ethyl-6-(1-(2-(3-hydroxypyrrolidin-1-yl)-2-oxoethyl)piperidin-4-yl)imidazo[1,2-a]pyrazin-3-yl)(methyl)amino)-4-(4-fluorophenyl)thiazole-5-carbonitrile,
- 2-(4-(2-ethyl-3-((4-(4-fluorophenyl)thiazol-2-yl)(methyl)amino)imidazo[1,2-b]pyridazin-6-yl)piperazin-1-yl)-1-(3-hydroxyazetidin-1-yl)ethanone,
- 2-((2-ethyl-6-(4-(2-(3-hydroxyazetidin-1-yl)-2-oxoethyl)piperazin-1-yl)imidazo[1,2-b]pyridazin-3-yl)(methyl)amino)-4-(4-fluorophenyl)thiazole-5-carbonitrile,
- 2-(4-(2-ethyl-3-((4-(4-fluorophenyl)thiazol-2-yl)(methyl)amino)imidazo[1,2-b]pyridazin-6-yl)piperazin-1-yl)-1-(2-methylpyrrolidin-1-yl)ethanone,
- 2-(4-(2-ethyl-3-((4-(4-fluorophenyl)thiazol-2-yl)(methyl)amino)imidazo[1,2-b]pyridazin-6-yl)piperazin-1-yl)-1-(2-(hydroxymethyl)pyrrolidin-1-yl)ethanone,
- 2-(4-(2-ethyl-3-((4-(4-fluorophenyl)thiazol-2-yl)(methyl)amino)imidazo[1,2-b]pyridazin-6-yl)piperazin-1-yl)-N-methylacetamide, 1-(3,3-difluoropyrrolidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone, 1-(2,5-dimethylpyrrolidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone, (R)-2-(4-(2-ethyl-3-((4-(4-fluorophenyl)thiazol-2-yl)(methyl)amino)imidazo[1,2-b]pyridazin-6-yl)piperazin-1-yl)-1-(3-hydroxypyrrolidin-1-yl)ethanone, (S)-2-(4-(2-ethyl-3-((4-(4-fluorophenyl)thiazol-2-yl)(methyl)amino)imidazo[1,2-b]pyridazin-6-yl)piperazin-1-yl)-1-(3-hydroxypyrrolidin-1-yl)ethanone, 2-(4-(2-ethyl-3-((4-(4-fluorophenyl)thiazol-2-yl)(methyl)amino)imidazo[1,2-b]pyridazin-6-yl)piperazin-1-yl)-N-(2-hydroxyethyl)acetamide, 1-(azetidin-1-yl)-2-(4-(2-ethyl-3-((4-(4-fluorophenyl)thiazol-2-yl)(methyl)amino)imidazo[1,2-b]pyridazin-6-yl)piperazin-1-yl)ethanone, 2-(4-(2-ethyl-3-((4-(4-fluorophenyl)thiazol-2-yl)(methyl)amino)imidazo[1,2-b]pyridazin-6-yl)piperazin-1-yl)-N-isopropyl-N-methylacetamide, N-(2-ethyl-6-(4-(oxetan-3-yl)piperazin-1-yl)imidazo[1,2-b]pyridazin-3-yl)-4-(4-fluorophenyl)-N-methylthiazol-2-amine, N-(2-ethyl-6-(4-(tetrahydro-2H-pyran-4-yl)piperazin-1-yl)imidazo[1,2-b]pyridazin-3-yl)-4-(4-fluorophenyl)-N-methylthiazol-2-amine, 5-((4-(2-ethyl-3-((4-(4-fluorophenyl)thiazol-2-yl)(methyl)amino)imidazo[1,2-b]pyridazin-6-yl)piperazin-1-yl)methyl)oxazolidin-2-one, 5-((4-(2-ethyl-3-((4-(4-fluorophenyl)-5-(hydroxymethyl)thiazol-2-yl)(methyl)amino)imidazo[1,2-b]pyridazin-6-yl)piperazin-1-yl)methyl)oxazolidin-2-one, 2-(4-(2-ethyl-3-((4-(4-fluorophenyl)thiazol-2-yl)(methyl)amino)imidazo[1,2-b]pyridazin-6-yl)piperazin-1-yl)-N,N-dimethylacetamide, 2-(4-(2-ethyl-3-((4-(4-fluorophenyl)-5-(hydroxymethyl)thiazol-2-yl)(methyl)amino)imidazo[1,2-b]pyridazin-6-yl)piperazin-1-yl)-N,N-dimethylacetamide, 2-(4-(3-((5-cyano-4-(4-fluorophenyl)thiazol-2-yl)(methyl)amino)-2-ethylimidazo[1,2-b]pyridazin-6-yl)piperazin-1-yl)-N,N-dimethylacetamide, 2-(4-(2-ethyl-3-((4-(4-fluorophenyl)-5-(2,2,2-trifluoroacetoyl)thiazol-2-yl)(methyl)amino)imidazo[1,2-b]pyridazin-6-yl)piperazin-1-yl)-N,N-dimethylacetamide, 1-(2-(4-(2-ethyl-3-((4-(4-fluorophenyl)thiazol-2-yl)(methyl)amino)imidazo[1,2-b]pyridazin-6-yl)piperazin-1-yl)ethyl)pyrrolidin-2-one, (4-(2-ethyl-3-((4-(4-fluorophenyl)thiazol-2-yl)(methyl)amino)imidazo[1,2-b]pyridazin-6-yl)piperazin-1-yl)(tetrahydrofuran-2-yl)methanone, N-(2-ethyl-6-(4-((tetrahydrofuran-2-yl)methyl)piperazin-1-yl)imidazo[1,2-b]pyridazin-3-yl)-4-(4-fluorophenyl)-N-methylthiazol-2-amine, 3-(4-(2-ethyl-3-((4-(4-fluorophenyl)thiazol-2-yl)(methyl)amino)imidazo[1,2-b]pyridazin-6-yl)piperazin-1-yl)propan-1-ol, 3-(4-(2-ethyl-3-((4-(4-fluorophenyl)-5-(hydroxymethyl)thiazol-2-yl)(methyl)amino)imidazo[1,2-b]pyridazin-6-yl)piperazin-1-yl)propan-1-ol, 3-(4-(2-ethyl-3-((4-(4-fluorophenyl)thiazol-2-yl)(methyl)amino)imidazo[1,2-b]pyridazin-6-yl)piperazin-1-yl)propanenitrile, 3-(4-(2-ethyl-3-((4-(4-fluorophenyl)thiazol-2-yl)(methyl)amino)imidazo[1,2-b]pyridazin-6-yl)piperazin-1-yl)propanamide, N-(2-ethyl-6-(4-(2-methoxyethyl)piperazin-1-yl)imidazo[1,2-b]pyridazin-3-yl)-4-(4-fluorophenyl)-N-methyl-thiazol-2-amine, 2-(4-(2-ethyl-3-((4-(4-fluorophenyl)thiazol-2-yl)(methyl)amino)imidazo[1,2-b]pyridazin-6-yl)piperazin-1-yl)-N-isopropylacetamide, 2-(4-(2-ethyl-3-((4-(4-fluorophenyl)thiazol-2-yl)(methyl)amino)imidazo[1,2-b]pyridazin-6-yl)piperazin-1-yl)-1-(pyrrolidin-1-yl)ethanone, tert-butyl 2-(4-(2-ethyl-3-((4-(4-fluorophenyl)thiazol-2-yl)(methyl)amino)imidazo[1,2-b]pyridazin-6-yl)piperazin-1-yl)ethylcarbamate, N-(2-(4-(2-ethyl-3-((4-(4-fluorophenyl)thiazol-2-yl)(methyl)amino)imidazo[1,2-b]pyridazin-6-yl)piperazin-1-yl)ethyl)acetamide, ethyl 2-(4-(2-ethyl-3-((4-(4-fluorophenyl)thiazol-2-yl)(methyl)amino)imidazo[1,2-b]pyridazin-6-yl)piperazin-1-yl)ethylcarbamate, (S)-tert-butyl 4-(2-ethyl-3-((4-(4-fluorophenyl)thiazol-2-yl)(methyl)amino)imidazo[1,2-b]pyridazin-6-yl)-2-(hydroxymethyl)piperazine-1-carboxylate, (S)-(4-(2-ethyl-3-((4-(4-fluorophenyl)thiazol-2-yl)(methyl)amino)imidazo[1,2-b]pyridazin-6-yl)piperazin-2-yl)methanol, (S)-7-(2-ethyl-3-((4-(4-fluorophenyl)thiazol-2-yl)(methyl)amino)imidazo[1,2-b]pyridazin-6-yl)tetrahydro-1H-oxazolo[3,4-a]pyrazin-3 (5H)-one, (S)—N-(2-ethyl-6-(3-(methoxymethyl)-4-(methylsulfonyl)piperazin-1-yl)imidazo[1,2-b]pyridazin-3-yl)-4-(4-fluorophenyl)-N-methylthiazol-2-amine, (S)-(1-(3-(dimethylamino)propylsulfonyl)-4-(2-ethyl-3-((4-(4-fluorophenyl)thiazol-2-yl)(methyl)amino)imidazo[1,2-b]pyridazin-6-yl)piperazin-2-yl)methanol, (S)-2-(4-(2-ethyl-3-((4-(4-fluorophenyl)thiazol-2-yl)(methyl)amino)imidazo[1,2-b]pyridazin-6-yl)-2-(hydroxymethyl)piperazin-1-yl)-1-(pyrrolidin-1-yl)ethanone, (S)-2-(4-(2-ethyl-3-((4-(4-fluorophenyl)thiazol-2-yl)(methyl)amino)imidazo[1,2-b]pyridazin-6-yl)-2-(hydroxymethyl)piperazin-1-yl)-1-morpholinoethanone, (S)-8-(2-ethyl-3-((4-(4-fluorophenyl)thiazol-2-yl)(methyl)amino)imidazo[1,2-b]pyridazin-6-yl)hexahydropyrazino[2,1-c][1,4]oxazin-4(1H)-one, (S)-(4-(2-ethyl-3-((4-(4-fluorophenyl)thiazol-2-yl)(methyl)amino)imidazo[1,2-b]pyridazin-6-yl)-1-(methylsulfonyl)piperazin-2-yl)methanol, (S)-(4-(2-ethyl-3-((4-(4-fluorophenyl)-5-(hydroxymethyl)thiazol-2-yl)(methyl)amino)imidazo[1,2-b]pyridazin-6-yl)-1-(methylsulfonyl)piperazin-2-yl)methanol, (R)-(4-(2-ethyl-3-((4-(4-fluorophenyl)thiazol-2-yl)(methyl)amino)imidazo[1,2-b]pyridazin-6-yl)-1-(methylsulfonyl)piperazin-2-yl)methanol, 3-(4-(2-ethyl-3-((4-(4-fluorophenyl)thiazol-2-yl)(methyl)amino)imidazo[1,2-b]pyridazin-6-yl)piperazin-1-yl)-1-(4-methoxybenzyl)pyrrolidin-2-one, N-(2-ethyl-6-(4-(ethylsulfonyl)piperazin-1-yl)imidazo[1,2-b]pyridazin-3-yl)-4-(4-fluorophenyl)-N-methylthiazol-2-amine, 2-(4-(2-ethyl-3-((4-(4-fluorophenyl)thiazol-2-yl)(methyl)amino)imidazo[1,2-b]pyridazin-6-yl)-1-(methylsulfonyl)piperazin-2-yl)ethanol, 2-(4-(2-ethyl-3-((4-(4-fluoro-2-methylphenyl)thiazol-2-yl)(methyl)amino)imidazo[1,2-b]pyridazin-6-yl)piperazin-1-yl)-N,N-dimethylacetamide, tert-butyl-(1R,4S)-5-(2-ethyl-3-((4-(4-fluorophenyl)thiazol-2-yl)(methyl)amino)imidazo[1,2-b]pyridazin-6-yl)-2,5-diazabicyclo[2.2.1]heptane-2-carboxylate,
1-((1R,4S)-5-(2-ethyl-3-((4-(4-fluorophenyl)thiazol-2-yl)(methyl)amino)imidazo[1,2-b]pyridazin-6-yl)-2,5-diazabicyclo[2.2.1]heptan-2-yl)ethanone,
N-(2-ethyl-6-((1 S,4R)-5-(methylsulfonyl)-2,5-diazabicyclo[2.2.1]heptan-2-yl)imidazo[1,2-b]pyridazin-3-yl)-4-(4-fluorophenyl)-N-methylthiazol-2-amine,
N-(2-ethyl-6-(3-azaspiro[5.5]undecan-3-yl)imidazo[1,2-b]pyridazin-3-yl)-4-(4-fluorophenyl)-N-methylthiazol-2-amine,
N-(2-ethyl-6-morpholinoimidazo[1,2-b]pyridazin-3-yl)-4-(4-fluorophenyl)-N-methylthiazol-2-amine,
6-(1,1-Dioxo-thiomorpholin-4-yl)-2-ethyl-imidazo[1,2-b]pyridazin-3-yl]-[4-(4-fluoro-phenyl)-thiazol-2-yl]-methyl-amine,
N-(6-(4-(dimethylamino)piperidin-1-yl)-2-ethylimidazo[1,2-b]pyridazin-3-yl)-4-(4-fluorophenyl)-N-methylthiazol-2-amine,
tert-butyl 1-(2-ethyl-3-((4-(4-fluorophenyl)thiazol-2-yl)(methyl)amino)imidazo[1,2-b]pyridazin-6-yl)piperidin-4-ylcarbamate,
N-(6-(4-aminopiperidin-1-yl)-2-ethylimidazo[1,2-b]pyridazin-3-yl)-4-(4-fluorophenyl)-N-methylthiazol-2-amine,
N-(1-(2-ethyl-3-((4-(4-fluorophenyl)thiazol-2-yl)(methyl)amino)imidazo[1,2-b]pyridazin-6-yl)piperidin-4-yl)methane sulfonamide,
N-(1-(2-ethyl-3-((4-(4-fluorophenyl)thiazol-2-yl)(methyl)amino)imidazo[1,2-b]pyridazin-6-yl)piperidin-4-yl)tetrahydro-2H-pyran-4-carboxamide,
N-(1-(2-ethyl-3-((4-(4-fluorophenyl)thiazol-2-yl)(methyl)amino)imidazo[1,2-b]pyridazin-6-yl)piperidin-4-yl)-2-hydroxyacetamide,
N-(1-(2-ethyl-3-((4-(4-fluorophenyl)thiazol-2-yl)(methyl)amino)imidazo[1,2-b]pyridazin-6-yl)piperidin-4-yl)-3-methyloxetane-3-carboxamide,
tert-butyl 4-(1-(2-ethyl-3-((4-(4-fluorophenyl)thiazol-2-yl)(methyl)amino)imidazo[1,2-b]pyridazin-6-yl)piperidin-4-ylcarbamoyl)piperidine-1-carboxylate,
N-(1-(2-ethyl-3-((4-(4-fluorophenyl)thiazol-2-yl)(methyl)amino)imidazo[1,2-b]pyridazin-6-yl)piperidin-4-yl)piperidine-4-carboxamide,
N-(1-(2-ethyl-3-((4-(4-fluorophenyl)thiazol-2-yl)(methyl)amino)imidazo[1,2-b]pyridazin-6-yl)piperidin-4-yl)pyrrolidine-1-carboxamide,
1-(2-ethyl-3-((4-(4-fluorophenyl)thiazol-2-yl)(methyl)amino)imidazo[1,2-b]pyridazin-6-yl)piperidin-4-ol,
1-(2-ethyl-3-((4-(4-fluorophenyl)thiazol-2-yl)(methyl)amino)imidazo[1,2-b]pyridazin-6-yl)piperidin-3-ol,
N-ethyl-2-(1-(2-ethyl-3-((4-(4-fluorophenyl)thiazol-2-yl)(methyl)amino)imidazo[1,2-b]pyridazin-6-yl)piperidin-3-yloxy)acetamide,
(1-(2-ethyl-3-((4-(4-fluorophenyl)thiazol-2-yl)(methyl)amino)imidazo[1,2-b]pyridazin-6-yl)piperidin-4-yl)methanol,
(1-(2-ethyl-3-((4-(4-fluorophenyl)thiazol-2-yl)(methyl)amino)imidazo[1,2-b]pyridazin-6-yl)piperidin-3-yl)methanol,
1-(2-Ethyl-3-{[4-(4-fluoro-phenyl)-thiazol-2-yl]-methyl-amino}-imidazo[1,2-b]pyridazin-6-yl)-piperidine-4-carboxylic acid ethyl ester,
1-(2-ethyl-3-((4-(4-fluorophenyl)thiazol-2-yl)(methyl)amino)imidazo[1,2-b]pyridazin-6-yl)piperidine-4-carboxylic acid,
1-(2-ethyl-3-((4-(4-fluorophenyl)thiazol-2-yl)(methyl)amino)imidazo[1,2-b]pyridazin-6-yl)-N-(2-hydroxyethyl)piperidine-4-carboxamide,
1-(2-ethyl-3-((4-(4-fluorophenyl)thiazol-2-yl)(methyl)amino)imidazo[1,2-b]pyridazin-6-yl)piperidine-4-carboxamide,
1-(2-ethyl-3-((4-(4-fluorophenyl)thiazol-2-yl)(methyl)amino)imidazo[1,2-b]pyridazin-6-yl)piperidine-3-carboxamide,
[1-(2-Ethyl-3-{[4-(4-fluoro-phenyl)-thiazol-2-yl]-methyl-amino}-imidazo[1,2-b]pyridazin-6-yl)-piperidin-3-ylmethyl]-carbamic acid tert-butyl ester,
N-(6-(3-(aminomethyl)piperidin-1-yl)-2-ethylimidazo[1,2-b]pyridazin-3-yl)-4-(4-fluorophenyl)-N-methylthiazol-2-amine,
N-((1-(2-ethyl-3-((4-(4-fluorophenyl)thiazol-2-yl)(methyl)amino)imidazo[1,2-b]pyridazin-6-yl)piperidin-3-yl)methyl)methanesulfonamide,
[1-(2-Ethyl-3-{[4-(4-fluoro-phenyl)-thiazol-2-yl]-methyl-amino}-imidazo[1,2-b]pyridazin-6-yl)-piperidin-4-ylmethyl]-carbamic acid tert-butyl ester,
N-(6-(4-(aminomethyl)piperidin-1-yl)-2-ethylimidazo[1,2-b]pyridazin-3-yl)-4-(4-fluorophenyl)-N-methylthiazol-2-amine,
N-((1-(2-ethyl-3-((4-(4-fluorophenyl)thiazol-2-yl)(methyl)amino)imidazo[1,2-b]pyridazin-6-yl)piperidin-4-yl)methyl)methanesulfonamide,
3-((1-(2-ethyl-3-((4-(4-fluorophenyl)thiazol-2-yl)(methyl)amino)imidazo[1,2-b]pyridazin-6-yl)piperidin-4-yl)methyl)-1,1-dimethylurea,
N-((1-(2-ethyl-3-((4-(4-fluorophenyl)thiazol-2-yl)(methyl)amino)imidazo[1,2-b]pyridazin-6-yl)piperidin-4-yl)methyl)tetrahydro-2H-pyran-4-carboxamide,
2-(1-(2-ethyl-3-((4-(4-fluorophenyl)thiazol-2-yl)(methyl)amino)imidazo[1,2-b]pyridazin-6-yl)piperidin-4-yl)-N,N-dimethylacetamide,
N-(2-ethyl-6-(4-morpholinopiperidin-1-yl)imidazo[1,2-b]pyridazin-3-yl)-4-(4-fluorophenyl)-N-methylthiazol-2-amine,
N-(2-ethyl-6-(3-morpholinopiperidin-1-yl)imidazo[1,2-b]pyridazin-3-yl)-4-(4-fluorophenyl)-N-methylthiazol-2-amine,
N-(6-(1,4'-bipiperidin-1'-yl)-2-ethylimidazo[1,2-b]pyridazin-3-yl)-4-(4-fluorophenyl)-N-methylthiazol-2-amine,
1'-(2-ethyl-3-((4-(4-fluorophenyl)thiazol-2-yl)(methyl)amino)imidazo[1,2-b]pyridazin-6-yl)-1,3'-bipiperidin-4-ol,
N-(2-ethyl-6-(4-phenylpiperidin-1-yl)imidazo[1,2-b]pyridazin-3-yl)-4-(4-fluorophenyl)-N-methylthiazol-2-amine,
N-cyclopropyl-1-(2-ethyl-3-((4-(4-fluorophenyl)thiazol-2-yl)(methyl)amino)imidazo[1,2-b]pyridazin-6-yl)piperidine-4-sulfonamide,
1-(4-(2-ethyl-3-((4-(4-fluorophenyl)thiazol-2-yl)(methyl)amino)imidazo[1,2-b]pyridazin-6-yl)-1,4-diazepan-1-yl)ethanone,
N-(2-ethyl-6-(4-(methylsulfonyl)-1,4-diazepan-1-yl)imidazo[1,2-b]pyridazin-3-yl)-4-(4-fluorophenyl)-N-methylthiazol-2-amine,
N-(2-ethyl-6-(8-oxa-2-azaspiro[4.5]decan-2-yl)imidazo[1,2-b]pyridazin-3-yl)-4-(4-fluorophenyl)-N-methylthiazol-2-amine,
7-(2-ethyl-3-((4-(4-fluorophenyl)thiazol-2-yl)(methyl)amino)imidazo[1,2-b]pyridazin-6-yl)-1-oxa-3,7-diazaspiro[4.4]nonan-2-one, 7-(2-ethyl-3-((4-(4-fluorophenyl)thiazol-2-yl)(methyl) amino)imidazo[1,2-b]pyridazin-6-yl)-3-methyl-1-oxa-3,7-diazaspiro[4.4]nonan-2-one, 7-(2-ethyl-3-((4-(4-fluorophenyl)-5-(hydroxymethyl)thiazol-2-yl)(methyl)amino)imidazo[1,2-b]pyridazin-6-yl)-3-methyl-1-oxa-3, 7-diazaspiro[4.4]nonan-2-one, 7-(2-ethyl-3-((4-(4-fluorophenyl)thiazol-2-yl)(methyl) amino)imidazo[1,2-b]pyridazin-6-yl)-2,7-diazaspiro [4.4]nonane-1,3-dione, tert-butyl 5-(2-ethyl-3-((4-(4-fluorophenyl)thiazol-2-yl) (methyl)amino)imidazo[1,2-b]pyridazin-6-yl)hexahydropyrrolo[3,4-c]pyrrole-2(1H)-carboxylate, N-(2-ethyl-6-(5-(methylsulfonyl)hexahydropyrrolo[3,4-c]pyrrol-2(1H)-yl)imidazo[1,2-b]pyridazin-3-yl)-4-(4-fluorophenyl)-N-methylthiazol-2-amine, 1-(5-(2-ethyl-3-((4-(4-fluorophenyl)thiazol-2-yl)(methyl) amino)imidazo[1,2-b]pyridazin-6-yl)hexahydropyrrolo[3,4-c]pyrrol-2(1H)-yl)ethanone, N-(6-(5-(3-chloropropylsulfonyl)hexahydropyrrolo[3,4-c]pyrrol-2(1H)-yl)-2-ethylimidazo[1,2-b]pyridazin-3-yl)-4-(4-fluorophenyl)-N-methylthiazol-2-amine, N-(6-(5-(3-(dimethylamino)propylsulfonyl)hexahydropyrrolo[3,4-c]pyrrol-2(1H)-yl)-2-ethylimidazo[1,2-b] pyridazin-3-yl)-4-(4-fluorophenyl)-N-methylthiazol-2-amine, N-(2-ethyl-6-(5-(3-morpholinopropylsulfonyl)hexahydropyrrolo[3,4-c]pyrrol-2(1H)-yl)imidazo[1,2-b] pyridazin-3-yl)-4-(4-fluorophenyl)-N-methylthiazol-2-amine, (S)-1-(2-ethyl-3-((4-(4-fluorophenyl)thiazol-2-yl) (methyl)amino)imidazo[1,2-b]pyridazin-6-yl)pyrrolidine-3-carbonitrile, 1-(2-ethyl-3-((4-(4-fluorophenyl)thiazol-2-yl)(methyl) amino)imidazo[1,2-b]pyridazin-6-yl)pyrrolidin-3-ol, 1-(2-ethyl-3-((4-(4-fluorophenyl)thiazol-2-yl)(methyl) amino)imidazo[1,2-b]pyridazin-6-yl)pyrrolidin-3-yl formate, N-(2-ethyl-6-(3-thiomorpholinopyrrolidin-1-yl)imidazo [1,2-b]pyridazin-3-yl)-4-(4-fluorophenyl)-N-methylthiazol-2-amine, 1-(3-((5-chloro-4-(4-fluorophenyl)thiazol-2-yl)(methyl) amino)-2-ethylimidazo[1,2-b]pyridazin-6-yl)pyrrolidin-3-one, tert-butyl 1-(2-ethyl-3-((4-(4-fluorophenyl)thiazol-2-yl) (methyl)amino)imidazo[1,2-b]pyridazin-6-yl)pyrrolidin-3-ylcarbamate, N-(6-(3-aminopyrrolidin-1-yl)-2-ethylimidazo[1,2-b] pyridazin-3-yl)-4-(4-fluorophenyl)-N-methylthiazol-2-amine, methyl 2-(1-(2-ethyl-3-((4-(4-fluorophenyl)thiazol-2-yl) (methyl)amino)imidazo[1,2-b]pyridazin-6-yl)pyrrolidin-3-ylamino)acetate, N-(1-(2-ethyl-3-((4-(4-fluorophenyl)thiazol-2-yl) (methyl)amino)imidazo[1,2-b]pyridazin-6-yl)pyrrolidin-3-yl)-2-hydroxyacetamide, N-(1-(2-ethyl-3-((4-(4-fluorophenyl)thiazol-2-yl) (methyl)amino)imidazo[1,2-b]pyridazin-6-yl)pyrrolidin-3-yl)methane sulfonamide, (S)-1-(2-ethyl-3-((4-(4-fluorophenyl)thiazol-2-yl) (methyl)amino)imidazo[1,2-b]pyridazin-6-yl)pyrrolidine-2-carboxylic acid, 1-(2-Ethyl-3-{[4-(4-fluoro-phenyl)-thiazol-2-yl]-methylamino}-imidazo[1,2-b]pyridazin-6-yl)-pyrrolidine-3-carboxylic acid methyl ester, 1-(2-ethyl-3-((4-(4-fluorophenyl)thiazol-2-yl)(methyl) amino)imidazo[1,2-b]pyridazin-6-yl)-N-(2-hydroxyethyl)pyrrolidine-3-carboxamide, (1-(2-ethyl-3-((4-(4-fluorophenyl)thiazol-2-yl)(methyl) amino)imidazo[1,2-b]pyridazin-6-yl)pyrrolidin-3-yl) (morpholino)methanone, (1-(2-ethyl-3-((4-(4-fluorophenyl)thiazol-2-yl)(methyl) amino)imidazo[1,2-b]pyridazin-6-yl)pyrrolidin-2-yl) methanol, (1-(2-ethyl-3-((4-(4-fluorophenyl)thiazol-2-yl)(methyl) amino)imidazo[1,2-b]pyridazin-6-yl)pyrrolidin-3-yl) methanol, (1-(2-ethyl-3-((4-(4-fluorophenyl)-5-(hydroxymethyl)thiazol-2-yl)(methyl)amino)imidazo[1,2-b]pyridazin-6-yl)pyrrolidin-3-yl)methanol, 3-(4-(1-(2-ethyl-3-((4-(4-fluorophenyl)thiazol-2-yl) (methyl)amino)imidazo[1,2-b]pyridazin-6-yl)pyrrolidin-3-yl)piperazin-1-yl)propan-1-ol, 4-(1-(2-ethyl-3-((4-(4-fluorophenyl)thiazol-2-yl)(methyl) amino)imidazo[1,2-b]pyridazin-6-yl)pyrrolidin-3-yl) piperazin-2-one, N-(2-ethyl-6-(3-morpholinopyrrolidin-1-yl)imidazo[1,2-b]pyridazin-3-yl)-4-(4-fluorophenyl)-N-methylthiazol-2-amine, (2-((2-ethyl-6-(3-morpholinopyrrolidin-1-yl)imidazo[1,2-b]pyridazin-3-yl)(methyl)amino)-4-(4-fluorophenyl) thiazol-5-yl)methanol, 2-((2-ethyl-6-(3-morpholinopyrrolidin-1-yl)imidazo[1,2-b]pyridazin-3-yl)(methyl)amino)-4-(4-fluorophenyl) thiazole-5-carbonitrile, {6-[3-(1,1-Dioxo-thiomorpholin-4-yl)-pyrrolidin-1-yl]-2-ethyl-imidazo[1,2-b]pyridazin-3-yl}-[4-(4-fluoro-phenyl)-thiazol-2-yl]-methyl-amine, N-(2-ethyl-6-(3-(piperidin-1-yl)pyrrolidin-1-yl)imidazo [1,2-b]pyridazin-3-yl)-4-(4-fluorophenyl)-N-methylthiazol-2-amine, 1-(1-(2-ethyl-3-((4-(4-fluorophenyl)thiazol-2-yl)(methyl) amino)imidazo[1,2-b]pyridazin-6-yl)pyrrolidin-3-yl) piperidin-4-ol, (1-(2-ethyl-3-((4-(4-fluorophenyl)thiazol-2-yl)(methyl) amino)imidazo[1,2-b]pyridazin-6-yl)azetidin-3-yl) methanol,

[1-(2-Ethyl-3-{[4-(4-fluoro-phenyl)-thiazol-2-yl]-methyl-amino}-imidazo[1,2-b]pyridazin-6-yl)-azetidin-3-yl]-carbamic acid tert-butyl ester, 2-(1-(2-ethyl-3-((4-(4-fluorophenyl)thiazol-2-yl)(methyl) amino)imidazo[1,2-b]pyridazin-6-yl)azetidin-3-ylamino)-1-(3-hydroxyazetidin-1-yl)ethanone, 2-(1-(2-ethyl-3-((4-(4-fluorophenyl)thiazol-2-yl)(methyl) amino)imidazo[1,2-b]pyridazin-6-yl)azetidin-3-ylamino)-N,N-dimethylacetamide, 2-(1-(2-ethyl-3-((4-(4-fluorophenyl)thiazol-2-yl)(methyl) amino)imidazo[1,2-b]pyridazin-6-yl)azetidin-3-ylamino)-N-methylacetamide, N-(1-(2-ethyl-3-((4-(4-fluorophenyl)thiazol-2-yl) (methyl)amino)imidazo[1,2-b]pyridazin-6-yl)azetidin-3-yl)methane sulfonamide, (1-(2-ethyl-3-((4-(4-fluorophenyl)thiazol-2-yl)(methyl) amino)imidazo[1,2-b]pyridazin-6-yl)azetidin-3-yl)(3-hydroxypyrrolidin-1-yl)methanone, 2-((2-ethyl-6-(4-((2-oxooxazolidin-5-yl)methyl)piperazin-1-yl)imidazo[1,2-b]pyridazin-3-yl)(methyl) amino)-4-(4-fluorophenyl)thiazole-5-carbonitrile, (S)-2-((2-ethyl-6-(3-(hydroxymethyl)-4-(methylsulfonyl) piperazin-1-yl)imidazo[1,2-b]pyridazin-3-yl)(methyl) amino)-4-(4-fluorophenyl)thiazole-5-carbonitrile, 2-((2-ethyl-6-(2-oxo-1-oxa-3,7-diazaspiro[4.5]decan-7-yl)imidazo[1,2-b]pyridazin-3-yl)(methyl)amino)-4-(4-fluorophenyl)thiazole-5-carbonitrile, 2-((2-ethyl-6-(3-methyl-2-oxo-1-oxa-3,7-diazaspiro[4.5]decan-7-yl)imidazo[1,2-b]pyridazin-3-yl)(methyl)amino)-4-(4-fluorophenyl)thiazole-5-carbonitrile, 2-((2-ethyl-6-(3-methyl-2-oxo-1-oxa-3,7-diazaspiro[4.4]nonan-7-yl)imidazo[1,2-b]pyridazin-3-yl)(methyl)amino)-4-(4-fluorophenyl)thiazole-5-carbonitrile, tert-butyl 7-(3-((5-cyano-4-(4-fluorophenyl)thiazol-2-yl)(methyl)amino)-2-ethylimidazo[1,2-b]pyridazin-6-yl)-2,7-diazaspiro[4.4]nonane-2-carboxylate, 2-((2-ethyl-6-(2,7-diazaspiro[4.4]nonan-2-yl)imidazo[1,2-b]pyridazin-3-yl)(methyl)amino)-4-(4-fluorophenyl)thiazole-5-carbonitrile, 2-((6-(7-acetoyl-2,7-diazaspiro[4.4]nonan-2-yl)-2-ethylimidazo[1,2-b]pyridazin-3-yl)(methyl)amino)-4-(4-fluorophenyl)thiazole-5-carbonitrile, methyl (1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl), N-((1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl)methyl)acetamide, N-((1-(3-((5-cyano-4-(4-fluorophenyl)thiazol-2-yl)(methyl)amino)-2-ethylimidazo[1,2-b]pyridazin-6-yl)-3-hydroxypyrrolidin-3-yl)methyl)isobutyramide, 2-((2-ethyl-6-(3-hydroxypyrrolidin-1-yl)imidazo[1,2-b]pyridazin-3-yl)(methyl)amino)-4-(4-fluorophenyl)thiazole-5-carbonitrile, 2-((2-ethyl-6-(3-oxopyrrolidin-1-yl)imidazo[1,2-b]pyridazin-3-yl)(methyl)amino)-4-(4-fluorophenyl)thiazole-5-carbonitrile, 2-((2-ethyl-6-(3-(hydroxymethyl)pyrrolidin-1-yl)imidazo[1,2-b]pyridazin-3-yl)(methyl)amino)-4-(4-fluorophenyl)thiazole-5-carbonitrile, (S)-2-((2-ethyl-6-(3-(2-(3-hydroxyazetidin-1-yl)-2-oxoethylamino)pyrrolidin-1-yl)imidazo[1,2-b]pyridazin-3-yl)(methyl)amino)-4-(4-fluorophenyl)thiazole-5-carbonitrile, (S)-2-(1-(3-((5-cyano-4-(4-fluorophenyl)thiazol-2-yl)(methyl)amino)-2-ethylimidazo[1,2-b]pyridazin-6-yl)pyrrolidin-3-ylamino)-N,N-dimethylacetamide, (R)-2-((2-ethyl-6-(3-(2-(3-hydroxyazetidin-1-yl)-2-oxoethylamino)pyrrolidin-1-yl)imidazo[1,2-b]pyridazin-3-yl)(methyl)amino)-4-(4-fluorophenyl)thiazole-5-carbonitrile, (R)-2-(1-(3-((5-cyano-4-(4-fluorophenyl)thiazol-2-yl)(methyl)amino)-2-ethylimidazo[1,2-b]pyridazin-6-yl)pyrrolidin-3-ylamino)-N,N-dimethylacetamide, 2-((6-(3-((2S,6R)-2,6-dimethylmorpholino)pyrrolidin-1-yl)-2-ethylimidazo[1,2-b]pyridazin-3-yl)(methyl)amino)-4-(4-fluorophenyl)thiazole-5-carbonitrile, 2-((2-ethyl-6-(3-(4-(hydroxymethyl)piperidin-1-yl)pyrrolidin-1-yl)imidazo[1,2-b]pyridazin-3-yl)(methyl)amino)-4-(4-fluorophenyl)thiazole-5-carbonitrile, 2-((6-(3-(4-acetoylpiperazin-1-yl)pyrrolidin-1-yl)-2-ethylimidazo[1,2-b]pyridazin-3-yl)(methyl)amino)-4-(4-fluorophenyl)thiazole-5-carbonitrile, N-(1-(1-(3-((5-cyano-4-(4-fluorophenyl)thiazol-2-yl)(methyl)amino)-2-ethylimidazo[1,2-b]pyridazin-6-yl)pyrrolidin-3-yl)piperidin-4-yl)-N-methylacetamide, 2-((2-ethyl-6-(3-(4-hydroxypiperidin-1-yl)pyrrolidin-1-yl)imidazo[1,2-b]pyridazin-3-yl)(methyl)amino)-4-(4-fluorophenyl)thiazole-5-carbonitrile, 2-((2-ethyl-6-(3-(4-methoxypiperidin-1-yl)pyrrolidin-1-yl)imidazo[1,2-b]pyridazin-3-yl)(methyl)amino)-4-(4-fluorophenyl)thiazole-5-carbonitrile, 2-((2-ethyl-6-((3S,4S)-3-hydroxy-4-morpholinopyrrolidin-1-yl)imidazo[1,2-b]pyridazin-3-yl)(methyl)amino)-4-(4-fluorophenyl)thiazole-5-carbonitrile, 1-(2-ethyl-3-((4-(4-fluorophenyl)-5-(hydroxymethyl)thiazol-2-yl)(methyl)amino)imidazo[1,2-b]pyridazin-6-yl)pyrrolidin-3-ol, (2-((2-ethyl-6-(8-oxa-2-azaspiro[4.5]decan-2-yl)imidazo[1,2-b]pyridazin-3-yl)(methyl)amino)-4-(4-fluorophenyl)thiazol-5-yl)methanol,

[1-(3-{[5-Cyano-4-(4-fluoro-phenyl)-thiazol-2-yl]-methyl-amino}-2-ethyl-imidazo[1,2-b]pyridazin-6-yl)-azetidin-3-yl]-carbamic acid tert-butyl ester, 2-((6-(3-aminoazetidin-1-yl)-2-ethylimidazo[1,2-b]pyridazin-3-yl)(methyl)amino)-4-(4-fluorophenyl)thiazole-5-carbonitrile, 2-((2-ethyl-6-(3-(2-(3-hydroxyazetidin-1-yl)-2-oxoethylamino)azetidin-1-yl)imidazo[1,2-b]pyridazin-3-yl)(methyl)amino)-4-(4-fluorophenyl)thiazole-5-carbonitrile, N-(1-(3-((5-cyano-4-(4-fluorophenyl)thiazol-2-yl)(methyl)amino)-2-ethylimidazo[1,2-b]pyridazin-6-yl)azetidin-3-yl)methanesulfonamide, 2-((2-ethyl-6-(3-(morpholine-4-carbonyl)azetidin-1-yl)imidazo[1,2-b]pyridazin-3-yl)(methyl)amino)-4-(4-fluorophenyl)thiazole-5-carbonitrile, 2-((2-ethyl-6-(3-(3-hydroxypyrrolidine-1-carbonyl)azetidin-1-yl)imidazo[1,2-b]pyridazin-3-yl)(methyl)amino)-4-(4-fluorophenyl)thiazole-5-carbonitrile, 4-(2-Ethyl-3-{[4-(4-fluoro-phenyl)-thiazol-2-yl]-methyl-amino}-imidazo[1,2-b]pyridazin-6-yl)-3,6-dihydro-2H-pyridine-1-carboxylic acid tert-butyl ester, N-(2-ethyl-6-(1-(methylsulfonyl)-1,2,3,6-tetrahydropyridin-4-yl)imidazo[1,2-b]pyridazin-3-yl)-4-(4-fluorophenyl)-N-methylthiazol-2-amine, (3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)methanol, 2-(3-((4-(4-fluorophenyl)thiazol-2-yl)(methyl)amino)-6-(1-(methylsulfonyl)-1,2,3,6-tetrahydropyridin-4-yl)imidazo[1,2-b]pyridazin-2-yl)acetonitrile, 3-(3-((4-(4-fluorophenyl)thiazol-2-yl)(methyl)amino)-6-(1-(methylsulfonyl)piperidin-4-yl)imidazo[1,2-b]pyridazin-2-yl)propanamide, 3-(3-((4-(4-fluorophenyl)thiazol-2-yl)(methyl)amino)-6-(1-(methylsulfonyl)piperidin-4-yl)imidazo[1,2-b]pyridazin-2-yl)propanenitrile, 3-(3-((4-(4-fluorophenyl)-5-(2,2,2-trifluoroacetoyl)thiazol-2-yl)(methyl)amino)-6-(1-(methylsulfonyl)piperidin-4-yl)imidazo[1,2-b]pyridazin-2-yl)propanenitrile, 3-(3-((4-(4-fluorophenyl)thiazol-2-yl)(methyl)amino)-6-(1-(methylsulfonyl)piperidin-4-yl)imidazo[1,2-b]pyridazin-2-yl)propan-1-ol, 2-(4-(2-ethyl-3-((4-(4-fluorophenyl)thiazol-2-yl)(methyl)amino)imidazo[1,2-b]pyridazin-6-yl)piperidin-1-yl)-1-(3-hydroxyazetidin-1-yl)ethanone, 2-(4-(2-ethyl-3-((4-(4-fluorophenyl)thiazol-2-yl)(methyl)amino)imidazo[1,2-b]pyridazin-6-yl)piperidin-1-yl)-N,N-dimethylacetamide, 2-(4-(2-ethyl-3-((4-(4-fluorophenyl)-5-(hydroxymethyl)thiazol-2-yl)(methyl)amino)imidazo[1,2-b]pyridazin-6-yl)piperidin-1-yl)-N,N-dimethylacetamide, 2-(2-((2-ethyl-6-(1-(methylsulfonyl)-1,2,3,6-tetrahydropyridin-4-yl)imidazo[1,2-b]pyridazin-3-yl)(methyl)amino)thiazol-4-yl)-5-fluorobenzonitrile, 2-(2-((2-ethyl-6-(1-(methylsulfonyl)piperidin-4-yl)imidazo[1,2-b]pyridazin-3-yl)(methyl)amino)thiazol-4-yl)-5-fluorobenzonitrile, 2-(2-((2-ethyl-6-(1-(methylsulfonyl)piperidin-4-yl)imidazo[1,2-b]pyridazin-3-yl)(methyl)amino)-5-(hydroxymethyl)thiazol-4-yl)-5-fluorobenzonitrile, 2-(2-((2-ethyl-6-(1-(2-(3-hydroxyazetidin-1-yl)-2-oxoethyl)piperidin-4-yl)imidazo[1,2-b]pyridazin-3-yl)(methyl)amino)thiazol-4-yl)-5-fluorobenzonitrile, 2-(4-(3-((4-(2-cyano-4-fluorophenyl)thiazol-2-yl)(methyl)amino)-2-ethylimidazo[1,2-b]pyridazin-6-yl)piperidin-1-yl)-N,N-dimethylacetamide, 2-(4-(3-((4-(2-cyano-4-fluorophenyl)thiazol-2-yl)(methyl)amino)-2-ethylimidazo[1,2-b]pyridazin-6-yl)piperidin-1-yl)-N-methylacetamide, 2-(2-((2-ethyl-6-(1-(2-(3-hydroxyazetidin-1-yl)-2-oxoethyl)piperidin-4-yl)imidazo[1,2-b]pyridazin-3-yl)(methyl)amino)-5-methylthiazol-4-yl)-5-fluorobenzonitrile, 2-(4-(3-((4-(2-cyano-4-fluorophenyl)-5-methylthiazol-2-yl)(methyl)amino)-2-ethylimidazo[1,2-b]pyridazin-6-yl)piperidin-1-yl)-N-methylacetamide, 2-((2-ethyl-6-(1-(2-(3-hydroxyazetidin-1-yl)-2-oxoethyl)piperidin-4-yl)imidazo[1,2-b]pyridazin-3-yl)(methyl)amino)-4-(4-fluorophenyl)thiazole-5-carbonitrile, 2-(6-((2-ethyl-6-(1-(2-(3-hydroxyazetidin-1-yl)-2-oxoethyl)piperidin-4-yl)imidazo[1,2-b]pyridazin-3-yl)(methyl)amino)pyridin-2-yl)-5-fluorobenzonitrile, 2-(4-(2-ethyl-3-((6-(4-fluorophenyl)pyridin-2-yl)(methyl)amino)imidazo[1,2-b]pyridazin-6-yl)piperidin-1-yl)-1-(3-hydroxyazetidin-1-yl)ethanone, 2-(4-(2-ethyl-3-((4-(4-fluorophenyl)pyrimidin-2-yl)(methyl)amino)imidazo[1,2-b]pyridazin-6-yl)piperidin-1-yl)-1-(3-hydroxyazetidin-1-yl)ethanone, 2-(4-(2-ethyl-3-((2-(4-fluorophenyl)pyrimidin-4-yl)(methyl)amino)imidazo[1,2-b]pyridazin-6-yl)piperidin-1-yl)-1-(3-hydroxyazetidin-1-yl)ethanone, 2-((2-ethyl-6-(1-(2-(3-hydroxyazetidin-1-yl)-2-oxoethyl)piperidin-4-yl)imidazo[1,2-b]pyridazin-3-yl)(methyl)amino)-6-(4-fluorophenyl)nicotinonitrile, 6-((2-ethyl-6-(1-(2-(3-hydroxyazetidin-1-yl)-2-oxoethyl)piperidin-4-yl)imidazo[1,2-b]pyridazin-3-yl)(methyl)amino)-2-(4-fluorophenyl)nicotinonitrile, 2-(5-((2-ethyl-6-(piperidin-4-yl)imidazo[1,2-b]pyridazin-3-yl)(methyl)amino)-1,2,4-thiadiazol-3-yl)-5-fluorobenzonitrile, and 2-(5-((2-ethyl-6-(1-(2-(3-hydroxyazetidin-1-yl)-2-oxoethyl)piperidin-4-yl)imidazo[1,2-b]pyridazin-3-yl)(methyl)amino)-1,2,4-thiadiazol-3-yl)-5-fluorobenzonitrile.

14. A pharmaceutical composition comprising a pharmaceutically acceptable carrier and a pharmaceutically effective amount of a compound according to claim 1.

15. A method of inhibiting ectonucleotide pyrophosphatase/phosphodiesterase 2 (ENPP2), which method comprises contacting the ENPP2 with a compound or pharmaceutically acceptable salt thereof according to claim 1.

* * * * *

UNITED STATES PATENT AND TRADEMARK OFFICE
CERTIFICATE OF CORRECTION

PATENT NO. : 9,796,719 B2  
APPLICATION NO. : 14/898327  
DATED : October 24, 2017  
INVENTOR(S) : Desroy et al.

Page 1 of 1

It is certified that error appears in the above-identified patent and that said Letters Patent is hereby corrected as shown below:

Column 374, Line 21: Claim 1, Delete "-$NR^dC(=O)$-, -$NR^dC(=O)O$-," and insert
-- -$NR^dC(=O)$-, -$NR^jC(=O)O$-, --

Column 381, Line 7: Claim 13, Delete "N-(2-ethyl-6-((1 S,4R)-" and insert
-- N-(2-ethyl-6-((1S,4R)- --

Column 384, Line 54: Claim 13, Delete "3-yl)methane sulfonamide," and insert
-- 3-yl)methanesulfonamide, --

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*